US012173064B2

(12) United States Patent
Verona et al.

(10) Patent No.: US 12,173,064 B2
(45) Date of Patent: Dec. 24, 2024

(54) ANTIBODIES SPECIFICALLY BINDING PD-1, TIM-3 OR PD-1 AND TIM-3 AND THEIR USES

(71) Applicant: Janssen Biotech, Inc., Horsham, PA (US)

(72) Inventors: Raluca Verona, Spring House, PA (US); Gordon Powers, Spring House, PA (US); Nina Chi Sabins, Spring House, PA (US); Nikki A. DeAngelis, Spring House, PA (US); Sandra Santulli-Marotto, Spring House, PA (US); Karla R. Wiehagen, Spring House, PA (US); Sheng-Jiun Wu, Spring House, PA (US); Catherine Ferrante, Spring House, PA (US); Enrique Zudaire Ubani, Spring House, PA (US)

(73) Assignee: Janssen Biotech, Inc., Horsham, PA (US)

(*) Notice: Subject to any disclaimer, the term of this patent is extended or adjusted under 35 U.S.C. 154(b) by 738 days.

(21) Appl. No.: 17/090,961

(22) Filed: Nov. 6, 2020

(65) Prior Publication Data
US 2021/0277110 A1 Sep. 9, 2021

Related U.S. Application Data

(62) Division of application No. 15/340,109, filed on Nov. 1, 2016, now Pat. No. 10,894,830.

(60) Provisional application No. 62/250,095, filed on Nov. 3, 2015.

(51) Int. Cl.
| | |
|---|---|
| *C07K 16/28* | (2006.01) |
| *A61K 39/395* | (2006.01) |
| *A61K 45/06* | (2006.01) |
| *A61P 35/00* | (2006.01) |
| *C07K 16/10* | (2006.01) |
| *C07K 16/42* | (2006.01) |
| *A61K 39/00* | (2006.01) |

(52) U.S. Cl.
CPC ...... *C07K 16/2803* (2013.01); *A61K 39/3955* (2013.01); *A61K 45/06* (2013.01); *A61P 35/00* (2018.01); *C07K 16/1063* (2013.01); *C07K 16/2818* (2013.01); *C07K 16/4258* (2013.01); *A61K 2039/505* (2013.01); *C07K 2317/21* (2013.01); *C07K 2317/24* (2013.01); *C07K 2317/31* (2013.01); *C07K 2317/33* (2013.01); *C07K 2317/34* (2013.01); *C07K 2317/52* (2013.01); *C07K 2317/55* (2013.01); *C07K 2317/565* (2013.01); *C07K 2317/71* (2013.01); *C07K 2317/75* (2013.01); *C07K 2317/76* (2013.01); *C07K 2317/92* (2013.01)

(58) Field of Classification Search
CPC ............ C07K 16/2803; C07K 16/1063; C07K 16/2818; C07K 16/4258; C07K 2317/21; C07K 2317/24; C07K 2317/31; C07K 2317/33; C07K 2317/34; C07K 2317/52; C07K 2317/55; A61K 39/3955; A61K 45/06; A61K 2039/505; A61P 35/00
See application file for complete search history.

(56) References Cited

U.S. PATENT DOCUMENTS

| | | |
|---|---|---|
| 4,978,672 A | 12/1990 | Bowman et al. |
| 5,208,020 A | 5/1993 | Chari et al. |
| 5,223,409 A | 6/1993 | Ladner et al. |
| 5,225,539 A | 7/1993 | Winter |
| 5,403,484 A | 4/1995 | Ladner et al. |
| 5,416,064 A | 5/1995 | Chari et al. |
| 5,427,908 A | 6/1995 | Dower et al. |
| 5,571,698 A | 11/1996 | Ladner et al. |
| 5,580,717 A | 12/1996 | Dower et al. |
| 5,624,821 A | 4/1997 | Winter et al. |
| 5,635,483 A | 6/1997 | Pettit et al. |
| 5,688,690 A | 11/1997 | Valiante et al. |
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,877,296 A | 3/1999 | Hamann et al. |
| 5,885,793 A | 3/1999 | Griffiths et al. |
| 5,897,862 A | 4/1999 | Hardy et al. |
| 5,969,108 A | 10/1999 | McCafferty et al. |
| 6,054,297 A | 4/2000 | Carter et al. |
| 6,150,584 A | 11/2000 | Kucherlapati et al. |
| 6,172,197 B1 | 1/2001 | McCafferty et al. |

(Continued)

FOREIGN PATENT DOCUMENTS

| | | |
|---|---|---|
| CN | 1880446 A | 12/2006 |
| CN | 103721255 A | 4/2014 |

(Continued)

OTHER PUBLICATIONS

Mariuzza (Annu. Rev. Biophys. Biophys. Chem., 16: 139-159, 1987).*

(Continued)

*Primary Examiner* — Nelson B Moseley, II

(57) ABSTRACT

The present invention relates to antibodies specifically binding PD-1, TIM-3 or PD-1 and TIM-3, polynucleotides encoding the antibodies or fragments, and methods of making and using the foregoing.

30 Claims, 30 Drawing Sheets
Specification includes a Sequence Listing.

(56) References Cited

U.S. PATENT DOCUMENTS

| | | |
|---|---|---|
| 6,479,638 B1 | 11/2002 | Adema et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,582,959 B2 | 6/2003 | Kim |
| 6,593,081 B1 | 7/2003 | Griffiths et al. |
| 6,630,579 B2 | 10/2003 | Chari et al. |
| 6,703,020 B1 | 3/2004 | Thorpe et al. |
| 6,737,056 B1 | 5/2004 | Presta |
| 6,818,749 B1 | 11/2004 | Kashmiri et al. |
| 6,884,879 B1 | 4/2005 | Baca et al. |
| 7,029,674 B2 | 4/2006 | Carreno et al. |
| 7,060,269 B1 | 6/2006 | Baca et al. |
| 7,473,761 B2 | 1/2009 | Albert et al. |
| 7,479,544 B2 | 1/2009 | Clark et al. |
| 7,488,802 B2 | 2/2009 | Collins et al. |
| 7,498,298 B2 | 3/2009 | Doronina et al. |
| 7,595,048 B2 | 9/2009 | Honjo et al. |
| 7,709,226 B2 | 5/2010 | Foote |
| 7,867,493 B2 | 1/2011 | Damiano et al. |
| 7,888,477 B2 | 2/2011 | Bangur et al. |
| 7,931,896 B2 | 4/2011 | Chen |
| 7,943,743 B2 | 5/2011 | Korman et al. |
| 8,008,449 B2 | 8/2011 | Korman et al. |
| 8,034,953 B2 | 10/2011 | Combs et al. |
| 8,080,636 B2 | 12/2011 | Mikesell et al. |
| 8,101,719 B2 | 1/2012 | Kikuchi et al. |
| 8,168,757 B2 | 5/2012 | Finnefrock et al. |
| 8,188,232 B1 | 5/2012 | Murphy et al. |
| 8,188,238 B2 | 5/2012 | Pease et al. |
| 8,247,537 B2 | 8/2012 | Korman et al. |
| 8,354,509 B2 | 1/2013 | Carven et al. |
| 8,415,355 B2 | 4/2013 | Brain et al. |
| 8,546,541 B2 | 10/2013 | Murphy et al. |
| 8,552,002 B2 | 10/2013 | Ding et al. |
| 8,552,003 B2 | 10/2013 | Charest et al. |
| 8,563,694 B2 | 10/2013 | Mataraza et al. |
| 8,598,322 B2 | 12/2013 | Markel et al. |
| 8,609,816 B2 | 12/2013 | Korman et al. |
| 8,617,546 B2 | 12/2013 | Kang et al. |
| 8,728,474 B2 | 5/2014 | Honjo et al. |
| 8,735,553 B1 | 5/2014 | Li et al. |
| 8,685,980 B2 | 6/2014 | Raghunathan |
| 8,748,356 B2 | 6/2014 | Raghunathan |
| 8,961,967 B2 | 2/2015 | Strohl et al. |
| 8,993,731 B2 | 3/2015 | Tyson |
| 9,102,727 B2 | 8/2015 | Freeman et al. |
| 9,163,087 B2 | 10/2015 | Kuchroo et al. |
| 9,181,342 B2 | 11/2015 | Davis |
| 9,220,776 B2 | 12/2015 | Sharma et al. |
| 9,243,052 B2 | 1/2016 | Olive et al. |
| 9,387,247 B2 | 7/2016 | Korman et al. |
| 9,457,080 B2 | 10/2016 | Freeman et al. |
| 9,676,853 B2 | 6/2017 | Zhou et al. |
| 9,683,043 B2 | 6/2017 | Davis et al. |
| 9,683,048 B2 | 6/2017 | Freeman et al. |
| 9,771,425 B2 | 9/2017 | Wang et al. |
| 9,815,897 B2 | 11/2017 | King et al. |
| 9,856,320 B2 | 1/2018 | Cogswell et al. |
| 9,914,783 B1 | 3/2018 | Afar et al. |
| 9,982,053 B2 | 5/2018 | Pantaleo et al. |
| 9,987,500 B2 | 6/2018 | Papadopoulos et al. |
| 10,160,806 B2 | 12/2018 | Bonvini et al. |
| 2002/0068276 A1 | 6/2002 | Winter et al. |
| 2002/0160000 A1 | 10/2002 | Wood et al. |
| 2003/0040044 A1 | 2/2003 | Heavner et al. |
| 2003/0079253 A1 | 4/2003 | Hiatt et al. |
| 2003/0096977 A1 | 5/2003 | Koike et al. |
| 2003/0103976 A1 | 6/2003 | Serizawa et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2003/0226155 A1 | 12/2003 | Sadeghi et al. |
| 2004/0047858 A1 | 3/2004 | Blumberg et al. |
| 2004/0133357 A1 | 7/2004 | Zhong et al. |
| 2004/0137513 A1 | 7/2004 | Devaux et al. |
| 2004/0166544 A1 | 8/2004 | Morton et al. |
| 2004/0208887 A1 | 10/2004 | Drakenberg et al. |
| 2005/0009136 A1 | 1/2005 | Nixon et al. |
| 2005/0025763 A1 | 2/2005 | Williams et al. |
| 2005/0112126 A1 | 5/2005 | Baca et al. |
| 2005/0186208 A1 | 8/2005 | Fyfe et al. |
| 2005/0215770 A1 | 9/2005 | Bell et al. |
| 2006/0009360 A1 | 1/2006 | Pifer et al. |
| 2006/0014768 A1 | 1/2006 | Kawasaki et al. |
| 2006/0034834 A1 | 2/2006 | Marasco et al. |
| 2006/0110383 A1 | 5/2006 | Hongo et al. |
| 2006/0167015 A1 | 7/2006 | Brietenstein et al. |
| 2006/0222645 A1 | 10/2006 | Lee et al. |
| 2006/0241106 A1 | 10/2006 | Drysdale et al. |
| 2006/0263361 A1 | 11/2006 | Moretta et al. |
| 2007/0020267 A1 | 1/2007 | Fuh et al. |
| 2007/0036783 A1 | 2/2007 | Humeau et al. |
| 2007/0048315 A1 | 3/2007 | Presta |
| 2007/0048740 A1 | 3/2007 | Isogai et al. |
| 2007/0083334 A1 | 4/2007 | Mintz et al. |
| 2007/0141065 A1 | 6/2007 | Fuh et al. |
| 2007/0248801 A1 | 10/2007 | Nakao |
| 2007/0287170 A1 | 12/2007 | Davis et al. |
| 2008/0166352 A1 | 7/2008 | Siu et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0118127 A1 | 5/2009 | Raghunathan |
| 2009/0136490 A1 | 5/2009 | Pilkington et al. |
| 2009/0182127 A1 | 7/2009 | Kjaergaard et al. |
| 2009/0217401 A1 | 8/2009 | Korman et al. |
| 2009/0220485 A1 | 9/2009 | Tanha |
| 2010/0004269 A1 | 1/2010 | Price et al. |
| 2010/0011456 A1 | 1/2010 | Mathur et al. |
| 2010/0015133 A1 | 1/2010 | Igawa et al. |
| 2010/0021477 A1 | 1/2010 | Tsui et al. |
| 2010/0028637 A1 | 2/2010 | Tavsanli et al. |
| 2010/0105711 A1 | 4/2010 | Fairhurst et al. |
| 2010/0119516 A1 | 5/2010 | Wu |
| 2010/0150902 A1 | 6/2010 | Haeuw |
| 2010/0249126 A1 | 9/2010 | Burger et al. |
| 2010/0260754 A1 | 10/2010 | Chedid et al. |
| 2010/0261620 A1 | 10/2010 | Almagro et al. |
| 2011/0008369 A1 | 1/2011 | Finnefrock et al. |
| 2011/0027284 A1 | 2/2011 | Barske et al. |
| 2011/0077268 A1 | 3/2011 | Liu et al. |
| 2011/0112063 A1 | 5/2011 | Marsilje et al. |
| 2011/0123532 A1 | 5/2011 | Gurney et al. |
| 2011/0150892 A1 | 6/2011 | Thudium et al. |
| 2011/0172228 A1 | 7/2011 | Ren et al. |
| 2011/0230444 A1 | 9/2011 | Garcia-Echeverria et al. |
| 2011/0237573 A1 | 9/2011 | Cheng et al. |
| 2011/0271358 A1 | 11/2011 | Freeman et al. |
| 2011/0280866 A1 | 11/2011 | Didierlaurent et al. |
| 2011/0281866 A1 | 11/2011 | Ren et al. |
| 2012/0017292 A1 | 1/2012 | Kovalic et al. |
| 2012/0039906 A1 | 2/2012 | Olive |
| 2012/0045437 A1 | 2/2012 | Ma et al. |
| 2012/0100158 A1 | 4/2012 | Markel et al. |
| 2012/0108795 A1 | 5/2012 | Kehoe et al. |
| 2012/0114652 A1 | 5/2012 | Elvin et al. |
| 2012/0149876 A1 | 6/2012 | Von Kreudenstein et al. |
| 2012/0189617 A1 | 7/2012 | Takayangi et al. |
| 2013/0034559 A1 | 2/2013 | Queva et al. |
| 2013/0039913 A1 | 2/2013 | Labrijn et al. |
| 2013/0045202 A1 | 2/2013 | Irving et al. |
| 2013/0150342 A1 | 6/2013 | Brain et al. |
| 2013/0156774 A1 | 6/2013 | Kuchroo et al. |
| 2013/0195849 A1 | 8/2013 | Von Kreudenstein et al. |
| 2013/0281922 A1 | 10/2013 | Teige |
| 2014/0011798 A1 | 1/2014 | Furet et al. |
| 2014/0037551 A1 | 2/2014 | Zang et al. |
| 2014/0044738 A1 | 2/2014 | Langermann et al. |
| 2014/0056890 A1 | 2/2014 | Gurney et al. |
| 2014/0112915 A1 | 4/2014 | Bardroff et al. |
| 2014/0271618 A1 | 9/2014 | Markel et al. |
| 2014/0271629 A1 | 9/2014 | Corbit et al. |

(56) References Cited

U.S. PATENT DOCUMENTS

| | | |
|---|---|---|
| 2014/0294765 A1 | 10/2014 | Cojocaru et al. |
| 2014/0294860 A1 | 10/2014 | Platten et al. |
| 2014/0322218 A1 | 10/2014 | Xiao et al. |
| 2014/0341902 A1 | 11/2014 | Maecker et al. |
| 2015/0126485 A1 | 5/2015 | Furet et al. |
| 2015/0141427 A1 | 5/2015 | Furet et al. |
| 2015/0165025 A1 | 6/2015 | Korman et al. |
| 2015/0183801 A1 | 7/2015 | Furet et al. |
| 2015/0183874 A1 | 7/2015 | Liu et al. |
| 2015/0197505 A1 | 7/2015 | Lelais et al. |
| 2015/0216970 A1 | 8/2015 | Grogan et al. |
| 2015/0218274 A1 | 8/2015 | Sabatos-Peyton et al. |
| 2015/0259434 A1 | 9/2015 | Johnson et al. |
| 2015/0315275 A1 | 11/2015 | Langermann et al. |
| 2015/0353636 A1 | 12/2015 | Parren et al. |
| 2016/0017040 A1 | 1/2016 | Leong et al. |
| 2016/0032014 A1 | 2/2016 | Michaels et al. |
| 2016/0122707 A1 | 5/2016 | Swee et al. |
| 2016/0159905 A1 | 6/2016 | Abdiche et al. |
| 2016/0168236 A1 | 6/2016 | Shipp et al. |
| 2016/0222113 A1 | 8/2016 | Buchanan et al. |
| 2016/0251436 A1 | 9/2016 | Amirina et al. |
| 2016/0272708 A1 | 9/2016 | Chen |
| 2016/0311902 A1 | 10/2016 | Morsey et al. |
| 2016/0376367 A1 | 12/2016 | Yuan et al. |
| 2016/0376373 A1 | 12/2016 | Ahmadi et al. |
| 2017/0044259 A1 | 2/2017 | Tipton et al. |
| 2017/0044260 A1 | 2/2017 | Baruah et al. |
| 2017/0081409 A1 | 3/2017 | Dijk et al. |
| 2017/0088618 A1 | 3/2017 | Bennett et al. |
| 2017/0114135 A1 | 4/2017 | Codarri-Deak et al. |
| 2017/0121409 A1 | 5/2017 | Verona et al. |
| 2017/0137520 A1 | 5/2017 | Punnonen et al. |
| 2017/0145116 A1 | 5/2017 | Regula et al. |
| 2017/0158764 A1 | 6/2017 | Mizuno et al. |
| 2017/0166642 A1 | 6/2017 | Pantaleo et al. |
| 2017/0240644 A1 | 8/2017 | Zhou et al. |
| 2017/0247454 A1 | 8/2017 | Benz et al. |
| 2017/0267762 A1 | 9/2017 | Qiu et al. |
| 2018/0127502 A1 | 5/2018 | Brentjens et al. |
| 2018/0142022 A1 | 5/2018 | Yam et al. |
| 2018/0179285 A1 | 6/2018 | Bennett et al. |
| 2018/0214548 A1 | 8/2018 | Liu et al. |
| 2018/0282412 A1 | 10/2018 | Gu et al. |
| 2018/0339045 A1 | 11/2018 | Li et al. |
| 2018/0346569 A1 | 12/2018 | Wang et al. |
| 2019/0016797 A1 | 1/2019 | Arenas-Ramirez et al. |
| 2019/0127467 A1 | 5/2019 | Shah et al. |
| 2019/0144542 A1 | 5/2019 | Galler et al. |
| 2019/0388338 A1 | 12/2019 | Giesing et al. |

FOREIGN PATENT DOCUMENTS

| | | | |
|---|---|---|---|
| CN | 104024276 A | 9/2014 | |
| EP | 0296122 B1 | 12/1988 | |
| EP | 0590058 B1 | 11/2003 | |
| EP | 2360254 A | 8/2011 | |
| EP | 1817055 B1 | 12/2012 | |
| EP | 3505535 A1 | 7/2019 | |
| EP | 3514177 A1 | 7/2019 | |
| GB | 2408508 A | 6/2005 | |
| RU | 2420587 C2 | 12/2010 | |
| WO | WO 1988/001649 A1 | 3/1988 | |
| WO | WO 1990/04036 A1 | 4/1990 | |
| WO | WO 1990/007861 A1 | 7/1990 | |
| WO | WO 1992/22653 A1 | 12/1992 | |
| WO | WO 1994/10202 A1 | 5/1994 | |
| WO | WO 1994/11026 A2 | 5/1994 | |
| WO | WO 1996/30046 A1 | 10/1996 | |
| WO | WO 1997/11971 A1 | 4/1997 | |
| WO | WO 1998/045332 A2 | 10/1998 | |
| WO | WO 1999/003854 A1 | 1/1999 | |
| WO | WO 1999/45962 A1 | 9/1999 | |
| WO | WO 2011/110604 A1 | 9/2001 | |
| WO | WO 2002/010192 A3 | 2/2002 | |
| WO | WO 2002/043478 A2 | 6/2002 | |
| WO | WO 2002/066630 A1 | 8/2002 | |
| WO | WO 2003/037347 A1 | 5/2003 | |
| WO | WO 2003/064383 A1 | 8/2003 | |
| WO | WO 2003/077914 A1 | 9/2003 | |
| WO | WO 2004/004771 A1 | 1/2004 | |
| WO | WO 2004/005281 A1 | 1/2004 | |
| WO | WO 2004/045532 A2 | 6/2004 | |
| WO | WO 2004/056875 A1 | 7/2004 | |
| WO | WO 2004/072051 A1 | 8/2004 | |
| WO | WO 2005/012359 A2 | 2/2005 | |
| WO | WO 2005/039549 A1 | 5/2005 | |
| WO | WO 2005/044853 A2 | 5/2005 | |
| WO | WO 2005/073224 A2 | 8/2005 | |
| WO | WO 2005/113556 A1 | 12/2005 | |
| WO | WO 2005/121142 A1 | 12/2005 | |
| WO | WO 2006/121168 A1 | 11/2006 | |
| WO | WO 2006/122806 A1 | 11/2006 | |
| WO | WO 2007/005874 A2 | 1/2007 | |
| WO | WO 2007/030377 A1 | 3/2007 | |
| WO | WO 2007/070514 A1 | 6/2007 | |
| WO | WO 2007/084786 A1 | 7/2007 | |
| WO | WO 2007/095337 A2 | 8/2007 | |
| WO | WO 2007/131201 A2 | 11/2007 | |
| WO | WO 2008/024725 A1 | 2/2008 | |
| WO | WO 2008/073687 A2 | 6/2008 | |
| WO | WO 2008/132601 A1 | 11/2008 | |
| WO | WO 2008/156712 A1 | 12/2008 | |
| WO | WO 2007/04415 A1 | 1/2009 | |
| WO | WO 2009/018386 A1 | 2/2009 | |
| WO | WO 2009/080251 A1 | 7/2009 | |
| WO | WO 2009/080252 A1 | 7/2009 | |
| WO | WO 2009/080254 A1 | 7/2009 | |
| WO | WO 2009/085462 | * 7/2009 | ............. C40B 40/02 |
| WO | WO 2009/085462 A1 | 7/2009 | |
| WO | WO 2009/085983 A1 | 7/2009 | |
| WO | WO 2009/114335 A2 | 9/2009 | |
| WO | WO 2009/114870 A2 | 9/2009 | |
| WO | WO 2009/115562 A2 | 9/2009 | |
| WO | WO 2010/002655 A2 | 1/2010 | |
| WO | WO 2010/006086 A2 | 1/2010 | |
| WO | WO 2010/007120 A1 | 1/2010 | |
| WO | WO 2010/019570 A2 | 2/2010 | |
| WO | WO 2010/026124 A1 | 3/2010 | |
| WO | WO 2010/029082 A1 | 3/2010 | |
| WO | WO 2010/029435 A1 | 3/2010 | |
| WO | WO 2010/036380 A1 | 4/2010 | |
| WO | WO 2010/036959 A2 | 4/2010 | |
| WO | WO 2010/060937 A2 | 6/2010 | |
| WO | WO 2010/077634 A1 | 7/2010 | |
| WO | WO 2010/078580 A2 | 7/2010 | |
| WO | WO 2010/101849 A1 | 9/2010 | |
| WO | WO 2010/149755 A1 | 12/2010 | |
| WO | WO 2011/025927 A1 | 3/2011 | |
| WO | WO 2011/066501 A1 | 3/2011 | |
| WO | WO 2011/076786 A1 | 6/2011 | |
| WO | WO 2011/101409 A1 | 8/2011 | |
| WO | WO 2011/131746 A2 | 10/2011 | |
| WO | WO 2011/159877 A2 | 12/2011 | |
| WO | WO 2012/022814 A1 | 2/2012 | |
| WO | WO 2012/061448 A1 | 5/2012 | |
| WO | WO 2012/145493 A1 | 10/2012 | |
| WO | WO 2012/177624 A2 | 12/2012 | |
| WO | WO 2013/006490 A2 | 1/2013 | |
| WO | WO 2013/019906 A1 | 2/2013 | |
| WO | WO 2011/155607 A1 | 8/2013 | |
| WO | WO 2013/111105 A1 | 8/2013 | |
| WO | WO 2013/124826 A1 | 8/2013 | |
| WO | WO 2013/132044 A1 | 9/2013 | |
| WO | WO 2013/171639 A1 | 11/2013 | |
| WO | WO 2013/171640 A1 | 11/2013 | |
| WO | WO 2013/171641 A1 | 11/2013 | |
| WO | WO 2013/171642 A1 | 11/2013 | |
| WO | WO 2013/184757 A1 | 12/2013 | |
| WO | WO 2014/022332 A1 | 2/2014 | |
| WO | WO 2014/031718 A1 | 2/2014 | |
| WO | WO 2014/072493 A1 | 5/2014 | |
| WO | WO 2014/085318 A1 | 6/2014 | |
| WO | WO 2014/100483 A1 | 6/2014 | |

(56) References Cited

FOREIGN PATENT DOCUMENTS

| WO | WO 2014/108198 A1 | 7/2014 |
|----|---|---|
| WO | WO 2014/141104 A1 | 9/2014 |
| WO | WO 2014/144080 A2 | 9/2014 |
| WO | WO 2014/151616 A1 | 9/2014 |
| WO | WO 2014/159562 A1 | 10/2014 |
| WO | WO 2014/159835 A1 | 10/2014 |
| WO | WO 2014/160160 A2 | 10/2014 |
| WO | WO 2014/179664 A2 | 11/2014 |
| WO | WO 2014/183066 A2 | 11/2014 |
| WO | WO 2014/184360 A1 | 11/2014 |
| WO | WO 2014/194302 A2 | 12/2014 |
| WO | WO 2014/206107 A1 | 12/2014 |
| WO | WO 2015/013389 A2 | 1/2015 |
| WO | WO 2015/024060 A1 | 2/2015 |
| WO | WO 2015/035606 A1 | 3/2015 |
| WO | WO 2015/036394 A1 | 3/2015 |
| WO | WO 2015/058573 A1 | 4/2015 |
| WO | WO 2015/085847 A1 | 6/2015 |
| WO | WO 2015/095410 | 6/2015 |
| WO | WO 2015/097563 A2 | 7/2015 |
| WO | WO 2015/112800 A1 | 7/2015 |
| WO | WO 2015/112805 A1 | 7/2015 |
| WO | WO 2015/112900 A1 | 7/2015 |
| WO | WO 2015/117002 A1 | 8/2015 |
| WO | WO 2015/173756 A2 | 11/2015 |
| WO | WO 2015195163 A1 | 12/2015 |
| WO | WO 2016/077397 A2 | 5/2016 |
| WO | WO 2016/210223 A1 | 12/2016 |
| WO | WO 2017/024515 A1 | 2/2017 |
| WO | WO 2017/055404 A1 | 4/2017 |
| WO | WO 2017/055537 A1 | 4/2017 |
| WO | WO 2017/071625 A1 | 5/2017 |
| WO | WO 2017/079116 A2 | 5/2017 |
| WO | WO 2017/122130 A1 | 7/2017 |
| WO | WO 2017/196847 A1 | 11/2017 |
| WO | WO 2017/214182 A1 | 12/2017 |
| WO | WO 2018/026248 A1 | 2/2018 |
| WO | WO 2018/028383 A1 | 2/2018 |
| WO | WO 2018/036472 A1 | 3/2018 |
| WO | WO 2018/050027 A1 | 3/2018 |
| WO | WO 2018/053709 A1 | 3/2018 |

OTHER PUBLICATIONS

International Search Report relating to International Patent Application No. PCT/US2016/059833, filed on Nov. 1, 2016. Date of Mailing of International Search Report: Apr. 13, 2017.
Written Opinion of the International Search Authority relating to International Patent Application No. PCT/US2016/059833, filed on Nov. 1, 2016. Date of Mailing of Written Opinion: Apr. 13, 2017.
International Search Report relating to International Patent Application No. PCT/US2016/059836, filed on Nov. 1, 2016. Date of Mailing of International Search Report: Apr. 10, 2017.
Written Opinion of the International Search Authority relating to International Patent Application No. PCT/US2016/059836, filed on Nov. 1, 2016. Date of Mailing of Written Opinion: Apr. 10, 2017.
International Search Report relating to International Patent Application No. PCT/US2016/059837, filed on Nov. 1, 2016. Date of Mailing of International Search Report: May 22, 2017.
Written Opinion of the International Search Authority relating to International Patent Application No. PCT/US2016/059837, filed on Nov. 1, 2016. Date of Mailing of Written Opinion: May 22, 2017.
Supplementary European Search Report, EP 16862773.5, Mailed Jun. 26, 2019.
Supplementary European Search Report, EP 16862775.0, Mailed Apr. 24, 2019.
Supplementary European Search Report, EP 16862776.8, Mailed Jun. 18, 2019.
Blank et al., "Interaction of PD-L1 on tumor cells with PD-1 on tumor-specific T cells as a mechanism of immune evasion: implications for tumor immunotherapy.", Cancer Immunol Immunother, 2005, pp. 307-314, vol. 54.
Bolt et al., "The generation of a humanized, non-mitogenic CD3 monoclonal antibody which retains in vitro immunosuppressive properties.", Eur J Immunol, 1993, pp. 403-411, vol. 23.
Borch et al., "Reorienting the immune system in the treatment of cancer by using anti-PD-1 and anti-PD-L1 antibodies.", Drug Discovery Today, Sep. 2015, pp. 1127-1134, vol. 20(9).
Brown et al., "Blockade of Programmed Death-1 Ligands on Dendritic Cells Enhances T Cell Activation and Cytokine Production.", J Immunol, 2003, pp. 1257-1266, vol. 170.
Brüggemann and Taussig, "Production of human antibody repertoires in transgenic mice.", Curr Opin Biotechnol, 1997, pp. 455-458, vol. 8.
Brüggemann et al., "Human antibody production in transgenic mice: expression from 100 kb of the human IgH locus.", Eur J Immunol, 1991, pp. 1323-1326, vol. 21.
Brusasco, V., "Book Review, Airway Smooth Muscle: Modelling the Asthmatic Response In Vitro.", Respiratiory Medicine, 1997, p. 179, vol. 91.
Cai et al., "C-Terminal Lysine Processing of Human Immunoglobulin G2 Heavy Chain In Vivo.", Biotechnol Bioeng, Feb. 2011, pp. 404-412, vol. 108(2).
Chames and Baty, "Bispecific antibodies for cancer therapy.", Curr Opin Drug Disc Dev, 2009, pp. 276-283, vol. 12(2).
Chari et al., "Immunoconjugates Containing Novel Maytansinoids: Promising Anticancer Drugs.", Cancer Res, Jan. 1, 1992, pp. 127-131, vol. 52.
Chen et al., "Molecular Pathways: Next-Generation Immunotherapy-Inhibiting Programmed Death-Ligand 1 and Programmed Death-1.", Clin Cancer Res, 2012, pp. 6580-6587, vol. 8(24).
Chien et al., "Significant structural and functional change of an antigen-binding site by a distant amino acid substitution: Proposal of a structural mechanism.", Proc. Natl. Acad. Sci., Jul. 1989, pp. 5532-5536, vol. 86.
Chothia and Lesk, "Canonical Structures for the Hypervariable Regions of Immunoglobulins.", Mol Biol, 1987, pp. 901-917, vol. 196.
Clayton, et al., "T cell Ig and Mucin Domain-Containing Protein 3 Is Recruited to the Immune Synapse, Disrupts Stable Synapse Formation, and Associates Receptor Phosphates.", J Immunol, 2014, pp. 782-791, vol. 192(2).
Cole et al., "HuM291, A Humanized ANTI-CD3 Antibody, is Immunosuppressive to T Cells While Exhibiting Reduced Mitogenicity in Vitro[1].", Transplantation, 1999, pp. 563-571, vol. 68(4).
Cook, R. C., "Economic and Clinical Impact of Multiple Myeloma to Managed Care.", J Manag Care Pharm., 2008, pp. S18-S25, vol. 14(7).
Da Silva et al., "Reversal of NK-Cell Exhaustion in Advanced Melanoma by Tim-3 Blockade.", Cancer Immunol Res, 2014, pp. 410-422, vol. 2(5).
Dall'Acqua et al., "Properties of Human IgG1s Engineered for Enhanced Binding to the Neonatal Fc Receptor (FcRn).", J Biol Chem, 2006, pp. 23514-23524, vol. 281(33).
Datta-Mannan et al., "Humanized IgG1 Variants with Differential Binding Properties to the Neonatal Fc Receptor: Relationship to Pharmacokinetics in Mice and Primates.", Drug Metab Dispos, 2007, pp. 86-94, vol. 35(1).
Diebolder et al., "Complement Is Activated by IgG Hexamers Assembled at the Cell Surface.", Science, Mar. 13, 2014, pp. 1260-1263, vol. 343.
Dong et al., "B7-H1 pathway and its role in the evasion of tumor immunity.", J Mol Med, 2003, pp. 281-287, vol. 81.
Dranoff et al., "Vaccination with irradiated tumor cells engineered to secrete murin granulocyte-macrophage colony-stimulating factor stimulates potent, specific, and long-lasting anti-tumor activity.", Proc Natl Acad Sci U.S.A., 1993, pp. 3539-3543, vol. 90.
Dubowchik et al., "Doxorubicin Immunoconjugates Containing Bivalent, Lysosomally-Cleavable Dipeptide Linkages.", Bioorg. & Med. Chem. Letters, 2002, pp. 1529-1532, vol. 12: 1529-1532.
Faghfuri et al., "Nivolumab and pembrolizumab as immune-modulating monoclonal antibodies targeting the PD-1 receptor to treat melanoma.", Expert Rev. Anticancer Ther., 2015, pp. 981-993, vol. 15(9).

(56) References Cited

OTHER PUBLICATIONS

Ferrara et al., "Modulation of Therapeutic Antibody Effector Functions by Glycosylation Engineering: Influence of Golgi Enzyme Localization Domain and Co-Expression of Heterologous β1,4-N-acetylglucosaminyltransferase III and Golgi α-mannosidase II.", Biotechnol Bioeng, 2006, pp. 851-861, vol. 93.
Ferrara et al., "The Carbohydrate at FcY RIIIa Asn-162. An Element Required for High Affinity Binding to Non-Fuscosylated IgG Glycoforms.", J Biol Chem, 2006, pp. 5032-5036, vol. 281(8).
Ferris et al., "Too Much of a Good Thing? Tim-3 and TCR Signaling in T Cell Exhaustion.", J Immunol, 2004, pp. 1525-1530, vol. 193(4).
Fishwild et al., "High-avidity human IgGK monoclonal antibodies from a novel strain of minilocus transgenic mice.", Nat Biotechnol, 1996, pp. 845-851, vol. 14.
Fourcade et al., "Upregulation of Tim-3 and PD-1 expression is associated with tumor antigen-specific CD8+ T cell dysfunction in melanoma patients.", J Exp Med, 2010, pp. 2175-2186, vol. 207.
Fransson et al., "Human Framework Adaptation of a Mouse Anti-Human IL-13 Antibody.", J Mol Biol, 2010, pp. 214-231, vol. 398.
Freeman et al., "Protect the killer: CTLs need defenses against the tumor.", Nat Med, 2002, pp. 787-789, vol. 8(8).
Gautron et al., "Enhanced suppressor function of TIM-3+FoxP3+ regulatory T cells.", Eur J Immunol, 2014, pp. 2703-2711, vol. 44(9).
Ghevaert et al., "Developing recombinant HPA-1a-specific antibodies with abrogated FcY receptor binding for the treatment of fetomaternal alloimmune thrombocytopenia.", J Clin Invest, 2008, pp. 2929-2938, vol. 118(8).
Goding, *Monoclonal Antibodies: Principles and Practice*, Chapter 3, pp. 59-103, Academic Press, 1986.
Golden-Mason et al., "Negative Immune Regulator Tim-3 Is Overexpressed on T Cells in Hepatitis C Virus Infection and Its Blockade Rescues Dysfunctional CD4+ and CD8+ T cells.", J Virol, Sep. 2009, pp. 9122-9130, vol. 83(18).
Green and Jakobovits, "Regulation of B Cell Development by Variable Gene Complexity in Mice Reconstituted with Human Immunoglobulin Yeast Artificial Chromosomes.", J. Exp. Med., Aug. 1998, pp. 483-495, vol. 188(3).
Green et al., "Antigen-specific human monoclonal antibodies from mice engineered with human Ig heavy and light chain YACs.", Nature Genet., 1994, pp. 13-21, vol. 7.
Gupta et al., "Development of a Multidose Formulation for a Humanized Monoclonal Antibody Using Experimental Design Techniques.", AAPS PharmSci, 2003, pp. 1-9, vol. 5(2), Article 8.
Hallett et al., "Immunosuppressive Effects of Multiple Myeloma Are Overcome by PD-L1 Blockade.", J of American Society for Blood and Marrow Transplantation, 2011, pp. 1133-1145, vol. 17(1).
Hastings et al., "TIM-3 is expressed on activated human CD41 T cells and regulates Th1 and Th17 cytokines.", Eur J Immunol, 2009, pp. 2492-2501, vol. 39.
Hinman et al., "Preparation and Characterization of Monoclonal Antibody Conjugates of the Calicheamicins: A Novel and Potent Family of Antitumor Antibiotics.", Jul. 1993, Cancer Res, pp. 3336-3342, vol. 53.
Hinton et al., "An Engineered Human IgG1 Antibody with Longer Serum Half-Life.", J Immunol, 2005, pp. 346-356, vol. 176.
Hinton et al., "Engineered Human IgG Antibodies with Longer Half-lives in Primates.", J Biol Chem, 2004, pp. 6213-6216, vol. 279(8).
Honda et al., "Tuning of Antigen Sensitivity by T Cell Receptor-Dependent Negative Feedback Controls T Cell Effector Function in Inflamed Tissues.", Immunity, Feb. 20, 2014, pp. 235-247, vol. 40(2).
Hoogenboom and Winter, "By-passing Immunisation. Human Antibodies from Synthetic Repertoires of Germline $V_H$ Gene Segments Rearranged in Virto.", J Mol Biol, 1992, pp. 381-388, vol. 227.

Hudes et al., "Temsirolimus, Interferon Alfa, or Both for Advanced Renal-Cell Carcinoma.", N Engl J Med, May 2007, pp. 2271-2281, vol. 356(22).
Idusogie et al., "Engineered Antibodies with Increased Activity to Recruit Complement.", J Immunol, 2001, pp. 2571-2575, vol. 166.
Iwai et al., "Involvement of PD-L1 on tumor cells in the escape from host immune system and tumor immunotherapy by PD-L1 blockade.", ProcNatl Acad Sci, Sep. 17, 2002, pp. 12293-12297, vol. 99.
Jeffrey et al., "Dipeptide-based highly potent doxorubicin antibody conjugates.", Bioorganic & Med Chem Letters, 2006, pp. 358-362, vol. 16.
Jones et al., "Tim-3 expression defines a novel population of dysfunctional T cells with highly elevated frequencies in progressive HIV-1 infection.", J Exp Med, 2008, pp. 2763-2779, vol. 205(12).
Kaas, et al., "IMGT/3Dstructure-DB IMGT/Structural Query, a database and a tool for immunoglobulin, T cell receptor and MHC structural data.", Nucl Acids Res, 2004, pp. D208-D210, vol. 32.
Kim et al., "Scientific Association of Human Telomerase Activity with Immortal Cells and Cancer.", Science, 1994, pp. 2011-2013, vol. 266.
Kim et al., "Mapping the site on human IgG for binding of the MHC class I-related receptor, FcRn.", Eur J Immunol, 1999, pp. 2819-2825, vol. 29.
King et al., "Monoclonal Antibody Conjugates of Doxorubicin Prepared with Branched Peptide Linkers: Inhibition of Aggregation by Methoxytriethyleneglycol Chains.", J Med Chem, 2002, pp. 4336-4343, vol. 45.
Klinger et al., "Multiplex Identification of Antigen-Specific T Cell Receptors Using a Combination of Immune Assays and Immune Receptor Sequencing.", PLoS One, Oct. 28, 2015, pp. 1-21, vol. 8(9).
Knappik et al., "Fully Snythetic Human Combinatorial Antibody Libraries (HuCAL) Based on Modular Consensus Frameworks and CDRs Randomized with Trinucleotides.", J Mol Biol, 2000, pp. 57-86, vol. 296.
Knight et al., "Pharmacodynamic enhancement of the anti-platelet antibody Fab abciximab by site-specific pegylation.", Platelet, 2004, pp. 409-418, vol. 15(7).
Kobrin et al., "A V region mutation in a phosphocholine-binding monoclonal antibody results in loss of antigen binding.", The Journal of Immunology, 1991, pp. 2017-2020, vol. 146.
Kohler and Milstein, "Continuous cultures of fused cells secreting antibody of predefined specificity.", Nature, 1975, pp. 495-497, vol. 256.
Konishi et al., "B7-H1 Expression on Non-Small Cell Lung Cancer Cells and Its Relationship with Tumor-Infiltrating Lymphocytes and Their PD-1 Expression.", Clin Cancer Res, Aug. 1, 2004, pp. 5094-5510, vol. 10.
Konno et al., "Fucose content of monoclonal antibodies can be controlled by culture medium osmolality for high antibody-dependent cellular cytotoxicity.", Cytotechnology, 2012, pp. 249-265, vol. 64.
Kratz et al., "Prodrugs of Anthracyclines in Cancer Chemotherapy.", Current Med. Chem, 2006, pp. 477-523, vol. 13.
Krebs et al., "High-Throughput generation and engineering of recombinant human antibodies.", J Immunol Meth, 2001, pp. 67-84, vol. 254.
Kugler et al., "Retraction: Regression of human metastatic renal cell carcinoma after vaccination with tumor cell-dendritic cell hybrids.", Nature Medicine, 2000, pp. 332-336, vol. 6."
Lazar et al., "Engineered antibody Fc variants with enhanced effector function.", Proc Natal Acad Sci, Mar. 14, 2006, pp. 4005-4010, vol. 103(11).
Lefranc et al., "IMGT unique numbering for immunoglobulin and T cell receptor variable domains and Ig superfamily V-like domains.", Dev Comparat Immunol, 2003, pp. 55-77, vol. 27.
Lefranc et al., "IMGT, the international ImMunoGeneTics information system®.", Nucl Acid Res, 2005, pp. D593-D597, vol. 33.
Leong et al., "Adapting Pharmacokinetic Properties of a Humanized Anti-Interleukin-8 Antibody for Therapeutic Applications Using Site-Specific Pegylation.", Cytokine, 2001, pp. 106-119, vol. 16(3).

(56) References Cited

OTHER PUBLICATIONS

Lepenies et al., "The Role of Negative Costimulators During Parasitic Infections.", Endocr Metab Immune Disord Drug Targets, 2008, pp. 279-288, vol. 8.

Li et al., "Design and Synthesis of Paclitaxel Conjugated with an ErfB2-Recognizing Peptide, EC-1.", Biopolymers, 2007, pp. 225-230, vol. 87.

Liu et al., "Synthesis of 20-paclitaxel methyl 2-glucopyranosyl succinate for specific targeted delivery to cancer cells.", Bioorganic & Medicinal Chemistry Letters, 2007, pp. 617-620, vol. 17.

Lode et al., "Targeted Therapy with a Novel Enediyene Antibiotic Calicheamicin ⊖I1 Effectively Suppress Growth and Dissemination of Liver Metastases in a Syngenic Model of Murine Neuroblastoma.", Cancer Res, 1998, pp. 2925-2928, vol. 58.

Lonberg and Huszar, "Human Antibodies from Transgenic Mice.", Int Rev Immunol, 1995, pp. 65-93, vol. 13.

Lonberg et al., "Antigen-specific human antibodies from mice comprising four distinct genetic modifications.", Nature, 1994, pp. 856-859, vol. 368.

Lote et al., "PD-1 and PD-L1 blockage in gastrointestinal malignancies.", Cancer Treatment Reviews, 2015, pp. 893-903, vol. 41.

Maa et al., "Aggregation of recombinant human growth hormone induced by phenolic compounds.", Int J Pharm, 1996, pp. 155-168, vol. 140.

MacLennan et al., "Structure-Function Relationships in the Ca2+-Binding and Translocation Domain of SERCA1: physiological correlates in Brody disease.", Acta Physiol Scand, 1998, pp. 55-67, Suppl 643.

Mahoney et al., "Combination cancer immunotherapy and new immunomodulatory targets.", Nature Reviews, Aug. 2015, pp. 561-587, vol. 14.

Marks et al., "By-passing Immunization. Human antibodies from V-gene Libraries Displayed on Phage.", J Mol Biol, 1991, pp. 581-587, vol. 222.

McDermott et al., "Pembrolizumab: PD-1 Inhibition as a Therapeutic Strategy in Cancer.", Drugs of Today, 2015, pp. 7-19, vol. 51(1).

Mendez et al., "Functional transplant of megabase human immunoglobulin loci recapitulates human antibody response in mice.", Nat Genet, Feb. 15, 1997, pp. 146-156, vol. 15.

Mokyr et al., "Realization of the Therapeutic Potential of CTLA-4 Blockade in Low-Dose Chemotherapy-treated Tumor-bearing Mice.", Cancer Research, 1998, pp. 5301-5304, vol. 58.

Monney et al., "Th1-specific cell surface protein Tim-3 regulates macrophage activation and severity of an autoimmune disease.", Nature, 2002, pp. 536-541, vol. 415(6871).

Moore et al., "Engineered Fc variant antibodies with enhanced ability to recruit complement and mediate effector functions.", Mabs, 2010, pp. 181-189, vol. 2.

Mori et al., "Engineering Chinese Hamster Ovary Cells to Maximize Effector Function of Produced Antibodies Using FUT8 siRNA.", Biotechnol Bioeng, 2004, pp. 901-908, vol. 88(7).

Nagy et al., "Stability of cytotoxic luteinizing hormone-releasing hormone conjugate (AN-152) containing doxorubicin 14-O-hemiglutarate in mouse and human serum in vitro: Implications for the design of preclinical studies.", Proc Natl Acad Sci, Jan. 18, 2000, USA, pp. 829-834, vol. 97.

Nestle et al., "Vaccination of melanoma patients with peptide- or tumor lysate-pulsed dendritic cells.", Nature Medicine, 1998, pp. 328-332, vol. 4(3).

Ngiow et al., "Anti-TIM3 Antibody Promotes T Cell IFN-g-Mediated Antitumor Immunity and Suppresses Established Tumors.", Cancer Res, May 15, 2011, pp. 3540-3551, vol. 71(10).

Nunez-Prado et al., "The coming of age of engineered multivalent antibodies.", Drug Discovery Today, May 2015, pp. 588-594, vol. 20(5).

Olivier et al., "EB66 cell line, a duck embryonic stem cell-derived substrate for the industrial production of therapeutic monoclonal antibodies with enhanced ADCC activity.", Mabs, 2010, pp. 405-415, vol. 2(4).

Padlan, E., "A Possible Procedure for Reducing the Immunogenicity of Antibody Variable Domains While Preserving Their Ligand-Binding Properties.", Mol Immunol, 1991, pp. 489-499, vol. 28(4/5).

Pal et al., "Programmed Death-1 Inhibition in Renal Cell Carcinoma: Clinical Insights and Future Directions.", Clin Advances in Hematology & Oncology, Feb. 2014, pp. 90-99, vol. 12(2).

Panka et al., "Defining The Structural Correlates Responsible for Loss of Arsonate Affinity in an ID$^{CR}$ Antibody Isolated From an Autoimmune Mouse.", 1993, pp. 1013-1020, vol. 30(11).

Pauken_Wherry, "Overcoming T cell exhaustion in infection and cancer.", Trends in Immunology, Apr. 2015, pp. 265-276, vol. 36(4).

Petkova et al., "Enhanced half-life of genetically engineered human IgG1 antibodies in a humanized FcRn mouse model: potential application in humorally mediated autoimmune disease.", Int Immunol, 2006, pp. 1759-1769, vol. 18(12).

Pol et al., "Trial Watch: DNA vaccines for cancer therapy.", Oncoimmunology, Feb. 2014, pp. e28185-1-e28185-10, vol. 3.

Popkov et al., "Human/mouse cross-reactive anti-VEGF receptor 2 recombinant antibodies selected from an immune b9 allotype rabbit antibody library.", Journal of Immunological Methods, 2004, pp. 149-164, vol. 288.

Remmele et al., "Differential Scanning Calorimetry. A Practical Tool for Elucidating Stability of Liquid Biopharmaceuticals.", Biopharm, Jun. 2000, pp. 36-46.

Remmele et al., "Interleukin-1 Receptor (IL-1R) Liquid Formulation Development Using Differential Scanning Calorimetry.", Pharm Res, 1998, pp. 200-208, vol. 15(2).

Richards et al., "Optimization of antibody binding to FcγRIIa enhances macrophage phagocytosis of tumor cells.", Mol Cancer Ther, Aug. 2008, pp. 2517-2527, vol. 7(8).

Rini et al., "Phase III Trial of Bevacizumab Plus Interferon Alfa Versus Interferon Alfa Monotherapy in Patients With Metastatic Renal Cell Carcinoma: Final Results of CALGB 90206.", J Clin Oncol, May 1, 2010, pp. 2137-2143, vol. 28(13).

Rong et al., "Tim-3 expression on periphal monocytes and CD3+ CD16/CD56+ natural killer-like T cells in patients with chronic hepatitis B.", Tissue Antigens, 2014, pp. 76-81, vol. 83(2).

Rother et al., "Discovery and Development of the complement inhibitor eculizumab for the treatment of paroxysmal nocturnal hemoglobinuria.", Nat Biotechnol, Nov. 7, 2002, pp. 1256-1264, vol. 25(11).

Rudikoff et al., "Single Amino Acid Substitution Altering Antigen-Binding Specificity.", PNAS, 1982, pp. 1979-1983, vol. 79.

Sabatos et al., "Interaction of Tim-3 and Tim-3 ligand regulates T helper type 1 responses and induction of periphal tolerance.", Nat Immunol, Nov. 2003, pp. 1102-1110, vol. 4(11).

Sakuishi et al., "Targeting Tim-3 and PD-1 pathways to reverse T cell exhaustion and restore anti-tumor immunity.", J Exp Med, 2010, pp. 2187-2194, vol. 207(10).

Sakuishi et al., "TIM3$^+$FOXP3$^+$ regulatory T cells are tissue-specific promoters of T-cell dysfunction in cancer.", Oncoimmunology, 2013, pp. e23849-1-e23849-9, vol. 2(4).

Sakuishi, K. and A. C. Anderson (2014). Tim-3 Regulation of Cancer Immunity. Tumor-Induced Immune Suppression. D. I. Gabrilovich and A. A. Hurwitz, Springer New York: 239-261.

Sanchez-Fueyo et al., "Tim-3 inhibits T helper type 1-mediated auto- and alloimmune responses and promotes immunlogical tolerance.", Nat Immunol, 2003, pp. 1093-1101, vol. 4(11).

Sasaki et al., "Stucture-Mutation Analysis of the ATPase Site of *Dictyostellium discoideum Myosin II*.", Adv Biophys, 1998, pp. 1-24, vol. 35.

Sheets et al., "Efficient construction of a large nonimmune phage antibody library: The production of high-affinity human single-chain antibodies to protein antigens.", PTAS (USA), May 1998, pp. 6157-6162, vol. 95.

Shi et al., "De Novo Selection of High-Affinity Antibodies from Synthetic Fab Libraries Displayed on Phage as pIX Fusion Proteins.", J Mol Biol, 2010, pp. 385-396, vol. 397.

Shields et al., "High Resolution Mapping of the Binding Site on Human IgG1 for FcγRI, FcγRII, FcγRIII, and FcRn and Design of IgG1 Variants with Improved Binding to the FcγR.", J Biol Chem, Mar. 2, 2001, pp. 6591-6604, vol. 276.

(56) References Cited

OTHER PUBLICATIONS

Shields et al., "Lack of Fucose on Human IgG1 N-Linked Oligosaccharide Improves Binding to Human FcRIII and Antibody-dependent Cellular Toxicity.", J Biol Chem, 2002, pp. 26733-26740, vol. 277(30).
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity.", J Biol Chem, 2003, pp. 3466-3473, vol. 278.
Stavenhagen et al., "Fc Optimization of Therapeutic Antibodies Enhances Their Ability to Kill Tumor Cells In vitro and Controls Tumor Expansion In vivo via Low-Affinity Activating Fc; Receptors.", Cancer Res, 2007, pp. 8882-8890, vol. 67.
Stickler et al., "The human G1m1 allotype associates with CD4+ T-cell responsiveness to a highly conserved IgG1 constant region peptide and confers an asparaginyl endopeptidase cleavage site.", Genes and Immunity, 2011, pp. 213-221, vol. 12.
Suto and Srivastava, "A Mechanism for the Specific Immunogenicity of Heat Shock Protein-Chaperoned Peptides.", Science, 1995, pp. 1585-1588, vol. 269.
Swaika et al., "Current state of anti-PD-L1 and anti-PD-1 agents in cancer therapy.", Mol Immunol, 2015, pp. 4-17, vol. 67.
Tamura et al., "Immunotherapy of Tumors with Autologous Tumor-Derived Heat Shock Protein Preparations.", Science, 1997, vol. 117-120, vol. 278.
Torgov et al., "Generation of an Intensely Potent Anthracycline by a Monoclonal Antibody-β-Galactosidase Conjugate.", Bioconj Chem, 2005, pp. 717-721, vol. 16.
UniProtKB Accession No. A0A0D9XEF3, 9ORYZ Uncharacterized protein. May 27, 2015 [found online Apr. 4, 2017 at http://www.uniprolorg/uniprot/A0A0D9XEF3] aa residues 111-118.
UniProtKB Accession No. E5ATZ2, PARRH Non-ribosomal peptide synthetase modules (EC 6.3.2.-) Feb. 8, 2011 [found online Apr. 5, 2017 athttp://www.uniprotorg/uniprot/E5ATZ2] aa residues 4403-4414.
UniProtKB Accession No. F4GQK8, PUSST Amino acid adenylation. Jun. 28, 2011 [found online Apr. 4, 2017 at http://www.uniprot.org/uniprot/F4GQK8] aa residues 482-490.
UniProtKB Accession No. W7MRS3, GIBM7 Uncharacterized protein. Apr. 16, 2014 [found online Apr. 5, 2017 at http://www.uniprot.org/uniprot/W7MRS3] aa residues 643-655.
Vaccaro et al., "Engineering the Fc Region of immunoglobin G to modulate in vivo antibody levels.", Nat Biotechnol, 2005, pp. 1283-1288, vol. 23.
Vaughan et al., "Human Antibodies with Sub-nanomolar Affinities Isolated from a large Non-immunized Phage Display Library.,", Nature Biotechnology, 1996, pp. 309-314, vol. 14.
Vitetta et al., "Redesigning Nature's Poisons to Create Anti-Tumor Reagents.", Science, Nov. 20, 1987, pp. 1098-1104, vol. 238.
Wang et al., "VISTA, a novel mouse Ig superfamily ligand that negatively regulates T cell responses.", J Exp Med, Mar. 14, 2011, pp. 577-592, vol. 208(3).
Winkler et al., "Changing the Antigen Binding Specificity by Single Point Mutations of an Anti-p24 (HIV-1) Antibody.", The Journal of Immunology, 2000, pp. 4505-4513, Vol.
Wolfl et al., "Activation-induced expression of CD137 permits detection, isolation, and expansion of the full repertoire of CD8+T cells responding to antigen without requiring knowledge of epitope specificities.", Blood, 2007, pp. 201-210, vol. 110(1).
Worn et al., "Stability engineering of antibody single-chain Fv fragments.", J Mol Biol, 2001, pp. 989-1010, vol. 305.
Wranik et al., "LUZ-Y, a Novel Platform for the Mammalian Cell Production of Full-length IgG-bispecific Antibodies.", J Biol Chem, 2012, pp. 43331-43339, vol. 287(52).
Wu and Kabat, "An Analysis of the Sequences of the Variable Regions of Bence Jones Proteins and Myeloma Light Chains and Their Implications for Anti-body Complementarity.", J Exp Med, 1970, pp. 211-250, vol. 132.

Xu et al., "In Vitro Characterization of Five Humanized OKT3 Effector Function Variant Antibodies.", Cell Immunol, 2000, pp. 16-26, vol. 200.
Yan et al., "Tim-3 Expression Defines Regulatory T Cells in Human Tumors.", PLoS One, Mar. 2013, pp. 1-10, vol. 8(3):e58006.
Yang et al., "Eradication of Established Tumors by a Fully Human Monoclonal Antibody to the Epidermal Growth Factor Receptor without Concomitant Chemotherapy.", Cancer Res, Mar. 15, 1999, pp. 1236-1243, vol. 59.
Yang et al., "Tailoring structure-function and pharmacokinetic properties of single-chain Fv proteins by site-specific PEGylation.", Protein Eng, 2003, pp. 761-770. vol. 16.
Yeung et al., "A Therapeutic Anti-VEGF Antibody with Increased Potency Independent of Pharmacokinetic Half-life.", Cancer Res, Apr. 15, 2010, pp. 3269-3277, vol. 70(8).
Yi, Q., "Novel Immunotherapies.", Cancer J, 2009, pp. 502-510, vol. 15(6).
Zalevsky et al., "Enhanced antibody half-life improves in vivo activity.", Nat Biotechnol, 2010, pp. 157-159, vol. 28.
Zhang et al., "Mechanism for Benzyl Alcohol-Induced Aggregation of Recombinant Human Interkeukin-1 Receptor Antagonist in Aqueous Solution.", J Pharm Sci, Dec. 2004, pp. 3076-3089, vol. 93(12).
Zhou et al., "Development of a Simple and Rapid Method for Producing Non-Fucosylated Oligomannose Containing Antibodies With Increased Effector Function.", Biotechnol Bioeng, Feb. 15, 2008, pp. 652-665, vol. 99(3).
Zhuang et al., "Ectopic Expression of TIM-3 in Lung Cancers. A Potential Independent Prognostice Factor for Patients With NSCLC.", Am J Clin Pathol, 2012, pp. 978-985, vol. 137(6).
Alegre et al., "A Non-Activating "Humanized" Anti-CD3 Monoclonal Antibody Retains Immunosuppressive Properties In Vivo.", Transplantation, Jun. 1994, pp. 1537-1543, vol. 57(11).
An et al., "IgG2m4, an engineered antibody isotype with reduced Fc function.", mAbs, 2009, pp. 572-579, vol. 1(6).
Baert et al., "Influence of Immunogenicity on the Long-Term Efficacy of Infliximab in Crohn's Disease.", N. Engl. J. Med, 2003, pp. 602-608, vol. 348(7).
Beduaddo et al., "Use of Biophysical Characterization in Preformulation Development of a Heavy-Chain Fragment of Botulinum Serotype B: Evaluation of Suitable Purification Process Conditions.", Pharm Res., Aug. 2004, pp. 1353-1361, vol. 21(8).
Dardalhon et al., "Tim-3/Galectin-9 Pathway: Regulation of Th1 Immunity through Promotion of CD11b+Ly-6G= Myeloid Cells.", J. of Immunology, Jun. 23, 2020, pp. 1383-1392, vol. 185(3).
UniProtKB/TrEMBL Accession No. A0A068NMJ6, Jul. 22, 2015 [online]. [Retrieved on Mar. 1-3, 17-19, 25, 28<URL: http://www.uniprot.org/uniprot/A0A068NMJ6.txt?version=6> entire document.
UniProtKB/TrEMBL Accession No. A0A068NN74, Jul. 22, 2015 [online]. [Retrieved on Mar. 1-3, 17-19, 25, 28, 2017]. Retrieved from the internet: <URL: http://www.uniprotorg/uniprot/A0A068NN74.txt?version=6> entire document.
UniProtKB/TrEMBL Accession No. F4GQK8, Jul. 22, 2015 [online]. [Retrieved on Mar. 28, 2017]. Retrieved from the internet: <URL: 1-3, 17-19, 25 http://www.uniprot.org/uniprot1F4GQK8.txt?version=25> entire document.
UniProtKB/TrEMBL Accession No. A0A087NGW6, Apr. 29, 2015 [online]. [Retrieved on Mar. 28, 2017]. Retrieved from the internet: <URL: 1-3, 17-19, 25 http://www.uniprotorg/uniprot/A0A087NGW6.txt?version=3> entire document.
UniProtKB/TrEMBL Accession No. E5ATZ2, Jan. 7, 2015 [online]. [Retrieved on Mar. 28, 2017]. Retrieved from the Internet: <URL: 1-3, 17-19, 25 http://www.uniprot.org/uniprot/E5ATZ2.txt?version=24> entire document.
UniProtKB/TrEMBL Accession No. G9POK7, Jan. 7, 2015 [online]. [Retrieved on Mar. 28, 2017). Retrieved from the internet: <URL: 1-3, 17-19, 25 http://www.uniprot.org/uniprot/G9POK7.txt?version=13> entire document.
Kang et al., "Apoptosis of tumor infiltrating effector TIM-3+CD8+ T cells in colon cancer.", Scientific Reports, Oct. 23, 2015, 15659, pp. 1-12, vol. 5(1).

(56) References Cited

OTHER PUBLICATIONS

Kikushige et al., "TIM-3 as a novel therapeutic target for eradicating acute myelogenous leukemia stem cells.", International Journal of Hematology, Sep. 18, 2013, pp. 627-633, vol. 98.

Wang et al., "Tim-3 signaling pathway as a novel negative mediator in lipopolysaccharide-induced endotoxic shock.", Human Immunology, May 2014, pp. 470-478, vol. 75(5).

Heon et al., "IL-15 induces strong but short-lived tumor-infiltrating CD8 T cell responses through the regulation of Tim-3 in breast cancer.", Biochemical and Biophysical Research Communications, Aug. 2015, pp. 360-366, vol. 464(1).

Li et al., "The Galectin-9/Tim-3 pathway is involved in the regulation of NK cell function at the maternal-fetal interface in early pregnancy.", Cellular & Molecular Immunology, 2016, pp. 73-81, Vol.

Morei da Silva et al., "Nivolumab: Anti-PD-1 monoclonal antibody cancer immunotherapy.", Drugs of the Future, Jan. 1, 2014, pp. 15-24, vol. 39(1).

Zhou et al., "Coexpression of Tim-3 and PD-1 identifies a CD8+ T-cell exhaustion phenotype in mice with disseminated acute myelogenous leukemia.", Blood, 2011, pp. 4501-4510, vol. 117(17).

Marwick et al., "Blockade of PD1 and TIM3 Restores Innate and Adaptive Immunity in Patients With Acute Alcoholic Hepatitis.", Gastroenterology: Official Publication of the American Gastroenterological Association, Mar. 1, 2015, pp. 590-610, vol. 148(3).

Collin, M., "Immune checkpoint inhibitors: a patent review (2010-2015).", Expert Opin. on Therapeuitc Agents, Apr. 18, 2016, pp. 555-564, vol. 26(5).

Green, L., "Antibody engineering via genetic engineering of the mouse: XenoMouse strains are a vehicle for the facile generation of therapeutic human monoclonal antibodies.", J Immunol Methods, 1999, pp. 11-23, vol. 231.

Anonymous: HNCT02908906 a Study to Evaluate the Safety, Pharmacokinetics, Pharmacodynamics, and Clinical Activity of JNJ-63723283, an Anti-PD-1 Monoclonal Antibody, in Participants With Advanced Cancers-H, Jan. 4, 2018 (Jan. 4, 2018), XP055579182, Retrieved from the Internet: URL:https://clinicaltrials.gov/ct2/history/NCT02908906?V 15=View#StudyPageTop [retrieved on Apr. 9, 2019], the whole document.

Tian et al: "Small-Angle X-ray 37-46 Scattering Screening Complements Conventional Biophysical Analysis: Comparative Structural and Biophysical Analysis of Monoclonal Antibodies IgGI, IgG2, and IgG4", Journal of Pharmaceutical Sciences, vol. 103, No. 6, Jun. 1, 2014 (Jun. 1, 2014), pp. 1701-1710, XP055576640, US ISSN: 0022-3549.

Freshwater et al: "Evaluation of dosing strategy for pembrolizumab for oncology indications", Journal for Immunotherapy of Cancer, Biomed Central Ltd, London, UK, vol. 5, No. 1, May 16, 2017 (May 16, 2017), pp. 1-9, XP021245121, DOI: 10.1186/S40425-017-0242-5 the whole document.

Hendrikx et al: "Fixed 1-36 Dosing of Monoclonal Antibodies in Oncology", The Oncologist, vol. 22, No. 10, Jul. 28, 2017 (Jul. 28, 2017), pp. 1212-1221, XP055579196, US ISSN: 1083-7159, DOI: 10.1634/theoncologist.2017-0167 the whole document.

Mackiewicz and Mackiewicz, "BRAF and MEK inhibitors in the era of immunotherapy in melanoma patients.", Contem Oncol, 2018, pp. 68-72, vol. 22.

Martin and Thornton, "Structural Families in Loops of Homologous Proteins: Automatic Classification, Modelling and Application to Antibodies.", J Bmol Biol, 1996, pp. 800-815, vol. 263.

Motzer et al., "Efficacy of everolimus in advanced renal cell carcinoma: a double-blind, randomised, placebo-controlled phase III trial.", Lancet, Aug. 9, 2008, pp. 449-456, vol. 372(9637).

Wolchok et al., "Guidelines for the Evaluation of Immune Therapy Activity in Solid Tumors: Immune-Related Response Criteria.", (2009) Clin Cancer Res, pp. 7412-7420, vol. 15(23).

\* cited by examiner

Figure 6.

| Antibody | HCDR1 | | | | | |
|---|---|---|---|---|---|---|
| | Sequence | | | | | SEQ ID NO: |
| PD1B114 | S | Y | A | I | S | 10 |
| PD1B149 | S | Y | A | I | S | 10 |
| PD1B160 | S | Y | A | I | S | 10 |
| PD1B162 | S | Y | A | I | S | 10 |
| PD1B164 | S | Y | A | I | S | 10 |
| PD1B11 | S | Y | A | I | S | 10 |
| PD1B183 | S | Y | A | I | S | 10 |
| PD1B184 | S | Y | A | I | S | 10 |
| PD1B185 | S | Y | A | I | S | 10 |
| PD1B187 | S | Y | A | I | S | 10 |
| PD1B71 | S | Y | A | I | S | 10 |
| PD1B177 | D | Y | V | I | S | 11 |
| PD1B70 | S | Y | A | I | S | 10 |
| PD1B175 | S | Y | V | I | H | 12 |
| PD1B194 | S | Y | A | I | S | 10 |
| PD1B195 | S | Y | A | I | S | 10 |
| PD1B196 | S | Y | A | I | S | 10 |
| PD1B197 | S | Y | V | I | H | 12 |
| PD1B198 | S | Y | V | I | H | 12 |
| PD1B199 | D | Y | V | I | S | 11 |
| PD1B200 | D | Y | V | I | S | 11 |
| PD1B201 | D | Y | V | I | S | 11 |
| HCDR1 genus | $X_1$ | Y | $X_2$ | I | $X_3$ | 82 |

PD-1 mAb HCDR1 genus sequence:

$X_1YX_2IX_3$ (SEQ ID NO: 82), wherein $X_1$ is S or D;

$X_2$ is V or A; and $X_3$ is H or S.

Figure 7.

| Antibody | HCDR2 | | | | | | | | | | | | | | | SEQ ID NO: |
|---|---|---|---|---|---|---|---|---|---|---|---|---|---|---|---|---|
| | Sequence | | | | | | | | | | | | | | | |
| PD1B114 | G | I | I | P | I | F | G | T | A | N | Y | A | Q | K | F | Q | G | 13 |
| PD1B149 | G | I | I | P | I | F | G | T | A | N | Y | A | Q | K | F | Q | G | 13 |
| PD1B160 | G | I | I | P | I | F | D | T | A | N | Y | A | Q | K | F | Q | G | 14 |
| PD1B162 | G | I | I | P | I | F | D | T | A | N | Y | A | Q | K | F | Q | G | 14 |
| PD1B164 | G | I | I | P | I | F | D | T | A | N | Y | A | Q | K | F | Q | G | 14 |
| PD1B11 | G | I | I | P | I | F | G | T | A | N | Y | A | Q | K | F | Q | G | 13 |
| PD1B183 | G | I | I | P | I | F | G | T | A | N | Y | A | Q | K | F | Q | G | 13 |
| PD1B184 | G | I | I | P | I | F | G | T | A | N | Y | A | Q | K | F | Q | G | 13 |
| PD1B185 | G | I | I | P | I | F | G | T | A | N | Y | A | Q | K | F | Q | G | 13 |
| PD1B187 | G | I | I | P | I | F | G | T | A | N | Y | A | Q | K | F | Q | G | 13 |
| PD1B71 | G | I | I | P | I | F | G | T | A | N | Y | A | Q | K | F | Q | G | 13 |
| PD1B177 | G | I | I | P | I | Y | G | T | A | N | Y | A | Q | K | F | Q | G | 15 |
| PD1B70 | G | I | I | P | I | F | G | T | A | N | Y | A | Q | K | F | Q | G | 13 |
| PD1B175 | G | I | I | P | I | F | G | T | A | N | Y | A | Q | K | F | Q | G | 13 |
| PD1B194 | G | I | I | P | I | F | D | T | A | N | Y | A | Q | K | F | Q | G | 14 |
| PD1B195 | G | I | I | P | I | F | D | T | A | N | Y | A | Q | K | F | Q | G | 14 |
| PD1B196 | G | I | I | P | I | F | D | T | A | N | Y | A | Q | K | F | Q | G | 14 |
| PD1B197 | G | I | I | P | I | F | G | T | A | N | Y | A | Q | K | F | Q | G | 13 |
| PD1B198 | G | I | I | P | I | F | G | T | A | N | Y | A | Q | K | F | Q | G | 13 |
| PD1B199 | G | I | I | P | I | Y | G | T | A | N | Y | A | Q | K | F | Q | G | 15 |
| PD1B200 | G | I | I | P | I | Y | G | T | A | N | Y | A | Q | K | F | Q | G | 15 |
| PD1B201 | G | I | I | P | I | Y | G | T | A | N | Y | A | Q | K | F | Q | G | 15 |
| HCDR2 genus | G | I | I | P | I | $X_4$ | $X_5$ | T | A | N | Y | A | Q | K | F | Q | G | 83 |

PD-1 mAb HCDR2 genus sequence

GIIPIX$_4$X$_5$TANYAQKFQG (SEQ ID NO: 83), wherein $X_4$ is Y or F; and $X_5$ is G or D.

Figure 8.

| Antibody | HCDR3 Sequence | | | | | | | | | | | | SEQ ID NO: |
|---|---|---|---|---|---|---|---|---|---|---|---|---|---|
| PD1B114 | P | G | L | A | A | A | Y | D | T | G | N | L | D | Y | 16 |
| PD1B149 | P | G | L | A | A | A | Y | D | T | G | N | L | D | Y | 16 |
| PD1B160 | P | G | L | A | A | A | Y | D | T | G | N | L | D | Y | 16 |
| PD1B162 | P | G | L | A | A | A | Y | D | T | G | N | L | D | Y | 16 |
| PD1B164 | P | G | L | A | A | A | Y | D | T | G | N | L | D | Y | 16 |
| PD1B11 | P | G | L | A | A | A | Y | D | T | G | S | L | D | Y | 17 |
| PD1B183 | P | G | L | A | A | A | Y | D | T | G | S | L | D | Y | 17 |
| PD1B184 | P | G | L | A | A | A | Y | D | T | G | S | L | D | Y | 17 |
| PD1B185 | P | G | L | A | A | A | Y | D | T | G | S | L | D | Y | 17 |
| PD1B187 | P | G | L | A | A | A | Y | D | T | G | S | L | D | Y | 17 |
| PD1B194 | P | G | L | A | A | A | Y | D | T | G | S | L | D | Y | 17 |
| PD1B195 | P | G | L | A | A | A | Y | D | T | G | S | L | D | Y | 17 |
| PD1B196 | P | G | L | A | A | A | Y | D | T | G | S | L | D | Y | 17 |
| HCDR3 genus 1 | P | G | L | A | A | A | Y | D | T | G | $X_6$ | L | D | Y | 84 |

PD-1 mAb HCDR3 genus 1

PGLAAAYDTGX$_6$LDY (SEQ ID NO: 84), wherein $X_6$ is N or S.

Figure 9.

| Antibody | HCDR3 | | | | | | | | | | SEQ ID NO: |
|---|---|---|---|---|---|---|---|---|---|---|---|
| | Sequence | | | | | | | | | | |
| PD1B71 | G | T | L | D | R | T | G | H | L | D | Y | 18 |
| PD1B177 | G | T | L | D | R | T | G | H | L | D | Y | 18 |
| PD1B70 | G | Y | V | R | A | T | G | M | L | D | Y | 19 |
| PD1B175 | G | Y | V | R | A | T | G | M | L | D | Y | 19 |
| PD1B197 | G | Y | V | R | A | T | G | M | L | D | Y | 19 |
| PD1B198 | G | Y | V | R | A | T | G | M | L | D | Y | 19 |
| PD1B199 | G | T | L | D | R | T | G | H | L | D | Y | 18 |
| PD1B200 | G | T | L | D | R | T | G | H | L | D | Y | 18 |
| PD1B201 | G | T | L | D | R | T | G | H | L | D | Y | 18 |
| HCDR3 genus 2 | G | $X_7$ | $X_8$ | $X_9$ | $X_{10}$ | T | G | $X_{11}$ | L | D | Y | 85 |

PD-1 mAb HCDR3 genus 2

$GX_7X_8X_9X_{10}TGX_{11}LDY$ (SEQ ID NO; 85), wherein $X_7$ is T or Y;

$X_8$ is L or V;

$X_9$ is D or R;

$X_{10}$ is R or A; and $X_{11}$ is H or M.

Figure 10.

| Antibody | LCDR1 | | | | | | | | | | SEQ ID NO: |
|---|---|---|---|---|---|---|---|---|---|---|---|
| | Sequence | | | | | | | | | | |
| PD1B114 | R | A | S | Q | S | V | S | S | Y | L | A | 20 |
| PD1B149 | R | A | S | Q | S | V | R | N | Y | L | A | 21 |
| PD1B160 | R | A | S | Q | S | V | D | S | Y | L | A | 22 |
| PD1B162 | R | A | S | Q | S | V | D | S | Y | L | A | 22 |
| PD1B164 | R | A | S | Q | S | V | R | S | Y | L | A | 23 |
| PD1B11 | R | A | S | Q | S | V | S | S | Y | L | A | 20 |
| PD1B183 | R | A | S | Q | S | V | S | S | Y | L | A | 20 |
| PD1B184 | R | A | S | Q | S | V | R | N | Y | L | A | 21 |
| PD1B185 | R | A | S | Q | S | V | R | N | Y | L | A | 21 |
| PD1B187 | R | A | S | Q | S | V | R | S | Y | L | A | 23 |
| PD1B71 | R | A | S | Q | S | V | S | S | Y | L | A | 20 |
| PD1B177 | R | A | S | Q | S | V | S | S | Y | L | A | 20 |
| PD1B70 | R | A | S | Q | S | V | S | S | Y | L | A | 20 |
| PD1B175 | R | A | S | Q | S | V | S | S | Y | L | A | 20 |
| PD1B194 | R | A | S | Q | S | V | R | S | Y | L | A | 23 |
| PD1B195 | R | A | S | Q | S | V | D | S | Y | L | A | 22 |
| PD1B196 | R | A | S | Q | S | V | R | S | Y | L | A | 23 |
| PD1B197 | R | A | S | Q | S | V | S | N | Y | L | A | 24 |
| PD1B198 | R | A | S | Q | S | V | S | S | Y | L | A | 20 |
| PD1B199 | R | A | S | Q | S | V | S | S | Y | L | A | 20 |
| PD1B200 | R | A | S | Q | S | V | D | N | Y | L | A | 25 |
| PD1B201 | R | A | S | Q | S | V | S | N | Y | L | A | 24 |
| LCDR1 genus | R | A | S | Q | S | V | $X_{12}$ | $X_{13}$ | Y | L | A | 86 |

PD-1 mAb LCDR1 genus

RASQSV$X_{12}X_{13}$YLA (SEQ ID NO: 86), wherein $X_{12}$ is S, R or D; and $X_{13}$ is S or N.

Figure 11.

| Antibody | LCDR2 | | | | | | | SEQ ID NO: |
|---|---|---|---|---|---|---|---|---|
| | Sequence | | | | | | | |
| PD1B114 | D | A | S | N | R | A | T | 26 |
| PD1B149 | D | A | S | N | R | A | T | 26 |
| PD1B160 | D | A | S | D | R | A | T | 27 |
| PD1B162 | D | A | S | N | R | A | T | 26 |
| PD1B164 | D | A | S | Y | R | A | T | 28 |
| PD1B11 | D | A | S | N | R | A | T | 26 |
| PD1B183 | D | A | S | N | R | A | T | 26 |
| PD1B184 | D | A | S | N | R | A | T | 26 |
| PD1B185 | D | A | S | D | R | A | T | 27 |
| PD1B187 | D | A | S | N | R | A | T | 26 |
| PD1B71 | D | A | S | N | R | A | T | 26 |
| PD1B177 | D | A | S | N | R | A | T | 26 |
| PD1B70 | D | A | S | N | R | A | T | 26 |
| PD1B175 | D | A | S | N | R | A | T | 26 |
| PD1B194 | D | A | S | Y | R | A | T | 28 |
| PD1B195 | D | A | S | N | R | A | T | 26 |
| PD1B196 | D | A | S | N | R | A | T | 26 |
| PD1B197 | D | A | S | N | R | A | T | 26 |
| PD1B198 | D | A | S | S | R | A | T | 29 |
| PD1B199 | D | A | S | T | R | A | T | 30 |
| PD1B200 | D | A | S | N | R | A | T | 26 |
| PD1B201 | D | A | S | N | R | A | T | 26 |
| LCDR2 genus | D | A | S | $X_{14}$ | R | A | T | 87 |

PD-1 mAb LCDR2 genus

DASX$_{14}$RAT (SEQ ID NO: 87), wherein $X_{14}$ is N, D, Y, S or T.

Figure 12.

| Antibody | LCDR3 | | | | | | | | | |
|---|---|---|---|---|---|---|---|---|---|---|
| | Sequence | | | | | | | | | SEQ ID NO: |
| PD1B114 | Q | Q | R | S | N | W | P | L | T | 31 |
| PD1B149 | Q | Q | R | N | Y | W | P | L | T | 32 |
| PD1B160 | Q | Q | R | G | N | W | P | L | T | 33 |
| PD1B162 | Q | Q | R | E | Y | W | P | L | T | 34 |
| PD1B164 | Q | Q | R | D | Y | W | P | L | T | 35 |
| PD1B11 | Q | Q | R | S | N | W | P | L | T | 31 |
| PD1B183 | Q | Q | R | G | Y | W | P | L | T | 36 |
| PD1B184 | Q | Q | R | N | Y | W | P | L | T | 32 |
| PD1B185 | Q | Q | R | W | N | W | P | L | T | 37 |
| PD1B187 | Q | Q | R | N | Y | W | P | L | T | 32 |
| PD1B71 | Q | Q | R | S | N | W | P | L | T | 31 |
| PD1B177 | Q | Q | R | S | N | W | P | L | T | 31 |
| PD1B70 | Q | Q | R | S | N | W | P | L | T | 31 |
| PD1B175 | Q | Q | R | S | N | W | P | L | T | 31 |
| PD1B194 | Q | Q | R | D | Y | W | P | L | T | 35 |
| PD1B195 | Q | Q | R | E | Y | W | P | L | T | 34 |
| PD1B196 | Q | Q | R | N | Y | W | P | L | T | 32 |
| PD1B197 | Q | Q | R | A | Y | W | P | L | T | 38 |
| PD1B198 | Q | Q | R | A | E | W | P | L | T | 39 |
| PD1B199 | Q | Q | R | N | Y | W | P | L | T | 32 |
| PD1B200 | Q | Q | R | S | A | W | P | L | T | 40 |
| PD1B201 | Q | Q | R | N | Y | W | P | L | T | 32 |
| LCDR3 genus | Q | Q | R | $X_{15}$ | $X_{16}$ | W | P | L | T | 88 |

PD-1 mAb LCDR3 genus:

QQR$X_{15}X_{16}$WPLT (SEQ ID NO: 88), wherein $X_{15}$ is S, N, G, E, D, W, E or A; and $X_{16}$ is N, Y, E or A.

Figure 13.

| mAb name | HCDR1 | | | | | |
|---|---|---|---|---|---|---|
| | Sequence | | | | | SEQ ID NO: |
| TM3B103 | N | Y | W | M | S | 90 |
| TM3B105 | S | Y | A | M | S | 91 |
| TM3B109 | S | Y | A | M | S | 91 |
| TM3B108 | G | Y | W | M | H | 92 |
| TM3B113 | D | Y | W | M | S | 93 |
| HCDR1 genus | $X_{17}$ | Y | $X_{18}$ | M | $X_{19}$ | 164 |

TIM3 mAb HCDR1 genus:

$X_{17}YX_{18}MX_{19}$ (SEQ ID NO: 164),

Wherein $X_{17}$ is N, S, G or D;

$X_{18}$ is W or A; and $X_{19}$ is S or H.

Figure 14.

| mAb | HCDR2 | | | | | | | | | | | | | | | SEQ ID NO: |
|---|---|---|---|---|---|---|---|---|---|---|---|---|---|---|---|---|
| | Sequence | | | | | | | | | | | | | | | |
| TM3B103 | A | I | S | G | S | G | G | S | T | Y | Y | A | D | S | V | K | G | 99 |
| TM3B105 | A | I | S | G | S | G | G | S | T | Y | Y | A | D | S | V | K | G | 99 |
| TM3B109 | A | I | S | G | S | G | G | S | T | Y | Y | A | D | S | V | K | G | 99 |
| TM3B108 | A | I | S | Y | S | G | G | S | T | Y | Y | A | D | S | V | K | G | 100 |
| TM3B113 | V | I | K | Y | S | G | G | S | K | Y | Y | A | D | S | V | K | G | 101 |
| HCDR2 genus | $X_{20}$ | I | $X_{21}$ | $X_{22}$ | S | G | G | S | $X_{23}$ | Y | Y | A | D | S | V | K | G | 165 |

TIM-3 mAb HCDR2 genus $X_{20}IX_{21}X_{22}SGGSX_{23}YYADSVKG$ (SEQ ID NO: 165), wherein $X_{20}$ is A or V;

$X_{21}$ is S or K;

$X_{22}$ is G or Y; and $X_{23}$ is T or K.

Figure 15.

| mAb | HCDR3 | | | | | | | | | SEQ ID NO: |
|---|---|---|---|---|---|---|---|---|---|---|
| | Sequence | | | | | | | | | |
| TM3B103 | D | H | W | D | P | N | F | L | D | Y | 107 |
| TM3B105 | S | P | - | - | Y | A | P | L | D | Y | 108 |
| TM3B109 | N | E | E | P | D | D | R | L | D | Y | 109 |
| TM3B108 | G | T | N | | | | W | L | D | Y | 110 |
| TM3B113 | E | L | E | | | G | V | F | D | Y | 111 |
| HCDR3 genus | $X_{24}$ | $X_{25}$ | $X_{26}$ | $X_{27}$ | $X_{28}$ | $X_{29}$ | $X_{30}$ | $X_{31}$ | D | Y | 166 |

$X_{24}X_{25}X_{26}X_{27}X_{28}X_{29}X_{30}X_{31}DY$ (SEQ ID NO: 166), wherein $X_{24}$ is D, S, N, G or E;

$X_{25}$ is H, P, E, T or L;

$X_{26}$ is W, E, N or deleted;

$X_{27}$ is D, P or deleted;

$X_{28}$ is P, Y, D or deleted;

$X_{29}$ is N, A, D, G or deleted;

$X_{30}$ is F, P, R, W or V; and $X_{31}$ is L or F.

Figue 16.

| mAb | LCDR1 ||||||||||||||||| SEQ ID NO: |
|---|---|---|---|---|---|---|---|---|---|---|---|---|---|---|---|---|---|
| | Sequence |||||||||||||||||
| TM3B103 | R | A | S | Q | S | V | S | S | - | | | | S | Y | L | A | 117 |
| TM3B105 | R | A | S | Q | S | V | N | - | | | | | D | Y | L | A | 118 |
| TM3B109 | K | S | S | Q | S | V | L | A | S | S | N | N | K | N | Y | L | A | 119 |
| TM3B108 | R | A | S | Q | S | V | S | S | | | | | S | Y | L | A | 117 |
| TM3B113 | R | A | S | Q | S | V | S | N | | | | | S | T | L | A | 120 |
| LCDR1 genus | $X_{32}$ | $X_{33}$ | S | Q | S | V | $X_{34}$ | $X_{35}$ | $X_{36}$ | $X_{37}$ | $X_{38}$ | $X_{39}$ | $X_{40}$ | $X_{41}$ | $X_{42}$ | L | A | 167 |

$X_{32}X_{33}SQSVX_{34}X_{35}X_{36}X_{37}X_{38}X_{39}X_{40}X_{41}X_{42}LA$ (SEQ ID NO: 167), wherein $X_{32}$ is R or K;

$X_{33}$ is A or S;

$X_{34}$ is S, N or L;

$X_{35}$ s S, A, N or deleted;

$X_{36}$ is S or deleted;

$X_{37}$ is S or deleted;

$X_{38}$ is N or deleted;

$X_{39}$ is N or deleted;

$X_{40}$ is K or deleted;

$X_{41}$ is S, D or N; and $X_{42}$ is Y or T.

Figure 17.

| mAb | LCDR2 | | | | | | |
|---|---|---|---|---|---|---|---|
| | Sequence | | | | | | SEQ ID NO: |
| TM3B103 | G | A | S | S | R | A | T | 126 |
| TM3B105 | D | A | S | N | R | A | T | 127 |
| TM3B109 | W | A | S | T | R | E | S | 128 |
| TM3B108 | G | A | S | S | R | A | T | 126 |
| TM3B113 | T | A | S | S | R | A | T | 129 |
| LCDR2 genus | $X_{43}$ | A | S | $X_{44}$ | R | $X_{45}$ | $X_{46}$ | 168 |

TIM-3 mAb LCDR2 genus $X_{43}ASX_{44}RX_{45}X_{46}$ (SEQ ID NO: 168), wherein $X_{43}$ is G, D, W or T;

$X_{44}$ is S, N or T;

$X_{45}$ is A or E; and $X_{46}$ is T or S.

Figure 18.

| mAb | LCDR3 | | | | | | | | SEQ ID NO: |
|---|---|---|---|---|---|---|---|---|---|
| | Sequence | | | | | | | | |
| TM3B103 | Q | Q | Y | G | S | S | P | L | T | 135 |
| TM3B105 | Q | Q | G | G | H | A | P | I | T | 136 |
| TM3B109 | Q | Q | Y | Y | S | T | P | L | T | 137 |
| TM3B108 | Q | Q | Y | G | S | S | P | L | T | 138 |
| TM3B113 | Q | Q | S | Y | T | S | P | W | T | 139 |
| LCDR3 genus | Q | Q | $X_{47}$ | $X_{48}$ | $X_{49}$ | $X_{50}$ | P | $X_{51}$ | T | 169 |

$QQX_{47}X_{48}X_{49}X_{50}PX_{51}T$ (SEQ ID NO: 169), wherein $X_{47}$ is Y, G or S;

$X_{48}$ is G or Y;

$X_{49}$ is S, H or T;

$X_{50}$ is S, A or T; and $X_{51}$ is L, I or W.

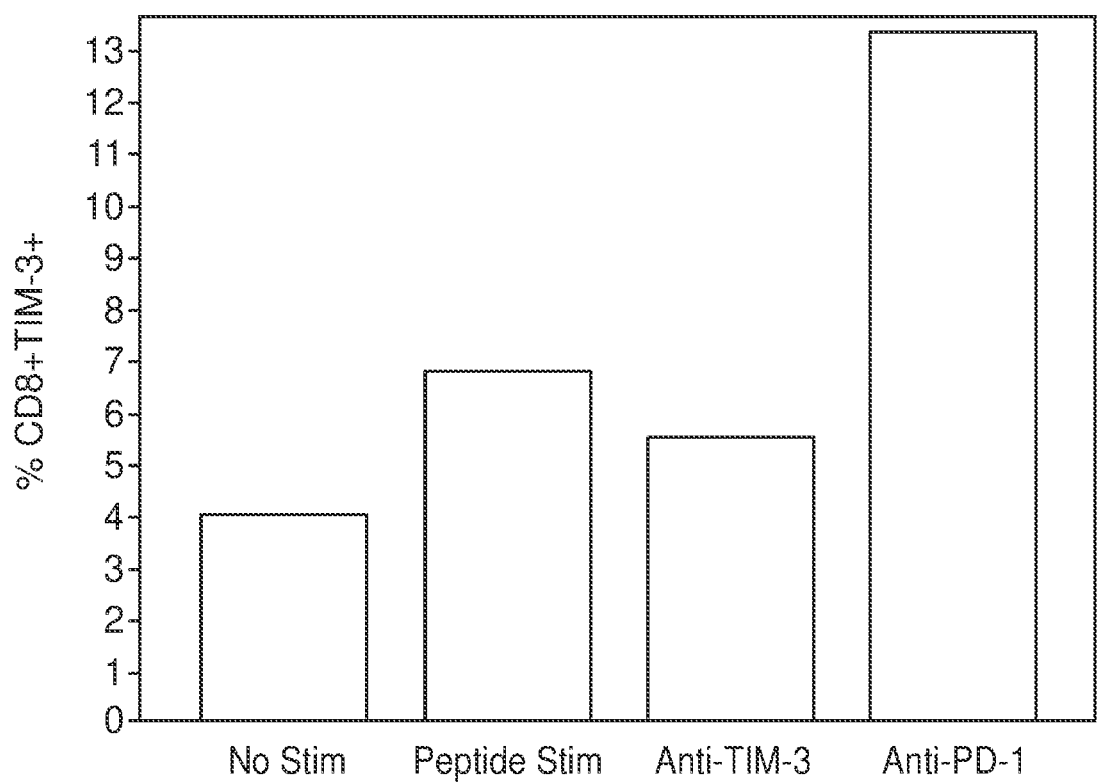

SEQUENCE LISTING

```
<160> NUMBER OF SEQ ID NOS: 312

<210> SEQ ID NO 1
<211> LENGTH: 268
<212> TYPE: PRT
<213> ORGANISM: Homo sapiens

<400> SEQUENCE: 1

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Val Pro Cys Val Pro Glu
```

```
                210                 215                 220
Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
            245                 250                 255

Leu Arg Pro Glu Asp Gly His Cys Ser Trp Pro Leu
        260                 265
```

<210> SEQ ID NO 2
<211> LENGTH: 149
<212> TYPE: PRT
<213> ORGANISM: Homo sapiens

<400> SEQUENCE: 2

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu
145
```

<210> SEQ ID NO 3
<211> LENGTH: 268
<212> TYPE: PRT
<213> ORGANISM: Macaca fascicularis

<400> SEQUENCE: 3

```
Pro Gly Trp Phe Leu Glu Ser Pro Asp Arg Pro Trp Asn Ala Pro Thr
1               5                   10                  15

Phe Ser Pro Ala Leu Leu Leu Val Thr Glu Gly Asp Asn Ala Thr Phe
            20                  25                  30

Thr Cys Ser Phe Ser Asn Ala Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Arg Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
```

```
            115                 120                 125
Ala Glu Val Pro Thr Ala His Pro Ser Pro Ser Pro Arg Pro Ala Gly
    130                 135                 140

Gln Phe Gln Ala Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Gln Gly Thr Ile Glu Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Ala Pro Cys Val Pro Glu
    210                 215                 220

Gln Thr Glu Tyr Ala Thr Ile Val Phe Pro Ser Gly Leu Gly Thr Ser
225                 230                 235                 240

Ser Pro Ala Arg Arg Gly Ser Ala Asp Gly Pro Arg Ser Pro Arg Pro
                245                 250                 255

Leu Arg Pro Glu Asp Gly His Cys Ser Trp Pro Leu
            260                 265

<210> SEQ ID NO 4
<211> LENGTH: 149
<212> TYPE: PRT
<213> ORGANISM: Macaca fascicularis

<400> SEQUENCE: 4

Pro Gly Trp Phe Leu Glu Ser Pro Asp Arg Pro Trp Asn Ala Pro Thr
1               5                   10                  15

Phe Ser Pro Ala Leu Leu Leu Val Thr Glu Gly Asp Asn Ala Thr Phe
            20                  25                  30

Thr Cys Ser Phe Ser Asn Ala Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Arg Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Ala Leu
145

<210> SEQ ID NO 5
<211> LENGTH: 220
<212> TYPE: PRT
<213> ORGANISM: Homo sapiens

<400> SEQUENCE: 5

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
```

-continued

```
                20                  25                  30
Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
    210                 215                 220
```

<210> SEQ ID NO 6
<211> LENGTH: 221
<212> TYPE: PRT
<213> ORGANISM: Homo sapiens

<400> SEQUENCE: 6

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175
```

```
Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr
    210                 215                 220

<210> SEQ ID NO 7
<211> LENGTH: 222
<212> TYPE: PRT
<213> ORGANISM: Macaca fascicularis

<400> SEQUENCE: 7

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Thr Ser Leu Ile Val Tyr Trp Glu Met Glu Asp Lys Asn Ile Ile
        35                  40                  45

Gln Phe Val His Gly Glu Glu Asp Leu Lys Val Gln His Ser Asn Tyr
    50                  55                  60

Arg Gln Arg Ala Gln Leu Leu Lys Asp Gln Leu Ser Leu Gly Asn Ala
65                  70                  75                  80

Ala Leu Arg Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
            100                 105                 110

Val Asn Ala Pro Tyr Asn Lys Ile Asn Gln Arg Ile Leu Val Val Asp
        115                 120                 125

Pro Val Thr Ser Glu His Glu Leu Thr Cys Gln Ala Glu Gly Tyr Pro
    130                 135                 140

Lys Ala Glu Val Ile Trp Thr Ser Ser Asp His Gln Val Leu Ser Gly
145                 150                 155                 160

Lys Thr Thr Thr Thr Asn Ser Lys Arg Glu Glu Lys Leu Leu Asn Val
                165                 170                 175

Thr Ser Thr Leu Arg Ile Asn Thr Thr Ala Asn Glu Ile Phe Tyr Cys
            180                 185                 190

Ile Phe Arg Arg Leu Asp Pro Glu Glu Asn His Thr Ala Glu Leu Val
        195                 200                 205

Ile Pro Glu Leu Pro Leu Ala Leu Pro Pro Asn Glu Arg Thr
    210                 215                 220

<210> SEQ ID NO 8
<211> LENGTH: 201
<212> TYPE: PRT
<213> ORGANISM: Homo sapiens

<400> SEQUENCE: 8

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60
```

-continued

```
Lys Ala Ser Phe His Ile Pro Gln Val Gln Val Arg Asp Glu Gly Gln
 65                  70                  75                  80

Tyr Gln Cys Ile Ile Ile Tyr Gly Val Ala Trp Asp Tyr Lys Tyr Leu
                 85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr
        195                 200

<210> SEQ ID NO 9
<211> LENGTH: 143
<212> TYPE: PRT
<213> ORGANISM: Mus musculus

<400> SEQUENCE: 9

Leu Glu Val Pro Asn Gly Pro Trp Arg Ser Leu Thr Phe Tyr Pro Ala
  1               5                  10                  15

Trp Leu Thr Val Ser Glu Gly Ala Asn Ala Thr Phe Thr Cys Ser Leu
                 20                  25                  30

Ser Asn Trp Ser Glu Asp Leu Met Leu Asn Trp Asn Arg Leu Ser Pro
             35                  40                  45

Ser Asn Gln Thr Glu Lys Gln Ala Ala Phe Cys Asn Gly Leu Ser Gln
         50                  55                  60

Pro Val Gln Asp Ala Arg Phe Gln Ile Ile Gln Leu Pro Asn Arg His
 65                  70                  75                  80

Asp Phe His Met Asn Ile Leu Asp Thr Arg Arg Asn Asp Ser Gly Ile
                 85                  90                  95

Tyr Leu Cys Gly Ala Ile Ser Leu His Pro Lys Ala Lys Ile Glu Glu
            100                 105                 110

Ser Pro Gly Ala Glu Leu Val Val Thr Glu Arg Ile Leu Glu Thr Ser
        115                 120                 125

Thr Arg Tyr Pro Ser Pro Ser Pro Lys Pro Glu Gly Arg Phe Gln
    130                 135                 140

<210> SEQ ID NO 10
<211> LENGTH: 5
<212> TYPE: PRT
<213> ORGANISM: Artificial sequence
<220> FEATURE:
<223> OTHER INFORMATION: PD-1 antibody HCDR1

<400> SEQUENCE: 10

Ser Tyr Ala Ile Ser
 1               5

<210> SEQ ID NO 11
<211> LENGTH: 5
<212> TYPE: PRT
```

```
<213> ORGANISM: Artificial sequence
<220> FEATURE:
<223> OTHER INFORMATION: PD-1 antibody HCDR1

<400> SEQUENCE: 11

Asp Tyr Val Ile Ser
1               5

<210> SEQ ID NO 12
<211> LENGTH: 5
<212> TYPE: PRT
<213> ORGANISM: Artificial sequence
<220> FEATURE:
<223> OTHER INFORMATION: PD-1 antibody HCDR1

<400> SEQUENCE: 12

Ser Tyr Val Ile His
1               5

<210> SEQ ID NO 13
<211> LENGTH: 17
<212> TYPE: PRT
<213> ORGANISM: Artificial sequence
<220> FEATURE:
<223> OTHER INFORMATION: PD-1 antibody HCDR2

<400> SEQUENCE: 13

Gly Ile Ile Pro Ile Phe Gly Thr Ala Asn Tyr Ala Gln Lys Phe Gln
1               5                   10                  15

Gly

<210> SEQ ID NO 14
<211> LENGTH: 17
<212> TYPE: PRT
<213> ORGANISM: Artificial sequence
<220> FEATURE:
<223> OTHER INFORMATION: PD-1 antibody HCDR2

<400> SEQUENCE: 14

Gly Ile Ile Pro Ile Phe Asp Thr Ala Asn Tyr Ala Gln Lys Phe Gln
1               5                   10                  15

Gly

<210> SEQ ID NO 15
<211> LENGTH: 17
<212> TYPE: PRT
<213> ORGANISM: Artificial sequence
<220> FEATURE:
<223> OTHER INFORMATION: PD-1 antibody HCDR2

<400> SEQUENCE: 15

Gly Ile Ile Pro Ile Tyr Gly Thr Ala Asn Tyr Ala Gln Lys Phe Gln
1               5                   10                  15

Gly

<210> SEQ ID NO 16
<211> LENGTH: 14
<212> TYPE: PRT
<213> ORGANISM: Artificial sequence
<220> FEATURE:
<223> OTHER INFORMATION: PD-1 antibody HCDR3

<400> SEQUENCE: 16

Pro Gly Leu Ala Ala Ala Tyr Asp Thr Gly Asn Leu Asp Tyr
1               5                   10
```

```
<210> SEQ ID NO 17
<211> LENGTH: 14
<212> TYPE: PRT
<213> ORGANISM: Artificial sequence
<220> FEATURE:
<223> OTHER INFORMATION: PD-1 antibody HCDR3

<400> SEQUENCE: 17

Pro Gly Leu Ala Ala Ala Tyr Asp Thr Gly Ser Leu Asp Tyr
1               5                   10

<210> SEQ ID NO 18
<211> LENGTH: 11
<212> TYPE: PRT
<213> ORGANISM: Artificial sequence
<220> FEATURE:
<223> OTHER INFORMATION: PD-1 antibody HCDR3

<400> SEQUENCE: 18

Gly Thr Leu Asp Arg Thr Gly His Leu Asp Tyr
1               5                   10

<210> SEQ ID NO 19
<211> LENGTH: 11
<212> TYPE: PRT
<213> ORGANISM: Artificial sequence
<220> FEATURE:
<223> OTHER INFORMATION: PD-1 antibody HCDR3

<400> SEQUENCE: 19

Gly Tyr Val Arg Ala Thr Gly Met Leu Asp Tyr
1               5                   10

<210> SEQ ID NO 20
<211> LENGTH: 11
<212> TYPE: PRT
<213> ORGANISM: Artificial sequence
<220> FEATURE:
<223> OTHER INFORMATION: PD-1 antibody LCDR1

<400> SEQUENCE: 20

Arg Ala Ser Gln Ser Val Ser Ser Tyr Leu Ala
1               5                   10

<210> SEQ ID NO 21
<211> LENGTH: 11
<212> TYPE: PRT
<213> ORGANISM: Artificial sequence
<220> FEATURE:
<223> OTHER INFORMATION: PD-1 antibody LCDR1

<400> SEQUENCE: 21

Arg Ala Ser Gln Ser Val Arg Asn Tyr Leu Ala
1               5                   10

<210> SEQ ID NO 22
<211> LENGTH: 11
<212> TYPE: PRT
<213> ORGANISM: Artificial sequence
<220> FEATURE:
<223> OTHER INFORMATION: PD-1 antibody LCDR1

<400> SEQUENCE: 22

Arg Ala Ser Gln Ser Val Asp Ser Tyr Leu Ala
1               5                   10
```

<210> SEQ ID NO 23
<211> LENGTH: 11
<212> TYPE: PRT
<213> ORGANISM: Artificial sequence
<220> FEATURE:
<223> OTHER INFORMATION: PD-1 antibody LCDR1

<400> SEQUENCE: 23

Arg Ala Ser Gln Ser Val Arg Ser Tyr Leu Ala
1               5                   10

<210> SEQ ID NO 24
<211> LENGTH: 11
<212> TYPE: PRT
<213> ORGANISM: Artificial sequence
<220> FEATURE:
<223> OTHER INFORMATION: PD-1 antibody LCDR1

<400> SEQUENCE: 24

Arg Ala Ser Gln Ser Val Ser Asn Tyr Leu Ala
1               5                   10

<210> SEQ ID NO 25
<211> LENGTH: 11
<212> TYPE: PRT
<213> ORGANISM: Artificial sequence
<220> FEATURE:
<223> OTHER INFORMATION: PD-1 antibody LCDR1

<400> SEQUENCE: 25

Arg Ala Ser Gln Ser Val Asp Asn Tyr Leu Ala
1               5                   10

<210> SEQ ID NO 26
<211> LENGTH: 7
<212> TYPE: PRT
<213> ORGANISM: Artificial sequence
<220> FEATURE:
<223> OTHER INFORMATION: PD-1 antibody LCDR2

<400> SEQUENCE: 26

Asp Ala Ser Asn Arg Ala Thr
1               5

<210> SEQ ID NO 27
<211> LENGTH: 7
<212> TYPE: PRT
<213> ORGANISM: Artificial sequence
<220> FEATURE:
<223> OTHER INFORMATION: PD-1 antibody LCDR2

<400> SEQUENCE: 27

Asp Ala Ser Asp Arg Ala Thr
1               5

<210> SEQ ID NO 28
<211> LENGTH: 7
<212> TYPE: PRT
<213> ORGANISM: Artificial sequence
<220> FEATURE:
<223> OTHER INFORMATION: PD-1 antibody LCDR2

<400> SEQUENCE: 28

Asp Ala Ser Tyr Arg Ala Thr
1               5

-continued

```
<210> SEQ ID NO 29
<211> LENGTH: 7
<212> TYPE: PRT
<213> ORGANISM: Artificial sequence
<220> FEATURE:
<223> OTHER INFORMATION: PD-1 antibody LCDR2

<400> SEQUENCE: 29

Asp Ala Ser Ser Arg Ala Thr
1               5

<210> SEQ ID NO 30
<211> LENGTH: 7
<212> TYPE: PRT
<213> ORGANISM: Artificial sequence
<220> FEATURE:
<223> OTHER INFORMATION: PD-1 antibody LCDR2

<400> SEQUENCE: 30

Asp Ala Ser Thr Arg Ala Thr
1               5

<210> SEQ ID NO 31
<211> LENGTH: 9
<212> TYPE: PRT
<213> ORGANISM: Artificial sequence
<220> FEATURE:
<223> OTHER INFORMATION: PD-1 antibody LCDR3

<400> SEQUENCE: 31

Gln Gln Arg Ser Asn Trp Pro Leu Thr
1               5

<210> SEQ ID NO 32
<211> LENGTH: 9
<212> TYPE: PRT
<213> ORGANISM: Artificial sequence
<220> FEATURE:
<223> OTHER INFORMATION: PD-1 antibody LCDR3

<400> SEQUENCE: 32

Gln Gln Arg Asn Tyr Trp Pro Leu Thr
1               5

<210> SEQ ID NO 33
<211> LENGTH: 9
<212> TYPE: PRT
<213> ORGANISM: Artificial sequence
<220> FEATURE:
<223> OTHER INFORMATION: PD-1 antibody LCDR3

<400> SEQUENCE: 33

Gln Gln Arg Gly Asn Trp Pro Leu Thr
1               5

<210> SEQ ID NO 34
<211> LENGTH: 9
<212> TYPE: PRT
<213> ORGANISM: Artificial sequence
<220> FEATURE:
<223> OTHER INFORMATION: PD-1 antibody LCDR3

<400> SEQUENCE: 34

Gln Gln Arg Glu Tyr Trp Pro Leu Thr
1               5

<210> SEQ ID NO 35
```

```
<211> LENGTH: 9
<212> TYPE: PRT
<213> ORGANISM: Artificial sequence
<220> FEATURE:
<223> OTHER INFORMATION: PD-1 antibody LCDR3

<400> SEQUENCE: 35

Gln Gln Arg Asp Tyr Trp Pro Leu Thr
1               5

<210> SEQ ID NO 36
<211> LENGTH: 9
<212> TYPE: PRT
<213> ORGANISM: Artificial sequence
<220> FEATURE:
<223> OTHER INFORMATION: PD-1 antibody LCDR3

<400> SEQUENCE: 36

Gln Gln Arg Gly Tyr Trp Pro Leu Thr
1               5

<210> SEQ ID NO 37
<211> LENGTH: 9
<212> TYPE: PRT
<213> ORGANISM: Artificial sequence
<220> FEATURE:
<223> OTHER INFORMATION: PD-1 antibody LCDR3

<400> SEQUENCE: 37

Gln Gln Arg Trp Asn Trp Pro Leu Thr
1               5

<210> SEQ ID NO 38
<211> LENGTH: 9
<212> TYPE: PRT
<213> ORGANISM: Artificial sequence
<220> FEATURE:
<223> OTHER INFORMATION: PD-1 antibody LCDR3

<400> SEQUENCE: 38

Gln Gln Arg Ala Tyr Trp Pro Leu Thr
1               5

<210> SEQ ID NO 39
<211> LENGTH: 9
<212> TYPE: PRT
<213> ORGANISM: Artificial sequence
<220> FEATURE:
<223> OTHER INFORMATION: PD-1 antibody LCDR3

<400> SEQUENCE: 39

Gln Gln Arg Ala Glu Trp Pro Leu Thr
1               5

<210> SEQ ID NO 40
<211> LENGTH: 9
<212> TYPE: PRT
<213> ORGANISM: Artificial sequence
<220> FEATURE:
<223> OTHER INFORMATION: PD-1 antibody LCDR3

<400> SEQUENCE: 40

Gln Gln Arg Ser Ala Trp Pro Leu Thr
1               5

<210> SEQ ID NO 41
<211> LENGTH: 123
```

<212> TYPE: PRT
<213> ORGANISM: Artificial sequence
<220> FEATURE:
<223> OTHER INFORMATION: PD1H24

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Ala Tyr Asp Thr Gly Asn Leu Asp Tyr
            100                 105                 110

Trp Gly Gln Gly Thr Leu Val Thr Val Ser Ser
        115                 120

<210> SEQ ID NO 42
<211> LENGTH: 123
<212> TYPE: PRT
<213> ORGANISM: Artificial sequence
<220> FEATURE:
<223> OTHER INFORMATION: PD1H131

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Ala Tyr Asp Thr Gly Asn Leu Asp Tyr
            100                 105                 110

Trp Gly Gln Gly Thr Leu Val Thr Val Ser Ser
        115                 120

<210> SEQ ID NO 43
<211> LENGTH: 123
<212> TYPE: PRT
<213> ORGANISM: Artificial sequence
<220> FEATURE:
<223> OTHER INFORMATION: PD1H3

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr

```
                    20                  25                  30
Ala Ile Ser Trp Val Arg Gln Ala Pro Gly Gln Gly Leu Glu Trp Met
            35                  40                  45
Gly Gly Ile Ile Pro Ile Phe Gly Thr Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Pro Gly Leu Ala Ala Ala Tyr Asp Thr Gly Ser Leu Asp Tyr
            100                 105                 110
Trp Gly Gln Gly Thr Leu Val Thr Val Ser Ser
        115                 120

<210> SEQ ID NO 44
<211> LENGTH: 120
<212> TYPE: PRT
<213> ORGANISM: Artificial sequence
<220> FEATURE:
<223> OTHER INFORMATION: PD1H108

<400> SEQUENCE: 44

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Thr Leu Asp Arg Thr Gly His Leu Asp Tyr Trp Gly Gln
            100                 105                 110
Gly Thr Leu Val Thr Val Ser Ser
        115                 120

<210> SEQ ID NO 45
<211> LENGTH: 120
<212> TYPE: PRT
<213> ORGANISM: Artificial sequence
<220> FEATURE:
<223> OTHER INFORMATION: PD1H164

<400> SEQUENCE: 45

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Asp Tyr
            20                  25                  30
Val Ile Ser Trp Val Arg Gln Ala Pro Gly Gln Gly Leu Glu Trp Met
        35                  40                  45
Gly Gly Ile Ile Pro Ile Tyr Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Thr Leu Asp Arg Thr Gly His Leu Asp Tyr Trp Gly Gln
            100                 105                 110

Gly Thr Leu Val Thr Val Ser Ser
        115                 120

<210> SEQ ID NO 46
<211> LENGTH: 120
<212> TYPE: PRT
<213> ORGANISM: Artificial sequence
<220> FEATURE:
<223> OTHER INFORMATION: PD1H107

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Arg Ala Thr Gly Met Leu Asp Tyr Trp Gly Gln
            100                 105                 110

Gly Thr Leu Val Thr Val Ser Ser
        115                 120

<210> SEQ ID NO 47
<211> LENGTH: 120
<212> TYPE: PRT
<213> ORGANISM: Artificial sequence
<220> FEATURE:
<223> OTHER INFORMATION: PD1H163

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Lys Ser Tyr
            20                  25                  30

Val Ile His Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Val Arg Ala Thr Gly Met Leu Asp Tyr Trp Gly Gln
            100                 105                 110

Gly Thr Leu Val Thr Val Ser Ser
        115                 120

<210> SEQ ID NO 48
```

-continued

<211> LENGTH: 123
<212> TYPE: PRT
<213> ORGANISM: Artificial sequence
<220> FEATURE:
<223> OTHER INFORMATION: PD1H170

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Ala Tyr Asp Thr Gly Ser Leu Asp Tyr
            100                 105                 110

Trp Gly Gln Gly Thr Leu Val Thr Val Ser Ser
        115                 120

<210> SEQ ID NO 49
<211> LENGTH: 107
<212> TYPE: PRT
<213> ORGANISM: Artificial sequence
<220> FEATURE:
<223> OTHER INFORMATION: PH9L3

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 50
<211> LENGTH: 107
<212> TYPE: PRT
<213> ORGANISM: Artificial sequence
<220> FEATURE:
<223> OTHER INFORMATION: PD1L128

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Asn Tyr
            20                  25                  30

-continued

```
Leu Ala Trp Tyr Gln Gln Lys Pro Gly Gln Ala Pro Arg Leu Leu Ile
         35                  40                  45

His Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Tyr Trp Pro Leu
                 85                  90                  95

Thr Phe Gly Gln Gly Thr Lys Val Glu Ile Lys
                100                 105

<210> SEQ ID NO 51
<211> LENGTH: 107
<212> TYPE: PRT
<213> ORGANISM: Artificial sequence
<220> FEATURE:
<223> OTHER INFORMATION: PD1L101

<400> SEQUENCE: 51

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asp Ser Tyr
                 20                  25                  30

Leu Ala Trp Tyr Gln Gln Lys Pro Gly Gln Ala Pro Arg Leu Leu Ile
         35                  40                  45

Lys Asp Ala Ser Asp Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Gly Asn Trp Pro Leu
                 85                  90                  95

Thr Phe Gly Gln Gly Thr Lys Val Glu Ile Lys
                100                 105

<210> SEQ ID NO 52
<211> LENGTH: 107
<212> TYPE: PRT
<213> ORGANISM: Artificial sequence
<220> FEATURE:
<223> OTHER INFORMATION: PD1L67

<400> SEQUENCE: 52

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asp Ser Tyr
                 20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Glu Tyr Trp Pro Leu
                 85                  90                  95

Thr Phe Gly Gln Gly Thr Lys Val Glu Ile Lys
                100                 105

<210> SEQ ID NO 53
```

```
<211> LENGTH: 107
<212> TYPE: PRT
<213> ORGANISM: Artificial sequence
<220> FEATURE:
<223> OTHER INFORMATION: PD1L71

<400> SEQUENCE: 53

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Tyr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asp Tyr Trp Pro Leu
                85                  90                  95

Thr Phe Gly Gln Gly Thr Lys Val Glu Ile Lys
            100                 105

<210> SEQ ID NO 54
<211> LENGTH: 107
<212> TYPE: PRT
<213> ORGANISM: Artificial sequence
<220> FEATURE:
<223> OTHER INFORMATION: PD1L109

<400> SEQUENCE: 54

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Lys Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Gly Tyr Trp Pro Leu
                85                  90                  95

Thr Phe Gly Gln Gly Thr Lys Val Glu Ile Lys
            100                 105

<210> SEQ ID NO 55
<211> LENGTH: 107
<212> TYPE: PRT
<213> ORGANISM: Artificial sequence
<220> FEATURE:
<223> OTHER INFORMATION: PD1L132

<400> SEQUENCE: 55

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Asn Tyr
            20                  25                  30

Leu Ala Trp Tyr Gln Gln Lys Pro Gly Gln Ala Pro Arg Leu Leu Ile
        35                  40                  45
```

```
Tyr Asp Ala Ser Asp Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Trp Asn Trp Pro Leu
                 85                  90                  95

Thr Phe Gly Gln Gly Thr Lys Val Glu Ile Lys
            100                 105
```

<210> SEQ ID NO 56
<211> LENGTH: 107
<212> TYPE: PRT
<213> ORGANISM: Artificial sequence
<220> FEATURE:
<223> OTHER INFORMATION: PD1L148

<400> SEQUENCE: 56

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Arg Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Tyr Trp Pro Leu
                 85                  90                  95

Thr Phe Gly Gln Gly Thr Lys Val Glu Ile Lys
            100                 105
```

<210> SEQ ID NO 57
<211> LENGTH: 107
<212> TYPE: PRT
<213> ORGANISM: Artificial sequence
<220> FEATURE:
<223> OTHER INFORMATION: PD1L133

<400> SEQUENCE: 57

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asp Ser Tyr
                 20                  25                  30

Leu Ala Trp Tyr Gln Gln Lys Pro Gly Gln Ala Pro Arg Leu Leu Ile
             35                  40                  45

His Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Tyr Trp Pro Leu
                 85                  90                  95

Thr Phe Gly Gln Gly Thr Lys Val Glu Ile Lys
            100                 105
```

<210> SEQ ID NO 58
<211> LENGTH: 107
<212> TYPE: PRT
<213> ORGANISM: Artificial sequence

<220> FEATURE:
<223> OTHER INFORMATION: PD1L185

<400> SEQUENCE: 58

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Tyr Trp Pro Leu
                85                  90                  95

Thr Phe Gly Gln Gly Thr Lys Val Glu Ile Lys
            100                 105

<210> SEQ ID NO 59
<211> LENGTH: 107
<212> TYPE: PRT
<213> ORGANISM: Artificial sequence
<220> FEATURE:
<223> OTHER INFORMATION: PD1L187

<400> SEQUENCE: 59

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Glu Asp Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Glu Trp Pro Leu
                85                  90                  95

Thr Phe Gly Gln Gly Thr Lys Val Glu Ile Lys
            100                 105

<210> SEQ ID NO 60
<211> LENGTH: 107
<212> TYPE: PRT
<213> ORGANISM: Artificial sequence
<220> FEATURE:
<223> OTHER INFORMATION: PD1L86

<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

His Asp Ala Ser Thr Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Tyr Trp Pro Leu
                 85                  90                  95

Thr Phe Gly Gln Gly Thr Lys Val Glu Ile Lys
            100                 105
```

<210> SEQ ID NO 61
<211> LENGTH: 107
<212> TYPE: PRT
<213> ORGANISM: Artificial sequence
<220> FEATURE:
<223> OTHER INFORMATION: PD1L168

<400> SEQUENCE: 61

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asp Asn Tyr
                20                  25                  30

Leu Ala Trp Tyr Gln Gln Lys Pro Gly Gln Ala Pro Arg Leu Leu Ile
             35                  40                  45

His Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Ala Trp Pro Leu
                 85                  90                  95

Thr Phe Gly Gln Gly Thr Lys Val Glu Ile Lys
            100                 105
```

<210> SEQ ID NO 62
<211> LENGTH: 107
<212> TYPE: PRT
<213> ORGANISM: Artificial sequence
<220> FEATURE:
<223> OTHER INFORMATION: PD1L190

<400> SEQUENCE: 62

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Asn Tyr
                20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Tyr Trp Pro Leu
                 85                  90                  95

Thr Phe Gly Gln Gly Thr Lys Val Glu Ile Lys
            100                 105
```

<210> SEQ ID NO 63
<211> LENGTH: 117
<212> TYPE: PRT
<213> ORGANISM: Artificial sequence
<220> FEATURE:
<223> OTHER INFORMATION: PD1H130

-continued

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Arg Tyr
            20                  25                  30

Asp Met Ser Trp Ile Arg Leu Ala Pro Gly Lys Gly Leu Glu Ser Val
        35                  40                  45

Ala Tyr Ile Ser Gly Gly Gly Ala Asn Thr Tyr Tyr Leu Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Leu Ser Tyr Phe Asp Val Trp Gly Gln Gly Thr Leu
            100                 105                 110

Val Thr Val Ser Ser
        115

<210> SEQ ID NO 64
<211> LENGTH: 117
<212> TYPE: PRT
<213> ORGANISM: Artificial sequence
<220> FEATURE:
<223> OTHER INFORMATION: PD1H129

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Arg Tyr
            20                  25                  30

Asp Met Ser Trp Val Arg Gln Ala Pro Gly Lys Gly Leu Glu Ser Val
        35                  40                  45

Ala Tyr Ile Ser Gly Gly Gly Ala Asn Thr Tyr Tyr Leu Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Leu Ser Tyr Phe Asp Val Trp Gly Gln Gly Thr Leu
            100                 105                 110

Val Thr Val Ser Ser
        115

<210> SEQ ID NO 65
<211> LENGTH: 107
<212> TYPE: PRT
<213> ORGANISM: Artificial sequence
<220> FEATURE:
<223> OTHER INFORMATION: PD1L62

<400> SEQUENCE: 65

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Leu Ser Asp Tyr
            20                  25                  30

Leu His Trp Tyr Gln Gln Lys Pro Gly Gln Ala Pro Arg Leu Leu Ile
        35                  40                  45

```
Lys Ser Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Asn Gly His Ser Phe Pro Tyr
                85                  90                  95

Thr Phe Gly Gln Gly Thr Lys Leu Glu Ile Lys
                100                 105
```

<210> SEQ ID NO 66
<211> LENGTH: 5
<212> TYPE: PRT
<213> ORGANISM: Artificial sequence
<220> FEATURE:
<223> OTHER INFORMATION: PD1 antibody HCDR1

<400> SEQUENCE: 66

```
Arg Tyr Asp Met Ser
1               5
```

<210> SEQ ID NO 67
<211> LENGTH: 17
<212> TYPE: PRT
<213> ORGANISM: Artificial sequence
<220> FEATURE:
<223> OTHER INFORMATION: PD1 antibody HCDR2

<400> SEQUENCE: 67

```
Tyr Ile Ser Gly Gly Gly Ala Asn Thr Tyr Tyr Leu Asp Asn Val Lys
1               5                   10                  15

Gly
```

<210> SEQ ID NO 68
<211> LENGTH: 8
<212> TYPE: PRT
<213> ORGANISM: Artificial sequence
<220> FEATURE:
<223> OTHER INFORMATION: PD1 antibody HCDR3

<400> SEQUENCE: 68

```
Pro Tyr Leu Ser Tyr Phe Asp Val
1               5
```

<210> SEQ ID NO 69
<211> LENGTH: 11
<212> TYPE: PRT
<213> ORGANISM: Artificial sequence
<220> FEATURE:
<223> OTHER INFORMATION: PD1 antibody LCDR1

<400> SEQUENCE: 69

```
Arg Ala Ser Gln Ser Leu Ser Asp Tyr Leu His
1               5                   10
```

<210> SEQ ID NO 70
<211> LENGTH: 7
<212> TYPE: PRT
<213> ORGANISM: Artificial sequence
<220> FEATURE:
<223> OTHER INFORMATION: PD1 antibody LCDR2

<400> SEQUENCE: 70

```
Ser Ala Ser Gln Ser Ile Ser
1               5
```

<210> SEQ ID NO 71
<211> LENGTH: 9
<212> TYPE: PRT
<213> ORGANISM: Artificial sequence
<220> FEATURE:
<223> OTHER INFORMATION: PD1 antibody LCDR3

<400> SEQUENCE: 71

Gln Asn Gly His Ser Phe Pro Tyr Thr
1               5

<210> SEQ ID NO 72
<211> LENGTH: 450
<212> TYPE: PRT
<213> ORGANISM: Artificial sequence
<220> FEATURE:
<223> OTHER INFORMATION: PD1B244 HC

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Ala Tyr Asp Thr Gly Ser Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

```
Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
                435                 440                 445

Gly Lys
    450

<210> SEQ ID NO 73
<211> LENGTH: 214
<212> TYPE: PRT
<213> ORGANISM: Artificial sequence
<220> FEATURE:
<223> OTHER INFORMATION: PD1B244 LC

<400> SEQUENCE: 73

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Tyr Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 74
<211> LENGTH: 444
<212> TYPE: PRT
<213> ORGANISM: Artificial sequence
<220> FEATURE:
<223> OTHER INFORMATION: PD1B243 HC

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Arg Tyr
            20                  25                  30

Asp Met Ser Trp Val Arg Gln Ala Pro Gly Lys Gly Leu Glu Ser Val
        35                  40                  45

Ala Tyr Ile Ser Gly Gly Gly Ala Asn Thr Tyr Tyr Leu Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Leu Ser Tyr Phe Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

```
Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 75
<211> LENGTH: 214
<212> TYPE: PRT
<213> ORGANISM: Artificial sequence
<220> FEATURE:
<223> OTHER INFORMATION: PD1B243 LC

<400> SEQUENCE: 75

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Leu Ser Asp Tyr
            20                  25                  30

Leu His Trp Tyr Gln Gln Lys Pro Gly Gln Ala Pro Arg Leu Leu Ile
        35                  40                  45

Lys Ser Ala Ser Gln Ser Ile Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Asn Gly His Ser Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 76
<211> LENGTH: 447
<212> TYPE: PRT
<213> ORGANISM: Artificial sequence
<220> FEATURE:
<223> OTHER INFORMATION: PD1B245 HC
```

<400> SEQUENCE: 76

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Asp Tyr
            20                  25                  30
Val Ile Ser Trp Val Arg Gln Ala Pro Gly Gln Gly Leu Glu Trp Met
        35                  40                  45
Gly Gly Ile Ile Pro Ile Tyr Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Thr Leu Asp Arg Thr Gly His Leu Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
```

```
Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 77
<211> LENGTH: 214
<212> TYPE: PRT
<213> ORGANISM: Artificial sequence
<220> FEATURE:
<223> OTHER INFORMATION: PD1B245 LC

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

His Asp Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Tyr Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 78
<211> LENGTH: 443
<212> TYPE: PRT
<213> ORGANISM: Artificial sequence
<220> FEATURE:
<223> OTHER INFORMATION: TIM3 antibody heavy chain

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Tyr Ala Pro Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Ala Ala Ala Ser Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Ala Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 79
<211> LENGTH: 214
<212> TYPE: PRT
<213> ORGANISM: Artificial sequence

```
<220> FEATURE:
<223> OTHER INFORMATION: TIM-3 antibody light chain

<400> SEQUENCE: 79

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Asp Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Gly His Ala Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 80
<211> LENGTH: 450
<212> TYPE: PRT
<213> ORGANISM: Artificial sequence
<220> FEATURE:
<223> OTHER INFORMATION: TIM-3 antibody heavy chain

<400> SEQUENCE: 80

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Gln Trp Val Arg Gln Met Pro Gly Lys Gly Leu Glu Trp Met
        35                  40                  45

Gly Ala Ile Tyr Pro Gly Asp Gly Asp Ile Arg Tyr Thr Gln Asn Phe
50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Glu Lys Ser Thr Thr Val Val Gln Arg Asn Tyr Phe Asp
            100                 105                 110

Tyr Trp Gly Gln Gly Thr Thr Val Thr Val Ser Ser Ala Ser Thr Lys
```

```
              115                 120                 125
Gly Pro Ser Val Phe Pro Leu Ala Pro Cys Ser Arg Ser Thr Ser Glu
        130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Ala Ala Ala
225                 230                 235                 240

Ser Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Ala Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 81
<211> LENGTH: 213
<212> TYPE: PRT
<213> ORGANISM: Artificial sequence
<220> FEATURE:
<223> OTHER INFORMATION: TIM-3 antibody light chain

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Gly Thr Phe
```

```
                20                  25                  30
Val Ser Trp Tyr Gln Gln Lys Pro Gly Lys Ala Pro Lys Leu Leu Ile
            35                  40                  45
Tyr Gly Ala Ser Asn Arg Tyr Thr Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gly Gln Ser Tyr Ser Tyr Pro Thr
                85                  90                  95
Phe Gly Gln Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
            115                 120                 125
Ala Ser Val Val Cys Leu Leu Asn Asn Phe Tyr Pro Arg Glu Ala Lys
        130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
            195                 200                 205
Asn Arg Gly Glu Cys
    210

<210> SEQ ID NO 82
<211> LENGTH: 5
<212> TYPE: PRT
<213> ORGANISM: Artificial sequence
<220> FEATURE:
<223> OTHER INFORMATION: PD-1 HCDR1 genus
<220> FEATURE:
<221> NAME/KEY: 1MISC_FEATURE
<222> LOCATION: (1)..(1)
<223> OTHER INFORMATION: Xaa may be Ser or Asp
<220> FEATURE:
<221> NAME/KEY: 1MISC_FEATURE
<222> LOCATION: (3)..(3)
<223> OTHER INFORMATION: Xaa may be Val or Ala
<220> FEATURE:
<221> NAME/KEY: 1MISC_FEATURE
<222> LOCATION: (5)..(5)
<223> OTHER INFORMATION: Xaa may be His or Ser

<400> SEQUENCE: 82

Xaa Tyr Xaa Ile Xaa
 1               5

<210> SEQ ID NO 83
<211> LENGTH: 17
<212> TYPE: PRT
<213> ORGANISM: Artificial sequence
<220> FEATURE:
<223> OTHER INFORMATION: PD-1 HCDR2 genus
<220> FEATURE:
<221> NAME/KEY: MISC_FEATURE
<222> LOCATION: (6)..(6)
<223> OTHER INFORMATION: Xaa may be Tyr or Phe
<220> FEATURE:
<221> NAME/KEY: MISC_FEATURE
<222> LOCATION: (7)..(7)
<223> OTHER INFORMATION: Xaa may be Gly or Asp
```

```
<400> SEQUENCE: 83

Gly Ile Ile Pro Ile Xaa Xaa Thr Ala Asn Tyr Ala Gln Lys Phe Gln
1               5                   10                  15

Gly

<210> SEQ ID NO 84
<211> LENGTH: 14
<212> TYPE: PRT
<213> ORGANISM: Artificial sequence
<220> FEATURE:
<223> OTHER INFORMATION: PD-1 HCDR3 genus 1
<220> FEATURE:
<221> NAME/KEY: MISC_FEATURE
<222> LOCATION: (11)..(11)
<223> OTHER INFORMATION: Xaa is Asn or Ser

<400> SEQUENCE: 84

Pro Gly Leu Ala Ala Ala Tyr Asp Thr Gly Xaa Leu Asp Tyr
1               5                   10

<210> SEQ ID NO 85
<211> LENGTH: 11
<212> TYPE: PRT
<213> ORGANISM: Artificial sequence
<220> FEATURE:
<223> OTHER INFORMATION: PD-1 HCDR3 genus 2
<220> FEATURE:
<221> NAME/KEY: MISC_FEATURE
<222> LOCATION: (2)..(2)
<223> OTHER INFORMATION: Xaa is Thr or Tyr
<220> FEATURE:
<221> NAME/KEY: MISC_FEATURE
<222> LOCATION: (3)..(3)
<223> OTHER INFORMATION: Xaa is Leu or Val
<220> FEATURE:
<221> NAME/KEY: MISC_FEATURE
<222> LOCATION: (4)..(4)
<223> OTHER INFORMATION: Xaa is Asp or Arg
<220> FEATURE:
<221> NAME/KEY: MISC_FEATURE
<222> LOCATION: (5)..(5)
<223> OTHER INFORMATION: Xaa is Arg or Ala
<220> FEATURE:
<221> NAME/KEY: MISC_FEATURE
<222> LOCATION: (8)..(8)
<223> OTHER INFORMATION: Xaa is His or Met

<400> SEQUENCE: 85

Gly Xaa Xaa Xaa Xaa Thr Gly Xaa Leu Asp Tyr
1               5                   10

<210> SEQ ID NO 86
<211> LENGTH: 11
<212> TYPE: PRT
<213> ORGANISM: Artificial sequence
<220> FEATURE:
<223> OTHER INFORMATION: PD-1 LCDR1 genus
<220> FEATURE:
<221> NAME/KEY: MISC_FEATURE
<222> LOCATION: (7)..(7)
<223> OTHER INFORMATION: Xaa is Ser, Arg or Asp
<220> FEATURE:
<221> NAME/KEY: MISC_FEATURE
<222> LOCATION: (8)..(8)
<223> OTHER INFORMATION: Xaa is Ser or Asn

<400> SEQUENCE: 86

Arg Ala Ser Gln Ser Val Xaa Xaa Tyr Leu Ala
1               5                   10
```

```
<210> SEQ ID NO 87
<211> LENGTH: 7
<212> TYPE: PRT
<213> ORGANISM: Artificial sequence
<220> FEATURE:
<223> OTHER INFORMATION: PD-1 LCDR2 genus
<220> FEATURE:
<221> NAME/KEY: MISC_FEATURE
<222> LOCATION: (4)..(4)
<223> OTHER INFORMATION: Xaa is Asn, Asp, Tyr, Ser or Thr

<400> SEQUENCE: 87

Asp Ala Ser Xaa Arg Ala Thr
1               5

<210> SEQ ID NO 88
<211> LENGTH: 9
<212> TYPE: PRT
<213> ORGANISM: Artificial sequence
<220> FEATURE:
<223> OTHER INFORMATION: PD-1 LCDR3 genus
<220> FEATURE:
<221> NAME/KEY: MISC_FEATURE
<222> LOCATION: (4)..(4)
<223> OTHER INFORMATION: Xaa is Ser, Asn, Gly, Glu, Asp, Trp or Ala
<220> FEATURE:
<221> NAME/KEY: MISC_FEATURE
<222> LOCATION: (5)..(5)
<223> OTHER INFORMATION: Xaa is Asn, Tyr, Glu or Ala

<400> SEQUENCE: 88

Gln Gln Arg Xaa Xaa Trp Pro Leu Thr
1               5

<210> SEQ ID NO 89
<211> LENGTH: 179
<212> TYPE: PRT
<213> ORGANISM: Homo sapiens

<400> SEQUENCE: 89

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg
```

```
<210> SEQ ID NO 90
<211> LENGTH: 5
<212> TYPE: PRT
<213> ORGANISM: Artificial sequence
<220> FEATURE:
<223> OTHER INFORMATION: TIM-3 antibody HCDR1

<400> SEQUENCE: 90

Asn Tyr Trp Met Ser
1               5

<210> SEQ ID NO 91
<211> LENGTH: 5
<212> TYPE: PRT
<213> ORGANISM: Artificial sequence
<220> FEATURE:
<223> OTHER INFORMATION: TIM-3 antibody HCDR1

<400> SEQUENCE: 91

Ser Tyr Ala Met Ser
1               5

<210> SEQ ID NO 92
<211> LENGTH: 5
<212> TYPE: PRT
<213> ORGANISM: Artificial sequence
<220> FEATURE:
<223> OTHER INFORMATION: TIM-3 antibody HCDR1

<400> SEQUENCE: 92

Gly Tyr Trp Met His
1               5

<210> SEQ ID NO 93
<211> LENGTH: 5
<212> TYPE: PRT
<213> ORGANISM: Artificial sequence
<220> FEATURE:
<223> OTHER INFORMATION: TIM-3 antibody HCDR1

<400> SEQUENCE: 93

Asp Tyr Trp Met Ser
1               5

<210> SEQ ID NO 94
<211> LENGTH: 5
<212> TYPE: PRT
<213> ORGANISM: Artificial sequence
<220> FEATURE:
<223> OTHER INFORMATION: TIM-3 antibody HCDR1

<400> SEQUENCE: 94

Ser Tyr Val Met Tyr
1               5

<210> SEQ ID NO 95
<211> LENGTH: 6
<212> TYPE: PRT
<213> ORGANISM: Artificial sequence
<220> FEATURE:
<223> OTHER INFORMATION: TIM-3 antibody HCDR1

<400> SEQUENCE: 95

Ser Asp Tyr Ala Trp Asn
1               5
```

<210> SEQ ID NO 96
<211> LENGTH: 5
<212> TYPE: PRT
<213> ORGANISM: Artificial sequence
<220> FEATURE:
<223> OTHER INFORMATION: TIM-3 antibody HCDR1

<400> SEQUENCE: 96

Asp Thr Tyr Leu His
1               5

<210> SEQ ID NO 97
<211> LENGTH: 5
<212> TYPE: PRT
<213> ORGANISM: Artificial sequence
<220> FEATURE:
<223> OTHER INFORMATION: TIM-3 antibody HCDR1

<400> SEQUENCE: 97

Ser Tyr Trp Met Gln
1               5

<210> SEQ ID NO 98
<211> LENGTH: 5
<212> TYPE: PRT
<213> ORGANISM: Artificial sequence
<220> FEATURE:
<223> OTHER INFORMATION: TIM-3 antibody HCDR1

<400> SEQUENCE: 98

Ser Tyr Gly Val His
1               5

<210> SEQ ID NO 99
<211> LENGTH: 17
<212> TYPE: PRT
<213> ORGANISM: Artificial sequence
<220> FEATURE:
<223> OTHER INFORMATION: TIM-3 antibody HCDR2

<400> SEQUENCE: 99

Ala Ile Ser Gly Ser Gly Gly Ser Thr Tyr Tyr Ala Asp Ser Val Lys
1               5                   10                  15

Gly

<210> SEQ ID NO 100
<211> LENGTH: 17
<212> TYPE: PRT
<213> ORGANISM: Artificial sequence
<220> FEATURE:
<223> OTHER INFORMATION: TIM-3 antibody HCDR2

<400> SEQUENCE: 100

Ala Ile Ser Tyr Ser Gly Ser Ser Thr Tyr Tyr Ala Asp Ser Val Lys
1               5                   10                  15

Gly

<210> SEQ ID NO 101
<211> LENGTH: 17
<212> TYPE: PRT
<213> ORGANISM: Artificial sequence
<220> FEATURE:
<223> OTHER INFORMATION: TIM-3 antibody HCDR2

<400> SEQUENCE: 101

```
Val Ile Lys Tyr Ser Gly Gly Ser Lys Tyr Tyr Ala Asp Ser Val Lys
1               5                   10                  15

Gly

<210> SEQ ID NO 102
<211> LENGTH: 17
<212> TYPE: PRT
<213> ORGANISM: Artificial sequence
<220> FEATURE:
<223> OTHER INFORMATION: TIM-3 antibody HCDR2

<400> SEQUENCE: 102

Tyr Ile Asn Pro Tyr Asn Asp Gly Thr Lys Tyr Asn Glu Lys Phe Lys
1               5                   10                  15

Gly

<210> SEQ ID NO 103
<211> LENGTH: 16
<212> TYPE: PRT
<213> ORGANISM: Artificial sequence
<220> FEATURE:
<223> OTHER INFORMATION: TIM-3 antibody HCDR2

<400> SEQUENCE: 103

Tyr Ile Asn Tyr Ser Gly Arg Thr Ser Tyr Asn Pro Ser Leu Lys Ser
1               5                   10                  15

<210> SEQ ID NO 104
<211> LENGTH: 17
<212> TYPE: PRT
<213> ORGANISM: Artificial sequence
<220> FEATURE:
<223> OTHER INFORMATION: TIM-3 antibody HCDR2

<400> SEQUENCE: 104

Arg Ile Asp Pro Thr Asn Gly Asn Ile Lys Tyr Asp Pro Lys Phe Gln
1               5                   10                  15

Gly

<210> SEQ ID NO 105
<211> LENGTH: 17
<212> TYPE: PRT
<213> ORGANISM: Artificial sequence
<220> FEATURE:
<223> OTHER INFORMATION: TIM-3 antibody HCDR2

<400> SEQUENCE: 105

Ala Ile Tyr Pro Gly Asp Gly Asp Ile Arg Tyr Thr Gln Asn Phe Lys
1               5                   10                  15

Gly

<210> SEQ ID NO 106
<211> LENGTH: 16
<212> TYPE: PRT
<213> ORGANISM: Artificial sequence
<220> FEATURE:
<223> OTHER INFORMATION: TIM-3 antibody HCDR2

<400> SEQUENCE: 106

Val Ile Trp Ser Asp Gly Ser Thr Thr Tyr Asn Ser Ala Leu Lys Ser
1               5                   10                  15

<210> SEQ ID NO 107
<211> LENGTH: 10
```

```
<212> TYPE: PRT
<213> ORGANISM: Artificial sequence
<220> FEATURE:
<223> OTHER INFORMATION: TIM-3 antibody HCDR2

<400> SEQUENCE: 107

Asp His Trp Asp Pro Asn Phe Leu Asp Tyr
1               5                   10

<210> SEQ ID NO 108
<211> LENGTH: 8
<212> TYPE: PRT
<213> ORGANISM: Artificial sequence
<220> FEATURE:
<223> OTHER INFORMATION: TIM-3 antibody HCDR3

<400> SEQUENCE: 108

Ser Pro Tyr Ala Pro Leu Asp Tyr
1               5

<210> SEQ ID NO 109
<211> LENGTH: 10
<212> TYPE: PRT
<213> ORGANISM: Artificial sequence
<220> FEATURE:
<223> OTHER INFORMATION: TIM-3 antibody HCDR3

<400> SEQUENCE: 109

Asn Glu Glu Pro Asp Asp Arg Leu Asp Tyr
1               5                   10

<210> SEQ ID NO 110
<211> LENGTH: 7
<212> TYPE: PRT
<213> ORGANISM: Artificial sequence
<220> FEATURE:
<223> OTHER INFORMATION: TIM-3 antibody HCDR3

<400> SEQUENCE: 110

Gly Thr Asn Trp Leu Asp Tyr
1               5

<210> SEQ ID NO 111
<211> LENGTH: 8
<212> TYPE: PRT
<213> ORGANISM: Artificial sequence
<220> FEATURE:
<223> OTHER INFORMATION: TIM-3 antibody HCDR3

<400> SEQUENCE: 111

Glu Leu Glu Gly Val Phe Asp Tyr
1               5

<210> SEQ ID NO 112
<211> LENGTH: 10
<212> TYPE: PRT
<213> ORGANISM: Artificial sequence
<220> FEATURE:
<223> OTHER INFORMATION: TIM-3 antibody HCDR3

<400> SEQUENCE: 112

Asp Asp Tyr Asp Val Ala Pro Phe Ala Tyr
1               5                   10

<210> SEQ ID NO 113
<211> LENGTH: 6
<212> TYPE: PRT
```

```
<213> ORGANISM: Artificial sequence
<220> FEATURE:
<223> OTHER INFORMATION: TIM-3 antibody HCDR3

<400> SEQUENCE: 113

Gly Gly Asn Phe Asp Tyr
1               5

<210> SEQ ID NO 114
<211> LENGTH: 8
<212> TYPE: PRT
<213> ORGANISM: Artificial sequence
<220> FEATURE:
<223> OTHER INFORMATION: TIM-3 antibody HCDR3

<400> SEQUENCE: 114

Pro Tyr Tyr Gly Phe Phe Asp Tyr
1               5

<210> SEQ ID NO 115
<211> LENGTH: 15
<212> TYPE: PRT
<213> ORGANISM: Artificial sequence
<220> FEATURE:
<223> OTHER INFORMATION: TIM-3 antibody HCDR3

<400> SEQUENCE: 115

Trp Glu Lys Ser Thr Thr Val Val Gln Arg Asn Tyr Phe Asp Tyr
1               5                   10                  15

<210> SEQ ID NO 116
<211> LENGTH: 12
<212> TYPE: PRT
<213> ORGANISM: Artificial sequence
<220> FEATURE:
<223> OTHER INFORMATION: TIM-3 antibody HCDR3

<400> SEQUENCE: 116

Gln Ala Asn Tyr Arg Tyr Asp Ser Ala Met Asp Tyr
1               5                   10

<210> SEQ ID NO 117
<211> LENGTH: 12
<212> TYPE: PRT
<213> ORGANISM: Artificial sequence
<220> FEATURE:
<223> OTHER INFORMATION: TIM-3 antibody LCDR1

<400> SEQUENCE: 117

Arg Ala Ser Gln Ser Val Ser Ser Ser Tyr Leu Ala
1               5                   10

<210> SEQ ID NO 118
<211> LENGTH: 11
<212> TYPE: PRT
<213> ORGANISM: Artificial sequence
<220> FEATURE:
<223> OTHER INFORMATION: TIM-3 antibody LCDR1

<400> SEQUENCE: 118

Arg Ala Ser Gln Ser Val Asn Asp Tyr Leu Ala
1               5                   10

<210> SEQ ID NO 119
<211> LENGTH: 17
<212> TYPE: PRT
<213> ORGANISM: Artificial sequence
```

```
<220> FEATURE:
<223> OTHER INFORMATION: TIM-3 antibody LCDR1

<400> SEQUENCE: 119

Lys Ser Ser Gln Ser Val Leu Ala Ser Ser Asn Asn Lys Asn Tyr Leu
1               5                   10                  15

Ala

<210> SEQ ID NO 120
<211> LENGTH: 12
<212> TYPE: PRT
<213> ORGANISM: Artificial sequence
<220> FEATURE:
<223> OTHER INFORMATION: TIM-3 antibody LCDR1

<400> SEQUENCE: 120

Arg Ala Ser Gln Ser Val Ser Asn Ser Thr Leu Ala
1               5                   10

<210> SEQ ID NO 121
<211> LENGTH: 15
<212> TYPE: PRT
<213> ORGANISM: Artificial sequence
<220> FEATURE:
<223> OTHER INFORMATION: TIM-3 antibody LCDR1

<400> SEQUENCE: 121

Arg Ala Ser Glu Ser Leu Asp Ser Tyr Gly Asn Ser Tyr Ile His
1               5                   10                  15

<210> SEQ ID NO 122
<211> LENGTH: 11
<212> TYPE: PRT
<213> ORGANISM: Artificial sequence
<220> FEATURE:
<223> OTHER INFORMATION: TIM-3 antibody LCDR1

<400> SEQUENCE: 122

Gln Ala Thr Gln Asp Ile Val Lys Asn Leu Asn
1               5                   10

<210> SEQ ID NO 123
<211> LENGTH: 11
<212> TYPE: PRT
<213> ORGANISM: Artificial sequence
<220> FEATURE:
<223> OTHER INFORMATION: TIM-3 antibody LCDR1

<400> SEQUENCE: 123

Lys Ala Ser Gln Asp Val Asn Thr Ala Val Ala
1               5                   10

<210> SEQ ID NO 124
<211> LENGTH: 11
<212> TYPE: PRT
<213> ORGANISM: Artificial sequence
<220> FEATURE:
<223> OTHER INFORMATION: TIM-3 antibody LCDR1

<400> SEQUENCE: 124

Lys Ala Ser Glu Asn Val Gly Thr Phe Val Ser
1               5                   10

<210> SEQ ID NO 125
<211> LENGTH: 15
<212> TYPE: PRT
```

```
<213> ORGANISM: Artificial sequence
<220> FEATURE:
<223> OTHER INFORMATION: TIM-3 antibody LCDR1

<400> SEQUENCE: 125

Lys Ala Ser Gln Ser Val Asp Tyr Asp Gly Asp Ser Tyr Met Asn
1               5                   10                  15

<210> SEQ ID NO 126
<211> LENGTH: 7
<212> TYPE: PRT
<213> ORGANISM: Artificial sequence
<220> FEATURE:
<223> OTHER INFORMATION: TIM-3 antibody LCDR2

<400> SEQUENCE: 126

Gly Ala Ser Ser Arg Ala Thr
1               5

<210> SEQ ID NO 127
<211> LENGTH: 7
<212> TYPE: PRT
<213> ORGANISM: Artificial sequence
<220> FEATURE:
<223> OTHER INFORMATION: TIM-3 antibody LCDR2

<400> SEQUENCE: 127

Asp Ala Ser Asn Arg Ala Thr
1               5

<210> SEQ ID NO 128
<211> LENGTH: 7
<212> TYPE: PRT
<213> ORGANISM: Artificial sequence
<220> FEATURE:
<223> OTHER INFORMATION: TIM-3 antibody LCDR2

<400> SEQUENCE: 128

Trp Ala Ser Thr Arg Glu Ser
1               5

<210> SEQ ID NO 129
<211> LENGTH: 7
<212> TYPE: PRT
<213> ORGANISM: Artificial sequence
<220> FEATURE:
<223> OTHER INFORMATION: TIM-3 antibody LCDR2

<400> SEQUENCE: 129

Thr Ala Ser Ser Arg Ala Thr
1               5

<210> SEQ ID NO 130
<211> LENGTH: 7
<212> TYPE: PRT
<213> ORGANISM: Artificial sequence
<220> FEATURE:
<223> OTHER INFORMATION: TIM-3 antibody LCDR2

<400> SEQUENCE: 130

Leu Ala Ser Asn Leu Glu Ser
1               5

<210> SEQ ID NO 131
<211> LENGTH: 7
<212> TYPE: PRT
<213> ORGANISM: Artificial sequence
```

```
<220> FEATURE:
<223> OTHER INFORMATION: TIM-3 antibody LCDR2

<400> SEQUENCE: 131

Tyr Val Thr Glu Leu Ala Glu
1               5

<210> SEQ ID NO 132
<211> LENGTH: 7
<212> TYPE: PRT
<213> ORGANISM: Artificial sequence
<220> FEATURE:
<223> OTHER INFORMATION: TIM-3 antibody LCDR2

<400> SEQUENCE: 132

Ser Ala Thr Tyr Arg Tyr Thr
1               5

<210> SEQ ID NO 133
<211> LENGTH: 7
<212> TYPE: PRT
<213> ORGANISM: Artificial sequence
<220> FEATURE:
<223> OTHER INFORMATION: TIM-3 antibody LCDR2

<400> SEQUENCE: 133

Gly Ala Ser Asn Arg Tyr Thr
1               5

<210> SEQ ID NO 134
<211> LENGTH: 7
<212> TYPE: PRT
<213> ORGANISM: Artificial sequence
<220> FEATURE:
<223> OTHER INFORMATION: TIM-3 antibody LCDR2

<400> SEQUENCE: 134

Thr Ala Ala Asn Leu Gln Ser
1               5

<210> SEQ ID NO 135
<211> LENGTH: 9
<212> TYPE: PRT
<213> ORGANISM: Artificial sequence
<220> FEATURE:
<223> OTHER INFORMATION: TIM-3 antibody LCDR3

<400> SEQUENCE: 135

Gln Gln Tyr Gly Ser Ser Pro Leu Thr
1               5

<210> SEQ ID NO 136
<211> LENGTH: 9
<212> TYPE: PRT
<213> ORGANISM: Artificial sequence
<220> FEATURE:
<223> OTHER INFORMATION: TIM-3 antibody LCDR3

<400> SEQUENCE: 136

Gln Gln Gly Gly His Ala Pro Ile Thr
1               5

<210> SEQ ID NO 137
<211> LENGTH: 9
<212> TYPE: PRT
<213> ORGANISM: Artificial sequence
<220> FEATURE:
```

<223> OTHER INFORMATION: TIM-3 antibody LCDR3

<400> SEQUENCE: 137

Gln Gln Tyr Tyr Ser Thr Pro Leu Thr
1               5

<210> SEQ ID NO 138
<211> LENGTH: 280
<212> TYPE: PRT
<213> ORGANISM: Homo sapiens

<400> SEQUENCE: 138

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
                20                  25                  30

Gly Lys Gly Ala Cys Pro Val Phe Glu Cys Gly Asn Val Val Leu Arg
            35                  40                  45

Thr Asp Glu Arg Asp Val Asn Tyr Trp Thr Ser Arg Tyr Trp Leu Asn
        50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
                100                 105                 110

Val Thr Pro Ala Pro Thr Arg Gln Arg Asp Phe Thr Ala Ala Phe Pro
            115                 120                 125

Arg Met Leu Thr Thr Arg Gly His Gly Pro Ala Glu Thr Gln Thr Leu
        130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly Ile Tyr Ile Gly Ala Gly Ile Cys Ala Gly Leu
            180                 185                 190

Ala Leu Ala Leu Ile Phe Gly Ala Leu Ile Phe Lys Trp Tyr Ser His
        195                 200                 205

Ser Lys Glu Lys Ile Gln Asn Leu Ser Leu Ile Ser Leu Ala Asn Leu
    210                 215                 220

Pro Pro Ser Gly Leu Ala Asn Ala Val Ala Glu Gly Ile Arg Ser Glu
225                 230                 235                 240

Glu Asn Ile Tyr Thr Ile Glu Glu Asn Val Tyr Glu Val Glu Glu Pro
                245                 250                 255

Asn Glu Tyr Tyr Cys Tyr Val Ser Ser Arg Gln Gln Pro Ser Gln Pro
                260                 265                 270

Leu Gly Cys Arg Phe Ala Met Pro
            275                 280

<210> SEQ ID NO 139
<211> LENGTH: 9
<212> TYPE: PRT
<213> ORGANISM: Artificial sequence
<220> FEATURE:
<223> OTHER INFORMATION: TIM-3 antibody LCDR3

<400> SEQUENCE: 139

Gln Gln Ser Tyr Thr Ser Pro Trp Thr
1               5

<210> SEQ ID NO 140
<211> LENGTH: 9
<212> TYPE: PRT
<213> ORGANISM: Artificial sequence
<220> FEATURE:
<223> OTHER INFORMATION: TIM-3 antibody LCDR3

<400> SEQUENCE: 140

Gln Gln Asn Asn Glu Asp Pro Phe Thr
1               5

<210> SEQ ID NO 141
<211> LENGTH: 9
<212> TYPE: PRT
<213> ORGANISM: Artificial sequence
<220> FEATURE:
<223> OTHER INFORMATION: TIM-3 antibody LCDR3

<400> SEQUENCE: 141

Leu Gln Phe Tyr Glu Phe Pro Leu Thr
1               5

<210> SEQ ID NO 142
<211> LENGTH: 9
<212> TYPE: PRT
<213> ORGANISM: Artificial sequence
<220> FEATURE:
<223> OTHER INFORMATION: TIM-3 antibody LCDR3

<400> SEQUENCE: 142

Gln Gln His Tyr Ser Thr Pro Tyr Thr
1               5

<210> SEQ ID NO 143
<211> LENGTH: 8
<212> TYPE: PRT
<213> ORGANISM: Artificial sequence
<220> FEATURE:
<223> OTHER INFORMATION: TIM-3 antibody LCDR3

<400> SEQUENCE: 143

Gly Gln Ser Tyr Ser Tyr Pro Thr
1               5

<210> SEQ ID NO 144
<211> LENGTH: 8
<212> TYPE: PRT
<213> ORGANISM: Artificial sequence
<220> FEATURE:
<223> OTHER INFORMATION: TIM-3 antibody LCDR3

<400> SEQUENCE: 144

Gly Gln Ser Tyr Ser Tyr Pro Thr
1               5

<210> SEQ ID NO 145
<211> LENGTH: 119
<212> TYPE: PRT
<213> ORGANISM: Artificial sequence
<220> FEATURE:
<223> OTHER INFORMATION: TM3H21

<400> SEQUENCE: 145

Glu Val Gln Leu Leu Glu Ser Gly Gly Gly Leu Val Gln Pro Gly Gly

```
                1               5                   10                  15
            Ser Leu Arg Leu Ser Cys Ala Ala Ser Gly Phe Thr Phe Ser Asn Tyr
                        20                  25                  30

Trp Met Ser Trp Val Arg Gln Ala Pro Gly Lys Gly Leu Glu Trp Val
                        35                  40                  45

Ser Ala Ile Ser Gly Ser Gly Gly Ser Thr Tyr Tyr Ala Asp Ser Val
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Ala Lys Asp His Trp Asp Pro Asn Phe Leu Asp Tyr Trp Gly Gln Gly
                        100                 105                 110

Thr Leu Val Thr Val Ser Ser
                        115
```

<210> SEQ ID NO 146
<211> LENGTH: 117
<212> TYPE: PRT
<213> ORGANISM: Artificial sequence
<220> FEATURE:
<223> OTHER INFORMATION: TM3H24

<400> SEQUENCE: 146

```
            Glu Val Gln Leu Leu Glu Ser Gly Gly Gly Leu Val Gln Pro Gly Gly
             1               5                   10                  15

Ser Leu Arg Leu Ser Cys Ala Ala Ser Gly Phe Thr Phe Ser Ser Tyr
                        20                  25                  30

Ala Met Ser Trp Val Arg Gln Ala Pro Gly Lys Gly Leu Glu Trp Val
                        35                  40                  45

Ser Ala Ile Ser Gly Ser Gly Gly Ser Thr Tyr Tyr Ala Asp Ser Val
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Ala Lys Ser Pro Tyr Ala Pro Leu Asp Tyr Trp Gly Gln Gly Thr Leu
                        100                 105                 110

Val Thr Val Ser Ser
                        115
```

<210> SEQ ID NO 147
<211> LENGTH: 116
<212> TYPE: PRT
<213> ORGANISM: Artificial sequence
<220> FEATURE:
<223> OTHER INFORMATION: TM3H30

<400> SEQUENCE: 147

```
            Glu Val Gln Leu Leu Glu Ser Gly Gly Gly Leu Val Gln Pro Gly Gly
             1               5                   10                  15

Ser Leu Arg Leu Ser Cys Ala Ala Ser Gly Phe Thr Phe Ser Gly Tyr
                        20                  25                  30

Trp Met His Trp Val Arg Gln Ala Pro Gly Lys Gly Leu Glu Trp Val
                        35                  40                  45

Ser Ala Ile Ser Tyr Ser Gly Ser Thr Tyr Tyr Ala Asp Ser Val
                        50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Thr Asn Trp Leu Asp Tyr Trp Gly Gln Gly Thr Leu Val
            100                 105                 110

Thr Val Ser Ser
        115

<210> SEQ ID NO 148
<211> LENGTH: 119
<212> TYPE: PRT
<213> ORGANISM: Artificial sequence
<220> FEATURE:
<223> OTHER INFORMATION: TM3H31

<400> SEQUENCE: 148

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asn Glu Glu Pro Asp Asp Arg Leu Asp Tyr Trp Gly Gln Gly
            100                 105                 110

Thr Leu Val Thr Val Ser Ser
        115

<210> SEQ ID NO 149
<211> LENGTH: 117
<212> TYPE: PRT
<213> ORGANISM: Artificial sequence
<220> FEATURE:
<223> OTHER INFORMATION: TM3H65

<400> SEQUENCE: 149

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Trp Met Ser Trp Val Arg Gln Ala Pro Gly Lys Gly Leu Glu Trp Val
         35                  40                  45

Ser Val Ile Lys Tyr Ser Gly Gly Ser Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Leu Glu Gly Val Phe Asp Tyr Trp Gly Gln Gly Thr Leu
            100                 105                 110

Val Thr Val Ser Ser
        115
```

<210> SEQ ID NO 150
<211> LENGTH: 119
<212> TYPE: PRT
<213> ORGANISM: Artificial sequence
<220> FEATURE:
<223> OTHER INFORMATION: TM3H141

<400> SEQUENCE: 150

```
Glu Val Gln Leu Gln Gln Ser Gly Pro Glu Leu Leu Lys Pro Gly Ala
1               5                   10                  15

Ser Val Lys Met Ser Cys Lys Ala Ser Gly Tyr Thr Phe Thr Ser Tyr
            20                  25                  30

Val Met Tyr Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Arg Leu Thr Ser Glu Asp Ser Ala Val Tyr Cys
                85                  90                  95

Thr Arg Asp Asp Tyr Asp Val Ala Pro Phe Ala Tyr Trp Gly Gln Gly
            100                 105                 110

Thr Leu Val Thr Val Ser Ala
        115
```

<210> SEQ ID NO 151
<211> LENGTH: 115
<212> TYPE: PRT
<213> ORGANISM: Artificial sequence
<220> FEATURE:
<223> OTHER INFORMATION: TM3H96

<400> SEQUENCE: 151

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Arg Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Thr Ser Gly Gly Asn Phe Asp Tyr Trp Gly Gln Gly Thr Thr Leu Thr
            100                 105                 110

Val Ser Ser
        115
```

<210> SEQ ID NO 152
<211> LENGTH: 117
<212> TYPE: PRT
<213> ORGANISM: Artificial sequence
<220> FEATURE:
<223> OTHER INFORMATION: TM3H99

<400> SEQUENCE: 152

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe His Ile Lys Asp Thr
            20                  25                  30

Tyr Leu His Trp Val Lys Gln Arg Pro Glu Gln Gly Leu Glu Trp Ile
        35                  40                  45

Gly Arg Ile Asp Pro Thr Asn Gly Asn Ile Lys Tyr Asp Pro Lys Phe
50                  55                  60

Gln Gly Lys Ala Thr Ile Thr Ser Asp Thr Ser Asn Thr Ala Tyr
65                  70                  75                  80

Leu Gln Leu Ser Ser Leu Thr Ser Glu Asp Thr Ala Val Tyr Tyr Cys
            85                  90                  95

Ala Arg Pro Tyr Tyr Gly Phe Phe Asp Tyr Trp Gly Gln Gly Thr Thr
                100                 105                 110

Leu Thr Val Ser Ser
            115

<210> SEQ ID NO 153
<211> LENGTH: 130
<212> TYPE: PRT
<213> ORGANISM: Artificial sequence
<220> FEATURE:
<223> OTHER INFORMATION: TM3H144

<400> SEQUENCE: 153

Glu Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Ile Arg Tyr Thr Gln Asn Phe
50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
            85                  90                  95

Ala Arg Trp Glu Lys Ser Thr Thr Val Val Gln Arg Asn Tyr Phe Asp
                100                 105                 110

Tyr Trp Gly Gln Gly Thr Thr Leu Thr Val Ser Ser Cys Arg Arg Glu
            115                 120                 125

Cys Thr
    130

<210> SEQ ID NO 154
<211> LENGTH: 120
<212> TYPE: PRT
<213> ORGANISM: Artificial sequence
<220> FEATURE:
<223> OTHER INFORMATION: TM3H102

<400> SEQUENCE: 154

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Ser Tyr
            20                  25                  30

Gly Val His Trp Val Arg Gln Pro Pro Gly Lys Gly Leu Glu Trp Leu
        35                  40                  45

```
Val Val Ile Trp Ser Asp Gly Ser Thr Thr Tyr Asn Ser Ala Leu Lys
 50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Met Tyr Tyr Cys Ala
                 85                  90                  95

Arg Gln Ala Asn Tyr Arg Tyr Asp Ser Ala Met Asp Tyr Trp Gly Gln
                100                 105                 110

Gly Thr Ser Val Thr Val Ser Ser
                115                 120

<210> SEQ ID NO 155
<211> LENGTH: 108
<212> TYPE: PRT
<213> ORGANISM: Artificial sequence
<220> FEATURE:
<223> OTHER INFORMATION: PH9L1

<400> SEQUENCE: 155

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gln Gly Thr Lys Val Glu Ile Lys
                100                 105

<210> SEQ ID NO 156
<211> LENGTH: 107
<212> TYPE: PRT
<213> ORGANISM: Artificial sequence
<220> FEATURE:
<223> OTHER INFORMATION: TM3L33

<400> SEQUENCE: 156

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asn Asp Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Gly Gly His Ala Pro Ile
                 85                  90                  95

Thr Phe Gly Gln Gly Thr Lys Val Glu Ile Lys
                100                 105
```

-continued

```
<210> SEQ ID NO 157
<211> LENGTH: 113
<212> TYPE: PRT
<213> ORGANISM: Artificial sequence
<220> FEATURE:
<223> OTHER INFORMATION: PYYL6

<400> SEQUENCE: 157

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ala Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys

<210> SEQ ID NO 158
<211> LENGTH: 108
<212> TYPE: PRT
<213> ORGANISM: Artificial sequence
<220> FEATURE:
<223> OTHER INFORMATION: TM3L12

<400> SEQUENCE: 158

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
            20                  25                  30

Thr Leu Ala Trp Tyr Gln Gln Lys Pro Gly Gln Ala Pro Arg Leu Leu
        35                  40                  45

Ile Tyr Thr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Thr Ser Pro
                85                  90                  95

Trp Thr Phe Gly Gln Gly Thr Lys Val Glu Ile Lys
            100                 105

<210> SEQ ID NO 159
<211> LENGTH: 111
<212> TYPE: PRT
<213> ORGANISM: Artificial sequence
<220> FEATURE:
<223> OTHER INFORMATION: TM3L61

<400> SEQUENCE: 159

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Leu Asp Ser Tyr
            20                  25                  30
```

```
Gly Asn Ser Tyr Ile His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
 50                  55                  60

Arg Phe Ser Gly Ser Gly Ser Lys Thr Asp Phe Thr Leu Thr Ile Asp
 65                  70                  75                  80

Pro Val Glu Ala Asp Asp Pro Ala Thr Tyr Tyr Cys Gln Gln Asn Asn
                 85                  90                  95

Glu Asp Pro Phe Thr Phe Gly Ser Gly Thr Lys Leu Glu Ile Lys
                100                 105                 110

<210> SEQ ID NO 160
<211> LENGTH: 107
<212> TYPE: PRT
<213> ORGANISM: Artificial sequence
<220> FEATURE:
<223> OTHER INFORMATION: TM3L62

<400> SEQUENCE: 160

Asp Ile Val Met Thr Gln Ser Pro Ser Ser Met Ser Ala Ser Leu Gly
 1               5                  10                  15

Asp Arg Ile Thr Ile Thr Cys Gln Ala Thr Gln Asp Ile Val Lys Asn
                20                  25                  30

Leu Asn Trp Tyr Gln Gln Lys Pro Gly Lys Pro Pro Ser Phe Leu Ile
            35                  40                  45

His Tyr Val Thr Glu Leu Ala Glu Gly Val Pro Ser Arg Phe Ser Gly
 50                  55                  60

Ser Gly Ser Gly Ser Asp Tyr Ser Leu Thr Ile Ser Asn Leu Glu Ser
 65                  70                  75                  80

Glu Asp Phe Ala Asp Tyr Tyr Cys Leu Gln Phe Tyr Glu Phe Pro Leu
                 85                  90                  95

Thr Phe Gly Ala Gly Thr Lys Leu Glu Leu Lys
                100                 105

<210> SEQ ID NO 161
<211> LENGTH: 107
<212> TYPE: PRT
<213> ORGANISM: Artificial sequence
<220> FEATURE:
<223> OTHER INFORMATION: TM3L52

<400> SEQUENCE: 161

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Asn Thr Ala
                20                  25                  30

Val Ala Trp Tyr Gln Gln Lys Pro Gly Gln Ser Pro Lys Leu Leu Ile
            35                  40                  45

Tyr Ser Ala Thr Tyr Arg Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Tyr
                 85                  90                  95

Thr Phe Gly Ser Gly Thr Lys Leu Glu Ile Lys
                100                 105

<210> SEQ ID NO 162
```

```
<211> LENGTH: 105
<212> TYPE: PRT
<213> ORGANISM: Artificial sequence
<220> FEATURE:
<223> OTHER INFORMATION: TM3L67

<400> SEQUENCE: 162

Asp Val Gln Met Ile Gln Ser Pro Lys Ser Met Ser Met Ser Val Gly
1               5                   10                  15

Glu Arg Val Thr Leu Ser Cys Lys Ala Ser Glu Asn Val Gly Thr Phe
            20                  25                  30

Val Ser Trp Tyr Gln Gln Lys Pro Asp Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Thr
                85                  90                  95

Phe Gly Ser Gly Thr Lys Leu Glu Met
            100                 105

<210> SEQ ID NO 163
<211> LENGTH: 111
<212> TYPE: PRT
<213> ORGANISM: Artificial sequence
<220> FEATURE:
<223> OTHER INFORMATION: TM3L64

<400> SEQUENCE: 163

Asp Ile Gln Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Thr Ala Ala Asn Leu Gln Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Ser Gly Thr Lys Leu Glu Ile Lys
            100                 105                 110

<210> SEQ ID NO 164
<211> LENGTH: 5
<212> TYPE: PRT
<213> ORGANISM: Artificial sequence
<220> FEATURE:
<223> OTHER INFORMATION: TIM-3 HCDR1 genus
<220> FEATURE:
<221> NAME/KEY: MISC_FEATURE
<222> LOCATION: (1)..(1)
<223> OTHER INFORMATION: Xaa is Asn, Ser, Gly or Asp
<220> FEATURE:
<221> NAME/KEY: MISC_FEATURE
<222> LOCATION: (3)..(3)
<223> OTHER INFORMATION: Xaa is Trp or Ala
<220> FEATURE:
<221> NAME/KEY: MISC_FEATURE
<222> LOCATION: (5)..(5)
<223> OTHER INFORMATION: Xaa is Ser or His
```

```
<400> SEQUENCE: 164

Xaa Tyr Xaa Met Xaa
1               5

<210> SEQ ID NO 165
<211> LENGTH: 17
<212> TYPE: PRT
<213> ORGANISM: Artificial sequence
<220> FEATURE:
<223> OTHER INFORMATION: TIM-3 HCDR2 genus
<220> FEATURE:
<221> NAME/KEY: MISC_FEATURE
<222> LOCATION: (1)..(1)
<223> OTHER INFORMATION: Xaa is Ala or Val
<220> FEATURE:
<221> NAME/KEY: MISC_FEATURE
<222> LOCATION: (3)..(3)
<223> OTHER INFORMATION: Xaa is Ser or Lys
<220> FEATURE:
<221> NAME/KEY: MISC_FEATURE
<222> LOCATION: (4)..(4)
<223> OTHER INFORMATION: Xaa is Gly or Tyr
<220> FEATURE:
<221> NAME/KEY: MISC_FEATURE
<222> LOCATION: (9)..(9)
<223> OTHER INFORMATION: Xaa is Thr or Lys

<400> SEQUENCE: 165

Xaa Ile Xaa Xaa Ser Gly Gly Ser Xaa Tyr Tyr Ala Asp Ser Val Lys
1               5                   10                  15

Gly

<210> SEQ ID NO 166
<211> LENGTH: 10
<212> TYPE: PRT
<213> ORGANISM: Artificial sequence
<220> FEATURE:
<223> OTHER INFORMATION: TIM-3 HCDR3 genus
<220> FEATURE:
<221> NAME/KEY: MISC_FEATURE
<222> LOCATION: (1)..(1)
<223> OTHER INFORMATION: Xaa is Asp, Ser, Asn, Gly or Glu
<220> FEATURE:
<221> NAME/KEY: MISC_FEATURE
<222> LOCATION: (2)..(2)
<223> OTHER INFORMATION: Xaa is His, Pro, Glu, Thr or Leu
<220> FEATURE:
<221> NAME/KEY: MISC_FEATURE
<222> LOCATION: (3)..(3)
<223> OTHER INFORMATION: Xaa isTrp, Glu, Asn or deleted
<220> FEATURE:
<221> NAME/KEY: MISC_FEATURE
<222> LOCATION: (4)..(4)
<223> OTHER INFORMATION: Xaa is Asp, Pro, or depeted
<220> FEATURE:
<221> NAME/KEY: MISC_FEATURE
<222> LOCATION: (5)..(5)
<223> OTHER INFORMATION: Xaa is Pro, Tyr, Asp or deleted
<220> FEATURE:
<221> NAME/KEY: MISC_FEATURE
<222> LOCATION: (6)..(6)
<223> OTHER INFORMATION: Xaa is Asn, Ala, Asp, Gly or deleted
<220> FEATURE:
<221> NAME/KEY: MISC_FEATURE
<222> LOCATION: (7)..(7)
<223> OTHER INFORMATION: Xaa is Phe, Pro, Arg, Trp or Val
<220> FEATURE:
<221> NAME/KEY: MISC_FEATURE
<222> LOCATION: (8)..(8)
<223> OTHER INFORMATION: Xaa is Leu or Phe

<400> SEQUENCE: 166
```

```
Xaa Xaa Xaa Xaa Xaa Xaa Xaa Xaa Asp Tyr
 1               5                  10
```

<210> SEQ ID NO 167
<211> LENGTH: 17
<212> TYPE: PRT
<213> ORGANISM: Artificial sequence
<220> FEATURE:
<223> OTHER INFORMATION: TIM-3 LCDR1 genus
<220> FEATURE:
<221> NAME/KEY: MISC_FEATURE
<222> LOCATION: (1)..(1)
<223> OTHER INFORMATION: Xaa is Arg or Lys
<220> FEATURE:
<221> NAME/KEY: MISC_FEATURE
<222> LOCATION: (2)..(2)
<223> OTHER INFORMATION: Xaa is Ala or Ser
<220> FEATURE:
<221> NAME/KEY: MISC_FEATURE
<222> LOCATION: (7)..(7)
<223> OTHER INFORMATION: Xaa is Ser, Asn or Leu
<220> FEATURE:
<221> NAME/KEY: MISC_FEATURE
<222> LOCATION: (8)..(8)
<223> OTHER INFORMATION: Xaa is Ser, Ala, Asn or deleted
<220> FEATURE:
<221> NAME/KEY: MISC_FEATURE
<222> LOCATION: (9)..(9)
<223> OTHER INFORMATION: Xaa is Ser or deleted
<220> FEATURE:
<221> NAME/KEY: MISC_FEATURE
<222> LOCATION: (10)..(10)
<223> OTHER INFORMATION: Xaa is Ser or deleted
<220> FEATURE:
<221> NAME/KEY: MISC_FEATURE
<222> LOCATION: (11)..(11)
<223> OTHER INFORMATION: Xaa is Asn or deleted
<220> FEATURE:
<221> NAME/KEY: MISC_FEATURE
<222> LOCATION: (12)..(12)
<223> OTHER INFORMATION: Xaa is Asn or deleted
<220> FEATURE:
<221> NAME/KEY: MISC_FEATURE
<222> LOCATION: (13)..(13)
<223> OTHER INFORMATION: Xaa is Lys or deleted
<220> FEATURE:
<221> NAME/KEY: MISC_FEATURE
<222> LOCATION: (14)..(14)
<223> OTHER INFORMATION: Xaa is Ser, Asn or Asp
<220> FEATURE:
<221> NAME/KEY: MISC_FEATURE
<222> LOCATION: (15)..(15)
<223> OTHER INFORMATION: Xaa is Tyr or Thr

<400> SEQUENCE: 167

```
Xaa Xaa Ser Gln Ser Val Xaa Xaa Xaa Xaa Xaa Xaa Xaa Xaa Leu
 1               5                  10                  15

Ala
```

<210> SEQ ID NO 168
<211> LENGTH: 7
<212> TYPE: PRT
<213> ORGANISM: Artificial sequence
<220> FEATURE:
<223> OTHER INFORMATION: TIM-3 LCDR2 genus
<220> FEATURE:
<221> NAME/KEY: MISC_FEATURE
<222> LOCATION: (1)..(1)
<223> OTHER INFORMATION: Xaa is Gly, Asp, Trp or Thr
<220> FEATURE:
<221> NAME/KEY: MISC_FEATURE
<222> LOCATION: (4)..(4)
<223> OTHER INFORMATION: Xaa is Ser, Asn or Thr
<220> FEATURE:
<221> NAME/KEY: MISC_FEATURE

```
<222> LOCATION: (6)..(6)
<223> OTHER INFORMATION: Xaa is Ala or Glu
<220> FEATURE:
<221> NAME/KEY: MISC_FEATURE
<222> LOCATION: (7)..(7)
<223> OTHER INFORMATION: Xaa is Thr or Ser

<400> SEQUENCE: 168

Xaa Ala Ser Xaa Arg Xaa Xaa
1               5

<210> SEQ ID NO 169
<211> LENGTH: 9
<212> TYPE: PRT
<213> ORGANISM: Artificial sequence
<220> FEATURE:
<223> OTHER INFORMATION: TIM-3 LCDR3 genus
<220> FEATURE:
<221> NAME/KEY: MISC_FEATURE
<222> LOCATION: (3)..(3)
<223> OTHER INFORMATION: Xaa is Tyr, Gly or Ser
<220> FEATURE:
<221> NAME/KEY: MISC_FEATURE
<222> LOCATION: (4)..(4)
<223> OTHER INFORMATION: Xaa is Gly or Tyr
<220> FEATURE:
<221> NAME/KEY: MISC_FEATURE
<222> LOCATION: (5)..(5)
<223> OTHER INFORMATION: Xaa is Ser, His or Thr
<220> FEATURE:
<221> NAME/KEY: MISC_FEATURE
<222> LOCATION: (6)..(6)
<223> OTHER INFORMATION: Xaa is Ser, Ala or Thr
<220> FEATURE:
<221> NAME/KEY: MISC_FEATURE
<222> LOCATION: (8)..(8)
<223> OTHER INFORMATION: Xaa is Leu, Ile or Trp

<400> SEQUENCE: 169

Gln Gln Xaa Xaa Xaa Xaa Pro Xaa Thr
1               5

<210> SEQ ID NO 170
<211> LENGTH: 98
<212> TYPE: PRT
<213> ORGANISM: Homo sapiens

<400> SEQUENCE: 170

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 171
<211> LENGTH: 95
<212> TYPE: PRT
<213> ORGANISM: Homo sapiens
```

<400> SEQUENCE: 171

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 172
<211> LENGTH: 124
<212> TYPE: PRT
<213> ORGANISM: Artificial sequence
<220> FEATURE:
<223> OTHER INFORMATION: TM3H162

<400> SEQUENCE: 172

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Gln Trp Val Arg Gln Met Pro Gly Lys Gly Leu Glu Trp Met
        35                  40                  45

Gly Ala Ile Tyr Pro Gly Asp Gly Asp Ile Arg Tyr Thr Gln Asn Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Glu Lys Ser Thr Thr Val Val Gln Arg Asn Tyr Phe Asp
            100                 105                 110

Tyr Trp Gly Gln Gly Thr Thr Val Thr Val Ser Ser
        115                 120

<210> SEQ ID NO 173
<211> LENGTH: 106
<212> TYPE: PRT
<213> ORGANISM: Artificial sequence
<220> FEATURE:
<223> OTHER INFORMATION: TM3L85

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Gly Thr Phe
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gly Gln Ser Tyr Ser Tyr Pro Thr
             85                  90                  95

Phe Gly Gln Gly Thr Lys Leu Glu Ile Lys
            100                 105

<210> SEQ ID NO 174
<211> LENGTH: 98
<212> TYPE: PRT
<213> ORGANISM: Homo sapiens

<400> SEQUENCE: 174

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 175
<211> LENGTH: 98
<212> TYPE: PRT
<213> ORGANISM: Homo sapiens

<400> SEQUENCE: 175

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg

<210> SEQ ID NO 176
<211> LENGTH: 99
<212> TYPE: PRT
<213> ORGANISM: Homo sapiens

<400> SEQUENCE: 176

Gln Val Gln Leu Gln Glu Ser Gly Pro Gly Leu Val Lys Pro Ser Gln
1               5                  10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45
```

```
Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg

<210> SEQ ID NO 177
<211> LENGTH: 98
<212> TYPE: PRT
<213> ORGANISM: Homo sapiens

<400> SEQUENCE: 177

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Ala Met His Trp Val Arg Gln Ala Pro Gly Gln Arg Leu Glu Trp Met
             35                  40                  45

Gly Trp Ile Asn Ala Gly Asn Gly Asn Thr Lys Tyr Ser Gln Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 178
<211> LENGTH: 100
<212> TYPE: PRT
<213> ORGANISM: Homo sapiens

<400> SEQUENCE: 178

Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Asn Ala
                 20                  25                  30

Arg Met Gly Val Ser Trp Ile Arg Gln Pro Pro Gly Lys Ala Leu Glu
             35                  40                  45

Trp Leu Ala His Ile Phe Ser Asn Asp Glu Lys Ser Tyr Ser Thr Ser
 50                  55                  60

Leu Lys Ser Arg Leu Thr Ile Ser Lys Asp Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Ala Arg Ile
            100

<210> SEQ ID NO 179
<211> LENGTH: 98
<212> TYPE: PRT
<213> ORGANISM: Homo sapiens

<400> SEQUENCE: 179

Glu Val Gln Leu Val Gln Ser Gly Ala Glu Val Lys Lys Pro Gly Glu
 1               5                  10                  15
```

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg

<210> SEQ ID NO 180
<211> LENGTH: 96
<212> TYPE: PRT
<213> ORGANISM: Homo sapiens

<400> SEQUENCE: 180

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

<210> SEQ ID NO 181
<211> LENGTH: 96
<212> TYPE: PRT
<213> ORGANISM: Homo sapiens

<400> SEQUENCE: 181

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

<210> SEQ ID NO 182
<211> LENGTH: 96
<212> TYPE: PRT
<213> ORGANISM: Homo sapiens

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

<210> SEQ ID NO 183
<211> LENGTH: 95
<212> TYPE: PRT
<213> ORGANISM: Homo sapiens

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 184
<211> LENGTH: 127
<212> TYPE: PRT
<213> ORGANISM: Artificial sequence
<220> FEATURE:
<223> OTHER INFORMATION: VH of gp120 binding mAb

<400> SEQUENCE: 184

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
            35                  40                  45

Gly Trp Ile Asn Pro Tyr Asn Gly Asn Lys Glu Phe Ser Ala Lys Phe
    50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
                100                 105                 110

Tyr Met Asp Val Trp Gly Lys Gly Thr Thr Val Ile Val Ser Ser
            115                 120                 125

<210> SEQ ID NO 185
<211> LENGTH: 108

```
<212> TYPE: PRT
<213> ORGANISM: Artificial sequence
<220> FEATURE:
<223> OTHER INFORMATION: VL of gp120 binding mAb

<400> SEQUENCE: 185

Glu Ile Val Leu Thr Gln Ser Pro Gly Thr Leu Ser Leu Ser Pro Gly
1               5                   10                  15

Glu Arg Ala Thr Phe Ser Cys Arg Ser His Ser Ile Arg Ser Arg
            20                  25                  30

Arg Val Ala Trp Tyr Gln His Lys Pro Gly Gln Ala Pro Arg Leu Val
            35                  40                  45

Ile His Gly Val Ser Asn Arg Ala Ser Gly Ile Ser Asp Arg Phe Ser
50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
            100                 105

<210> SEQ ID NO 186
<211> LENGTH: 449
<212> TYPE: PRT
<213> ORGANISM: Artificial sequence
<220> FEATURE:
<223> OTHER INFORMATION: Bispecific mAb HC1

<400> SEQUENCE: 186

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Asp Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Tyr Asp Thr Gly Ser Leu Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
            195                 200                 205

Asp His Lys Pro Ser Asn Thr Lys Val Asp Lys Thr Val Glu Arg Lys
        210                 215                 220
```

Cys Cys Val Glu Cys Pro Pro Cys Pro Ala Pro Ala Ala Ala Ser
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Ala Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Leu Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 187
<211> LENGTH: 443
<212> TYPE: PRT
<213> ORGANISM: Artificial sequence
<220> FEATURE:
<223> OTHER INFORMATION: Bispecific mAb HC1

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Arg Tyr
            20                  25                  30

Asp Met Ser Trp Val Arg Gln Ala Pro Gly Lys Gly Leu Glu Ser Val
        35                  40                  45

Ala Tyr Ile Ser Gly Gly Gly Ala Asn Thr Tyr Tyr Leu Asp Asn Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Leu Ser Tyr Phe Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Thr Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Ala Ala Ala Ser Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Ala Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Leu Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 188
<211> LENGTH: 214
<212> TYPE: PRT
<213> ORGANISM: Artificial sequence
<220> FEATURE:
<223> OTHER INFORMATION: Bispecific mAb LC1

<400> SEQUENCE: 188

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Tyr Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 189
<211> LENGTH: 214
<212> TYPE: PRT
<213> ORGANISM: Artificial sequence
<220> FEATURE:
<223> OTHER INFORMATION: Bispecific mAb LC1

<400> SEQUENCE: 189

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Leu Ser Asp Tyr
                20                  25                  30

Leu His Trp Tyr Gln Gln Lys Pro Gly Gln Ala Pro Arg Leu Leu Ile
            35                  40                  45

Lys Ser Ala Ser Gln Ser Ile Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Asn Gly His Ser Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
            195                 200                 205

Phe Asn Arg Gly Glu Cys
            210

<210> SEQ ID NO 190
<211> LENGTH: 450
<212> TYPE: PRT
<213> ORGANISM: Artificial sequence
<220> FEATURE:
<223> OTHER INFORMATION: Bispecific mAb HC2

<400> SEQUENCE: 190

Glu Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Ile Arg Tyr Thr Gln Asn Phe
    50                  55                  60

Lys Gly Lys Ala Thr Leu Thr Ala Asp Lys Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Trp Glu Lys Ser Thr Thr Val Val Gln Arg Asn Tyr Phe Asp
            100                 105                 110

Tyr Trp Gly Gln Gly Thr Thr Leu Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Thr Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Ala Ala Ala
225                 230                 235                 240

Ser Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Ala Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335
```

```
Lys Thr Ile Ser Lys Thr Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 191
<211> LENGTH: 443
<212> TYPE: PRT
<213> ORGANISM: Artificial sequence
<220> FEATURE:
<223> OTHER INFORMATION: Bispecific mAb HC2

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Tyr Ala Pro Leu Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Thr Ser Ser Asn
                180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
        210                 215                 220

Pro Cys Pro Ala Pro Pro Ala Ala Ser Ser Val Phe Leu Phe Pro
225                 230                 235                 240
```

Pro Lys Pro Lys Asp Thr Leu Met Ile Ser Arg Thr Pro Glu Val Thr
            245                 250                 255

Cys Val Val Asp Val Ser Ala Glu Asp Pro Glu Val Gln Phe Asn
        260                 265                 270

Trp Tyr Val Asp Gly Val Glu Val His Asn Ala Lys Thr Lys Pro Arg
            275                 280                 285

Glu Glu Gln Phe Asn Ser Thr Phe Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Met Leu Asp Ser Asp Gly Ser Phe
385                 390                 395                 400

Phe Leu Tyr Ser Arg Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 192
<211> LENGTH: 450
<212> TYPE: PRT
<213> ORGANISM: Artificial sequence
<220> FEATURE:
<223> OTHER INFORMATION: Bispecific mAb HC2

<400> SEQUENCE: 192

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Gln Trp Val Arg Gln Met Pro Gly Lys Gly Leu Glu Trp Met
        35                  40                  45

Gly Ala Ile Tyr Pro Gly Asp Gly Asp Ile Arg Tyr Thr Gln Asn Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Glu Lys Ser Thr Thr Val Val Gln Arg Asn Tyr Phe Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
165                 170                 175

Phe Pro Ala Val Leu Gln Ser Ser Gly Leu Tyr Ser Leu Ser Ser Val
            180                 185                 190

Val Thr Val Thr Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Ala Ala Ala
225                 230                 235                 240

Ser Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Ala Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 193
<211> LENGTH: 213
<212> TYPE: PRT
<213> ORGANISM: Artificial sequence
<220> FEATURE:
<223> OTHER INFORMATION: Bispecific mAb LC2

<400> SEQUENCE: 193

Asp Val Gln Met Ile Gln Ser Pro Lys Ser Met Ser Met Ser Val Gly
1               5                   10                  15

Glu Arg Val Thr Leu Ser Cys Lys Ala Ser Glu Asn Val Gly Thr Phe
            20                  25                  30

Val Ser Trp Tyr Gln Gln Lys Pro Asp Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

```
Ser Gly Ser Ala Thr Asp Phe Thr Leu Thr Ile Ser Ser Val Gln Ala
 65                  70                  75                  80

Glu Asp Leu Ala Asp Tyr His Cys Gly Gln Ser Tyr Ser Tyr Pro Thr
                 85                  90                  95

Phe Gly Ser Gly Thr Lys Leu Glu Met Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 194
<211> LENGTH: 214
<212> TYPE: PRT
<213> ORGANISM: Artificial sequence
<220> FEATURE:
<223> OTHER INFORMATION: Bispecific mAb LC2

<400> SEQUENCE: 194

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asn Asp Tyr
             20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Gly Gly His Ala Pro Ile
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205
```

```
Phe Asn Arg Gly Glu Cys
    210
```

<210> SEQ ID NO 195
<211> LENGTH: 213
<212> TYPE: PRT
<213> ORGANISM: Artificial sequence
<220> FEATURE:
<223> OTHER INFORMATION: Bispecific mAb LC2

<400> SEQUENCE: 195

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Gly Thr Phe
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Tyr Ser Tyr Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 196
<211> LENGTH: 369
<212> TYPE: DNA
<213> ORGANISM: Artificial sequence
<220> FEATURE:
<223> OTHER INFORMATION: DNA of PD1H170

<400> SEQUENCE: 196

```
caggtgcagc tggtgcagag cggcgcggaa gtgaaaaaac cgggcagcag cgtgaaagtg      60
agctgcaaag cgagcggcgg caccttttagc agctatgcga ttagctgggt gcgccaggcg    120
ccgggccagg gcctggaatg gatgggcggc attattccga ttttttgacac cgcgaactat    180 gcgcagaaat ttcagggccg cgtgaccatt accgcggatg aaagcaccag caccgcgtat    240
atggaactga gcagcctgcg cagcgaagat accgcggtgt attattgcgc gcgccctggt    300
ctcgctgcgg cttatgatac tggttccttg gactattggg gccagggcac cctggtgacc    360
gtgagcagc                                                             369
```

```
<210> SEQ ID NO 197
<211> LENGTH: 321
<212> TYPE: DNA
<213> ORGANISM: Artificial sequence
<220> FEATURE:
<223> OTHER INFORMATION: DNA of PD1L148

<400> SEQUENCE: 197
gaaattgtgc tgacccagag cccggcgacc ctgagcctga gcccgggcga acgcgcgacc      60
ctgagctgcc gcgcgagcca gagcgttcgc tcctacctgg cgtggtatca gcagaaaccg     120
ggccaggcgc cgcgcctgct gatctacgac gcgagcaatc gtgcgaccgg cattccggcg     180
cgctttagcg gctccggtag cggcaccgat tttaccctga ccattagcag cctggaaccg     240
gaagattttg cggtgtatta ttgccagcaa cgtaattatt ggccgctgac ctttggccag     300
ggcaccaaag tggaaattaa a                                                321

<210> SEQ ID NO 198
<211> LENGTH: 351
<212> TYPE: DNA
<213> ORGANISM: Artificial sequence
<220> FEATURE:
<223> OTHER INFORMATION: DNA of PD1H129

<400> SEQUENCE: 198
gaagtgcagc tggtggaatc tggcggcgga ctggtgcagc ctggcggatc tctgagactg      60
agctgtgccg ccagcggctt cgccttcagc agatacgaca tgagctgggt gcgccaggcc     120
cctggcaaag actggaaag cgtggcctac atctctggcg aggcgccaa cacctactac       180 ctggacaacg tgaagggccg gttcaccatc agccgggaca cgccaagaa cagcctgtac      240 ctgcagatga actccctgcg ggccgaggac accgccgtgt actattgcgc ctcccccctac    300 ctgagctact cgacgtgtg gggccagggc acactcgtga ccgtgtcatc t                351

<210> SEQ ID NO 199
<211> LENGTH: 321
<212> TYPE: DNA
<213> ORGANISM: Artificial sequence
<220> FEATURE:
<223> OTHER INFORMATION: DNA of PD1L62

<400> SEQUENCE: 199
gagatcgtga tgacccagag ccctgccacc ctgtccgtgt ctccaggcga aagagccacc      60
ctgagctgca gagccagcca gagcctgagc gactacctgc actggtatca gcagaagccc     120
ggccaggccc ccagactgct gatcaagtct gccagccagt ccatcagcgg catccccgcc     180 agatttctg gcagcggctc cggcaccgag ttcaccctga caatcagcag cctgcagagc      240
gaggacttcg ccgtgtacta ctgccagaac ggccacagct cccttacac cttcggccag     300 ggcaccaagc tggaaatcaa g                                                321

<210> SEQ ID NO 200
<211> LENGTH: 360
<212> TYPE: DNA
<213> ORGANISM: Artificial sequence
<220> FEATURE:
<223> OTHER INFORMATION: DNA of PD1H163

<400> SEQUENCE: 200
caggtgcagc tggtgcagag cggcgcggaa gtgaaaaaac cgggcagcag cgtgaaagtg      60
agctgcaaag cgagcggcgg caccttcaag tcctatgtga ttcattgggt gcgccaggcg     120
```

```
ccgggccagg gcctggaatg gatgggcggt attatcccaa ttttggcac cgccaattat    180 gcgcagaaat tcagggccg cgtgaccatt accgctgatg aaagcaccag caccgcgtat    240
atggaactga gcagcctgcg cagcgaagat accgcggtgt attattgcgc gcgcggttat    300
gtgcgggcta cgggcatgtt ggactattgg ggccagggca ccctggtgac cgtgagcagc    360
```

<210> SEQ ID NO 201
<211> LENGTH: 321
<212> TYPE: DNA
<213> ORGANISM: Artificial sequence
<220> FEATURE:
<223> OTHER INFORMATION: DNA of PD1L185

<400> SEQUENCE: 201

```
gaaattgtgc tgacccagag cccggcgacc ctgagcctga gcccgggcga acgcgcgacc     60
ctgagctgcc gcgcgagcca gagcgttagc aattatctgg cgtggtatca gcagaaaccg    120
ggccaggcgc cgcgcctgct gatctacgac gccagcaatc gcgcgaccgg cattccggcg    180
cgctttagcg gctccggtag cggcaccgat tttaccctga ccattagcag cctggaaccg    240
gaagattttg cggtgtatta ttgccagcaa cgtgcatatt ggccgctgac ctttggccag    300
ggcaccaaag tggaaattaa a                                              321
```

<210> SEQ ID NO 202
<211> LENGTH: 360
<212> TYPE: DNA
<213> ORGANISM: Artificial sequence
<220> FEATURE:
<223> OTHER INFORMATION: DNA of PD1H164

<400> SEQUENCE: 202

```
caggtgcagc tggtgcagag cggcgcggaa gtgaaaaaac cgggcagcag cgtgaaagtg     60
agctgcaaag cgagcggcgg caccttcagc gattatgtga tttcctgggt gcgccaggcg    120
ccgggccagg gcctggaatg gatgggcggt attatcccga tttacgggac cgctaactat    180
gcgcagaaat tcagggccg cgtgaccatt accgctgatg aaagcaccag caccgcgtat    240
atggaactga gcagcctgcg cagcgaagat accgcggtgt attattgcgc gcgcggtacc    300
ctcgaccgga ccgggcattt ggactattgg ggccagggca ccctggtgac cgtgagcagc    360
```

<210> SEQ ID NO 203
<211> LENGTH: 321
<212> TYPE: DNA
<213> ORGANISM: Artificial sequence
<220> FEATURE:
<223> OTHER INFORMATION: DNA of PD1L86

<400> SEQUENCE: 203

```
gaaattgtgc tgacccagag cccggcgacc ctgagcctga gcccgggcga acgcgcgacc     60
ctgagctgcc gcgcgagcca gagcgtctcc tcctacttg cgtggtatca gcagaaaccg    120
ggccaggcgc cgcgcctgct gatccacgac gcctctacgc gtgcgaccgg cattccggcg    180
cgctttagcg gctccggtag cggcaccgat tttaccctga ccattagcag cctggaaccg    240
gaagattttg cggtgtatta ttgccagcaa cgtaattatt ggccgctcac ctttggccag    300
ggcaccaaag tggaaattaa a                                              321
```

<210> SEQ ID NO 204
<211> LENGTH: 351
<212> TYPE: DNA

```
<213> ORGANISM: Artificial sequence
<220> FEATURE:
<223> OTHER INFORMATION: DNA of TM3H24

<400> SEQUENCE: 204
gaagtgcagc tgctggaaag cggcggcggc ctggtgcagc cgggcggcag cctgcgcctg      60
agctgcgcgg caagcggctt tacctttagc agctatgcga tgagctgggt gcgccaggcg     120
ccgggcaaag gcctggaatg ggtgagcgcg attagcggca gcggcggcag cacctattat     180
gcggatagcg tgaaaggccg ctttaccatt agccgcgata cagcaaaaa caccctgtat      240 ctgcagatga acagcctgcg cgcggaagat accgcggtgt attattgcgc gaaatccccg     300
tacgcgccct tggactattg gggccagggc accctggtga ccgtgagcag c              351

<210> SEQ ID NO 205
<211> LENGTH: 321
<212> TYPE: DNA
<213> ORGANISM: Artificial sequence
<220> FEATURE:
<223> OTHER INFORMATION: DNA of TM3L33

<400> SEQUENCE: 205
gaaattgtgc tgacccagag cccggcgacc ctgagcctga gcccgggcga acgcgcgacc      60
cttagctgcc gtgcaagtca gagtgtgaac gactacctgg cgtggtatca gcagaaaccg     120
ggccaggcgc cgcgcctgct gatttatgat gcgagcaacc gcgcgaccgg cattccggcg     180
cgctttagcg gcagcggcag cggcaccgat tttaccctga ccattagcag cctggaaccg     240
gaagattttg cggtgtatta ttgccagcag ggtggtcacg cgccgatcac ctttggccag     300
ggcaccaaag tggaaattaa a                                                321

<210> SEQ ID NO 206
<211> LENGTH: 372
<212> TYPE: DNA
<213> ORGANISM: Artificial sequence
<220> FEATURE:
<223> OTHER INFORMATION: DNA of TM3H162

<400> SEQUENCE: 206
gaagtgcagc tggtgcagtc tggcgccgaa gtgaagaagc tggcgagag cctgaagatc       60 agctgcaagg gcagcggcta cagcttcacc agctactgga tgcagtgggt gcgccagatg     120
cctggcaagg gcctggaatg gatgggcgcc atctatcccg gcgacggcga catcagatac     180
acccagaact tcaagggcca agtgaccatc agccgccgaca agagcatcag caccgcctac     240
ctgcagtggt ccagcctgaa ggccagcgac accgccatgt actactgtgc cagatgggag     300
aagtccacca ccgtggtgca gcggaactac ttcgactact ggggccaggg caccacagtg     360
accgtgtcta gt                                                           372

<210> SEQ ID NO 207
<211> LENGTH: 318
<212> TYPE: DNA
<213> ORGANISM: Artificial sequence
<220> FEATURE:
<223> OTHER INFORMATION: DNA of TM3L85

<400> SEQUENCE: 207
gacatccaga tgacccagag ccccagcagc ctgtctgcca gcgtgggcga cagagtgacc      60
atcacatgca aggccagcga gaacgtgggc accttcgtgt cctggtatca gcagaagccc     120
ggcaaggccc ccaagctgct gatctacggc gccagcaaca gatacaccgg cgtgcccagc     180
```
agattcagcg gctctggcag cggcaccgac ttcaccctga ccatctctag cctgcagccc    240
gaggacttcg ccacctacta ctgcggccag agctacagct accccacctt tggccagggc    300
accaagctgg aaatcaag                                                  318

<210> SEQ ID NO 208
<211> LENGTH: 357
<212> TYPE: DNA
<213> ORGANISM: Artificial sequence
<220> FEATURE:
<223> OTHER INFORMATION: DNA of TM3H21

<400> SEQUENCE: 208
gaagtgcagc tgctggaaag cggcggcggc ctggtgcagc cgggcggcag cctgcgcctg     60
agctgcgcgg cgagcggctt tacctttagc aactattgga tgagctgggt gcgccaggcg    120
ccgggcaaag gcctggaatg ggtgagcgcg attagcggca gcggcggcag cacctattat    180
gcggatagcg tgaaaggccg ctttaccatt agccgcgata caagcaaaaa cacccctgtat   240 ctgcagatga acagcctgcg cgcggaagat accgcggtgt attattgcgc gaaagatcat    300
tgggatccca attttttgga ctattggggc cagggcaccc tggtgaccgt gagcagc       357

<210> SEQ ID NO 209
<211> LENGTH: 324
<212> TYPE: DNA
<213> ORGANISM: Artificial sequence
<220> FEATURE:
<223> OTHER INFORMATION: DNA of PH9L1

<400> SEQUENCE: 209
gaaattgtgc tgacccagag cccgggcacc ctgagcctga gcccgggcga acgcgcgacc     60
ctgagctgcc gcgcgagcca gagcgtgagc agcagctatc tggcgtggta tcagcagaaa    120
ccgggccagg cgccgcgcct gctgatttat ggcgcgagca gccgcgcgac cggcattccg    180
gatcgcttta gcggcagcgg cagcggcacc gattttaccc tgaccattag ccgcctggaa    240
ccggaagatt ttgcggtgta ttattgccag cagtatggca gcagcccgct gacctttggc    300
cagggcacca aagtggaaat taaa                                            324

<210> SEQ ID NO 210
<211> LENGTH: 351
<212> TYPE: DNA
<213> ORGANISM: Artificial sequence
<220> FEATURE:
<223> OTHER INFORMATION: DNA of TM3H65

<400> SEQUENCE: 210
gaagtgcagc tgctggaaag cggcggcggc ctggtgcagc cgggcggcag cctgcgcctg     60
agctgcgcgg cgagcggctt tacctttagc gactattgga tgagctgggt gcgccaggcg    120
ccgggcaaag gcctggaatg ggtgagcgtg atcaagtata gcgtggctc caaatattat     180 gcggatagcg tgaaaggccg ctttaccatt agccgcgata caagcaaaaa cacccctgtat   240 ctgcagatga acagcctgcg cgcggaagat accgcggtgt attattgcgc gaaagagctg    300 gaggggggtgt tcgactattg gggccagggc accctggtga ccgtgagcag c            351

<210> SEQ ID NO 211
<211> LENGTH: 324
<212> TYPE: DNA
<213> ORGANISM: Artificial sequence
<220> FEATURE:

<223> OTHER INFORMATION: DNA of TM3L12

<400> SEQUENCE: 211

```
gaaattgtgc tgacccagag cccgggcacc ctgagcctga gcccgggcga acgcgcgacc    60
ctgagctgcc gcgcgagcca gagcgttagc aatagcactc tggcgtggta tcagcagaaa   120
ccgggccagg cgccgcgcct gctgatttat actgcgagca gccgcgcgac cggcattccg   180
gatcgcttta gcggcagcgg cagcggcacc gattttaccc tgaccattag ccgcctggaa   240
ccggaagatt ttgcggtgta ttattgccag cagtcttaca catctccgtg gacttttggc   300
cagggcacca aagtggaaat taaa                                          324
```

<210> SEQ ID NO 212
<211> LENGTH: 449
<212> TYPE: PRT
<213> ORGANISM: Artificial sequence
<220> FEATURE:
<223> OTHER INFORMATION: HC of PD1B114

<400> SEQUENCE: 212

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Ala Tyr Asp Thr Gly Asn Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Ala Ala Ala Ser
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Ala Glu Asp
            260                 265                 270

Pro Glu Val Gln Phe Asn Trp Tyr Val Asp Gly Val Glu Val His Asn
        275                 280                 285

```
Ala Lys Thr Lys Pro Arg Glu Glu Gln Phe Asn Ser Thr Phe Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Thr Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 213
<211> LENGTH: 214
<212> TYPE: PRT
<213> ORGANISM: Artificial sequence
<220> FEATURE:
<223> OTHER INFORMATION: LC of PD1B114

<400> SEQUENCE: 213

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

Ala Cys Glu Val Thr His Gln Gly Leu Ser Ser Pro Val Thr Lys Ser
            195                 200                 205

Phe Asn Arg Gly Glu Cys
    210

<210> SEQ ID NO 214
<211> LENGTH: 449
<212> TYPE: PRT
<213> ORGANISM: Artificial sequence
<220> FEATURE:
<223> OTHER INFORMATION: HC of PD1B149

<400> SEQUENCE: 214

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Ala Tyr Asp Thr Gly Asn Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Ala Ala Ala Ser
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Ala Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

```
Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 215
<211> LENGTH: 214
<212> TYPE: PRT
<213> ORGANISM: Artificial sequence
<220> FEATURE:
<223> OTHER INFORMATION: LC of PD1B149

<400> SEQUENCE: 215

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Asn Tyr
            20                  25                  30

Leu Ala Trp Tyr Gln Gln Lys Pro Gly Gln Ala Pro Arg Leu Leu Ile
            35                  40                  45

His Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Tyr Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 216
<211> LENGTH: 449
<212> TYPE: PRT
```

<213> ORGANISM: Artificial sequence
<220> FEATURE:
<223> OTHER INFORMATION: HC of PD1B160

<400> SEQUENCE: 216

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Tyr Asp Thr Gly Asn Leu Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Ala Ala Ala Ser
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Ala Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
```

```
                385                 390                 395                 400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 217
<211> LENGTH: 214
<212> TYPE: PRT
<213> ORGANISM: Artificial sequence
<220> FEATURE:
<223> OTHER INFORMATION: LC of PD1B160

<400> SEQUENCE: 217

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Ser Tyr
                20                  25                  30

Leu Ala Trp Tyr Gln Gln Lys Pro Gly Gln Ala Pro Arg Leu Leu Ile
            35                  40                  45

Lys Asp Ala Ser Asp Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Gly Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 218
<211> LENGTH: 449
<212> TYPE: PRT
<213> ORGANISM: Artificial sequence
<220> FEATURE:
<223> OTHER INFORMATION: HC of PD1B162

<400> SEQUENCE: 218

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
            20                  25                  30
Ala Ile Ser Trp Val Arg Gln Ala Pro Gly Gln Gly Leu Glu Trp Met
        35                  40                  45
Gly Gly Ile Ile Pro Ile Phe Asp Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Pro Gly Leu Ala Ala Tyr Asp Thr Gly Asn Leu Asp Tyr
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Cys Ser Arg Ser Thr Ser Glu Ser
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Thr Ser Ser Asn Phe Gly Thr Gln Thr Tyr Thr Cys Asn Val
        195                 200                 205
Asp His Lys Pro Ser Asn Thr Lys Val Asp Lys Thr Val Glu Arg Lys
    210                 215                 220
Cys Cys Val Glu Cys Pro Pro Cys Pro Ala Pro Pro Ala Ala Ala Ser
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Ala Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Phe Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Thr Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Met Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
```

```
<210> SEQ ID NO 219
<211> LENGTH: 214
<212> TYPE: PRT
<213> ORGANISM: Artificial sequence
<220> FEATURE:
<223> OTHER INFORMATION: LC of PD1B162

<400> SEQUENCE: 219

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Glu Tyr Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 220
<211> LENGTH: 449
<212> TYPE: PRT
<213> ORGANISM: Artificial sequence
<220> FEATURE:
<223> OTHER INFORMATION: HC of PD1B164

<400> SEQUENCE: 220

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80
```

-continued

Met Glu Leu Ser Ser Leu Arg Ser Glu Asp Thr Ala Val Tyr Tyr Cys
                85                  90                  95

Ala Arg Pro Gly Leu Ala Ala Tyr Asp Thr Gly Asn Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
210                 215                 220

Cys Cys Val Glu Cys Pro Pro Cys Pro Ala Pro Pro Ala Ala Ala Ser
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Ala Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 221
<211> LENGTH: 214
<212> TYPE: PRT
<213> ORGANISM: Artificial sequence
<220> FEATURE:
<223> OTHER INFORMATION: LC of PD1B164

<400> SEQUENCE: 221

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Tyr Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asp Tyr Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 222
<211> LENGTH: 449
<212> TYPE: PRT
<213> ORGANISM: Artificial sequence
<220> FEATURE:
<223> OTHER INFORMATION: HC of PD1B183

<400> SEQUENCE: 222

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Ala Tyr Asp Thr Gly Ser Leu Asp Tyr
            100                 105                 110

Trp Gly Gln Gly Thr Leu Val Thr Val Ser Ser Ala Ser Thr Lys Gly
        115                 120                 125

```
Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Thr Ser Ser Asn Phe Gly Thr Gln Thr Tyr Thr Cys Asn Val
            195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Ala Ala Ala Ser
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Ala Glu Asp
                260                 265                 270

Pro Glu Val Gln Phe Asn Trp Tyr Val Asp Gly Val Glu Val His Asn
    275                 280                 285

Ala Lys Thr Lys Pro Arg Glu Glu Gln Phe Asn Ser Thr Phe Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Thr Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 223
<211> LENGTH: 214
<212> TYPE: PRT
<213> ORGANISM: Artificial sequence
<220> FEATURE:
<223> OTHER INFORMATION: LC of PD1B183

<400> SEQUENCE: 223

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
```

```
            35                  40                  45
Lys Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Gly Tyr Trp Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 224
<211> LENGTH: 449
<212> TYPE: PRT
<213> ORGANISM: Artificial sequence
<220> FEATURE:
<223> OTHER INFORMATION: HC of PD1B184

<400> SEQUENCE: 224

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Pro Gly Leu Ala Ala Ala Tyr Asp Thr Gly Ser Leu Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
                180              185              190
Thr Val Thr Ser Ser Asn Phe Gly Thr Gln Thr Tyr Thr Cys Asn Val
            195              200              205
Asp His Lys Pro Ser Asn Thr Lys Val Asp Lys Thr Val Glu Arg Lys
        210              215              220
Cys Cys Val Glu Cys Pro Pro Cys Pro Ala Pro Ala Ala Ala Ser
225             230              235              240
Ser Val Phe Leu Phe Pro Pro Lys Pro Lys Asp Thr Leu Met Ile Ser
                245              250              255
Arg Thr Pro Glu Val Thr Cys Val Val Asp Val Ser Ala Glu Asp
            260              265              270
Pro Glu Val Gln Phe Asn Trp Tyr Val Asp Gly Val Glu Val His Asn
        275              280              285
Ala Lys Thr Lys Pro Arg Glu Glu Gln Phe Asn Ser Thr Phe Arg Val
        290              295              300
Val Ser Val Leu Thr Val Leu His Gln Asp Trp Leu Asn Gly Lys Glu
305             310              315              320
Tyr Lys Cys Lys Val Ser Asn Lys Gly Leu Pro Ser Ser Ile Glu Lys
                325              330              335
Thr Ile Ser Lys Thr Lys Gly Gln Pro Arg Glu Pro Gln Val Tyr Thr
                340              345              350
Leu Pro Pro Ser Arg Glu Glu Met Thr Lys Asn Gln Val Ser Leu Thr
            355              360              365
Cys Leu Val Lys Gly Phe Tyr Pro Ser Asp Ile Ala Val Glu Trp Glu
        370              375              380
Ser Asn Gly Gln Pro Glu Asn Asn Tyr Lys Thr Thr Pro Pro Met Leu
385             390              395              400
Asp Ser Asp Gly Ser Phe Phe Leu Tyr Ser Lys Leu Thr Val Asp Lys
                405              410              415
Ser Arg Trp Gln Gln Gly Asn Val Phe Ser Cys Ser Val Met His Glu
            420              425              430
Ala Leu His Asn His Tyr Thr Gln Lys Ser Leu Ser Leu Ser Pro Gly
        435              440              445
Lys

<210> SEQ ID NO 225
<211> LENGTH: 214
<212> TYPE: PRT
<213> ORGANISM: Artificial sequence
<220> FEATURE:
<223> OTHER INFORMATION: LC of PD1B184

<400> SEQUENCE: 225

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Arg Asn Tyr
            20                  25                  30
Leu Ala Trp Tyr Gln Gln Lys Pro Gly Gln Ala Pro Arg Leu Leu Ile
        35                  40                  45
His Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Asn Tyr Trp Pro Leu
                85                  90                  95
```

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 226
<211> LENGTH: 449
<212> TYPE: PRT
<213> ORGANISM: Artificial sequence
<220> FEATURE:
<223> OTHER INFORMATION: HC of PD1B185

<400> SEQUENCE: 226

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Tyr Asp Thr Gly Ser Leu Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
            195                 200                 205

Asp His Lys Pro Ser Asn Thr Lys Val Asp Lys Thr Val Glu Arg Lys
            210                 215                 220

Cys Cys Val Glu Cys Pro Pro Cys Pro Ala Pro Ala Ala Ala Ser
225                 230                 235                 240
```

```
Ser Val Phe Leu Phe Pro Pro Lys Pro Lys Asp Thr Leu Met Ile Ser
            245             250             255

Arg Thr Pro Glu Val Thr Cys Val Val Val Asp Val Ser Ala Glu Asp
            260             265             270

Pro Glu Val Gln Phe Asn Trp Tyr Val Asp Gly Val Glu Val His Asn
            275             280             285

Ala Lys Thr Lys Pro Arg Glu Glu Gln Phe Asn Ser Thr Phe Arg Val
            290             295             300

Val Ser Val Leu Thr Val Leu His Gln Asp Trp Leu Asn Gly Lys Glu
305             310             315             320

Tyr Lys Cys Lys Val Ser Asn Lys Gly Leu Pro Ser Ser Ile Glu Lys
            325             330             335

Thr Ile Ser Lys Thr Lys Gly Gln Pro Arg Glu Pro Gln Val Tyr Thr
            340             345             350

Leu Pro Pro Ser Arg Glu Glu Met Thr Lys Asn Gln Val Ser Leu Thr
            355             360             365

Cys Leu Val Lys Gly Phe Tyr Pro Ser Asp Ile Ala Val Glu Trp Glu
            370             375             380

Ser Asn Gly Gln Pro Glu Asn Asn Tyr Lys Thr Thr Pro Pro Met Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys

<210> SEQ ID NO 227
<211> LENGTH: 214
<212> TYPE: PRT
<213> ORGANISM: Artificial sequence
<220> FEATURE:
<223> OTHER INFORMATION: LC of PD1B185

<400> SEQUENCE: 227

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Asn Tyr
            20                  25                  30

Leu Ala Trp Tyr Gln Gln Lys Pro Gly Gln Ala Pro Arg Leu Leu Ile
            35                  40                  45

Tyr Asp Ala Ser Asp Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Val Tyr Tyr Cys Gln Gln Arg Trp Asn Trp Pro Leu
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 228
<211> LENGTH: 449
<212> TYPE: PRT
<213> ORGANISM: Artificial sequence
<220> FEATURE:
<223> OTHER INFORMATION: HC of PD1B192

<400> SEQUENCE: 228

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Ala Tyr Asp Thr Gly Ser Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Ala Ala Ala Ser
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Ala Glu Asp
            260                 265                 270

Pro Glu Val Gln Phe Asn Trp Tyr Val Asp Gly Val Glu Val His Asn
        275                 280                 285
```

```
Ala Lys Thr Lys Pro Arg Glu Glu Gln Phe Asn Ser Thr Phe Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 229
<211> LENGTH: 214
<212> TYPE: PRT
<213> ORGANISM: Artificial sequence
<220> FEATURE:
<223> OTHER INFORMATION: LC or PD1B192

<400> SEQUENCE: 229

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Ser Tyr
            20                  25                  30

Leu Ala Trp Tyr Gln Gln Lys Pro Gly Gln Ala Pro Arg Leu Leu Ile
        35                  40                  45

His Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Tyr Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
                   195                 200                 205

Phe Asn Arg Gly Glu Cys
    210

<210> SEQ ID NO 230
<211> LENGTH: 120
<212> TYPE: PRT
<213> ORGANISM: Artificial sequence
<220> FEATURE:
<223> OTHER INFORMATION: Keytryda VH

<400> SEQUENCE: 230

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 231
<211> LENGTH: 111
<212> TYPE: PRT
<213> ORGANISM: Artificial sequence
<220> FEATURE:
<223> OTHER INFORMATION: Keytruda VL

<400> SEQUENCE: 231

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 232
<211> LENGTH: 113
<212> TYPE: PRT
<213> ORGANISM: Artificial sequence
<220> FEATURE:
<223> OTHER INFORMATION: Nivolumab VH

<400> SEQUENCE: 232
```

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 233
<211> LENGTH: 107
<212> TYPE: PRT
<213> ORGANISM: Artificial sequence
<220> FEATURE:
<223> OTHER INFORMATION: Nivolumab VL

<400> SEQUENCE: 233

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 234
<211> LENGTH: 121
<212> TYPE: PRT
<213> ORGANISM: Artificial sequence
<220> FEATURE:
<223> OTHER INFORMATION: Durvalumab VH

<400> SEQUENCE: 234

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 235
<211> LENGTH: 108
<212> TYPE: PRT
<213> ORGANISM: Artificial sequence
<220> FEATURE:
<223> OTHER INFORMATION: Durvalumab VL

<400> SEQUENCE: 235

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 236
<211> LENGTH: 118
<212> TYPE: PRT
<213> ORGANISM: Artificial sequence
<220> FEATURE:
<223> OTHER INFORMATION: Atezolizumab VH

<400> SEQUENCE: 236

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 237
<211> LENGTH: 107
<212> TYPE: PRT

<213> ORGANISM: Artificial sequence
<220> FEATURE:
<223> OTHER INFORMATION: Atezolizumab VL

<400> SEQUENCE: 237

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 238
<211> LENGTH: 120
<212> TYPE: PRT
<213> ORGANISM: Artificial sequence
<220> FEATURE:
<223> OTHER INFORMATION: Avelumab VH

<400> SEQUENCE: 238

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 239
<211> LENGTH: 110
<212> TYPE: PRT
<213> ORGANISM: Artificial sequence
<220> FEATURE:
<223> OTHER INFORMATION: Avelumab VL

<400> SEQUENCE: 239

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

```
Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 240
<211> LENGTH: 443
<212> TYPE: PRT
<213> ORGANISM: Artificial Sequence
<220> FEATURE:
<223> OTHER INFORMATION: TM3B105 Heavy chain

<400> SEQUENCE: 240

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Tyr Ala Pro Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Thr Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Ala Ala Ala Ser Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Ala Glu Asp Pro Glu Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300
```

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Thr Lys
            325                 330                 335

Gly Gln Pro Arg Glu Pro Gln Val Tyr Thr Leu Pro Pro Ser Arg Glu
        340                 345                 350

Glu Met Thr Lys Asn Gln Val Ser Leu Thr Cys Leu Val Lys Gly Phe
    355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
        420                 425                 430

Thr Gln Lys Ser Leu Ser Leu Ser Pro Gly Lys
    435                 440

<210> SEQ ID NO 241
<211> LENGTH: 449
<212> TYPE: PRT
<213> ORGANISM: Artificial sequence
<220> FEATURE:
<223> OTHER INFORMATION: Bispecific mAb HC1

<400> SEQUENCE: 241

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Tyr Asp Thr Gly Ser Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Leu Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 242
<211> LENGTH: 444
<212> TYPE: PRT
<213> ORGANISM: Artificial sequence
<220> FEATURE:
<223> OTHER INFORMATION: Bispecific mAb HC1

<400> SEQUENCE: 242

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Arg Tyr
            20                  25                  30

Asp Met Ser Trp Val Arg Gln Ala Pro Gly Lys Gly Leu Glu Ser Val
        35                  40                  45

Ala Tyr Ile Ser Gly Gly Gly Ala Asn Thr Tyr Tyr Leu Asp Asn Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Leu Ser Tyr Phe Asp Val Trp Gly Gln Gly Thr Leu
            100                 105                 110

Val Thr Val Ser Ser Ala Ser Thr Lys Gly Pro Ser Val Phe Pro Leu
        115                 120                 125

```
Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 243
<211> LENGTH: 450
<212> TYPE: PRT
<213> ORGANISM: Artificial sequence
<220> FEATURE:
<223> OTHER INFORMATION: Bispecific mAb HC1

<400> SEQUENCE: 243

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45
```

```
Gly Gly Ile Ile Pro Ile Phe Asp Thr Ala Asn Tyr Ala Gln Lys Phe
 50                  55                      60

Gln Gly Arg Val Thr Ile Thr Ala Asp Glu Ser Thr Ser Thr Ala Tyr
 65                  70                      75                  80

Met Glu Leu Ser Ser Leu Arg Ser Glu Asp Thr Ala Val Tyr Tyr Cys
                 85                      90                  95

Ala Arg Pro Gly Leu Ala Ala Tyr Asp Thr Gly Ser Leu Asp Tyr
             100                 105                 110

Trp Gly Gln Gly Thr Leu Val Thr Val Ser Ser Ala Ser Thr Lys Gly
             115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Lys Thr Tyr Thr Cys Asn Val
             195                 200                 205

Asp His Lys Pro Ser Asn Thr Lys Val Asp Lys Arg Val Glu Ser Lys
210                 215                 220

Tyr Gly Pro Pro Cys Pro Cys Pro Ala Pro Glu Phe Leu Gly Gly
225                 230                 235                 240

Pro Ser Val Phe Leu Phe Pro Pro Lys Pro Lys Asp Thr Leu Met Ile
             245                 250                 255

Ser Arg Thr Pro Glu Val Thr Cys Val Val Val Asp Val Ser Gln Glu
             260                 265                 270

Asp Pro Glu Val Gln Phe Asn Trp Tyr Val Asp Gly Val Glu Val His
             275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Gln Glu Glu Met Thr Lys Asn Gln Val Ser Leu
             355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                 405                 410                 415

Lys Ser Arg Trp Gln Glu Gly Asn Val Phe Ser Cys Ser Val Met His
                 420                 425                 430

Glu Ala Leu His Asn His Tyr Thr Gln Lys Ser Leu Ser Leu Ser Leu
             435                 440                 445

Gly Lys
450
```

```
<210> SEQ ID NO 244
<211> LENGTH: 450
<212> TYPE: PRT
<213> ORGANISM: Artificial sequence
<220> FEATURE:
<223> OTHER INFORMATION: Bispecific mAb HC2

<400> SEQUENCE: 244
```

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Pro | Gly | Glu |
| 1 | | | | 5 | | | | | 10 | | | | | 15 |
| Ser | Leu | Lys | Ile | Ser | Cys | Lys | Gly | Ser | Gly | Tyr | Ser | Phe | Thr | Ser | Tyr |
| | | | 20 | | | | | 25 | | | | | 30 |
| Trp | Met | Gln | Trp | Val | Arg | Gln | Met | Pro | Gly | Lys | Gly | Leu | Glu | Trp | Met |
| | | 35 | | | | | 40 | | | | | 45 |
| Gly | Ala | Ile | Tyr | Pro | Gly | Asp | Gly | Asp | Ile | Arg | Tyr | Thr | Gln | Asn | Phe |
| 50 | | | | | 55 | | | | | 60 |
| Lys | Gly | Gln | Val | Thr | Ile | Ser | Ala | Asp | Lys | Ser | Ile | Ser | Thr | Ala | Tyr |
| 65 | | | | | 70 | | | | | 75 | | | | | 80 |
| Leu | Gln | Trp | Ser | Ser | Leu | Lys | Ala | Ser | Asp | Thr | Ala | Met | Tyr | Tyr | Cys |
| | | | | 85 | | | | | 90 | | | | | 95 |
| Ala | Arg | Trp | Glu | Lys | Ser | Thr | Thr | Val | Val | Gln | Arg | Asn | Tyr | Phe | Asp |
| | | | 100 | | | | | 105 | | | | | 110 |
| Tyr | Trp | Gly | Gln | Gly | Thr | Thr | Val | Thr | Val | Ser | Ser | Ala | Ser | Thr | Lys |
| | | | 115 | | | | | 120 | | | | | 125 |
| Gly | Pro | Ser | Val | Phe | Pro | Leu | Ala | Pro | Cys | Ser | Arg | Ser | Thr | Ser | Glu |
| 130 | | | | | 135 | | | | | 140 |
| Ser | Thr | Ala | Ala | Leu | Gly | Cys | Leu | Val | Lys | Asp | Tyr | Phe | Pro | Glu | Pro |
| 145 | | | | | 150 | | | | | 155 | | | | | 160 |
| Val | Thr | Val | Ser | Trp | Asn | Ser | Gly | Ala | Leu | Thr | Ser | Gly | Val | His | Thr |
| | | | | 165 | | | | | 170 | | | | | 175 |
| Phe | Pro | Ala | Val | Leu | Gln | Ser | Ser | Gly | Leu | Tyr | Ser | Leu | Ser | Ser | Val |
| | | | 180 | | | | | 185 | | | | | 190 |
| Val | Thr | Val | Pro | Ser | Ser | Asn | Phe | Gly | Thr | Gln | Thr | Tyr | Thr | Cys | Asn |
| | | | 195 | | | | | 200 | | | | | 205 |
| Val | Asp | His | Lys | Pro | Ser | Asn | Thr | Lys | Val | Asp | Lys | Thr | Val | Glu | Arg |
| 210 | | | | | 215 | | | | | 220 |
| Lys | Cys | Cys | Val | Glu | Cys | Pro | Pro | Cys | Pro | Ala | Pro | Pro | Val | Ala | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 |
| Ser | Arg | Thr | Pro | Glu | Val | Thr | Cys | Val | Val | Val | Asp | Val | Ser | His | Glu |
| | | | 260 | | | | | 265 | | | | | 270 |
| Asp | Pro | Glu | Val | Gln | Phe | Asn | Trp | Tyr | Val | Asp | Gly | Val | Glu | Val | His |
| | | | 275 | | | | | 280 | | | | | 285 |
| Asn | Ala | Lys | Thr | Lys | Pro | Arg | Glu | Glu | Gln | Phe | Asn | Ser | Thr | Phe | Arg |
| 290 | | | | | 295 | | | | | 300 |
| Val | Val | Ser | Val | Leu | Thr | Val | Val | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Gly | Leu | Pro | Ala | Pro | Ile | Glu |
| | | | | 325 | | | | | 330 | | | | | 335 |
| Lys | Thr | Ile | Ser | Lys | Thr | Lys | Gly | Gln | Pro | Arg | Glu | Pro | Gln | Val | Tyr |
| | | | 340 | | | | | 345 | | | | | 350 |
| Thr | Leu | Pro | Pro | Ser | Arg | Glu | Glu | Met | Thr | Lys | Asn | Gln | Val | Ser | Leu |
| | | | | 355 | | | | | 360 | | | | | 365 |
| Thr | Cys | Leu | Val | Lys | Gly | Phe | Tyr | Pro | Ser | Asp | Ile | Ala | Val | Glu | Trp |

```
                    370                 375                 380
Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 245
<211> LENGTH: 443
<212> TYPE: PRT
<213> ORGANISM: Artificial sequence
<220> FEATURE:
<223> OTHER INFORMATION: Bispecific mAb HC2

<400> SEQUENCE: 245

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Tyr Ala Pro Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
```

```
              275                 280                 285
Glu Glu Gln Phe Asn Ser Thr Phe Arg Val Val Ser Val Leu Thr Val
    290                 295                 300
Val His Gln Asp Trp Leu Asn Gly Lys Glu Tyr Lys Cys Lys Val Ser
305                 310                 315                 320
Asn Lys Gly Leu Pro Ala Pro Ile Glu Lys Thr Ile Ser Lys Thr Lys
                325                 330                 335
Gly Gln Pro Arg Glu Pro Gln Val Tyr Thr Leu Pro Pro Ser Arg Glu
                340                 345                 350
Glu Met Thr Lys Asn Gln Val Ser Leu Thr Cys Leu Val Lys Gly Phe
                355                 360                 365
Tyr Pro Ser Asp Ile Ala Val Glu Trp Glu Ser Asn Gly Gln Pro Glu
                370                 375                 380
Asn Asn Tyr Lys Thr Thr Pro Pro Met Leu Asp Ser Asp Gly Ser Phe
385                 390                 395                 400
Phe Leu Tyr Ser Arg Leu Thr Val Asp Lys Ser Arg Trp Gln Gln Gly
                405                 410                 415
Asn Val Phe Ser Cys Ser Val Met His Glu Ala Leu His Asn His Tyr
                420                 425                 430
Thr Gln Lys Ser Leu Ser Leu Ser Pro Gly Lys
                435                 440

<210> SEQ ID NO 246
<211> LENGTH: 444
<212> TYPE: PRT
<213> ORGANISM: Artificial sequence
<220> FEATURE:
<223> OTHER INFORMATION: Bispecific mAb HC2

<400> SEQUENCE: 246

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Ser Pro Tyr Ala Pro Leu Asp Tyr Trp Gly Gln Gly Thr Leu
                100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Lys Thr Tyr Thr Cys Asn Val Asp His Lys Pro Ser Asn
```

```
                    195                 200                 205
Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Leu Leu Tyr Ser Lys Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 247
<211> LENGTH: 451
<212> TYPE: PRT
<213> ORGANISM: Artificial sequence
<220> FEATURE:
<223> OTHER INFORMATION: Bispecific mAb HC2

<400> SEQUENCE: 247

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Met Gln Trp Val Arg Gln Met Pro Gly Lys Gly Leu Glu Trp Met
            35                  40                  45

Gly Ala Ile Tyr Pro Gly Asp Gly Asp Ile Arg Tyr Thr Gln Asn Phe
        50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Glu Lys Ser Thr Thr Val Val Gln Arg Asn Tyr Phe Asp
            100                 105                 110

Tyr Trp Gly Gln Gly Thr Thr Val Thr Val Ser Ser Ala Ser Thr Lys
```

```
            115                 120                 125
Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Leu Leu Tyr Ser Lys Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 248
<211> LENGTH: 443
<212> TYPE: PRT
<213> ORGANISM: Artificial sequence
<220> FEATURE:
<223> OTHER INFORMATION: Bispecific mAb HC2

<400> SEQUENCE: 248

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20                  25                  30
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Tyr Ala Pro Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Ala Ala Ser Ser Val Phe Leu Phe Pro Pro
225                 230                 235                 240

Pro Lys Pro Lys Asp Thr Leu Met Ile Ser Arg Thr Pro Glu Val Thr
                245                 250                 255

Cys Val Val Val Asp Val Ser Ala Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Arg Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440
```

<210> SEQ ID NO 249
<211> LENGTH: 455
<212> TYPE: PRT
<213> ORGANISM: Artificial sequence
<220> FEATURE:
<223> OTHER INFORMATION: EM1 mAb HC1

<400> SEQUENCE: 249

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365
```

```
Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 250
<211> LENGTH: 214
<212> TYPE: PRT
<213> ORGANISM: Artificial sequence
<220> FEATURE:
<223> OTHER INFORMATION: EM1 mAb LC1

<400> SEQUENCE: 250

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 251
<211> LENGTH: 449
<212> TYPE: PRT
<213> ORGANISM: Artificial sequence
<220> FEATURE:
<223> OTHER INFORMATION: EM1 mAb HC2
```

<400> SEQUENCE: 251

Gln Val Gln Leu Val Gln Ser Gly Ala Glu Val Lys Lys Pro Gly Ala
1               5                   10                  15

Ser Val Lys Val Ser Cys Glu Thr Ser Gly Tyr Thr Phe Thr Ser Tyr
            20                  25                  30

Gly Ile Ser Trp Val Arg Gln Ala Pro Gly His Gly Leu Glu Trp Met
        35                  40                  45

Gly Trp Ile Ser Ala Tyr Asn Gly Tyr Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Arg Gly Thr Asn Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 252
<211> LENGTH: 214
<212> TYPE: PRT
<213> ORGANISM: Artificial sequence
<220> FEATURE:
<223> OTHER INFORMATION: EM1 mAb LC2

<400> SEQUENCE: 252

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 253
<211> LENGTH: 1807
<212> TYPE: DNA
<213> ORGANISM: Artificial sequence
<220> FEATURE:
<223> OTHER INFORMATION: PTBB28 HC1 DNA

<400> SEQUENCE: 253
cagctgagtt gttgtgttct gataagagtc agaggtaact cccgttgcgg tgctgttaac    60
ggtggagggc agtgtagtct gagcagtact cgttgctgcc gcgcgcgcca ccagacataa   120
tagctgacag actaacagac tgttcctttc catgggtctt ttctgcagtc accgtccttg   180
acacgaagct tgccgccacc atggcttggg tgtggacctt gctattcctg atggcagctg   240

| | |
|---|---|
| cccaaagtat acaggcccag gtgcagctgg tgcagagcgg cgcggaagtg aaaaaaccgg | 300 |
| gcagcagcgt gaaagtgagc tgcaaagcga gcggcggcac ctttagcagc tatgcgatta | 360 |
| gctgggtgcg ccaggcgccg ggccagggcc tggaatggat gggcggcatt attccgattt | 420 |
| ttgacaccgc gaactatgcg cagaaatttc agggccgcgt gaccattacc gcggatgaaa | 480 |
| gcaccagcac cgcgtatatg aactgagca gcctgcgcag cgaagatacc gcggtgtatt | 540 |
| attgcgcgcg ccctggtctc gctgcggctt atgatactgg ttccttggac tattggggcc | 600 |
| agggcaccct ggtgaccgtg agcagcgcct ccaccaaggg cccatcggtc ttccccctgg | 660 |
| cgccctgctc caggagcacc tccgagagca gcccgccct gggctgcctg gtcaaggact | 720 |
| acttccccga accggtgacg gtgtcgtgga actcaggcgc tctgaccagc ggcgtgcaca | 780 |
| ccttcccagc tgtcctacag tcctcaggac tctactccct cagcagcgtg gtgaccgtgc | 840 |
| cctccagcaa cttcggcacc cagacctaca cctgcaacgt agatcacaag cccagcaaca | 900 |
| ccaaggtgga caagacagtt gagcgcaaat gttgtgtcga gtgcccaccg tgcccagcac | 960 |
| cacctgtggc aggaccgtca gtcttcctct tccccccaaa acccaaggac accctcatga | 1020 |
| tctcccggac ccctgaggtc acgtgcgtgg tggtggacgt gagccacgaa gaccccgagg | 1080 |
| tccagttcaa ctggtacgtg gacggcgtgg aggtgcataa tgccaagaca aagccacggg | 1140 |
| aggagcagtt caacagcacg ttccgtgtgg tcagcgtcct caccgttgtg caccaggact | 1200 |
| ggctgaacgg caaggagtac aagtgcaagg tctccaacaa aggcctccca gcccccatcg | 1260 |
| agaaaaccat ctccaaaacc aaagggcagc ccgagaacc acaggtgtac accctgcccc | 1320 |
| catcccggga ggagatgacc aagaaccagg tcagcctgac ctgcctggtc aaaggcttct | 1380 |
| accccagcga catcgccgtg gagtgggaga gcaatgggca gccggagaac aactacaaga | 1440 |
| ccacacctcc catgctggac tccgacggct ccttcctgct ctacagcaag ctcaccgtgg | 1500 |
| acaagagcag gtggcagcag gggaacgtct tctcatgctc cgtgatgcat gaggctctgc | 1560 |
| acaaccacta cacgcagaag agcctctccc tgtctccggg taaatgatag ttcgaattca | 1620 |
| ttgatcataa tcagccatac cacatttgta gaggttttac ttgctttaaa aaacctccca | 1680 |
| cacctccccc tgaacctgaa acataaaatg aatgcaattg ttgttgttaa cttgtttatt | 1740 |
| gcagcttata atggttacaa ataaagcaat agcatcacaa atttcacaaa taaagcattt | 1800 |
| ttttcac | 1807 |

```
<210> SEQ ID NO 254
<211> LENGTH: 1105
<212> TYPE: DNA
<213> ORGANISM: Artificial sequence
<220> FEATURE:
<223> OTHER INFORMATION: PTBB28 LC1 DNA

<400> SEQUENCE: 254
```

| | |
|---|---|
| cagctgagtt gttgtgttct gataagagtc agaggtaact cccgttgcgg tgctgttaac | 60 |
| ggtggagggc agtgtagtct gagcagtact cgttgctgcc gcgcgcgcca ccagacataa | 120 |
| tagctgacag actaacagac tgttcctttc catgggtctt ttctgcagtc accgtccttg | 180 |
| acacgaagct tgccgccacc atggagacac attctcaggt cttttgtatac atgttgctgt | 240 |
| ggttgtctgg tgtcgaggga gaaattgtgc tgacccagag cccggcgacc ctgagcctga | 300 |
| gcccgggcga acgcgcgacc ctgagctgcc gcgcgagcca gagcgttcgc tcctacctgg | 360 |
| cgtggtatca gcagaaaccg ggccaggcgc gcgcctgct gatctacgac gcgagcaatc | 420 |
| gtgcgaccgg cattccggcg cgctttagcg gctccggtag cggcaccgat tttaccctga | 480 |

| | |
|---|---|
| ccattagcag cctggaaccg gaagattttg cggtgtatta ttgccagcaa cgtaattatt | 540 |
| ggccgctgac ctttggccag ggcaccaaag tggaaattaa acgtacggtg gctgcaccat | 600 |
| ctgtcttcat cttcccgcca tctgatgagc agttgaaatc tggaactgcc tctgttgtgt | 660 |
| gcctgctgaa taacttctat cccagagagg ccaaagtaca gtggaaggtg gataacgccc | 720 |
| tccaatcggg taactcccag gagagtgtca cagagcagga cagcaaggac agcacctaca | 780 |
| gcctcagcag cacccctgacg ctgagcaaag cagactacga gaaacacaaa gtctacgcct | 840 |
| gcgaagtcac ccatcagggc ctgagctcgc ccgtcacaaa gagcttcaac aggggagagt | 900 |
| gttagtgatt cgaatgatca taatcagcca taccacattt gtagaggttt tacttgcttt | 960 |
| aaaaaacctc ccacacctcc ccctgaacct gaaacataaa atgaatgcaa ttgttgttgt | 1020 |
| taacttgttt attgcagctt ataatggtta caaataaagc aatagcatca caaatttcac | 1080 |
| aaataaagca ttttttttcac tgcat | 1105 |

<210> SEQ ID NO 255
<211> LENGTH: 1789
<212> TYPE: DNA
<213> ORGANISM: Artificial sequence
<220> FEATURE:
<223> OTHER INFORMATION: PTBB28 HC2 DNA

<400> SEQUENCE: 255

| | |
|---|---|
| cagctgagtt gttgtgttct gataagagtc agaggtaact cccgttgcgg tgctgttaac | 60 |
| ggtggagggc agtgtagtct gagcagtact cgttgctgcc gcgcgcgcca ccagacataa | 120 |
| tagctgacag actaacagac tgttcctttc catgggtctt ttctgcagtc accgtccttg | 180 |
| acacgaagct tgccgccacc atggcttggg tgtggacctt gctattcctg atggcagctg | 240 |
| cccaaagtat acaggccgaa gtgcagctgc tggaaagcgg cggcggcctg gtgcagccgg | 300 |
| gcggcagcct gcgcctgagc tgcgcggcaa gcggctttac ctttagcagc tatgcgatga | 360 |
| gctgggtgcg ccaggcgccg ggcaaaggcc tggaatgggt gagcgcgatt agcggcagcg | 420 |
| gcggcagcac ctattatgcg gatagcgtga aaggccgctt taccattagc cgcgataaca | 480 |
| gcaaaaacac cctgtatctg cagatgaaca gcctgcgcgc ggaagatacc gcggtgtatt | 540 |
| attgcgcgaa atccccgtac gcgcccttgg actattgggg ccagggcacc ctggtgaccg | 600 |
| tgagcagcgc ctccaccaag ggcccatcgg tcttccccct ggcgccctgc tccaggagca | 660 |
| cctccgagag cacagccgcc ctgggctgcc tggtcaagga ctacttcccc gaaccggtga | 720 |
| cggtgtcgtg gaactcaggc gctctgacca gcggcgtgca caccttccca gctgtcctac | 780 |
| agtcctcagg actctactcc ctcagcagcg tggtgaccgt gccctccagc aacttcggca | 840 |
| cccagaccta cacctgcaac gtagatcaca agcccagcaa caccaaggtg gacaagacag | 900 |
| ttgagcgcaa atgttgtgtc gagtgcccac cgtgcccagc accacctgtg gcaggaccgt | 960 |
| cagtcttcct cttccccca aaacccaagg acaccctcat gatctcccgg acccctgagg | 1020 |
| tcacgtgcgt ggtggtggac gtgagccacg aagacccga ggtccagttc aactggtacg | 1080 |
| tggacggcgt ggaggtgcat aatgccaaga caaagccacg ggaggagcag ttcaacagca | 1140 |
| cgttccgtgt ggtcagcgtc ctcaccgttg tgcaccagga ctggctgaac ggcaaggagt | 1200 |
| acaagtgcaa ggtctccaac aaaggcctcc cagcccccat cgagaaaacc atctccaaaa | 1260 |
| ccaaagggca gccccgagaa ccacaggtgt acaccctgcc cccatcccgg gaggagatga | 1320 |
| ccaagaacca ggtcagcctg acctgcctgg tcaaaggctt ctaccccagc gacatcgccg | 1380 |

| | |
|---|---|
| tggagtggga gagcaatggg cagccggaga acaactacaa gaccacacct cccatgctgg | 1440 |
| actccgacgg ctccttcttc ctctacagcc ggctcaccgt ggacaagagc aggtggcagc | 1500 |
| aggggaacgt cttctcatgc tccgtgatgc atgaggctct gcacaaccac tacacgcaga | 1560 |
| agagcctctc cctgtctccg ggtaaatgat agttcgaatt cattgatcat aatcagccat | 1620 |
| accacatttg tagaggtttt acttgcttta aaaaacctcc cacacctccc cctgaacctg | 1680 |
| aaacataaaa tgaatgcaat tgttgttgtt aacttgttta ttgcagctta taatggttac | 1740 |
| aaataaagca atagcatcac aaatttcaca aataaagcat ttttttcac | 1789 |

<210> SEQ ID NO 256
<211> LENGTH: 1105
<212> TYPE: DNA
<213> ORGANISM: Artificial sequence
<220> FEATURE:
<223> OTHER INFORMATION: PTBB28 LC2 DNA

<400> SEQUENCE: 256

| | |
|---|---|
| cagctgagtt gttgtgttct gataagagtc agaggtaact cccgttgcgg tgctgttaac | 60 |
| ggtggagggc agtgtagtct gagcagtact cgttgctgcc gcgcgcgcca ccagacataa | 120 |
| tagctgacag actaacagac tgttcctttc catgggtctt ttctgcagtc accgtccttg | 180 |
| acacgaagct tgccgccacc atggagacac attctcaggt cttgtatac atgttgctgt | 240 |
| ggttgtctgg tgtcgaggga gaaattgtgc tgacccagag cccggcgacc ctgagcctga | 300 |
| gcccgggcga acgcgcgacc cttagctgcc gtgcaagtca gagtgtgaac gactacctgg | 360 |
| cgtggtatca gcagaaaccg ggccaggcgc gcgcctgct gatttatgat gcgagcaacc | 420 |
| gcgcgaccgg cattccggcg cgctttagcg gcagcggcag cggcaccgat tttaccctga | 480 |
| ccattagcag cctggaaccg gaagattttg cggtgtatta ttgccagcag ggtggtcacg | 540 |
| cgccgatcac ctttggccag ggcaccaaag tggaaattaa acgtacggtg gctgcaccat | 600 |
| ctgtcttcat cttcccgcca tctgatgagc agttgaaatc tggaactgcc tctgttgtgt | 660 |
| gcctgctgaa taacttctat cccagagagg ccaaagtaca gtggaaggtg gataacgccc | 720 |
| tccaatcggg taactcccag gagagtgtca cagagcagga cagcaaggac agcacctaca | 780 |
| gcctcagcag caccctgacg ctgagcaaag cagactacga gaaacacaaa gtctacgcct | 840 |
| gcgaagtcac ccatcagggc ctgagctcgc ccgtcacaaa gagcttcaac aggggagagt | 900 |
| gttagtgatt cgaatgatca taatcagcca taccacattt gtagaggttt tacttgctt | 960 |
| aaaaaacctc ccacacctcc cctgaacct gaaacataaa atgaatgcaa ttgttgttgt | 1020 |
| taacttgttt attgcagctt ataatggtta caaataaagc aatagcatca caaatttcac | 1080 |
| aaataaagca ttttttcac tgcat | 1105 |

<210> SEQ ID NO 257
<211> LENGTH: 1807
<212> TYPE: DNA
<213> ORGANISM: Artificial sequence
<220> FEATURE:
<223> OTHER INFORMATION: PTBB30 HC1 DNA

<400> SEQUENCE: 257

| | |
|---|---|
| cagctgagtt gttgtgttct gataagagtc agaggtaact cccgttgcgg tgctgttaac | 60 |
| ggtggagggc agtgtagtct gagcagtact cgttgctgcc gcgcgcgcca ccagacataa | 120 |
| tagctgacag actaacagac tgttcctttc catgggtctt ttctgcagtc accgtccttg | 180 |
| acacgaagct tgccgccacc atggcttggg tgtggacctt gctattcctg atggcagctg | 240 |

```
cccaaagtat acaggcccag gtgcagctgg tgcagagcgg cgcggaagtg aaaaaaccgg      300
gcagcagcgt gaaagtgagc tgcaaagcga gcggcggcac ctttagcagc tatgcgatta      360
gctgggtgcg ccaggcgccg ggccagggcc tggaatggat gggcggcatt attccgattt      420
ttgacaccgc gaactatgcg cagaaatttc agggccgcgt gaccattacc gcggatgaaa      480
gcaccagcac cgcgtatatg gaactgagca gcctgcgcag cgaagatacc gcggtgtatt      540
attgcgcgcg ccctggtctc gctgcggctt atgatactgg ttccttggac tattggggcc      600
agggcaccct ggtgaccgtg agcagcgcct ccaccaaggg cccatcggtc ttccccctgg      660
cgccctgctc caggagcacc tccgagagca gcccgccct gggctgcctg gtcaaggact       720
acttccccga accggtgacg gtgtcgtgga actcaggcgc tctgaccagc ggcgtgcaca      780
ccttcccagc tgtcctacag tcctcaggac tctactccct cagcagcgtg gtgaccgtgc      840
cctccagcaa cttcggcacc cagacctaca cctgcaacgt agatcacaag cccagcaaca      900
ccaaggtgga caagacagtt gagcgcaaat gttgtgtcga gtgcccaccg tgcccagcac      960
cacctgccgc agccagctca gtcttcctct tccccccaaa acccaaggac accctcatga     1020
tctcccggac ccctgaggtc acgtgcgtgg tggtggacgt gagcgccgaa gaccccgagg     1080
tccagttcaa ctggtacgtg gacggcgtgg aggtgcataa tgccaagaca aagccacggg     1140
aggagcagtt caacagcacg ttccgtgtgg tcagcgtcct caccgttctg caccaggact     1200
ggctgaacgg caaggagtac aagtgcaagg tctccaacaa aggcctccca tcctccatcg     1260
agaaaaccat ctccaaaacc aaagggcagc ccgagaacc acaggtgtac accctgcccc      1320
catcccggga ggagatgacc aagaaccagg tcagcctgac ctgcctggtc aaaggcttct     1380
accccagcga catcgccgtg gagtgggaga gcaatgggca gccggagaac aactacaaga     1440
ccacacctcc catgctggac tccgacggct ccttcctgct ctacagcaag ctcaccgtgg     1500
acaagagcag gtggcagcag gggaacgtct tctcatgctc cgtgatgcat gaggctctgc     1560
acaaccacta cacgcagaag agcctctccc tgtctccggg taaatgatag ttcgaattca     1620
ttgatcataa tcagccatac cacatttgta gaggttttac ttgctttaaa aaacctccca     1680
cacctccccc tgaacctgaa acataaaatg aatgcaattg ttgttgttaa cttgtttatt     1740
gcagcttata atggttacaa ataaagcaat agcatcacaa atttcacaaa taaagcattt     1800
ttttcac                                                               1807
```

<210> SEQ ID NO 258
<211> LENGTH: 1105
<212> TYPE: DNA
<213> ORGANISM: Artificial sequence
<220> FEATURE:
<223> OTHER INFORMATION: PTBB30 LC1 DNA

<400> SEQUENCE: 258

```
cagctgagtt gttgtgttct gataagagtc agaggtaact cccgttgcgg tgctgttaac       60
ggtggagggc agtgtagtct gagcagtact cgttgctgcc gcgcgcgcca ccagacataa      120
tagctgacag actaacagac tgttcctttc catgggtctt ttctgcagtc accgtccttg      180
acacgaagct tgccgccacc atggagacac attctcaggt ctttgtatac atgttgctgt      240
ggttgtctgg tgtcgaggga gaaattgtgc tgacccagag cccggcgacc ctgagcctga      300
gcccgggcga acgcgcgacc ctgagctgcc gcgcagccca gagcgttcgc tcctacctgg      360
cgtggtatca gcagaaaccg ggccaggcgc cgcgcctgct gatctacgac gcgagcaatc      420
```

| | |
|---|---|
| gtgcgaccgg cattccggcg cgctttagcg gctccggtag cggcaccgat tttaccctga | 480 |
| ccattagcag cctggaaccg gaagattttg cggtgtatta ttgccagcaa cgtaattatt | 540 |
| ggccgctgac ctttggccag ggcaccaaag tggaaattaa acgtacggtg ctgcaccat | 600 |
| ctgtcttcat cttcccgcca tctgatgagc agttgaaatc tggaactgcc tctgttgtgt | 660 |
| gcctgctgaa taacttctat cccagagagg ccaaagtaca gtggaaggtg gataacgccc | 720 |
| tccaatcggg taactcccag gagagtgtca cagagcagga cagcaaggac agcacctaca | 780 |
| gcctcagcag caccctgacg ctgagcaaag cagactacga gaaacacaaa gtctacgcct | 840 |
| gcgaagtcac ccatcagggc ctgagctcgc ccgtcacaaa gagcttcaac aggggagagt | 900 |
| gttagtgatt cgaatgatca taatcagcca taccacattt gtagaggttt tacttgcttt | 960 |
| aaaaaacctc ccacacctcc ccctgaacct gaaacataaa atgaatgcaa ttgttgttgt | 1020 |
| taacttgttt attgcagctt ataatggtta caaataaagc aatagcatca caaatttcac | 1080 |
| aaataaagca ttttttcac tgcat | 1105 |

```
<210> SEQ ID NO 259
<211> LENGTH: 1789
<212> TYPE: DNA
<213> ORGANISM: Artificial sequence
<220> FEATURE:
<223> OTHER INFORMATION: PTBB30 HC2 DNA

<400> SEQUENCE: 259
```

| | |
|---|---|
| cagctgagtt gttgtgttct gataagagtc agaggtaact cccgttgcgg tgctgttaac | 60 |
| ggtggagggc agtgtagtct gagcagtact cgttgctgcc gcgcgcgcca ccagacataa | 120 |
| tagctgacag actaacagac tgttcctttc catgggtctt ttctgcagtc accgtccttg | 180 |
| acacgaagct tgccgccacc atggcttggg tgtggacctt gctattcctg atggcagctg | 240 |
| cccaaagtat acaggccgaa gtgcagctgc tggaaagcgg cggcggcctg gtgcagccgg | 300 |
| gcggcagcct cgcgcctgagc tgcgcggcaa gcggctttac cttttagcagc tatgcgatga | 360 |
| gctgggtgcg ccaggcgccg ggcaaaggcc tggaatgggt gagcgcgatt agcggcagcg | 420 |
| gcggcagcac ctattatgcg gatagcgtga aaggccgctt taccattagc cgcgataaca | 480 |
| gcaaaaacac cctgtatctg cagatgaaca gcctgcgcgc ggaagatacc gcggtgtatt | 540 |
| attgcgcgaa atccccgtac gcgcccttgg actattgggg ccagggcacc ctggtgaccg | 600 |
| tgagcagcgc ctccaccaag ggcccatcgg tcttcccccct ggcgccctgc tccaggagca | 660 |
| cctccgagag cacagccgcc ctgggctgcc tggtcaagga ctacttcccc gaaccggtga | 720 |
| cggtgtcgtg gaactcaggc gctctgacca gcggcgtgca caccttccca gctgtcctac | 780 |
| agtcctcagg actctactcc ctcagcagcg tggtgaccgt gccctccagc aacttcggca | 840 |
| cccagaccta cacctgcaac gtagatcaca agcccagcaa caccaaggtg gacaagacag | 900 |
| ttgagcgcaa atgttgtgtc gagtgcccac cgtgcccagc accacctgcc gcagccagct | 960 |
| cagtcttcct cttccccca aaacccaagg acaccctcat gatctcccgg acccctgagg | 1020 |
| tcacgtgcgt ggtggtggac gtgagcgccg aagaccccga ggtccagttc aactggtacg | 1080 |
| tggacggcgt ggaggtgcat aatgccaaga caaagccacg ggaggagcag ttcaacagca | 1140 |
| cgttccgtgt ggtcagcgtc ctcaccgttc tgcaccagga ctggctgaac ggcaaggagt | 1200 |
| acaagtgcaa ggtctccaac aaaggcctcc catcctccat cgagaaaacc atctccaaaa | 1260 |
| ccaaagggca gccccgagaa ccacaggtgt acaccctgcc cccatcccgg gaggagatga | 1320 |
| ccaagaacca ggtcagcctg acctgcctgg tcaaaggctt ctaccccagc gacatcgccg | 1380 |

```
tggagtggga gagcaatggg cagccggaga acaactacaa gaccacacct cccatgctgg    1440
actccgacgg ctccttcttc ctctacagcc ggctcaccgt ggacaagagc aggtggcagc    1500
aggggaacgt cttctcatgc tccgtgatgc atgaggctct gcacaaccac tacacgcaga    1560
agagcctctc cctgtctccg ggtaaatgat agttcgaatt cattgatcat aatcagccat    1620
accacatttg tagaggtttt acttgcttta aaaaacctcc cacacctccc cctgaacctg    1680
aaacataaaa tgaatgcaat tgttgttgtt aacttgttta ttgcagctta taatggttac    1740
aaataaagca atagcatcac aaatttcaca aataaagcat tttttttcac                1789

<210> SEQ ID NO 260
<211> LENGTH: 1105
<212> TYPE: DNA
<213> ORGANISM: Artificial sequence
<220> FEATURE:
<223> OTHER INFORMATION: PTBB30 LC2 DNA

<400> SEQUENCE: 260
cagctgagtt gttgtgttct gataagagtc agaggtaact cccgttgcgg tgctgttaac      60
ggtggagggc agtgtagtct gagcagtact cgttgctgcc gcgcgcgcca ccagacataa     120
tagctgacag actaacagac tgttcctttc catgggtctt ttctgcagtc accgtccttg     180
acacgaagct tgccgccacc atggagacac attctcaggt cttgtatac atgttgctgt      240 ggttgtctgg tgtcgaggga gaaattgtgc tgacccagag cccggcgacc ctgagcctga     300
gcccgggcga acgcgcgacc cttagctgcc gtgcaagtca gagtgtgaac gactacctgg     360
cgtggtatca gcagaaaccg ggccaggcgc cgcgcctgct gatttatgat gcgagcaacc     420
gcgcgaccgg cattccggcg cgcttttagcg gcagcggcag cggcaccgat tttaccctga    480
ccattagcag cctggaaccg gaagattttg cggtgtatta ttgccagcag ggtggtcacg     540
cgccgatcac ctttggccag ggcaccaaag tggaaattaa acgtacggtg gctgcaccat     600
ctgtcttcat cttcccgcca tctgatgagc agttgaaatc tggaactgcc tctgttgtgt     660
gcctgctgaa taacttctat cccagagagg ccaaagtaca gtggaaggtg gataacgccc     720
tccaatcggg taactcccag gagagtgtca cagagcagga cagcaaggac agcacctaca     780
gcctcagcag caccctgacg ctgagcaaag cagactacga aaacacaaa gtctacgcct      840 gcgaagtcac ccatcagggc ctgagctcgc ccgtcacaaa gagcttcaac aggggagagt     900
gttagtgatt cgaatgatca taatcagcca taccacatttt gtagaggttt tacttgcttt    960
aaaaaacctc ccacacctcc ccctgaacct gaaacataaa tgaatgcaa ttgttgttgt     1020 taacttgttt attgcagctt ataatggtta caaataaagc aatagcatca caaatttcac    1080
aaataaagca ttttttttcac tgcat                                          1105

<210> SEQ ID NO 261
<211> LENGTH: 16
<212> TYPE: PRT
<213> ORGANISM: Homo sapiens

<400> SEQUENCE: 261

Trp Gly Lys Gly Ala Cys Pro Val Phe Glu Cys Gly Asn Val Val Leu
1               5                   10                  15

<210> SEQ ID NO 262
<211> LENGTH: 7
<212> TYPE: PRT
<213> ORGANISM: Homo sapiens
```

-continued

<400> SEQUENCE: 262

Asp Glu Arg Asp Val Asn Tyr
1               5

<210> SEQ ID NO 263
<211> LENGTH: 13
<212> TYPE: PRT
<213> ORGANISM: Homo sapiens

<400> SEQUENCE: 263

Arg Ile Gln Ile Pro Gly Ile Met Asn Asp Glu Lys Phe
1               5                   10

<210> SEQ ID NO 264
<211> LENGTH: 306
<212> TYPE: PRT
<213> ORGANISM: Homo sapiens

<400> SEQUENCE: 264

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Asp His Ile Pro
    210                 215                 220

Trp Ile Thr Ala Val Leu Pro Thr Val Ile Ile Cys Val Met Val Phe
225                 230                 235                 240

Cys Leu Ile Leu Trp Lys Trp Lys Lys Lys Arg Pro Arg Asn Ser
                245                 250                 255

Tyr Lys Cys Gly Thr Asn Thr Met Glu Arg Glu Glu Ser Glu Gln Thr
            260                 265                 270

Lys Lys Arg Glu Lys Ile His Ile Pro Glu Arg Ser Asp Glu Ala Gln
        275                 280                 285

```
Arg Val Phe Lys Ser Ser Lys Thr Ser Ser Cys Asp Lys Ser Asp Thr
    290                 295                 300

Cys Phe
305

<210> SEQ ID NO 265
<211> LENGTH: 254
<212> TYPE: PRT
<213> ORGANISM: Homo sapiens

<400> SEQUENCE: 265

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
            35                  40                  45

Ile Trp Pro Glu Tyr Lys Asn Arg Thr Ile Phe Asp Ile Thr Asn Asn
        50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Leu Leu Pro Ser Trp Ala Ile Thr Leu Ile Ser Val Asn Gly Ile Phe
    210                 215                 220

Val Ile Cys Cys Leu Thr Tyr Cys Phe Ala Pro Arg Cys Arg Glu Arg
225                 230                 235                 240

Arg Arg Asn Glu Arg Leu Arg Arg Glu Ser Val Arg Pro Val
                245                 250

<210> SEQ ID NO 266
<211> LENGTH: 202
<212> TYPE: PRT
<213> ORGANISM: Homo sapiens

<400> SEQUENCE: 266

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
                20                  25                  30

Phe Arg Ala Ser Leu His Lys Gly Leu Asp Ser Ala Val Glu Val Cys
            35                  40                  45
```

```
Val Val Tyr Gly Asn Tyr Ser Gln Gln Leu Gln Val Tyr Ser Lys Thr
 50                  55                  60

Gly Phe Asn Cys Asp Gly Lys Leu Gly Asn Glu Ser Val Thr Phe Tyr
 65                  70                  75                  80

Leu Gln Asn Leu Tyr Val Asn Gln Thr Asp Ile Tyr Phe Cys Lys Ile
                 85                  90                  95

Glu Val Met Tyr Pro Pro Pro Tyr Leu Asp Asn Glu Lys Ser Asn Gly
                100                 105                 110

Thr Ile Ile His Val Lys Gly Lys His Leu Cys Pro Ser Pro Leu Phe
                115                 120                 125

Pro Gly Pro Ser Lys Pro Phe Trp Val Leu Val Val Val Gly Gly Val
130                 135                 140

Leu Ala Cys Tyr Ser Leu Leu Val Thr Val Ala Phe Ile Ile Phe Trp
145                 150                 155                 160

Val Arg Ser Lys Arg Ser Arg Leu Leu His Ser Asp Tyr Met Asn Met
                165                 170                 175

Thr Pro Arg Arg Pro Gly Pro Thr Arg Lys His Tyr Gln Pro Tyr Ala
                180                 185                 190

Pro Pro Arg Asp Phe Ala Ala Tyr Arg Ser
                195                 200

<210> SEQ ID NO 267
<211> LENGTH: 179
<212> TYPE: PRT
<213> ORGANISM: Homo sapiens

<400> SEQUENCE: 267

Glu Ile Asn Gly Ser Ala Asn Tyr Glu Met Phe Ile Phe His Asn Gly
 1                   5                  10                  15

Gly Val Gln Ile Leu Cys Lys Tyr Pro Asp Ile Val Gln Gln Phe Lys
                 20                  25                  30

Met Gln Leu Leu Lys Gly Gly Gln Ile Leu Cys Asp Leu Thr Lys Thr
                 35                  40                  45

Lys Gly Ser Gly Asn Thr Val Ser Ile Lys Ser Leu Lys Phe Cys His
 50                  55                  60

Ser Gln Leu Ser Asn Asn Ser Val Ser Phe Phe Leu Tyr Asn Leu Asp
 65                  70                  75                  80

His Ser His Ala Asn Tyr Tyr Phe Cys Asn Leu Ser Ile Phe Asp Pro
                 85                  90                  95

Pro Pro Phe Lys Val Thr Leu Thr Gly Gly Tyr Leu His Ile Tyr Glu
                100                 105                 110

Ser Gln Leu Cys Cys Gln Leu Lys Phe Trp Leu Pro Ile Gly Cys Ala
                115                 120                 125

Ala Phe Val Val Val Cys Ile Leu Gly Cys Ile Leu Ile Cys Trp Leu
                130                 135                 140

Thr Lys Lys Lys Tyr Ser Ser Ser Val His Asp Pro Asn Gly Glu Tyr
145                 150                 155                 160

Met Phe Met Arg Ala Val Asn Thr Ala Lys Lys Ser Arg Leu Thr Asp
                165                 170                 175

Val Thr Leu

<210> SEQ ID NO 268
<211> LENGTH: 284
<212> TYPE: PRT
<213> ORGANISM: Homo sapiens
```

<400> SEQUENCE: 268

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
                20                  25                  30

Tyr Val Tyr Trp Gln Thr Ser Glu Ser Lys Thr Val Thr Tyr His
            35                  40                  45

Ile Pro Gln Asn Ser Ser Leu Glu Asn Val Asp Ser Arg Tyr Arg Asn
        50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
                100                 105                 110

Thr Leu His Val Ala Ala Asn Phe Ser Val Pro Val Val Ser Ala Pro
            115                 120                 125

His Ser Pro Ser Gln Asp Glu Leu Thr Phe Thr Cys Thr Ser Ile Asn
        130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
210                 215                 220

Thr Glu Asn Pro Val Ser Thr Gly Glu Lys Asn Ala Ala Thr Trp Ser
225                 230                 235                 240

Ile Leu Ala Val Leu Cys Leu Val Val Val Ala Val Ala Ile Gly
                245                 250                 255

Trp Val Cys Arg Asp Arg Cys Leu Gln His Ser Tyr Ala Gly Ala Trp
                260                 265                 270

Ala Val Ser Pro Glu Thr Glu Leu Thr Gly His Val
            275                 280

<210> SEQ ID NO 269
<211> LENGTH: 260
<212> TYPE: PRT
<213> ORGANISM: Homo sapiens

<400> SEQUENCE: 269

Leu Ser Val Gln Gln Gly Pro Asn Leu Leu Gln Val Arg Gln Gly Ser
1               5                   10                  15

Gln Ala Thr Leu Val Cys Gln Val Asp Gln Ala Thr Ala Trp Glu Arg
                20                  25                  30

Leu Arg Val Lys Trp Thr Lys Asp Gly Ala Ile Leu Cys Gln Pro Tyr
            35                  40                  45

Ile Thr Asn Gly Ser Leu Ser Leu Gly Val Cys Gly Pro Gln Gly Arg
        50                  55                  60

Leu Ser Trp Gln Ala Pro Ser His Leu Thr Leu Gln Leu Asp Pro Val
65                  70                  75                  80

```
Ser Leu Asn His Ser Gly Ala Tyr Val Cys Trp Ala Ala Val Glu Ile
             85                  90                  95

Pro Glu Leu Glu Glu Ala Glu Gly Asn Ile Thr Arg Leu Phe Val Asp
        100                 105                 110

Pro Asp Asp Pro Thr Gln Asn Arg Asn Arg Ile Ala Ser Phe Pro Gly
        115                 120                 125

Phe Leu Phe Val Leu Leu Gly Val Gly Ser Met Gly Val Ala Ala Ile
130                 135                 140

Val Trp Gly Ala Trp Phe Trp Gly Arg Arg Ser Cys Gln Gln Arg Asp
145                 150                 155                 160

Ser Gly Asn Ser Pro Gly Asn Ala Phe Tyr Ser Asn Val Leu Tyr Arg
                165                 170                 175

Pro Arg Gly Ala Pro Lys Lys Ser Glu Asp Cys Ser Gly Glu Gly Lys
            180                 185                 190

Asp Gln Arg Gly Gln Ser Ile Tyr Ser Thr Ser Phe Pro Gln Pro Ala
        195                 200                 205

Pro Arg Gln Pro His Leu Ala Ser Arg Pro Cys Pro Ser Pro Arg Pro
        210                 215                 220

Cys Pro Ser Pro Arg Pro Gly His Pro Val Ser Met Val Arg Val Ser
225                 230                 235                 240

Pro Arg Pro Ser Pro Thr Gln Pro Arg Pro Lys Gly Phe Pro Lys
                245                 250                 255

Val Gly Glu Glu
        260

<210> SEQ ID NO 270
<211> LENGTH: 257
<212> TYPE: PRT
<213> ORGANISM: Homo sapiens

<400> SEQUENCE: 270

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys His Pro Trp
130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg Ala Leu Val
                165                 170                 175

Val Ile Pro Ile Ile Phe Gly Ile Leu Phe Ala Ile Leu Leu Val Leu
            180                 185                 190
```

-continued

Val Phe Ile Lys Lys Val Ala Lys Pro Thr Asn Lys Ala Pro His
        195                 200                 205

Pro Lys Gln Glu Pro Gln Glu Ile Asn Phe Pro Asp Asp Leu Pro Gly
    210                 215                 220

Ser Asn Thr Ala Ala Pro Val Gln Glu Thr Leu His Gly Cys Gln Pro
225                 230                 235                 240

Val Thr Gln Glu Asp Gly Lys Glu Ser Arg Ile Ser Val Gln Glu Arg
                245                 250                 255

Gln

<210> SEQ ID NO 271
<211> LENGTH: 216
<212> TYPE: PRT
<213> ORGANISM: Homo sapiens

<400> SEQUENCE: 271

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
            20                  25                  30

Cys Arg Asp Tyr Pro Gly Glu Glu Cys Cys Ser Glu Trp Asp Cys Met
        35                  40                  45

Cys Val Gln Pro Glu Phe His Cys Gly Asp Pro Cys Cys Thr Thr Cys
    50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu Pro Leu Gly Trp Leu Thr Val Val
    130                 135                 140

Leu Leu Ala Val Ala Ala Cys Val Leu Leu Leu Thr Ser Ala Gln Leu
145                 150                 155                 160

Gly Leu His Ile Trp Gln Leu Arg Ser Gln Cys Met Trp Pro Arg Glu
                165                 170                 175

Thr Gln Leu Leu Leu Glu Val Pro Pro Ser Thr Glu Asp Ala Arg Ser
            180                 185                 190

Cys Gln Phe Pro Glu Glu Glu Arg Gly Glu Arg Ser Ala Glu Glu Lys
        195                 200                 205

Gly Arg Leu Gly Asp Leu Trp Val
    210                 215

<210> SEQ ID NO 272
<211> LENGTH: 254
<212> TYPE: PRT
<213> ORGANISM: Homo sapiens

<400> SEQUENCE: 272

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Ala Ala Ala Cys Ala Val Phe
         35                  40                  45

Leu Ala Cys Pro Trp Ala Val Ser Gly Ala Arg Ala Ser Pro Gly Ser
 50                  55                  60

Ala Ala Ser Pro Arg Leu Arg Glu Gly Pro Glu Leu Ser Pro Asp Asp
 65                  70                  75                  80

Pro Ala Gly Leu Leu Asp Leu Arg Gln Gly Met Phe Ala Gln Leu Val
                 85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 273
<211> LENGTH: 183
<212> TYPE: PRT
<213> ORGANISM: Homo sapiens

<400> SEQUENCE: 273

Met Glu Arg Val Gln Pro Leu Glu Glu Asn Val Gly Asn Ala Ala Arg
 1               5                  10                  15

Pro Arg Phe Glu Arg Asn Lys Leu Leu Leu Val Ala Ser Val Ile Gln
                20                  25                  30

Gly Leu Gly Leu Leu Leu Cys Phe Thr Tyr Ile Cys Leu His Phe Ser
            35                  40                  45

Ala Leu Gln Val Ser His Arg Tyr Pro Arg Ile Gln Ser Ile Lys Val
 50                  55                  60

Gln Phe Thr Glu Tyr Lys Lys Glu Lys Gly Phe Ile Leu Thr Ser Gln
 65                  70                  75                  80

Lys Glu Asp Glu Ile Met Lys Val Gln Asn Asn Ser Val Ile Ile Asn
                 85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
130                 135                 140

Tyr Lys Asp Lys Val Tyr Leu Asn Val Thr Thr Asp Asn Thr Ser Leu
145                 150                 155                 160

```
Asp Asp Phe His Val Asn Gly Glu Leu Ile Leu Ile His Gln Asn
                165                 170                 175

Pro Gly Glu Phe Cys Val Leu
            180

<210> SEQ ID NO 274
<211> LENGTH: 155
<212> TYPE: PRT
<213> ORGANISM: Homo sapiens

<400> SEQUENCE: 274

Gln Arg Phe Ala Gln Ala Gln Gln Leu Pro Leu Glu Ser Leu Gly
1               5                   10                  15

Trp Asp Val Ala Glu Leu Gln Leu Asn His Thr Gly Pro Gln Gln Asp
                20                  25                  30

Pro Arg Leu Tyr Trp Gln Gly Gly Pro Ala Leu Gly Arg Ser Phe Leu
            35                  40                  45

His Gly Pro Glu Leu Asp Lys Gly Gln Leu Arg Ile His Arg Asp Gly
    50                  55                  60

Ile Tyr Met Val His Ile Gln Val Thr Leu Ala Ile Cys Ser Ser Thr
65              70                  75                  80

Thr Ala Ser Arg His His Pro Thr Thr Leu Ala Val Gly Ile Cys Ser
                85                  90                  95

Pro Ala Ser Arg Ser Ile Ser Leu Leu Arg Leu Ser Phe His Gln Gly
            100                 105                 110

Cys Thr Ile Ala Ser Gln Arg Leu Thr Pro Leu Ala Arg Gly Asp Thr
        115                 120                 125

Leu Cys Thr Asn Leu Thr Gly Thr Leu Leu Pro Ser Arg Asn Thr Asp
    130                 135                 140

Glu Thr Phe Phe Gly Val Gln Trp Val Arg Pro
145                 150                 155

<210> SEQ ID NO 275
<211> LENGTH: 240
<212> TYPE: PRT
<213> ORGANISM: Homo sapiens

<400> SEQUENCE: 275

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65              70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Asn Asn Leu Val Thr Leu Glu Asn Gly Lys Gln Leu Thr Val Lys Arg
    130                 135                 140
```

```
Gln Gly Leu Tyr Tyr Ile Tyr Ala Gln Val Thr Phe Cys Ser Asn Arg
145                 150                 155                 160

Glu Ala Ser Ser Gln Ala Pro Phe Ile Ala Ser Leu Cys Leu Lys Ser
            165                 170                 175

Pro Gly Arg Phe Glu Arg Ile Leu Leu Arg Ala Ala Asn Thr His Ser
            180                 185                 190

Ser Ala Lys Pro Cys Gly Gln Gln Ser Ile His Leu Gly Gly Val Phe
            195                 200                 205

Glu Leu Gln Pro Gly Ala Ser Val Phe Val Asn Val Thr Asp Pro Ser
            210                 215                 220

Gln Val Ser His Gly Thr Gly Phe Thr Ser Phe Gly Leu Leu Lys Leu
225                 230                 235                 240

<210> SEQ ID NO 276
<211> LENGTH: 393
<212> TYPE: PRT
<213> ORGANISM: Homo sapiens

<400> SEQUENCE: 276

Gln Gly Gly Thr Arg Ser Pro Arg Cys Asp Cys Ala Gly Asp Phe His
1               5                   10                  15

Lys Lys Ile Gly Leu Phe Cys Cys Arg Gly Cys Pro Ala Gly His Tyr
            20                  25                  30

Leu Lys Ala Pro Cys Thr Glu Pro Cys Gly Asn Ser Thr Cys Leu Val
            35                  40                  45

Cys Pro Gln Asp Thr Phe Leu Ala Trp Glu Asn His His Asn Ser Glu
50                  55                  60

Cys Ala Arg Cys Gln Ala Cys Asp Glu Gln Ala Ser Gln Val Ala Leu
65                  70                  75                  80

Glu Asn Cys Ser Ala Val Ala Asp Thr Arg Cys Gly Cys Lys Pro Gly
            85                  90                  95

Trp Phe Val Glu Cys Gln Val Ser Gln Cys Val Ser Ser Ser Pro Phe
            100                 105                 110

Tyr Cys Gln Pro Cys Leu Asp Cys Gly Ala Leu His Arg His Thr Arg
            115                 120                 125

Leu Leu Cys Ser Arg Arg Asp Thr Asp Cys Gly Thr Cys Leu Pro Gly
130                 135                 140

Phe Tyr Glu His Gly Asp Gly Cys Val Ser Cys Pro Thr Ser Thr Leu
145                 150                 155                 160

Gly Ser Cys Pro Glu Arg Cys Ala Ala Val Cys Gly Trp Arg Gln Met
            165                 170                 175

Phe Trp Val Gln Val Leu Leu Ala Gly Leu Val Val Pro Leu Leu Leu
            180                 185                 190

Gly Ala Thr Leu Thr Tyr Thr Tyr Arg His Cys Trp Pro His Lys Pro
            195                 200                 205

Leu Val Thr Ala Asp Glu Ala Gly Met Glu Ala Leu Thr Pro Pro Pro
            210                 215                 220

Ala Thr His Leu Ser Pro Leu Asp Ser Ala His Thr Leu Leu Ala Pro
225                 230                 235                 240

Pro Asp Ser Ser Glu Lys Ile Cys Thr Val Gln Leu Val Gly Asn Ser
            245                 250                 255

Trp Thr Pro Gly Tyr Pro Glu Thr Gln Glu Ala Leu Cys Pro Gln Val
            260                 265                 270

Thr Trp Ser Trp Asp Gln Leu Pro Ser Arg Ala Leu Gly Pro Ala Ala
```

```
                275                 280                 285
Ala Pro Thr Leu Ser Pro Glu Ser Pro Ala Gly Ser Pro Ala Met Met
    290                 295                 300

Leu Gln Pro Gly Pro Gln Leu Tyr Asp Val Met Asp Ala Val Pro Ala
305                 310                 315                 320

Arg Arg Trp Lys Glu Phe Val Arg Thr Leu Gly Leu Arg Glu Ala Glu
                325                 330                 335

Ile Glu Ala Val Glu Val Glu Ile Gly Arg Phe Arg Asp Gln Gln Tyr
            340                 345                 350

Glu Met Leu Lys Arg Trp Arg Gln Gln Pro Ala Gly Leu Gly Ala
                355                 360                 365

Val Tyr Ala Ala Leu Glu Arg Met Gly Leu Asp Gly Cys Val Glu Asp
        370                 375                 380

Leu Arg Ser Arg Leu Gln Arg Gly Pro
385                 390

<210> SEQ ID NO 277
<211> LENGTH: 240
<212> TYPE: PRT
<213> ORGANISM: Homo sapiens

<400> SEQUENCE: 277

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 278
<211> LENGTH: 199
```

```
<212> TYPE: PRT
<213> ORGANISM: Homo sapiens

<400> SEQUENCE: 278

Met Thr Leu His Pro Ser Pro Ile Thr Cys Glu Phe Leu Phe Ser Thr
1               5                   10                  15

Ala Leu Ile Ser Pro Lys Met Cys Leu Ser His Leu Glu Asn Met Pro
                20                  25                  30

Leu Ser His Ser Arg Thr Gln Gly Ala Gln Arg Ser Ser Trp Lys Leu
            35                  40                  45

Trp Leu Phe Cys Ser Ile Val Met Leu Leu Phe Leu Cys Ser Phe Ser
        50                  55                  60

Trp Leu Ile Phe Ile Phe Leu Gln Leu Glu Thr Ala Lys Glu Pro Cys
65                  70                  75                  80

Met Ala Lys Phe Gly Pro Leu Pro Ser Lys Trp Gln Met Ala Ser Ser
                85                  90                  95

Glu Pro Pro Cys Val Asn Lys Val Ser Asp Trp Lys Leu Glu Ile Leu
            100                 105                 110

Gln Asn Gly Leu Tyr Leu Ile Tyr Gly Gln Val Ala Pro Asn Ala Asn
        115                 120                 125

Tyr Asn Asp Val Ala Pro Phe Glu Val Arg Leu Tyr Lys Asn Lys Asp
    130                 135                 140

Met Ile Gln Thr Leu Thr Asn Lys Ser Lys Ile Gln Asn Val Gly Gly
145                 150                 155                 160

Thr Tyr Glu Leu His Val Gly Asp Thr Ile Asp Leu Ile Phe Asn Ser
                165                 170                 175

Glu His Gln Val Leu Lys Asn Asn Thr Tyr Trp Gly Ile Ile Leu Leu
            180                 185                 190

Ala Asn Pro Gln Phe Ile Ser
        195

<210> SEQ ID NO 279
<211> LENGTH: 277
<212> TYPE: PRT
<213> ORGANISM: Homo sapiens

<400> SEQUENCE: 279

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
        130                 135                 140
```

```
Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
        210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
            275

<210> SEQ ID NO 280
<211> LENGTH: 260
<212> TYPE: PRT
<213> ORGANISM: Homo sapiens

<400> SEQUENCE: 280

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
                20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys His Tyr Ser Cys Pro Arg Glu Glu
225                 230                 235                 240
```

```
Glu Gly Ser Thr Ile Pro Ile Gln Glu Asp Tyr Arg Lys Pro Glu Pro
                245                 250                 255

Ala Cys Ser Pro
            260
```

<210> SEQ ID NO 281
<211> LENGTH: 255
<212> TYPE: PRT
<213> ORGANISM: Homo sapiens

<400> SEQUENCE: 281

```
Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 282
<211> LENGTH: 216
<212> TYPE: PRT
<213> ORGANISM: Homo sapiens

<400> SEQUENCE: 282

```
Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
                20                  25                  30

Arg Trp Gln Lys Gln Arg Cys Pro Val Val Lys Ser Lys Cys Arg Glu
            35                  40                  45
```

```
Asn Ala Ser Pro Phe Phe Cys Cys Phe Ile Ala Val Ala Met Gly
    50              55                  60

Ile Arg Phe Ile Ile Met Val Ala Ile Trp Ser Ala Val Phe Leu Asn
65              70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Cys Tyr Gln
                100                 105                 110

Phe Phe Asp Glu Ser Lys Asn Trp Tyr Glu Ser Gln Ala Ser Cys Met
        115                 120                 125

Ser Gln Asn Ala Ser Leu Leu Lys Val Tyr Ser Lys Glu Asp Gln Asp
        130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
        195                 200                 205

Tyr Ile Cys Met Gln Arg Thr Val
    210                 215

<210> SEQ ID NO 283
<211> LENGTH: 194
<212> TYPE: PRT
<213> ORGANISM: Homo sapiens

<400> SEQUENCE: 283

Gln Gly His Leu Val His Met Thr Val Val Ser Gly Ser Asn Val Thr
1               5                   10                  15

Leu Asn Ile Ser Glu Ser Leu Pro Glu Asn Tyr Lys Gln Leu Thr Trp
                20                  25                  30

Phe Tyr Thr Phe Asp Gln Lys Ile Val Glu Trp Asp Ser Arg Lys Ser
            35                  40                  45

Lys Tyr Phe Glu Ser Lys Phe Lys Gly Arg Val Arg Leu Asp Pro Gln
    50                  55                  60

Ser Gly Ala Leu Tyr Ile Ser Lys Val Gln Lys Glu Asp Asn Ser Thr
65                  70                  75                  80

Tyr Ile Met Arg Val Leu Lys Lys Thr Gly Asn Glu Gln Glu Trp Lys
                85                  90                  95

Ile Lys Leu Gln Val Leu Asp Pro Val Pro Lys Pro Val Ile Lys Ile
                100                 105                 110

Glu Lys Ile Glu Asp Met Asp Asp Asn Cys Tyr Leu Lys Leu Ser Cys
        115                 120                 125

Val Ile Pro Gly Glu Ser Val Asn Tyr Thr Trp Tyr Gly Asp Lys Arg
        130                 135                 140

Pro Phe Pro Lys Glu Leu Gln Asn Ser Val Leu Glu Thr Thr Leu Met
145                 150                 155                 160

Pro His Asn Tyr Ser Arg Cys Tyr Thr Cys Gln Val Ser Asn Ser Val
                165                 170                 175

Ser Ser Lys Asn Gly Thr Val Cys Leu Ser Pro Pro Cys Thr Leu Ala
            180                 185                 190

Arg Ser
```

<210> SEQ ID NO 284
<211> LENGTH: 318
<212> TYPE: PRT
<213> ORGANISM: Homo sapiens

<400> SEQUENCE: 284

Glu Glu Val Leu Trp His Thr Ser Val Pro Phe Ala Glu Asn Met Ser
1               5                   10                  15

Leu Glu Cys Val Tyr Pro Ser Met Gly Ile Leu Thr Gln Val Glu Trp
            20                  25                  30

Phe Lys Ile Gly Thr Gln Gln Asp Ser Ile Ala Ile Phe Ser Pro Thr
        35                  40                  45

His Gly Met Val Ile Arg Lys Pro Tyr Ala Glu Arg Val Tyr Phe Leu
    50                  55                  60

Asn Ser Thr Met Ala Ser Asn Asn Met Thr Leu Phe Phe Arg Asn Ala
65                  70                  75                  80

Ser Glu Asp Asp Val Gly Tyr Tyr Ser Cys Ser Leu Tyr Thr Tyr Pro
                85                  90                  95

Gln Gly Thr Trp Gln Lys Val Ile Gln Val Val Gln Ser Asp Ser Phe
            100                 105                 110

Glu Ala Ala Val Pro Ser Asn Ser His Ile Val Ser Glu Pro Gly Lys
        115                 120                 125

Asn Val Thr Leu Thr Cys Gln Pro Gln Met Thr Trp Pro Val Gln Ala
130                 135                 140

Val Arg Trp Glu Lys Ile Gln Pro Arg Gln Ile Asp Leu Leu Thr Tyr
145                 150                 155                 160

Cys Asn Leu Val His Gly Arg Asn Phe Thr Ser Lys Phe Pro Arg Gln
                165                 170                 175

Ile Val Ser Asn Cys Ser His Gly Arg Trp Ser Val Ile Val Ile Pro
            180                 185                 190

Asp Val Thr Val Ser Asp Ser Gly Leu Tyr Arg Cys Tyr Leu Gln Ala
        195                 200                 205

Ser Ala Gly Glu Asn Glu Thr Phe Val Met Arg Leu Thr Val Ala Glu
    210                 215                 220

Gly Lys Thr Asp Asn Gln Tyr Thr Leu Phe Val Ala Gly Gly Thr Val
225                 230                 235                 240

Leu Leu Leu Leu Phe Val Ile Ser Ile Thr Thr Ile Ile Val Ile Phe
                245                 250                 255

Leu Asn Arg Arg Arg Arg Arg Glu Arg Arg Asp Leu Phe Thr Glu Ser
            260                 265                 270

Trp Asp Thr Gln Lys Ala Pro Asn Asn Tyr Arg Ser Pro Ile Ser Thr
        275                 280                 285

Ser Gln Pro Thr Asn Gln Ser Met Asp Asp Thr Arg Glu Asp Ile Tyr
    290                 295                 300

Val Asn Tyr Pro Thr Phe Ser Arg Arg Pro Lys Thr Arg Val
305                 310                 315

<210> SEQ ID NO 285
<211> LENGTH: 360
<212> TYPE: PRT
<213> ORGANISM: Homo sapiens

<400> SEQUENCE: 285

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
 50                  55                  60

Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser Gly Lys Val Leu Val Leu Gln Ser His Trp Gln Thr Phe His
        275                 280                 285

Val Ser Ala Val Ala Ala Ala Ile Phe Val Ile Ile Ile Phe Tyr
290                 295                 300

Val Arg Cys Cys Lys Lys Lys Thr Ser Ala Ala Glu Gly Pro Glu Leu
305                 310                 315                 320

Val Ser Leu Gln Val Leu Asp Gln His Pro Val Gly Thr Ser Asp His
                325                 330                 335

Arg Asp Ala Thr Gln Leu Gly Phe Gln Pro Leu Met Ser Asp Leu Gly
            340                 345                 350

Ser Thr Gly Ser Thr Glu Gly Ala
        355                 360

<210> SEQ ID NO 286
<211> LENGTH: 279
<212> TYPE: PRT
<213> ORGANISM: Homo sapiens

<400> SEQUENCE: 286

Phe Lys Val Ala Thr Pro Tyr Ser Leu Tyr Val Cys Pro Glu Gly Gln
1               5                   10                  15

Asn Val Thr Leu Thr Cys Arg Leu Leu Gly Pro Val Asp Lys Gly His

```
                20                  25                  30
Asp Val Thr Phe Tyr Lys Thr Trp Tyr Arg Ser Ser Arg Gly Glu Val
            35                  40                  45

Gln Thr Cys Ser Glu Arg Arg Pro Ile Arg Asn Leu Thr Phe Gln Asp
        50                  55                  60

Leu His Leu His His Gly Gly His Gln Ala Ala Asn Thr Ser His Asp
65                  70                  75                  80

Leu Ala Gln Arg His Gly Leu Glu Ser Ala Ser Asp His His Gly Asn
                85                  90                  95

Phe Ser Ile Thr Met Arg Asn Leu Thr Leu Leu Asp Ser Gly Leu Tyr
            100                 105                 110

Cys Cys Leu Val Val Glu Ile Arg His His Ser Glu His Arg Val
        115                 120                 125

His Gly Ala Met Glu Leu Gln Val Gln Thr Gly Lys Asp Ala Pro Ser
    130                 135                 140

Asn Cys Val Val Tyr Pro Ser Ser Gln Asp Ser Glu Asn Ile Thr
145                 150                 155                 160

Ala Ala Ala Leu Ala Thr Gly Ala Cys Ile Val Gly Ile Leu Cys Leu
                165                 170                 175

Pro Leu Ile Leu Leu Leu Val Tyr Lys Gln Arg Gln Ala Ala Ser Asn
            180                 185                 190

Arg Arg Ala Gln Glu Leu Val Arg Met Asp Ser Asn Ile Gln Gly Ile
        195                 200                 205

Glu Asn Pro Gly Phe Glu Ala Ser Pro Pro Ala Gln Gly Ile Pro Glu
    210                 215                 220

Ala Lys Val Arg His Pro Leu Ser Tyr Val Ala Gln Arg Gln Pro Ser
225                 230                 235                 240

Glu Ser Gly Arg His Leu Leu Ser Glu Pro Ser Thr Pro Leu Ser Pro
                245                 250                 255

Pro Gly Pro Gly Asp Val Phe Phe Pro Ser Leu Asp Pro Val Pro Asp
            260                 265                 270

Ser Pro Asn Phe Glu Val Ile
            275

<210> SEQ ID NO 287
<211> LENGTH: 432
<212> TYPE: PRT
<213> ORGANISM: Homo sapiens

<400> SEQUENCE: 287

Lys Gln Ser Glu Asp Phe Arg Val Ile Gly Pro Ala His Pro Ile Leu
1               5                   10                  15

Ala Gly Val Gly Glu Asp Ala Leu Leu Thr Cys Gln Leu Leu Pro Lys
            20                  25                  30

Arg Thr Thr Met His Val Glu Val Arg Trp Tyr Arg Ser Glu Pro Ser
        35                  40                  45

Thr Pro Val Phe Val His Arg Asp Gly Val Glu Val Thr Glu Met Gln
    50                  55                  60

Met Glu Glu Tyr Arg Gly Trp Val Glu Trp Ile Glu Asn Gly Ile Ala
65                  70                  75                  80

Lys Gly Asn Val Ala Leu Lys Ile His Asn Ile Gln Pro Ser Asp Asn
                85                  90                  95

Gly Gln Tyr Trp Cys His Phe Gln Asp Gly Asn Tyr Cys Gly Glu Thr
            100                 105                 110
```

```
Ser Leu Leu Leu Lys Val Ala Gly Leu Gly Ser Ala Pro Ser Ile His
            115                 120                 125

Met Glu Gly Pro Gly Glu Ser Gly Val Gln Leu Val Cys Thr Ala Arg
        130                 135                 140

Gly Trp Phe Pro Glu Pro Gln Val Tyr Trp Glu Asp Ile Arg Gly Glu
145                 150                 155                 160

Lys Leu Leu Ala Val Ser Glu His Arg Ile Gln Asp Lys Asp Gly Leu
                165                 170                 175

Phe Tyr Ala Glu Ala Thr Leu Val Val Arg Asn Ala Ser Ala Glu Ser
            180                 185                 190

Val Ser Cys Leu Val His Asn Pro Val Leu Thr Glu Glu Lys Gly Ser
        195                 200                 205

Val Ile Ser Leu Pro Glu Lys Leu Gln Thr Glu Leu Ala Ser Leu Lys
    210                 215                 220

Val Asn Gly Pro Ser Gln Pro Ile Leu Val Arg Val Gly Glu Asp Ile
225                 230                 235                 240

Gln Leu Thr Cys Tyr Leu Ser Pro Lys Ala Asn Ala Gln Ser Met Glu
                245                 250                 255

Val Arg Trp Asp Arg Ser His Arg Tyr Pro Ala Val His Val Tyr Met
            260                 265                 270

Asp Gly Asp His Val Ala Gly Glu Gln Met Ala Glu Tyr Arg Gly Arg
        275                 280                 285

Thr Val Leu Val Ser Asp Ala Ile Asp Glu Gly Arg Leu Thr Leu Gln
    290                 295                 300

Ile Leu Ser Ala Arg Pro Ser Asp Asp Gly Gln Tyr Arg Cys Leu Phe
305                 310                 315                 320

Glu Lys Asp Asp Val Tyr Gln Glu Ala Ser Leu Asp Leu Lys Val Val
                325                 330                 335

Ser Leu Gly Ser Ser Pro Leu Ile Thr Val Glu Gly Gln Glu Asp Gly
            340                 345                 350

Glu Met Gln Pro Met Cys Ser Ser Asp Gly Trp Phe Pro Gln Pro His
        355                 360                 365

Val Pro Trp Arg Asp Met Glu Gly Lys Thr Ile Pro Ser Ser Ser Gln
370                 375                 380

Ala Leu Thr Gln Gly Ser His Gly Leu Phe His Val Gln Thr Leu Leu
385                 390                 395                 400

Arg Val Thr Asn Ile Ser Ala Val Asp Val Thr Cys Ser Ile Ser Ile
                405                 410                 415

Pro Phe Leu Gly Glu Lys Ile Ala Thr Phe Ser Leu Ser Gly Trp
            420                 425                 430

<210> SEQ ID NO 288
<211> LENGTH: 506
<212> TYPE: PRT
<213> ORGANISM: Homo sapiens

<400> SEQUENCE: 288

Leu Glu Val Gln Val Pro Glu Asp Pro Val Ala Leu Val Gly Thr
1               5                   10                  15

Asp Ala Thr Leu Cys Cys Ser Phe Ser Pro Glu Pro Gly Phe Ser Leu
                20                  25                  30

Ala Gln Leu Asn Leu Ile Trp Gln Leu Thr Asp Thr Lys Gln Leu Val
            35                  40                  45

His Ser Phe Ala Glu Gly Gln Asp Gln Gly Ser Ala Tyr Ala Asn Arg
        50                  55                  60
```

-continued

```
Thr Ala Leu Phe Pro Asp Leu Ala Gln Gly Asn Ala Ser Leu Arg
 65                  70                  75                  80

Leu Gln Arg Val Arg Val Ala Asp Glu Gly Ser Phe Thr Cys Phe Val
                 85                  90                  95

Ser Ile Arg Asp Phe Gly Ser Ala Ala Val Ser Leu Gln Val Ala Ala
            100                 105                 110

Pro Tyr Ser Lys Pro Ser Met Thr Leu Glu Pro Asn Lys Asp Leu Arg
        115                 120                 125

Pro Gly Asp Thr Val Thr Ile Thr Cys Ser Ser Tyr Gln Gly Tyr Pro
    130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Ile Leu Arg Val Val Leu Gly Ala Asn Gly Thr Tyr Ser Cys
            180                 185                 190

Leu Val Arg Asn Pro Val Leu Gln Gln Asp Ala His Ser Ser Val Thr
        195                 200                 205

Ile Thr Pro Gln Arg Ser Pro Thr Gly Ala Val Glu Val Gln Val Pro
210                 215                 220

Glu Asp Pro Val Val Ala Leu Val Gly Thr Asp Ala Thr Leu Arg Cys
225                 230                 235                 240

Ser Phe Ser Pro Glu Pro Gly Phe Ser Leu Ala Gln Leu Asn Leu Ile
                245                 250                 255

Trp Gln Leu Thr Asp Thr Lys Gln Leu Val His Ser Phe Thr Glu Gly
            260                 265                 270

Arg Asp Gln Gly Ser Ala Tyr Ala Asn Arg Thr Ala Leu Phe Pro Asp
        275                 280                 285

Leu Leu Ala Gln Gly Asn Ala Ser Leu Arg Leu Gln Arg Val Arg Val
    290                 295                 300

Ala Asp Glu Gly Ser Phe Thr Cys Phe Val Ser Ile Arg Asp Phe Gly
305                 310                 315                 320

Ser Ala Ala Val Ser Leu Gln Val Ala Ala Pro Tyr Ser Lys Pro Ser
                325                 330                 335

Met Thr Leu Glu Pro Asn Lys Asp Leu Arg Pro Gly Asp Thr Val Thr
            340                 345                 350

Ile Thr Cys Ser Ser Tyr Arg Gly Tyr Pro Glu Ala Glu Val Phe Trp
        355                 360                 365

Gln Asp Gly Gln Gly Val Pro Leu Thr Gly Asn Val Thr Thr Ser Gln
    370                 375                 380

Met Ala Asn Glu Gln Gly Leu Phe Asp Val His Ser Val Leu Arg Val
385                 390                 395                 400

Val Leu Gly Ala Asn Gly Thr Tyr Ser Cys Leu Val Arg Asn Pro Val
                405                 410                 415

Leu Gln Gln Asp Ala His Gly Ser Val Thr Ile Thr Gly Gln Pro Met
            420                 425                 430

Thr Phe Pro Pro Glu Ala Leu Trp Val Thr Val Gly Leu Ser Val Cys
        435                 440                 445

Leu Ile Ala Leu Leu Val Ala Leu Ala Phe Val Cys Trp Arg Lys Ile
    450                 455                 460

Lys Gln Ser Cys Glu Glu Glu Asn Ala Gly Ala Glu Asp Gln Asp Gly
465                 470                 475                 480
```

```
Glu Gly Glu Gly Ser Lys Thr Ala Leu Gln Pro Leu Lys His Ser Asp
            485                 490                 495
Ser Lys Glu Asp Asp Gly Gln Glu Ile Ala
            500                 505

<210> SEQ ID NO 289
<211> LENGTH: 258
<212> TYPE: PRT
<213> ORGANISM: Homo sapiens

<400> SEQUENCE: 289

Leu Ile Ile Gly Phe Gly Ile Ser Gly Arg His Ser Ile Thr Val Thr
1               5                   10                  15
Thr Val Ala Ser Ala Gly Asn Ile Gly Glu Asp Gly Ile Leu Ser Cys
            20                  25                  30
Thr Phe Glu Pro Asp Ile Lys Leu Ser Asp Ile Val Ile Gln Trp Leu
        35                  40                  45
Lys Glu Gly Val Leu Gly Leu Val His Glu Phe Lys Glu Gly Lys Asp
    50                  55                  60
Glu Leu Ser Glu Gln Asp Glu Met Phe Arg Gly Arg Thr Ala Val Phe
65                  70                  75                  80
Ala Asp Gln Val Ile Val Gly Asn Ala Ser Leu Arg Leu Lys Asn Val
                85                  90                  95
Gln Leu Thr Asp Ala Gly Thr Tyr Lys Cys Tyr Ile Ile Thr Ser Lys
            100                 105                 110
Gly Lys Gly Asn Ala Asn Leu Glu Tyr Lys Thr Gly Ala Phe Ser Met
        115                 120                 125
Pro Glu Val Asn Val Asp Tyr Asn Ala Ser Ser Glu Thr Leu Arg Cys
130                 135                 140
Glu Ala Pro Arg Trp Phe Pro Gln Pro Thr Val Val Trp Ala Ser Gln
145                 150                 155                 160
Val Asp Gln Gly Ala Asn Phe Ser Glu Val Ser Asn Thr Ser Phe Glu
                165                 170                 175
Leu Asn Ser Glu Asn Val Thr Met Lys Val Val Ser Val Leu Tyr Asn
            180                 185                 190
Val Thr Ile Asn Asn Thr Tyr Ser Cys Met Ile Glu Asn Asp Ile Ala
        195                 200                 205
Lys Ala Thr Gly Asp Ile Lys Val Thr Glu Ser Glu Ile Lys Arg Arg
    210                 215                 220
Ser His Leu Gln Leu Leu Asn Ser Lys Ala Ser Leu Cys Val Ser Ser
225                 230                 235                 240
Phe Phe Ala Ile Ser Trp Ala Leu Leu Pro Leu Ser Pro Tyr Leu Met
                245                 250                 255
Leu Lys

<210> SEQ ID NO 290
<211> LENGTH: 245
<212> TYPE: PRT
<213> ORGANISM: Homo sapiens

<400> SEQUENCE: 290

Leu Pro Ser Cys Lys Glu Asp Glu Tyr Pro Val Gly Ser Glu Cys Cys
1               5                   10                  15
Pro Lys Cys Ser Pro Gly Tyr Arg Val Lys Glu Ala Cys Gly Glu Leu
            20                  25                  30
Thr Gly Thr Val Cys Glu Pro Cys Pro Pro Gly Thr Tyr Ile Ala His
```

```
            35                  40                  45
Leu Asn Gly Leu Ser Lys Cys Leu Gln Cys Gln Met Cys Asp Pro Ala
 50                  55                  60
Met Gly Leu Arg Ala Ser Arg Asn Cys Ser Arg Thr Glu Asn Ala Val
 65                  70                  75                  80
Cys Gly Cys Ser Pro Gly His Phe Cys Ile Val Gln Asp Gly Asp His
                 85                  90                  95
Cys Ala Ala Cys Arg Ala Tyr Ala Thr Ser Pro Gly Gln Arg Val
            100                 105                 110
Gln Lys Gly Gly Thr Glu Ser Gln Asp Thr Leu Cys Gln Asn Cys Pro
            115                 120                 125
Pro Gly Thr Phe Ser Pro Asn Gly Thr Leu Glu Glu Cys Gln His Gln
            130                 135                 140
Thr Lys Cys Ser Trp Leu Val Thr Lys Ala Gly Ala Gly Thr Ser Ser
145                 150                 155                 160
Ser His Trp Val Trp Phe Leu Ser Gly Ser Leu Val Ile Val Ile
                165                 170                 175
Val Cys Ser Thr Val Gly Leu Ile Ile Cys Val Lys Arg Arg Lys Pro
            180                 185                 190
Arg Gly Asp Val Val Lys Val Ile Val Ser Val Gln Arg Lys Arg Gln
            195                 200                 205
Glu Ala Glu Gly Glu Ala Thr Val Ile Glu Ala Leu Gln Ala Pro Pro
            210                 215                 220
Asp Val Thr Thr Val Ala Val Glu Glu Thr Ile Pro Ser Phe Thr Gly
225                 230                 235                 240
Arg Ser Pro Asn His
                245

<210> SEQ ID NO 291
<211> LENGTH: 392
<212> TYPE: PRT
<213> ORGANISM: Homo sapiens

<400> SEQUENCE: 291

Ile Phe Pro Leu Ala Phe Phe Ile Tyr Val Pro Met Asn Glu Gln Ile
 1               5                  10                  15
Val Ile Gly Arg Leu Asp Glu Asp Ile Ile Leu Pro Ser Ser Phe Glu
             20                  25                  30
Arg Gly Ser Glu Val Val Ile His Trp Lys Tyr Gln Asp Ser Tyr Lys
             35                  40                  45
Val His Ser Tyr Tyr Lys Gly Ser Asp His Leu Glu Ser Gln Asp Pro
 50                  55                  60
Arg Tyr Ala Asn Arg Thr Ser Leu Phe Tyr Asn Glu Ile Gln Asn Gly
 65                  70                  75                  80
Asn Ala Ser Leu Phe Phe Arg Arg Val Ser Leu Leu Asp Glu Gly Ile
                 85                  90                  95
Tyr Thr Cys Tyr Val Gly Thr Ala Ile Gln Val Ile Thr Asn Lys Val
            100                 105                 110
Val Leu Lys Val Gly Val Phe Leu Thr Pro Val Met Lys Tyr Glu Lys
            115                 120                 125
Arg Asn Thr Asn Ser Phe Leu Ile Cys Ser Val Leu Ser Val Tyr Pro
            130                 135                 140
Arg Pro Ile Ile Thr Trp Lys Met Asp Asn Thr Pro Ile Ser Glu Asn
145                 150                 155                 160
```

```
Asn Met Glu Glu Thr Gly Ser Leu Asp Ser Phe Ser Ile Asn Ser Pro
                165                 170                 175

Leu Asn Ile Thr Gly Ser Asn Ser Ser Tyr Glu Cys Thr Ile Glu Asn
            180                 185                 190

Ser Leu Leu Lys Gln Thr Trp Thr Gly Arg Trp Thr Met Lys Asp Gly
        195                 200                 205

Leu His Lys Met Gln Ser Glu His Val Ser Leu Ser Cys Gln Pro Val
    210                 215                 220

Asn Asp Tyr Phe Ser Pro Asn Gln Asp Phe Lys Val Thr Trp Ser Arg
225                 230                 235                 240

Met Lys Ser Gly Thr Phe Ser Val Leu Ala Tyr Tyr Leu Ser Ser Ser
                245                 250                 255

Gln Asn Thr Ile Ile Asn Glu Ser Arg Phe Ser Trp Asn Lys Glu Leu
            260                 265                 270

Ile Asn Gln Ser Asp Phe Ser Met Asn Leu Met Asp Leu Asn Leu Ser
        275                 280                 285

Asp Ser Gly Glu Tyr Leu Cys Asn Ile Ser Ser Asp Glu Tyr Thr Leu
    290                 295                 300

Leu Thr Ile His Thr Val His Val Glu Pro Ser Gln Glu Thr Ala Ser
305                 310                 315                 320

His Asn Lys Gly Leu Trp Ile Leu Val Pro Ser Ala Ile Leu Ala Ala
                325                 330                 335

Phe Leu Leu Ile Trp Ser Val Lys Cys Cys Arg Ala Gln Leu Glu Ala
            340                 345                 350

Arg Arg Ser Arg His Pro Ala Asp Gly Ala Gln Gln Glu Arg Cys Cys
        355                 360                 365

Val Pro Pro Gly Glu Arg Cys Pro Ser Ala Pro Asp Asn Gly Glu Glu
    370                 375                 380

Asn Val Pro Leu Ser Gly Lys Val
385                 390

<210> SEQ ID NO 292
<211> LENGTH: 188
<212> TYPE: PRT
<213> ORGANISM: Homo sapiens

<400> SEQUENCE: 292

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp Phe Leu
        115                 120                 125

Leu Trp Ile Leu Ala Ala Val Ser Ser Gly Leu Phe Phe Tyr Ser Phe
    130                 135                 140
```

```
Leu Leu Thr Ala Val Ser Leu Ser Lys Met Leu Lys Lys Arg Ser Pro
145                 150                 155                 160

Leu Thr Thr Gly Val Tyr Val Lys Met Pro Thr Glu Pro Glu Cys
            165                 170                 175

Glu Lys Gln Phe Gln Pro Tyr Phe Ile Pro Ile Asn
        180                 185

<210> SEQ ID NO 293
<211> LENGTH: 497
<212> TYPE: PRT
<213> ORGANISM: Homo sapiens

<400> SEQUENCE: 293

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

Pro Gly Gly Gly Pro Asp Leu Leu Val Thr Gly Asp Asn Gly Asp Phe
        275                 280                 285

Thr Leu Arg Leu Glu Asp Val Ser Gln Ala Gln Ala Gly Thr Tyr Thr
    290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
```

```
                    325                 330                 335
Gly Lys Leu Leu Cys Glu Val Thr Pro Val Ser Gly Gln Glu Arg Phe
                340                 345                 350

Val Trp Ser Ser Leu Asp Thr Pro Ser Gln Arg Ser Phe Ser Gly Pro
            355                 360                 365

Trp Leu Glu Ala Gln Glu Ala Gln Leu Leu Ser Gln Pro Trp Gln Cys
        370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu Leu Phe Leu Ile Leu Gly Val Leu Ser
                420                 425                 430

Leu Leu Leu Leu Val Thr Gly Ala Phe Gly Phe His Leu Trp Arg Arg
            435                 440                 445

Gln Trp Arg Pro Arg Arg Phe Ser Ala Leu Glu Gln Gly Ile His Pro
        450                 455                 460

Pro Gln Ala Gln Ser Lys Ile Glu Glu Leu Glu Gln Glu Pro Glu Pro
465                 470                 475                 480

Glu Pro Glu Pro Glu Pro Glu Pro Glu Pro Glu Pro Glu Pro Glu Gln
                485                 490                 495

Leu

<210> SEQ ID NO 294
<211> LENGTH: 259
<212> TYPE: PRT
<213> ORGANISM: Homo sapiens

<400> SEQUENCE: 294

Lys Glu Ser Cys Asp Val Gln Leu Tyr Ile Lys Arg Gln Ser Glu His
1               5                   10                  15

Ser Ile Leu Ala Gly Asp Pro Phe Glu Leu Glu Cys Pro Val Lys Tyr
                20                  25                  30

Cys Ala Asn Arg Pro His Val Thr Trp Cys Lys Leu Asn Gly Thr Thr
            35                  40                  45

Cys Val Lys Leu Glu Asp Arg Gln Thr Ser Trp Lys Glu Glu Lys Asn
        50                  55                  60

Ile Ser Phe Phe Ile Leu His Phe Glu Pro Val Leu Pro Asn Asp Asn
65                  70                  75                  80

Gly Ser Tyr Arg Cys Ser Ala Asn Phe Gln Ser Asn Leu Ile Glu Ser
                85                  90                  95

His Ser Thr Thr Leu Tyr Val Thr Asp Val Lys Ser Ala Ser Glu Arg
            100                 105                 110

Pro Ser Lys Asp Glu Met Ala Ser Arg Pro Trp Leu Leu Tyr Arg Leu
        115                 120                 125

Leu Pro Leu Gly Gly Leu Pro Leu Leu Ile Thr Thr Cys Phe Cys Leu
    130                 135                 140

Phe Cys Cys Leu Arg Arg His Gln Gly Lys Gln Asn Glu Leu Ser Asp
145                 150                 155                 160

Thr Ala Gly Arg Glu Ile Asn Leu Val Asp Ala His Leu Lys Ser Glu
                165                 170                 175

Gln Thr Glu Ala Ser Thr Arg Gln Asn Ser Gln Val Leu Leu Ser Glu
            180                 185                 190

Thr Gly Ile Tyr Asp Asn Asp Pro Asp Leu Cys Phe Arg Met Gln Glu
```

```
                195                 200                 205
Gly Ser Glu Val Tyr Ser Asn Pro Cys Leu Glu Glu Asn Lys Pro Gly
    210                 215                 220

Ile Val Tyr Ala Ser Leu Asn His Ser Val Ile Gly Pro Asn Ser Arg
225                 230                 235                 240

Leu Ala Arg Asn Val Lys Glu Ala Pro Thr Glu Tyr Ala Ser Ile Cys
                245                 250                 255

Val Arg Ser

<210> SEQ ID NO 295
<211> LENGTH: 133
<212> TYPE: PRT
<213> ORGANISM: Homo sapiens

<400> SEQUENCE: 295

Ile Asn Ile Thr Ser Ser Ala Ser Gln Glu Gly Thr Arg Leu Asn Leu
1               5                   10                  15

Ile Cys Thr Val Trp His Lys Lys Glu Ala Glu Gly Phe Val Val
                20                  25                  30

Phe Leu Cys Lys Asp Arg Ser Gly Asp Cys Ser Pro Glu Thr Ser Leu
            35                  40                  45

Lys Gln Leu Arg Leu Lys Arg Asp Pro Gly Ile Asp Gly Val Gly Glu
    50                  55                  60

Ile Ser Ser Gln Leu Met Phe Thr Ile Ser Gln Val Thr Pro Leu His
65                  70                  75                  80

Ser Gly Thr Tyr Gln Cys Cys Ala Arg Ser Gln Lys Ser Gly Ile Arg
                85                  90                  95

Leu Gln Gly His Phe Phe Ser Ile Leu Phe Thr Glu Thr Gly Asn Tyr
            100                 105                 110

Thr Val Thr Gly Leu Lys Gln Arg Gln His Leu Glu Phe Ser His Asn
    115                 120                 125

Glu Gly Thr Leu Ser
        130

<210> SEQ ID NO 296
<211> LENGTH: 492
<212> TYPE: PRT
<213> ORGANISM: Homo sapiens

<400> SEQUENCE: 296

Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
                20                  25                  30

Trp Tyr Lys Gly Glu Arg Val Asp Gly Asn Arg Gln Ile Val Gly Tyr
            35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
    115                 120                 125
```

Val Ala Phe Thr Cys Glu Pro Glu Thr Gln Asp Thr Thr Tyr Leu Trp
    130                 135                 140

Trp Ile Asn Asn Gln Ser Leu Pro Val Ser Pro Arg Leu Gln Leu Ser
145                 150                 155                 160

Asn Gly Asn Arg Thr Leu Thr Leu Leu Ser Val Thr Arg Asn Asp Thr
                165                 170                 175

Gly Pro Tyr Glu Cys Glu Ile Gln Asn Pro Val Ser Ala Asn Arg Ser
            180                 185                 190

Asp Pro Val Thr Leu Asn Val Thr Tyr Gly Pro Asp Thr Pro Thr Ile
        195                 200                 205

Ser Pro Ser Asp Thr Tyr Tyr Arg Pro Gly Ala Asn Leu Ser Leu Ser
210                 215                 220

Cys Tyr Ala Ala Ser Asn Pro Pro Ala Gln Tyr Ser Trp Leu Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys His Ala Asn Asn Ser Val Thr
            260                 265                 270

Gly Cys Asn Arg Thr Thr Val Lys Thr Ile Ile Val Thr Glu Leu Ser
        275                 280                 285

Pro Val Val Ala Lys Pro Gln Ile Lys Ala Ser Lys Thr Thr Val Thr
290                 295                 300

Gly Asp Lys Asp Ser Val Asn Leu Thr Cys Ser Thr Asn Asp Thr Gly
305                 310                 315                 320

Ile Ser Ile Arg Trp Phe Phe Lys Asn Gln Ser Leu Pro Ser Ser Glu
                325                 330                 335

Arg Met Lys Leu Ser Gln Gly Asn Thr Thr Leu Ser Ile Asn Pro Val
            340                 345                 350

Lys Arg Glu Asp Ala Gly Thr Tyr Trp Cys Glu Val Phe Asn Pro Ile
        355                 360                 365

Ser Lys Asn Gln Ser Asp Pro Ile Met Leu Asn Val Asn Tyr Asn Ala
370                 375                 380

Leu Pro Gln Glu Asn Gly Leu Ser Pro Gly Ala Ile Ala Gly Ile Val
385                 390                 395                 400

Ile Gly Val Val Ala Leu Val Ala Leu Ile Ala Val Ala Leu Ala Cys
                405                 410                 415

Phe Leu His Phe Gly Lys Thr Gly Arg Ala Ser Asp Gln Arg Asp Leu
            420                 425                 430

Thr Glu His Lys Pro Ser Val Ser Asn His Thr Gln Asp His Ser Asn
        435                 440                 445

Asp Pro Pro Asn Lys Met Asn Glu Val Thr Tyr Ser Thr Leu Asn Phe
450                 455                 460

Glu Ala Gln Gln Pro Thr Gln Pro Thr Ser Ala Ser Pro Ser Leu Thr
465                 470                 475                 480

Ala Thr Glu Ile Ile Tyr Ser Glu Val Lys Lys Gln
                485                 490

<210> SEQ ID NO 297
<211> LENGTH: 266
<212> TYPE: PRT
<213> ORGANISM: Homo sapiens

<400> SEQUENCE: 297

Gln Glu Glu Asp Leu Pro Arg Pro Ser Ile Ser Ala Glu Pro Gly Thr

```
                1               5                   10                  15
            Val Ile Pro Leu Gly Ser His Val Thr Phe Val Cys Arg Gly Pro Val
                                20                  25                  30
            Gly Val Gln Thr Phe Arg Leu Glu Arg Glu Ser Arg Ser Thr Tyr Asn
                                35                  40                  45
            Asp Thr Glu Asp Val Ser Gln Ala Ser Pro Ser Glu Ser Glu Ala Arg
                 50                      55                  60
            Phe Arg Ile Asp Ser Val Ser Glu Gly Asn Ala Gly Pro Tyr Arg Cys
             65                      70                  75                  80
            Ile Tyr Tyr Lys Pro Pro Lys Trp Ser Glu Gln Ser Asp Tyr Leu Glu
                                85                  90                  95
            Leu Leu Val Lys Glu Thr Ser Gly Gly Pro Asp Ser Pro Asp Thr Glu
                            100                 105                 110
            Pro Gly Ser Ser Ala Gly Pro Thr Gln Arg Pro Ser Asp Asn Ser His
                            115                 120                 125
            Asn Glu His Ala Pro Ala Ser Gln Gly Leu Lys Ala Glu His Leu Tyr
                     130                     135                 140
            Ile Leu Ile Gly Val Ser Val Val Phe Leu Phe Cys Leu Leu Leu Leu
            145                     150                 155                 160
            Val Leu Phe Cys Leu His Arg Gln Asn Gln Ile Lys Gln Gly Pro Pro
                                165                 170                 175
            Arg Ser Lys Asp Glu Glu Gln Lys Pro Gln Gln Arg Pro Asp Leu Ala
                            180                 185                 190
            Val Asp Val Leu Glu Arg Thr Ala Asp Lys Ala Thr Val Asn Gly Leu
                        195                 200                 205
            Pro Glu Lys Asp Arg Glu Thr Asp Thr Ser Ala Leu Ala Ala Gly Ser
                210                     215                 220
            Ser Gln Glu Val Thr Tyr Ala Gln Leu Asp His Trp Ala Leu Thr Gln
            225                     230                 235                 240
            Arg Thr Ala Arg Ala Val Ser Pro Gln Ser Thr Lys Pro Met Ala Glu
                                245                 250                 255
            Ser Ile Thr Tyr Ala Ala Val Ala Arg His
                            260                 265

<210> SEQ ID NO 298
<211> LENGTH: 390
<212> TYPE: PRT
<213> ORGANISM: Homo sapiens

<400> SEQUENCE: 298

Met Pro Pro Ser Gly Leu Arg Leu Leu Leu Leu Leu Pro Leu Leu
             1               5                   10                  15
            Trp Leu Leu Val Leu Thr Pro Gly Arg Pro Ala Ala Gly Leu Ser Thr
                                20                  25                  30
            Cys Lys Thr Ile Asp Met Glu Leu Val Lys Arg Lys Arg Ile Glu Ala
                                35                  40                  45
            Ile Arg Gly Gln Ile Leu Ser Lys Leu Arg Leu Ala Ser Pro Pro Ser
                     50                      55                  60
            Gln Gly Glu Val Pro Pro Gly Pro Leu Pro Glu Ala Val Leu Ala Leu
             65                      70                  75                  80
            Tyr Asn Ser Thr Arg Asp Arg Val Ala Gly Glu Ser Ala Glu Pro Glu
                                85                  90                  95
            Pro Glu Pro Glu Ala Asp Tyr Tyr Ala Lys Glu Val Thr Arg Val Leu
                            100                 105                 110
```

Met Val Glu Thr His Asn Glu Ile Tyr Asp Lys Phe Lys Gln Ser Thr
115                 120                 125

His Ser Ile Tyr Met Phe Phe Asn Thr Ser Glu Leu Arg Glu Ala Val
130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
            165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
195                 200                 205

Ser Arg Gly Gly Glu Ile Glu Gly Phe Arg Leu Ser Ala His Cys Ser
210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
275                 280                 285

Thr Glu Lys Asn Cys Cys Val Arg Gln Leu Tyr Ile Asp Phe Arg Lys
290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
355                 360                 365

Tyr Val Gly Arg Lys Pro Lys Val Glu Gln Leu Ser Asn Met Ile Val
370                 375                 380

Arg Ser Cys Lys Cys Ser
385                 390

<210> SEQ ID NO 299
<211> LENGTH: 160
<212> TYPE: PRT
<213> ORGANISM: Homo sapiens

<400> SEQUENCE: 299

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

```
Asn Leu Lys Thr Leu Arg Leu Arg Leu Arg Arg Cys His Arg Phe Leu
                100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
        130                 135                 140

Ile Phe Ile Asn Tyr Ile Glu Ala Tyr Met Thr Met Lys Ile Arg Asn
145                 150                 155                 160

<210> SEQ ID NO 300
<211> LENGTH: 564
<212> TYPE: PRT
<213> ORGANISM: Homo sapiens

<400> SEQUENCE: 300

Val Trp Glu Lys Thr Val Asn Thr Glu Glu Asn Val Tyr Ala Thr Leu
1               5                   10                  15

Gly Ser Asp Val Asn Leu Thr Cys Gln Thr Gln Thr Val Gly Phe Phe
            20                  25                  30

Val Gln Met Gln Trp Ser Lys Val Thr Asn Lys Ile Asp Leu Ile Ala
        35                  40                  45

Val Tyr His Pro Gln Tyr Gly Phe Tyr Cys Ala Tyr Gly Arg Pro Cys
    50                  55                  60

Glu Ser Leu Val Thr Phe Thr Glu Thr Pro Glu Asn Gly Ser Lys Trp
65                  70                  75                  80

Thr Leu His Leu Arg Asn Met Ser Cys Ser Val Ser Gly Arg Tyr Glu
                85                  90                  95

Cys Met Leu Val Leu Tyr Pro Glu Gly Ile Gln Thr Lys Ile Tyr Asn
            100                 105                 110

Leu Leu Ile Gln Thr His Val Thr Ala Asp Glu Trp Asn Ser Asn His
        115                 120                 125

Thr Ile Glu Ile Glu Ile Asn Gln Thr Leu Glu Ile Pro Cys Phe Gln
    130                 135                 140

Asn Ser Ser Ser Lys Ile Ser Ser Glu Phe Thr Tyr Ala Trp Ser Val
145                 150                 155                 160

Glu Asn Ser Ser Thr Asp Ser Trp Val Leu Leu Ser Lys Gly Ile Lys
                165                 170                 175

Glu Asp Asn Gly Thr Gln Glu Thr Leu Ile Ser Gln Asn His Leu Ile
            180                 185                 190

Ser Asn Ser Thr Leu Leu Lys Asp Arg Val Lys Leu Gly Thr Asp Tyr
        195                 200                 205

Arg Leu His Leu Ser Pro Val Gln Ile Phe Asp Asp Gly Arg Lys Phe
    210                 215                 220

Ser Cys His Ile Arg Val Gly Pro Asn Lys Ile Leu Arg Ser Ser Thr
225                 230                 235                 240

Thr Val Lys Val Phe Ala Lys Pro Glu Ile Pro Val Ile Val Glu Asn
                245                 250                 255

Asn Ser Thr Asp Val Leu Val Glu Arg Arg Phe Thr Cys Leu Leu Lys
            260                 265                 270

Asn Val Phe Pro Lys Ala Asn Ile Thr Trp Phe Ile Asp Gly Ser Phe
        275                 280                 285

Leu His Asp Glu Lys Glu Gly Ile Tyr Ile Thr Asn Glu Glu Arg Lys
    290                 295                 300

Gly Lys Asp Gly Phe Leu Glu Leu Lys Ser Val Leu Thr Arg Val His
```

```
                305                 310                 315                 320
        Ser Asn Lys Pro Ala Gln Ser Asp Asn Leu Thr Ile Trp Cys Met Ala
                        325                 330                 335

Leu Ser Pro Val Pro Gly Asn Lys Val Trp Asn Ile Ser Ser Glu Lys
                        340                 345                 350

Ile Thr Phe Leu Leu Gly Ser Glu Ile Ser Ser Thr Asp Pro Pro Leu
                        355                 360                 365

Ser Val Thr Glu Ser Thr Leu Asp Thr Gln Pro Ser Pro Ala Ser Ser
                    370                 375                 380

Val Ser Pro Ala Arg Tyr Pro Ala Thr Ser Ser Val Thr Leu Val Asp
        385                 390                 395                 400

Val Ser Ala Leu Arg Pro Asn Thr Thr Pro Gln Pro Ser Asn Ser Ser
                        405                 410                 415

Met Thr Thr Arg Gly Phe Asn Tyr Pro Trp Thr Ser Ser Gly Thr Asp
                        420                 425                 430

Thr Lys Lys Ser Val Ser Arg Ile Pro Ser Glu Thr Tyr Ser Ser Ser
                        435                 440                 445

Pro Ser Gly Ala Gly Ser Thr Leu His Asp Asn Val Phe Thr Ser Thr
                        450                 455                 460

Ala Arg Ala Phe Ser Glu Val Pro Thr Thr Ala Asn Gly Ser Thr Lys
        465                 470                 475                 480

Thr Asn His Val His Ile Thr Gly Ile Val Val Asn Lys Pro Lys Asp
                        485                 490                 495

Gly Met Ser Trp Pro Val Ile Val Ala Ala Leu Leu Phe Cys Cys Met
                        500                 505                 510

Ile Leu Phe Gly Leu Gly Val Arg Lys Trp Cys Gln Tyr Gln Lys Glu
                        515                 520                 525

Ile Met Glu Arg Pro Pro Pro Phe Lys Pro Pro Pro Pro Pro Ile Lys
                        530                 535                 540

Tyr Thr Cys Ile Gln Glu Pro Asn Glu Ser Asp Leu Pro Tyr His Glu
        545                 550                 555                 560

Met Glu Thr Leu

<210> SEQ ID NO 301
<211> LENGTH: 223
<212> TYPE: PRT
<213> ORGANISM: Homo sapiens

<400> SEQUENCE: 301

Met Met Thr Gly Thr Ile Glu Thr Gly Asn Ile Ser Ala Glu Lys
        1               5                   10                  15

Gly Gly Ser Ile Ile Leu Gln Cys His Leu Ser Ser Thr Thr Ala Gln
                        20                  25                  30

Val Thr Gln Val Asn Trp Glu Gln Gln Asp Gln Leu Leu Ala Ile Cys
                        35                  40                  45

Asn Ala Asp Leu Gly Trp His Ile Ser Pro Ser Phe Lys Asp Arg Val
                    50                  55                  60

Ala Pro Gly Pro Gly Leu Gly Leu Thr Leu Gln Ser Leu Thr Val Asn
        65                  70                  75                  80

Asp Thr Gly Glu Tyr Phe Cys Ile Tyr His Thr Tyr Pro Asp Gly Thr
                        85                  90                  95

Tyr Thr Gly Arg Ile Phe Leu Glu Val Leu Glu Ser Ser Val Ala Glu
                        100                 105                 110

His Gly Ala Arg Phe Gln Ile Pro Leu Leu Gly Ala Met Ala Ala Thr
```

-continued

```
            115                 120                 125
Leu Val Val Ile Cys Thr Ala Val Ile Val Val Ala Leu Thr Arg
    130                 135                 140
Lys Lys Lys Ala Leu Arg Ile His Ser Val Glu Gly Asp Leu Arg Arg
145                 150                 155                 160
Lys Ser Ala Gly Gln Glu Glu Trp Ser Pro Ser Ala Pro Ser Pro Pro
                165                 170                 175
Gly Ser Cys Val Gln Ala Glu Ala Ala Pro Ala Gly Leu Cys Gly Glu
            180                 185                 190
Gln Arg Gly Glu Asp Cys Ala Glu Leu His Asp Tyr Phe Asn Val Leu
        195                 200                 205
Ser Tyr Arg Ser Leu Gly Asn Cys Ser Phe Phe Thr Glu Thr Gly
    210                 215                 220

<210> SEQ ID NO 302
<211> LENGTH: 233
<212> TYPE: PRT
<213> ORGANISM: Homo sapiens

<400> SEQUENCE: 302

Met Asp Asn Gln Gly Val Ile Tyr Ser Asp Leu Asn Leu Pro Pro Asn
1               5                   10                  15
Pro Lys Arg Gln Gln Arg Lys Pro Lys Gly Asn Lys Asn Ser Ile Leu
            20                  25                  30
Ala Thr Glu Gln Glu Ile Thr Tyr Ala Glu Leu Asn Leu Gln Lys Ala
        35                  40                  45
Ser Gln Asp Phe Gln Gly Asn Asp Lys Thr Tyr His Cys Lys Asp Leu
    50                  55                  60
Pro Ser Ala Pro Glu Lys Leu Ile Val Gly Ile Leu Gly Ile Ile Cys
65                  70                  75                  80
Leu Ile Leu Met Ala Ser Val Val Thr Ile Val Val Ile Pro Ser Thr
                85                  90                  95
Leu Ile Gln Arg His Asn Asn Ser Ser Leu Asn Thr Arg Thr Gln Lys
            100                 105                 110
Ala Arg His Cys Gly His Cys Pro Glu Glu Trp Ile Thr Tyr Ser Asn
        115                 120                 125
Ser Cys Tyr Tyr Ile Gly Lys Glu Arg Arg Thr Trp Glu Glu Ser Leu
    130                 135                 140
Leu Ala Cys Thr Ser Lys Asn Ser Ser Leu Leu Ser Ile Asp Asn Glu
145                 150                 155                 160
Glu Glu Met Lys Phe Leu Ser Ile Ile Ser Pro Ser Ser Trp Ile Gly
                165                 170                 175
Val Phe Arg Asn Ser Ser His His Pro Trp Val Thr Met Asn Gly Leu
            180                 185                 190
Ala Phe Lys His Glu Ile Lys Asp Ser Asp Asn Ala Glu Leu Asn Cys
        195                 200                 205
Ala Val Leu Gln Val Asn Arg Leu Lys Ser Ala Gln Cys Gly Ser Ser
    210                 215                 220
Ile Ile Tyr His Cys Lys His Lys Leu
225                 230

<210> SEQ ID NO 303
<211> LENGTH: 507
<212> TYPE: PRT
<213> ORGANISM: Homo sapiens
```

```
<400> SEQUENCE: 303

Gln Asp Val Arg Val Gln Val Leu Pro Glu Val Arg Gly Gln Leu Gly
1               5                   10                  15

Gly Thr Val Glu Leu Pro Cys His Leu Leu Pro Pro Val Pro Gly Leu
            20                  25                  30

Tyr Ile Ser Leu Val Thr Trp Gln Arg Pro Asp Ala Pro Ala Asn His
        35                  40                  45

Gln Asn Val Ala Ala Phe His Pro Lys Met Gly Pro Ser Phe Pro Ser
    50                  55                  60

Pro Lys Pro Gly Ser Glu Arg Leu Ser Phe Val Ser Ala Lys Gln Ser
65                  70                  75                  80

Thr Gly Gln Asp Thr Glu Ala Glu Leu Gln Asp Ala Thr Leu Ala Leu
                85                  90                  95

His Gly Leu Thr Val Glu Asp Glu Gly Asn Tyr Thr Cys Glu Phe Ala
            100                 105                 110

Thr Phe Pro Lys Gly Ser Val Arg Gly Met Thr Trp Leu Arg Val Ile
        115                 120                 125

Ala Lys Pro Lys Asn Gln Ala Glu Ala Gln Lys Val Thr Phe Ser Gln
    130                 135                 140

Asp Pro Thr Thr Val Ala Leu Cys Ile Ser Lys Glu Gly Arg Pro Pro
145                 150                 155                 160

Ala Arg Ile Ser Trp Leu Ser Ser Leu Asp Trp Glu Ala Lys Glu Thr
                165                 170                 175

Gln Val Ser Gly Thr Leu Ala Gly Thr Val Thr Val Thr Ser Arg Phe
            180                 185                 190

Thr Leu Val Pro Ser Gly Arg Ala Asp Gly Val Thr Val Thr Cys Lys
        195                 200                 205

Val Glu His Glu Ser Phe Glu Glu Pro Ala Leu Ile Pro Val Thr Leu
    210                 215                 220

Ser Val Arg Tyr Pro Pro Glu Val Ser Ile Ser Gly Tyr Asp Asp Asn
225                 230                 235                 240

Trp Tyr Leu Gly Arg Thr Asp Ala Thr Leu Ser Cys Asp Val Arg Ser
                245                 250                 255

Asn Pro Glu Pro Thr Gly Tyr Asp Trp Ser Thr Thr Ser Gly Thr Phe
            260                 265                 270

Pro Thr Ser Ala Val Ala Gln Gly Ser Gln Leu Val Ile His Ala Val
        275                 280                 285

Asp Ser Leu Phe Asn Thr Thr Phe Val Cys Thr Val Thr Asn Ala Val
    290                 295                 300

Gly Met Gly Arg Ala Glu Gln Val Ile Phe Val Arg Glu Thr Pro Asn
305                 310                 315                 320

Thr Ala Gly Ala Gly Ala Thr Gly Gly Ile Ile Gly Gly Ile Ile Ala
                325                 330                 335

Ala Ile Ile Ala Thr Ala Val Ala Ala Thr Gly Ile Leu Ile Cys Arg
            340                 345                 350

Gln Gln Arg Lys Glu Gln Thr Leu Gln Gly Ala Glu Glu Asp Glu Asp
        355                 360                 365

Leu Glu Gly Pro Pro Ser Tyr Lys Pro Pro Thr Pro Lys Ala Lys Leu
    370                 375                 380

Glu Ala Gln Glu Met Pro Ser Gln Leu Phe Thr Leu Gly Ala Ser Glu
385                 390                 395                 400

His Ser Pro Leu Lys Thr Pro Tyr Phe Asp Ala Gly Ala Ser Cys Thr
                405                 410                 415
```

```
Glu Gln Glu Met Pro Arg Tyr His Glu Leu Pro Thr Leu Glu Arg
            420             425             430

Ser Gly Pro Leu His Pro Gly Ala Thr Ser Leu Gly Ser Pro Ile Pro
        435                 440                 445

Val Pro Pro Gly Pro Pro Ala Val Glu Asp Val Ser Leu Asp Leu Glu
450                 455                 460

Asp Glu Glu Gly Glu Glu Glu Glu Tyr Leu Asp Lys Ile Asn Pro
465             470              475             480

Ile Tyr Asp Ala Leu Ser Tyr Ser Ser Pro Ser Asp Ser Tyr Gln Gly
                485             490             495

Lys Gly Phe Val Met Ser Arg Ala Met Tyr Val
            500             505

<210> SEQ ID NO 304
<211> LENGTH: 305
<212> TYPE: PRT
<213> ORGANISM: Homo sapiens

<400> SEQUENCE: 304

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
                20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
        50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile Leu Ile Val
        115                 120                 125

Ile Phe Pro Ile Phe Ala Ile Leu Leu Phe Trp Gly Gln Phe Gly Ile
    130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
                165                 170                 175

Ile Leu Phe Val Pro Gly Glu Tyr Ser Leu Lys Asn Ala Thr Gly Leu
            180                 185                 190

Gly Leu Ile Val Thr Ser Thr Gly Ile Leu Ile Leu Leu His Tyr Tyr
        195                 200                 205

Val Phe Ser Thr Ala Ile Gly Leu Thr Ser Phe Val Ile Ala Ile Leu
    210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
            260                 265                 270

Phe Val Ala Ser Asn Gln Lys Thr Ile Gln Pro Pro Arg Lys Ala Val
```

```
                275                 280                 285
Glu Glu Pro Leu Asn Ala Phe Lys Glu Ser Lys Gly Met Met Asn Asp
    290                 295                 300
Glu
305

<210> SEQ ID NO 305
<211> LENGTH: 474
<212> TYPE: PRT
<213> ORGANISM: Homo sapiens

<400> SEQUENCE: 305

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335
```

```
Ser Asn Glu Arg Asn Ile Tyr Ile Val Val Gly Val Cys Thr Leu
                340                 345                 350

Leu Val Ala Leu Leu Met Ala Ala Leu Tyr Leu Val Arg Ile Arg Gln
    355                 360                 365

Lys Lys Ala Gln Gly Ser Thr Ser Ser Thr Arg Leu His Glu Pro Glu
    370                 375                 380

Lys Asn Ala Arg Glu Ile Thr Gln Asp Thr Asn Asp Ile Thr Tyr Ala
385                 390                 395                 400

Asp Leu Asn Leu Pro Lys Gly Lys Lys Pro Ala Pro Gln Ala Ala Glu
                405                 410                 415

Pro Asn Asn His Thr Glu Tyr Ala Ser Ile Gln Thr Ser Pro Gln Pro
                420                 425                 430

Ala Ser Glu Asp Thr Leu Thr Tyr Ala Asp Leu Asp Met Val His Leu
            435                 440                 445

Asn Arg Thr Pro Lys Gln Pro Ala Pro Lys Pro Glu Pro Ser Phe Ser
            450                 455                 460

Glu Tyr Ala Ser Val Gln Val Pro Arg Lys
465                 470

<210> SEQ ID NO 306
<211> LENGTH: 349
<212> TYPE: PRT
<213> ORGANISM: Homo sapiens

<400> SEQUENCE: 306

Cys Gln Gly Ser Ala Asp His Val Val Ser Ile Ser Gly Val Pro Leu
1               5                   10                  15

Gln Leu Gln Pro Asn Ser Ile Gln Thr Lys Val Asp Ser Ile Ala Trp
                20                  25                  30

Lys Lys Leu Leu Pro Ser Gln Asn Gly Phe His His Ile Leu Lys Trp
            35                  40                  45

Glu Asn Gly Ser Leu Pro Ser Asn Thr Ser Asn Asp Arg Phe Ser Phe
        50                  55                  60

Ile Val Lys Asn Leu Ser Leu Leu Ile Lys Ala Ala Gln Gln Gln Asp
65                  70                  75                  80

Ser Gly Leu Tyr Cys Leu Glu Val Thr Ser Ile Ser Gly Lys Val Gln
                85                  90                  95

Thr Ala Thr Phe Gln Val Phe Val Phe Glu Ser Leu Leu Pro Asp Lys
                100                 105                 110

Val Glu Lys Pro Arg Leu Gln Gly Gln Gly Lys Ile Leu Asp Arg Gly
            115                 120                 125

Arg Cys Gln Val Ala Leu Ser Cys Leu Val Ser Arg Asp Gly Asn Val
130                 135                 140

Ser Tyr Ala Trp Tyr Arg Gly Ser Lys Leu Ile Gln Thr Ala Gly Asn
145                 150                 155                 160

Leu Thr Tyr Leu Asp Glu Glu Val Asp Ile Asn Gly Thr His Thr Tyr
                165                 170                 175

Thr Cys Asn Val Ser Asn Pro Val Ser Trp Glu Ser His Thr Leu Asn
            180                 185                 190

Leu Thr Gln Asp Cys Gln Asn Ala His Gln Glu Phe Arg Phe Trp Pro
        195                 200                 205

Phe Leu Val Ile Ile Val Ile Leu Ser Ala Leu Phe Leu Gly Thr Leu
    210                 215                 220

Ala Cys Phe Cys Val Trp Arg Arg Lys Arg Lys Glu Lys Gln Ser Glu
225                 230                 235                 240
```

```
Thr Ser Pro Lys Glu Phe Leu Thr Ile Tyr Glu Asp Val Lys Asp Leu
                245                 250                 255

Lys Thr Arg Arg Asn His Glu Gln Glu Gln Thr Phe Pro Gly Gly Gly
            260                 265                 270

Ser Thr Ile Tyr Ser Met Ile Gln Ser Gln Ser Ser Ala Pro Thr Ser
            275                 280                 285

Gln Glu Pro Ala Tyr Thr Leu Tyr Ser Leu Ile Gln Pro Ser Arg Lys
        290                 295                 300

Ser Gly Ser Arg Lys Arg Asn His Ser Pro Ser Phe Asn Ser Thr Ile
305                 310                 315                 320

Tyr Glu Val Ile Gly Lys Ser Gln Pro Lys Ala Gln Asn Pro Ala Arg
                325                 330                 335

Leu Ser Arg Lys Glu Leu Glu Asn Phe Asp Val Tyr Ser
            340                 345
```

<210> SEQ ID NO 307
<211> LENGTH: 651
<212> TYPE: PRT
<213> ORGANISM: Homo sapiens

<400> SEQUENCE: 307

```
Lys Leu Thr Ile Glu Ser Thr Pro Phe Asn Val Ala Glu Gly Lys Glu
1               5                   10                  15

Val Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
            35                  40                  45

Val Ile Gly Thr Gln Gln Ala Thr Pro Gly Pro Ala Tyr Ser Gly Arg
        50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
        115                 120                 125

Val Ala Phe Thr Cys Glu Pro Glu Thr Gln Asp Ala Thr Tyr Leu Trp
130                 135                 140

Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
                165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
        195                 200                 205

Ser Pro Leu Asn Thr Ser Tyr Arg Ser Gly Glu Asn Leu Asn Leu Ser
210                 215                 220

Cys His Ala Ala Ser Asn Pro Pro Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
```

```
                260                 265                 270
Gly Leu Asn Arg Thr Thr Val Thr Thr Ile Thr Val Tyr Ala Glu Pro
            275                 280                 285

Pro Lys Pro Phe Ile Thr Ser Asn Asn Ser Asn Pro Val Glu Asp Glu
        290                 295                 300

Asp Ala Val Ala Leu Thr Cys Glu Pro Glu Ile Gln Asn Thr Thr Tyr
305                 310                 315                 320

Leu Trp Trp Val Asn Asn Gln Ser Leu Pro Val Ser Pro Arg Leu Gln
                325                 330                 335

Leu Ser Asn Asp Asn Arg Thr Leu Thr Leu Leu Ser Val Thr Arg Asn
            340                 345                 350

Asp Val Gly Pro Tyr Glu Cys Gly Ile Gln Asn Lys Leu Ser Val Asp
        355                 360                 365

His Ser Asp Pro Val Ile Leu Asn Val Leu Tyr Gly Pro Asp Asp Pro
    370                 375                 380

Thr Ile Ser Pro Ser Tyr Thr Tyr Tyr Arg Pro Gly Val Asn Leu Ser
385                 390                 395                 400

Leu Ser Cys His Ala Ala Ser Asn Pro Pro Ala Gln Tyr Ser Trp Leu
                405                 410                 415

Ile Asp Gly Asn Ile Gln Gln His Thr Gln Glu Leu Phe Ile Ser Asn
            420                 425                 430

Ile Thr Glu Lys Asn Ser Gly Leu Tyr Thr Cys Gln Ala Asn Asn Ser
        435                 440                 445

Ala Ser Gly His Ser Arg Thr Thr Val Lys Thr Ile Thr Val Ser Ala
    450                 455                 460

Glu Leu Pro Lys Pro Ser Ile Ser Ser Asn Asn Ser Lys Pro Val Glu
465                 470                 475                 480

Asp Lys Asp Ala Val Ala Phe Thr Cys Glu Pro Glu Ala Gln Asn Thr
                485                 490                 495

Thr Tyr Leu Trp Trp Val Asn Gly Gln Ser Leu Pro Val Ser Pro Arg
            500                 505                 510

Leu Gln Leu Ser Asn Gly Asn Arg Thr Leu Thr Leu Phe Asn Val Thr
        515                 520                 525

Arg Asn Asp Ala Arg Ala Tyr Val Cys Gly Ile Gln Asn Ser Val Ser
    530                 535                 540

Ala Asn Arg Ser Asp Pro Val Thr Leu Asp Val Leu Tyr Gly Pro Asp
545                 550                 555                 560

Thr Pro Ile Ile Ser Pro Pro Asp Ser Ser Tyr Leu Ser Gly Ala Asn
                565                 570                 575

Leu Asn Leu Ser Cys His Ser Ala Ser Asn Pro Ser Pro Gln Tyr Ser
            580                 585                 590

Trp Arg Ile Asn Gly Ile Pro Gln Gln His Thr Gln Val Leu Phe Ile
        595                 600                 605

Ala Lys Ile Thr Pro Asn Asn Asn Gly Thr Tyr Ala Cys Phe Val Ser
    610                 615                 620

Asn Leu Ala Thr Gly Arg Asn Asn Ser Ile Val Lys Ser Ile Thr Val
625                 630                 635                 640

Ser Ala Ser Gly Thr Ser Pro Gly Leu Ser Ala
                645                 650

<210> SEQ ID NO 308
<211> LENGTH: 355
<212> TYPE: PRT
<213> ORGANISM: Homo sapiens
```

<400> SEQUENCE: 308

```
Met Ala Phe Ser Gly Ser Gln Ala Pro Tyr Leu Ser Pro Ala Val Pro
1               5                   10                  15
Phe Ser Gly Thr Ile Gln Gly Gly Leu Gln Asp Gly Leu Gln Ile Thr
            20                  25                  30
Val Asn Gly Thr Val Leu Ser Ser Gly Thr Arg Phe Ala Val Asn
        35                  40                  45
Phe Gln Thr Gly Phe Ser Gly Asn Asp Ile Ala Phe His Phe Asn Pro
    50                  55                  60
Arg Phe Glu Asp Gly Gly Tyr Val Val Cys Asn Thr Arg Gln Asn Gly
65                  70                  75                  80
Ser Trp Gly Pro Glu Glu Arg Lys Thr His Met Pro Phe Gln Lys Gly
                85                  90                  95
Met Pro Phe Asp Leu Cys Phe Leu Val Gln Ser Ser Asp Phe Lys Val
            100                 105                 110
Met Val Asn Gly Ile Leu Phe Val Gln Tyr Phe His Arg Val Pro Phe
        115                 120                 125
His Arg Val Asp Thr Ile Ser Val Asn Gly Ser Val Gln Leu Ser Tyr
130                 135                 140
Ile Ser Phe Gln Asn Pro Arg Thr Val Pro Val Gln Pro Ala Phe Ser
145                 150                 155                 160
Thr Val Pro Phe Ser Gln Pro Val Cys Phe Pro Pro Arg Pro Arg Gly
                165                 170                 175
Arg Arg Gln Lys Pro Pro Gly Val Trp Pro Ala Asn Pro Ala Pro Ile
            180                 185                 190
Thr Gln Thr Val Ile His Thr Val Gln Ser Ala Pro Gly Gln Met Phe
        195                 200                 205
Ser Thr Pro Ala Ile Pro Pro Met Met Tyr Pro His Pro Ala Tyr Pro
210                 215                 220
Met Pro Phe Ile Thr Thr Ile Leu Gly Gly Leu Tyr Pro Ser Lys Ser
225                 230                 235                 240
Ile Leu Leu Ser Gly Thr Val Leu Pro Ser Ala Gln Arg Phe His Ile
                245                 250                 255
Asn Leu Cys Ser Gly Asn His Ile Ala Phe His Leu Asn Pro Arg Phe
            260                 265                 270
Asp Glu Asn Ala Val Val Arg Asn Thr Gln Ile Asp Asn Ser Trp Gly
        275                 280                 285
Ser Glu Glu Arg Ser Leu Pro Arg Lys Met Pro Phe Val Arg Gly Gln
290                 295                 300
Ser Phe Ser Val Trp Ile Leu Cys Glu Ala His Cys Leu Lys Val Ala
305                 310                 315                 320
Val Asp Gly Gln His Leu Phe Glu Tyr Tyr His Arg Leu Arg Asn Leu
                325                 330                 335
Pro Thr Ile Asn Arg Leu Glu Val Gly Gly Asp Ile Gln Leu Thr His
            340                 345                 350
Val Gln Thr
        355
```

<210> SEQ ID NO 309
<211> LENGTH: 119
<212> TYPE: PRT
<213> ORGANISM: Artificial sequence
<220> FEATURE:
<223> OTHER INFORMATION: OX40 antiboyd VH

<400> SEQUENCE: 309

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
50                  55                  60

Lys Gly Arg Ala Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 310
<211> LENGTH: 107
<212> TYPE: PRT
<213> ORGANISM: Artificial sequence
<220> FEATURE:
<223> OTHER INFORMATION: OX40 antibody VL

<400> SEQUENCE: 310

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gln Gly Thr Lys Val Glu Ile Lys
            100                 105

<210> SEQ ID NO 311
<211> LENGTH: 121
<212> TYPE: PRT
<213> ORGANISM: Artificial sequence
<220> FEATURE:
<223> OTHER INFORMATION: OX40 antibody VH

<400> SEQUENCE: 311

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Met
        35                  40                  45

Gly Gly Ile Tyr Pro Asn Asn Gly Gly Ser Thr Tyr Asn Gln Asn Phe
50                  55                  60

```
Lys Asp Arg Val Thr Ile Thr Ala Asp Lys Ser Thr Ser Thr Ala Tyr
 65              70                  75                  80

Met Glu Leu Ser Ser Leu Arg Ser Glu Asp Thr Ala Val Tyr Tyr Cys
                 85                  90                  95

Ala Arg Met Gly Tyr His Gly Pro His Leu Asp Phe Asp Val Trp Gly
            100             105                 110

Gln Gly Thr Thr Val Thr Val Ser Ser
            115             120

<210> SEQ ID NO 312
<211> LENGTH: 107
<212> TYPE: PRT
<213> ORGANISM: Artificial sequence
<220> FEATURE:
<223> OTHER INFORMATION: OX40 antibody VL

<400> SEQUENCE: 312

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Gly Ala Ala
             20                  25                  30

Val Ala Trp Tyr Gln Gln Lys Pro Gly Lys Ala Pro Lys Leu Leu Ile
         35                  40                  45

Tyr Trp Ala Ser Thr Arg His Thr Gly Val Pro Ser Arg Phe Ser Gly
     50                  55                  60

Ser Gly Ser Gly Thr Asp Phe Thr Leu Thr Ile Ser Ser Leu Gln Pro
 65              70                  75                  80

Glu Asp Phe Ala Thr Tyr Tyr Cys Gln Gln Tyr Ile Asn Tyr Pro Leu
                 85                  90                  95

Thr Phe Gly Gly Gly Thr Lys Val Glu Ile Lys
            100             105
```

ANTIBODIES SPECIFICALLY BINDING PD-1, TIM-3 OR PD-1 AND TIM-3 AND THEIR USES

CROSS-REFERENCE TO RELATED APPLICATIONS

This application is a divisional application of U.S. patent application Ser. No. 15/340,109, filed on 1 Nov. 2016, and which claims the benefit of U.S. Provisional Application 62/250,095, filed 3 Nov. 2015, the entire contents of the aforementioned applications are incorporated herein by reference herein their entireties.

SEQUENCE LISTING

This application contains a Sequence Listing submitted via EFS-Web, the entire content incorporated herein by reference in its entirety. The ASCII text file, created on 28 Oct. 2016, is named JBJ5071USNP_ST25.txt and is 416 kilobytes in size.

FIELD OF THE INVENTION

The present invention relates antibodies specifically binding PD-1, TIM-3 or PD-1 and TIM-3, polynucleotides encoding the antibodies or fragments, and methods of making and using the foregoing.

BACKGROUND OF THE INVENTION

The immune system is tightly controlled by a network of costimulatory and co-inhibitory ligands and receptors. These molecules provide secondary signals for T cell activation and provide a balanced network of positive and negative signals to maximize immune responses against infection and tumors, while limiting immunity to self (Wang et al., (Epub Mar. 7, 2011) *J Exp Med* 208(3):577-92; Lepenies et al., (2008) *Endocr Metab Immune Disord Drug Targets* 8:279-288).

Immune checkpoint therapy, targeting co-inhibitory pathways in T cells to promote antitumor immune responses, has led to advances in clinical care of cancer patients.

PD-1 is a negative immune checkpoint molecule that suppresses $CD4^+$ and $CD8^+$ T cell functions in the tumor microenvironment (TME). PD-1 engagement with its ligands (PD-L1 and PD-L2) drives T cell anergy and exhaustion in tumors by inhibiting multiple pathways downstream of the T cell receptor signaling, resulting in decreased T cell survival, growth and proliferation, compromised effector function, and altered metabolism. Preclinical studies have demonstrated that the PD-1 pathway blockade can reverse T cell exhaustion and stimulate anti-tumor immunity.

The PD-1 pathway hence contributes to downregulation of T cell functions in the (TME) and evasion of tumors via immune destruction. In the TME, exhausted T cells, in addition to expressing high levels of PD-1, express other inhibitory receptors including CTLA-4, TIM-3, LAG-3, CD244, TIGIT and CD160 (see e.g., Pauken & Wherry; 2015, *Trends in Immunology* 36(4): 265-276).

TIM-3 is a transmembrane receptor that is expressed on Th1 (T helper 1) $CD4^+$ cells and cytotoxic $CD8^+$ T cells that secrete IFN-γ. TIM-3 is generally not expressed on naïve T cells but rather upregulated on activated, effector T cells. TIM-3 has a role in regulating immunity and tolerance in vivo (see Hastings et al., (2009) *Eur J Immunol* 39(9):2492-501).

PD-1 antibodies have been described for example in: U.S. Pat. Nos. 5,897,862 and 7,488,802, and in Int. Patent Publ. Nos. WO2004/004771, WO2004/056875, WO2006/121168, WO2008/156712, WO2010/029435, WO2010/036959, WO2011/110604, WO2012/145493, WO2014/194302, WO2014/206107, WO2015/036394, WO2015/035606, WO2015/085847, WO2015/112900 and WO2015/112805.

TIM-3 antibodies have been described for example in: Monney et al., *Nature* (2002) 415(6871):536-41, and in Int. Patent Publ. Nos. WO2011/155607, WO2013/006490 and WO2015/117002.

Combinations with TIM-3 antibody and a PD-L1 antibody have been evaluated in for example in Int. Patent Publ. No. WO2011/159877.

While anti-PD-1/PD-L1 antibodies are demonstrating encouraging clinical responses in patients with multiple solid tumors, the response rates are still fairly low, about 15%-20% in pretreated patients (Swaika et al., (2015) *Mol Immunol*. doi: 10.1016/j.molimm.2015.02.009).

Therefore, there is a need for new therapeutics that inhibit the immunosuppressive activity of checkpoint inhibitors such as PD-1 and TIM-3, to be used for cancer immunotherapy and treatment of other conditions that would benefit from enhancement of an immune response, such as chronic infections.

BRIEF SUMMARY OF THE INVENTION

The invention provides an isolated antagonistic antibody specifically binding PD-1, comprising a heavy chain complementarity determining region 1 (HCDR1), a HCDR2 and a HCDR3 of SEQ ID NOs: 82, 83 and 84, respectively, or SEQ ID NOs: 82, 83 and 85, respectively.

The invention also provides an isolated antagonistic antibody specifically binding PD-1, comprising a heavy chain complementarity determining region 1 (HCDR1), a HCDR2 and a HCDR3 of SEQ ID NOs: 82, 83 and 84, respectively, and a light chain complementarity determining region 1 (LCDR1), a LCDR2 and a LCDR3 of SEQ ID NOs: 86, 87 and 88, respectively.

The invention also provides an isolated antagonistic antibody specifically binding PD-1, comprising a heavy chain complementarity determining region 1 (HCDR1), a HCDR2 and a HCDR3 of SEQ ID NOs: 82, 83 and 85, respectively, and a light chain complementarity determining region 1 (LCDR1), a LCDR2 and a LCDR3 of SEQ ID NOs: 86, 87 and 88, respectively.

The invention also provides an isolated antagonistic antibody specifically binding PD-1, comprising certain HCDR1, HCDR2, HCDR3, LCDR1, LCDR2 and LCDR3 amino acid sequences as described herein.

The invention also provides an isolated antagonistic antibody specifically binding PD-1, comprising certain VH and VL amino acid sequences as described herein.

The invention also provides an isolated antagonistic antibody specifically binding TIM-3, comprising a heavy chain complementarity determining region 1 (HCDR1), a HCDR2 and a HCDR3 of SEQ ID NOs: 164, 165 and 166, respectively.

The invention also provides an isolated antagonistic antibody specifically binding TIM-3, comprising the HCDR1, the HCDR2 and the HCDR3 of SEQ ID NOs: 164, 165 and 166, respectively, and the LCDR1, the LCDR2 and the LCDR3 of SEQ ID NOs: 167, 168 and 169 respectively.

The invention also provides an isolated antagonistic antibody specifically binding TIM-3, comprising certain HCDR1, HCDR2, HCDR3, LCDR1, LCDR2 and LCDR3 amino acid sequences as described herein.

The invention also provides an isolated antagonistic antibody specifically binding TIM-3, comprising certain VH and VL amino acid sequences as described herein.

The invention also provides an isolated antagonistic bispecific PD1/TIM-3 antibody comprising a first domain specifically binding PD-1 and a second domain specifically binding TIM-3.

The invention also provides an isolated antagonistic bispecific PD1/TIM-3 antibody comprising a first domain specifically binding PD-1 and a second domain specifically binding TIM-3, comprising certain HCDR1, HCDR2, HCDR3, LCDR1, LCDR2, LCDR3, VH, VL, heavy chain or light chain amino acids sequences as described herein.

The invention also provides an isolated antagonistic bispecific PD1/TIM-3 antibody comprising a first domain specifically binding PD-1 and a second domain specifically binding TIM-3, wherein the first domain comprises the HCDR1, the HCDR2, the HCDR3, the LCDR1, the LCDR2 and the LCDR3 of SEQ ID NOs: 10, 14, 17, 23, 26 and 32, respectively, and the second domain comprises the HCDR1, the HCDR2, the HCDR3, the LCDR1, the LCDR2 and the LCDR3 of SEQ ID NOs: 97, 105, 115, 124, 133 and 143, respectively.

The invention also provides an isolated antagonistic bispecific PD1/TIM-3 antibody comprising a first domain specifically binding PD-1 and a second domain specifically binding TIM-3, wherein the first domain comprises the HCDR1, the HCDR2, the HCDR3, the LCDR1, the LCDR2 and the LCDR3 of SEQ ID NOs: 10, 14, 17, 23, 26 and 32, respectively, and the second domain comprises the HCDR1, the HCDR2, the HCDR3, the LCDR1, the LCDR2 and the LCDR3 of SEQ ID NOs: 91, 99, 108, 118, 127 and 136, respectively.

The invention also provides an isolated antagonistic bispecific PD1/TIM-3 antibody comprising a first domain specifically binding PD-1 and a second domain specifically binding TIM-3, wherein the first domain comprises the HCDR1, the HCDR2, the HCDR3, the LCDR1, the LCDR2 and the LCDR3 of SEQ ID NOs: 66, 67, 68, 69, 70 and 71, respectively, and the second domain comprises the HCDR1, the HCDR2, the HCDR3, the LCDR1, the LCDR2 and the LCDR3 of SEQ ID NOs: 97, 105, 115, 124, 133 and 143, respectively.

The invention also provides an isolated antagonistic bispecific PD1/TIM-3 antibody comprising a first domain specifically binding PD-1 and a second domain specifically binding TIM-3, wherein the first domain comprises the HCDR1, the HCDR2, the HCDR3, the LCDR1, the LCDR2 and the LCDR3 of SEQ ID NOs: 66, 67, 68, 69, 70 and 71, respectively, and the second domain comprises the HCDR1, the HCDR2, the HCDR3, the LCDR1, the LCDR2 and the LCDR3 of SEQ ID NOs: 91, 99, 108, 118, 127 and 136, respectively.

The invention also provides an isolated antagonistic bispecific PD1/TIM-3 antibody comprising a first domain specifically binding PD-1 and a second domain specifically binding TIM-3, wherein the first domain comprises the HCDR1, the HCDR2, the HCDR3, the LCDR1, the LCDR2 and the LCDR3 of SEQ ID NOs: 10, 14, 16, 723, 26 and 32, respectively, and the second domain comprises the HCDR1, the HCDR2, the HCDR3, the LCDR1, the LCDR2 and the LCDR3 of SEQ ID NOs: 97, 105, 115, 124, 133 and 143, respectively.

The invention also provides an isolated antagonistic bispecific PD1/TIM-3 antibody comprising a first domain specifically binding PD-1 and a second domain specifically binding TIM-3, wherein the first domain comprises a heavy chain variable region (VH) of SEQ ID NO: 48 and a light chain variable region (VL) of SEQ ID NO: 56, and the second domain comprises the VH of SEQ ID NO: 153 and the VL of SEQ ID NO: 162.

The invention also provides an isolated antagonistic bispecific PD1/TIM-3 antibody comprising a first domain specifically binding PD-1 and a second domain specifically binding TIM-3, wherein the first domain comprises the VH of SEQ ID NO: 48 and the VL of SEQ ID NO: 56, and the second domain comprises the VH of SEQ ID NO: 146 and the VL of SEQ ID NO: 156.

The invention also provides an isolated antagonistic bispecific PD1/TIM-3 antibody comprising a first domain specifically binding PD-1 and a second domain specifically binding TIM-3, wherein the first domain comprises the VH of SEQ ID NO: 64 and the VL of SEQ ID NO: 65, and the second domain comprises the VH of SEQ ID NO: 153 and the VL of SEQ ID NO: 162.

The invention also provides an isolated antagonistic bispecific PD1/TIM-3 antibody comprising a first domain specifically binding PD-1 and a second domain specifically binding TIM-3, wherein the first domain comprises the VH of SEQ ID NO: 64 and the VL of SEQ ID NO: 65, and the second domain comprises the VH of SEQ ID NO: 146 and the VL of SEQ ID NO: 156.

The invention also provides an isolated antagonistic bispecific PD1/TIM-3 antibody comprising a first domain specifically binding PD-1 and a second domain specifically binding TIM-3, wherein the first domain comprises the VH of SEQ ID NO: 48 and the VL of SEQ ID NO: 56, and the second domain comprises the VH of SEQ ID NO: 172 and the VL of SEQ ID NO: 173.

The invention also provides an immunoconjugate comprising the antibody or antigen-binding portion thereof of the invention linked to a therapeutic agent or to an imaging agent.

The invention also provides a pharmaceutical composition comprising the antibody of the invention and a pharmaceutically accepted carrier.

The invention also provides a polynucleotide encoding the antibody VH, the antibody VL or the antibody VH and the antibody VL of the invention.

The invention also provides a vector comprising the polynucleotide encoding the antibody VH, the antibody VL or the antibody VH and the VL of the invention.

The invention also provides a host cell comprising the vector of the invention.

The invention also provides a method of producing the antibody of the invention, comprising culturing the host cell of the invention in conditions that the antibody is expressed, and recovering the antibody produced by the host cell.

The invention also provides a method of treating a cancer in a subject, comprising administering a therapeutically effective amount of the isolated antibody of the invention to the subject in need thereof for a time sufficient to treat the cancer.

The invention also provides a method of enhancing an immune response in a subject, comprising administering a therapeutically effective amount of the isolated antibody of the invention to the subject in need thereof for a time sufficient to enhance the immune response.

The invention also provides an anti-idiotypic antibody binding to the antibody of the invention.

The invention also provides a kit comprising the antibody of the invention.

BRIEF DESCRIPTION OF THE DRAWINGS

FIG. 6 shows the HCDR1 sequences of select anti-PD-1 antibodies and the HCDR1 genus sequence.

FIG. 7 shows the HCDR2 sequences of select anti-PD-1 antibodies and the HCDR2 genus sequence.

FIG. 8 shows the HCDR3 sequences of select anti-PD-1 antibodies and the first HCDR3 genus sequence.

FIG. 9 shows the HCDR3 sequences of select anti-PD-1 antibodies and the second HCDR3 genus sequence.

FIG. 10 shows the LCDR1 sequences of select anti-PD-1 antibodies and the LCDR1 genus sequence.

FIG. 11 shows the LCDR2 sequences of select anti-PD-1 antibodies and the LCDR2 genus sequence.

FIG. 12 shows the LCDR3 sequences of select anti-PD-1 antibodies and the LCDR3 genus sequence.

FIG. 13 shows the HCDR1 sequences of select anti-TIM-3 antibodies and the HCDR1 genus sequence. The genus sequence was determined by generating molecular models for all Fv (VH/VL pairs) in MOE (CCG, Montreal) using a default protocol for antibody modeling. For CDRs that have different lengths, these structural models were aligned based upon the structurally conserved regions and the structurally equivalent CDRs positions were identified.

FIG. 14 shows the HCDR2 sequences of select anti-TIM-3 antibodies and the HCDR2 genus sequence. The HCDR2 genus sequence was generated as described for FIG. 10.

FIG. 15 shows the HCDR3 sequences of select anti-TIM-3 antibodies and the first HCDR3 genus sequence. The HCDR3 genus sequence was generated as described for FIG. 10.

FIG. 16 shows the LCDR1 sequences of select anti-TIM-3 antibodies and the LCDR1 genus sequence. The LCDR1 genus sequence was generated as described for FIG. 10.

FIG. 17 shows the LCDR2 sequences of select anti-TIM-3 antibodies and the LCDR2 genus sequence. The LCDR2 genus sequence was generated as described for FIG. 10.

FIG. 18 shows the LCDR3 sequences of select anti-TIM-3 antibodies and the LCDR3 genus sequence. The LCDR3 genus sequence was generated as described for FIG. 10.

FIG. 21 shows upregulation of TIM-3 expression on peripheral T cells in melanoma patients PBMCs from treatment naïve melanoma patients stimulated with melanoma antigen peptide pools (NY-ESO, gp100, MART-1) in the presence or absence of anti-PD-1 or anti-TIM-3 function blocking antibodies. Expression of TIM-3 was determined by flow cytometry on restimulated cells on day 6.

DETAILED DESCRIPTION OF THE INVENTION

Figure 1A:
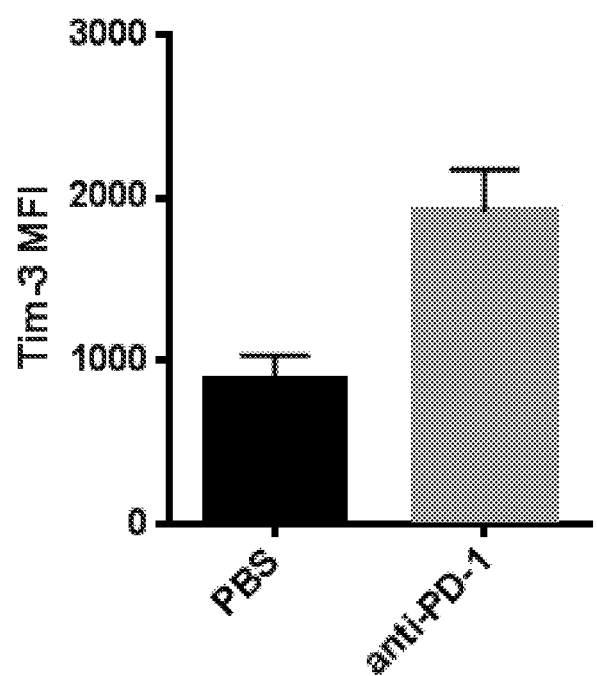
FIG. 1A shows that TIM-3 surface expression is elevated in tumors after treatment with anti-PD-1 antibodies. Balb/c mice with established CT26 colon carcinoma tumors were treated biweekly with anti-PD-1 antibody or vehicle. Tumors were harvested at day 22 and TIM-3 expression was evaluated on tumor-infiltrating T cells using flow cytometry. MFI: mean fluorescent intensity. PBS: control

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

"Specific binding" or "specifically binds" or "binds" refers to an antibody binding to an antigen or an epitope within the antigen with greater affinity than for other antigens. Typically, the antibody binds to the antigen or the epitope within the antigen with an equilibrium dissociation constant ($K_D$) of about $1 \times 10^{-8}$ M or less, for example about $1 \times 10^{-9}$ M or less, about $1 \times 10^{-10}$ M or less, about $1 \times 10^{-11}$ M or less, or about $1 \times 10^{-12}$ M or less, typically with the $K_D$ that is at least one hundred fold less than its $K_D$ for binding to a non-specific antigen (e.g., BSA, casein). The dissociation constant may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset). While a monospecific antibody specifically binds one antigen or one epitope, a bispecific antibody specifically binds two distinct antigens or two distinct epitopes.

"Antibodies" is meant in a broad sense and includes immunoglobulin molecules including monoclonal antibodies including murine, human, humanized and chimeric monoclonal antibodies, antigen-binding fragments, bispecific or multispecific antibodies, dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy (H) chains and two light (L) chains inter-connected by disulfide bonds as well as multimers thereof (for example IgM). Each heavy chain is comprised of a heavy chain variable region (VH) and a heavy chain constant region (comprised of domains CH1, hinge CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-terminus to carboxy-terminus in the following order: FR1, CDR1, FR2, CDR2, FR3, CDR3, and FR4.

"Complementarity determining regions (CDR)" are "antigen binding sites" in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu and Kabat, (1970) *J Exp Med* 132:211-50; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk, (1987) *Mol Biol* 196:901-17). The International ImMunoGeneTics (IMGT) database (http://www_imgt_org) provides a standardized numbering and definition of antigen-binding sites. The correspondence between CDRs, HVs and IMGT delineations is described in Lefranc et al., (2003) *Dev Comparat Immunol* 27:55-77. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may assigned to one of two clearly distinct types, namely kappa (κ) and lambda (λ), based on the amino acid sequences of their constant domains.

"Antibody fragments" or "antigen-binding portion" refers to a portion of an immunoglobulin molecule that retains the antigen binding properties of the parental full length antibody. Exemplary antigen-binding portions are heavy chain complementarity determining regions (HCDR) 1, 2 and 3, light chain complementarity determining regions (LCDR) 1, 2 and 3, a heavy chain variable region (VH), a light chain variable region (VL), Fab, F(ab')2, Fd and Fv fragments as well as domain antibodies (dAb) consisting of either one VH or VL domain. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"Monoclonal antibody" refers to an antibody population with single amino acid composition in each heavy and each light chain, except for possible well known alterations such as removal of C-terminal lysine from the antibody heavy chain. Monoclonal antibodies typically bind one antigenic epitope, except that multispecific monoclonal antibodies bind two or more distinct antigens or epitopes. Bispecific monoclonal antibodies bind two distinct antigenic epitopes. Monoclonal antibodies may have heterogeneous glycosylation within the antibody population. Monoclonal antibodies may be monospecific or multispecific, or monovalent, bivalent or multivalent. A multispecific antibody, such as a bispecific antibody or a trispecific antibody is included in the term monoclonal antibody.

"Isolated antibody" refers to an antibody or antibody fragment that is substantially free of other antibodies having different antigenic specificities (e.g., an isolated antibody specifically binding PD-1 is substantially free of antibodies that specifically bind antigens other than PD-1). An isolated antibody specifically binding TIM-3 is substantially free of antibodies that specifically bind antigens other than TIM-3. In case of bispecific PD-1/TIM-3 antibodies, the bispecific antibody specifically binds both PD-1 and TIM-3, and is substantially free of antibodies that specifically bind antigens other that PD-1 and TIM-3. "Isolated antibody" encompasses antibodies that are isolated to a higher purity, such as antibodies that are 80%, 81%, 82%, 83%, 84%, 85%, 86%, 87%, 88%, 89%, 90%, 91%, 92%, 93%, 94%, 95%, 96%, 97%, 98%, 99% or 100% pure.

"Humanized antibodies" refers to antibodies in which at least one CDR is derived from non-human species and the variable region frameworks are derived from human immunoglobulin sequences. Humanized antibodies may include intentionally introduced mutations in the framework regions so that the framework may not be an exact copy of expressed human immunoglobulin or germline gene sequences.

"Human antibody" refers to an antibody having heavy and light chain variable regions in which both the framework and all 6 CDRs are derived from sequences of human origin. If the antibody contains a constant region or a portion of the constant region, the constant region also is derived from sequences of human origin.

Human antibody comprises heavy or light chain variable regions that are "derived from" sequences of human origin if the variable regions of the antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci as described herein. "Human antibody" may contain amino acid differences when compared to the human germline immunoglobulin or rearranged immunoglobulin genes due to for example naturally occurring somatic mutations or intentional introduction of substitutions into the framework or antigen binding site, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) *J Mol Biol* 296:57-86, or synthetic HCDR3 incorporated into human immunoglobulin gene libraries displayed on phage, for example as described in Shi et al., (2010) *J Mol Biol* 397:385-96, and in Int. Patent Publ. No. WO2009/085462.

Human antibodies derived from human immunoglobulin sequences may be generated using systems such as phage display incorporating synthetic CDRs and/or synthetic frameworks, or may be subjected to in vitro mutagenesis to improve antibody properties, resulting in antibodies that are not expressed by the human antibody germline repertoire in vivo.

"Recombinant" refers to antibodies and other proteins that are prepared, expressed, created or isolated by recombinant means.

"Epitope" refers to a portion of an antigen to which an antibody specifically binds. Epitopes typically consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule. Antibody "epitope" depends on the methodology used to identify the epitope.

"Multispecific" refers to an antibody that specifically binds at least two distinct antigens or two distinct epitopes within the antigens, for example three, four or five distinct antigens or epitopes.

"Bispecific" refers to an antibody that specifically binds two distinct antigens or two distinct epitopes within the same antigen. The bispecific antibody may have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset), or may bind an epitope that is shared between two or more distinct antigens.

"Variant" refers to a polypeptide or a polynucleotide that differs from a reference polypeptide or a reference polynucleotide by one or more modifications for example, substitutions, insertions or deletions.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide. Small polypeptides of less than 50 amino acids may be referred to as "peptides".

PD-1 refers to human programmed cell death protein 1, PD-1. PD-1 is also known as CD279 or PDCD1. The amino acid sequence of the mature human PD-1 (without signal sequence) is shown in SEQ ID NO: 1. The extracellular domain spans residues 1-150, the transmembrane domain spans residues 151-171 and the cytoplasmic domain spans residues 172-268 of SEQ ID NO: 1. Throughout the specification, "the extracellular domain of human PD-1 "huPD1-ECD" refers to protein having amino acid sequence of residues 1-149 of SEQ ID NO: 1, and shown in SEQ ID NO:2. "PD-1" in the specification refers to human mature PD-1, unless explicitly stated to the contrary.

TIM-3 refers to human hepatitis A virus cellular receptor 2, also called HAVCR2. The amino acid sequence of the mature human TIM-3 (without signal sequence) is shown in SEQ ID NO: 138. The extracellular domain spans residues 1-181, the transmembrane domain spans residues 182-202 and the cytoplasmic domain spans residues 203-280 of SEQ ID NO: 138. Throughout the specification, "the extracellular domain of human TIM-3 "huTIM-3-ECD" refers to protein having amino acid sequence of residues 1-179 of SEQ ID NO: 138, and shown in SEQ ID NO: 89. TIM-3 in the specification refers to human mature TIM-3, unless explicitly stated to the contrary.

"In combination with" means that two or more therapeutics are administered to a subject together in a mixture, concurrently as single agents or sequentially as single agents in any order.

"Overexpress", "overexpressed" and "overexpressing" is used interchangeably and refers to a sample such as a cancer cell, malignant cell or cancer tissue that has measurably higher levels of PD-1, TIM-3, PD-L1, PD-L2 or TIM-3 ligand when compared to a reference sample. The overexpression may be caused by gene amplification or by increased transcription or translation. Expression and overexpression of protein in the sample may be measured using well know assays using for example ELISA, immunofluorescence, flow cytometry or radioimmunoassay on live or lysed cells. Expression and overexpression of a polynucleotide in the sample may be measured for example using fluorescent in situ hybridization, Southern blotting, or PCR techniques. A protein or a polynucleotide is overexpressed when the level of the protein or the polynucleotide in the sample at least 1.5-fold higher or statistically significant when compared to the reference sample. Selection of the reference sample is known.

"Sample" refers to a collection of similar fluids, cells, or tissues isolated from a subject, as well as fluids, cells, or tissues present within a subject. Exemplary samples are biological fluids such as blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage, liquid solutions contacted with a subject or biological source, for example, cell and organ culture medium including cell or organ conditioned medium, lavage fluids and the like, tissue biopsies, fine needle aspirations or surgically resected tumor tissue.

A "cancer cell" or a "tumor cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid, uptake of exogenous nucleic acid or it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo (Freshney, Culture of Animal Cells: A Manual of Basic Technique (3rd ed. 1994)).

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Bispecific PD-1/TIM-3 antibody", "PD-1/TIM-3 antibody", "bispecific anti-PD-1/TIM-3 antibody" or "anti-PD-1/TIM-3 antibody" refers to a molecule comprising at least one binding domain specifically binding PD-1 and at least one binding domain specifically binding TIM-3. The domains specifically binding PD-1 and TIM-3 are typically VH/VL pairs. The bispecific anti-PD-1/TIM-3 antibody may be monovalent in terms of its binding to either PD-1 or TIM-3.

"Valent" refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"An antigen specific $CD4^+$ or $CD8^+$ T cell" refers to a $CD4^+$ or $CD8^+$ T cell activated by a specific antigen, or immunostimulatory epitope thereof.

"CD137" (also called tumor necrosis factor receptor superfamily member 9, TNFRSF9, 4-1BBL) refers to a human CD137 molecule having the amino acid sequence shown in SEQ ID NO: 281.

SEQ ID NO: 281
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL

"TIGIT" (also called T-cell immunoreceptor with Ig and ITIM domains) refers to human TIGIT molecule having the amino acid sequence shown in SEQ ID NO: 301.

SEQ ID NO: 301
MMTGTIETTGNISAEKGGSIILQCHLSSTTAQVTQVNWEQQDQLLAICNA

DLGWHISPSFKDRVAPGPGLGLTLQSLTVNDTGEYFCIYHTYPDGTYTGR

IFLEVLESSVAEHGARFQIPLLGAMAATLVVICTAVIVVVALTRKKKALR

IHSVEGDLRRKSAGQEEWSPSAPSPPGSCVQAEAAPAGLCGEQRGEDCAE

LHDYFNVLSYRSLGNCSFFTETG

"Agonist" refers to a molecule that, when bound to a cellular protein, induces at least one reaction or activity that is induced by a natural ligand of the protein. The molecule is an agonist when the at least one reaction or activity is induced by at least about 30%, 40%, 45%, 50%, 55%, 60%, 65%, 70%, 75%, 80%, 85%, 90%, 95%, or 100% greater than the at least one reaction or activity induced in the absence of the agonist (e.g., negative control), or when the induction is statistically significant when compared to the induction in the absence of the agonist. Agonist may be an antibody, a soluble ligand, or a small molecule. An exemplary agonist is an agonistic antibody that specifically binds a T cell activating molecule.

"Antagonist" refers to a molecule that, when bound to a cellular protein, suppresses at least one reaction or activity that is induced by a natural ligand of the protein. A molecule is an antagonist when the at least one reaction or activity is suppressed by at least about 30%, 40%, 45%, 50%, 55%, 60%, 65%, 70%, 75%, 80%, 85%, 90%, 95%, or 100% more than the at least one reaction or activity suppressed in the absence of the antagonist (e.g., negative control), or when the suppression is statistically significant when compared to the suppression in the absence of the antagonist. Antagonist may be an antibody, a soluble ligand, a small molecule, a DNA or RNA such as siRNA. Exemplary antagonists are an antagonistic antibody specifically binding PD-1, an antagonistic antibody specifically binding TIM-3, an antagonistic bispecific PD-1/TIM-3 antibody or an antagonistic antibody specifically binding a T cell inhibitory molecule. A typical reaction or activity that is induced by PD-1 binding to its receptor PD-L1 or PD-L2 may be reduced antigen-specific CD4$^+$ or CD8$^+$ cell proliferation or reduced interferon-γ (IFN-γ) production by T cells, resulting in suppression of immune responses against for example tumor. A typical reaction or activity that is induced by TIM-3 binding to its receptor, such as galectin-9, may be reduced antigen specific CD4$^+$ or CD8$^+$ cell proliferation, reduced IFN-γ production by T cells, or reduced CD137 surface expression on CD4$^+$ or CD8$^+$ cells, resulting in suppression of immune responses against for example tumor. Similarly, a typical reaction or activity that is induced by a T cell inhibitory molecule is immunosuppression. Hence, an antagonistic PD-1 antibody specifically binding PD-1, an antagonistic antibody specifically binding TIM-3, an antagonistic bispecific PD-1/TIM-3 antibody, or an antagonistic antibody specifically binding a T cell inhibitory molecule induces immune responses by inhibiting the inhibitory pathways.

"Subject" includes any human or nonhuman animal. "Nonhuman animal" includes all vertebrates, e.g., mammals and non-mammals, such as nonhuman primates, sheep, dogs, cats, horses, cows chickens, amphibians, reptiles, etc. Except when noted, the terms "patient" or "subject" are used interchangeably.

The numbering of amino acid residues in the antibody constant region throughout the specification is according to the EU index as described in Kabat et al., Sequences of Proteins of Immunological Interest, 5th Ed. Public Health Service, National Institutes of Health, Bethesda, MD. (1991), unless otherwise explicitly stated.

Conventional one and three-letter amino acid codes are used herein as shown in Table 1.

TABLE 1

| Amino acid | Three-letter code | One-letter code |
|---|---|---|
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Compositions of Matter

The present invention provides antagonistic antibodies specifically binding PD-1, antagonistic antibodies specifically binding TIM-3, and antagonistic bispecific PD-1/TIM-3 antibodies. The present invention provides polypeptides and polynucleotides encoding the antibodies of the invention or complementary nucleic acids thereof, vectors, host cells, and methods of making and using them.

Antagonistic Antibodies Specifically Binding PD-1

PD-1, upon ligand engagement, suppresses T cell functions through multiple mechanisms (Pauken & Wherry (2015) *Trends in Immunology* 36(4): 265-276). PD-1 engagement directly inhibits T cell receptor (TCR) signaling through co-localization with the TCR and subsequent induction of dephosphorylation of TCR proximal signaling molecules, inhibition of Ras/MEK/ERK pathway leading to inhibition of the cell cycle progression and T cell proliferation, inhibition of cell growth and survival and reprogramming of T cell metabolism through suppression of PI3K/AKT pathway, leading to the upregulation of the BATF transcription factor, and modulation of development, maintenance and function of regulatory T cells. PD-1 has also been proposed to increase T cell motility and to limit duration of interaction between T cells and target cells, thereby reducing the extent of T cell activation (Honda et al., (2014) *Immunity* 40(2):235-47).

Tumors have co-opted the PD-1 pathway to downregulate T cell function in the tumor microenvironment (TME) and to evade immune destruction. In the TME, under conditions of persistent antigen and inflammation, T cells become exhausted, or dysfunctional, and progressively lose their effector function and proliferative capacity. Exhausted T cells express high levels of PD-1, often together with other inhibitory receptors such as TIM-3 or LAG-3 (Pauken & Wherry (2015) *Trends in Immunology* 36(4): 265-276). One of the PD-1 ligands, PD-L1, is also upregulated in various tumors. PD-L1 expression occurs on the cancer cells themselves and/or infiltrating immune cells, including tumor associated macrophages, dendritic cells, fibroblasts and activated T cells (Chen et al., 2012 *Clin Cancer Res* 18(24): 6580-7). In this setting, PD-1 engagement is hypothesized to limit anti-tumor T cell responses and lead to immune evasion. Recent studies have shown that a higher frequency and level of PD-1 expression occurs on tumor infiltrating lymphocytes (TILs) in multiple solid tumors. Importantly, these PD-1+ TILs are functionally impaired, as evidenced by lower proliferation and effector functions (Pauken & Wherry; 2015, *Trends in Immunology* 36(4): 265-276) These data support the hypothesis that PD-1 mediates immune suppression in the TME.

T cell exhaustion in tumors is reversible, at least partially, by PD-1 pathway blockade. Anti-PD-1/PD-L1 antibodies have been shown to enhance T cell function and lead to improved anti-tumor immunity in a number of preclinical tumor models. PD-1/PD-L1 antibodies have also shown encouraging clinical responses in multiple solid tumors, with 20-40% overall response rate (ORR) in melanoma, 10-24% in non-small cell lung cancer (NSCLC), 12-31% in renal cell carcinoma (RCC), 24-52% in bladder cancer, and 20% in head and neck cancer (Swaika et al., (2015) *Mol Immunol* 67(2 Pt A):4-17).

The invention provides an isolated antagonistic antibody specifically binding PD-1 or an antigen-binding portion thereof comprising a heavy chain complementarity determining region 1 (HCDR1), a HCDR2 and a HCDR3 of SEQ ID NOs: 82, 83 and 84, respectively, or SEQ ID NOs: 82, 83 and 85, respectively.

The invention also provides an isolated antagonistic antibody specifically binding PD-1 or an antigen-binding portion thereof comprising a light chain complementarity determining region 1 (LCDR1), a LCDR2 and a LCDR3 of SEQ ID NOs: 86, 87 and 88, respectively.

The invention also provides an isolated antagonistic antibody specifically binding PD-1 or an antigen-binding portion thereof comprising the HCDR1, the HCDR2 and the HCDR3 of SEQ ID NOs: 82, 83 and 84, respectively, and the LCDR1, the LCDR2 and the LCDR3 of SEQ ID NOs: 86, 87 and 88, respectively.

The invention also provides an isolated antagonistic antibody specifically binding PD-1 or an antigen-binding portion thereof comprising the HCDR1, the HCDR2 and the HCDR3 of SEQ ID NOs: 82, 83 and 85, respectively, and the LCDR1, the LCDR2 and the LCDR3 of SEQ ID NOs: 86, 87 and 88, respectively.

SEQ ID NOs: 82, 83, 84, 85, 86, 87 and 88 represent the HCDR1, the HCDR2, the HCDR3, the LCDR1, the LCDR2 and the LCDR3 genus sequences of affinity-matured variants of antagonistic antibodies specifically binding PD-1 having similar HCDR1, HCDR2, LCDR1, LCDR2 and LCDR3 sequences, and two similar HCDR3 groups of sequences. Antibodies within the genus bind PD-1 with the $K_D$ of less than about $1 \times 10^{-7}$ M, such as less than about $1 \times 10^{-8}$ M, for example less than about $1 \times 10^{-9}$ M, or for example less than about $1 \times 10^{-10}$ M. Exemplary such antibodies are antibodies having the HCDR1, the HCDR2, the HCDR3, the LCDR1, the LCDR2 and the LCDR3 amino acid sequences of antibodies PD1B114, PD1B149, PD1B160, PD1B162, PD1B164, PD1B11, PD1B183, PD1B184, PD1B185, PD1B187, PD1B71, PD1B177, PD1B70, PD1B175, PD1B194, PD1B195, PD1B196, PD1B197, PD1B198, PD1B199, PD1B200, PD1B201 and PD1B244 as described herein.

SEQ ID NO: 82
$X_1YX_2IX_3$,
wherein
$X_1$ is S or D;
$X_2$ is V or A; and
$X_3$ is H or S.
SEQ ID NO: 83
GIIPIX$_4$X$_5$TANYAQKFQG,
wherein
$X_4$ is Y or F; and
$X_5$ is G or D.
SEQ ID NO: 84
PGLAAAYDTGX$_6$LDY,
wherein
$X_6$ is N or S.
SEQ ID NO: 85
GX$_7$X$_8$X$_9$X$_{10}$TGX$_{11}$LDY,
wherein
$X_7$ is T or Y;
$X_8$ is L or V;
$X_9$ is D or R;
$X_{10}$ is R or A; and
$X_{11}$ is H or M.
SEQ ID NO: 86
RASQSVX$_{12}$X$_{13}$YLA,
wherein
$X_{12}$ is S, R or D; and
$X_{13}$ is S or N.
SEQ ID NO: 87
DASX$_{14}$RAT,
wherein
$X_{14}$ is N, D, Y, S or T.
SEQ ID NO: 88
QQRX$_{15}$X$_{16}$WPLT,
wherein
$X_{15}$ is S, N, G, E, D, W or A; and
$X_{16}$ is N, Y, E or A.

In some embodiments, the isolated antagonistic antibody specifically binding PD-1 or the antigen-binding portion thereof has one, two, three, four or five of the following properties:

a) enhances an activation of antigen specific CD4+ or CD8+ T cells in a dose dependent manner, wherein the activation is measured using a cytomegalovirus antigen recall assay (CMV assay) as described in Example 1;
b) binds human PD-1 with an equilibrium dissociation constant ($K_D$) of less than about 100 nM, wherein the $K_D$ is measured using ProteOn XPR36 system at +25° C.;
c) binds human PD-1 with the $K_D$ of less than about 1 nM, wherein the $K_D$ is measured using ProteOn XPR36 system at +25° C.;
d) binds cynomolgus PD-1 with the $K_D$ of less than about 100 nM, wherein the $K_D$ is measured using ProteOn XPR36 system at +25° C., or
e) binds cynomolgus PD-1 with the $K_D$ of less than about 1 nM, wherein the $K_D$ is measured using ProteOn XPR36 system at +25° C.

Exemplary such antibodies are PD-1 antibodies PD1B114, PD1B149, PD1B160, PD1B162, PD1B164, PD1B11, PD1B183, PD1B184, PD1B185, PD1B187, PD1B71, PD1B177, PD1B70, PD1B175, PD1B194, PD1B195, PD1B196, PD1B197, PD1B198, PD1B199, PD1B200, PD1B201 and PD1B244 as described herein.

In some embodiments, the isolated antagonistic antibody specifically binding PD-1 or the antigen-binding portion thereof enhances an activation of antigen specific CD4+ or CD8+ T cells in a dose dependent manner, wherein the activation is measured using a cytomegalovirus antigen recall assay (CMV assay) as described in Example 1, and binds human PD-1 with an equilibrium dissociation constant ($K_D$) of less than about 100 nM, wherein the $K_D$ is measured using ProteOn XPR36 system at +25° C.

In some embodiments, the isolated antagonistic antibody specifically binding PD-1 or the antigen-binding portion thereof enhances an activation of antigen specific $CD4^+$ or $CD8^+$ T cells in dose dependent manner, wherein the activation is measured using a cytomegalovirus antigen recall assay (CMV assay) as described in Example 1, and binds human PD-1 with an equilibrium dissociation constant ($K_D$) of less than about 10 nM, wherein the $K_D$ is measured using ProteOn XPR36 system at +25° C.

In some embodiments, the isolated antagonistic antibody specifically binding PD-1 or the antigen-binding portion thereof enhances an activation of antigen specific $CD4^+$ or $CD8^+$ T cells in dose dependent manner, wherein the activation is measured using a cytomegalovirus antigen recall assay (CMV assay) as described in Example 1, and binds cynomolgus PD-1 with an equilibrium dissociation constant ($K_D$) of less than about 100 nM, wherein the $K_D$ is measured using ProteOn XPR36 system at +25° C.

In some embodiments, the isolated antagonistic antibody specifically binding PD-1 or the antigen-binding portion thereof enhances an activation of antigen specific $CD4^+$ or $CD8^+$ T cells in dose dependent manner, wherein the activation is measured using a cytomegalovirus antigen recall assay (CMV assay) as described in Example 1, and binds cynomolgus PD-1 with an equilibrium dissociation constant ($K_D$) of less than about 10 nM, wherein the $K_D$ is measured using ProteOn XPR36 system at +25° C.

Activation of antigen specific $CD4^+$ or $CD8^+$ T cells may be assessed by measuring increased T cell proliferation in a Mixed Lymphocyte Reaction (MLR) assay, increased interferon-γ (IFN-γ) secretion in the MLR assay, increased TNF-α secretion in the MLR assay, increased IFN-γ secretion in a cytomegalovirus antigen assay (CMV assay) or increased TNF-α secretion in the CMV assay using known protocols and those described in Example 1. Antibodies of the invention enhance the activation of antigen specific $CD4^+$ or $CD8^+$ T when the measured T cell functionality is increased by the antibodies of the invention in a dose-dependent manner.

The affinity of an antibody to human or cynomolgus PD-1 may be determined experimentally using any suitable method. Such methods may utilize ProteOn XPR36, Biacore 3000 or KinExA instrumentation, ELISA or competitive binding assays known to those skilled in the art. The measured affinity of a particular antibody/PD-1 interaction may vary if measured under different conditions (e.g., osmolarity, pH). Thus, measurements of affinity and other binding parameters (e.g., $K_D$, $K_{on}$, $K_{off}$) are typically made with standardized conditions and a standardized buffer, such as the buffer described herein. Skilled in the art will appreciate that the internal error for affinity measurements for example using Biacore 3000 or ProteOn (measured as standard deviation, SD) may typically be within 5-33% for measurements within the typical limits of detection. Therefore the term "about" in the context of $K_D$ reflects the typical standard deviation in the assay. For example, the typical SD for a $K_D$ of $1 \times 10^{-9}$ M is up to $\pm 0.33 \times 10^{-9}$ M.

In some embodiments, the antagonistic antibody specifically binding PD-1 or the antigen-binding portion thereof comprises the HCDR1, the HCDR2 and the HCDR3 contained within a heavy chain variable region (VH) of SEQ ID NOs: 41, 42, 43, 44, 45, 46, 47 or 48, wherein the HCDR1, the HCDR2 and the HCDR3 are defined by Chothia, Kabat, or IMGT.

In some embodiments, the antagonistic antibody specifically binding PD-1 or the antigen-binding portion thereof of the invention comprises the LCDR1, the LCDR2 and the LCDR3 contained within a light chain variable region (VL) of SEQ ID NOs: 49, 50, 51, 52, 53, 54, 55, 56, 57, 58, 59, 60, 61 or 62, wherein the LCDR1, the LCDR2 and the LCDR are defined by Chothia, Kabat, or IMGT.

In some embodiments, the antagonistic antibody specifically binding PD-1 or the antigen-binding portion thereof of the invention comprises
the HCDR1 of SEQ ID NOs: 10, 11 or 12;
the HCDR2 of SEQ ID NOs: 13, 14 or 15; and
the HCDR3 of SEQ ID NOs: 16, 17, 18 or 19.

In some embodiments, the antagonistic antibody specifically binding PD-1 or the antigen-binding portion thereof of the invention comprises
the LCDR1 of SEQ ID NOs: 20, 21, 22, 23, 24 or 25;
the LCDR2 of SEQ ID NOs: 26, 27, 28, 29 or 30; and
the LCDR3 of SEQ ID NOs: 31, 32, 33, 34, 35, 36, 37, 38, 39, or 40.

In some embodiments, the antagonistic antibody specifically binding PD-1 or the antigen-binding portion thereof of the invention comprises
the HCDR1 of SEQ ID NOs: 10, 11 or 12;
the HCDR2 of SEQ ID NOs: 13, 14 or 15;
the HCDR3 of SEQ ID NOs: 16, 17, 18 or 19;
the LCDR1 of SEQ ID NOs: 20, 21, 22, 23, 24 or 25;
the LCDR2 of SEQ ID NOs: 26, 27, 28, 29 or 30; and
the LCDR3 of SEQ ID NOs: 31, 32, 33, 34, 35, 36, 37, 38, 39 or 40.

In some embodiments, the antagonistic antibody specifically binding PD-1 or the antigen-binding portion thereof of the invention comprises the HCDR1, the HCDR2 and the HCDR3 of
SEQ ID NOs: 10, 13 and 16, respectively;
SEQ ID NOs: 10, 14 and 16, respectively;
SEQ ID NOs: 10, 13 and 17, respectively;
SEQ ID NOs: 10, 13 and 18, respectively;
SEQ ID NOs: 11, 15 and 18, respectively;
SEQ ID NOs: 10, 13 and 19, respectively;
SEQ ID NOs: 10, 14 and 17, respectively; or
SEQ ID NOs: 12, 13 and 19, respectively.

In some embodiments, the antagonistic antibody specifically binding PD-1 or the antigen-binding portion thereof of the invention comprises the LCDR1, the LCDR2 and the LCDR3 of
SEQ ID NOs: 20, 26 and 31, respectively;
SEQ ID NOs: 21, 26 and 32, respectively;
SEQ ID NOs: 22, 27 and 33, respectively;
SEQ ID NOs: 22, 26 and 34, respectively;
SEQ ID NOs: 23, 28 and 35, respectively;
SEQ ID NOs: 20, 26 and 36, respectively;
SEQ ID NOs: 21, 27 and 37, respectively;
SEQ ID NOs: 23, 26 and 32, respectively;
SEQ ID NOs: 22, 26 and 32, respectively;
SEQ ID NOs: 24, 26 and 38, respectively;
SEQ ID NOs: 20, 29 and 39, respectively;
SEQ ID NOs: 20, 30 and 32, respectively;
SEQ ID NOs: 25, 26 and 40, respectively; or
SEQ ID NOs: 24, 26 and 32, respectively.

The invention also provides an antagonistic antibody specifically binding PD-1 or an antigen-binding portion thereof comprising the HCDR1, the HCDR2, the HCDR3, the LCDR1, the LCDR2 and the LCDR3 of SEQ ID NOs: 10, 14, 17, 23, 26 and 32, respectively.

In some embodiments, the antibody or the antigen-binding portion thereof binds human PD-1 with an equilibrium dissociation constant ($K_D$) of less than about 100 nM, optionally less than about 10 nM, for example less than about 1 nM such as less than about 500 pM, wherein the $K_D$ is measured using ProteOn XPR36 system at +25° C.

In some embodiments, the antibody or the antigen-binding portion thereof binds cynomolgous PD-1 with an equilibrium dissociation constant ($K_D$) of less than about 100 nM, optionally less than about 10 nM, for example less than about 1 nM such as less than about 500 pM, wherein the $K_D$ is measured using ProteOn XPR36 system at +25° C.

In some embodiments, the antibody or the antigen-binding portion thereof comprises the VH of SEQ ID NO: 48 and the VL of SEQ ID NO: 56.

In some embodiments, the VH and the VL are encoded by polynucleotide sequences of SEQ ID NOs: 196 and 197, respectively.

In some embodiments, the antibody is an IgG4 isotype, optionally comprising a S228P substitution when compared to the wild type IgG4.

In some embodiments, the antibody is an IgG4/κ isotype, optionally comprising the S228P substitution when compared to the wild type IgG4.

In some embodiments, the antibody comprises the VH of SEQ ID NO: 48 and the VL of SEQ ID NO: 56 and is an IgG4 isotype, optionally comprising the S228P substitution when compared to the wild type IgG4.

In some embodiments, the antibody comprises the VH of SEQ ID NO: 48 and the VL of SEQ ID NO: 56 and is an IgG4/κ isotype comprising the S228P substitution when compared to the wild type IgG4.

In some embodiments, the antibody comprises a heavy chain (HC) of SEQ ID NO: 72 and a light chain (LC) of SEQ ID NO: 73.

In some embodiments, the antibody is an IgG2 isotype, optionally comprising V234A, G237A, P238S, H268A, V309L, A330S and P331S substitutions when compared to the wild type IgG2.

In some embodiments, the antibody is an IgG2/x isotype, optionally comprising V234A, G237A, P238S, H268A, V309L, A330S and P331S substitutions when compared to the wild type IgG2.

In some embodiments, the antibody comprises the VH of SEQ ID NO: 48 and the VL of SEQ ID NO: 56 and is an IgG2/x isotype, optionally comprising V234A, G237A, P238S, H268A, V309L, A330S and P331S substitutions when compared to the wild type IgG2.

In some embodiments, the antibody comprises the VH of SEQ ID NO: 48 and the VL of SEQ ID NO: 56 and is an IgG2/x isotype comprising V234A, G237A, P238S, H268A, V309L, A330S and P331S substitutions when compared to the wild type IgG2.

In some embodiments, the antibody is an IgG1 isotype.

In some embodiments, the antibody is an IgG3 isotype.

In some embodiments, the antibody is a bispecific antibody, such as a bispecific PD-1/TIM-3 antibody.

The antibody is suitable for use in therapy, for example in treating cancer.

The antibody is suitable for use in therapy, for example in treating a solid tumor.

The antibody is suitable for use in therapy, for example in treating a melanoma.

The antibody is suitable for use in therapy, for example in treating a lung cancer.

The antibody is suitable for use in therapy, for example in treating non-small cell lung cancer (NSCLC).

The antibody is suitable for use in therapy, for example in treating a squamous NSCLC.

The antibody is suitable for use in therapy, for example in treating a non-squamous NSCLC.

The antibody is suitable for use in therapy, for example in treating a lung adenocarcinoma.

The antibody is suitable for use in therapy, for example in treating a renal cell carcinoma (RCC).

The antibody is suitable for use in therapy, for example in treating a mesothelioma.

The antibody is suitable for use in therapy, for example in treating a nasopharyngeal carcinoma (NPC).

The antibody is suitable for use in therapy, for example in treating a colorectal cancer.

The antibody is suitable for use in therapy, for example in treating a prostate cancer.

The antibody is suitable for use in therapy, for example in treating a castration-resistant prostate cancer.

The antibody is suitable for use in therapy, for example in treating a stomach cancer.

The antibody is suitable for use in therapy, for example in treating an ovarian cancer.

The antibody is suitable for use in therapy, for example in treating a gastric cancer.

The antibody is suitable for use in therapy, for example in treating a liver cancer.

The antibody is suitable for use in therapy, for example in treating a pancreatic cancer.

The antibody is suitable for use in therapy, for example in treating a thyroid cancer.

The antibody is suitable for use in therapy, for example in treating a squamous cell carcinoma of the head and neck.

The antibody is suitable for use in therapy, for example in treating a carcinomas of the esophagus or gastrointestinal tract.

The antibody is suitable for use in therapy, for example in treating a breast cancer.

The antibody is suitable for use in therapy, for example in treating a fallopian tube cancer.

The antibody is suitable for use in therapy, for example in treating a brain cancer.

The antibody is suitable for use in therapy, for example in treating an urethral cancer.

The antibody is suitable for use in therapy, for example in treating an endometriosis.

The antibody is suitable for use in therapy, for example in treating a cervical cancer.

The antibody is suitable for use in therapy, for example in treating a metastatic lesion of the cancer.

The antibody is suitable for use in therapy, for example in treating a hematological malignancy.

The antibody is suitable for use in therapy, for example in treating a non-Hodgkin's lymphoma.

The antibody is suitable for use in therapy, for example in treating a chronic lymphocytic leukemia.

The antibody is suitable for use in therapy, for example in treating a cancer, in combination with an antagonistic antibody specifically binding TIM-3.

The antibody is suitable for use in therapy, for example in treating a cancer, in combination with an antagonistic antibody specifically binding TIM-3 comprising the VH of SEQ ID NO: 146 and the VL of SEQ ID NO: 156.

The antibody is suitable for use in therapy, for example in treating a cancer, in combination with an antagonistic antibody specifically binding TIM-3 comprising the VH of SEQ ID NO: 145 and the VL of SEQ ID NO: 155.

The antibody is suitable for use in therapy, for example in treating a cancer, in combination with an antagonistic antibody specifically binding TIM-3 comprising the VH of SEQ ID NO: 172 and the VL of SEQ ID NO: 173.

The antibody is suitable for use in therapy, for example in treating cancer, such as a solid tumor, in combination with a FGFR inhibitor.

The antibody is suitable for use in therapy, for example in treating cancer, such as a solid tumor, in combination with a vaccine.

The antibody is suitable for use in therapy, for example in treating cancer, such as a solid tumor, in combination with an agonistic antibody specifically binding GITR (SEQ ID NO: 271).

The antibody is suitable for use in therapy, for example in treating cancer, such as a solid tumor, in combination with an agonistic antibody specifically binding CD137 (SEQ ID NO: 281).

The antibody is suitable for use in therapy, for example in treating cancer, such as a solid tumor, in combination with an agonistic antibody specifically binding OX-40 (SEQ ID NO: 279).

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 66, 67, 68, 69, 70 and 71, respectively.

In some embodiments, the antibody comprises the VH of SEQ ID NO: 64 and the VL of SEQ ID NO: 65.

In some embodiments, the VH and the VL are encoded by polynucleotide sequences of SEQ ID NOs: 198 and 199, respectively.

In some embodiments, the antibody comprises the VH of SEQ ID NO: 63 and the VL of SEQ ID NO: 65.

In some embodiments, the antibody or the antigen-binding portion thereof binds human PD-1 with an equilibrium dissociation constant ($K_D$) of less than about 100 nM, optionally less than about 10 nM, for example less than about 1 nM such as less than about 100 pM, wherein the $K_D$ is measured using ProteOn XPR36 system at +25° C.

In some embodiments, the antibody is an IgG4 isotype, optionally comprising a S228P substitution when compared to the wild type IgG4.

In some embodiments, the antibody is an IgG4/κ isotype, optionally comprising the S228P substitution when compared to the wild type IgG4.

In some embodiments, the antibody comprises the VH of SEQ ID NO: 64 and the VL of SEQ ID NO: 65 and is an IgG4 isotype, optionally comprising the S228P substitution when compared to the wild type IgG4.

In some embodiments, the antibody comprises the VH of SEQ ID NO: 64 and the VL of SEQ ID NO: 65 and is an IgG4κ isotype, comprising the S228P substitution when compared to the wild type IgG4.

In some embodiments, the antibody comprises the HC of SEQ ID NO: 74 and the LC of SEQ ID NO: 75.

In some embodiments, the antibody is an IgG2 isotype, optionally comprising V234A, G237A, P238S, H268A, V309L, A330S and P331S substitutions when compared to the wild type IgG2.

In some embodiments, the antibody is an IgG2/x isotype, optionally comprising V234A, G237A, P238S, H268A, V309L, A330S and P331S substitution when compared to the wild type IgG2.

In some embodiments, the antibody comprises the VH of SEQ ID NO: 64 and the VL of SEQ ID NO: 65 and is an IgG2/x isotype, optionally comprising V234A, G237A, P238S, H268A, V309L, A330S and P331S substitution when compared to the wild type IgG2.

In some embodiments, the antibody comprises the VH of SEQ ID NO: 64 and the VL of SEQ ID NO: 65 and is an IgG2/x isotype comprising V234A, G237A, P238S, H268A, V309L, A330S and P331S substitution when compared to the wild type IgG2.

In some embodiments, the antibody is an IgG1 isotype.

In some embodiments, the antibody is an IgG3 isotype.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The antibody is suitable for use in therapy, for example in treating a melanoma.

The antibody is suitable for use in therapy, for example in treating a lung cancer.

The antibody is suitable for use in therapy, for example in treating non-small cell lung cancer (NSCLC).

The antibody is suitable for use in therapy, for example in treating a squamous NSCLC.

The antibody is suitable for use in therapy, for example in treating a non-squamous NSCLC.

The antibody is suitable for use in therapy, for example in treating a lung adenocarcinoma.

The antibody is suitable for use in therapy, for example in treating a renal cell carcinoma (RCC).

The antibody is suitable for use in therapy, for example in treating a mesothelioma.

The antibody is suitable for use in therapy, for example in treating a nasopharyngeal carcinoma (NPC).

The antibody is suitable for use in therapy, for example in treating a colorectal cancer.

The antibody is suitable for use in therapy, for example in treating a prostate cancer.

The antibody is suitable for use in therapy, for example in treating a castration-resistant prostate cancer.

The antibody is suitable for use in therapy, for example in treating a stomach cancer.

The antibody is suitable for use in therapy, for example in treating an ovarian cancer.

The antibody is suitable for use in therapy, for example in treating a gastric cancer.

The antibody is suitable for use in therapy, for example in treating a liver cancer.

The antibody is suitable for use in therapy, for example in treating a pancreatic cancer.

The antibody is suitable for use in therapy, for example in treating a thyroid cancer.

The antibody is suitable for use in therapy, for example in treating a squamous cell carcinoma of the head and neck.

The antibody is suitable for use in therapy, for example in treating a carcinomas of the esophagus or gastrointestinal tract.

The antibody is suitable for use in therapy, for example in treating a breast cancer.

The antibody is suitable for use in therapy, for example in treating a fallopian tube cancer.

The antibody is suitable for use in therapy, for example in treating a brain cancer.

The antibody is suitable for use in therapy, for example in treating an urethral cancer.

The antibody is suitable for use in therapy, for example in treating an endometriosis.

The antibody is suitable for use in therapy, for example in treating a cervical cancer.

The antibody is suitable for use in therapy, for example in treating a metastatic lesion of the cancer.

The antibody is suitable for use in therapy, for example in treating a hematological malignancy.

The antibody is suitable for use in therapy, for example in treating a non-Hodgkin's lymphoma.

The antibody is suitable for use in therapy, for example in treating a chronic lymphocytic leukemia.

The antibody is suitable for use in therapy, for example in treating a cancer, in combination with an antagonistic antibody specifically binding TIM-3.

The antibody is suitable for use in therapy, for example in treating a cancer, in combination with an antagonistic antibody specifically binding TIM-3 comprising the VH of SEQ ID NO: 146 and the VL of SEQ ID NO: 156.

The antibody is suitable for use in therapy, for example in treating a cancer, in combination with an antagonistic antibody specifically binding TIM-3 comprising the VH of SEQ ID NO: 145 and the VL of SEQ ID NO: 155.

The antibody is suitable for use in therapy, for example in treating a cancer, in combination with an antagonistic antibody specifically binding TIM-3 comprising the VH of SEQ ID NO: 172 and the VL of SEQ ID NO: 173.

The antibody is suitable for use in therapy, for example in treating cancer, such as a solid tumor, in combination with a FGFR inhibitor.

The antibody is suitable for use in therapy, for example in treating cancer, such as a solid tumor, in combination with a vaccine.

The antibody is suitable for use in therapy, for example in treating cancer, such as a solid tumor, in combination with an agonistic antibody specifically binding GITR (SEQ ID NO: 271).

The antibody is suitable for use in therapy, for example in treating cancer, such as a solid tumor, in combination with an agonistic antibody specifically binding CD137 (SEQ ID NO: 281).

The antibody is suitable for use in therapy, for example in treating cancer, such as a solid tumor, in combination with an agonistic antibody specifically binding OX-40 (SEQ ID NO: 279).

The invention also provides an antagonistic antibody specifically binding PD-1 or an antigen-biding portion thereof, comprising the HCDR1, the HCDR2, the HCDR3, the LCDR1, the LCDR2 and the LCDR3 of SEQ ID NOs: 12, 13, 19, 24, 26 and 38, respectively.

In some embodiments, the antibody or the antigen-biding portion thereof comprises the VH of SEQ ID NO: 47 and the VL of SEQ ID NO: 58.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-biding portion thereof comprising the HCDR1, the HCDR2, the HCDR3, the LCDR1, the LCDR2 and the LCDR3 of SEQ ID NOs: 11, 15, 18, 20, 30 and 32, respectively.

In some embodiments, the antibody or the antigen-binding portion thereof comprises the VH of SEQ ID NO: 45 and the VL of SEQ ID NO: 60.

In some embodiments, the VH and the VL are encoded by polynucleotide sequences of SEQ ID NOs: 202 and 203, respectively.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody comprises the HC of SEQ ID NO: 76 and the LC of SEQ ID NO: 77.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-biding portion thereof, comprising the HCDR1, the HCDR2, the HCDR3, the LCDR1, the LCDR2 and the LCDR3 of SEQ ID NOs: 10, 13, 16, 20, 26 and 31, respectively.

In some embodiments, the antibody or the antigen-biding portion thereof comprises the VH of SEQ ID NO: 41 and the VL of SEQ ID NO: 49.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody comprises the HC of SEQ ID NO: 212 and the LC of SEQ ID NO: 213.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-biding portion thereof, comprising the HCDR1, the HCDR2, the HCDR3, the LCDR1, the LCDR2 and the LCDR3 of SEQ ID NOs: 10, 13, 16, 21, 26 and 32, respectively.

In some embodiments, the antibody or the antigen-biding portion thereof comprises the VH of SEQ ID NO: 41 and the VL of SEQ ID NO: 50.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody comprises the HC of SEQ ID NO: 214 and the LC of SEQ ID NO: 215.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-biding portion thereof, comprising the HCDR1, the HCDR2, the HCDR3, the LCDR1, the LCDR2 and the LCDR3 of SEQ ID NOs: 10, 14, 16, 22, 27 and 33, respectively.

In some embodiments, the antibody or the antigen-binding portion thereof comprises the VH of SEQ ID NO: 42 and the VL of SEQ ID NO: 51.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody comprises the HC of SEQ ID NO: 216 and the LC of SEQ ID NO: 217.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-biding portion thereof, comprising the HCDR1, the HCDR2, the HCDR3, the LCDR1, the LCDR2 and the LCDR3 of SEQ ID NOs: 10, 14, 16, 22, 26 and 34, respectively.

In some embodiments, the antibody or the antigen-biding portion thereof comprises the VH of SEQ ID NO: 42 and the VL of SEQ ID NO: 52.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody comprises the HC of SEQ ID NO: 218 and the LC of SEQ ID NO: 219.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 10, 14, 16, 23, 28 and 35, respectively.

In some embodiments, the antibody or the antigen-binding portion thereof comprises the VH of SEQ ID NO: 42 and the VL of SEQ ID NO: 53.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody comprises the HC of SEQ ID NO: 220 and the LC of SEQ ID NO: 221.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 10, 13, 17, 20, 26 and 31, respectively.

In some embodiments, the antibody or the antigen-binding portion thereof comprises the VH of SEQ ID NO: 43 and the VL of SEQ ID NO: 49.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 10, 13, 17, 20, 26 and 36, respectively.

In some embodiments, the antibody or the antigen-binding portion thereof comprises the VH of SEQ ID NO: 43 and the VL of SEQ ID NO: 54.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody comprises the HC of SEQ ID NO: 222 and the LC of SEQ ID NO: 223.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 10, 13, 17, 21, 26 and 32, respectively.

In some embodiments, the antibody or the antigen-binding portion thereof comprises the VH of SEQ ID NO: 43 and the VL of SEQ ID NO: 50.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody comprises the HC of SEQ ID NO: 224 and the LC of SEQ ID NO: 225.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR1, the HCDR2, the HCDR3, the LCDR1, the LCDR2 and the LCDR3 of SEQ ID NOs: 10, 13, 17, 21, 27 and 37, respectively.

In some embodiments, the antibody or the antigen-binding portion thereof comprises the VH of SEQ ID NO: 43 and the VL of SEQ ID NO: 55.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody comprises the HC of SEQ ID NO: 226 and the LC of SEQ ID NO: 227.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 10, 13, 17, 23, 26 and 32, respectively.

In some embodiments, the antibody or the antigen-binding portion thereof comprises the VH of SEQ ID NO: 43 and the VL of SEQ ID NO: 56.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 10, 13, 17, 22, 26 and 32, respectively.

In some embodiments, the antibody comprises the VH of SEQ ID NO: 43 and the VL of SEQ ID NO: 57.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody comprises the HC of SEQ ID NO: 228 and the LC of SEQ ID NO: 229.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 10, 13, 18, 20, 26 and 31, respectively.

In some embodiments, the antibody or the antigen-binding portion thereof comprises the VH of SEQ ID NO: 44 and the VL of SEQ ID NO: 49.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 11, 15, 18, 20, 26 and 31, respectively.

In some embodiments, the antibody or the antigen-binding portion thereof comprises the VH of SEQ ID NO: 45 and the VL of SEQ ID NO: 49.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 10, 13, 19, 20, 26 and 31, respectively.

In some embodiments, the antibody or the antigen-binding portion thereof comprises the VH of SEQ ID NO: 46 and the VL of SEQ ID NO: 49.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 12, 13, 19, 20, 26 and 31, respectively.

In some embodiments, the antibody or the antigen-binding portion thereof comprises the VH of SEQ ID NO: 47 and the VL of SEQ ID NO: 49.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 10, 14, 17, 23, 28 and 35, respectively.

In some embodiments, the antibody comprises the VH of SEQ ID NO: 48 and the VL of SEQ ID NO: 53.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 10, 14, 17, 22, 26 and 34, respectively.

In some embodiments, the antibody or the antigen-binding portion thereof comprises the VH of SEQ ID NO: 48 and the VL of SEQ ID NO: 52.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 12, 13, 19, 20, 29 and 39, respectively.

In some embodiments, the antibody or the antigen-binding portion thereof comprises the VH of SEQ ID NO: 47 and the VL of SEQ ID NO: 59.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 11, 15, 18, 25, 26 and 40, respectively.

In some embodiments, the antibody or the antigen-binding portion thereof comprises the VH of SEQ ID NO: 45 and the VL of SEQ ID NO: 61.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 11, 15, 18, 24, 26 and 32, respectively.

In some embodiments, the antibody of the antigen-binding portion thereof comprises the VH of SEQ ID NO: 45 and the VL of SEQ ID NO: 62.

In some embodiments, the antibody is an IgG1 isotype.

In some embodiments, the antibody is an IgG2 isotype.

In some embodiments, the antibody is an IgG2 isotype comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype.

In some embodiments, the antibody is an IgG4 isotype comprising the S228P substitution when compared to the wild type IgG4.

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The invention also provides an antagonistic antibody specifically binding PD-1 or an antigen-binding portion thereof, comprising the VH of SEQ ID NOs: 41, 42, 43, 44, 45, 46, 47, 48, 63 or 64.

The invention also provides an antagonistic antibody specifically binding PD-1 or an antigen-binding portion thereof, comprising the VL of SEQ ID NOs: 49, 50, 51, 52, 53, 54, 55, 56, 57, 58, 59, 60, 61, 62 or 65.

The invention also provides an antagonistic antibody specifically binding PD-1 or an antigen-binding portion thereof, comprising the VH of SEQ ID NOs: 41, 42, 43, 44, 45, 46, 47, 48, 63 or 64 and the VL of SEQ ID NOs: 49, 50, 51, 52, 53, 54, 55, 56, 57, 58, 59, 60, 61, 62 or 65.

The VH, the VL, the HCDR and the LCDR sequences of exemplary antagonistic antibodies specifically binding PD-1 of the invention are shown in Table 2.

Although the embodiments illustrated in the Examples comprise pairs of variable regions, one from a heavy chain and one from a light chain, a skilled artisan will recognize that alternative embodiments may comprise single heavy or light chain variable regions. The single variable region may be used to screen for variable domains capable of forming a two-domain specific antigen-binding fragment capable of, for example, binding to human PD-1. The screening may be accomplished by phage display screening methods using for example hierarchical dual combinatorial approach disclosed in Int. Patent Publ. No. WO1992/01047. In this approach, an individual colony containing either a VH or a VL chain clone is used to infect a complete library of clones encoding the other chain (VL or VH), and the resulting two-chain specific antigen-binding domain is selected in accordance with phage display techniques using known methods and those described herein. Therefore, the individual VH and VL polypeptide chains are useful in identifying additional antibodies specifically binding to human PD-1 using the methods disclosed in Int. Patent Publ. No. WO1992/01047.

In some embodiments, the antagonistic antibody specifically binding PD-1 is a multispecific antibody.

In some embodiments, the antagonistic antibody specifically binding PD-1 is a bispecific antibody.

In some embodiments, antagonistic bispecific antibody specifically binding PD-1 binds PD-L1 (SEQ ID NO: 5), PD-L2 (SEQ ID NO: 8), LAG-3 (SEQ ID NO: 293), TIM-3 (SEQ ID NO: 138), CEACAM-1 (SEQ ID NO: 296), CEACAM-5 (SEQ ID NO: 307), OX-40 (SEQ ID NO: 279), GITR (SEQ ID NO: 271), CD27 (SEQ ID NO: 280), VISTA (SEQ ID NO: 286), CD137 (SEQ ID NO: 281), TIGIT (SEQ ID NO: 301) or CTLA-4 (SEQ ID NO: 292). Bispecific and multispecific antibodies may be generated using methods described herein.

TABLE 2

| Antibody | HCDR1 | HCDR2 | HCDR3 | LCDR1 | LCDR2 | LCDR3 | VH | VL |
|---|---|---|---|---|---|---|---|---|
| PD1B114 | 10 | 13 | 16 | 20 | 26 | 31 | 41 | 49 |
| PD1B149 | 10 | 13 | 16 | 21 | 26 | 32 | 41 | 50 |
| PD1B160 | 10 | 14 | 16 | 22 | 27 | 33 | 42 | 51 |
| PD1B162 | 10 | 14 | 16 | 22 | 26 | 34 | 42 | 52 |
| PD1B164 | 10 | 14 | 16 | 23 | 28 | 35 | 42 | 53 |
| PD1B11 | 10 | 13 | 17 | 20 | 26 | 31 | 43 | 49 |
| PD1B183 | 10 | 13 | 17 | 20 | 26 | 36 | 43 | 54 |
| PD1B184 | 10 | 13 | 17 | 21 | 26 | 32 | 43 | 50 |
| PD1B185 | 10 | 13 | 17 | 21 | 27 | 37 | 43 | 55 |
| PD1B187 | 10 | 13 | 17 | 23 | 26 | 32 | 43 | 56 |
| PD1B192 | 10 | 13 | 17 | 22 | 26 | 32 | 43 | 57 |
| PD1B71 | 10 | 13 | 18 | 20 | 26 | 31 | 44 | 49 |
| PD1B177 | 11 | 15 | 18 | 20 | 26 | 31 | 45 | 49 |
| PD1B70 | 10 | 13 | 19 | 20 | 26 | 31 | 46 | 49 |
| PD1B175 | 12 | 13 | 19 | 20 | 26 | 31 | 47 | 49 |
| PD1B194 | 10 | 14 | 17 | 23 | 28 | 35 | 48 | 53 |
| PD1B195 | 10 | 14 | 17 | 22 | 26 | 34 | 48 | 52 |
| PD1B196 | 10 | 14 | 17 | 23 | 26 | 32 | 48 | 56 |
| PD1B197 | 12 | 13 | 19 | 24 | 26 | 38 | 47 | 58 |
| PD1B198 | 12 | 13 | 19 | 20 | 29 | 39 | 47 | 59 |
| PD1B199 | 11 | 15 | 18 | 20 | 30 | 32 | 45 | 60 |
| PD1B200 | 11 | 15 | 18 | 25 | 26 | 40 | 45 | 61 |
| PD1B201 | 11 | 15 | 18 | 24 | 26 | 32 | 45 | 62 |
| PD1B131 | 66 | 67 | 68 | 69 | 70 | 71 | 63 | 65 |
| PD1B132 | 66 | 67 | 68 | 69 | 70 | 71 | 64 | 65 |

Homologous Antibodies

Variants of the antagonistic antibodies specifically binding PD-1 or the antigen-binding portion thereof of the invention comprising the VH, the VL or the VH and the VL amino acid sequences shown in Table 2, Table 21 and Table 22 are within the scope of the invention. For example, variants may comprise one, two, three, four, five, six, seven, eight, nine, ten, eleven, twelve, thirteen, fourteen or fifteen amino acid substitutions in the VH and/or the VL as long as the homologous antibodies retain or have improved functional properties when compared to the parental antibodies. In some embodiments, the sequence identity may be about 90%, 91%, 92%, 93%, 94%, 95%, 96%, 97%, 98% or 99% to a VH or the VL amino acid sequence of the invention. Optionally, any variation of the variant compared to the parental antibody is not within the CDRs of the variant.

The invention also provides an antagonistic antibody specifically binding PD-1 or an antigen-binding portion thereof, comprising the VH of SEQ ID NOs: 41, 42, 43, 44, 45, 46, 47, 48, 63 or 64, the VH optionally having one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding PD-1 or an antigen-binding portion thereof, comprising the VL of SEQ ID NOs: 49, 50, 51, 52, 53, 54, 55, 56, 57, 58, 59, 60, 61, 62 or 65, the VL optionally having one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding PD-1 or an antigen-binding portion thereof, comprising the VH of SEQ ID NO: 48 and the VL of SEQ ID NO: 56, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding PD-1 or an antigen-binding portion thereof, comprising the VH of SEQ ID NO: 64 and the VL of SEQ ID NO: 65, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding PD-1 or an antigen-binding portion thereof, comprising the VH of SEQ ID NO: 41 and the VL of SEQ ID NO: 49;
  the VH of SEQ ID NO: 41 and the VL of SEQ ID NO: 50;
  the VH of SEQ ID NO: 42 and the VL of SEQ ID NO: 51;
  the VH of SEQ ID NO: 42 and the VL of SEQ ID NO: 52;
  the VH of SEQ ID NO: 42 and the VL of SEQ ID NO: 53;
  the VH of SEQ ID NO: 43 and the VL of SEQ ID NO: 49;
  the VH of SEQ ID NO: 43 and the VL of SEQ ID NO: 54;
  the VH of SEQ ID NO: 43 and the VL of SEQ ID NO: 50;
  the VH of SEQ ID NO: 43 and the VL of SEQ ID NO: 55;
  the VH of SEQ ID NO: 43 and the VL of SEQ ID NO: 56;
  the VH of SEQ ID NO: 43 and the VL of SEQ ID NO: 57;
  the VH of SEQ ID NO: 44 and the VL of SEQ ID NO: 49;
  the VH of SEQ ID NO: 45 and the VL of SEQ ID NO: 49;
  the VH of SEQ ID NO: 46 and the VL of SEQ ID NO: 49;
  the VH of SEQ ID NO: 47 and the VL of SEQ ID NO: 49;
  the VH of SEQ ID NO: 48 and the VL of SEQ ID NO: 53;
  the VH of SEQ ID NO: 48 and the VL of SEQ ID NO: 52;
  the VH of SEQ ID NO: 47 and the VL of SEQ ID NO: 58;
  the VH of SEQ ID NO: 47 and the VL of SEQ ID NO: 59;
  the VH of SEQ ID NO: 45 and the VL of SEQ ID NO: 60;
  the VH of SEQ ID NO: 45 and the VL of SEQ ID NO: 61;
  the VH of SEQ ID NO: 45 and the VL of SEQ ID NO: 62;
  or
  the VH of SEQ ID NO: 63 and the VL of SEQ ID NO: 65, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding PD-1 or an antigen-binding portion thereof, comprising the VH having the amino acid sequence at least 90%, 91%, 92%, 93%, 94%, 95%, 96%, 97%, 98% or 99% identical to the VH of SEQ ID NOs: 41, 42, 43, 44, 45, 46, 47, 48, 64 or 65. Optionally, any variation from the sequences of the SEQ ID NOs is not within the CDRs.

The invention also provides an antagonistic antibody specifically binding PD-1 or an antigen-binding portion thereof, comprising the VL having the amino acid sequence at least 90%, 91%, 92%, 93%, 94%, 95%, 96%, 97%, 98% or 99% identical to the VL of SEQ ID NOs: 49, 50, 51, 52, 53, 54, 55, 56, 57, 58, 59, 60, 61, 62 or 65. Optionally, any variation from the sequences of the SEQ ID NOs is not within the CDRs.

The invention also provides an antagonistic antibody specifically binding PD-1 or an antigen-binding portion thereof, comprising the VH having the amino acid sequence at least 90%, 91%, 92%, 93%, 94%, 95%, 96%, 97%, 98% or 99% identical to the VH of SEQ ID NOs: 41, 42, 43, 44, 45, 46, 47, 48, 63 or 64 and the VL having the amino acid sequence at least 90%, 91%, 92%, 93%, 94%, 95%, 96%, 97%, 98% or 99% identical to the VL of SEQ ID NOs: 49, 50, 51, 52, 53, 54, 55, 56, 57, 58, 59, 60, 61, 62 or 65. Optionally, any variation from the sequences of the SEQ ID NOs is not within the CDRs.

The invention also provides an antagonistic antibody specifically binding PD-1 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 48 and the VL of SEQ ID NO: 56. Optionally, any variation from the sequences of the SEQ ID NOs is not within the CDRs.

The invention also provides an antagonistic antibody specifically binding PD-1 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 64 and the VL of SEQ ID NO: 65. Optionally, any variation from the sequences of the SEQ ID NOs is not within the CDRs.

The invention also provides an antagonistic antibody specifically binding PD-1 or an antigen-binding portion thereof, comprising the VH and the VL having the amino acid sequences at least 90%, 91%, 92%, 93%, 94%, 95%, 96%, 97%, 98% or 99% identical to the VH and the VL of SEQ ID NOs:
  41 and 49, respectively;
  41 and 50, respectively;
  42 and 51, respectively;
  42 and 52, respectively;
  42 and 53, respectively;
  43 and 49, respectively;
  43 and 54, respectively;
  43 and 50, respectively;
  43 and 55, respectively;
  43 and 56, respectively;
  43 and 57, respectively;
  44 and 49, respectively;
  45 and 49, respectively;
  46 and 49, respectively;
  47 and 49, respectively;
  48 and 53, respectively;
  48 and 52, respectively;
  47 and 58, respectively;
  47 and 59, respectively;
  45 and 60, respectively;
  45 and 61, respectively;
  45 and 62, respectively; or
  63 and 65, respectively. Optionally, any variation from the sequences of the SEQ ID NOs is not within the CDRs.

The homologous antagonistic antibodies specifically binding PD-1 or the antigen-binding portions thereof of the invention have one, two, three, four or five of the following properties:

a) enhance an activation of antigen specific $CD4^+$ or $CD8^+$ T cells in a dose dependent manner, wherein the activation is measured using a cytomegalovirus antigen recall assay (CMV assay) as described in Example 1;

b) bind human PD-1 with an equilibrium dissociation constant ($K_D$) of less than about 100 nM, wherein the $K_D$ is measured using ProteOn XPR36 system at +25° C.;

c) bind human PD-1 with the $K_D$ of less than about 1 nM, wherein the $K_D$ is measured using ProteOn XPR36 system at +25° C.;

d) bind cynomolgus PD-1 of SEQ ID NO: 3 with the $K_D$ of less than about 100 nM, wherein the $K_D$ is measured using ProteOn XPR36 system at +25° C., or e) bind cynomolgus PD-1 of SEQ ID NO: 3 with the $K_D$ of less than about 1 nM, wherein the $K_D$ is measured using ProteOn XPR36 system at +25° C.

In some embodiments, the antibody enhances activation of antigen specific $CD4^+$ or $CD8^+$ T cells in a dose dependent manner, wherein activation is measured using a cytomegalovirus antigen recall assay (CMV assay) as described in Example 1, and binds human PD-1 with an equilibrium dissociation constant ($K_D$) of less than about 100 nM, wherein the $K_D$ is measured using ProteOn XPR36 system at +25° C.

In some embodiments, the antibody enhances activation of antigen specific $CD4^+$ or $CD8^+$ T cells in dose dependent manner, wherein activation is measured using a cytomegalovirus antigen recall assay (CMV assay) as described in Example 1, and binds human PD-1 with an equilibrium dissociation constant ($K_D$) of less than about 10 nM, wherein the $K_D$ is measured using ProteOn XPR36 system at +25° C.

The percent identity between the two sequences is a function of the number of identical positions shared by the sequences (i.e., % identity=number of identical positions/total number of positions×100), taking into account the number of gaps, and the length of each gap, which need to be introduced for optimal alignment of the two sequences.

The percent identity between two amino acid sequences may be determined using the algorithm of E. Meyers and W. Miller (*Comput Appl Biosci* 4:11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch (*J Mol Biol* 48:444-453 (1970)) algorithm which has been incorporated into the GAP program in the GCG software package (available at http://_www_gcg_com), using either a Blossum 62 matrix or a PAM250 matrix, and a gap weight of 16, 14, 12, 10, 8, 6, or 4 and a length weight of 1, 2, 3, 4, 5, or 6.

Antibodies with Conservative Modifications

The invention also provides antagonistic antibodies specifically binding PD-1 or antigen-binding portions thereof comprising the VH comprising the HCDR1, the HCDR2 and the HCDR3 sequences and the VL comprising the LCDR1, the LCDR2 and the LCDR3 sequences, wherein one or more of the CDR sequences comprise specified amino acid sequences based on the antibodies described herein (e.g., antibodies shown in Table 2, Table 21 and Table 22, or conservative modifications thereof, and wherein the antibodies retain the desired functional properties of the parental antagonistic antibodies specifically binding PD-1 of the invention.

The antibodies with conservative modifications have one, two, three, four or five of the following properties:
  a) enhance an activation of antigen specific $CD4^+$ or $CD8^+$ T cells in dose dependent manner, wherein the activation is measured using a cytomegalovirus antigen recall assay (CMV assay) as described in Example 1;
  b) bind human PD-1 with an equilibrium dissociation constant ($K_D$) of less than about 100 nM, wherein the $K_D$ is measured using ProteOn XPR36 system at +25° C.;
  c) bind human PD-1 with the $K_D$ of less than about 1 nM, wherein the $K_D$ is measured using ProteOn XPR36 system at +25° C.;
  d) bind cynomolgus PD-1 of SEQ ID NO: 3 with the $K_D$ of less than about 100 nM, wherein the $K_D$ is measured using ProteOn XPR36 system at +25° C., or e) bind cynomolgus PD-1 of SEQ ID NO: 3 with the $K_D$ of less than about 1 nM, wherein the $K_D$ is measured using ProteOn XPR36 system at +25° C.

In some embodiments, the antibody enhances activation of antigen specific $CD4^+$ or $CD8^+$ T cells in dose dependent manner, wherein activation is measured using a cytomegalovirus antigen recall assay (CMV assay) as described in Example 1, and binds human PD-1 with an equilibrium dissociation constant ($K_D$) of less than about 100 nM, wherein the $K_D$ is measured using ProteOn XPR36 system at +25° C.

In some embodiments, the antibody enhances activation of antigen specific $CD4^+$ or $CD8^+$ T cells in dose dependent manner, wherein activation is measured using a cytomegalovirus antigen recall assay (CMV assay) as described in Example 1, and binds human PD-1 with an equilibrium dissociation constant ($K_D$) of less than about 10 nM, wherein the $K_D$ is measured using ProteOn XPR36 system at +25° C.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 10, 14, 17, 23, 26 and 32, respectively, and conservative modifications thereof.

The invention also provides an antagonistic antibody specifically binding PD-1 or an antigen-binding portion thereof, comprising the HCDR1, the HCDR2, the HCDR3, the LCDR1, the LCDR2 and the LCDR3 of SEQ ID NOs: 66, 67, 68, 69, 70 and 71, respectively, and conservative modifications thereof.

The invention also provides an antagonistic antibody specifically binding PD-1 or an antigen-binding portion thereof, comprising the HCDR1, the HCDR2, the HCDR3, the LCDR1, the LCDR2 and the LCDR3 of
  SEQ ID NOs: 10, 13, 16, 20, 26 and 31, respectively;
  SEQ ID NOs: 10, 13, 16, 21, 26 and 32, respectively;
  SEQ ID NOs: 10, 14, 16, 22, 27 and 33, respectively;
  SEQ ID NOs: 10, 14, 16, 22, 26 and 34, respectively;
  SEQ ID NOs: 10, 14, 16, 23, 28 and 35, respectively;
  SEQ ID NOs: 10, 13, 17, 20, 26 and 31, respectively;
  SEQ ID NOs: 10, 13, 17, 20, 26 and 36, respectively;
  SEQ ID NOs: 10, 13, 17, 21, 26 and 32, respectively;
  SEQ ID NOs: 10, 13, 17, 21, 27 and 37, respectively;
  SEQ ID NOs: 10, 13, 17, 23, 26 and 32, respectively;
  SEQ ID NOs: 10, 13, 17, 22, 26 and 32, respectively;
  SEQ ID NOs: 10, 13, 18, 20, 26 and 31, respectively;
  SEQ ID NOs: 11, 15, 18, 20, 26 and 31, respectively;
  SEQ ID NOs: 10, 13, 19, 20, 26 and 31, respectively;
  SEQ ID NOs: 12, 13, 19, 20, 26 and 31, respectively;
  SEQ ID NOs: 10, 14, 17, 23, 28 and 35, respectively;
  SEQ ID NOs: 10, 14, 17, 22, 26 and 34, respectively;
  SEQ ID NOs: 12, 13, 19, 24, 26 and 38, respectively;
  SEQ ID NOs: 12, 13, 19, 20, 29 and 39, respectively;
  SEQ ID NOs: 11, 15, 18, 20, 30 and 32, respectively;
  SEQ ID NOs: 11, 15, 18, 25, 26 and 40, respectively;
  SEQ ID NOs: 11, 15, 18, 24, 26 and 32, respectively, and
    conservative modifications thereof.

"Conservative modification" refers to amino acid modifications that do not significantly affect or alter the binding characteristics of the antibody containing the amino acid sequences. Conservative modifications include amino acid substitutions, additions and deletions. Conservative substitutions are those in which the amino acid is replaced with an amino acid residue having a similar side chain. The families of amino acid residues having similar side chains are well defined and include amino acids with acidic side chains (for example, aspartic acid, glutamic acid), basic side chains (for example, lysine, arginine, histidine), nonpolar side chains (for example, alanine, valine, leucine, isoleucine, proline, phenylalanine, methionine), uncharged polar side chains (for example, glycine, asparagine, glutamine, cysteine, serine, threonine, tyrosine, tryptophan), aromatic side chains (for example, phenylalanine, tryptophan, histidine, tyrosine), aliphatic side chains (for example, glycine, alanine, valine, leucine, isoleucine, serine, threonine), amide (for example, asparagine, glutamine), beta-branched side chains (for example, threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., Acta Physiol. Scand. Suppl. 643:55-67, 1998; Sasaki et al., Adv. Biophys. 35:1-24, 1998). Amino acid substitutions to the antibodies of the invention may be made by well-known methods for example by PCR mutagenesis (U.S. Pat. No. 4,683,195). Alternatively, libraries of variants may be generated using known methods, for example using random (NNK) or non-random codons, for example DVK codons, which encode 11 amino acids (Ala, Cys, Asp, Glu, Gly, Lys, Asn, Arg, Ser, Tyr, Trp). The resulting antibody variants may be tested for their characteristics using assays described herein.

Antagonistic Antibodies Specifically Binding TIM-3

T-cell immunoglobulin domain and mucin domain 3 (TIM-3, also known as Hepatitis A virus cellular receptor 2 (HAVCR2)) is a co-inhibitory immune checkpoint receptor that has been proposed to negatively regulate both adaptive and innate immune responses. TIM-3 is expressed on specific subsets of $CD4^+$ and $CD8^+$ T cells and functions to limit the duration and magnitude of T cell responses.

Multiple lines of evidence support the inhibitory role of TIM-3 in regulating T cell responses. Tim-3-deficient mice exhibit defects in the induction of both antigen-specific and transplantation tolerance, consistent with TIM-3 inhibiting effector T cells during normal immune responses (Sabatos et al., (2003) *Nat Immunol* 4(11):1102-1110, Sanchez-Fueyo et al., (2003) *Nat Immunol* 4(11):1093-1101). Anti-TIM-3 antibodies exacerbate experimental autoimmune encephalomyelitis (EAE) in animal models (Monney et al., (2002) *Nature* 415(6871):536-541). TIM-3 has been shown to be a critical driver of the dysfunctional or exhausted T cell state that occurs in chronic infection and cancer (Sakuishi, K. and A. C. Anderson (2014). Tim-3 Regulation of Cancer Immunity. Tumor-Induced Immune Suppression. D. I. Gabrilovich and A. A. Hurwitz, Springer New York: 239-261).

Blockade of TIM-3 has been shown to restore activity in effector cells, such as cytokine secretion and proliferation. In virally exhausted cell populations, e.g., cells infected with HCV, TIM-3-expressing cells (TIM-3⁺ cells) express less TNF-α and IFN-γ cytokines than TIM-3 negative cells in both effector cell populations, CD4⁺ and CD8⁺ T cells (Golden-Mason et al., (2009) *J Virol* 83:9122). Blockade of TIM-3 restored proliferation in CD8⁺ T cells from an HIV patient, or in cells that recapitulated viral exhaustion (Jones et al., (2008) *J Exp Med* 205:2763), or proliferation and IFN-γ and/or TNF-α secretion in NY-ESO-1 specific T cells from PBMCs from metastatic patients (Fourcade et al., (2010) *J Exp Med* 207:2175). TIM-3⁺ T cells have been found to be concentrated in tumors, and contribute to the immunosuppressive tumor environment (Sakuishi et al., (2013) *Oncoimmunology*, 2:e23849).

Blockade of TIM-3 (partially alone and additively or synergistically in combination with PD-1 pathway blockade) has shown anti-tumor efficacy in several preclinical cancer models, including CT26 colon carcinoma (Sakuishi et al., (2010) *J Exp Med* 207(10):2187-94), WT3 sarcoma and TRAMP-C1 prostate carcinoma (Ngiow et al., (2011) *Cancer Res* 71(10):3540-3551).

The mechanisms through which TIM-3 inhibits T cell responses are not fully understood. The cytoplasmic tail of TIM-3 contains multiple tyrosine residues (Ferris et al., (2014) *J Immunol* 193(4): 1525-1530) but lacks inhibitory signaling motifs such as ITIMs or ITSMs that are found in the PD-1 intracellular tail. The Src family tyrosine kinases Fyn and Lck have been shown to bind to TIM-3, although the exact consequences of these interactions remain to be confirmed in vivo. Two opposing models have been proposed for how TIM-3 regulates T cell signaling. On one hand, TIM-3 has been postulated to negatively regulate TCR signaling by recruiting a phosphatase to the immunological synapse, and de-phosphorylating Lck (Clayton, et al., (2014) *J Immunol* 192(2):782-791). In contrast, TIM-3 has also been proposed to enhance TCR signaling and paradoxically drive T cells towards a more exhausted state, through increased activation of NFAT activity and NFκB signaling.

In addition to expression on effector T cells, TIM-3 is also expressed on regulatory T cells (T-regs) and has been shown to mark a suppressive T-reg subset in tumors. Analyses using both primary human cells and mouse preclinical models have shown that TIM-3⁺ T-regs are more effective at inhibiting T helper1 (Th1) and T helper 17 (Th17) T cell responses than TIM-3⁻ T-regs (Gautron et al., (2014) *Eur J Immunol* 44(9): 2703-2711; Sakuishi et al., (2013) *Oncoimmunology*, 2:e23849). Since TIM-3 is expressed on highly suppressive Tregs, it can directly inhibit CD4⁺ and CD8⁺ T cell responses. In addition, TIM-3⁺ Tregs express high levels of IL-10, which has been proposed to drive exhaustion of effector T cells in the TME as an additional indirect mechanism of suppressing anti-tumor immune responses (Sakuishi et al., (2013) *Oncoimmunology*, 2:e23849).

TIM-3 is expressed on several innate immune cell types, including monocytes/macrophages, dendritic cells, and NK cells. Existing data are consistent with a suppressive role for TIM-3 in these different cell types.

TIM-3 is constitutively expressed by circulating CD14⁺ monocytes in healthy donors, and its expression on peripheral monocytes is significantly increased in patients with chronic inflammation and cancer (Rong et al., (2014) *Tissue Antigens* 83(2):76-81). TIM-3 levels are also upregulated on macrophages that infiltrate hepatocellular carcinoma (HCC) tumors, compared to macrophages from adjacent tissues, and is proposed to play a role in driving the polarization of macrophages to an M2 tumor-promoting phenotype.

Recently, TIM-3 was reported to be expressed on dendritic cells that infiltrate mouse tumors. In this setting, interaction of TIM-3 with HMBG1 was proposed to suppress innate immunity by interfering with the recognition of and response to immunostimulatory nucleic acid (Chiba et al., (2012) *Immunol* 13(9): 832-842). TIM-3 is also constitutively expressed on NK cells in peripheral blood. A recent study showed that NK cells from advanced melanoma patients express high levels of TIM-3 on peripheral NK cells. Importantly, TIM-3⁺ NK cells were functionally exhausted and anti-TIM-3 blockade was able to reverse the exhaustion and enhance NK cell functionality (da Silva et al., (2014) *Cancer Immunol Res* 2(5): 410-422).

TIM-3 binds ligands galectin-9 (Gal-9), phosphatidylserine (PtdSer), HMGB1 and CEACAM-1. S-type lectin galectin-9 can inhibit TIM-3-associated Th1 effector function and induce apoptosis on TIM-3-expressing T cells in murine models. PtdSer usually resides on the intracellular side of the plasma membrane, but is flipped to the extracellular side during apoptosis. PtdSer binds a preserved cleft in all three human TIM family members (TIM-1, 3, 4). Inhibition of PtdSer binding to TIM-3 may activate T-cell response. Galectin-9 is secreted by tumor cells and can contribute to evasion from anti-tumor immunity. DNA alarmin HMGB1, for which TIM-3 may act as a "sink," can prevent the HMGB1/RAGE interactions that stimulate innate immunity. CEACAM-1 can interact with TIM-3 both in cis as a heterodimer on T cells and in trans as a ligand. Interaction between CEACAM-1 and TIM-3 may help mediate block immune response signaling. Co-blockade of TIM-3 and CEACAM-1 in CT26 colon carcinoma showed similar efficacy to that seen for co-blockade of PD-L1 and TIM-3.

Thus, blockade of TIM-3 using the antibodies of the invention described herein that inhibit TIM-3 function may improve the immune response against infection and anti-tumor immunity.

The invention also provides an isolated antagonistic antibody specifically binding TIM-3 or an antigen-binding portion thereof, wherein the antibody inhibits binding of TIM-3 to galectin-9.

Inhibition of binding of TIM-3 to galectin-9 by the antibodies of the invention may be assessed using competition ELISA. In an exemplary assay, 1 µg/ml recombinant human Fc-TIM-3 is bound on wells of microtiter plates, the wells are washed and blocked, and 10 µg/ml of the test antibody is added. Without washing, 7.5 µg/ml galectin-9 is added into the wells and incubated for 30 min, after which 0.5 µg/ml anti-galectin-9-biotin antibody is added and incubated for 30 min. The plates are washed and 0.5 µg/mL neutravidin-HRP conjugate polyclonal antibody is added and incubated for 30 minutes. The plates are washed and POD Chemiluminescence substrate added immediately prior to reading the luminescence signal. Antibodies of the invention inhibit binding of TIM-3 to galectin-9 when the binding of galectin-9 is reduced by at least about 50%, 55%, 60%, 65%, 70%, 75%, 80%, 85%, 90%, 95% or 100% using an assay described herein and in Example 1. Exemplary antibodies that inhibit TIM-3 binding to galectin-9 are antibodies TM3B103, TM3B105, TM3B107, TM3B108, TM3B109, TM3B113, TM3B189, TM3B190 and TM3B196.

In some embodiments, the antagonistic antibody specifically binding TIM-3 or the antigen-binding portion thereof enhances activation of antigen specific CD4$^+$ or CD8$^+$ T cells.

In some embodiments, the antagonistic antibody specifically binding TIM-3 or the antigen-binding portion thereof enhances an activation of antigen specific CD4$^+$ or CD8$^+$ T cells, wherein the activation of antigen-specific CD4$^+$ or CD8$^+$ T cells is assessed by measuring a statistically significant enhancement of CD137 surface expression on antigen specific CD4$^+$ or CD8$^+$ T cells according to methods described in Example 14.

Use of CD137 as a marker of antigen specific CD8$^+$ and CD4$^+$ T cells that expand in response to CMV antigen stimulation allowed the detection of the functional effects of the antagonistic TIM-3 antibodies of the invention.

In some embodiments, the antagonistic antibody specifically binding TIM-3 or the antigen-binding portion thereof binds TIM-3 within TIM-3 residues 32-47 (WGKGACPVFECGNVVL) (SEQ ID NO: 261).

In some embodiments, the antagonistic antibody specifically binding TIM-3 or the antigen-binding portion thereof binds TIM-3 within TIM-3 residues 32-47 (WGKGACPVFECGNVVL) (SEQ ID NO: 261) and residues 50-56 (DERDVNY) (SEQ ID NO: 262).

In some embodiments, the antagonistic antibody specifically binding TIM-3 or the antigen-binding portion thereof binds TIM-3 within TIM-3 residues 90-102 (RIQIPGIMNDEKF) (SEQ ID NO: 263).

In some embodiments, the antagonistic antibody specifically binding TIM-3 or the antigen-binding portion thereof binds TIM-3 within TIM-3 residues 90-102 (RIQIPGIMNDEKF) (SEQ ID NO: 263) and residues 50-56 (DERDVNY) SEQ ID NO: 262.

"Within" means that 80% or more of the epitope residues the antibody binds to reside within the recited amino acid stretches, and that up to 20% of the epitope residues the antibody binds to reside outside of the recited amino acid stretches.

The Tim-3 epitope the antibody binds to may be resolved for example using hydrogen/deuterium exchange (H/D exchange) or by analyzing a crystal structure of the antibody in complex with TIM-3. The epitope residues are those which are protected by the antibody by at least 5% difference in deuteration levels through H/D exchange or those surface exposed amino acid residues determined to bind the antibody in a crystal structure of a complex of the antibody and TIM-3. In the crystal structure of a complex of the antibody and TIM-3, the epitope residues are those TIM-3 residues that reside within 4 Å distance or less from any of the antibody CDR residues.

In an H/D exchange assay, TIM-3 protein is incubated in the presence or absence of the antibody in deuterated water for predetermined times resulting in deuterium incorporation at exchangeable hydrogen atoms which are unprotected by the antibody, followed by protease digestion of the protein and analyses of the peptide fragments using LC-MS. In an exemplary assay, 5 µL of the test antibody (10 µg) or 5 µL of the complex of TIM-3 and the test antibody (10 and 7.35 µg, respectively) is incubated with 120 µL deuterium oxide labeling buffer (50 mM phosphate, 100 mM sodium chloride at pH 7.4) for 0 sec, 60 sec, 300 sec, 1800 sec, 7200 sec, and 14400 sec. Deuterium exchange is quenched by adding 63 µL of 5 M guanidine hydrochloride and final pH is 2.5. The quenched sample is subjected to on-column pepsin/protease type XIII digestion and LC-MS analysis. For pepsin/protease type XIII digestion, 5 µg of the samples in 125 µL control buffer (50 mM phosphate, 100 mM sodium chloride at pH 7.4) are denatured by adding 63 µL of 5 M guanidine hydrochloride (final pH is 2.5) and incubating the mixture for 3 min. Then, the mixture is subjected to on-column pepsin/protease type XIII digestion and the resultant peptides analyzed using an UPLC-MS system comprised of a Waters Acquity UPLC coupled to a Q Exactive™ Hybrid Quadrupole-Orbitrap Mass Spectrometer (Thermo). Raw MS data is processed using HDX WorkBench, software for the analysis of H/D exchange MS data. The deuterium levels are calculated using the average mass difference between the deuteriated peptide and its native form (to). Peptide identification is done through searching MS/MS data against the TIM-3 sequence with Mascot. The mass tolerance for the precursor and product ions is 20 ppm and 0.05 Da, respectively.

For X-ray crystallography, TIM-3 and the test antibody are expressed and purified using standard protocols. The TIM-3/test antibody complex is incubated overnight at 4° C., concentrated, and separated from the uncomplexed species using size-exclusion chromatography. The complex is crystallized by the vapor-diffusion method from various known test solutions for example solutions containing PEG3350, ammonium citrate and 2-(N-Morpholino)ethanesulfonic acid (MES).

Antibodies binding within Tim-3 residues 32-47 (WGKGACPVFECGNVVL) (SEQ ID NO: 261), 90-102 (RIQIPGIMNDEKF) (SEQ ID NO: 263) and/or 50-56 (DERDVNY) (SEQ ID NO: 262) may be generated by isolating antibodies binding TIM-3 using phage display libraries, selecting those antibodies that compete with the reference antibody TM3B105 (VH of SEQ ID NO: 146 and VL of SEQ ID NO: 156) or TM3B291 (VH of SEQ ID NO: 172 and VL of SEQ ID NO: 173) for binding to TIM-3 by 100%, and confirming the epitope of the generated antibodies by solving the crystal structure of the antibody/TIM-3 complex. Alternatively, mice, rats or rabbits may be immunized using peptides encompassing residues 32-47, 90-102 and/or 50-56 of TIM-3 and the generated antibodies may be evaluated for their binding within the recited region.

The invention also provides an antagonistic antibody specifically binding TIM-3 or an antigen-binding portion thereof comprising a heavy chain complementarity determining region 1 (HCDR1), a HCDR2 and a HCDR3 of SEQ ID NOs: 164, 165 and 166, respectively.

The invention also provides an antagonistic antibody specifically binding TIM-3 or an antigen-binding portion thereof comprising a light chain complementarity determining region 1 (LCDR1), LCDR2 and LCDR3 of SEQ ID NOs: 167, 168 and 169 respectively.

The invention also provides an antagonistic antibody specifically binding TIM-3 or an antigen-binding portion thereof comprising the HCDR1, the HCDR2 and the HCDR3 of SEQ ID NOs: 164, 165 and 166, respectively, and the LCDR1, the LCDR2 and the LCDR3 of SEQ ID NOs: 167, 168 and 169 respectively.

SEQ ID NOs: 164, 165, 166, 167, 168 and 169 represent the HCDR1, the HCDR2, the HCDR3, the LCDR1, the LCDR2 and the LCDR3 genus sequences of TIM-3 antagonists derived from phage display libraries. The genus sequences were generated based on structural models that resulted in the sequence alignments given in FIG. 13, FIG. 14, FIG. 15, FIG. 16, FIG. 17 and FIG. 18 and summarized herein.

SEQ ID NO: 164
$X_{17}YX_{18}MX_{19}$,
wherein
$X_{17}$ is N, S, G or D;
$X_{18}$ is W or A; and
$X_{19}$ is S or H.
SEQ ID NO: 165
$X_{20}IX_{21}X_{22}SGGSX_{23}YYADSVKG$,
wherein
$X_{20}$ is A or V;
$X_{21}$ is S or K;
$X_{22}$ is G or Y; and
$X_{23}$ is T or K.
SEQ ID NO: 166
$X_{24}X_{25}X_{26}X_{27}X_{28}X_{29}X_{30}X_{31}DY$,
wherein
$X_{24}$ is D, S, N, G or E;
$X_{25}$ is H, P, E, T or L;
$X_{26}$ is W, E, N or deleted;
$X_{27}$ is D, P or deleted;
$X_{28}$ is P, Y, D or deleted;
$X_{29}$ is N, A, D, G or deleted;
$X_{30}$ is F, P, R, W or V; and
$X_{31}$ is L or F.
SEQ ID NO: 167
$X_{32}X_{33}SQSVX_{34}X_{35}X_{36}X_{37}X_{38}X_{39}X_{40}X_{41}X_{42}LA$,
wherein
$X_{32}$ is R or K;
$X_{33}$ is A or S;
$X_{34}$ is S, N or L;
$X_{35}$ is S, A, N or deleted;
$X_{36}$ is S or deleted;
$X_{37}$ is S or deleted;
$X_{38}$ is N or deleted;
$X_{39}$ is N or deleted;
$X_{40}$ is K or deleted;
$X_{41}$ is S, D or N; and
$X_{42}$ is Y or T.
SEQ ID NO: 168
$X_{43}ASX_{44}RX_{45}X_{46}$,
wherein
$X_{43}$ is G, D, W or T;
$X_{44}$ is S, N or T;
$X_{45}$ is A or E; and
$X_{46}$ is T or S.
SEQ ID NO: 169
$QQX_{47}X_{48}X_{49}X_{50}PX_{51}T$ (SEQ ID NO: 169),
wherein
$X_{47}$ is Y, G or S;
$X_{48}$ is G or Y;
$X_{49}$ is S, H or T;
$X_{50}$ is S, A or T; and
$X_{51}$ is L, I or W.

The invention also provides an antagonistic antibody specifically binding TIM-3 or an antigen-binding portion thereof comprising the HCDR1, the HCDR2 and the HCDR3 contained within a heavy chain variable region (VH) of SEQ ID NOs: 145, 146, 147, 148 or 149, wherein the HCDR1, the HCDR2 and the HCDR3 are defined by Chothia, Kabat, or IMGT.

The invention also provides an antagonistic antibody specifically binding TIM-3 or an antigen-binding portion thereof comprising the LCDR1, the LCDR2 and the LCDR3 contained within a light chain variable region (VL) of SEQ ID NOs: 155, 156, 157 or 158, wherein the LCDR1, the LCDR2 and the LCDR3 are defined by Chothia, Kabat, or IMGT.

In some embodiments, the antagonistic antibody specifically binding TIM-3 or the antigen-binding portion thereof comprises
the HCDR1 of SEQ ID NOs: 90, 91, 92 or 93;
the HCDR2 of SEQ ID NOs: 99, 100 or 101; and
the HCDR3 of SEQ ID NOs: 107, 108, 109, 110 or 111.

In some embodiments, the antagonistic antibody specifically binding TIM-3 or the antigen-binding portion thereof of the invention comprises
the LCDR1 of SEQ ID NOs: 117, 118, 119 or 120;
the LCDR2 of SEQ ID NOs: 126, 127, 128 or 129; and
the LCDR3 of SEQ ID NOs: 135, 136, 137 or 139.

In some embodiments, the antagonistic antibody specifically binding TIM-3 or the antigen-binding portion thereof comprises
the HCDR1 of SEQ ID NOs: 90, 91, 92 or 93;
the HCDR2 of SEQ ID NOs: 99, 100 or 101;
the HCDR3 of SEQ ID NOs: 107, 108, 109, 110 or 111;
the LCDR1 of SEQ ID NOs: 117, 118, 119 or 120;
the LCDR2 of SEQ ID NOs: 126, 127, 128 or 129; or
the LCDR3 of SEQ ID NOs: 135, 136, 137 or 139.

In some embodiments, the antagonistic antibody specifically binding TIM-3 or the antigen-binding portion thereof comprises the HCDR1, the HCDR2 and the HCDR3 of
SEQ ID NOs: 90, 99 and 107, respectively;
SEQ ID NOs: 91, 99 and 108, respectively;
SEQ ID NOs: 91, 99 and 109, respectively;
SEQ ID NOs: 92, 100 and 110, respectively; or
SEQ ID NOs: 93, 101 and 111, respectively;

In some embodiments, the antagonistic antibody specifically binding TIM-3 or the antigen-binding portion thereof comprises the LCDR1, the LCDR2 and the LCDR3 of
SEQ ID NOs: 117, 126 and 135, respectively;
SEQ ID NOs: 118, 127 and 136, respectively;
SEQ ID NOs: 119, 128 and 137, respectively; or
SEQ ID NOs: 120, 129 and 139, respectively.

In some embodiments, the antagonistic antibody specifically binding TIM-3 or the antigen-binding portion thereof comprises the HCDR1, the HCDR2, the HCDR3, the LCDR1, the LCDR2 and the LCDR3 of
SEQ ID NOs: 90, 99, 107, 117, 126 and 135, respectively;
SEQ ID NOs: 91, 99, 108, 118, 127 and 136, respectively;
SEQ ID NOs: 91, 99, 109, 119, 128 and 137, respectively;
SEQ ID NOs: 92, 100, 110, 117, 126 and 135, respectively; or
SEQ ID NOs: 93, 101, 111, 120, 129 and 139, respectively.

The invention also provides an isolated antagonistic antibody specifically binding TIM-3 or an antigen-binding portion thereof, comprising the HCDR1, the HCDR2 and, the HCDR3 of SEQ ID NOs: 164, 165 and 108, respectively, and the LCDR1, the LCDR2 and the LCDR3 of SEQ ID NOs: 118, 168 and 169 respectively.

The invent ion also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 91, 99, 108, 118, 127 and 136, respectively.

In some embodiments, the antibody specifically binding TIM-3 or the antigen-binding portion thereof binds TIM-3 within TIM-3 residues 32-47 (WGKGACPVFECGNVVL) (SEQ ID NO: 261).

In some embodiments, the antibody specifically binding TIM-3 or the antigen-binding portion thereof binds TIM-3 within TIM-3 residues 32-47 (WGKGACPVFECGNVVL) (SEQ ID NO: 261) and residues 50-56 (DERDVNY) SEQ ID NO: 262.

In some embodiments, the antibody specifically binding TIM-3 or the antigen-binding portion thereof inhibits binding of TIM-3 to galectin-9.

In some embodiments, the antibody or the antigen-binding portion thereof comprises a heavy chain framework derived from IGHV3-23 (SEQ ID NO: 174) and a light chain framework derived from IGKV3-11 (SEQ ID NO: 171).

In some embodiments, the antibody or the antigen-binding portion thereof comprises the VH of SEQ ID NO: 146 and the VL of SEQ ID NO: 156.

In some embodiments, the VH and the VL are encoded by polynucleotide sequences of SEQ ID NOs: 204 and 205, respectively.

In some embodiments, the antibody or the antigen-binding portion thereof enhances activation of antigen specific CD4$^+$ or CD8$^+$ T cells, wherein activation of antigen-specific CD4$^+$ or CD8$^+$ T cells is assessed by measuring a statistically significant enhancement of CD137 surface expression on antigen specific CD4$^+$ or CD8$^+$ T cells according to methods described in Example 14.

In some embodiments, the antibody is an IgG1 isotype.

In some embodiments, the antibody is an IgG3 isotype.

In some embodiments, the antibody is an IgG4 isotype, optionally comprising a S228P substitution when compared to the wild type IgG4.

In some embodiments, the antibody is an IgG4/κ isotype, optionally comprising the S228P substitution when compared to the wild type IgG4.

In some embodiments, the antibody comprises the VH of SEQ ID NO: 146 and the VL of SEQ ID NO: 156 and is an IgG4 isotype, optionally comprising the S228P substitution when compared to the wild type IgG4.

In some embodiments, the antibody comprises the VH of SEQ ID NO: 146 and the VL of SEQ ID NO: 156 and is an IgG4κ isotype comprising the S228P substitution when compared to the wild type IgG4.

In some embodiments, the antibody is an IgG2 isotype, optionally comprising V234A, G237A, P238S, H268A, V309L, A330S and P331S substitutions when compared to the wild type IgG2.

In some embodiments, the antibody is an IgG2/x isotype, optionally comprising V234A, G237A, P238S, H268A, V309L, A330S and P331S substitutions when compared to the wild type IgG2.

In some embodiments, the antibody comprises the VH of SEQ ID NO: 146 and the VL of SEQ ID NO: 156 and is an IgG2/x isotype, optionally comprising V234A, G237A, P238S, H268A, V309L, A330S and P331S substitutions when compared to the wild type IgG2.

In some embodiments, the antibody comprises the VH of SEQ ID NO: 146 and the VL of SEQ ID NO: 156 and is an IgG2/x isotype comprising V234A, G237A, P238S, H268A, V309L, A330S and P331S substitutions when compared to the wild type IgG2.

In some embodiments, the antibody comprises the HC of SEQ ID NO: 78 and the LC of SEQ ID NO: 79.

In some embodiments, the antibody comprises the HC of SEQ ID NO: 240 and the LC of SEQ ID NO: 79.

SEQ ID NO: 78
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSP

YAPLDYWGQGTLVTVSSASTKGPSVFPLAPCSRSTSESTAALGCLVKDYF

-continued
PEPVTVSWNSGALTSGVHTFPAVLQSSGLYSLSSVVTVPSSNFGTQTYTC

NVDHKPSNTKVDKTVERKCCVECPPCPAPPAAASSVFLFPPKPKDTLMIS

RTPEVTCVVVDVSAEDPEVQFNWYVDGVEVHNAKTKPREEQFNSTFRVVS

VLTVLHQDWLNGKEYKCKVSNKGLPSSIEKTISKTKGQPREPQVYTLPPS

REEMTKNQVSLTCLVKGFYPSDIAVEWESNGQPENNYKTTPPMLDSDGSF

FLYSKLTVDKSRWQQGNVFSCSVMHEALHNHYTQKSLSLSPGK

SEQ ID NO: 79
EIVLTQSPATLSLSPGERATLSCRASQSVNDYLAWYQQKPGQAPRLLIYD

ASNRATGIPARFSGSGSGTDFTLTISSLEPEDFAVYYCQQGGHAPITFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO: 240
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSP

YAPLDYWGQGTLVTVSSASTKGPSVFPLAPCSRSTSESTAALGCLVKDYF

PEPVTVSWNSGALTSGVHTFPAVLQSSGLYSLSSVVTVTSSNFGTQTYTC

NVDHKPSNTKVDKTVERKCCVECPPCPAPPAAASSVFLFPPKPKDTLMIS

RTPEVTCVVVDVSAEDPEVQFNWYVDGVEVHNAKTKPREEQFNSTFRVVS

VLTVLHQDWLNGKEYKCKVSNKGLPSSIEKTISKTKGQPREPQVYTLPPS

REEMTKNQVSLTCLVKGFYPSDIAVEWESNGQPENNYKTTPPMLDSDGSF

FLYSKLTVDKSRWQQGNVFSCSVMHEALHNHYTQKSLSLSPGK

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The antibody is suitable for use in therapy, for example in treating a melanoma.

The antibody is suitable for use in therapy, for example in treating a lung cancer.

The antibody is suitable for use in therapy, for example in treating non-small cell lung cancer (NSCLC).

The antibody is suitable for use in therapy, for example in treating a squamous NSCLC.

The antibody is suitable for use in therapy, for example in treating a non-squamous NSCLC.

The antibody is suitable for use in therapy, for example in treating a lung adenocarcinoma.

The antibody is suitable for use in therapy, for example in treating a renal cell carcinoma (RCC).

The antibody is suitable for use in therapy, for example in treating a mesothelioma.

The antibody is suitable for use in therapy, for example in treating a nasopharyngeal carcinoma (NPC).

The antibody is suitable for use in therapy, for example in treating a colorectal cancer.

The antibody is suitable for use in therapy, for example in treating a prostate cancer.

The antibody is suitable for use in therapy, for example in treating a castration-resistant prostate cancer.

The antibody is suitable for use in therapy, for example in treating a stomach cancer.

The antibody is suitable for use in therapy, for example in treating an ovarian cancer.

The antibody is suitable for use in therapy, for example in treating a gastric cancer.

The antibody is suitable for use in therapy, for example in treating a liver cancer.

The antibody is suitable for use in therapy, for example in treating a pancreatic cancer.

The antibody is suitable for use in therapy, for example in treating a thyroid cancer.

The antibody is suitable for use in therapy, for example in treating a squamous cell carcinoma of the head and neck.

The antibody is suitable for use in therapy, for example in treating a carcinomas of the esophagus or gastrointestinal tract.

The antibody is suitable for use in therapy, for example in treating a breast cancer.

The antibody is suitable for use in therapy, for example in treating a fallopian tube cancer.

The antibody is suitable for use in therapy, for example in treating a brain cancer.

The antibody is suitable for use in therapy, for example in treating an urethral cancer.

The antibody is suitable for use in therapy, for example in treating an endometriosis.

The antibody is suitable for use in therapy, for example in treating a cervical cancer.

The antibody is suitable for use in therapy, for example in treating a metastatic lesion of the cancer.

The antibody is suitable for use in therapy, for example in treating a cancer, in combination with an antagonistic antibody that specifically binds PD-1.

The antibody is suitable for use in therapy, for example in treating a cancer, in combination with the antagonistic antibody that specifically binds PD-1 comprising the VH of SEQ ID NO: 48 and the VL of SEQ ID NO: 56.

The antibody is suitable for use in therapy, for example in treating a cancer, in combination with the antagonistic antibody that specifically binds PD-1 comprising the VH of SEQ ID NO: 47 and the VL of SEQ ID NO: 58.

The antibody is suitable for use in therapy, for example in treating a cancer, in combination with the antagonistic antibody that specifically binds PD-1 comprising the VH of SEQ ID NO: 45 and the VL of SEQ ID NO: 60.

The antibody is suitable for use in therapy, for example in treating a cancer, in combination with the antagonistic antibody that specifically binds PD-1 comprising the VH of SEQ ID NO: 64 and the VL of SEQ ID NO: 65.

The antibody is suitable for use in therapy, for example in treating cancer, such as a solid tumor, in combination with an antagonistic antibody specifically binding TIGIT (SEQ ID NO: 301).

The antibody is suitable for use in therapy, for example in treating cancer, such as a solid tumor, in combination with a FGFR inhibitor.

The antibody is suitable for use in therapy, for example in treating cancer, such as a solid tumor, in combination with a vaccine.

The antibody is suitable for use in therapy, for example in treating cancer, such as a solid tumor, in combination with an agonistic antibody specifically binding GITR (SEQ ID NO: 271).

The antibody is suitable for use in therapy, for example in treating cancer, such as a solid tumor, in combination with an agonistic antibody specifically binding CD137 (SEQ ID NO: 281).

The antibody is suitable for use in therapy, for example in treating cancer, such as a solid tumor, in combination with an agonistic antibody specifically binding OX-40 (SEQ ID NO: 279).

The antibody is suitable for use in therapy in a subject who is being treated or who has been treated with an antagonistic antibody specifically binding PD-1 comprising the VH of SEQ ID NO: 230 and the VL of SEQ ID NO: 231. (e.g. KEYTRUDA® (pembrolizumab)).

The antibody is suitable for use in therapy in a subject who is being treated or who has been treated with an antagonistic antibody specifically binding PD-1 comprising the VH of SEQ ID NO: 232 and the VL of SEQ ID NO: 233. (e.g. OPDIVO® (nivolumab)).

The antibody is suitable for use in therapy in a subject who is refractory to treatment with the antagonistic antibody specifically binding PD-1 comprising the VH of SEQ ID NO: 230 and the VL of SEQ ID NO: 231. (e.g. KEYTRUDA® (pembrolizumab)).

The antibody is suitable for use in therapy in a subject who is refractory to treatment with the antagonistic antibody specifically binding PD-1 comprising the VH of SEQ ID NO: 232 and the VL of SEQ ID NO: 233. (e.g. OPDIVO® (nivolumab)).

The antibody is suitable for use in therapy in a subject who has a relapsed tumor after treatment with the antagonistic antibody specifically binding PD-1 comprising the VH of SEQ ID NO: 230 and the VL of SEQ ID NO: 231. (e.g. KEYTRUDA® (pembrolizumab).

The antibody is suitable for use in therapy in a subject who has a relapsed tumor after treatment with the antagonistic antibody specifically binding PD-1 comprising the VH of SEQ ID NO: 232 and the VL of SEQ ID NO: 233. (e.g. OPDIVO® (nivolumab)).

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 97, 105, 115, 124, 133 and 143, respectively.

In some embodiments, the antibody or the antigen-binding portion thereof comprises a heavy chain framework derived from IGHV5-51 (SEQ ID NO: 179) and a light chain framework derived from IGKV1-39 (SEQ ID NO: 182).

In some embodiments, the antibody comprises the VH of SEQ ID NO: 172 and the VL of SEQ ID NO: 173.

In some embodiments, the VH and the VL are encoded by polynucleotide sequences of SEQ ID NOs: 206 and 207, respectively.

In some embodiments, the antibody or the antigen-binding portion thereof enhances activation of antigen specific CD4$^+$ or CD8$^+$ T cells, wherein the activation of antigen-specific CD4$^+$ or CD8$^+$ T cells is assessed by measuring a statistically significant enhancement of CD137 surface expression on antigen specific CD4$^+$ or CD8$^+$ T cells according to methods described in Example 14.

In some embodiments, the antibody specifically binding TIM-3 or the antigen-binding portion thereof binds TIM-3 within TIM-3 residues 90-102 (RIQIPGIMNDEKF) (SEQ ID NO: 263).

In some embodiments, the antibody specifically binding TIM-3 or the antigen-binding portion thereof binds TIM-3 within TIM-3 residues 90-102 (RIQIPGIMNDEKF) (SEQ ID NO: 263) and residues 50-56 (DERDVNY) SEQ ID NO: 262.

In some embodiments, the antibody specifically binding TIM-3 or the antigen-binding portion thereof inhibits binding of TIM-3 to galectin-9.

In some embodiments, the antibody is an IgG1 isotype.

In some embodiments, the antibody is an IgG3 isotype.

In some embodiments, the antibody is an IgG4 isotype, optionally comprising a S228P substitution when compared to the wild type IgG4.

In some embodiments, the antibody is an IgG4/κ isotype, optionally comprising the S228P substitution when compared to the wild type IgG4.

In some embodiments, the antibody comprises the VH of SEQ ID NO: 172 and the VL of SEQ ID NO: 173 and is an IgG4 isotype, optionally comprising the S228P substitution when compared to the wild type IgG4.

In some embodiments, the antibody comprises the VH of SEQ ID NO: 172 and the VL of SEQ ID NO: 173 and is an IgG4κ isotype comprising the S228P substitution when compared to the wild type IgG4.

In some embodiments, the antibody is an IgG2 isotype, optionally comprising V234A, G237A, P238S, H268A, V309L, A330S and P331S substitutions when compared to the wild type IgG2.

In some embodiments, the antibody is an IgG2/x isotype, optionally comprising V234A, G237A, P238S, H268A, V309L, A330S and P331S substitutions when compared to the wild type IgG2.

In some embodiments, the antibody comprises the VH of SEQ ID NO: 172 and the VL of SEQ ID NO: 173 and is an IgG2/x isotype, optionally comprising V234A, G237A, P238S, H268A, V309L, A330S and P331S substitutions when compared to the wild type IgG2.

In some embodiments, the antibody comprises the VH of SEQ ID NO: 172 and the VL of SEQ ID NO: 173 and is an IgG2/x isotype comprising V234A, G237A, P238S, H268A, V309L, A330S and P331S substitutions when compared to the wild type IgG2.

In some embodiments, the antibody comprises the HC of SEQ ID NO: 80 and the LC of SEQ ID NO: 81.

```
                                                    SEQ ID NO: 80
EVQLVQSGAEVKKPGESLKISCKGSGYSFTSYWMQWVRQMPGKGLEWMGA

IYPGDGDIRYTQNFKGQVTISADKSISTAYLQWSSLKASDTAMYYCARWE

KSTTVVQRNYFDYWGQGTTVTVSSASTKGPSVFPLAPCSRSTSESTAALG

CLVKDYFPEPVTVSWNSGALTSGVHTFPAVLQSSGLYSLSSVVTVPSSNF

GTQTYTCNVDHKPSNTKVDKTVERKCCVECPPCPAPPAAASSVFLFPPKP

KDTLMISRTPEVTCVVVDVSAEDPEVQFNWYVDGVEVHNAKTKPREEQFN

STFRVVSVLTVLHQDWLNGKEYKCKVSNKGLPSSIEKTISKTKGQPREPQ

VYTLPPSREEMTKNQVSLTCLVKGFYPSDIAVEWESNGQPENNYKTTPPM

LDSDGSFFLYSRLTVDKSRWQQGNVFSCSVMHEALHNHYTQKSLSLSPGK

SEQ IN NO: 81
DIQMTQSPSSLSASVGDRVTITCKASENVGTFVSWYQQKPGKAPKLLIYG

ASNRYTGVPSRFSGSGSGTDFTLTISSLQPEDFATYYCGQSYSYPTFGQG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC
```

In some embodiments, the antibody is a bispecific antibody, such as a bispecific PD-1/TIM-3 antibody.

The antibody is suitable for use in therapy, for example in treating a cancer.

The antibody is suitable for use in therapy, for example in treating a solid tumor.

The antibody is suitable for use in therapy, for example in treating a melanoma.

The antibody is suitable for use in therapy, for example in treating a lung cancer.

The antibody is suitable for use in therapy, for example in treating non-small cell lung cancer (NSCLC).

The antibody is suitable for use in therapy, for example in treating a squamous NSCLC.

The antibody is suitable for use in therapy, for example in treating a non-squamous NSCLC.

The antibody is suitable for use in therapy, for example in treating a lung adenocarcinoma.

The antibody is suitable for use in therapy, for example in treating a renal cell carcinoma (RCC).

The antibody is suitable for use in therapy, for example in treating a mesothelioma.

The antibody is suitable for use in therapy, for example in treating a nasopharyngeal carcinoma (NPC).

The antibody is suitable for use in therapy, for example in treating a colorectal cancer.

The antibody is suitable for use in therapy, for example in treating a prostate cancer.

The antibody is suitable for use in therapy, for example in treating a castration-resistant prostate cancer.

The antibody is suitable for use in therapy, for example in treating a stomach cancer.

The antibody is suitable for use in therapy, for example in treating an ovarian cancer.

The antibody is suitable for use in therapy, for example in treating a gastric cancer.

The antibody is suitable for use in therapy, for example in treating a liver cancer.

The antibody is suitable for use in therapy, for example in treating a pancreatic cancer.

The antibody is suitable for use in therapy, for example in treating a thyroid cancer.

The antibody is suitable for use in therapy, for example in treating a squamous cell carcinoma of the head and neck.

The antibody is suitable for use in therapy, for example in treating a carcinomas of the esophagus or gastrointestinal tract.

The antibody is suitable for use in therapy, for example in treating a breast cancer.

The antibody is suitable for use in therapy, for example in treating a fallopian tube cancer.

The antibody is suitable for use in therapy, for example in treating a brain cancer.

The antibody is suitable for use in therapy, for example in treating an urethral cancer.

The antibody is suitable for use in therapy, for example in treating an endometriosis.

The antibody is suitable for use in therapy, for example in treating a cervical cancer.

The antibody is suitable for use in therapy, for example in treating a metastatic lesion of the cancer.

The antibody is suitable for use in therapy, for example in treating a hematological malignancy.

The antibody is suitable for use in therapy, for example in treating an acute lymphoblastic leukemia (ALL).

The antibody is suitable for use in therapy, for example in treating a cancer, in combination with an antagonistic antibody that specifically binds PD-1.

The antibody is suitable for use in therapy, for example in treating a cancer, in combination with the antagonistic antibody that specifically binds PD-1 comprising the VH of SEQ ID NO: 48 and the VL of SEQ ID NO: 56.

The antibody is suitable for use in therapy, for example in treating a cancer, in combination with the antagonistic antibody that specifically binds PD-1 comprising the VH of SEQ ID NO: 47 and the VL of SEQ ID NO: 58.

The antibody is suitable for use in therapy, for example in treating a cancer, in combination with the antagonistic antibody that specifically binds PD-1 comprising the VH of SEQ ID NO: 45 and the VL of SEQ ID NO: 60.

The antibody is suitable for use in therapy, for example in treating a cancer, in combination with the antagonistic antibody that specifically binds PD-1 comprising the VH of SEQ ID NO: 65 and the VL of SEQ ID NO: 65.

The antibody is suitable for use in therapy, for example in treating cancer, such as a solid tumor, in combination with an antagonistic antibody specifically binding TIGIT (SEQ ID NO: 301).

The antibody is suitable for use in therapy, for example in treating cancer, such as a solid tumor, in combination with a FGFR inhibitor.

The antibody is suitable for use in therapy, for example in treating cancer, such as a solid tumor, in combination with a vaccine.

The antibody is suitable for use in therapy, for example in treating cancer, such as a solid tumor, in combination with an agonistic antibody specifically binding GITR (SEQ ID NO: 271).

The antibody is suitable for use in therapy, for example in treating cancer, such as a solid tumor, in combination with an agonistic antibody specifically binding CD137 (SEQ ID NO: 281).

The antibody is suitable for use in therapy, for example in treating cancer, such as a solid tumor, in combination with an agonistic antibody specifically binding OX-40 (SEQ ID NO: 279).

The antibody is suitable for use in therapy in a subject who is being treated or who has been treated with an antagonistic antibody specifically binding PD-1 comprising the VH of SEQ ID NO: 230 and the VL of SEQ ID NO: 231. (e.g. KEYTRUDA® (pembrolizumab)).

The antibody is suitable for use in therapy in a subject who is being treated or who has been treated with an antagonistic antibody specifically binding PD-1 comprising the VH of SEQ ID NO: 232 and the VL of SEQ ID NO: 233. (e.g. OPDIVO® (nivolumab)).

The antibody is suitable for use in therapy in a subject who is refractory to treatment with the antagonistic antibody specifically binding PD-1 comprising the VH of SEQ ID NO: 230 and the VL of SEQ ID NO: 231. (e.g. KEYTRUDA® (pembrolizumab)).

The antibody is suitable for use in therapy in a subject who is refractory to treatment with the antagonistic antibody specifically binding PD-1 comprising the VH of SEQ ID NO: 232 and the VL of SEQ ID NO: 233. (e.g. OPDIVO® (nivolumab)).

The antibody is suitable for use in therapy in a subject who has a relapsed tumor after treatment with the antagonistic antibody specifically binding PD-1 comprising the VH of SEQ ID NO: 230 and the VL of SEQ ID NO: 231. (e.g. KEYTRUDA® (pembrolizumab).

The antibody is suitable for use in therapy in a subject who has a relapsed tumor after treatment with the antagonistic antibody specifically binding PD-1 comprising the VH of SEQ ID NO: 232 and the VL of SEQ ID NO: 233. (e.g. OPDIVO® (nivolumab)).

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 90, 99, 107, 117, 126 and 135, respectively.

In some embodiments, the antibody or the antigen-binding portion thereof comprises a heavy chain framework derived from IGHV3-23 (SEQ ID NO: 174) and a light chain framework derived from IGKV3-20 (SEQ ID NO: 180).

In some embodiments, the antibody or the antigen-binding portion thereof comprises the VH of SEQ ID NO: 145 and the VL of SEQ ID NO: 155.

In some embodiments, the VH and the VL are encoded by polynucleotide sequences of SEQ ID NOs: 208 and 209, respectively.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 91, 99, 109, 119, 128 and 137, In some embodiments, the antibody or the antigen-binding portion thereof comprises a heavy chain framework derived from IGHV3-23 (SEQ ID NO: 174) and a light chain framework derived from IGKV4-1 (SEQ ID NO: 181).

In some embodiments, the antibody or the antigen-binding portion thereof comprises the VH of SEQ ID NO: 148 and the VL of SEQ ID NO: 157.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 92, 100, 110, 117, 126 and 135, respectively.

In some embodiments, the antibody or the antigen-binding portion thereof comprises a heavy chain framework derived from IGHV3-23 (SEQ ID NO: 174) and a light chain framework derived from IGKV3-20 (SEQ ID NO: 180).

In some embodiments, the antibody or the antigen-binding portion thereof comprises the VH of SEQ ID NO: 147 and the VL of SEQ ID NO: 155.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 93, 101, 111, 120, 129 and 139, respectively.

In some embodiments, the antibody or the antigen-binding portion thereof comprises a heavy chain framework derived from IGHV3-23 (SEQ ID NO: 174) and a light chain framework derived from IGKV3-20 (SEQ ID NO: 180).

In some embodiments, the antibody or the antigen-binding portion thereof comprises the VH of SEQ ID NO: 149 and the VL of SEQ ID NO: 158.

In some embodiments, the VH and the VL are encoded by polynucleotide sequences of SEQ ID NOs: 201 and 211, respectively.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 94, 102, 112, 121, 130 and 140, respectively.

In some embodiments, the antibody or the antigen-binding portion thereof comprises a heavy chain framework derived from IGHV1-02 (SEQ ID NO: 175) and a light chain framework derived from IGKV4-1 (SEQ ID NO: 181).

In some embodiments, the antibody or the antigen-binding portion thereof comprises the VH of SEQ ID NO: 150 and the VL of SEQ ID NO: 159.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 95, 103, 113, 122, 131 and 141, respectively.

In some embodiments, the antibody or the antigen-binding portion thereof comprises a heavy chain framework derived from IGHV4-30-4 (SEQ ID NO: 176) and a light chain framework derived from IGKV1-39 (SEQ ID NO: 182).

In some embodiments, the antibody or the antigen-binding portion thereof comprises the VH of SEQ ID NO: 151 and the VL of SEQ ID NO: 160.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 96, 104, 114, 123, 132 and 142, respectively.

In some embodiments, the antibody or the antigen-binding portion thereof comprises a heavy chain framework derived from IGHV1-03 (SEQ ID NO: 177) and a light chain framework derived from IGKV1-33 (SEQ ID NO: 183).

In some embodiments, the antibody or the antigen-binding portion thereof comprises the VH of SEQ ID NO: 152 and the VL of SEQ ID NO: 161.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 97, 105, 115, 124, 133 and 143, respectively.

In some embodiments, the antibody or the antigen-binding portion thereof comprises a heavy chain framework derived from IGHV1-03 (SEQ ID NO: 177) and a light chain framework derived from IGKV1-39 (SEQ ID NO: 182).

In some embodiments, the antibody or the antigen-binding portion thereof comprises the VH of SEQ ID NO: 153 and the VL of SEQ ID NO: 162.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 98, 106, 116, 125, 134 and 144, respectively.

In some embodiments, the antibody or the antigen-binding portion thereof comprises a heavy chain framework derived from IGHV2-26 (SEQ ID NO: 178) and a light chain framework derived from IGKV4-1 (SEQ ID NO: 181).

In some embodiments, the antibody or the antigen-binding portion thereof comprises the VH of SEQ ID NO: 154 and the VL of SEQ ID NO: 163.

In some embodiments, the antibody or the antigen-binding portion thereof enhances activation of antigen specific $CD4^+$ or $CD8^+$ T cells, wherein activation of antigen-specific $CD4^+$ or $CD8^+$ T cells is assessed by measuring a statistically significant enhancement of CD137 surface expression on antigen specific $CD4^+$ or $CD8^+$ T cells according to methods described in Example 14.

In some embodiments, the antibody is an IgG1 isotype.

In some embodiments, the antibody is an IgG3 isotype.

In some embodiments, the antibody is an IgG4 isotype, optionally comprising a S228P substitution when compared to the wild type IgG4.

In some embodiments, the antibody is an IgG2 isotype, optionally comprising V234A, G237A, P238S, H268A, V309L, A330S and P331S substitutions when compared to the wild type IgG2.

The VH, the VL, the HCDR and the LCDR sequences of exemplary antagonistic antibodies specifically binding TIM-3 of the invention are shown in Table 3.

Although the embodiments illustrated in the Examples comprise pairs of variable regions, one from a heavy chain and one from a light chain, a skilled artisan will recognize that alternative embodiments may comprise single heavy or light chain variable regions. The single variable region may be used to screen for variable domains capable of forming a two-domain specific antigen-binding fragment capable of, for example, binding to human TIM-3. The screening may be accomplished by phage display screening methods similarly as described herein.

In some embodiments, the antagonistic antibody specifically binding TIM-3 is a multispecific antibody.

In some embodiments, the antagonistic antibody specifically binding TIM-3 is a bispecific antibody.

In some embodiments, the bispecific or the multispecific antibody binds PD-1 (SEQ ID NO: 1), PD-L1 (SEQ ID NO: 5), PD-L2 (SEQ ID NO: 8), LAG-3 (SEQ ID NO: 293), CEACAM-1 (SEQ ID NO: 296), CEACAM-5 (SEQ ID NO: 307), NKG2D (SEQ ID NO: 282), or TIGIT (SEQ ID NO: 301). Bispecific and multispecific antibodies may be generated using methods described herein.

TABLE 3

| mAb name | HCDR1 | HCDR2 | HCDR3 | LCDR1 | LCDR2 | LCDR3 | VH | VL |
|---|---|---|---|---|---|---|---|---|
| TM3B103 | 90 | 99 | 107 | 117 | 126 | 135 | 145 | 155 |
| TM3B105 | 91 | 99 | 108 | 118 | 127 | 136 | 146 | 156 |
| TM3B109 | 91 | 99 | 109 | 119 | 128 | 137 | 148 | 157 |
| TM3B108 | 92 | 100 | 110 | 117 | 126 | 135 | 147 | 155 |
| TM3B113 | 93 | 101 | 111 | 120 | 129 | 139 | 149 | 158 |
| TM3B189 | 94 | 102 | 112 | 121 | 130 | 140 | 150 | 159 |
| TM3B190 | 95 | 103 | 113 | 122 | 131 | 141 | 151 | 160 |
| TM3B193 | 96 | 104 | 114 | 123 | 132 | 142 | 152 | 161 |
| TM3B195 | 97 | 105 | 115 | 124 | 133 | 143 | 153 | 162 |
| TM3B196 | 98 | 106 | 116 | 125 | 134 | 144 | 154 | 163 |
| TM3B291 | 97 | 105 | 115 | 124 | 133 | 143 | 172 | 173 |

Homologous Antibodies

Variants of the antagonistic antibodies specifically binding TIM-3 of the invention comprising VH or VL amino acid sequences shown in Table 3, Table 36 and Table 37 are within the scope of the invention. For example, variants may comprise one, two, three, four, five, six, seven, eight, nine, ten, eleven, twelve, thirteen, fourteen or fifteen amino acid substitutions in the VH and/or the VL as long as the homologous antibodies retain or have improved functional properties when compared to the parental antibodies. In some embodiments, the sequence identity may be about 90%, 91%, 92%, 93%, 94%, 95%, 96%, 97%, 98% or 99% to a VH or the VL amino acid sequence of the invention.

The invention also provides an antagonistic antibody specifically binding TIM-3 or an antigen-binding portion thereof, comprising the VH of SEQ ID NO: 145 and the VL of SEQ ID NO: 155, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding TIM-3 or an antigen-binding portion thereof, comprising the VH of SEQ ID NO: 146 and the VL of SEQ ID NO: 156, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding TIM-3 or an antigen-binding portion thereof, comprising the VH of SEQ ID NO: 148 and the VL of SEQ ID NO: 157, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding TIM-3 or an antigen-binding portion thereof, comprising the VH of SEQ ID NO: 147 and the VL of SEQ ID NO: 155, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding TIM-3 or an antigen-binding portion thereof, comprising the VH of SEQ ID NO: 149 and the VL of SEQ ID NO: 158, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding TIM-3 or an antigen-binding portion thereof, comprising the VH of SEQ ID NO: 150 and the VL of SEQ ID NO: 159, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding TIM-3 or an antigen-binding portion thereof, comprising the VH of SEQ ID NO: 151 and the VL of SEQ ID NO: 160, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding TIM-3 or an antigen-binding portion thereof, comprising the VH of SEQ ID NO: 152 and the VL of SEQ ID NO: 161, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding TIM-3 or an antigen-binding portion thereof, comprising the VH of SEQ ID NO: 153 and the VL of SEQ ID NO: 162, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding TIM-3 or an antigen-binding portion thereof, comprising the VH of SEQ ID NO: 154 and the VL of SEQ ID NO: 163, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding TIM-3 or an antigen-binding portion thereof, comprising the VH of SEQ ID NO: 172 and the VL of SEQ ID NO: 173, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an antagonistic antibody specifically binding TIM-3 or an antigen-binding portion thereof, comprising the VH having the amino acid sequence at least 90%, 91%, 92%, 93%, 94%, 95%, 96%, 97%, 98% or 99% identical to the VH of SEQ ID NOs: 145, 146, 147, 148, 149, 150, 151, 152, 153, 154 or 172. Optionally, any variation from the sequences of the SEQ ID NOs is not within the CDRs.

The invention also provides an antagonistic antibody specifically binding TIM-3 or an antigen-binding portion thereof, comprising the VL having the amino acid sequence at least 90%, 91%, 92%, 93%, 94%, 95%, 96%, 97%, 98% or 99% identical to the VL of SEQ IS NOs: 155, 156, 157, 158, 159, 160, 161, 162, 163 or 173. Optionally, any variation from the sequences of the SEQ ID NOs is not within the CDRs.

The invention also provides an antagonistic antibody specifically binding TIM-3 or an antigen-binding portion thereof, comprising the VH having the amino acid sequence at least 90%, 91%, 92%, 93%, 94%, 95%, 96%, 97%, 98% or 99% identical to the VH of SEQ ID NOs: 145, 146, 147, 148, 149, 150, 151, 152, 153, 154 or 172 and the VL having the amino acid sequence at least 90%, 91%, 92%, 93%, 94%, 95%, 96%, 97%, 98% or 99% identical to the VL of SEQ ID NOs: 155, 156, 157, 158, 159, 160, 161, 162, 163 or 173. Optionally, any variation from the sequences of the SEQ ID NOs is not within the CDRs.

The invention also provides an antagonistic antibody specifically binding TIM-3 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 145 and the VL of SEQ ID NO: 155. Optionally, any variation from the sequences of the SEQ ID NOs is not within the CDRs.

The invention also provides an antagonistic antibody specifically binding TIM-3 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO:

146 and the VL of SEQ ID NO: 156. Optionally, any variation from the sequences of the SEQ ID NOs is not within the CDRs.

The invention also provides an antagonistic antibody specifically binding TIM-3 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 148 and the VL of SEQ ID NO: 157. Optionally, any variation from the sequences of the SEQ ID NOs is not within the CDRs.

The invention also provides an antagonistic antibody specifically binding TIM-3 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 147 and the VL of SEQ ID NO: 155. Optionally, any variation from the sequences of the SEQ ID NOs is not within the CDRs.

The invention also provides an antagonistic antibody specifically binding TIM-3 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 149 and the VL of SEQ ID NO: 158. Optionally, any variation from the sequences of the SEQ ID NOs is not within the CDRs.

The invention also provides an antagonistic antibody specifically binding TIM-3 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 150 and the VL of SEQ ID NO: 159. Optionally, any variation from the sequences of the SEQ ID NOs is not within the CDRs.

The invention also provides an antagonistic antibody specifically binding TIM-3 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 151 and the VL of SEQ ID NO: 160. Optionally, any variation from the sequences of the SEQ ID NOs is not within the CDRs.

The invention also provides an antagonistic antibody specifically binding TIM-3 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 152 and the VL of SEQ ID NO: 161. Optionally, any variation from the sequences of the SEQ ID NOs is not within the CDRs.

The invention also provides an antagonistic antibody specifically binding TIM-3 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 153 and the VL of SEQ ID NO: 162. Optionally, any variation from the sequences of the SEQ ID NOs is not within the CDRs.

The invention also provides an antagonistic antibody specifically binding TIM-3 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 154 and the VL of SEQ ID NO: 163. Optionally, any variation from the sequences of the SEQ ID NOs is not within the CDRs.

The invention also provides an antagonistic antibody specifically binding TIM-3 or an antigen-binding portion thereof, comprising the VH and the VL having the amino acid sequences at least 90%, 91%, 92%, 93%, 94%, 95%, 96%, 97%, 98% or 99% identical to the VH of SEQ ID NO: 172 and the VL of SEQ ID NO: 173. Optionally, any variation from the sequences of the SEQ ID NOs is not within the CDRs.

The homologous antibodies of the invention described herein have substantially similar functionality when compared to the parental TIM-3 antibodies.

Antagonistic Antibodies Specifically Binding TIM-3 of the Invention with Conservative Modifications The invention also provides an antagonistic antibody specifically binding TIM-3 or an antigen-binding portion thereof, comprising the VH comprising the HCDR1, the HCDR2 and the HCDR3 sequences and the VL comprising the LCDR1, the LCDR2 and the LCDR3 sequences, wherein one or more of the CDR sequences comprise specified amino acid sequences based on the antibodies described herein (e.g., antibodies shown in Table 3, Table 36 or Table 37 or conservative modifications thereof, and wherein the antibodies retain the desired functional properties of the parental antagonistic antibodies specifically binding TIM-3 of the invention.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 90, 99, 107, 117, 126 and 135, respectively, and conservative modifications thereof.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 91, 99, 108, 118, 127 and 136, respectively, and conservative modifications thereof.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 91, 99, 109, 119, 128 and 137, respectively, and conservative modifications thereof.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 92, 100, 110, 117, 126 and 135, respectively, and conservative modifications thereof.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 93, 101, 111, 120, 129 and 139, respectively, and conservative modifications thereof.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 94, 102, 112, 121, 130 and 140, respectively, and conservative modifications thereof.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 95, 103, 113, 122, 131 and 141, respectively, and conservative modifications thereof.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 96, 104, 114, 123, 132 and 142, respectively, and conservative modifications thereof.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 97, 105, 115, 124, 133 and 143, respectively, and conservative modifications thereof.

The invention also provides an antagonistic antibody specifically binding TIM-3 or an antigen-binding portion thereof, comprising the HCDR1, the HCDR2, the HCDR3, the LCDR1, the LCDR2 and the LCDR3 of SEQ ID NOs: 98, 106, 116, 125, 134 and 144, respectively, and conservative modifications thereof.

"Conservative modification" refers to modifications as described herein.

Antagonistic Antibodies Specifically Binding TIM-3 of the Invention with Specific Framework Sequences The invention also provides an antagonistic antibody specifically binding TIM-3 or an antigen-binding portion thereof, comprising the VH and the VL derived from particular human germline immunoglobulin sequences.

The invention also provides an antagonistic antibody specifically binding TIM-3 or an antigen-binding portion thereof, comprising the VH framework derived from IGHV3-23 (SEQ ID NO: 174), IGHV1-02 (SEQ ID NO: 175), IGHV4-30-4 (SEQ ID NO: 176), IGHV1-03 (SEQ ID NO: 177), IGHV2-26 (SEQ ID NO: 178) or IGHV5-51 (SEQ ID NO: 179).

The invention also provides an antagonistic antibody specifically binding TIM-3 or an antigen-binding portion thereof, comprising the VL framework derived from IGKV3-20 (A27) (SEQ ID NO: 180), IGKV3-11 (L6) (SEQ ID NO: 171), IGKV4-1 (B3) (SEQ ID NO: 181), IGKV1-39 (O12) (SEQ ID NO: 182) or IGKV1-33 (O18) (SEQ ID NO: 183).

The invention also provides an antagonistic antibody specifically binding TIM-3 or an antigen-binding portion thereof, comprising the VH framework derived from IGHV3-23 (SEQ ID NO: 174) and the VL framework derived from IGKV3-20 (SEQ ID NO: 180).

The invention also provides an antagonistic antibody specifically binding TIM-3 or an antigen-binding portion thereof, comprising the VH framework derived from IGHV3-23 (SEQ ID NO: 174) and the VL framework derived from IGKV3-11 (SEQ ID NO: 171).

The invention also provides an antagonistic antibody specifically binding TIM-3 or an antigen-binding portion thereof, comprising the VH framework derived from IGHV3-23 (SEQ ID NO: 174) and the VL framework derived from IGKV4-1 (SEQ ID NO: 181).

The invention also provides an antagonistic antibody specifically binding TIM-3 or an antigen-binding portion thereof, comprising the VH framework derived from IGHV1-02 (SEQ ID NO: 175) and the VL framework derived from IGKV4-1 (SEQ ID NO: 181).

The invention also provides an antagonistic antibody specifically binding TIM-3 or an antigen-binding portion thereof, comprising the VH framework derived from IGHV4-30-4 (SEQ ID NO: 176) and the VL framework derived from IGKV1-39 (SEQ ID NO: 182).

The invention also provides an antagonistic antibody specifically binding TIM-3 or an antigen-binding portion thereof, comprising the VH framework derived from IGHV1-03 (SEQ ID NO: 177) and the VL framework derived from IGKV1-33 (SEQ ID NO: 183).

The invention also provides an antagonistic antibody specifically binding TIM-3 or an antigen-binding portion thereof, comprising the VH framework derived from IGHV1-03 (SEQ ID NO: 177) and the VL framework derived from IGKV1-39 (SEQ ID NO: 182).

The invention also provides an antagonistic antibody specifically binding TIM-3 or an antigen-binding portion thereof, comprising the VH framework derived from IGHV2-26 (SEQ ID NO: 178) and the VL framework derived from IGKV4-1 (SEQ ID NO: 181).

The invention also provides an antagonistic antibody specifically binding TIM-3 or an antigen-binding portion thereof, comprising the VH framework derived from IGHV5-51 (SEQ ID NO: 179) and the VL framework derived from IGKV1-39 (SEQ ID NO: 182).

The antibodies of the invention comprising heavy or light chain variable regions "derived from" a particular framework or germline sequence refer to antibodies obtained from a system that uses human germline immunoglobulin genes, such as from transgenic mice or from phage display libraries as discussed herein. An antibody that is "derived from" a particular framework or germline sequence may contain amino acid differences as compared to the sequence it was derived from, due to, for example, naturally-occurring somatic mutations or intentional substitutions.

Exemplary antagonistic antibodies specifically binding TIM-3 having certain VH and VL framework sequences are shown in Table 38.

Bispecific Anti-PD-1/TIM-3 Antibodies

The invention also provides antagonistic bispecific PD-1/TIM-3 antibodies.

The invention also provides an isolated antagonistic bispecific PD-1/TIM-3 antibody comprising a first domain specifically binding PD-1 and a second domain specifically binding TIM-3.

In some embodiments, the antagonistic bispecific PD-1/TIM-3 antibody of the invention enhances activation of antigen-specific CD4$^+$ or CD8$^+$ T cells.

In some embodiments, the antagonistic bispecific PD-1/TIM-3 antibody of the invention enhances activation of antigen-specific CD4$^+$ or CD8$^+$ T cells, wherein enhanced activation of antigen-specific CD4$^+$ or CD8$^+$ T cells is assessed by measuring a statistically significant increase of CD137 surface expression on antigen-specific CD4$^+$ or CD8$^+$ T cells.

In some embodiments, the antagonistic bispecific PD-1/TIM-3 antibody of the invention inhibits TIM-3 binding to galectin-9.

In some embodiments, the antagonistic bispecific PD-1/TIM-3 antibody of the invention
  binds human PD-1 with an equilibrium dissociation constant ($K_D$) of less than about 100 nM, wherein the $K_D$ is measured using ProteOn XPR36 system at +25° C.;
  binds human PD-1 with the $K_D$ of less than about 1 nM, wherein the $K_D$ is measured using ProteOn XPR36 system at +25° C.;
  binds cynomolgus PD-1 with the $K_D$ of less than about 100 nM, wherein the $K_D$ is measured using ProteOn XPR36 system at +25° C.; or
  binds cynomolgus PD-1 with the $K_D$ of less than about 1 nM;
  wherein the $K_D$ is measured using ProteOn XPR36 system at +25° C.

In some embodiments, the antagonistic bispecific PD-1/TIM-3 antibody of the invention enhances an activation of antigen-specific CD4+ or CD8+ T cells, wherein the activation of antigen-specific CD4+ or CD8+ T cells is assessed by measuring a statistically significant increase of CD137 surface expression on antigen-specific CD4+ or CD8+ T cells and binds human PD-1 with an equilibrium dissociation constant ($K_D$) of less than about 100 nM, wherein the $K_D$ is measured using ProteOn XPR36 system at +25° C.

In some embodiments, the antagonistic bispecific PD-1/TIM-3 antibody of the invention enhances the activation of antigen-specific CD4+ or CD8+ T cells, wherein the activation of antigen-specific CD4+ or CD8+ T cells is assessed by measuring a statistically significant increase of CD137 surface expression on antigen-specific CD4+ or CD8+ T cells, and binds human PD-1 with an equilibrium dissociation constant ($K_D$) of less than about 1 nM, wherein the $K_D$ is measured using ProteOn XPR36 system at +25° C.

In some embodiments, the antagonistic bispecific PD-1/TIM-3 antibody of the invention enhances the activation of antigen-specific CD4+ or CD8+ T cells, wherein the activation of antigen-specific CD4+ or CD8+ T cells is assessed by measuring a statistically significant increase of CD137 surface expression on antigen-specific CD4+ or CD8+ T cells and binds cynomolgus PD-1 with an equilibrium dissociation constant ($K_D$) of less than about 100 nM, wherein the $K_D$ is measured using ProteOn XPR36 system at +25° C.

In some embodiments, the antagonistic bispecific PD-1/TIM-3 antibody of the invention enhances the activation of antigen-specific CD4+ or CD8+ T cells, wherein the activation of antigen-specific CD4+ or CD8+ T cells is assessed by measuring a statistically significant increase of CD137 surface expression on antigen-specific CD4+ or CD8+ T cells, and binds cynomolgus PD-1 with an equilibrium dissociation constant ($K_D$) of less than about 1 nM, wherein the $K_D$ is measured using ProteOn XPR36 system at +25° C.

The antagonistic bispecific PD-1/TIM-3 antibodies of the invention described herein may be evaluated for their ability to enhance antigen specific CD4+ or CD8+ T cell activation, to inhibit TIM-3 binding to galectin-9, and binding kinetics to human or cynomolgus PD-1 or TIM-3 may be assessed using methods described herein.

For example, CD137 may be used as a marker for activation of antigen specific CD4+ or CD8+ T cells. CD137 surface expression may be measured on T cells cultured in the presence or in the absence of a test antibody, such as the bispecific PD-1/TIM-3 antibody, using anti-CD137 antibody and a secondary antibody conjugated for example to a fluorescent dye. The statistically significant difference in the obtained signal on T cells cultured in the presence or in the absence of the test antibody is evaluated.

In some embodiments, the antagonistic bispecific PD-1/TIM-3 antibody of the invention binds TIM-3 within TIM-3 residues 32-47 (WGKGACPVFECGNVVL) (SEQ ID NO: 261).

In some embodiments, the antagonistic bispecific PD-1/TIM-3 antibody of the invention binds TIM-3 within TIM-3 residues 32-47 (WGKGACPVFECGNVVL) (SEQ ID NO: 261) and residues 50-56 (DERDVNY) SEQ ID NO: 262.

In some embodiments, the antagonistic bispecific PD-1/TIM-3 antibody of the invention binds TIM-3 within TIM-3 residues 90-102 (RIQIPGIMNDEKF) (SEQ ID NO: 263).

In some embodiments, the antagonistic bispecific PD-1/TIM-3 antibody of the invention binds TIM-3 within TIM-3 residues 90-102 (RIQIPGIMNDEKF) (SEQ ID NO: 263) and residues 50-56 (DERDVNY) SEQ ID NO: 262.

In some embodiments, the first domain comprises a heavy chain complementarity determining region (HCDR) 1 a HCDR2 and a HCDR3 of SEQ ID NOs: 82, 83 and 84, respectively.

In some embodiments, the first domain comprises the HCDR1, the HCDR2 and the HCDR3 of SEQ ID NOs: 82, 83 and 85, respectively.

In some embodiments, the first domain comprises a light chain complementarity determining regions (LCDR) 1, a LCDR2 and a LCDR3 of SEQ ID NOs: 86, 87 and 88, respectively.

In some embodiments, the first domain comprises the HCDR1, the HCDR2 and the HCDR3 of SEQ ID NOs: 82, 83 and 84, respectively, and the LCDR1, the LCDR2 and the LCDR3 of SEQ ID NOs: 86, 87 and 88, respectively.

In some embodiments, the first domain comprises the HCDR1, the HCDR2 and the HCDR3 of SEQ ID NOs: 82, 83 and 85, respectively, and the LCDR1, the LCDR2 and the LCDR3 of SEQ ID NOs: 86, 87 and 88, respectively.

In some embodiments, the second domain comprises the HCDR1, the HCDR2 and the HCDR3 amino acid sequences of SEQ ID NOs: 164, 165 and 166, respectively.

In some embodiments, the second domain comprises the LCDR1, the LCDR2 and the LCDR3 amino acid sequences of SEQ ID NOs: 167, 168 and 169, respectively.

In some embodiments, the second domain comprises the HCDR1, the HCDR2 and the HCDR3 amino acid sequences of SEQ ID NOs: 164, 165 and 166, respectively, and the LCDR1, the LCDR2 and the LCDR3 amino acid sequences of SEQ ID NOs: 167, 168 and 169 respectively.

In some embodiments, the first domain comprises the HCDR1, the HCDR2, the HCDR3, the LCDR1, the LCDR2 and the LCDR3 of
SEQ ID NOs: 10, 13, 16, 20, 26 and 31, respectively;
SEQ ID NOs: 10, 13, 16, 21, 26 and 32, respectively;
SEQ ID NOs: 10, 14, 16, 22, 27 and 33, respectively;
SEQ ID NOs: 10, 14, 16, 22, 26 and 34, respectively;
SEQ ID NOs: 10, 14, 16, 23, 28 and 35, respectively;
SEQ ID NOs: 10, 13, 17, 20, 26 and 31, respectively;
SEQ ID NOs: 10, 13, 17, 20, 26 and 36, respectively;
SEQ ID NOs: 10, 13, 17, 21, 26 and 32, respectively;
SEQ ID NOs: 10, 13, 17, 21, 27 and 37, respectively;
SEQ ID NOs: 10, 13, 17, 23, 26 and 32, respectively;
SEQ ID NOs: 10, 13, 17, 22, 26 and 32, respectively;
SEQ ID NOs: 10, 13, 18, 20, 26 and 31, respectively;
SEQ ID NOs: 11, 15, 18, 20, 26 and 31, respectively;
SEQ ID NOs: 10, 13, 19, 20, 26 and 31, respectively;
SEQ ID NOs: 12, 13, 19, 20, 26 and 31, respectively;
SEQ ID NOs: 10, 14, 17, 23, 28 and 35, respectively;
SEQ ID NOs: 10, 14, 17, 22, 26 and 34, respectively;
SEQ ID NOs: 10, 14, 17, 23, 26 and 32, respectively;
SEQ ID NOs: 12, 13, 19, 24, 26 and 38, respectively;
SEQ ID NOs: 12, 13, 19, 20, 29 and 39, respectively;
SEQ ID NOs: 11, 15, 18, 20, 30 and 32, respectively;
SEQ ID NOs: 11, 15, 18, 25, 26 and 40, respectively;
SEQ ID NOs: 11, 15, 18, 24, 26 and 32, respectively; or
SEQ ID NOs: 66, 67, 68, 69, 70 and 71, respectively.

In some embodiments, the second domain comprises the HCDR1, the HCDR2, the HCDR3, the LCDR1, the LCDR2 and the LCDR3 of
SEQ ID NOs: 90, 99, 107, 117, 126 and 135, respectively;
SEQ ID NOs: 91, 99, 108, 118, 127 and 136, respectively;
SEQ ID NOs: 91, 99, 109, 119, 128 and 137, respectively;
SEQ ID NOs: 92, 100, 110, 117, 126 and 135, respectively;
SEQ ID NOs: 93, 101, 111, 120, 129 and 139, respectively;

SEQ ID NOs: 94, 102, 112, 121, 130 and 140, respectively;

SEQ ID NOs: 95, 103, 113, 122, 131 and 141, respectively;

SEQ ID NOs: 96, 104, 114, 123, 132 and 142, respectively;

SEQ ID NOs: 97, 105, 115, 124, 133 and 143, respectively; or

SEQ ID NOs: 98, 106, 116, 125, 134 and 144, respectively.

In some embodiments, the first domain comprises the VH of SEQ ID NOs: 41, 42, 43, 44, 45, 46, 47, 48, 63 or 64, the VH optionally having one, two, three, four, five, six, seven, eight, nine, ten, eleven, twelve, thirteen, fourteen or fifteen conservative amino acid substitutions. Optionally, any substitutions are not within the CDRs.

In some embodiments, the first domain comprises the VL of SEQ ID NOs: 49, 50, 51, 52, 53, 54, 55, 56, 57, 58, 59, 60, 61, 62 or 65, the VL optionally having one, two, three, four, five, six, seven, eight, nine, ten, eleven, twelve, thirteen, fourteen or fifteen conservative amino acid substitutions. Optionally, any substitutions are not within the CDRs.

In some embodiments, the first domain comprises the VH of SEQ ID NOs: 41, 42, 43, 44, 45, 46, 47, 48, 63 or 64 and the VL of SEQ ID NOs: 49, 50, 51, 52, 53, 54, 55, 56, 57, 58, 59, 60, 61, 62 and 65, the VH, the VL, or the VH and the VL optionally having one, two, three, four, five, six, seven, eight, nine, ten, eleven, twelve, thirteen, fourteen or fifteen conservative amino acid substitutions. Optionally, any substitutions are not within the CDRs.

In some embodiments, the second domain comprises the VH of SEQ ID NOs: 145, 146, 147, 148, 149, 150, 151, 152, 153, 154 or 172, the VH optionally having one, two, three, four, five, six, seven, eight, nine, ten, eleven, twelve, thirteen, fourteen or fifteen conservative amino acid substitutions. Optionally, any substitutions are not within the CDRs.

In some embodiments, the second domain comprises the VL of SEQ IS NOs: 155, 156, 157, 158, 159, 160, 161, 162, 163 or 173, the VL optionally having one, two, three, four, five, six, seven, eight, nine, ten, eleven, twelve, thirteen, fourteen or fifteen conservative amino acid substitutions. Optionally, any substitutions are not within the CDRs.

In some embodiments, the second domain comprises the VH of SEQ ID NOs: 145, 146, 147, 148, 149, 150, 151, 152, 153, 154 or 172 and the VL of SEQ ID NOs: 155, 156, 157, 158, 159, 160, 161, 162, 163 or 173, the VH and the VL optionally having one, two, three, four, five, six, seven, eight, nine, ten, eleven, twelve, thirteen, fourteen or fifteen conservative amino acid substitutions. Optionally, any substitutions are not within the CDRs.

In some embodiments, the first domain comprises the VH of SEQ ID NO: 41 and the VL of SEQ ID NO: 49.

In some embodiments, the first domain comprises the VH of SEQ ID NO: 41 and the VL of SEQ ID NO: 50.

In some embodiments, the first domain comprises the VH of SEQ ID NO: 42 and the VL of SEQ ID NO: 51.

In some embodiments, the first domain comprises the VH of SEQ ID NO: 42 and the VL of SEQ ID NO: 52.

In some embodiments, the first domain comprises the VH of SEQ ID NO: 42 and the VL of SEQ ID NO: 53.

In some embodiments, the first domain comprises the VH of SEQ ID NO: 43 and the VL of SEQ ID NO: 49.

In some embodiments, the first domain comprises the VH of SEQ ID NO: 43 and the VL of SEQ ID NO: 54.

In some embodiments, the first domain comprises the VH of SEQ ID NO: 43 and the VL of SEQ ID NO: 50.

In some embodiments, the first domain comprises the VH of SEQ ID NO: 43 and the VL of SEQ ID NO: 55.

In some embodiments, the first domain comprises the VH of SEQ ID NO: 43 and the VL of SEQ ID NO: 56.

In some embodiments, the first domain comprises the VH of SEQ ID NO: 43 and the VL of SEQ ID NO: 57.

In some embodiments, the first domain comprises the VH of SEQ ID NO: 44 and the VL of SEQ ID NO: 49.

In some embodiments, the first domain comprises the VH of SEQ ID NO: 45 and the VL of SEQ ID NO: 49.

In some embodiments, the first domain comprises the VH of SEQ ID NO: 46 and the VL of SEQ ID NO: 49.

In some embodiments, the first domain comprises the VH of SEQ ID NO: 47 and the VL of SEQ ID NO: 49.

In some embodiments, the first domain comprises the VH of SEQ ID NO: 48 and the VL of SEQ ID NO: 53.

In some embodiments, the first domain comprises the VH of SEQ ID NO: 48 and the VL of SEQ ID NO: 52.

In some embodiments, the first domain comprises the VH of SEQ ID NO: 48 and the VL of SEQ ID NO: 56.

In some embodiments, the first domain comprises the VH of SEQ ID NO: 47 and the VL of SEQ ID NO: 58.

In some embodiments, the first domain comprises the VH of SEQ ID NO: 47 and the VL of SEQ ID NO: 59.

In some embodiments, the first domain comprises the VH of SEQ ID NO: 45 and the VL of SEQ ID NO: 60.

In some embodiments, the first domain comprises the VH of SEQ ID NO: 45 and the VL of SEQ ID NO: 61.

In some embodiments, the first domain comprises the VH of SEQ ID NO: 45 and the VL of SEQ ID NO: 62.

In some embodiments, the first domain comprises the VH of SEQ ID NO: 63 and the VL of SEQ ID NO: 65.

In some embodiments, the first domain comprises the VH of SEQ ID NO: 64 and the VL of SEQ ID NO: 65.

In some embodiments, the second domain comprises the VH of SEQ ID NO: 145 and the VL of SEQ ID NO: 155.

In some embodiments, the second domain comprises the VH of SEQ ID NO: 146 and the VL of SEQ ID NO: 156.

In some embodiments, the second domain comprises the VH of SEQ ID NO: 148 and the VL of SEQ ID NO: 157.

In some embodiments, the second domain comprises the VH of SEQ ID NO: 147 and the VL of SEQ ID NO: 155.

In some embodiments, the second domain comprises the VH of SEQ ID NO: 149 and the VL of SEQ ID NO: 158.

In some embodiments, the second domain comprises the VH of SEQ ID NO: 150 and the VL of SEQ ID NO: 159.

In some embodiments, the second domain comprises the VH of SEQ ID NO: 151 and the VL of SEQ ID NO: 160.

In some embodiments, the second domain comprises the VH of SEQ ID NO: 152 and the VL of SEQ ID NO: 161.

In some embodiments, the second domain comprises the VH of SEQ ID NO: 153 and the VL of SEQ ID NO: 162.

In some embodiments, the second domain comprises the VH of SEQ ID NO: 154 and the VL of SEQ ID NO: 163.

In some embodiments, the second domain comprises the VH of SEQ ID NO: 172 and the VL of SEQ ID NO: 173.

The invention also provides an isolated antagonistic bispecific PD-1/TIM-3 antibody comprising a first domain specifically binding PD-1 and a second domain specifically binding TIM-3, wherein the first domain comprises the HCDR1, the HCDR2, the HCDR3, the LCDR1, the LCDR2 and the LCDR3 of SEQ ID NOs: 10, 14, 17, 23, 26 and 32, respectively, and the second domain comprises the HCDR1, the HCDR2, the HCDR3, the LCDR1, the LCDR2 and the LCDR3 of SEQ ID NOs: 91, 99, 108, 118, 127 and 136, respectively.

In some embodiments, the antagonistic bispecific PD-1/TIM-3 antibody binds TIM-3 within TIM-3 residues 32-47 (WGKGACPVFECGNVVL) (SEQ ID NO: 261).

In some embodiments, the antagonistic bispecific PD-1/TIM-3 antibody binds TIM-3 within TIM-3 residues 32-47 (WGKGACPVFECGNVVL) (SEQ ID NO: 261) and residues 50-56 (DERDVNY) SEQ ID NO: 262.

In some embodiments, the antagonistic bispecific PD-1/TIM-3 antibody inhibits TIM-3 binding to galectin-9.

In some embodiments, the first domain comprises the VH of SEQ ID NO: 48 and the VL of SEQ ID NO: 56 and the second domain comprises the VH of SEQ ID NO: 146 and the VL of SEQ ID NO: 156.

In some embodiments, the antibody is an IgG1 isotype.

In some embodiments, the antibody is an IgG2 isotype.

In some embodiments, the antibody is an IgG2 isotype comprising a F405L and/or a K409R substitution.

In some embodiments, the antibody is an IgG2 isotype, optionally comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype, optionally comprising a S228P substitution when compared to the wild type IgG4.

In some embodiments, the antibody is an IgG4 isotype comprising a F405L and a K409R substitution.

In some embodiments, the antibody is an IgG4 isotype comprising a heavy chain substitution S228P when compared to the wild type IgG4.

In some embodiments, the isolated antagonistic bispecific PD-1/TIM-3 antibody comprises a first heavy chain (HC1) a first light chain (LC1), a second heavy chain (HC2) and a second light chain (LC2) of SEQ ID NOs: 241, 188, 245 or 194, respectively.

In some embodiments, the isolated antagonistic bispecific PD-1/TIM-3 antibody comprises the HC1, the LC1, the HC2 and the LC2 of SEQ ID NOs: 186, 188, 191 or 194, respectively.

In some embodiments, the isolated antagonistic bispecific PD-1/TIM-3 antibody comprises the HC1, the LC1, the HC2 and the LC2 of SEQ ID NOs: 186, 188, 248 or 194, respectively.

In some embodiments, the isolated antagonistic bispecific PD-1/TIM-3 antibody comprises the HC1, the LC1, the HC2 and the LC2 of SEQ ID NOs: 243, 188, 246 or 194, respectively.

The antibody is suitable for use in therapy, for example in treating a cancer.

The antibody is suitable for use in therapy, for example in treating a solid tumor.

The antibody is suitable for use in therapy, for example in treating a melanoma.

The antibody is suitable for use in therapy, for example in treating a lung cancer.

The antibody is suitable for use in therapy, for example in treating a non-small cell lung cancer (NSCLC).

The antibody is suitable for use in therapy, for example in treating a squamous NSCLC.

The antibody is suitable for use in therapy, for example in treating a non-squamous NSCLC.

The antibody is suitable for use in therapy, for example in treating a lung adenocarcinoma.

The antibody is suitable for use in therapy, for example in treating a renal cell carcinoma (RCC).

The antibody is suitable for use in therapy, for example in treating a mesothelioma.

The antibody is suitable for use in therapy, for example in treating a nasopharyngeal carcinoma (NPC).

The antibody is suitable for use in therapy, for example in treating a colorectal cancer.

The antibody is suitable for use in therapy, for example in treating a prostate cancer.

The antibody is suitable for use in therapy, for example in treating a castration-resistant prostate cancer.

The antibody is suitable for use in therapy, for example in treating a stomach cancer.

The antibody is suitable for use in therapy, for example in treating an ovarian cancer.

The antibody is suitable for use in therapy, for example in treating a gastric cancer.

The antibody is suitable for use in therapy, for example in treating a liver cancer.

The antibody is suitable for use in therapy, for example in treating pancreatic cancer.

The antibody is suitable for use in therapy, for example in treating a thyroid cancer.

The antibody is suitable for use in therapy, for example in treating a squamous cell carcinoma of the head and neck.

The antibody is suitable for use in therapy, for example in treating a carcinomas of the esophagus or gastrointestinal tract.

The antibody is suitable for use in therapy, for example in treating a breast cancer.

The antibody is suitable for use in therapy, for example in treating a fallopian tube cancer.

The antibody is suitable for use in therapy, for example in treating a brain cancer.

The antibody is suitable for use in therapy, for example in treating an urethral cancer.

The antibody is suitable for use in therapy, for example in treating an endometriosis.

The antibody is suitable for use in therapy, for example in treating a cervical cancer.

The antibody is suitable for use in therapy, for example in treating a metastatic lesion of the cancer.

The antibody is suitable for use in therapy in a subject who is being treated or who has been treated with anti-PD-1 antibody comprising the VH of SEQ ID NO: 230 and the VL of SEQ ID NO: 231. (e.g. KEYTRUDA® (pembrolizumab)).

The antibody is suitable for use in therapy in a subject who is being treated or who has been treated with anti-PD-1 antibody comprising the VH of SEQ ID NO: 232 and the VL of SEQ ID NO: 233. (e.g. OPDIVO® (nivolumab)).

The antibody is suitable for use in therapy in a subject who is refractory to treatment with the anti-PD-1 antibody comprising the VH of SEQ ID NO: 230 and the VL of SEQ ID NO: 231. (e.g. KEYTRUDA® (pembrolizumab)).

The antibody is suitable for use in therapy in a subject who is refractory to treatment with the anti-PD-1 antibody comprising the VH of SEQ ID NO: 232 and the VL of SEQ ID NO: 233. (e.g. OPDIVO® (nivolumab)).

The antibody is suitable for use in therapy in a subject who has a relapsed tumor after treatment with the anti-PD-1 antibody comprising the VH of SEQ ID NO: 230 and the VL of SEQ ID NO: 231. (e.g. KEYTRUDA® (pembrolizumab).

The antibody is suitable for use in therapy in a subject who has a relapsed tumor after treatment with the anti-PD-1 antibody comprising the VH of SEQ ID NO: 232 and the VL of SEQ ID NO: 233. (e.g. OPDIVO® (nivolumab)).

The invention also provides an isolated antagonistic bispecific PD-1/TIM-3 antibody comprising a first domain specifically binding PD-1 and a second domain specifically binding TIM-3, wherein the first domain comprises the HCDR1, the HCDR2, the HCDR3, the LCDR1, the LCDR2 and the LCDR3 of SEQ ID NOs: 66, 67, 68, 69, 70 and 71, respectively, and the second domain comprises the HCDR1, the HCDR2, the HCDR3, the LCDR1, the LCDR2 and the LCDR3 of SEQ ID NOs 97, 105, 115, 124, 133 and 143, respectively.

In some embodiments, the antagonistic bispecific PD-1/TIM-3 antibody binds TIM-3 within TIM-3 residues 90-102 (RIQIPGIMNDEKF) (SEQ ID NO: 263).

In some embodiments, the bispecific PD-1/TIM-3 antibody binds TIM-3 within TIM-3 residues 90-102 (RIQIPGIMNDEKF) (SEQ ID NO: 263) and residues 50-56 (DERDVNY) SEQ ID NO: 262.

In some embodiments, the bispecific PD-1/TIM-3 antibody inhibits binding of TIM-3 to galectin-9.

In some embodiments, the first domain comprises the VH of SEQ ID NO: 64 and the VL of SEQ ID NO: 65 and the second domain comprises the VH of SEQ ID NO: 153 and the VL of SEQ ID NO: 162.

In some embodiments, the antibody is an IgG1 isotype.

In some embodiments, the antibody is an IgG2 isotype.

In some embodiments, the antibody is an IgG2 isotype comprising a F405L and/or a K409R substitution.

In some embodiments, the antibody is an IgG2 isotype, optionally comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype, optionally comprising a S228P substitution when compared to the wild type IgG4.

In some embodiments, the antibody is an IgG4 isotype comprising a F405L and a K409R substitution.

In some embodiments, the antibody is an IgG4 isotype comprising a heavy chain substitution S228P when compared to the wild type IgG4.

In some embodiments, the isolated bispecific PD-1/TIM-3 antibody comprises the HC1, the LC1, the HC2 and the LC2 of SEQ ID NOs: 187, 189, 190 and 193, respectively.

The invention also provides an isolated antagonistic bispecific PD-1/TIM-3 antibody comprising a first domain specifically binding PD-1 and a second domain specifically binding TIM-3, wherein the first domain comprises the HCDR1, the HCDR2, the HCDR3, the LCDR1, the LCDR2 and the LCDR3 of SEQ ID NOs: 66, 67, 68, 69, 70 and 71, respectively, and the second domain comprises the HCDR1, the HCDR2, the HCDR3, the LCDR1, the LCDR2 and the LCDR3 of SEQ ID NOs: 91, 99, 108, 118, 127 and 136, respectively.

In some embodiments, the first domain comprises the VH of SEQ ID NO: 64 and the VL of SEQ ID NO: 65 and the second domain comprises the VH of SEQ ID NO: 146 and the VL of SEQ ID NO: 156.

In some embodiments, the antibody is an IgG1 isotype.

In some embodiments, the antibody is an IgG2 isotype.

In some embodiments, the antibody is an IgG2 isotype comprising a F405L and/or a K409R substitution.

In some embodiments, the antibody is an IgG2 isotype, optionally comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype, optionally comprising a S228P substitution when compared to the wild type IgG4.

In some embodiments, the antibody is an IgG4 isotype comprising a F405L and a K409R substitution.

In some embodiments, the antibody is an IgG4 isotype comprising a heavy chain substitution S228P when compared to the wild type IgG4.

In some embodiments, the isolated antagonistic bispecific PD-1/TIM-3 antibody comprises the HC1, the LC1, the HC2 and the LC2 of SEQ ID NOs: 187, 189, 191 and 194, respectively.

In some embodiments, the isolated bispecific PD-1/TIM-3 antibody comprises the HC1, the LC1, the HC2 and the LC2 of SEQ ID NOs: 242, 189, 246 and 194, respectively.

The invention also provides an isolated antagonistic bispecific PD-1/TIM-3 antibody comprising a first domain specifically binding PD-1 and a second domain specifically binding TIM-3, wherein the first domain comprises the HCDR1, the HCDR2, the HCDR3, the LCDR1, the LCDR2 and the LCDR3 of SEQ ID NOs: 10, 14, 17, 23, 26 and 32, respectively, and the second domain comprises the HCDR1, the HCDR2, the HCDR3, the LCDR1, the LCDR2 and the LCDR3 of SEQ ID NOs: 97, 105, 115, 124, 133 and 143, respectively.

In some embodiments, the first domain comprises the VH of SEQ ID NO: 48 and the VL of SEQ ID NO: 56 and the second domain comprises the VH of SEQ ID NO: 172 and the VL of SEQ ID NO: 173.

In some embodiments, the antibody is an IgG1 isotype.

In some embodiments, the antibody is an IgG2 isotype.

In some embodiments, the antibody is an IgG2 isotype comprising a F405L and/or a K409R substitution.

In some embodiments, the antibody is an IgG2 isotype, optionally comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype, optionally comprising a S228P substitution when compared to the wild type IgG4.

In some embodiments, the antibody is an IgG4 isotype comprising a F405L and a K409R substitution.

In some embodiments, the antibody is an IgG4 isotype comprising a heavy chain substitution S228P when compared to the wild type IgG4.

In some embodiments, the isolated antagonistic bispecific PD-1/TIM-3 antibody comprises the HC1, the LC1, the HC2 and the LC2 of SEQ ID NOs: 186, 188, 192 and 195, respectively.

In some embodiments, the isolated antagonistic bispecific PD-1/TIM-3 antibody comprises the HC1, the LC1, the HC2 and the LC2 of SEQ ID NOs: 241, 188, 244 and 195, respectively.

In some embodiments, the isolated antagonistic bispecific PD-1/TIM-3 antibody comprises the HC1, the LC1, the HC2 and the LC2 of SEQ ID NOs: 243, 188, 247 and 195, respectively.

In some embodiments, the antibody enhances activation of antigen specific $CD4^+$ or $CD8^+$ T cells, wherein activation of antigen-specific $CD4^+$ or $CD8^+$ T cells is assessed by measuring a statistically significant enhancement of CD137 surface expression on antigen specific $CD4^+$ or $CD8^+$ T cells according to methods described in Example 14.

The invention also provides an isolated antagonistic bispecific PD-1/TIM-3 antibody comprising a first domain specifically binding PD-1 and a second domain specifically binding TIM-3, wherein the first domain comprises the HCDR1, the HCDR2, the HCDR3, the LCDR1, the LCDR2 and the LCDR3 of SEQ ID NOs: 10, 14, 17, 23, 26 and 32, respectively, and the second domain comprises the HCDR1, the HCDR2, the HCDR3, the LCDR1, the LCDR2 and the LCDR3 of SEQ ID NOs: 97, 105, 115, 124, 133 and 143, respectively.

In some embodiments, the first domain comprises the VH of SEQ ID NO: 48 and the VL of SEQ ID NO: 56 and the second domain comprises the VH of SEQ ID NO: 153 and the VL of SEQ ID NO: 156.

In some embodiments, the antibody is an IgG1 isotype.

In some embodiments, the antibody is an IgG2 isotype.

In some embodiments, the antibody is an IgG2 isotype comprising a F405L and/or a K409R substitution.

In some embodiments, the antibody is an IgG2 isotype, optionally comprising V234A, G237A, P238S, H268A, V309L, A330S and P331S substitutions when compared to the wild type IgG2.

In some embodiments, the antibody is an IgG3 isotype.

In some embodiments, the antibody is an IgG4 isotype, optionally comprising a S228P substitution when compared to the wild type IgG4.

In some embodiments, the antibody is an IgG4 isotype comprising a F405L and a K409R substitution.

In some embodiments, the antibody is an IgG4 isotype comprising a heavy chain substitution S228P when compared to the wild type IgG4.

In some embodiments, the isolated bispecific PD-1/TIM-3 antibody comprises the HC1, the LC1, the HC2 and the LC2 of SEQ ID NOs: 186, 188, 190 and 193, respectively.

Exemplary antagonistic bispecific PD-1/TIM-3 antibodies of the invention having certain VH, VL, HCDR and LCDR sequences as shown in Table 4 and Table 5.

TABLE 4

PD-1 binding arm SEQ ID NOs:

| mAb | VH | VL | HCDRs | | | LCDRs | | |
|---|---|---|---|---|---|---|---|---|
| | | | 1 | 2 | 3 | 1 | 2 | 3 |
| PTBB14 | 48 | 56 | 10 | 14 | 17 | 23 | 26 | 32 |
| PTBB15 | 48 | 56 | 10 | 14 | 17 | 23 | 26 | 32 |
| PTBB16 | 64 | 65 | 66 | 67 | 68 | 69 | 70 | 71 |
| PTBB17 | 64 | 65 | 66 | 67 | 68 | 69 | 70 | 71 |
| PTBB24 | 48 | 56 | 10 | 14 | 17 | 23 | 26 | 32 |
| PTBB30 | 48 | 56 | 10 | 14 | 17 | 23 | 26 | 32 |
| PTBB27 | 48 | 56 | 10 | 14 | 17 | 23 | 26 | 32 |
| PTBB28 | 48 | 56 | 10 | 14 | 17 | 23 | 26 | 32 |
| PTBB18 | 64 | 65 | 66 | 67 | 68 | 69 | 70 | 71 |
| PTBB20 | 48 | 56 | 10 | 14 | 17 | 23 | 26 | 32 |
| PTBB21 | 48 | 56 | 10 | 14 | 17 | 23 | 26 | 32 |

TABLE 5

TIM-3 binding arm SEQ ID NOs:

| mAb | VH | VL | HCDRs | | | LCDR2 | | |
|---|---|---|---|---|---|---|---|---|
| | | | 1 | 2 | 3 | 1 | 2 | 3 |
| PTBB14 | 153 | 162 | 97 | 105 | 115 | 124 | 133 | 143 |
| PTBB15 | 146 | 156 | 91 | 99 | 108 | 118 | 127 | 136 |
| PTBB16 | 153 | 162 | 97 | 105 | 115 | 124 | 133 | 143 |
| PTBB17 | 146 | 156 | 91 | 99 | 108 | 118 | 127 | 136 |
| PTBB24 | 172 | 173 | 97 | 105 | 115 | 124 | 133 | 143 |
| PTBB30 | 146 | 156 | 91 | 99 | 108 | 118 | 127 | 136 |
| PTBB27 | 172 | 173 | 97 | 105 | 115 | 124 | 133 | 143 |
| PTBB28 | 146 | 156 | 91 | 99 | 108 | 118 | 127 | 136 |
| PTBB18 | 146 | 156 | 91 | 99 | 108 | 118 | 127 | 136 |
| PTBB20 | 146 | 156 | 91 | 99 | 108 | 118 | 127 | 136 |
| PTBB21 | 172 | 173 | 97 | 105 | 115 | 124 | 133 | 143 |

Engineered and Modified Antibodies

The antibodies of the invention may further be engineered to generate modified antibodies with similar or altered properties when compared to the parental antibodies. The VH, the VL, the VH and the VL, the constant regions, VH framework, VL framework, or any or all of the six CDRs may be engineered in the antibodies of the invention.

"The antibodies of the invention" as used herein refers to the antagonistic antibodies specifically binding PD-1, the antagonistic antibodies specifically binding TIM-3, and the antagonistic bispecific PD-1/TIM-3 antibodies comprising a first domain specifically binding PD-1 and a second domain specifically binding TIM-3 (e.g. bispecific PD-1/TIM-3 antibodies) as described herein.

The antibodies of the invention may be engineered by CDR grafting. One or more CDR sequences of the antibodies of the invention described herein may be grafted to a different framework sequence. CDR grafting may be done using known methods and methods described herein.

In some embodiments, the antagonistic antibodies specifically binding PD-1 or the bispecific PD-1/TIM-3 antibodies of the invention comprise the VH that comprises the HDCR1 of SEQ ID NOs: 10, 11 or 12, the HCDR2 of SEQ ID NOs: 13, 14 or 15, the HCDR3 of SEQ ID NOs: 16, 17, 18 or 19, and the VL that comprises the LCDR1 of SEQ ID NOs: 20, 21, 22, 23, 24 or 25, the LCDR2 of SEQ ID NOs: 26, 27, 28, 29 or 30, and/or the LCDR3 of SEQ ID NOs: 31, 32, 33, 34, 35, 36, 37, 38, 39 or 40, wherein the VH framework is derived from the VH framework other than VH1-69 (SEQ ID NO: 170) and the VL framework is derived from the VL framework other than IGKV3-11 (SEQ ID NO: 171).

In some embodiments, the antagonistic antibodies specifically binding TIM-3 or the bispecific PD-1/TIM-3 antibodies of the invention comprise the HDCR1 of SEQ ID NOs: 90, 91, 92, 93, 94, 95, 96, 97 or 98, the HCDR2 of SEQ ID NOs: 99, 100, 101, 102, 10, 104, 105 or 106, the HCDR3 of SEQ ID NOs: 107, 108, 109, 110, 111, 112, 113, 114, 115 or 116, and the VL that comprises the LCDR1 of SEQ ID NOs: 117, 118, 119, 120, 121, 122, 123, 124 or 125, the LCDR2 of SEQ ID NOs: 126, 127, 128, 129, 130, 131, 132, 133 or 134, and/or the LCDR3 of SEQ ID NOs: 135, 136, 137, 139, 140, 141, 142, 143 or 144, wherein the VH framework is derived from the human VH germline gene sequences other than those of IGHV3-23 (SEQ ID NO: 174), IGHV1-02 (SEQ ID NO: 175), IGHV4-30-4 (SEQ ID NO: 176), IGHV1-03 (SEQ ID NO: 177), IGHV2-26 (SEQ ID NO: 178) or IGHV5-51 (SEQ ID NO: 179), and the VL framework is derived from the human VL germline gene sequences other than those of IGKV3-20 (A27) (SEQ ID NO: 180), IGKV3-11 (L6) (SEQ ID NO: 171), IGKV4-1 (B3) (SEQ ID NO: 181), IGKV1-39 (012) (SEQ ID NO: 182) or IGKV1-33 (018) (SEQ ID NO: 183).

The framework sequences to be used may be obtained from public DNA databases or published references that include germline antibody gene sequences. For example, germline DNA and the encoded protein sequences of human heavy and light chain variable region genes may be found at IMGT®, the international ImMunoGeneTics information System® (http://_www-imgt_org). Framework sequences that may be used to replace the existing framework sequences in the antibodies of the invention may be those that show the highest percent identity to the parental frameworks over the entire length of the VH or the VL, or over the length of the FR1, FR2, FR3 and FR4. In addition, suitable frameworks may further be selected based on the VH and the VL CDR1 and CDR2 lengths or identical LCDR1, LCDR2, LCDR3, HCDR1 and HCDR2 canonical structure. Suitable frameworks may be selected using known methods, such as human framework adaptation described in U.S. Pat. No. 8,748,356 or superhumanization described in U.S. Pat. No. 7,709,226.

The framework sequences of the parental and engineered antibodies may further be modified, for example by back-mutations to restore and/or improve binding of the generated antibody to the antigen as described for example in U.S. Pat. No. 6,180,370. The framework sequences of the parental or engineered antibodies may further be modified by mutating one or more residues within the framework region, or within one or more CDR regions, to remove T-cell epitopes to thereby reduce the potential immunogenicity of the antibody. This approach is also referred to as "deimmunization" and described in further detail in U.S. Patent Publ. No. US20070014796.

The CDR residues of the antibodies of the invention may be mutated to improve affinity of the antibodies to PD-1, TIM-3, or PD-1 and TIM-3.

The CDR residues of the antibodies of the invention may be mutated for example to minimize risk of post-translational modifications. Amino acid residues of putative motifs for deamination (NS), acid-catalyzed hydrolysis (DP), isomerization (DS), or oxidation (W) may be substituted with any of the naturally occurring amino acids to mutagenize the motifs, and the resulting antibodies may be tested for their functionality and stability using methods described herein.

Fc substitutions may be made to the antibodies of the invention to modulate antibody effector functions and pharmacokinetic properties. In traditional immune function, the interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All of these interactions are initiated through the binding of the Fc domain of antibodies or immune complexes to specialized cell surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are "activating Fcγ receptors" (i e, immune system enhancing); FcγRIIB (CD32B) is an inhibiting Fcγ receptor" (i.e., immune system dampening). Binding to the FcRn receptor modulates antibody half-life.

In some embodiments, the antagonistic antibodies of the invention comprise at least one substitution in an Fc region In some embodiments, the antagonistic antibodies of the invention comprise one, two, three, four, five, six, seven, eight, nine, ten, eleven, twelve, thirteen, fourteen or Fc positions that may be substituted to modulate antibody half-life are those described for example in Dall'Acqua et al., (2006) *J Biol Chem* 281:23514-240, Zalevsky et al., (2010) *Nat Biotechnol* 28:157-159, Hinton et al., (2004) *J Biol Chem* 279(8):6213-6216, Hinton et al., (2006) *J Immunol* 176:346-356, Shields et al. (2001) *J Biol Chem* 276: 6591-6607, Petkova et al., (2006). *Int Immunol* 18:1759-1769, Datta-Mannan et al., (2007) *Drug Metab Dispos,* 35:86-94, 2007, Vaccaro et al., (2005) *Nat Biotechnol* 23:1283-1288, Yeung et al., (2010) *Cancer Res,* 70:3269-3277 and Kim et al., (1999) *Eur J Immunol* 29: 2819, and include positions 250, 252, 253, 254, 256, 257, 307, 376, 380, 428, 434 and 435. Exemplary substitutions that may be made singularly or in combination are substitutions T250Q, M252Y, I253A, S254T, T256E, P257I, T307A, D376V, E380A, M428L, H433K, N434S, N434A, N434H, N434F, H435A and H435R. Exemplary singular or combination substitutions that may be made to increase the half-life of the antibody are substitutions M428L/N434S, M252Y/S254T/T256E, T250Q/M428L, N434A and T307A/E380A/N434A. Exemplary singular or combination substitutions that may be made to reduce the half-life of the antibody are substitutions H435A, P257I/N434H, D376V/N434H, M252Y/S254T/T256E/H433K/N434F, T308P/N434A and H435R.

In some embodiments, the antibodies of the invention comprise at least one substitution in the antibody Fc at amino acid position 250, 252, 253, 254, 256, 257, 307, 376, 380, 428, 434 or 435.

In some embodiments, the antibodies of the invention comprise at least one substitution in the antibody Fc selected from the group consisting of T250Q, M252Y, I253A, S254T, T256E, P257I, T307A, D376V, E380A, M428L, H433K, N434S, N434A, N434H, N434F, H435A and H435R.

In some embodiments, the antibodies of the invention comprise at least one substitution in the antibody Fc selected from the group consisting of M428L/N434S, M252Y/S254T/T256E, T250Q/M428L, N434A, T307A/E380A/N434A, H435A, P257I/N434H, D376V/N434H, M252Y/S254T/T256E/H433K/N434F, T308P/N434A and H435R.

In some embodiments, the antibodies of the invention comprise at least one substitution in the antibody Fc that reduces binding of the antibody to an activating Fcγ receptor (FcγR) and/or reduces Fc effector functions such as C1q binding, complement dependent cytotoxicity (CDC), antibody-dependent cell-mediated cytotoxicity (ADCC) or phagocytosis (ADCP).

Fc positions that may be substituted to reduce binding of the antibody to the activating FcγR and subsequently to reduce effector function are those described for example in Shields et al., (2001) *J Biol Chem* 276:6591-6604, Intl. Patent Publ. No. WO2011/066501, U.S. Pat. Nos. 6,737,056 and 5,624,821, Xu et al., (2000) *Cell Immunol,* 200:16-26, Alegre et al., (1994) *Transplantation* 57:1537-1543, Bolt et al., (1993) *Eur J Immunol* 23:403-411, Cole et al., (1999) *Transplantation,* 68:563-571, Rother et al., (2007) *Nat Biotechnol* 25:1256-1264, Ghevaert et al., (2008) *J Clin Invest* 118:2929-2938, An et al., (2009) mAbs, 1:572-579) and include positions 214, 233, 234, 235, 236, 237, 238, 265, 267, 268, 270, 295, 297, 309, 327, 328, 329, 330, 331 and 365. Exemplary substitutions that may be made singularly or in combination are substitutions K214T, E233P, L234V, L234A, deletion of G236, V234A, F234A, L235A, G237A, P238A, P238S, D265A, S267E, H268A, H268Q, Q268A, N297A, A327Q, P329A, D270A, Q295A, V309L, A327S, L328F, A330S and P331S in IgG1, IgG2, IgG3 or IgG4. Exemplary combination substitutions that result in antibodies with reduced ADCC are substitutions L234A/L235A on IgG1, V234A,/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4. Hybrid IgG2/4 Fc domains may also be used, such as Fc with residues 117-260 from IgG2 and residues 261-447 from IgG4.

Well-known S228P substitution may be made in IgG4 antibodies to enhance IgG4 stability.

In some embodiments, the antibodies of the invention comprise a substitution in at least one residue position 214, 233, 234, 235, 236, 237, 238, 265, 267, 268, 270, 295, 297, 309, 327, 328, 329, 330, 331 or 365, wherein residue numbering is according to the EU Index.

In some embodiments, the antibodies of the invention comprise at least one substitution selected from the group consisting of K214T, E233P, L234V, L234A, deletion of G236, V234A, F234A, L235A, G237A, P238A, P238S, D265A, S267E, H268A, H268Q, Q268A, N297A, A327Q, P329A, D270A, Q295A, V309L, A327S, L328F, A330S and P331S, wherein residue numbering is according to the EU Index.

In some embodiments, the antibodies of the invention comprise a substitution in at least one residue position 228, 234, 235, 237, 238, 268, 330 or 331, wherein residue numbering is according to the EU Index.

In some embodiments, the antibodies of the invention comprise a S228P substitution, wherein residue numbering is according to the EU Index.

In some embodiments, the antibodies of the invention comprise a V234A substitution, wherein residue numbering is according to the EU Index.

In some embodiments, the antibodies of the invention comprise a F234A substitution, wherein residue numbering is according to the EU Index.

In some embodiments, the antibodies of the invention comprise a G237A substitution, wherein residue numbering is according to the EU Index.

In some embodiments, the antibodies of the invention comprise a P238S substitution, wherein residue numbering is according to the EU Index.

In some embodiments, the antibodies of the invention comprise a H268A substitution, wherein residue numbering is according to the EU Index.

In some embodiments, the antibodies of the invention comprise a Q268A substitution, wherein residue numbering is according to the EU Index.

In some embodiments, the antibodies of the invention comprise an A330S substitution, wherein residue numbering is according to the EU Index.

In some embodiments, the antibodies of the invention comprise a P331S substitution, wherein residue numbering is according to the EU Index.

In some embodiments, the antibodies of the invention comprise L234A, L235A, G237A, P238S, H268A, A330S and P331S substitutions, wherein residue numbering is according to the EU Index.

In some embodiments, the antibodies of the invention comprise V234A, G237A, P238S, H268A, V309L, A330S and P331S substitutions, wherein residue numbering is according to the EU Index.

In some embodiments, the antibodies of the invention comprise F234A, L235A, G237A, P238S and Q268A substitutions, wherein residue numbering is according to the EU Index.

In some embodiments, the antibodies of the invention comprise L234A, L235A or L234A and L235A substitutions, wherein residue numbering is according to the EU Index.

In some embodiments, the antibodies of the invention comprise F234A, L235A or F234A and L235A substitutions, wherein residue numbering is according to the EU Index.

In some embodiments, the antibodies of the invention comprise S228P, F234A and L235A substitutions, wherein residue numbering is according to the EU Index.

In some embodiments, the antibodies of the invention comprise at least one substitution in an antibody Fc that enhances binding of the antibody to an Fcγ receptor (FcγR) and/or enhances Fc effector functions such as C1q binding, complement dependent cytotoxicity (CDC), antibody-dependent cell-mediated cytotoxicity (ADCC) or phagocytosis (ADCP).

In addition to their immunomodulatory activity, the PD-1 or the TIM-3 antibodies of the invention may kill tumor cells expressing PD-1 and/or TIM-3 directly via antibody-mediated effector functions, for example by ADCC, ADCP or CDC.

Fc positions that may be substituted to increase binding of the antibody to the activating Fcγ and/or enhance antibody effector functions are those described for example in U.S. Pat. No. 6,737,056, U.S. Patent Publ. No. 2015/0259434, Shields et al., (2001) *J Biol Chem* 276:6591-6604, Lazar et al., (2006) *Proc Natal Acad Sci,* 103:4005-4010, Stavenhagen et al., (2007) *Cancer Res* 67:8882-8890, Richards et al., (2008) *Mol Cancer Ther* 7:2517-2527, Diebolder et al., *Science*; published online Mar. 13, 2014; doi:10.1126/science.1248943, and include positions 236, 239, 243, 256, 290, 292, 298, 300, 305, 312, 326, 330, 332, 333, 334, 345, 360, 339, 378, 396 or 430 (residue numbering according to the EU index). Exemplary substitutions that may be made singularly or in combination are G236A, S239D, F243L, T256A, K290A, R292P, S298A, Y300L, V305L, K326A, A330K, I332E, E333A, K334A, A339T and P396L. Exemplary combination substitutions that result in antibodies with increased ADCC or ADCP are substitutions S239D/I332E, S298A/E333A/K334A, F243L/R292P/Y300L, F243L/R292P/Y300L/P396L, F243L/R292P/Y300L/V305I/P396L and G236A/S239D/I332E on IgG1.

Fc positions that may be substituted to enhance CDC of the antibody are those described for example in Int. Patent Appl. WO2014/108198, Idusogie et al., (2001) *J Immunol* 166:2571-2575 and Moore et al., (2010) *Mabs,* 2:181-189, and include positions 267, 268, 324, 326, 333, 345 and 430. Exemplary substitutions that may be made singularly or in combination are substitutions S267E, H268F, S324T, K326A, K326W, E333A, E345K, E345Q, E345R, E345Y, E430S, E430F and E430T. Exemplary combination substitutions that result in antibodies with increased CDC are substitutions K326A/E333A, K326W/E333A, H268F/S324T, S267E/H268F, S267E/S324T and S267E/H268F/S324T on IgG1.

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγRI, FcγRII and FcγRIIIa. Death of the antibody-coated target cell, such as PD-1 or TIM-3 expressing cells, occurs as a result of effector cell activity through the secretion of membrane pore-forming proteins and proteases. To assess ADCC activity of the antibody of the invention described herein, the antibody may be added to TIM-3 or PD-1 expressing cells in combination with immune effector cells, which may be activated by the antigen antibody complexes resulting in cytolysis of the target cell. Cytolysis may be detected by the release of label (e.g. radioactive substrates, fluorescent dyes or natural intracellular proteins) from the lysed cells. Exemplary effector cells for such assays include peripheral blood mononuclear cells (PBMC) and NK cells. Exemplary target cells include cells expressing TIM-3 or PD-1 either endogenously or recombinantly. In an exemplary assay, target cells are used with a ratio of 1 target cell to 50 effector cells. Target cells are pre-labeled with BATDA (PerkinElmer) for 20 minutes at 37° C., washed twice and resuspended in DMEM, 10% heat-inactivated FBS, 2 mM L-glutamine (all from Invitrogen). Target ($1 \times 10^4$ cells) and effector cells ($0.5 \times 10^6$ cells) are combined and 100 µl of cells are added to the wells of 96-well U-bottom plates. An additional 100 µl is added with or without the test antibodies. The plates are centrifuged at 200 g for 3 minutes, incubated at 37° C. for 2 hours, and then centrifuged again at 200 g for 3 minutes. A total of 20 µl of supernatant is removed per well and cell lysis is measured by the addition of 200 µl of the DELPHIA Europium-based reagent (PerkinElmer). Data is normalized to maximal cytotoxicity with 0.67% Triton X-100 (Sigma Aldrich) and minimal control determined by spontaneous release of BATDA from target cells in the absence of any antibody. The antibody of the invention may induce ADCC by about 20%, 25%, 30%, 35%, 40%, 45%, 50%, 55%, 60%, 65%, 70%, 75%, 80%, 85%, 90%, 95% or 100%.

"Antibody-dependent cellular phagocytosis" ("ADCP") refers to a mechanism of elimination of antibody-coated target cells by internalization by phagocytic cells, such as macrophages or dendritic cells. ADCP may be evaluated by using monocyte-derived macrophages as effector cells and Daudi cells (ATCC® CCL-213™) or B cell leukemia or lymphoma or tumor cells expressing TIM-3 or PD-1 as target cells engineered to express GFP or other labeled molecule. Effector:target cell ratio may be for example 4:1. Effector cells may be incubated with target cells for 4 hours with or without the antibody of the invention. After incubation, cells may be detached using accutase. Macrophages may be identified with anti-CD11b and anti-CD14 antibodies coupled to a fluorescent label, and percent phagocytosis may be determined based on % GFP fluorescence in the $CD11^+CD14^+$ macrophages using standard methods. The antibody of the invention may induce ADCP by about 20%, 25%, 30%, 35%, 40%, 45%, 50%, 55%, 60%, 65%, 70%, 75%, 80%, 85%, 90%, 95% or 100%.

"Complement-dependent cytotoxicity", or "CDC", refers to a mechanism for inducing cell death in which the Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes. CDC of TIM-3 or PD-1 expressing cells may be measured for example by plating Daudi cells at $1 \times 10^5$ cells/well (50 µl/well) in RPMI-B (RPMI supplemented with 1% BSA), adding 50 µl of test antibodies to the wells at final concentration between 0-100 µg/ml, incubating the reaction for 15 min at room temperature, adding 11 µl of pooled human serum to the wells, and incubation the reaction for 45 min at 37° C. Percentage (%) lysed cells may be detected as % propidium iodide stained cells in FACS assay using standard methods. Antibodies of the invention may induce CDC by about 20%, 25%, 30%, 35%, 40%, 45%, 50%, 55%, 60%, 65%, 70%, 75%, 80%, 85%, 90%, 95% or 100%.

The ability of antibodies of the invention described herein to induce ADCC may be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs may be achieved using different methods reported to lead to the successful expression of relatively high defucosylated antibodies bearing the biantennary complex-type of Fc oligosaccharides such as control of culture osmolality (Konno et al., (2012) *Cytotechnology* 64:249-65), application of a variant CHO line Lec13 as the host cell line (Shields et al., (2002) *J Biol Chem* 277:26733-26740), application of a variant CHO line EB66 as the host cell line (Olivier et al., *MAbs*; 2(4), 2010; Epub ahead of print; PMID:20562582), application of a rat hybridoma cell line YB2/0 as the host cell line (Shinkawa et al., (2003) *J Biol Chem* 278:3466-3473), introduction of small interfering RNA specifically against the α 1,6-fucosyltrasferase (FUT8) gene (Mori et al., (2004) *Biotechnol Bioeng* 88:901-908), or coexpression of β-1,4-N-acetylglucosaminyltransferase III and Golgi α-mannosidase II or a potent alpha-mannosidase I inhibitor, kifunensine (Ferrara et al., (2006) *J Biol Chem* 281:5032-5036, Ferrara et al., (2006) *Biotechnol Bioeng* 93:851-861; Xhou et al., (2008) *Biotechnol Bioeng* 99:652-65).

In some embodiments, the antibodies of the invention comprise at least one substitution in the antibody Fc that enhances effector function of the antibody.

In some embodiments, the antibodies of the invention comprise at least one substitution in the antibody Fc at amino acid position 236, 239, 243, 256, 267, 268, 290, 292, 298, 300, 305, 312, 324, 326, 330, 332, 333, 334, 345, 360, 339, 378, 396 or 430.

In some embodiments, the antibodies of the invention comprise at least one substitution in the antibody Fc selected from the group consisting of G236A, S239D, F243L, T256A, K290A, R292P, S298A, Y300L, V305L, K326A, A330K, I332E, E333A, K334A, A339T, P396L, S267E, H268F, S324T, K326A, K326W, E333A, E345K, E345Q, E345R, E345Y, E430S, E430F and E430T.

In some embodiments, the antibodies of the invention comprise at least one substitution in the antibody Fc selected from the group consisting of S239D/I332E, S298A/E333A/K334A, F243L/R292P/Y300L, F243L/R292P/Y300L/P396L, F243L/R292P/Y300L/V305I/P396L, G236A/S239D/I332E, K326A/E333A, K326W/E333A, H268F/S324T, S267E/H268F, S267E/S324T and S267E/H268F/S324T.

In some embodiments, the antibodies of the invention have a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

In some embodiments, the antibodies of the invention have a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%.

Substitutions in the Fc and reduced fucose content may enhance the ADCC activity of the antagonistic antibodies specifically binding TIM-3 or PD-1 of the invention. TIM-3 or PD-1 antibodies with enhanced ADCC, ADCP and/or CDC activity may be useful in the treatment of patients with TIM-3 and/or PD-1 expressing tumors, including heme malignancies.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Intl. Patent Publ. No. WO2008/077546; 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS) or 5) separation of the mAb oligosaccharides from the mAb protein by specific enzymatic deglycosylation with PNGase F at Asn 297. The oligosaccharides released may be labeled with a fluorophore, separated and identified by various complementary techniques which allow fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosaccharide forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" refers to antibodies with fucose content of about 0%-15%.

"Normal fucose" or "normal fucose content" refers to antibodies with fucose content of about over 50%, typically about over 60%, 70%, 80% or over 85%.

The antibodies of the invention may be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention described herein may be conjugated to polyethylene glycol (PEGylated) to improve their pharmacokinetic profiles. Conjugation may be carried out by techniques known to those skilled in the art. Conjugation of therapeutic antibodies with PEG has been shown to enhance pharmacodynamics while not interfering with function (Knigh et al., (2004) *Platelets* 15:409-18; Leong et al., (2001) *Cytokine* 16:106-19; Yang et al., (2003) *Protein Eng* 16:761-70).

Antibodies of the invention may be modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn et al., (2001) *J Mol Biol* 305:989-1010). Potential structure destabilizing residues may be identified based upon the crystal structure of the antibody or by molecular modeling in certain cases, and the effect of the residues on antibody stability may be tested by generating and evaluating variants harboring mutations in the identified residues. One of the ways to increase antibody stability is to raise the thermal transition midpoint ($T_m$) as measured by differential scanning calorimetry (DSC). In general, the protein $T_m$ is correlated with its stability and inversely correlated with its susceptibility to unfolding and denaturation in solution and the degradation processes that depend on the tendency of the protein to unfold (Remmele et al., (2000) *Biopharm* 13:36-46). A number of studies have found correlation between the ranking of the physical stability of formulations measured as thermal stability by DSC and physical stability measured by other methods (Gupta et al., (2003) *AAPS PharmSci* 5E8; Zhang et al., (2004) *J Pharm Sci* 93:3076-89; Maa et al., (1996) *Int J Pharm* 140:155-68; Bedu-Addo et al., (2004) *Pharm Res* 21:1353-61; Remmele et al., (1997) Pharm Res 15:200-8). Formulation studies suggest that a Fab $T_m$ has implication for long-term physical stability of a corresponding mAb.

C-terminal lysine (CTL) may be removed from injected antibodies by endogenous circulating carboxypeptidases in the blood stream (Cai et al., (2011) *Biotechnol Bioeng* 108:404-412). During manufacturing, CTL removal may be controlled to less than the maximum level by control of concentration of extracellular $Zn^{2+}$, EDTA or EDTA—$Fe^{3+}$ as described in U.S. Patent Publ. No. US20140273092. CTL content in antibodies can be measured using known methods.

In some embodiments, the antibodies of the invention have a C-terminal lysine content of about 10% to about 90%, about 20% to about 80%, about 40% to about 70%, about 55% to about 70%, or about 60%.

In some embodiments, the antibodies of the invention have a C-terminal lysine content of about 0%, 5%, 10%, 20%, 30%, 40%, 50%, 60%, 70%, 80%, 90% or 100%.

Methods of Generating Homologous Antibodies, Antibodies with Conservative Modifications, and Engineered and Modified Antibodies The antibodies of the invention that have altered amino acid sequences when compared to the parental antibodies may be generated using standard cloning and expression technologies. For example, site-directed mutagenesis or PCR-mediated mutagenesis may be performed to introduce the mutation(s) and the effect on antibody binding or other property of interest, may be evaluated using well known methods and the methods described herein in the Examples.

Antibody Allotypes

The antibody of the invention may be an IgG1, IgG2, IgG3 or IgG4 isotype.

In some embodiments, the antibody of the invention is an IgG1 isotype.

In some embodiments, the antibody of the invention is an IgG2 isotype.

In some embodiments, the antibody of the invention is an IgG3 isotype.

In some embodiments, the antibody of the invention is an IgG4 isotype.

Immunogenicity of therapeutic antibodies is associated with increased risk of infusion reactions and decreased duration of therapeutic response (Baert et al., (2003) *N Engl J Med* 348:602-08). The extent to which therapeutic antibodies induce an immune response in the host may be determined in part by the allotype of the antibody (Stickler et al., (2011) *Genes and Immunity* 12:213-21). Antibody allotype is related to amino acid sequence variations at specific locations in the constant region sequences of the antibody.

Table 6 shows select IgG1, IgG2 and IgG4 allotypes.

In some embodiments, the antagonistic antibodies specifically binding PD-1 of the invention are of G2m(n), G2m(n-), G2m(n)/(n-), nG4m(a), G1m(17) or G1m(17,1) allotype.

In some embodiments, the antagonistic antibodies specifically binding TIM-3 of the invention are of G2m(n), G2m(n-), G2m(n)/(n-), nG4m(a), G1m(17) or G1m(17,1) allotype.

In some embodiments, the bispecific PD-1/TIM-3 antibodies of the invention are of G2m(n), G2m(n-), G2m(n)/(n-), nG4m(a), G1m(17) or G1m(17,1) allotype.

TABLE 6

Amino acid residue at position of diversity (residue numbering: EU Index)

| Allotype | IgG2 | | IgG4 | | IgG1 | | | |
|---|---|---|---|---|---|---|---|---|
| | 189 | 282 | 309 | 422 | 214 | 356 | 358 | 431 |
| G2m(n) | T | M | | | | | | |
| G2m(n-) | P | V | | | | | | |
| G2m(n)/(n-) | T | V | | | | | | |
| nG4m(a) | | | L | R | | | | |
| G1m(17) | | | | | K | E | M | A |
| G1m(17,1) | | | | | K | D | L | A |

Anti-Idiotypic Antibodies

The present invention provides an anti-idiotypic antibody binding to the antibody of the invention.

The invention also provides an anti-idiotypic antibody specifically binding to the anti-PD-1 antibody of the invention.

The invention also provides an anti-idiotypic antibody specifically binding the antibody comprising the VH of SEQ ID NO: 41 and the VL of SEQ ID NO: 49.

The invention also provides an anti-idiotypic antibody specifically binding the antibody comprising the VH of SEQ ID NO: 41 and the VL of SEQ ID NO: 50.

The invention also provides an anti-idiotypic antibody specifically binding the antibody comprising the VH of SEQ ID NO: 42 and the VL of SEQ ID NO: 51.

The invention also provides an anti-idiotypic antibody specifically binding the antibody comprising the VH of SEQ ID NO: 42 and the VL of SEQ ID NO: 52.

The invention also provides an anti-idiotypic antibody specifically binding the antibody comprising the VH of SEQ ID NO: 42 and the VL of SEQ ID NO: 53.

The invention also provides an anti-idiotypic antibody specifically binding the antibody comprising the VH of SEQ ID NO: 43 and the VL of SEQ ID NO: 49.

The invention also provides an anti-idiotypic antibody specifically binding the antibody comprising the VH of SEQ ID NO: 43 and the VL of SEQ ID NO: 54.

The invention also provides an anti-idiotypic antibody specifically binding the antibody comprising the VH of SEQ ID NO: 43 and the VL of SEQ ID NO: 50.

The invention also provides an anti-idiotypic antibody specifically binding the antibody comprising the VH of SEQ ID NO: 43 and the VL of SEQ ID NO: 55.

The invention also provides an anti-idiotypic antibody specifically binding the antibody comprising the VH of SEQ ID NO: 43 and the VL of SEQ ID NO: 56.

The invention also provides an anti-idiotypic antibody specifically binding the antibody comprising the VH of SEQ ID NO: 43 and the VL of SEQ ID NO: 57.

The invention also provides an anti-idiotypic antibody specifically binding the antibody comprising the VH of SEQ ID NO: 44 and the VL of SEQ ID NO: 49.

The invention also provides an anti-idiotypic antibody specifically binding the antibody comprising the VH of SEQ ID NO: 45 and the VL of SEQ ID NO: 49.

The invention also provides an anti-idiotypic antibody specifically binding the antibody comprising the VH of SEQ ID NO: 46 and the VL of SEQ ID NO: 49.

The invention also provides an anti-idiotypic antibody specifically binding the antibody comprising the VH of SEQ ID NO: 47 and the VL of SEQ ID NO: 49.

The invention also provides an anti-idiotypic antibody specifically binding the antibody comprising the VH of SEQ ID NO: 48 and the VL of SEQ ID NO: 53.

The invention also provides an anti-idiotypic antibody specifically binding the antibody comprising the VH of SEQ ID NO: 48 and the VL of SEQ ID NO: 52.

The invention also provides an anti-idiotypic antibody specifically binding the antibody comprising the VH of SEQ ID NO: 48 and the VL of SEQ ID NO: 56.

The invention also provides an anti-idiotypic antibody specifically binding the antibody comprising the VH of SEQ ID NO: 47 and the VL of SEQ ID NO: 58.

The invention also provides an anti-idiotypic antibody specifically binding the antibody comprising the VH of SEQ ID NO: 47 and the VL of SEQ ID NO: 59.

The invention also provides an anti-idiotypic antibody specifically binding the antibody comprising the VH of SEQ ID NO: 45 and the VL of SEQ ID NO: 60.

The invention also provides an anti-idiotypic antibody specifically binding the antibody comprising the VH of SEQ ID NO: 45 and the VL of SEQ ID NO: 61.

The invention also provides an anti-idiotypic antibody specifically binding the antibody comprising the VH of SEQ ID NO: 45 and the VL of SEQ ID NO: 62.

The invention also provides an anti-idiotypic antibody specifically binding the antibody comprising the VH of SEQ ID NO: 63 and the VL of SEQ ID NO: 65.

The invention also provides an anti-idiotypic antibody specifically binding the antibody comprising the VH of SEQ ID NO: 64 and the VL of SEQ ID NO: 65.

The invention also provides an anti-idiotypic antibody specifically binding the antagonistic antibody specifically binding TIM-3 of the invention.

The invention also provides an anti-idiotypic antibody specifically binding the antibody comprising the VH of SEQ ID NO: 145 and the VL of SEQ ID NO: 155.

The invention also provides an anti-idiotypic antibody specifically binding the antibody comprising the VH of SEQ ID NO: 146 and the VL of SEQ ID NO: 156.

The invention also provides an anti-idiotypic antibody specifically binding the antibody comprising the VH of SEQ ID NO: 148 and the VL of SEQ ID NO: 157.

The invention also provides an anti-idiotypic antibody specifically binding the antibody comprising the VH of SEQ ID NO: 147 and the VL of SEQ ID NO: 155.

The invention also provides an anti-idiotypic antibody specifically binding the antibody comprising the VH of SEQ ID NO: 149 and the VL of SEQ ID NO: 158.

The invention also provides an anti-idiotypic antibody specifically binding the antibody comprising the VH of SEQ ID NO: 150 and the VL of SEQ ID NO: 159.

The invention also provides an anti-idiotypic antibody specifically binding the antibody comprising the VH of SEQ ID NO: 151 and the VL of SEQ ID NO: 160.

The invention also provides an anti-idiotypic antibody specifically binding the antibody comprising the VH of SEQ ID NO: 152 and the VL of SEQ ID NO: 161.

The invention also provides an anti-idiotypic antibody specifically binding the antibody comprising the VH of SEQ ID NO: 153 and the VL of SEQ ID NO: 162.

The invention also provides an anti-idiotypic antibody specifically binding the antibody comprising the VH of SEQ ID NO: 154 and the VL of SEQ ID NO: 163.

In some embodiments, the kit comprises the antagonistic antibody specifically binding PD-1 comprising the VH of SEQ ID NO: 48 and the VL of SEQ ID NO: 56.

In some embodiments, the kit comprises the antagonistic antibody specifically binding PD-1 comprising the VH of SEQ ID NO: 64 and the VL of SEQ ID NO: 65.

The invention also provides an anti-idiotypic antibody specifically binding the antibody comprising the VH of SEQ ID NO: 172 and the VL of SEQ ID NO: 173.

In some embodiments, the anti-idiotypic antibody is used for detecting the level of the therapeutic antibodies (e.g. anti-PD-1, anti-TIM-3 or the bispecific PD-1/TIM-3 antibodies of the invention described herein) in a sample.

An anti-idiotypic (Id) antibody is an antibody which recognizes the antigenic determinants (e.g. the paratope or CDRs) of the antibody. The Id antibody may be antigen-blocking or non-blocking. The antigen-blocking Id may be used to detect the free antibody in a sample (e.g. anti-PD-1, anti-TIM-3 or the bispecific PD-1/TIM-3 antibody of the invention described herein). The non-blocking Id may be used to detect the total antibody (free, partially bond to antigen, or fully bound to antigen) in a sample. An Id antibody may be prepared by immunizing an animal with the antibody to which an anti-Id is being prepared.

An anti-Id antibody may also be used as an immunogen to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity. Anti-Id antibodies may be varied (thereby producing anti-Id antibody variants) and/or derivatized by any suitable technique, such as those described elsewhere herein with respect to the antibodies specifically binding PD-1 or TIM-3, or the bispecific PD-1/TIM-3 antibodies.

Immunoconjugates

An "immunoconjugate" refers to the antibody of the invention conjugated to one or more heterologous molecule(s).

In some embodiments, the antibody of the invention is conjugated to one or more cytotoxic agents or an imaging agent.

Exemplary cytotoxic agents include chemotherapeutic agents or drugs, growth inhibitory agents, toxins (e.g., protein toxins, enzymatically active toxins of bacterial, fungal, plant, or animal origin, or fragments thereof), and radionuclides.

The cytotoxic agent may be one or more drugs, such as to a mayatansinoid (see, e.g., U.S. Pat. No. 5,208,020, 5,416, 06), an auristatin such as monomethylauristatin drug moieties DE and DF (MMAE and MMAF) (see, e.g., U.S. Pat. Nos. 5,635,483 and 5,780,588, and 7,498,298), a dolastatin, a calicheamicin or derivative thereof (see, e.g., U.S. Pat. Nos. 5,712,374, 5,714,586, 5,739, 116, 5,767,285, 5,770, 701, 5,770,710, 5,773,001, and 5,877,296; Hinman et al., (1993) *Cancer Res* 53:3336-3342; and Lode et al., (1998) *Cancer Res* 58:2925-2928); an anthracycline such as daunomycin or doxorubicin (see, e.g., Kratz et al., (2006) *Current Med. Chem* 13:477-523; Jeffrey et al., (2006) Bioorganic & *Med Chem Letters* 16:358-362; Torgov et al., (2005) *Bioconj Chem* 16:717-721; Nagy et al., (2000) *Proc Natl Acad Sci USA* 97:829-834; Dubowchik et al, Bioorg. & Med. Chem. Letters 12: 1529-1532 (2002); King et al., (2002) *J Med Chem* 45:4336-4343; and U.S. Pat. No. 6,630,579), methotrexate, vindesine, a taxane such as docetaxel, paclitaxel, larotaxel, tesetaxel, and ortataxel.

The cytotoxic agent may also be an enzymatically active toxin or fragment thereof, such as diphtheria A chain, nonbinding active fragments of diphtheria toxin, exotoxin A chain (from *Pseudomonas aeruginosa*), ricin A chain, modeccin A chain, alpha-sarcin, *Aleurites fordii* proteins, dianthins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

The cytotoxic agent or an imaging agent may also be a radionuclide. Exemplary radionuclides include Ac-225, At-211, I-131, I-125, Y-90, Re-186, Re-188, Sm-153, Bi-212, P-32, Pb-212 and radioactive isotopes of Lu. When the radioconjugate is used for detection, it may comprise a radioactive atom for scintigraphic studies, for example Tc-99m or I-123, or a spin label for nuclear magnetic resonance (NMR) imaging (also known as magnetic resonance imaging, mri), such as I-123, I-131, In-111, F-19, C-13, N-15 or O-17.

Conjugates of the antibodies of the invention and the heterologous molecule may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HQ), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin may be prepared as described in Vitetta et al., (1987) *Science* 238: 1098. Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., (1992) *Cancer Res* 52: 127-131; U.S. Pat. No. 5,208,020) may be used.

Conjugates of the antibodies of the invention and the heterologous molecule may be prepared with cross-linker reagents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

The invention also provides an immunoconjugate comprising the antagonistic antibody specifically binding PD-1 of the invention linked to a therapeutic agent or an imaging agent.

The invention also provides an immunoconjugate comprising the antagonistic antibody specifically binding TIM-3 of the invention linked to a therapeutic agent or an imaging agent.

The invention also provides an immunoconjugate comprising the bispecific PD-1/TIM-3 antibody of the invention linked to a therapeutic agent or an imaging agent.

Generation of Monospecific Antibodies of the Invention

In some embodiments, the antibodies of the invention are human.

In some embodiments, the antibodies of the invention are humanized.

Monospecific antibodies of the invention described herein (e.g. antibodies specifically binding PD-1 or TIM-3) may be generated using various technologies. For example, the hybridoma method of Kohler and Milstein, Nature 256:495, 1975 may be used to generate monoclonal antibodies. In the hybridoma method, a mouse or other host animal, such as a hamster, rat or monkey, is immunized with human or cyno PD-1 or TIM-3 or fragments of PD-1 or TIM-3, such as the extracellular domain of PD-1 or TIM-3, followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding, cross-reactivity or lack thereof, and affinity for the antigen.

Various host animals may be used to produce the antibodies of the invention. For example, Balb/c mice may be used to generate mouse anti-human PD-1 or TIM-3 antibodies. The antibodies made in Balb/c mice and other non-human animals may be humanized using various technologies to generate more human-like sequences.

Exemplary humanization techniques including selection of human acceptor frameworks are known and include CDR grafting (U.S. Pat. No. 5,225,539), SDR grafting (U.S. Pat. No. 6,818,749), Resurfacing (Padlan, (1991) Mol Immunol 28:489-499), Specificity Determining Residues Resurfacing (U.S. Patent Publ. No. 2010/0261620), human framework adaptation (U.S. Pat. No. 8,748,356) or superhumanization (U.S. Pat. No. 7,709,226). In these methods, CDRs of parental antibodies are transferred onto human frameworks that may be selected based on their overall homology to the parental frameworks, based on similarity in CDR length, or canonical structure identity, or a combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1090/007861 and WO1992/22653, or by introducing variation at any of the CDRs for example to improve affinity of the antibody.

Transgenic animals, such as mice or rats carrying human immunoglobulin (Ig) loci in their genome may be used to generate human antibodies against a target protein, and are described in for example U.S. Pat. No. 6,150,584, Int. Patent Publ. No. WO99/45962, Int. Patent Publ. Nos. WO2002/066630, WO2002/43478, WO2002/043478 and WO1990/04036, Lonberg et al (1994) Nature 368:856-9; Green et al (1994) Nature Genet. 7:13-21; Green & Jakobovits (1998) Exp. Med. 188:483-95; Lonberg and Huszar (1995) Int Rev Immunol 13:65-93; Bruggemann et al., (1991) Eur J Immunol 21:1323-1326; Fishwild et al., (1996) Nat Biotechnol 14:845-851; Mendez et al., (1997) Nat Genet 15:146-156; Green (1999) J Immunol Methods 231:11-23; Yang et al., (1999) Cancer Res 59:1236-1243; Brüggemann and Taussig (1997) Curr Opin Biotechnol 8:455-458. The endogenous immunoglobulin loci in such animal may be disrupted or deleted, and at least one complete or partial human immunoglobulin locus may be inserted into the genome of the antimal using homologous or non-homologous recombination, using transchromosomes, or using minigenes. Companies such as Regeneron (http://_www_regeneron_com), Harbour Antibodies (http://_www_harbourantibodies_com), Open Monoclonal Technology, Inc. (OMT) (http://_www_omtinc_net), KyMab (http://_www_kymab_com), Trianni (http://_www.trianni_com) and Ablexis (http://_www-_ablexis_com) may be engaged to provide human antibodies directed against a selected antigen using technologies as described above.

Human antibodies may be selected from a phage display library, where the phage is engineered to express human immunoglobulins or portions thereof such as Fabs, single chain antibodies (scFv), or unpaired or paired antibody variable regions (Knappik et al., (2000) J Mol Biol 296:57-86; Krebs et al., (2001) J Immunol Meth 254:67-84; Vaughan et al., (1996) Nature Biotechnology 14:309-314; Sheets et al., (1998) PITAS (USA) 95:6157-6162; Hoogenboom and Winter (1991) J Mol Biol 227:381; Marks et al., (1991) J Mol Biol 222:581). The antibodies of the invention may be isolated for example from phage display library expressing antibody heavy and light chain variable regions as fusion proteins with bacteriophage pIX coat protein as described in Shi et al., (2010) J Mol Biol 397:385-96, and Int. Patent Publ. No. WO09/085462). The libraries may be screened for phage binding to human and/or cyno PD-1 or TIM-3 and the obtained positive clones may be further characterized, the Fabs isolated from the clone lysates, and expressed as full length IgGs. Such phage display methods for isolating human antibodies are described in for example: U.S. Pat. Nos. 5,223,409, 5,403,484, 5,571,698, 5,427,908, 5,580, 717, 5,969,108, 6,172,197, 5,885,793; 6,521,404; 6,544, 731; 6,555,313; 6,582,915 and 6,593,081.

Preparation of immunogenic antigens and monoclonal antibody production may be performed using any suitable technique, such as recombinant protein production. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

Generation of Bispecific PD-1/TIM-3 Antibodies of the Invention

The bispecific PD-1/TIM-3 antibodies of the invention (e.g. the bispecific antibodies comprising a first domain specifically binding PD-1 and a second domain specifically binding TIM-3) may be generated by combining PD-1 binding VH/VL domains with TIM-3 binding VH/VL domains isolated and characterized herein. Alternatively, the bispecific PD-1/TIM-3 antibodies may be engineered using VH/VL domains from publicly available monospecific anti-PD-1 and anti-TIM-3 antibodies, and/or by mix-matching the PD-1 or TIM-3 binding VH/VL domains identified herein with publicly available PD-1 or TIM-3 binding VH/VL domains.

Exemplary anti-PD-1 antibodies that may be used to engineer bispecific PD-1/TIM-3 molecules are for example those described in U.S. Pat. Nos. 5,897,862 and 7,488,802, and in Int. Patent Publ. Nos. WO2004/004771, WO2004/056875, WO2006/121168, WO2008/156712, WO2010/029435, WO2010/036959, WO2011/110604, WO2012/145493, WO2014/194302, WO2014/206107, WO2015/036394, WO2015/035606, WO2015/085847, WO2015/112900 and WO2015/112805. For example, the VH/VL domains of KEYTRUDA® (pembrolizumab) and OPDIVO® (nivolumab) may be used. These PD-1 VH/VL domains may be incorporated into bispecific antibodies comprising TIM-3 binding VH/VL domains described herein and in Table 3. For example, the VH/VL domains of the TIM-3 antibodies TM3B103, TM3B105, TM3B107, TM3B108, TM3B109, TM3B113, TM3B189, TM3B190 and TM3B196 described herein may be used to generate bispecific PD-1/TIM-3 antibodies.

Similarly, exemplary anti-TIM-3 antibodies that may be used to engineer bispecific PD-1/TIM-3 molecules are for example those described in Int. Patent Publ. Nos. WO2011/155607, WO2013/006490, and WO2015/117002. These TIM-3 VH/VL domains may be incorporated into bispecific antibodies comprising PD-1 binding VH/VL domains described herein and in Table 2. For example, the VH/VL domains of the PD-1 antibodies PD1B114, PD1B149, PD1B160, PD1B162, PD1B164, PD1B183, PD1B184, PD1B185, PD1B187, PD1B192, PD1B71, PD1B177, PD1B70, PD1B175, PD1B194, PD1B195, PD1B196, PD1B197, PD1B198, PD1B199, PD1B200, PD1B201, PD1B131 and PD1B132 described herein may be used to generate bispecific PD-1/TIM-3 antibodies.

The generated bispecific PD-1/TIM-3 antibodies may be tested for their binding to PD-1 and TIM-3, and for their desired functional characteristics, such as enhancement of activation of antigen specific $CD4^+$ and $CD4^+$ T cells using methods described herein.

Bispecific antibodies of the invention comprise antibodies having a full length antibody structure.

Full length bispecific antibodies may be generated for example using Fab arm exchange (e.g., half molecule exchange, exchanging on heavy chain—light chain pair) between two monospecific bivalent antibodies by introducing mutations at the heavy chain CH3 interface in each half-molecule to favor heterodimer formation of two antibody half-molecules having distinct specificity either in vitro in cell-free environment or using co-expression. The Fab arm exchange reaction is the result of a disulfide-bond isomerization reaction and dissociation-association of CH3 domains. The heavy chain disulfide bonds in the hinge regions of the parental monospecific antibodies are reduced. The resulting free cysteines of one of the parental monospecific antibodies form an inter heavy-chain disulfide bond with cysteine residues of a second parental monospecific antibody molecule and simultaneously CH3 domains of the parental antibodies release and reform by dissociation-association. The CH3 domains of the Fab arms may be engineered to favor heterodimerization over homodimerization. The resulting product is a bispecific antibody having two Fab arms r half molecules which each bind a distinct epitope. Mutations F405L in one heavy chain and K409R in the other heavy chain may be used in case of IgG1 antibodies. For IgG2 antibodies, a wild-type IgG2 and a IgG2 antibody with F405L and R409K substitutions may be used. To generate bispecific antibodies, first monospecific bivalent antibody and the second monospecific bivalent antibody are engineered to have a F405L or a K409R mutation in the Fc region, the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2 carboxyethyl)phosphine (TCEP), L-cysteine and beta-mercaptoethanol. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Bispecific antibodies may also be generated using designs such as the Knob-in-Hole (Genentech), CrossMAbs (Roche) and the electrostatically-matched (Chugai, Amgen, NovoNordisk, Oncomed), the LUZ-Y (Genentech), the Strand Exchange Engineered Domain body (SEEDbody) (EMD Serono), and the Biclonic (Merus).

The "knob-in-hole" strategy (see, e.g., Intl. Publ. No. WO 2006/028936) may be used to generate full length bispecific antibodies of the invention. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

The CrossMAb technology may be used to generate full length bispecific antibodies of the invention. CrossMAbs, in addition to utilizing the "knob-in-hole" strategy to promoter Fab arm exchange, have in one of the half arms the CH1 and the CL domains exchanged to ensure correct light chain pairing of the resulting bispecific antibody (see e.g. U.S. Pat. No. 8,242,247).

Other cross-over strategies may be used to generate full length bispecific antibodies of the invention by exchanging variable or constant, or both domains between the heavy chain and the light chain or within the heavy chain in the bispecific antibodies, either in one or both arms. These exchanges include for example VH-CH1 with VL-CL, VH with VL, CH3 with CL and CH3 with CH1 as described in Int. Patent Publ. Nos. WO2009/080254, WO2009/080251, WO2009/018386 and WO2009/080252.

Other strategies such as promoting heavy chain heterodimerization using electrostatic interactions by substituting positively charged residues at one CH3 surface and negatively charged residues at a second CH3 surface may be used, as described in US Patent Publ. No. US2010/0015133; US Patent Publ. No. US2009/0182127; US Patent Publ. No. US2010/028637 or US Patent Publ. No. US2011/0123532. In other strategies, heterodimerization may be promoted by following substitutions (expressed as modified positions in the first CH3 domain of the first heavy chain/modified position in the second CH3 domain of the second heavy chain): L351Y_F405A_Y407V/T394W, T3661K392M_T394W/F405A_Y407V, T366L_K392M_T394W/F405A_Y407V, L351Y_Y407A/

T366A_K409F, L351Y_Y407A/T366V_K409F, Y407A/ T366A_K409F, or T350V_L351Y_F405A_Y407V/ T350V_T366L_K392L_T394W as described in U.S. Patent Publ. No. US2012/0149876 or U.S. Patent Publ. No. US2013/0195849.

LUZ-Y technology may be utilized to generate bispecific antibodies of the invention. In this technology, a leucine zipper is added into the C terminus of the CH3 domains to drive the heterodimer assembly from parental mAbs that is removed post-purification as described in Wranik et al., (2012) *J Biol Chem* 287(52): 42221-9.

SEEDbody technology may be utilized to generate bispecific antibodies of the invention. SEEDbodies have, in their constant domains, select IgG residues substituted with IgA residues to promote heterodimerization as described in U.S. Patent No. US20070287170.

Mutations are typically made at the DNA level to a molecule such as the constant domain of the antibody using standard methods.

The antibodies of the invention may be engineered into various well known antibody formats.

In some embodiments, the bispecific antibodies include recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

Polynucleotides, Vectors and Host Cells

The invention also provides an antagonistic antibody that specifically binds PD-1, TIM-3 or PD-1 and TIM-3 having certain VH and VL sequences, wherein the antibody VH is encoded by a first polynucleotide and the antibody VL is encoded by a second polynucleotide. The polynucleotide may be a complementary deoxynucleic acid (cDNA), and may be codon optimized for expression in suitable host. Codon optimization is a well-known technology.

The invention also provides an isolated polynucleotide encoding the VH of the antibody of the invention, the VL of the antibody of the invention, the heavy chain of the antibody of the invention or the light chain of the antibody of the invention.

The invention also provides an isolated polynucleotide encoding the VH, the VL, or the VH and the VL of the antagonistic antibody specifically binding PD-1 of the invention.

The invention also provides an isolated polynucleotide encoding the VH of SEQ ID NOs: 41, 42, 43, 44, 45, 46, 47, 48, 63 or 64.

The invention also provides an isolated polynucleotide encoding the VL of SEQ ID NOs: 49, 50, 51, 52, 53, 54, 55, 56, 57, 58, 59, 60, 61, 62 or 65.

The invention also provides an isolated polynucleotide comprising the polynucleotide sequence of SEQ ID NOs: 196, 197, 198, 199, 200, 201, 202 or 203.

The invention also provides an isolated polynucleotide encoding the VH, the VL, or the VH and the VL of the antagonistic antibody specifically binding TIM-3 of the invention.

The invention also provides an isolated polynucleotide encoding the VH of SEQ ID NOs: 145, 146, 147, 148, 149, 150, 151, 152, 153, 154 or 172.

The invention also provides an isolated polynucleotide encoding the VL of SEQ ID NOs: 155, 156, 157, 158, 159, 160, 161, 162, 163 or 173.

The invention also provides an isolated polynucleotide comprising the polynucleotide sequence of SEQ ID NOs: 204, 205, 206, 207, 208, 209, 210 or 211.

The invention also provides an isolated polynucleotide encoding the HC1, the LC1, the HC2 or the LC2 of the antagonistic bispecific PD-1/TIM-3 antibody of the invention.

The invention also provides an isolated polynucleotide encoding the HC1 of SEQ ID NOs: 186, 187, 241, 242 or 243.

The invention also provides an isolated polynucleotide encoding the LC1 of SEQ ID NOs: 188 or 189.

The invention also provides an isolated polynucleotide encoding the HC2 of SEQ ID NOs: 190, 191, 192, 244, 245, 246, 247 or 248.

The invention also provides an isolated polynucleotide encoding the LC2 of SEQ ID NOs: 193, 194 or 195.

The invention also provides an isolated polynucleotide comprising the polynucleotide sequence of SEQ ID NOs: 253, 254, 255, 256, 257, 258, 259 and 260.

```
(PD1H170)
                                          SEQ ID NO: 196
CAGGTGCAGCTGGTGCAGAGCGGCGCGGAAGTGAAAAAACCGGGCAGCAG

CGTGAAAGTGAGCTGCAAAGCGAGCGGCGGCACCTTTAGCAGCTATGCGA

TTAGCTGGGTGCGCCAGGCGCCGGGCCAGGGCCTGGAATGGATGGGCGGC

ATTATTCCGATTTTTGACACCGCGAACTATGCGCAGAAATTTCAGGGCCG

CGTGACCATTACCGCGGATGAAAGCACCAGCACCGCGTATATGGAACTGA

GCAGCCTGCGCAGCGAAGATACCGCGGTGTATTATTGCGCGCGCCCTGGT

CTCGCTGCGGCTTATGATACTGGTTCCTTGGACTATTGGGGCCAGGGCAC

CCTGGTGACCGTGAGCAGC (PD1L148)
                                          SEQ ID NO: 197
GAAATTGTGCTGACCCAGAGCCCGGCGACCCTGAGCCTGAGCCCGGGCGA

ACGCGCGACCCTGAGCTGCCGCGCGAGCCAGAGCGTTCGCTCCTACCTGG

CGTGGTATCAGCAGAAACCGGGCCAGGCGCCGCGCCTGCTGATCTACGAC

GCGAGCAATCGTGCGACCGGCATTCCGGCGCGCTTTAGCGGCTCCGGTAG

CGGCACCGATTTTACCCTGACCATTAGCAGCCTGGAACCGGAAGATTTTG

CGGTGTATTATTGCCAGCAACGTAATTATTGGCCGCTGACCTTTGGCCAG

GGCACCAAAGTGGAAATTAAA (PD1H129)
                                          SEQ ID NO: 198
GAAGTGCAGCTGGTGGAATCTGGCGGCGGACTGGTGCAGCCTGGCGGATC

TCTGAGACTGAGCTGTGCCGCCAGCGGCTTCGCCTTCAGCAGATACGACA

TGAGCTGGGTGCGCCAGGCCCCTGGCAAAGGACTGGAAAGCGTGGCCTAC

ATCTCTGGCGGAGGCGCCAACACCTACTACCTGGACAACGTGAAGGGCCG
```

GTTCACCATCAGCCGGGACAACGCCAAGAACAGCCTGTACCTGCAGATGA
ACTCCCTGCGGGCCGAGGACACCGCCGTGTACTATTGCGCCTCCCCCTAC
CTGAGCTACTTCGACGTGTGGGGCCAGGGCACACTCGTGACCGTGTCATC
T (PD1L62)
SEQ ID NO: 199
GAGATCGTGATGACCCAGAGCCCTGCCACCCTGTCCGTGTCTCCAGGCGA
AAGAGCCACCCTGAGCTGCAGAGCCAGCCAGAGCCTGAGCGACTACCTGC
ACTGGTATCAGCAGAAGCCCGGCCAGGCCCCCAGACTGCTGATCAAGTCT
GCCAGCCAGTCCATCAGCGGCATCCCCGCCAGATTTTCTGGCAGCGGCTC
CGGCACCGAGTTCACCCTGACAATCAGCAGCCTGCAGAGCGAGGACTTCG
CCGTGTACTACTGCCAGAACGGCCACAGCTTCCCTTACACCTTCGGCCAG
GGCACCAAGCTGGAAATCAAG (PD1H163)
SEQ ID NO: 200
CAGGTGCAGCTGGTGCAGAGCGGCGCGGAAGTGAAAAAACCGGGCAGCAG
CGTGAAAGTGAGCTGCAAAGCGAGCGGCGGCACCTTCAAGTCCTATGTGA
TTCATTGGGTGCGCCAGGCGCCGGGCCAGGGCCTGGAATGGATGGGCGGT
ATTATCCCAATTTTTGGCACCGCCAATTATGCGCAGAAATTTCAGGGCCG
CGTGACCATTACCGCTGATGAAAGCACCAGCACCGCGTATATGGAACTGA
GCAGCCTGCGCAGCGAAGATACCGCGGTGTATTATTGCGCGCGCGGTTAT
GTGCGGGCTACGGGCATGTTGGACTATTGGGGCCAGGGCACCCTGGTGAC
CGTGAGCAGC (PD1L185)
SEQ ID NO: 201
GAAATTGTGCTGACCCAGAGCCCGGCGACCCTGAGCCTGAGCCCGGGCGA
ACGCGCGACCCTGAGCTGCCGCGCGAGCCAGAGCGTTAGCAATTATCTGG
CGTGGTATCAGCAGAAACCGGGCCAGGCGCCGCGCCTGCTGATCTACGAC
GCCAGCAATCGCGCGACCGGCATTCCGGCGCGCTTTAGCGGCTCCGGTAG
CGGCACCGATTTTACCCTGACCATTAGCAGCCTGGAACCGGAAGATTTTG
CGGTGTATTATTGCCAGCAACGTGCATATTGGCCGCTGACCTTTGGCCAG
GGCACCAAAGTGGAAATTAAA (PD1H164)
SEQ ID NO: 202
CAGGTGCAGCTGGTGCAGAGCGGCGCGGAAGTGAAAAAACCGGGCAGCAG
CGTGAAAGTGAGCTGCAAAGCGAGCGGCGGCACCTTCAGCGATTATGTGA
TTTCCTGGGTGCGCCAGGCGCCGGGCCAGGGCCTGGAATGGATGGGCGGT
ATTATCCCGATTTACGGGACCGCTAACTATGCGCAGAAATTTCAGGGCCG
CGTGACCATTACCGCTGATGAAAGCACCAGCACCGCGTATATGGAACTGA
GCAGCCTGCGCAGCGAAGATACCGCGGTGTATTATTGCGCGCGCGGTACC
CTCGACCGGACCGGGCATTTGGACTATTGGGGCCAGGGCACCCTGGTGAC
CGTGAGCAGC (PD1L86)
SEQ ID NO: 203
GAAATTGTGCTGACCCAGAGCCCGGCGACCCTGAGCCTGAGCCCGGGCGA
ACGCGCGACCCTGAGCTGCCGCGCGAGCCAGAGCGTCTCCTCCTACTTG

CGTGGTATCAGCAGAAACCGGGCCAGGCGCCGCGCCTGCTGATCCACGAC
GCCTCTACGCGTGCGACCGGCATTCCGGCGCGCTTTAGCGGCTCCGGTAG
CGGCACCGATTTTACCCTGACCATTAGCAGCCTGGAACCGGAAGATTTTG
CGGTGTATTATTGCCAGCAACGTAATTATTGGCCGCTCACCTTTGGCCAG
GGCACCAAAGTGGAAATTAAA (TM3H24)
SEQ ID NO: 204
GAAGTGCAGCTGCTGGAAAGCGGCGGCGGCCTGGTGCAGCCGGGCGGCAG
CCTGCGCCTGAGCTGCGCGGCAAGCGGCTTTACCTTTAGCAGCTATGCGA
TGAGCTGGGTGCGCCAGGCGCCGGGCAAAGGCCTGGAATGGGTGAGCGCG
ATTAGCGGCAGCGGCGGCAGCACCTATTATGCGGATAGCGTGAAAGGCCG
CTTTACCATTAGCCGCGATAACAGCAAAAACACCCTGTATCTGCAGATGA
ACAGCCTGCGCGCGGAAGATACCGCGGTGTATTATTGCGCGAAATCCCCG
TACGCGCCCTTGGACTATTGGGGCCAGGGCACCCTGGTGACCGTGAGCAG
C (TM3L33)
SEQ ID NO: 205
GAAATTGTGCTGACCCAGAGCCCGGCGACCCTGAGCCTGAGCCCGGGCGA
ACGCGCGACCCTTAGCTGCCGTGCAAGTCAGAGTGTGAACGACTACCTGG
CGTGGTATCAGCAGAAACCGGGCCAGGCGCCGCGCCTGCTGATTTATGAT
GCGAGCAACCGCGCGACCGGCATTCCGGCGCGCTTTAGCGGCAGCGGCAG
CGGCACCGATTTTACCCTGACCATTAGCAGCCTGGAACCGGAAGATTTTG
CGGTGTATTATTGCCAGCAGGGTGGTCACGCGCCGATCACCTTTGGCCAG
GGCACCAAAGTGGAAATTAAA (TM3H162)
SEQ ID NO: 206
GAAGTGCAGCTGGTGCAGTCTGGCGCCGAAGTGAAGAAGCCTGGCGAGAG
CCTGAAGATCAGCTGCAAGGGCAGCGGCTACAGCTTCACCAGCTACTGGA
TGCAGTGGGTGCGCCAGATGCCTGGCAAGGGCCTGGAATGGATGGGCGCC
ATCTATCCCGGCGACGGCGACATCAGATACACCCAGAACTTCAAGGGCCA
AGTGACCATCAGCGCCGACAAGAGCATCAGCACCGCCTACCTGCAGTGGT
CCAGCCTGAAGGCCAGCGACACCGCCATGTACTACTGTGCCAGATGGGAG
AAGTCCACCACCGTGGTGCAGCGGAACTACTTCGACTACTGGGGCCAGGG
CACCACAGTGACCGTGTCTAGT (TM3L85)
SEQ ID NO: 207
GACATCCAGATGACCCAGAGCCCCAGCAGCCTGTCTGCCAGCGTGGGCGA
CAGAGTGACCATCACATGCAAGGCCAGCGAGAACGTGGGCACCTTCGTGT
CCTGGTATCAGCAGAAGCCCGGCAAGGCCCCCAAGCTGCTGATCTACGGC
GCCAGCAACAGATACACCGGCGTGCCCAGCAGATTCAGCGGCTCTGGCAG
CGGCACCGACTTCACCCTGACCATCTCTAGCCTGCAGCCCGAGGACTTCG
CCACCTACTACTGCGGCCAGAGCTACAGCTACCCCACCTTTGGCCAGGGC
ACCAAGCTGGAAATCAAG

-continued (TM3H21)
SEQ ID NO: 208
GAAGTGCAGCTGCTGGAAAGCGGCGGCGGCCTGGTGCAGCCGGGCGGCAG

CCTGCGCCTGAGCTGCGCGGCGAGCGGCTTTACCTTTAGCAACTATTGGA

TGAGCTGGGTGCGCCAGGCGCCGGGCAAAGGCCTGGAATGGGTGAGCGCG

ATTAGCGGCAGCGGCGGCAGCACCTATTATGCGGATAGCGTGAAAGGCCG

CTTTACCATTAGCCGCGATAACAGCAAAAACACCCTGTATCTGCAGATGA

ACAGCCTGCGCGCGGAAGATACCGCGGTGTATTATTGCGCGAAAGATCAT

TGGGATCCCAATTTTTTGGACTATTGGGGCCAGGGCACCCTGGTGACCGT

GAGCAGC (PH9L1)
SEQ ID NO: 209
GAAATTGTGCTGACCCAGAGCCCGGGCACCCTGAGCCTGAGCCCGGGCGA

ACGCGCGACCCTGAGCTGCCGCGCGAGCCAGAGCGTGAGCAGCAGCTATC

TGGCGTGGTATCAGCAGAAACCGGGCCAGGCGCCGCGCCTGCTGATTTAT

GGCGCGAGCAGCCGCGCGACCGGCATTCCGGATCGCTTTAGCGGCAGCGG

CAGCGGCACCGATTTTACCCTGACCATTAGCCGCCTGGAACCGGAAGATT

TTGCGGTGTATTATTGCCAGCAGTATGGCAGCAGCCCGCTGACCTTTGGC

CAGGGCACCAAAGTGGAAATTAAA (TM3H65)
SEQ ID NO: 210
GAAGTGCAGCTGCTGGAAAGCGGCGGCGGCCTGGTGCAGCCGGGCGGCAG

CCTGCGCCTGAGCTGCGCGGCGAGCGGCTTTACCTTTAGCGACTATTGGA

TGAGCTGGGTGCGCCAGGCGCCGGGCAAAGGCCTGGAATGGGTGAGCGTG

ATCAAGTATAGCGGTGGCTCCAAATATTATGCGGATAGCGTGAAAGGCCG

CTTTACCATTAGCCGCGATAACAGCAAAAACACCCTGTATCTGCAGATGA

ACAGCCTGCGCGCGGAAGATACCGCGGTGTATTATTGCGCGAAAGAGCTG

GAGGGGGTGTTCGACTATTGGGGCCAGGGCACCCTGGTGACCGTGAGCAG

C (TM3L12)
SEQ ID NO: 211
GAAATTGTGCTGACCCAGAGCCCGGGCACCCTGAGCCTGAGCCCGGGCGA

ACGCGCGACCCTGAGCTGCCGCGCGAGCCAGAGCGTTAGCAATAGCACTC

TGGCGTGGTATCAGCAGAAACCGGGCCAGGCGCCGCGCCTGCTGATTTAT

ACTGCGAGCAGCCGCGCGACCGGCATTCCGGATCGCTTTAGCGGCAGCGG

CAGCGGCACCGATTTTACCCTGACCATTAGCCGCCTGGAACCGGAAGATT

TTGCGGTGTATTATTGCCAGCAGTCTTACACATCTCCGTGGACTTTTGGC

CAGGGCACCAAAGTGGAAATTAAA

The polynucleotide sequences encoding the VH or the VL or an antigen-binding fragment thereof of the antibodies of the invention, or the heavy chain and the light chain of the antibodies of the invention may be operably linked to one or more regulatory elements, such as a promoter or enhancer, that allow expression of the nucleotide sequence in the intended host cell. The polynucleotide may be a cDNA.

The invention also provides a vector comprising the polynucleotide of the invention. Such vectors may be plasmid vectors, viral vectors, vectors for baculovirus expression, transposon based vectors or any other vector suitable for introduction of the synthetic polynucleotide of the invention into a given organism or genetic background by any means. For example, polynucleotides encoding light and/or heavy chain variable regions of the antibodies of the invention, optionally linked to constant regions, are inserted into expression vectors. The light and/or heavy chains may be cloned in the same or different expression vectors. The DNA segments encoding immunoglobulin chains may be operably linked to control sequences in the expression vector(s) that ensure the expression of immunoglobulin polypeptides. Such control sequences include signal sequences, promoters (e.g. naturally associated or heterologous promoters), enhancer elements, and transcription termination sequences, and are chosen to be compatible with the host cell chosen to express the antibody. Once the vector has been incorporated into the appropriate host, the host is maintained under conditions suitable for high level expression of the proteins encoded by the incorporated polynucleotides.

In some embodiments, the vector comprises the polynucleotide of SEQ ID NO: 196 and 197.

In some embodiments, the vector comprises the polynucleotide of SEQ ID NO: 198 and 199.

In some embodiments, the vector comprises the polynucleotide of SEQ ID NO: 200 and 201.

In some embodiments, the vector comprises the polynucleotide of SEQ ID NO: 202 and 203.

In some embodiments, the vector comprises the polynucleotide of SEQ ID NO: 204 and 205.

In some embodiments, the vector comprises the polynucleotide of SEQ ID NO: 206 and 207.

In some embodiments, the vector comprises the polynucleotide of SEQ ID NO: 208 and 209.

In some embodiments, the vector comprises the polynucleotide of SEQ ID NO: 210 and 211.

In some embodiments, the vector comprises the polynucleotide of SEQ ID NO: 253 and 254.

In some embodiments, the vector comprises the polynucleotide of SEQ ID NO: 255 and 256.

In some embodiments, the vector comprises the polynucleotide of SEQ ID NO: 257 and 258.

In some embodiments, the vector comprises the polynucleotide of SEQ ID NO: 259 and 260.

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed with the desired DNA sequences.

Suitable promoter and enhancer elements are known in the art. For expression in a eukaryotic cell, exemplary promoters include light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various known tissue specific promoters. Selection of the appropriate vector and promoter is well within the level of ordinary skill in the art.

Exemplary vectors that may be used are Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia), pEE6.4 (Lonza) and pEE12.4 (Lonza).

The invention also provides a host cell comprising one or more vectors of the invention. "Host cell" refers to a cell into which a vector has been introduced. It is understood that the term host cell is intended to refer not only to the particular subject cell but to the progeny of such a cell, and also to a stable cell line generated from the particular subject cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic cells, plant cells or archeal cells. *Escherichia coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces* (for example, *S. cerevisiae*) and *Pichia* are examples of suitable yeast host cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, VA, CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHOK1SV (Lonza Biologics, Walkersville, MD), Potelligent® CHOK2SV (Lonza), CHO-K1 (ATCC CRL-61) or DG44.

The invention also provides a method of producing an antibody of the invention comprising culturing the host cell of the invention in conditions that the antibody is expressed, and recovering the antibody produced by the host cell. Methods of making antibodies and purifying them are well known in the art. Once synthesized (either chemically or recombinantly), the whole antibodies, their dimers, individual light and/or heavy chains, or other antibody fragments such as VH and/or VL, may be purified according to standard procedures, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody may be substantially pure, for example, at least about 80% to 85% pure, at least about 85% to 90% pure, at least about 90% to 95% pure, or at least about 98% to 99%, or more, pure, for example, free from contaminants such as cell debris, macromolecules, etc. other than the subject antibody.

The polynucleotide sequences of the invention may be incorporated into vectors using standard molecular biology methods. Host cell transformation, culture, antibody expression and purification are done using well known methods. Another embodiment of the invention is a method of producing the antagonistic antibody specifically binding PD-1 of the invention, comprising:
  incorporating the first polynucleotide encoding the VH of the antibody and the second polynucleotide encoding the VL of the antibody into an expression vector; transforming a host cell with the expression vector;
  culturing the host cell in culture medium under conditions wherein the VL and the VH are expressed and form the antibody; and
  recovering the antibody from the host cell or culture medium.

Another embodiment of the invention described herein is a method of producing the antagonistic antibody specifically binding TIM-3 of the invention, comprising: incorporating the first polynucleotide encoding the VH of the antibody and the second polynucleotide encoding the VL of the antibody into an expression vector; transforming a host cell with the expression vector;
  culturing the host cell in culture medium under conditions wherein the VL and the VH are expressed and form the antibody; and
  recovering the antibody from the host cell or culture medium.

The polynucleotides encoding certain VH or VL sequences of the invention described herein, and in some embodiments of each and every one of the numbered embodiments listed below, may be incorporated into vectors using standard molecular biology methods. Host cell transformation, culture, antibody expression and purification are done using well known methods.

Pharmaceutical Compositions/Administration

The invention provides pharmaceutical compositions comprising the antibodies of the invention and a pharmaceutically acceptable carrier. For therapeutic use, the antibodies of the invention may be prepared as pharmaceutical compositions containing an effective amount of the antibody as an active ingredient in a pharmaceutically acceptable carrier. "Carrier" refers to a diluent, adjuvant, excipient, or vehicle with which the antibody of the invention is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibodies of the invention in such pharmaceutical formulation may vary, from less than about 0.5%, usually to at least about 1% to as much as 15 or 20% by weight and may be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, PA 2006, Part 5, Pharmaceutical Manufacturing pp 691-1092, See especially pp. 958-989.

The mode of administration for therapeutic use of the antibodies of the invention may be any suitable route that delivers the antibody to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intratumoral, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

The antibodies of the invention may be administered to a subject by any suitable route, for example parentally by intravenous (i.v.) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hours.

The dose given to a subject is sufficient to alleviate or at least partially arrest the disease being treated ("therapeutically effective amount") and may be sometimes 0.005 mg to about 100 mg/kg, e.g. about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m$^2$. Usually between 1 and 8 doses, (e.g., 1, 2, 3, 4, 5, 6, 7 or 8) may be administered to treat the patient, but 9, 10, 11, 12, 13, 14, 15, 16, 17, 18, 19, 20 or more doses may be given.

The administration of the antibodies of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the antibodies of the invention may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

For example, the antibodies of the invention may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The antibodies of the invention, may also be administered prophylactically in order to reduce the risk of developing cancer, delay the onset of the occurrence of an event in cancer progression, and/or reduce the risk of recurrence when a cancer is in remission.

The antibodies of the invention may be lyophilized for storage and reconstituted in a suitable carrier prior to use. This technique has been shown to be effective with conventional protein preparations and well known lyophilization and reconstitution techniques can be employed.

Methods and Uses

The antibodies of the invention have in vitro and in vivo diagnostic, as well as therapeutic and prophylactic utilities.

For example, the antibodies of the invention may be administered to cells in culture, in vitro or ex vivo, or to a subject to treat, prevent, and/or diagnose a variety of disorders, such as cancers and infectious disorders.

The invention provides a method of modifying an immune response in a subject comprising administering to the subject the antibody of the invention for a time sufficient to modify the immune response.

In some embodiments, the immune response is enhanced, stimulated or upregulated.

In some embodiments described herein, the subject is a human patient.

In some embodiments described herein, the subject is a human patient in need of enhancement of the immune response.

In some embodiments, the subject is immunocompromised.

In some embodiments, the subject is at risk of being immunocompromised.

Immunocompromised subject may be undergoing, or has undergone a chemotherapeutic or radiation therapy.

In some embodiment, the subject is or is at risk of being immunocompromised as a result of an infection.

The antibodies of the invention are suitable for treating a subject having a disorder that may be treated by augmenting T-cell mediated immune responses.

In some embodiments, the antagonistic antibody specifically binding PD-1 used in the methods of the invention described herein is PD1B114, PD1B149, PD1B160, PD1B162, PD1B164, PD1B11, PD1B183, PD1B184, PD1B185, PD1B187, PD1B71, PD1B177, PD1B70, PD1B175, PD1B194, PD1B195, PD1B196, PD1B197, PD1B198, PD1B199, PD1B200, PD1B201, PD1B243, PD1B244, PD1B131 or PD1B132. The VH and the VL amino acid sequences of these antibodies are shown in Table 2.

In some embodiments, the antagonistic antibody specifically binding TIM-3 used in the methods of the invention described herein is TM3B103, TM3B105, TM3B109, TM3B108, TM3B113, TM3B189, TM3B190, TM3B193, TM3B195, TM3B196 or TM3B291. The VH and the VL amino acid sequences of these antibodies are shown in Table 3.

In some embodiments, the bispecific PD-1/TIM-3 antibody used in the methods of the invention is PTBB14, PTBB15, PTBB16, PTBB17, PTBB24, PTBB30, PTBB27, PTBB28, PTBB18, PTBB20 or PTBB21. The HC1, the LC1, the HC2 and the LC2 amino acid sequences of these antibodies are shown in Table 41 and Table 42.

In some embodiments, the antagonistic antibody specifically binding PD-1 used in the methods of the invention comprises the VH of SEQ ID NO: 41 and the VL of SEQ ID NO: 49.

In some embodiments, the antagonistic antibody specifically binding PD-1 used in the methods of the invention comprises the VH of SEQ ID NO: 41 and the VL of SEQ ID NO: 50.

In some embodiments, the antagonistic antibody specifically binding PD-1 used in the methods of the invention comprises the VH of SEQ ID NO: 42 and the VL of SEQ ID NO: 51.

In some embodiments, the antagonistic antibody specifically binding PD-1 used in the methods of the invention comprises the VH of SEQ ID NO: 42 and the VL of SEQ ID NO: 52.

In some embodiments, the antagonistic antibody specifically binding PD-1 used in the methods of the invention comprises the VH of SEQ ID NO: 42 and the VL of SEQ ID NO: 53.

In some embodiments, the antagonistic antibody specifically binding PD-1 used in the methods of the invention comprises the VH of SEQ ID NO: 43 and the VL of SEQ ID NO: 49.

In some embodiments, the antagonistic antibody specifically binding PD-1 used in the methods of the invention comprises the VH of SEQ ID NO: 43 and the VL of SEQ ID NO: 54.

In some embodiments, the antagonistic antibody specifically binding PD-1 used in the methods of the invention comprises the VH of SEQ ID NO: 43 and the VL of SEQ ID NO: 50.

In some embodiments, the antagonistic antibody specifically binding PD-1 used in the methods of the invention comprises the VH of SEQ ID NO: 43 and the VL of SEQ ID NO: 55.

In some embodiments, the antagonistic antibody specifically binding PD-1 used in the methods of the invention comprises the VH of SEQ ID NO: 43 and the VL of SEQ ID NO: 56.

In some embodiments, the antagonistic antibody specifically binding PD-1 used in the methods of the invention comprises the VH of SEQ ID NO: 43 and the VL of SEQ ID NO: 57.

In some embodiments, the antagonistic antibody specifically binding PD-1 used in the methods of the invention comprises the VH of SEQ ID NO: 44 and the VL of SEQ ID NO: 49.

In some embodiments, the antagonistic antibody specifically binding PD-1 used in the methods of the invention comprises the VH of SEQ ID NO: 45 and the VL of SEQ ID NO: 49.

In some embodiments, the antagonistic antibody specifically binding PD-1 used in the methods of the invention comprises the VH of SEQ ID NO: 46 and the VL of SEQ ID NO: 49.

In some embodiments, the antagonistic antibody specifically binding PD-1 used in the methods of the invention comprises the VH of SEQ ID NO: 47 and the VL of SEQ ID NO: 49.

In some embodiments, the antagonistic antibody specifically binding PD-1 used in the methods of the invention comprises the VH of SEQ ID NO: 48 and the VL of SEQ ID NO: 53.

In some embodiments, the antagonistic antibody specifically binding PD-1 used in the methods of the invention comprises the VH of SEQ ID NO: 48 and the VL of SEQ ID NO: 52.

In some embodiments, the antagonistic antibody specifically binding PD-1 used in the methods of the invention comprises the VH of SEQ ID NO: 48 and the VL of SEQ ID NO: 56.

In some embodiments, the antagonistic antibody specifically binding PD-1 used in the methods of the invention comprises the VH of SEQ ID NO: 47 and the VL of SEQ ID NO: 58.

In some embodiments, the antagonistic antibody specifically binding PD-1 used in the methods of the invention comprises the VH of SEQ ID NO: 47 and the VL of SEQ ID NO: 59.

In some embodiments, the antagonistic antibody specifically binding PD-1 used in the methods of the invention comprises the VH of SEQ ID NO: 45 and the VL of SEQ ID NO: 60.

In some embodiments, the antagonistic antibody specifically binding PD-1 used in the methods of the invention comprises the VH of SEQ ID NO: 45 and the VL of SEQ ID NO: 61.

In some embodiments, the antagonistic antibody specifically binding PD-1 used in the methods of the invention comprises the VH of SEQ ID NO: 45 and the VL of SEQ ID NO: 62.

In some embodiments, the antagonistic antibody specifically binding TIM-3 used in the methods of the invention comprises the VH of SEQ ID NO: 145 and the VL of SEQ ID NO: 155.

In some embodiments, the antagonistic antibody specifically binding TIM-3 used in the methods of the invention comprises the VH of SEQ ID NO: 146 and the VL of SEQ ID NO: 156.

In some embodiments, the antagonistic antibody specifically binding TIM-3 used in the methods of the invention comprises the VH of SEQ ID NO: 148 and the VL of SEQ ID NO: 157.

In some embodiments, the antagonistic antibody specifically binding TIM-3 used in the methods of the invention comprises the VH of SEQ ID NO: 147 and the VL of SEQ ID NO: 155.

In some embodiments, the antagonistic antibody specifically binding TIM-3 used in the methods of the invention comprises the VH of SEQ ID NO: 149 and the VL of SEQ ID NO: 158.

In some embodiments, the antagonistic antibody specifically binding TIM-3 used in the methods of the invention comprises the VH of SEQ ID NO: 150 and the VL of SEQ ID NO: 159.

In some embodiments, the antagonistic antibody specifically binding TIM-3 used in the methods of the invention comprises the VH of SEQ ID NO: 151 and the VL of SEQ ID NO: 160.

In some embodiments, the antagonistic antibody specifically binding TIM-3 used in the methods of the invention comprises the VH of SEQ ID NO: 152 and the VL of SEQ ID NO: 161.

In some embodiments, the antagonistic antibody specifically binding TIM-3 used in the methods of the invention comprises the VH of SEQ ID NO: 153 and the VL of SEQ ID NO: 162.

In some embodiments, the antagonistic antibody specifically binding TIM-3 used in the methods of the invention comprises the VH of SEQ ID NO: 154 and the VL of SEQ ID NO: 163.

In some embodiments, the antagonistic antibody specifically binding TIM-3 used in the methods of the invention comprises the VH of SEQ ID NO: 172 and the VL of SEQ ID NO: 173.

In some embodiments, the antagonistic bispecific PD-1/TIM-3 antibody comprising a first domain specifically binding PD-1 and a second domain specifically binding TIM-3 used in the methods of the invention comprises the VH of SEQ ID NO: 48 and the VL of SEQ ID NO: 56 in the first domain, and the VH of SEQ ID NO: 153 and the VL of SEQ ID NO: 162 in the second domain.

In some embodiments, the antagonistic bispecific PD-1/TIM-3 antibody comprising a first domain specifically binding PD-1 and a second domain specifically binding TIM-3 used in the methods of the invention comprises the VH of SEQ ID NO: 48 and the VL of SEQ ID NO: 56 in the first domain, and the VH of SEQ ID NO: 146 and the VL of SEQ ID NO: 156 in the second domain.

In some embodiments, the antagonistic bispecific PD-1/TIM-3 antibody comprising a first domain specifically binding PD-1 and a second domain specifically binding TIM-3 used in the methods of the invention comprises the VH of SEQ ID NO: 64 and the VL of SEQ ID NO: 65 in the first domain, and the VH of SEQ ID NO: 153 and the VL of SEQ ID NO: 162 in the second domain.

In some embodiments, the antagonistic bispecific PD-1/TIM-3 antibody comprising a first domain specifically binding PD-1 and a second domain specifically binding TIM-3 used in the methods of the invention, comprises the VH of SEQ ID NO: 64 and the VL of SEQ ID NO: 65 in the first domain, and the VH of SEQ ID NO: 146 and the VL of SEQ ID NO: 156 in the second domain.

In some embodiments, the antagonistic bispecific PD-1/TIM-3 antibody comprising a first domain specifically binding PD-1 and a second domain specifically binding TIM-3 used in the methods of the invention comprises the VH of SEQ ID NO: 48 and the VL of SEQ ID NO: 56 in the first domain, and the VH of SEQ ID NO: 172 and the VL of SEQ ID NO: 173 in the second domain.

Cancer

Blockade of PD-1 may enhance an immune response to cancerous cells in a subject. The ligand for PD-1, PD-L1, is abundantly expressed in a variety of human cancers (Dong et al., (2002) *Nat Med* 8:787-9). The interaction between PD-1 and PD-L1 can result in a decrease in tumor infiltrating lymphocytes, a decrease in T-cell receptor mediated proliferation, and/or immune evasion by the cancerous cells (Dong et al., (2003) *J Mol Med* 81:281-7; Blank et al., (2005) *Cancer Immunol Immunother* 54:307-314; Konishi et al., (2004) *Clin Cancer Res* 10:5094-100). Immune suppression may be reversed by inhibiting the local interaction of PD-1 to PD-L1; the effect is additive when the interaction of PD-1 to the second PD-1 ligand, PD-L2, is blocked as well (Iwai et al., (2002) *Porc Natl Acad Sci* 99:12293-7; Brown et al., (2003) *J Immunol* 170:1257-66). Thus, inhibition of PD-1 may result in augmenting an immune response.

TIM-3 is a coinhibitory protein expressed on activated T helper 1 (Th1) $CD4^+$ and cytotoxic $CD8^+$ T cells that secrete IFN-$\gamma$. TIM-3 is co-expressed on PD-1+ exhausted T cells as shown in preclinical models of cancer and viral exhaustion. Co-blockade of these pathways may restore effector T cell function (e.g., IFN-$\gamma$ secretion, proliferation) in several models as well as human PBMCs derived from metastatic melanoma patients and patients with HIV or HCV. TIM-3 is also enriched on Foxp3+ regulatory T cells and Tregs co-expressing TIM-3, LAG3 and CTLA4 have been shown to be highly efficient suppressors of effector T cells (Teff) (Galuton et al., (2014) *Eur J Immunol* 44(9):2703-11). TIM-3 expression has been correlated with poorer prognosis in NSCLC (Zhuang et al., (2012) Am J Clin Pathol 137(6): 978-85). Lymphocytes from tumor tissues of ovarian, colorectal, cervical and hepatocellular carcinoma patients exhibit higher proportion of TIM-$3^+$ CD4 T cells, which cells have impaired capacity to produce ILF-$\gamma$ (Yan et al., (2013) *PLoS One* 8(3):e58006).

The invention also provides a method of inhibiting growth of tumor cells in a subject, comprising administering to the subject a therapeutically effective amount of the antagonistic antibody specifically binding PD-1 of the invention for a time sufficient to inhibit growth of tumor cells.

The invention also provides a method of inhibiting growth of tumor cells in a subject, comprising administering to the subject a therapeutically effective amount of the antagonistic antibody specifically binding TIM-3 of the invention for a time sufficient to inhibit growth of tumor cells.

The invention also provides a method of inhibiting growth of tumor cells in a subject, comprising administering to the subject a therapeutically effective amount of the antagonistic bispecific PD-1/TIM-3 antibody of the invention for a time sufficient to inhibit growth of tumor cells.

The invention also provides a method of treating a cancer by administering to the subject in need thereof a therapeutically effective amount of the antagonistic antibody specifically binding PD-1 of the invention for a time sufficient to treat the cancer.

The invention also provides a method of treating a cancer by administering to the subject in need thereof a therapeutically effective amount of the antagonistic antibody specifically binding TIM-3 of the invention for a time sufficient to treat the cancer.

The invention also provides a method of treating a cancer by administering to the subject in need thereof a therapeutically effective amount of the bispecific PD-1/TIM-3 antibody of the invention for a time sufficient to treat the cancer.

Exemplary antibodies that may be used are antagonistic antibodies specifically binding PD-1, antagonistic antibodies specifically binding TIM-3, and antagonistic bispecific PD-1/TIM-3 antibodies PD1B114, PD1B149, PD1B160, PD1B162, PD1B164, PD1B11, PD1B183, PD1B184, PD1B185, PD1B187, PD1B71, PD1B177, PD1B70, PD1B175, PD1B194, PD1B195, PD1B196, PD1B197, PD1B198, PD1B199, PD1B200, PD1B201, TM3B103, TM3B105, TM3B109, TM3B108, TM3B113, TM3B189, TM3B190, TM3B193, TM3B195, TM3B196, TM3B291, PTBB14, PTBB15, PTBB16, PTBB17, PTBB24, PTBB30, PTBB27, PTBB28, PTBB18, PTBB20 and PTBB21 having the VH and the VL amino acid sequence and characteristics as described herein.

Cancer may be a hyperproliferative condition or disorder, a solid tumor, a hematological malignancy, a soft tissue tumor, or a metastatic lesion.

"Cancer" is meant to include all types of cancerous growths or oncogenic processes, metastatic tissues or malignantly transformed cells, tissues, or organs, irrespective of histopathology type or stage of invasiveness. Examples of cancers include solid tumors, hematological malignancies, soft tissue tumors, and metastatic lesions. Exemplary solid tumors include malignancies, e.g., sarcomas, and carcinomas (including adenocarcinomas and squamous cell carcinomas) of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, a rectal cancer, a renal-cell carcinoma, a liver cancer, a non-small cell carcinoma of the lung, a cancer of the small intestine and a cancer of the esophagus. Squamous cell carcinomas include malignancies, e.g., in the lung, esophagus, skin, head and neck region, oral cavity, anus, and cervix.

In some embodiments, the cancer is a melanoma.

Metastatic lesions of the aforementioned cancers may also be treated or prevented using the methods and antibodies of the invention described herein.

Exemplary cancers whose growth may be inhibited or reduced using the antibodies of the invention include cancers that may be responsive to immunotherapy. Exemplary such cancers include a melanoma, a renal cancer, a prostate cancer, a breast cancer, a colon cancer, a gastrointestinal cancer, a stomach cancer, an esophageal cancer, a lung cancer, a metastatic malignant melanoma, a clear cell carcinoma, a hormone refractory prostate adenocarcinoma, a non-small cell lung cancer or cancer of the head and neck. Refractory or recurrent malignancies may be treated using the antibodies of the invention described herein.

Exemplary other cancers that may be treated with the antibodies of the invention ae an anal cancer, a basal cell carcinoma, a biliary tract cancer, a bladder cancer, a bone cancer, brain and CNS cancers, a carcinoma of the fallopian tubes, carcinoma of the vagina, a carcinoma of the vulva, a cutaneous or intraocular malignant melanoma, a astro-esophageal cancer, a testicular cancer, an ovarian cancer, a pancreatic cancer, a rectal cancer, an uterine cancer, a primary CNS lymphoma; a neoplasm of the central nervous system (CNS), a cervical cancer, a choriocarcinoma, a rectum cancer, a connective tissue cancer, a cancer of the digestive system, an endometrial cancer, an eye cancer; an intra-epithelial neoplasm, a kidney cancer, a larynx cancer, a liver cancer; a small cell lung cancer, a neuroblastoma, an oral cavity cancer (e.g., lip, tongue, mouth, and pharynx), a nasopharyngeal cancer, a retinoblastoma, a rhabdomyosarcoma, a cancer of the respiratory system, a sarcoma, a thyroid cancer, a cancer of the urinary system, a hepatocarcinoma, a cancer of the anal region, a carcinoma of the fallopian tubes, a carcinoma of the vagina, a carcinoma of the vulva, a cancer of the small intestine, a cancer of the endocrine system, a cancer of the parathyroid gland, a cancer of the adrenal gland, a sarcoma of soft tissue, a cancer of the urethra, a cancer of the penis, solid tumors of childhood, a tumor angiogenesis, a spinal axis tumor, a brain stem glioma, a pituitary adenoma, Kaposi's sarcoma, Merkel cell cancer, an epidermoid cancer, a squamous cell cancer, an environmentally induced cancers including those induced by asbestos, as well as other carcinomas and sarcomas, and combinations of said cancers.

Exemplary hematological malignancies that may be treated with the antibodies of the invention include leukemias, lymphomas and myeloma, such as a precursor B-cell lymphoblastic leukemia/lymphoma and a B-cell non-Hodgkin's lymphoma, an acute promyelocytic leukemia, an acute lymphoblastic leukemia (ALL), a B-cell chronic lymphocytic leukemia(CLL)/small lymphocytic lymphoma (SLL), a B-cell acute lymphocytic leukemia, a B-cell prolymphocytic leukemia, a lymphoplasmacytic lymphoma, a mantle cell lymphoma (MCL), a follicular lymphoma (FL), including low-grade, intermediate-grade and high-grade FL, a cutaneous follicle center lymphoma, a marginal zone B-cell lymphoma (MALT type, nodal and splenic type), a hairy cell leukemia, a diffuse large B-cell lymphoma (DLBCL), Burkitt's lymphoma (BL), a plasmacytoma, a multiple myeloma (MM), a plasma cell leukemia, a post-transplant lymphoproliferative disorder, Waldenstrom's macroglobulinemia, plasma cell disorders, an anaplastic large-cell lymphoma (ALCL), a T-cell acute lymphocytic leukemia, a primary systemic amyloidosis (e.g. light chain amyloidosis), a pro-lymphocytic/myelocytic leukemia, an acute myeloid leukemia (AML), a chronic myeloid leukemia (CML), a large granular lymphocytic (LGL) leukemia, a NK-cell leukemia and Hodgkin's lymphoma.

"Plasma cell disorder" refers to disorders characterized by clonal plasma cells, and includes a multiple myeloma, a light chain amyloidosis and Waldenstrom's macroglobulinemia. Light chain amyloidosis and Waldenstrom's macroglobulinemia can arise independently from multiple myeloma. They may also present simultaneously with multiple myeloma, and develop either before or after the development of multiple myeloma.

Exemplary B-cell non-Hodgkin's lymphomas are a lymphomatoid granulomatosis, a primary effusion lymphoma, an intravascular large B-cell lymphoma, a mediastinal large B-cell lymphoma, heavy chain diseases (including γ, μ, and a disease), lymphomas induced by therapy with immunosuppressive agents, such as cyclosporine-induced lymphoma, and methotrexate-induced lymphoma.

Patients having cancer including metastatic cancer that express PD-L1 may be treated with the antibodies of the invention. The cancer may be a melanoma, a renal cell carcinoma, a squamous non-small cell lung cancer (NSCLC), a non-squamous NSCLC, a colorectal cancer, a castration-resistant prostate cancer, an ovarian cancer, a gastric cancer, an adenocarcinoma (ACA), a squamous cell carcinoma (SCC), a hepatocellular carcinoma (HCC), a pancreatic carcinoma, a squamous cell carcinoma of the head and neck, carcinomas of the esophagus, gastrointestinal tract and breast.

Patients having cancer that expresses TIM-3 may be treated with the antibodies of the invention. TIM-3-expressing cancers include a cervical cancer, a lung cancer, a NSCLC, an acute myeloid leukemia (AML), a diffuse large B cell lymphoma (DLBCL), a melanoma, a renal cancer, a renal cell carcinoma (RCC), a kidney clear cell carcinoma, a kidney papillary cell carcinoma, a metastatic renal cell carcinoma, a squamous cell carcinoma, an esophageal squamous cell carcinoma, a nasopharyngeal carcinoma, a colorectal cancer, a breast cancer (e.g., a breast cancer that does not express one, two or all of estrogen receptor, progesterone receptor, or Her2/neu, e.g., a triple negative breast cancer), a mesothelioma, a hepatocellular carcinoma, and an ovarian cancer. The TIM-3-expressing cancer may be a metastatic cancer.

In some embodiments, the subject has a solid tumor.

In some embodiments, the subject has a hematological malignancy.

In some embodiments, the solid tumor is a melanoma.

In some embodiments, the solid tumor is a lung cancer.

In some embodiments, the solid tumor is a non-small cell lung cancer (NSCLC).

In some embodiments, the solid tumor is a squamous non-small cell lung cancer (NSCLC).

In some embodiments, the solid tumor is a non-squamous NSCLC.

In some embodiments, the solid tumor is a lung adenocarcinoma.

In some embodiments, the solid tumor is a renal cell carcinoma (RCC).

In some embodiments, the solid tumor is a mesothelioma.

In some embodiments, the solid tumor is a nasopharyngeal carcinoma (NPC).

In some embodiments, the solid tumor is a colorectal cancer.

In some embodiments, the solid tumor is a prostate cancer.

In some embodiments, the solid tumor is castration-resistant prostate cancer.

In some embodiments, the solid tumor is a stomach cancer.

In some embodiments, the solid tumor is an ovarian cancer.

In some embodiments, the solid tumor is a gastric cancer.

In some embodiments, the solid tumor is a liver cancer.

In some embodiments, the solid tumor is pancreatic cancer.

In some embodiments, the solid tumor is a thyroid cancer.

In some embodiments, the solid tumor is a squamous cell carcinoma of the head and neck.

In some embodiments, the solid tumor is a carcinomas of the esophagus or gastrointestinal tract.

In some embodiments, the solid tumor is a breast cancer.

In some embodiments, the solid tumor is a fallopian tube cancer.

In some embodiments, the solid tumor is a brain cancer.

In some embodiments, the solid tumor is an urethral cancer.

In some embodiments, the solid tumor is a genitourinary cancer.

In some embodiments, the solid tumor is an endometriosis.

In some embodiments, the solid tumor is a cervical cancer.

In some embodiments, the solid tumor is a metastatic lesion of the cancer.

In some embodiments, the hematological malignancy is a lymphoma, a myeloma or a leukemia.

In some embodiments, the hematological malignancy is a B cell lymphoma.

In some embodiments, the hematological malignancy is Burkitt's lymphoma.

In some embodiments, the hematological malignancy is Hodgkin's lymphoma.

In some embodiments, the hematological malignancy is a non-Hodgkin's lymphoma.

In some embodiments, the hematological malignancy is a myelodysplastic syndrome.

In some embodiments, the hematological malignancy is an acute myeloid leukemia (AML).

In some embodiments, the hematological malignancy is a chronic myeloid leukemia (CML).

In some embodiments, the hematological malignancy is a chronic myelomoncytic leukemia (CMML).

In some embodiments, the hematological malignancy is a multiple myeloma (MM).

In some embodiments, the hematological malignancy is a plasmacytoma.

In some embodiments, the subject has a tumor that expresses PD-L1.

In some embodiments, the subject has tumor-infiltrating T lymphocytes (TILs) in the tumor tissue.

In some embodiments, the subject has PD-1$^+$ TIM-3$^+$ TILs in the tumor tissue.

In some embodiments, the subject has increased number of PD-1$^+$ TIM-3$^+$ tumor-infiltrating T lymphocytes (TILs) in the tumor tissue.

"Increased number" refers to statistically significant increase in a subject when compared to a control. "Increased number" for example refers to statistically significant increase in the number of TILs in a subject (e.g. patient) pre- and post-treatment with a PD-1 antibody or other therapeutic.

In some embodiments, the subject has increased expression or activity of interferon-gamma (IFN-γ).

In some embodiments, the subject has been treated with an anti-PD-1 antibody.

In some embodiments, the subject is refractory to treatment with the anti-PD-1 antibody.

In some embodiments, the subject has a relapsed tumor after treatment with the anti-PD-1 antibody.

In some embodiments, the subject has been treated with the anti-PD-1 antibody comprising the VH of SEQ ID NO: 230 and the VL of SEQ ID NO: 231 (e.g. KEYTRUDA® (pembrolizumab)).

In some embodiments, the subject has been treated with the anti-PD-1 antibody comprising the VH of SEQ ID NO: 232 and the VL of SEQ ID NO: 233 (e.g. OPDIVO® (nivolumab)).

In some embodiments, the subject is refractory to treatment with the anti-PD-1 antibody comprising the VH of SEQ ID NO: 230 and the VL of SEQ ID NO: 231 (e.g. KEYTRUDA® (pembrolizumab)).

In some embodiments, the subject is refractory to treatment with the anti-PD-1 antibody comprising the VH of SEQ ID NO: 232 and the VL of SEQ ID NO: 233 (e.g. OPDIVO® (nivolumab)).

In some embodiments, the subject has a relapsed tumor after treatment with the anti-PD-1 antibody comprising the VH of SEQ ID NO: 230 and the VL of SEQ ID NO: 231 (e.g. KEYTRUDA® (pembrolizumab).

In some embodiments, the subject has a relapsed tumor after treatment with the anti-PD-1 antibody comprising the VH of SEQ ID NO: 232 and the VL of SEQ ID NO: 233 (e.g. OPDIVO® (nivolumab)).

```
                                          SEQ ID NO: 230
QVQLVQSGVEVKKPGASVKVSCKASGYTFTNYYMYWVRQAPGQGLEWMGG

INPSNGGTNFNEKFKNRVTLTTDSSTTTAYMELKSLQFDDTAVYYCARRD

YRFDMGFDYWGQGTTVTVSS

SEQ ID NO: 231
EIVLTQSPATLSLSPGERATLSCRASKGVSTSGYSYLHWYQQKPGQAPRL

LIYLASYLESGVPARFSGSGSGTDFTLTISSLEPEDFAVYYCQHSRDLPL

TFGGGTKVEIK

SEQ ID NO: 232
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSS

SEQ ID NO: 233
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIK
```

In some embodiments, the subject has been treated or is being treated with a PD-L1 antibody.

In some embodiments, the subject is refractory to treatment with the PD-L1 antibody.

In some embodiments, the subject has a relapsed tumor after treatment with the PD-L1 antibody.

In some embodiments, the subject is refractory or relapsed after treatment with the PD-L1 antibody durvalumab (MEDI-4736). Durvalumab comprises the VH of SEQ ID NO: 234 and the VL of SEQ ID NO: 235.

```
                                          SEQ ID NO: 234
EVQLVESGGGLVQPGGSLRLSCAASGFTFSRYWMSWVRQAPGKGLEWVAN

IKQDGSEKYYVDSVKGRFTISRDNAKNSLYLQMNSLRAEDTAVYYCAREG

GWFGELAFDYWGQGTLVTVSS
```

-continued

SEQ ID NO: 235
EIVLTQSPGTLSLSPGERATLSCRASQRVSSSYLAWYQQKPGQAPRLLIY

DASSRATGIPDRFSGSGSGTDFTLTISRLEPEDFAVYYCQQYGSLPWTFG

QGTKVEIK

In some embodiments, the subject is refractory or relapsed after treatment with the PD-L1 antibody atezolizumab.
Atezolizumab comprises the VH of SEQ ID NO: 236 and the VL of SEQ ID NO: 237.

SEQ ID NO: 236
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS

SEQ ID NO: 237
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIK

In some embodiments, the subject is refractory or relapsed after treatment with the PD-L1 antibody avelumab. Avelumab comprises the VH of SEQ ID NO: 238 and the VL of SEQ ID NO: 239.

SEQ ID NO: 238
EVQLLESGGGLVQPGGSLRLSCAASGFTFSSYIMMWVRQAPGKGLEWVSS

IYPSGGITFYADTVKGRFTISRDNSKNTLYLQMNSLRAEDTAVYYCARIK

LGTVTTVDYWGQGTLVTVSS

SEQ ID NO: 239
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL

In some embodiments, the subject is refractory or relapsed after treatment with the PD-L1 antibody MDX-1105.

In some embodiments, the subject has been treated or is being treated with a PD-L2 antibody.

In some embodiments described herein, the subject is refractory to treatment with a PD-L2 antibody.

In some embodiments, the subject has a relapsed tumor after treatment with a PD-L2 antibody.

Various qualitative and/or quantitative methods may be used to determine relapse or refractory nature of the disease. Symptoms that may be associated with relapse or resistance are, for example, a decline or plateau of the well-being of the patient or re-establishment or worsening of various symptoms associated with solid tumors, and/or the spread of cancerous cells in the body from one location to other organs, tissues or cells.

TIM-3 expression was found herein to be elevated in CD8$^+$ T cells isolated from tumors after anti-PD-1 antibody treatment. Therefore, therapeutic administration of antagonistic antibodies specifically binding TIM-3 or antagonistic bispecific PD-1/TIM-3 antibodies described herein to a subject who has already received or is receiving anti-PD-1 antibody therapy, is refractory to the anti-PD-1 antibody treatment or has relapsed after or during the anti-PD-1 antibody treatment may improve the clinical outcome of the patients.

The invention also provides a method of treating a cancer in a subject, comprising administering to the subject a therapeutically effective amount of the antagonistic antibody specifically binding TIM-3 of the invention, wherein the subject is being treated or has been treated with an anti-PD-1 antibody.

In some embodiments, the antagonistic antibody specifically binding TIM-3 comprises the VH of SEQ ID NO: 146 and the VL of SEQ ID NO: 156.

The invention also provides a method of treating a cancer in a subject, comprising administering to the subject a therapeutically effective amount of the antagonistic antibody specifically binding TIM-3 comprising the VH of SEQ ID NO: 146 and the VL of SEQ ID NO: 156, wherein the subject is being treat or has been treated with the anti-PD-1 antibody KEYTRUDA® (pembrolizumab) comprising the VH of SEQ ID NO: 230 and the VL of SEQ ID NO: 231.

The invention also provides a method of treating a cancer in a subject, comprising administering to the subject a therapeutically effective amount of the antagonistic antibody specifically binding TIM-3 comprising the VH of SEQ ID NO: 146 and the VL of SEQ ID NO: 156, wherein the subject is being treat or has been treated with the anti-PD-1 antibody OPDIVO® (nivolumab) comprising the VH of SEQ ID NO: 232 and the VL of SEQ ID NO: 233.

The invention also provides a method of treating a cancer in a subject, comprising administering to the subject a therapeutically effective amount of the antagonistic antibody specifically binding TIM-3 of the invention, wherein the subject is being treated or has been treated with an anti-PD-L1 antibody.

The invention also provides a method of treating a cancer in a subject, comprising administering to the subject a therapeutically effective amount of the antagonistic antibody specifically binding TIM-3 of the invention, wherein the subject is being treated or has been treated with an anti-PD-L2 antibody.

The invention also provides a method of treating a cancer in a subject, comprising administering to the subject a therapeutically effective amount of the antagonistic bispecific PD-1/TIM-3 antibody the invention, wherein the subject is being treated or has been treated with an anti-PD-1 antibody.

The invention also provides a method of treating a cancer in a subject, comprising administering to the subject a therapeutically effective amount of the antagonistic bispecific PD-1/TIM-3 antibody the invention, wherein the subject is being treated or has been treated with an anti-PD-L1 antibody.

The invention also provides a method of treating a cancer in a subject, comprising administering to the subject a therapeutically effective amount of the antagonistic bispecific PD-1/TIM-3 antibody the invention, wherein the subject is being treated or has been treated with an anti-PD-L2 antibody.

The invention also provides a method of treating a cancer in a subject, comprising administering to the subject a therapeutically effective amount of the antagonistic antibody specifically binding PD-1 comprising the VH of SEQ ID NO: 48 and the VL of SEQ ID NO: 56 for a time sufficient to treat the cancer.

The invention also provides a method of treating a cancer in a subject, comprising administering to the subject a therapeutically effective amount of the antagonistic antibody specifically binding PD-1 comprising the VH of SEQ ID NO: 64 and the VL of SEQ ID NO: 65 for a time sufficient to treat the cancer.

Any of the PD-1, TIM-3 or bispecific PD-1/TIM-3 antibodies of the invention described herein may be used in the methods of the invention.

"Treat" or "treatment" refers to therapeutic treatment wherein the object is to slow down (lessen) an undesired physiological change or disease, such as the development or spread of tumor or tumor cells, or to provide a beneficial or desired clinical outcome during treatment. Beneficial or desired clinical outcomes include alleviation of symptoms, diminishment of extent of disease, stabilized (i.e., not worsening) state of disease, delay or slowing of disease progression, lack of metastasis, amelioration or palliation of the disease state, and remission (whether partial or total), whether detectable or undetectable. "Treatment" may also mean prolonging survival as compared to expected survival if a subject was not receiving treatment. Those in need of treatment include those subjects already with the undesired physiological change or diseases well as those subjects prone to have the physiological change or disease.

A "therapeutically effective amount" refers to an amount effective, at dosages and for periods of time necessary, to achieve a desired therapeutic result. A therapeutically effective amount of the antibody of the invention may vary according to factors such as the disease state, age, sex, and weight of the individual, and the ability of the antibody of the invention to elicit a desired response in the individual. Exemplary indicators of an effective therapeutic or combination of therapeutics include, for example, improved well-being of the patient, reduction in a tumor burden, arrested or slowed growth of a tumor, and/or absence of metastasis of cancer cells to other locations in the body.

Combination Therapies for Cancer Treatment

The antibodies of the invention may be administered in combination with a second therapeutic agent.

The antibodies of the invention may be administered in combination with one, two, three, four, five or six additional therapeutic agents.

Any of the antagonistic antibodies specifically binding PD-1, antagonistic antibodies specifically binding TIM-3 or antagonistic bispecific PD-1/TIM-3 antibodies of the invention may be used in combination with a second therapeutic agent.

Any of the antagonistic antibodies specifically binding PD-1, antagonistic antibodies specifically binding TIM-3 or antagonistic bispecific PD-1/TIM-3 antibodies of the invention may be used in combination with one, two, three, four, five or six additional therapeutic agents.

"In combination with" refers to administering of the antibodies of the invention and at least one second therapeutic agent concurrently as single agents or sequentially as single agents in any order. In general, each agent will be administered at a dose and/or on a time schedule determined for that agent.

In some embodiments, the second therapeutic agent modulates activity of a molecule involved in the cancer-immunity cycle, e.g. a molecule involved in stimulatory or inhibitory pathways functioning in release of cancer cell antigens, cancer antigen presentation, T cell priming and activation, trafficking of T cells to tumors, infiltration of T cells into tumors, recognition of cancer cells by T cells, and killing of cancer cells. The cancer-immunity cycle is described in Chen and Mellman (2013) *Immunity* 39:1-10. In some embodiments, the second therapeutic agend modulates activity of a molecule involved in regulation of activity of T regulatory cells (Treg), co-stimulatory or co-inhibitory ligands expressed on tumors, activating or inhibitory receptors on natural killer (NK) cells, or immunosuppressive factors in the tumor microenvironment. Combination cancer immunotherapies are described in Manoney et al., (2015) *Nature Reviews* 14:561-584.

The second therapeutic agent typically enhances the activity of stimulatory molecules and suppresses the activity of inhibitory molecules, as is well known. Thus, "modulate" refers to the enhancement of immune response by the second therapeutic agent, wheatear the agent itself is agonist or antagonist of a specific molecule.

In some embodiments, the antibodies of the invention are administered in combination with an inhibitor of a T cell inhibitory molecule.

In some embodiments, the antibodies of the invention are administered in combination with an inhibitor of a T cell inhibitory molecule PD-1, PD-L1, PD-L2, VISTA, BTNL2, B7-H3, B7-H4, HVEM, HHLA2, CTLA-4, LAG-3, TIM-3, BTLA, CD160, CEACAM-1, LAIR1, TGFβ, IL-10, Siglec family protein, KIR, CD96, TIGIT, NKG2A, CD112, CD47, SIRPA or CD244.

In some embodiments, KIR is KIR2DL1, KIR2DL2 or KIR2DL3.

Inhibition of inhibitory molecules may be performed by inhibition at the DNA, RNA or protein level. In some embodiments, an inhibitory nucleic acid (e.g., a dsRNA, siRNA or shRNA) is used to inhibit expression of the inhibitory molecule.

In some embodiments, the inhibitor of the inhibitory molecule is a soluble ligand of the inhibitory molecule.

In some embodiments, the inhibitor of the inhibitory molecule is an antagonistic antibody specifically binding the inhibitory molecule.

In some embodiments, the inhibitor of the inhibitory molecule is CTLA-4-Fc or TIM-3-Fc fusion protein.

In some embodiments, the inhibitor of the inhibitory molecule is an antibody or an antibody fragment that binds PD-1, PD-L1, PD-L2, VISTA, BTNL2, B7-H3, B7-H4, HVEM, HHLA2, CTLA-4, LAG-3, TIM-3, BTLA, CD160, CEACAM-1, LAIR1, TGFβ, IL-10, Siglec family protein, KIR, CD96, TIGIT, NKG2A, CD112, CD47, SIRPA or CD244.

Exemplary anti-PD-1 antibodies that may be used in the methods of the invention are those described herein and in U.S. Pat. Nos. 5,897,862 and 7,488,802, and in Int. Patent Publ. Nos. WO2004/004771, WO2004/056875, WO2006/121168, WO2008/156712, WO2010/029435, WO2010/036959, WO2011/110604, WO2012/145493, WO2014/194302, WO2014/206107, WO2015/036394, WO2015/035606, WO2015/085847, WO2015/112900 and WO2015/112805. Exemplary anti-PD1 antibodies include KEYTRUDA® (pembrolizumab) and OPDIVO® (nivolumab).

In some embodiments, the antibodies of the invention are administered in combination with a soluble PD-1 ligand.

In some embodiments, the soluble PD-1 ligand is soluble PD-L1 or soluble PD-L2 fused to an Fc.

In some embodiments, the soluble PD-1 ligand is AMP-224.

In some embodiments, the antibodies of the invention are administered in combination with an anti-PD-L1 antibody, or antigen-binding fragments thereof.

Exemplary PD-L1 antibodies that may be used in the methods of the invention are antibodies MDPL3280A (Genentech/Roche) and other human monoclonal antibodies disclosed in U.S. Pat. No. 7,943,743 and U.S Patent Publ.

No. 20120039906. Other anti-PD-L1 binding agents include YW243.55.570 (heavy and light chain variable regions are shown in SEQ ID NOs 20 and 21 in WO2010/077634) and MDX-1105 (also referred to as BMS-936559, and, e.g., anti-PD-L1 binding agents disclosed in WO2007/005874). The VH and the VL sequences of anti-PD-L1 antibodies durvalumab, atezolimumab and avelumab that may be used are disclosed herein.

Exemplary PD-L2 antibodies that may be used in the methods of the invention are those described in U.S. Pat. Nos. 8,080,636, 8,188,238, U.S. Patent Publ. No. 20110271358 and Int. Patent Publ. No. WO2012145493.

Exemplary B7-H4 antibodies that may be used in the methods of the invention are those described in U.S. Pat. Nos. 7,888,477, 8,609,816, 7,931,896, European Patent No. 1817055, U.S. Patent Publ. No. US20140037551 and US2014029486, and Int. Patent Publ. Nos. WO2014/100483 and WO2014/159835.

Exemplary anti-CTLA-4 antibodies that may be used in the methods of the invention are ipilimumab (MDX-010, CAS No. 477202-00-9) and tremelimumab (IgG2 monoclonal antibody available from Pfizer, formerly known as ticilimumab, CP-675,206).

Exemplary anti-LAG-3 antibodies that may be used in the methods of the invention are those described for example in Int. Patent Publ. Nos. WO2008/132601 and WO2010/019570.

Exemplary anti-CEACAM-1 antibodies that may be used in the methods of the invention are those described in U.S. Pat. No. 8,598,322 and in U.S. Patent Publ. Nos. US2004/0047858, US20140271618 and US20120100158. Without wishing to be bound by any particular theory, CEACAM-1 has been described as a ligand and partner of TIM-3 (see e.g., Int. Patent Publ. No. WO2014/022332). Synergistic in vivo effect of the combination of anti-TIM-3 and anti-CEACAM-1 antibodies have been detected in xenograft cancer models (see e.g., Int. Patent Publ. No. WO2014/022332). Tumors may use CEACAM-1 to inhibit the immune system. Therefore, anti-CEACAM-1 antibodies may be used in combination with the antibodies of the invention described herein.

Exemplary anti-LAIR1 antibodies that may be used in the methods of the invention are those described in U.S. Pat. No. 6,479,638 and Int. Patent Publ. No. WO2010/078580.

Exemplary anti-CD96 antibodies that may be used in the methods of the invention are those described in Int. Patent Publ. No. WO2015/024060.

Exemplary anti-TIM-3 antibodies that may be used in the methods of the invention are those described herein and in Int. Patent Publ. Nos. WO2011/155607, WO2013/006490 and WO2015/117002.

Exemplary anti-TIGIT antibodies that may be used in the methods of the invention are those described in U.S. Patent Publ. Nos. US20140056890 and US20150216970. An exemplary anti-TIGIT antibody is RG-6058 (MTIG-7192A).

TIGIT expression was found herein to be elevated in CD8$^+$ T cells isolated from tumors after anti-TIM-3 antibody treatment in animal models of cancer. Therefore, therapeutic administration of antagonistic antibodies specifically binding TIGIT to a subject who has already received or is receiving anti-TIM-3 antibody therapy, is refractory to the anti-TIM-3 antibody treatment or has relapsed after or during the anti-TIM-3 antibody treatment may improve the clinical outcome of the patients.

The invention also provides a method of treating a cancer in a subject, comprising administering to the subject in need thereof a therapeutically effective amount of an antagonistic antibody that specifically binds TIM-3 and an antagonistic antibody that specifically binds TIGIT for a time sufficient to treat the cancer.

In some embodiments, the antagonistic antibody that specifically binds TIGIT is administered after administration of the antagonistic antibody specifically binding TIM-3.

In some embodiments, the antagonistic antibody that specifically binds TIGIT and the antagonistic antibody specifically binding TIM-3 are administered concurrently as single agents or sequentially as single agents in any order.

Exemplary anti-BTLA antibodies that may be used in the methods of the invention are those described in U.S. Pat. Nos. 8,546,541, 7,479,544, 8,188,232, 8,247,537, 8,563,694 and in Int. Patent Publ. No. WO2014184360.

Exemplary anti-HVEM antibodies that may be used in the methods of the invention are those described in U.S. Patent Publ. No. US20110280866.

Exemplary CD47 antibodies that may be used in the methods of the invention are those described in U.S. Pat. No. 8,101,719.

Exemplary CD244 antibodies that may be used in the methods of the invention include those described in U.S. Pat. No. 5,688,690.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-TIM-3 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-PD-L1 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-PD-L2 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-VISTA antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-BTNL2 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-B7-H3 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-B7-H4 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-HVEM antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-HLA2 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CTLA-4 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-LAG-3 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-TIM-3 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-BTLA antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD160 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CEACAM-1 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-LAIR1 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-TGFβ antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-IL-10 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-TIGIT antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-KIR antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-NKG2A antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD112 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD47 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-SIRPA antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD244 antibody or antigen-binding fragment thereof.

The immune inhibitory molecules may regulate or synergistically regulate T-cell functions to promote tumoral immune escape. Therefore, combination therapies with two or more inhibitors of the inhibitory molecules may provide an improved therapy to a patient when compared to monotherapy alone.

In some embodiments, the antibodies of the invention are administered in combination with an activator of an activating molecule.

In some embodiments, the antibodies of the invention are administered in combination with an activator of an activating molecule CD86, CD80, CD28, ICOS, ICOS ligand, TMIGD2, CD40, GITR ligand, 4-1BB ligand, OX40 ligand, CD70, CD40L, TNFRSF25, LIGHT, GITR, OX-40, CD27, CD137, NKG2D, CD48, CD226 or MICA.

Activation of activating molecules may be performed using for example soluble ligands or ligand derivatives of the activating molecules, peptides or agonistic antibodies.

In some embodiments, the activator of the activating molecule is a soluble ligand of the T cell activating molecule.

In some embodiments, the activator of the activating molecule is an agonistic antibody specifically binding the activating molecule.

Exemplary anti-CD40 antibodies that may be used in the methods of the invention include CP-870,893 and humanized S2C6 described in U.S. Pat. No. 7,288,251 (antibody 21.4.1) and U.S. Pat. No. 8,303,955, respectively, and anti-CD40 antibodies described in Int. Patent Publ. Nos. WO2001/056603, WO2001/083755, WO2013/034904 and WO2014/070934.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No. 090505B1, U.S. Pat. No. 8,586,023, Int. Patent. Publ. Nos. WO2010/003118 and WO2011/090754, or an anti-GITR antibody described in U.S. Pat. Nos. 7,025,962, 7,812,135, 8,388,967, 8,591,886 and 7,618,632, European Patent Nos. 1947183 and 1866339, or Int. Patent Publ. Nos. WO2011/028683, WO2013/039954, WO2005/007190, WO2007/133822, WO2005/055808, WO1999/40196, WO2001/03720, WO1999/20758, WO2006/083289, WO2005/115451 and WO2011/051726.

GITR expression was found herein to be elevated in $CD8^+$ T cells isolated from tumors after anti-PD-1 antibody treatment in animal models of cancer. The restoration of GITR expression on TILs by anti-PD-1 treatment supports that combination therapy with anti-GITR and anti-PD-1 antibodies may improve the clinical outcome of the patients.

The invention also provides a method of treating a cancer in a subject, comprising administering to the subject in need thereof a therapeutically effective amount of an antagonistic antibody that specifically binds PD-1 and an agonistic antibody that specifically binds GITR for a time sufficient to treat the cancer.

In some embodiments, the agonistic antibody that specifically binds GITR is administered after administration of the antagonistic antibody specifically binding PD-1.

In some embodiments, the agonistic antibody that specifically binds GITR and the antagonistic antibody specifically binding PD-1 are administered concurrently as single agents or sequentially as single agents in any order.

Exemplary OX40 antibodies that may be used in the methods of the invention include those described in U.S. Pat. Nos. 8,133,983, 7,960,515, U.S. Patent Publ. No. 20130280275 and Int. Patent Publ. Nos. WO2013028231 and WO2014148895.

An exemplary OX40 antibody that may be used in the methods of the invention is an antibody comprising the VH of SEQ ID NO: 309 and the VL of SEQ ID NO: 310.

Another exemplary OX40 antibody that may be used in the methods of the invention is an antibody comprising the VH of SEQ ID NO: 311 and the VL of SEQ ID NO: 312.

OX40 expression was found herein to be elevated in $CD8^+$ T cells isolated from tumors after anti-PD-1 antibody treatment in animal models of cancer. The restoration of OX40 expression on TILs by anti-PD-1 treatment supports that combination therapy with anti-OX40 and anti-PD-1 antibodies may improve the clinical outcome of the patients. The invention also provides a method of treating a cancer in a subject, comprising administering to the subject in need thereof a therapeutically effective amount of an antagonistic antibody that specifically binds PD-1 and an agonistic antibody that specifically binds OX40 for a time sufficient to treat the cancer.

In some embodiments, the agonistic antibody that specifically binds OX40 is administered after administration of the antagonistic antibody specifically binding PD-1.

In some embodiments, the agonistic antibody that specifically binds OX40 and the antagonistic antibody specifically binding PD-1 are administered concurrently as single agents or sequentially as single agents in any order.

Exemplary CD70 antibodies that may be used in the methods of the invention include those described in U.S. Patent Publ. No. US20130336976.

Exemplary TNFRSF25 antibodies that may be used in the methods of the invention include those described in U.S. Pat. No. 7,708,996.

Exemplary CD27 antibodies that may be used in the methods of the invention include those described in U.S. Patent Publ. No. US20130336976.

Exemplary CD137 antibodies that may be used in the methods of the invention include those described in U.S. Pat. Nos. 6,974,863, 6,303,121, 7,138,500, 7,288,638, 8,716,452, 8,821,867 and in U.S. Patent Publ. No. US20130149301.

CD137 expression was found herein to be elevated in $CD8^+$ T cells isolated from tumors after anti-PD-1 antibody treatment in animal models of cancer. The restoration of CD137 expression on TILs by anti-PD-1 treatment supports that combination therapy with anti-CD137 and anti-PD-1 antibodies may improve the clinical outcome of the patients.

The invention also provides a method of treating a cancer in a subject, comprising administering to the subject in need thereof a therapeutically effective amount of an antagonistic antibody that specifically binds PD-1 and an agonistic antibody that specifically binds CD137 for a time sufficient to treat the cancer.

In some embodiments, the agonistic antibody that specifically binds CD137 is administered after administration of the antagonistic antibody specifically binding PD-1.

In some embodiments, the agonistic antibody that specifically binds CD137 and the antagonistic antibody specifically binding PD-1 are administered concurrently as single agents or sequentially as single agents in any order.

Exemplary NKG2D antibodies that may be used in the methods of the invention include those described in U.S. Patent Publ. No. US20110150870.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD86 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD80 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD28 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-ICOS antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-ICOS ligand antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-TMIGD2 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD40 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-GITR ligand antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-4-1BB ligand antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-OX40 ligand antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD70 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD40L antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-TNFRSF25 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-LIGHT antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-GITR antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-OX40 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD27 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD137 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-NKG2D antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD48 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-CD226 antibody or antigen-binding fragment thereof.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with an anti-MICA antibody or antigen-binding fragment thereof.

The combination of antibodies recited herein can be administered separately, e.g., as separate antibodies, or linked, e.g., as a bispecific or trispecific antibody molecule.

The efficacy of the combinations described herein may be tested in animal models known in the art.

Antibodies of the invention described herein may be administered in combination with a vaccine.

Exemplary vaccines are immunogenic agents, such as cancerous cells, purified tumor antigens (including recombinant proteins, antigen epitopes, peptides and carbohydrate molecules), tumor antigens delivered to a patient via gene therapy, cells, and cells transfected with genes encoding immune stimulating cytokines. Exemplary vaccines that may be used include peptides of melanoma antigens, such as peptides of gp100, MAGE antigens, Trp-2, MART1 and/or tyrosinase, or tumor cells transfected to express the cytokine GM-CSF, DNA-based vaccines, RNA-based vaccines, and viral transduction-based vaccines, peptides or prostate antigens or peptides of lung cancer antigens. The cancer vaccine may be prophylactic or therapeutic.

Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology.

Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., (1993) *Proc Natl Acad Sci* U.S.A. 90: 3539-43).

The antibodies of the invention described herein may be administered in combination with one or a collection of recombinant proteins and/or peptides expressed in or on a tumor in order to generate an immune response to these proteins. These proteins are normally viewed by the immune system as self-antigens and are therefore tolerant to them. The tumor antigen may also include the protein telomerase, which is required for the synthesis of telomeres of chromosomes and which is expressed in more than 85% of human cancers and in only a limited number of somatic tissues (Kim et al., (1994) *Science* 266: 2011-2013). Tumor antigens may also be "neo-antigens" expressed in or on cancer cells as a result of somatic mutations that alter protein sequence or create fusion proteins between two unrelated sequences (e.g., bcr-abl in the Philadelphia chromosome), or idiotype from B cell tumors. The tumor antigens may be antigen epitopes of prostate specific antigen (PSA), mesothelin, prostate-specific membrane antigen (PSMA), synovial sarcoma X2 (SSX2), NKX3.1, prostatic acidic phosphatase (PAP), or epidermal growth factor receptors, or peptides specific for variants of EGFR such as the well-known EGFRvIII overexpressed on tumor cells.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV), and Epstein-Barr virus (EBV). Another form of tumor specific antigens which may be used in combination with the antibodies of the invention described herein is purified heat shock proteins (HSP) isolated from the tumor tissue itself. HSP contain fragments of proteins from the tumor cells and are highly efficient at delivery to antigen presenting cells for eliciting tumor immunity (Suot and Srivastava (1995) *Science* 269: 1585-1588; Tamura et al., (1997) *Science* 278:117-120).

Dendritic cells (DC) are potent antigen presenting cells that may be used to prime antigen-specific responses. DC's may be produced ex vivo and loaded with various protein and peptide antigens as well as tumor cell extracts (Nestle et al., (1998) *Nature Medicine* 4: 328-332). DCs may also be transduced by genetic means to express these tumor antigens. DCs have also been fused directly to tumor cells for the purposes of immunization (Kugler et al., (2000) *Nature Medicine* 6:332-336). As a method of vaccination, DC immunization may be effectively combined with the antibodies of the invention described herein to activate more potent anti-tumor responses.

In some embodiments, the vaccine is a polypeptide or a fragment thereof, or a DNA or a RNA encoding the polypeptide or fragment thereof expressed on tumor cells.

In some embodiments, the polypeptide or fragment thereof expressed on tumor cells is PSMA.

In some embodiments, the polypeptide or fragment thereof expressed on tumor cells is mesothelin.

In some embodiments, the polypeptide or fragment thereof expressed on tumor cells is EGFR or EGFR variant such as EGFRvIII.

In some embodiments, the polypeptide or fragment thereof expressed on tumor cells is PAP.

In some embodiments, the polypeptide or fragment thereof expressed on tumor cells is synovial sarcoma X2 (SSX2).

In some embodiments, the polypeptide or fragment thereof expressed on tumor cells is NKX3.1.

In some embodiments, the tumor cells are melanoma, lung cancer, squamous non-small cell lung cancer (NSCLC), non-squamous NSCLC, colorectal cancer, prostate cancer, castration-resistant prostate cancer, ovarian cancer, gastric cancer, liver cancer, pancreatic cancer, thyroid cancer, squamous cell carcinoma of the head and neck, carcinomas of the esophagus or gastrointestinal tract or breast cancer cells.

In some embodiments, the antibodies of the invention are administered in combination with a renal carcinoma (RCC) vaccine.

In some embodiments, the antibodies of the invention are administered in combination with a lung cancer vaccine.

In some embodiments, the antibodies of the invention are administered in combination with a prostate cancer vaccine.

In some embodiments, the antibodies of the invention are administered in combination with a lung cancer vaccine.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with a tumor vaccine comprising a peptide fragment of EGFR or EGFRvIII, or a vector encoding the peptide fragment of EGFR or EGFRvIII.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with a tumor vaccine comprising a peptide fragment of mesothelin, or a vector encoding the peptide fragment of mesothelin.

In some embodiments, the antagonistic antibodies specifically binding PD-1 of the invention, the antagonistic antibodies specifically binding TIM-3 or the invention, or the antagonistic bispecific PD-1/TIM-3 antibodies of the invention are administered in combination with a tumor vaccine comprising a peptide fragment of prostate specific antigen, or a vector encoding the peptide fragment of prostate specific antigen.

Suitable vectors that may be used in the methods of the invention are well known and include lentiviral vectors, adenoviral vectors, minimal nucleic acid vector (MNAV), vaccinia virus, flow pox virus, Alpha virus-derived VRP, *Saccharomyces cerevisiae*, MVA, *Listeria* moonocytogenes, pVAX-based plasmid, see e.g. Pol et al., (2014) *Oncoimmunology* 1(3):e28185.

The antibodies of the invention may be administered in combination with a standard of care cancer treatment.

The antibodies of the invention described herein may be administered in combination with a standard of care cancer chemotherapeutic regimes. In these instances, it may be possible to reduce the dose of chemotherapeutic reagent administered (Mokyr et al., (1998) *Cancer Research* 58: 5301-5304).

In some embodiments, the antibodies of the invention may be administered in combination with one or more of other antibody molecules, chemotherapy, other anti-cancer therapy (e.g., targeted anti-cancer therapies, or oncolytic drugs), cytotoxic agents, cytokines, surgical and/or radiation procedures.

Exemplary cytotoxic agents that may be administered in combination with the antibodies of the invention include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation).

Standard of care therapeutics include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), vinorelbine (Navelbine®), Ibrutinib, idelalisib, and brentuximab vedotin.

Exemplary alkylating agents include, nitrogen mustards, ethylenimine derivatives, alkyl sulfonates, nitrosoureas and triazenes: uracil mustard (Aminouracil Mustard®, Chlorethaminacil®, Demethyldopan®, Desmethyldopan®, Haemanthamine®, Nordopan®, Uracil Nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), chlorambucil (Leukeran®), pipobroman (Amedel®, Vercyte®), triethylenemelamine (Hemel®, Hexalen®, Hexastat®), triethylenethiophosphoramine, temozolomide (Temodar®), thiotepa (Thioplex®), busulfan (Busilvex®, Myleran®), carmustine (BiCNU®), lomustine (CeeNU®) and streptozocin (Zanosar®). Additional exemplary alkylating agents include, oxaliplatin (Eloxatin®), temozolomide (Temodar® and Temodal®), dactinomycin (also known as actinomycin-D, Cosmegen®), altretamine (also known as hexamethylmelamine (HMM), Hexalen®), bendamustine (Treanda®), carboplatin (Paraplatin®), lomustine (also known as CCNU, CeeNU®), cisplatin (also known as CDDP, Platinol® and Platinol®-AQ), chlorambucil (Leukeran®), prednumustine, procarbazine (Matulane®), and thiotepa (also known as thiophosphoamide, TESPA and TSPA, Thioplex®).

Exemplary anthracyclines include, e.g., doxorubicin (Adriamycin® and Rubex®); bleomycin (Lenoxane®), daunorubicin (dauorubicin hydrochloride, daunomycin, and rubidomycin hydrochloride, Cerubidine®), daunorubicin liposomal (daunorubicin citrate liposome, DaunoXome®), mitoxantrone (DHAD, Novantrone®), epirubicin (Ellence™), idarubicin (Idamycin®, Idamycin PFS®), mitomycin C (Mutamycin®), geldanamycin, herbimycin, ravidomycin, and desacetylravidomycin.

Exemplary vinca alkaloids that may be used in combination with the antibodies of the invention include vinorelbine tartrate (Navelbine®), vincristine (Oncovin®), and vindesine (Eldisine®), vinblastine (also known as vinblastine sulfate, vincaleukoblastine and VLB, Alkaban-AQ® and Velban®) and vinorelbine (Navelbine®).

Exemplary proteosome inhibitors that may be used in combination with the antibodies of the invention are bortezomib (Velcade®); carfilzomib (Kyprolis®), ixazomib (Ninlaro®), marizomib (NPI-0052) and delanzomib (CEP-18770).

In some embodiments, the antibodies of the invention are administered in combination with a tyrosine kinase inhibitor (e.g., a receptor tyrosine kinase (RTK) inhibitor). Exemplary tyrosine kinase inhibitor include an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor), a platelet derived growth factor (PDGF) pathway inhibitor (e.g., a platelet derived growth factor receptor (PDGFR) inhibitor (e.g., a PDGFR-β inhibitor), a RAF-1 inhibitor, a KIT inhibitor and a RET inhibitor. In some embodiments, the second therapeutic is axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951 (tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, pazopanib hydrochloride, PD173074, Sorafenib Tosylate (Bay 43-9006), SU 5402, TSU-68 (SU6668), vatalanib, XL880 (GSK1363089, EXEL-2880). Selected tyrosine kinase inhibitors are chosen from sunitinib, erlotinib, gefitinib, or sorafenib. In some embodiments, the EGFR inhibitor is a bispecific EGFRc-Met antibody (EM-1 mAb) comprising the heavy and the light chains of SEQ ID NOs: 249, 250, 251 and 252 (US2014/0141000).

In some embodiments, the antibodies of the invention are administered in combination with Vascular Endothelial Growth Factor (VEGF) receptor inhibitors, including bevacizumab (Avastin®), axitinib (Inlyta®), brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy) propan-2-yl)2-aminopropanoate), sorafenib (Nexavar®); Pazopanib (Votrient®), sunitinib malate (Sutent®), cediranib (AZD2171, CAS 288383-20-1), vargatef (BIBF1120, CAS 928326-83-4), foretinib (GSK1363089), telatinib (BAY57-9352, CAS 332012-40-5), apatinib (YN968D1, CAS 811803-05-1), imatinib (Gleevec®), ponatinib (AP24534, CAS 943319-70-8), tivozanib (AV951, CAS 475108-18-0), regorafenib (BAY73-4506, CAS 755037-03-7), vatalanib dihydrochloride (PTK787, CAS 212141-51-0), brivanib (BMS-540215, CAS 649735-46-6), vandetanib (Caprelsa® or AZD6474), motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470), dovitinib dilactic acid (TK1258, CAS 852433-84-2), linfanib (ABT869, CAS 796967-16-3); Cabozantinib (XL184, CAS 849217-68-1), lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl) amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta [c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and aflibercept (Eylea®).

In some embodiments, the antibodies of the invention are administered in combination with a PI3K inhibitor. In one embodiment, the PI3K inhibitor is an inhibitor of delta and gamma isoforms of PI3K. Exemplary PI3K inhibitors that may be used are described in, e.g., WO 2010/036380, WO 2010/006086, WO 09/114870, WO 05/113556, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235).

In some embodiments, the antibodies of the invention are administered in combination with a mTOR inhibitor, e.g., one or more mTOR inhibitors chosen from one or more of rapamycin, temsirolimus (TORISEL®), AZD8055, BEZ235, BGT226, XL765, PF-4691502, GDC0980, SF1126, OSI-027, GSK1059615, KU-0063794, WYE-354, Palomid 529 (P529), PF-04691502, or PKI-587. ridaforolimus (formally known as deferolimus, (1R,2R,4S)-4-[(2R)-2 [(1R,9S,12S,15R,16E,18R,19R,21R,23S,24E,26E,28Z,30S, 32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.04,9] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl] methoxy]butyl]-L-arginylglycyl-L-α-aspartylL-serine-(SEQ ID NO: 237), inner salt (SF1126, CAS 936487-67-1), and XL765.

In some embodiments, the antibodies of the invention are administered in combination with a BRAF inhibitor, e.g., GSK2118436, RG7204, PLX4032, GDC-0879, PLX4720, and sorafenib tosylate (Bay 43-9006).

In some embodiments, the antibodies of the invention are administered in combination with a MEK inhibitor.

In some embodiments, the antibodies of the invention are administered in combination with a JAK2 inhibitor, e.g., CEP-701, INCB18424, CP-690550 (tasocitinib). In some embodiments, the antibodies of the invention are administered in combination with paclitaxel or a paclitaxel agent, e.g., TAXOL®, protein-bound paclitaxel (e.g., ABRAXANE®). Exemplary paclitaxel agents include nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87:225-230), and glucose-conjugated paclitaxel (e.g., 2'-paclitaxel methyl 2-glucopyranosyl succinate, see Liu et al., (2007) Bioorganic & Medicinal Chemistry Letters 17:617-620).

In some embodiments, the antibodies of the invention are administered in combination with a cellular immunotherapy (e.g., Provenge (e.g., Sipuleucel)), and optionally in combination with cyclophosphamide.

Exemplary therapeutic agents that may be used in combination with the antibodies of the invention for treatment of pancreatic cancer include a chemotherapeutic agent, e.g., paclitaxel or a paclitaxel agent (e.g., a paclitaxel formulation such as TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus), IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., RO5126766), Notch signaling inhibitor (e.g., MK0752), monoclonal antibody-antibody fusion protein (e.g., L19IL2), curcumin; HSP90 inhibitor (e.g., tanespimycin, STA-9090), rIL-2; denileukin diftitox; topoisomerase 1 inhibitor (e.g., irinotecan, PEP02); statin (e.g., simvastatin), Factor VIIa inhibitor (e.g., PCI-27483), AKT inhibitor (e.g., RX-0201), hypoxia-activated prodrug (e.g., TH-302), metformin hydrochloride, gamma-secretase inhibitor (e.g., R04929097), ribonucleotide reductase inhibitor (e.g., 3-AP), immunotoxin (e.g., HuC242-DM4), PARP inhibitor (e.g., KU-0059436, veliparib), CTLA-4 inhibitor (e.g., CP-675,206, ipilimumab), AdV-tk therapy, proteasome inhibitor (e.g., bortezomib (Velcade), NPI-0052), thiazolidinedione (e.g., pioglitazone), NPC-1C; Aurora kinase inhibitor (e.g., R763/AS703569), CTGF inhibitor (e.g., FG-3019), siG12D LODER and radiation therapy (e.g., tomotherapy, stereotactic radiation, proton therapy), surgery, and a combination thereof. In certain embodiments, a combination of paclitaxel or a paclitaxel agent, and gemcitabine can be used with the antibodies of the invention.

Exemplary therapeutic agents that may be used in combination with the antibodies of the invention for treatment of small cell lung cancer (SCLC) include approved drugs for treatment of SCLC such as methotrexate (Folex®, Mexate®), everolimus (Afinitor®), doxorubicin hydrochloride, etoposide phosphate (Etopophos®), topotecan hydrochloride (Hycamtin®), mechlorethamine hydrochloride (Mustargen®), topotecan hydrochloride. Other therapeutic agents that may be used are carboplatin, cisplatin, oxaliplatin, irinotecan, gemcitabine, liposomal SN-38, bendamustine, temozolomide, belotecan, NK012, FR901228, flavopiridol), tyrosine kinase inhibitor (e.g., EGFR inhibitor (e.g., erlotinib, gefitinib, cetuximab, panitumumab), multikinase inhibitor (e.g., sorafenib, sunitinib), VEGF inhibitor (e.g., bevacizumab, vandetanib), cancer vaccine (e.g., GVAX); Bcl-2 inhibitor (e.g., oblimersen sodium, ABT-263), proteasome inhibitor (e.g., bortezomib (Velcade), NPI-0052), paclitaxel or a paclitaxel agent; docetaxel, IGF-1 receptor inhibitor (e.g., AMG 479), HGF/SF inhibitor (e.g., AMG 102, MK-0646), chloroquine, Aurora kinase inhibitor (e.g., MLN8237), radioimmunotherapy (e.g., TF2), HSP90 inhibitor (e.g., tanespimycin, STA-9090), mTOR inhibitor (e.g., everolimus), Ep-CAM/CD3-bispecific antibody (e.g., MT110), CK-2 inhibitor (e.g., CX-4945), HDAC inhibitor (e.g., belinostat), SMO antagonist (e.g., BMS 833923), peptide cancer vaccine, and radiation therapy (e.g., intensity-modulated radiation therapy (IMRT), hypofractionated radiotherapy, hypoxia-guided radiotherapy), surgery, and combinations thereof.

Exemplary therapeutic agents that may be used in combination with the antibodies of the invention for treatment of non-small cell lung cancer include approved drugs for treatment of NSCLC including methotrexate (Folex®, Mexate®), paclitaxel (Abraxane®), afatinib (Gilotrif®), everolimus (Afinitor®), alectinib (Alecensa®), pemetrexed disodium (Alimta®), bevacizumab (Avastin®), carboplatin, ceritinib (Zykadia®), crizotinib (Xalkori®), ramucirumab (Cyramza®), docetaxel, everolimus (Afinitor®), gefitinib (Iressa®), afatinib dimaleate (Gilotrif®), gemcitabine hydrochloride (Gmezar®), pembrolizumab (Keytruda®), mechlorethamine hydrochloride (Mustargen®), vinorelbine tartrate (Navelbine®), necitumumab (Portrazza®), nivolumab (Opdivo®), osimertinib, paclitaxel (Taxol®), carboplatin, pemetrexed disodium, ramucirumab (Cyramza®), osimertinib (Tagrisso®). Other therapeutic agents that may be used are vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafur-gimeracil-oteracil potassium, sapacitabine), tyrosine kinase inhibitor (e.g., EGFR inhibitor (e.g., erlotinib, gefitinib, cetuximab, panitumumab, necitumumab, PF-00299804, nimotuzumab, RO5083945), MET inhibitor (e.g., PF-02341066, ARQ 197), PI3K kinase inhibitor (e.g., XL147, GDC-0941), Raf/MEK dual kinase inhibitor (e.g., RO5126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25 liposome vaccine, GVAX, recombinant DNA and adenovirus expressing L523S protein), Bcl-2 inhibitor (e.g., oblimersen sodium), proteasome inhibitor (e.g., bortezomib, carfilzomib, NPI-0052, MLN9708), paclitaxel or a paclitaxel agent, docetaxel, IGF-1 receptor inhibitor (e.g., cixutumumab, MK-0646, OSI 906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide (SEQ ID NO: 225)-TNF alpha conjugate, dichloroacetate (DCA), HGF inhibitor (e.g., SCH 900105), SAR240550, PPAR-gamma agonist (e.g., CS-7017), gamma-secretase inhibitor (e.g., RO4929097), epigenetic therapy (e.g., 5-azacitidine), nitroglycerin, MEK inhibitor (e.g., AZD6244), cyclin-dependent kinase inhibitor (e.g., UCN-01), cholesterol-Fus1, antitubulin agent (e.g., E7389), farnesyl-OH-transferase inhibitor (e.g., lonafarnib), immunotoxin (e.g., BB-10901, SS1 (dsFv) PE38), fondaparinux, vascular-disrupting agent (e.g., AVE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), EGFR/c-Met bispecific antibody EM-1 as described in US2014/0141000A1, radiation therapy, surgery, and combinations thereof.

Exemplary therapeutic agents that may be used in combination with the antibodies of the invention for treatment of ovarian cancer include approved drugs for treatment of ovarian cancer, such as melphalan (Alkeran®), bevacizumab (Avastin®), carboplatin, cyclophosphamide (Clafen®, Cytoxan®), cisplatin, doxorubicin hydrochloride, gemcitabine hydrochloride (Gemzar®), topotecan hydrochloride (Hycamtin®), Olaparib (Lynparza®), carboplatin, cisplatin, paclitaxel (Taxol®), thiotepa and topotecan hydrochloride. Other therapeutic agents that may be used are, ifosfamide, olaparib, oxaliplatin, pemetrexed disodium, SJG-136, etoposide, decitabine; immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), VEGF inhibitor (e.g., bevacizumab, BIBF 1120, cediranib, AZD2171), PDGFR inhibitor (e.g., IMC-3G3), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agent (e.g., Hu3S193), statin (e.g., lovastatin), topoisomerase 1 inhibitor (e.g., NKTR-102), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., RO04929097), Wee-1 inhibitor (e.g., MK-1775), antitubulin agent (e.g., vinorelbine, E7389), immunotoxin (e.g., denileukin diftitox), SB-485232, vascular-disrupting agent (e.g., AVE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy, and combinations thereof.

Exemplary therapeutic agents that may be used in combination with the antibodies of the invention for treatment of a myeloma include one or more of chemotherapy or other anti-cancer agents (e.g., thalidomide analogs, e.g., lenalidomide), HSCT (Cook, (2008) J *Manag Care Pharm.* 14(7 Suppl):19-25), an anti-TIM-3 antibody (Hallett et al,. (2011) *J of American Society for Blood and Marrow Transplantation* 17(8):1133-145), tumor antigen-pulsed dendritic cells, fusions (e.g., electrofusions) of tumor cells and dendritic cells, or vaccination with immunoglobulin idiotype produced by malignant plasma cells (reviewed in Yi (2009) *Cancer J* 15(6):502-10).

Exemplary therapeutics agents that may be used in combination with the antibodies of the invention for treatment of a renal cancer, e.g., a renal cell carcinoma (RCC) or metastatic RCC include drugs approved for treatment of RCC, including everolimus (Afinitor®), aldesleukin, bevacizumab (Avastin®), axitinib (Inlyta®), cabozantinib-S-Malate (Cabometyx®), aldesleukin (Proleukin®), lenvatinib mesylate (Lenvima®), sorafenib tosylate (Nexavar®), nivolumab (Opdivo®), pazopanib hydrochloride, sorafenib tosylate, sunitinib (Sutent®), temsirolimus (Torisel®) and pazopanib hydrochloride (Votrient®). Other therapeutics that may be used are a targeted agent (e.g., a VEGF inhibitor such as a monoclonal antibody to VEGF, e.g., bevacizumab, a VEGF tyrosine kinase inhibitor such as sorafenib, axitinib and pazopanib.

Exemplary therapeutic agents that may be used in combination with the antibodies of the invention for treatment of a chronic myelogenous leukemia (AML) include a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), dual inhibitor (e.g., dasatinib, bosutinib), multikinase inhibitor (e.g., DCC-2036, ponatinib, sorafenib, sunitinib, RGB-286638), interferon alfa, steroids, apoptotic agent (e.g., omacetaxine mepesuccinat), immunotherapy (e.g., allogeneic CD4+ memory Th1-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., RO5045337), Aurora B kinase inhibitor (e.g., TAK-901), radioimmunotherapy (e.g., actinium-225-labeled anti-CD33 antibody HuM 195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

Exemplary therapeutic agents that may be used in combination with the antibodies of the invention for treatment of a chronic lymphocytic leukemia (CLL) include a chemotherapeutic agent (e.g., fludarabine, cyclophosphamide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765 (ibrutinib), multikinase inhibitor (e.g., MGCD265, RGB-286638), CD-20 targeting agent (e.g., rituximab, ofatumumab, RO5072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Th1-like T cells/microparticle-bound anti-CD3/anti-CD28, autologous cytokine induced killer cells (CIK), HDAC inhibitor (e.g., vorinostat, valproic acid, LBH589, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac(Fv)-PE38 (LMB-2)), CD37 targeting agent (e.g., TRU-016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., RO5045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-CoA inhibitor (e.g., simvastatin), GNKG186, radiation therapy, bone marrow transplantation, stem cell transplantation, and a combination thereof.

Exemplary therapeutic agents that may be used in combination with the antibodies of the invention for treatment of an acute lymphocytic leukemia (ALL) include a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asparaginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., RO5045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, radiation therapy, steroid, bone marrow transplantation, stem cell transplantation, or a combination thereof.

Exemplary therapeutic agents that may be used in combination with the antibodies of the invention for treatment of an acute myeloid leukemia (AML) include a chemotherapeutic agent (e.g., cytarabine, daunorubicin, idarubicin, clofarabine, decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib), immunotoxin (e.g., gemtuzumab ozogamicin), DT388IL3 fusion protein, HDAC inhibitor (e.g., vorinostat, LBH589), plerixafor, mTOR inhibitor (e.g., everolimus), SRC inhibitor (e.g., dasatinib), HSP90 inhibitor (e.g., STA-9090), retinoid (e.g., bexarotene, Aurora kinase inhibitor (e.g., BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., RO5045337), mTOR inhibitor (e.g., everolimus), LY573636-sodium, ZRx-101, MLN4924, lenalidomide, immunotherapy (e.g., AHN-12), histamine dihydrochloride, radiation therapy, bone marrow transplantation, stem cell transplantation, and a combination thereof.

Exemplary therapeutic agents that may be used in combination with the antibodies of the invention for treatment of a multiple myeloma (MM) include a chemotherapeutic agent (e.g., melphalan, amifostine, cyclophosphamide, doxorubicin, clofarabine, bendamustine, fludarabine, adriamycin, SyB L-0501), thalidomide, lenalidomide, dexamethasone, prednisone, pomalidomide, proteasome inhibitor (e.g., bortezomib, carfilzomib, MLN9708), cancer vaccine (e.g., GVAX), CD-40 targeting agent (e.g., SGN-40, CHIR-12.12), perifosine, zoledronic acid, Immunotherapy (e.g., MAGE-A3, NY-ESO-1, HuMax-CD38), HDAC inhibitor (e.g., vorinostat, LBH589, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283), VEGF inhibitor (e.g., bevacizumab), plerixafor, MEK inhibitor (e.g., AZD6244), IPH2101, atorvastatin, immunotoxin (e.g., BB-10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945), an anti-CD38 antibody (e.g. DARZALEX® (daratumumab), radiation therapy, bone marrow transplantation, stem cell transplantation, and a combination thereof.

Exemplary therapeutic agents that may be used in combination with the antibodies of the invention for treatment of a prostate cancer are approved drugs for treatment of the prostate cancer, such as abiraterone acetate (Zytiga®), bicalutamide (Casodex®), cabazitaxel (Jevtana®), conjugated estrogens (Premarin®), stradiol (Estrace®), estradiol valerate (Delestrogen®), estrogens, esterified (Menest®), degarelix (Firmagon®), docetaxel (Taxotere®), enzalutamide (Xtandi®), flutamide, goserelin acetate (Zoladex®), Cabazitaxel (Jevtana®), leuprolide acetate (Lupron®), mitoxantrone hydrochloride, nilutamide (Nilandron®) Sipuleucel-T (Provenge®) and radium 223 dichloride (Xofigo®). Other drugs that may be used include a chemotherapeutic agent (e.g., carboplatin, fludarabine), hormonal therapy (e.g., cyproterone acetate, ketoconazole, aminoglutethimide, abarelix, degarelix, leuprolide, triptorelin, buserelin), tyrosine kinase inhibitor (e.g., dual kinase inhibitor (e.g., lapatanib), multikinase inhibitor (e.g., sorafenib, sunitinib), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-3G3, bafetinib, CP-675,206, radiation therapy, surgery, or a combination thereof.

Exemplary therapeutic agents that may be used in combination with the antibodies of the invention for treatment of a head and neck squamous cell carcinoma (HNSCC) include methotrexate (Folex®, Mexate®), bleomycin (Blenoxane®), docetaxel (Taxotere®), erbitux (Cetuximab®), hydroxyurea (Hydrea®) or pembrolizumab (Keytruda®), In some embodiments, the antibodies of the invention are administered in combination with a TLR agonist.

In some embodiments, the TLR3 agonist is TLR4 agonist.

In some embodiments, the TLR3 agonist is a TLR7/8 agonist.

Exemplary TLR agonists are Pam3Cys, a TLR-1/2 agonist; CFA, a TLR-2 agonist; MALP2, a TLR-2 agonist; Pam2Cys, a TLR-2 agonist; FSL-1, a TLR-2 agonist; Hib-OMPC, a TLR-2 agonist; polyribosinic:polyribocytidic acid (Poly I:C), a TLR-3 agonist; polyadenosine-polyuridylic acid (poly AU), a TLR-3 agonist; Polyinosinic-Polycytidylic acid stabilized with poly-L-lysine and carboxymethylcellulose (Hiltonol®), a TLR-3 agonist; monophosphoryl lipid A (MPL), a TLR-4 agonist; LPS, a TLR-4 agonist; bacterial flagellin, a TLR-5 agonist; sialyl-Tn (STn), a carbohydrate associated with the MUCI mucin on a number of human cancer cells and a TLR-4 agonist; imiquimod, a TLR-7 agonist; resiquimod, a TLR-7/8 agonist; loxoribine, a TLR-7/8 agonist; and unmethylated CpG dinucleotide (CpG-ODN), a TLR-9 agonist.

Exemplary TLR4 agonists are agonistic antibodies specifically binding TLR4.

In some embodiments described herein, the antibodies of the invention are administered in combination with an antibody that bids CSF-1R Exemplary antibodies that bind CSF-1R are those described in Int. Patent Publ. No. WO2013132044.

In some embodiments described herein, the antibodies of the invention are administered in combination with LXRβ agonist.

In some embodiments described herein, the antibodies of the invention are administered in combination with a DR4 agonist.

In some embodiments described herein, the antibodies of the invention are administered in combination with a DR5 agonist.

Suitable DR4 and DR5 agonists are described for example in Int. Patent Publ. No. WO2014159562.

In some embodiments described herein, the antibodies of the invention are administered in combination with an anti-galectin 1 antibody.

Exemplary anti-galectin 1 antibodies that may be used in combination with the antibodies of the invention are those described in Int. Patent Publ. No. WO2015013389.

In some embodiment described herein, the antibodies of the invention are administered in combination with a BTK inhibitor.

In some embodiments, the BTK inhibitor is IMBRUVICA® (ibrutinib).

In some embodiments described herein, the antibodies of the invention are administered in combination with an anti-HER2 antibody.

In some embodiments described herein, the antibodies of the invention are administered in combination with an anti-CD20 antibody.

In some embodiments, the antibodies of the invention are administered in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAM-PATH. In some embodiments, the antibodies of the invention may be administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive the antibodies of the invention.

In some embodiments described herein, the antibodies of the invention are administered before or following surgery.

In some embodiments described herein, the antibodies of the invention are administered in combination with radiation therapy.

Radiation therapy may be administered using various methods, including external-beam therapy, internal radiation therapy, implant radiation, stereotactic radiosurgery, systemic radiation therapy, radiotherapy and permanent or temporary interstitial brachytherapy. External-beam therapy involves three dimensional, conformal radiation therapy where the field of radiation is designed, local radiation (e.g., radiation directed to a preselected target or organ), or focused radiation. Focused radiation may be selected from stereotactic radiosurgery, fractionated stereotactic radiosurgery or intensity-modulated radiation therapy. Focused radiation may have particle beam (proton), cobalt-60 (photon) linear accelerator (x-ray) as a radiation source (see e.g. WO 2012/177624). "Brachytherapy," refers to radiation therapy delivered by a spatially confined radioactive material inserted into the body at or near a tumor or other proliferative tissue disease site, and includes exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner include both solids and liquids. The radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material may also be a fluid made from any solution of radionuclide(s), e.g., a solution of I-125 or I-131, or a radioactive fluid can be produced using a slurry of a suitable fluid containing small particles of solid radionuclides, such as Au-198, Y-90. The radionuclide(s) may be embodied in a gel or radioactive micro spheres.

In some embodiments, the antibodies of the invention are administered in combination with decarbazine for the treatment of melanoma. Without being bound by any particular theory, the combined use of PD-1 and/or TIM-3 blockade and chemotherapy is believed to be facilitated by cell death that is a consequence of the cytotoxic action of most chemotherapeutic compounds, which can result in increased levels of tumor antigen in the antigen presentation pathway. Other combination therapies that may result in synergy with PD-1 and/or TIM-3 blockade through cell death are radiation, surgery, and hormone deprivation. Each of these protocols creates a source of tumor antigen in the host. Angiogenesis inhibitors may also be combined with PD-1 and/or TIM-3 blockade. Inhibition of angiogenesis leads to tumor cell death which may feed tumor antigen into host antigen presentation pathways.

The monospecific PD-1 and/or TIM-3 antibodies of the invention may also be used in combination with bispecific antibodies. Bispecific antibodies may be used to target two separate antigens. For example anti-Fc receptor/anti-tumor antigen (e.g., Her-2/neu) bispecific antibodies have been used to target macrophages to sites of tumor. Bispecific targeting may more effectively activate tumor specific responses. The T cell arm of these responses would be augmented by the use of PD-1 and/or TIM-3 blockade. Alternatively, antigen may be delivered directly to DCs by the use of bispecific antibodies which bind to tumor antigen and a dendritic cell specific cell surface marker.

The antibodies of the invention may be used in unconjugated forms or conjugated to a second agent, e.g., a cytotoxic drug, radioisotope, or a protein, e.g., a protein toxin or a viral protein. The antibody molecules may be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g.; via a viral coat protein), or mixtures thereof.

Infectious Diseases

The invention also provides a method of treating a subject that has been exposed to particular toxins or pathogen with the antibodies of the invention for a time sufficient to treat the subject.

The invention also provides a method of treating a subject having an infectious disease, comprising administering a therapeutically efficient amount of the antibody of the invention to the subject in need thereof for a time sufficient to treat the infectious disease.

The invention also provides a method of treating a subject having a viral infection, comprising administering a therapeutically efficient amount of the antibody of the invention to the subject in need thereof for a time sufficient to treat the viral infection.

The invention also provides a method of treating a subject having a bacterial infection, comprising administering a therapeutically efficient amount of the antibody of the invention to the subject in need thereof for a time sufficient to treat the bacterial infection.

The invention also provides a method of treating a subject having a fungal infection, comprising administering a therapeutically efficient amount of the antibody of the invention to the subject in need thereof for a time sufficient to treat the fungal infection.

In the treatment of infection (e.g., acute and/or chronic), administration of the antibodies of the invention may be combined with conventional treatments in addition to or in lieu of stimulating natural host immune defenses to infection. Natural host immune defenses to infection include inflammation, fever, antibody-mediated host defense, T-lymphocyte-mediated host defenses, including lymphokine secretion and cytotoxic T-cells (especially during viral infection), complement mediated lysis and opsonization (facilitated phagocytosis), and phagocytosis. The ability of the antibodies of the invention to reactivate dysfunctional T-cells would be useful to treat chronic infections, in particular those in which cell-mediated immunity is important for complete recovery.

Similar to its application to tumors as discussed above, antibodies of the invention may be used alone, or as an adjuvant, in combination with vaccines, to stimulate the immune response to pathogens, toxins, and self-antigens. Examples of pathogens for which this therapeutic approach may be useful include pathogens for which there is currently no effective vaccine, or pathogens for which conventional vaccines are less than completely effective. These include HIV, Hepatitis (A, B, & C), Influenza, Herpes, Giardia, Malaria, *Leishmania, Staphylococcus aureus* and *Pseudomonas Aeruginosa*. PD-1 and/or TIM-3 blockade may be useful against established infections by agents such as HIV that present altered antigens over the course of the infections. These novel epitopes are recognized as foreign at the time of administration of the antibodies of the invention, thus provoking a strong T cell response that is not dampened by negative signals through PD-1 or TIM-3.

Viruses

For infections resulting from viral causes, the antibodies of the invention may be combined with standard therapies for treating viral infections. Such standard therapies vary depending upon type of virus, although in almost all cases, administration of human serum containing antibodies (e.g., IgA, IgG) specific to the virus can be effective.

Exemplary pathogenic viruses causing infections that may be treatable by the antibodies of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In some embodiments, the virus infection is an influenza virus infection. Influenza infection can result in fever, cough, myalgia, headache and malaise, which often occur in seasonal epidemics. Influenza is also associated with a number of postinfectious disorders, such as encephalitis, myopericarditis, Goodpasture's syndrome, and Reye's syndrome. Influenza infection also suppresses normal pulmonary antibacterial defenses, such that patients recovering from influenza have an increased risk of developing bacterial pneumonia. Influenza viral surface proteins show marked antigenic variation, resulting from mutation and recombination. Thus, cytolytic T lymphocytes are the host's primary vehicle for the elimination of virus after infection. Influenza is classified into three primary types: A, B and C. Influenza A is unique in that it infects both humans and many other animals (e.g., pigs, horses, birds and seals) and is the principal cause of pandemic influenza. A cell can be infected by two different influenza A strains, the segmented RNA genomes of two parental virus types mix during replication to create a hybrid replicant, resulting in new epidemic strains. Influenza B does not replicate in animals and thus has less genetic variation and influenza C has only a single serotype.

Most conventional therapies are palliatives of the symptoms resulting from infection, while the host's immune response actually clears the disease. However, certain strains (e.g., influenza A) can cause more serious illness and death. Influenza A may be treated both clinically and prophylactically by the administration of the cyclic amines inhibitors amantadine and rimantadine, which inhibit viral replication. However, the clinical utility of these drugs is limited due to the relatively high incidence of adverse reactions, their narrow anti-viral spectrum (influenza A only), and the propensity of the virus to become resistant. The administration of serum IgG antibody to the major influenza surface proteins, hemagglutinin and neuraminidase can prevent pulmonary infection, whereas mucosal IgA is required to prevent infection of the upper respiratory tract and trachea. The most effective current treatment for influenza is vaccination with the administration of virus inactivated with formalin or β-propiolactone.

In some embodiments, the infection is a hepatitis infection, e.g., a Hepatitis B or C infection.

Hepatitis B virus (HB-V) is the most infectious known blood borne pathogen. It is a major cause of acute and chronic hepatitis and hepatic carcinoma, as well as life-long, chronic infection. Following infection, the virus replicates in hepatocytes, which also then shed the surface antigen HBsAg. The detection of excessive levels of HBsAg in serum is used as a standard method for diagnosing a hepatitis B infection. An acute infection may resolve or it can develop into a chronic persistent infection. Current treatments for chronic HBV include α-interferon, which increases the expression of class I human leukocyte antigen (HLA) on the surface of hepatocytes, thereby facilitating their recognition by cytotoxic T lymphocytes. Additionally, the nucleoside analogs ganciclovir, famciclovir and lamivudine have also shown some efficacy in the treatment of HBV infection in clinical trials. Additional treatments for HBV include pegylated α-interferon, adenfovir, entecavir and telbivudine. While passive immunity can be conferred through parental administration of anti-HBsAg serum antibodies, vaccination with inactivated or recombinant HBsAg also confers resistance to infection. The antibodies of the invention may be combined with conventional treatments for hepatitis B infections for therapeutic advantage.

Hepatitis C virus (HC-V) infection may lead to a chronic form of hepatitis, resulting in cirrosis. While symptoms are similar to infections resulting from Hepatitis B, in distinct contrast to HB-V, infected hosts can be asymptomatic for 10-20 years. The antibodies of the invention can be administered as a monotherapy, or combined with the standard of care for hepatitis C infection. For example, the antibodies of the invention can be administered with one or more of Sovaldi (sofosbuvir) Olysio (simeprevir), plus ribavirin or pegylated interferon. Although regimens that include Incivek (telaprevir) or Victrelis (boceprevir) plus ribavirin and pegylated interferon are also approved, they are associated with increased side effects and longer duration of treatment.

Conventional treatment for HC-V infection includes the administration of a combination of α-interferon and ribavirin. A promising potential therapy for HC-V infection is the protease inhibitor telaprevir (VX-960). Additional treatments include bavituximab (an antibody that binds anionic phospholipid phosphatidylserine in a B2-glycoprotein I dependent manner, Peregrine Pharmaceuticals), anti-HPV viral coat protein E2 antibod(y)(ies) (e.g., ATL 6865-Ab68+ Ab65, XTL Pharmaceuticals) and Civacir® (polyclonal anti-HCV human immune globulin). The antibodies of the invention may be combined with one or more of these treatments for hepatitis C infections for therapeutic advantage. Protease, polymerase and NS5A inhibitors which may be used in combination with the antibodies of the invention to specifically treat Hepatitis C infection include those described in US 2013/0045202.

In another embodiment, the infection is a measles virus. After an incubation of 9-11 days, hosts infected with the measles virus develop fever, cough, coryza and conjunctivitis. Within 1-2 days, an erythematous, maculopapular rash develop, which quickly spreads over the entire body. Because infection also suppresses cellular immunity, the host is at greater risk for developing bacterial superinfections, including otitis media, pneumonia and postinfectious encephalomyelitis. Acute infection is associated with significant morbidity and mortality, especially in malnourished adolescents.

Treatment for measles includes the passive administration of pooled human IgG, which can prevent infection in non-immune subjects, even if given up to one week after exposure. However, prior immunization with live, attenuated virus is the most effective treatment and prevents disease in more than 95% of those immunized. As there is one serotype of this virus, a single immunization or infection typically results in protection for life from subsequent infection.

In a small proportion of infected hosts, measles can develop into SSPE, which is a chronic progressive neurologic disorder resulting from a persistent infection of the central nervous system. S SPE is caused by clonal variants of measles virus with defects that interfere with virion assembly and budding. For these patients, reactivation of T-cells with the antibodies of the invention so as to facilitate viral clearance would be desirable.

In another embodiment, the infection is HIV. HIV attacks $CD4^+$ cells, including T-lymphocytes, monocyte-macrophages, follicular dendritic cells and Langerhan's cells, and $CD4^+$ helper/inducer cells are depleted. As a result, the host acquires a severe defect in cell-mediated immunity. Infection with HIV results in AIDS in at least 50% of individuals, and is transmitted via sexual contact, administration of infected blood or blood products, artificial insemination with infected semen, exposure to blood-containing needles or syringes and transmission from an infected mother to infant during childbirth.

A host infected with HIV may be asymptomatic, or may develop an acute illness that resembling mononucleosis—fever, headache, sore throat, malaise and rash. Symptoms can progress to progressive immune dysfunction, including persistent fever, night sweats, weight loss, unexplained diarrhea, eczema, psoriasis, seborrheic dermatitis, herpes zoster, oral candidiasis and oral hairy leukoplakia. Opportunistic infections by a host of parasites are common in patients whose infections develop into AIDS.

Treatments for HIV include antiviral therapies including nucleoside analogs, zidovudine (AST) either alone or in combination with didanosine or zalcitabine, dideoxyinosine, dideoxycytidine, lamidvudine, stavudine; reverse transcriptive inhibitors such as delavirdine, nevirapine, loviride, and proteinase inhibitors such as saquinavir, ritonavir, indinavir and nelfinavir. Treatments for HIV include EDURANT® (rilpivirine). The antibodies of the invention may be combined with conventional treatments for HIV infections for therapeutic advantage.

In another embodiment, the infection is a Cytomegalovirus (CMV) infection. CMV infection is often associated with persistent, latent and recurrent infection. CMV infects and remains latent in monocytes and granulocyte-monocyte progenitor cells. The clinical symptoms of CMV include mononucleosis-like symptoms (i.e., fever, swollen glands, malaise), and a tendency to develop allergic skin rashes to antibiotics. The virus is spread by direct contact. The virus is shed in the urine, saliva, semen and to a lesser extent in other body fluids. Transmission can also occur from an infected mother to her fetus or newborn and by blood transfusion and organ transplants. CMV infection results in general impairment of cellular immunity, characterized by impaired blastogenic responses to nonspecific mitogens and specific CMV antigens and diminished cytotoxic ability.

Treatments of CMV infection include the anti-virals ganciclovir, foscarnet and cidovir, but these drugs are typically only prescribed in immunocompromised patients. The antibodies of the invention described herein may be combined with conventional treatments for cytomegalovirus infections for therapeutic advantage.

In another embodiment, the infection is Epstein-Barr virus (EBV) infection. EBV can establish persistent and latent infections and primarily attacks B cells. Infection with EBV results in the clinical condition of infectious mononucleosis, which includes fever, sore throat, often with exudate, generalized lymphadenopathy and splenomegaly. Hepatitis is also present, which can develop into jaundice.

While typical treatments for EBV infections are palliative of symptoms, EBV is associated with the development of certain cancers such as Burkitt's lymphoma and nasopharyngeal cancer. Thus, clearance of viral infection before the complications develop would be of great benefit. The antibodies of the invention may be combined with conventional treatments for Epstein-Barr virus infections for therapeutic advantage.

In another embodiment, the infection is Herpes simplex virus (HSV) infection. HSV is transmitted by direct contact with an infected host. A direct infection may be asymptomatic, but typically result in blisters containing infectious particles. The disease manifests as cycles of active periods of disease, in which lesions appear and disappear as the virus latently infects the nerve ganglion for subsequent outbreaks. Lesions may be on the face, genitals, eyes and/or hands. In some case, an infection can also cause encephalitis.

Treatments for herpes infections are directed primarily to resolving the symptomatic outbreaks, and include systemic antiviral medicines such as: acyclovir (e.g., Zovirax®), valaciclovir, famciclovir, penciclovir, and topical medications such as docosanol (Abreva®), tromantadine and zilactin. The clearance of latent infections of herpes would be of great clinical benefit. The antibodies of the invention may be combined with conventional treatments for herpes virus infections for therapeutic advantage.

In another embodiment, the infection is Human T-lymphotrophic virus (HTLV-1, HTLV-2). HTLV is transmitted via sexual contact, breast feeding or exposure to contaminated blood. The virus activates Th1 cells, resulting in their overproliferation and overproduction of Th1 related cytokines (e.g., IFN-γ and TNF-α). This in turn results in a suppression of Th2 lymphocytes and reduction of Th2 cytokine production (e.g., IL-4, IL-5, IL-10 and IL-13), causing a reduction in the ability of an infected host to mount an adequate immune response to invading organisms requiring a Th2-dependent response for clearance (e.g., parasitic infections, production of mucosal and humoral antibodies).

HTLV infections lead to opportunistic infections resulting in bronchiectasis, dermatitis and superinfections with *Staphylococcus* spp. and *Strongyloides* spp. resulting in death from polymicrobial sepsis. HTLV infection can also lead directly to adult T-cell leukemia/lymphoma and progressive demyelinating upper motor neuron disease known as HAM/TSP. The clearance of HTLV latent infections would be of great clinical benefit. The antibodies of the invention may be combined with conventional treatments for HTLV infections for therapeutic advantage.

In another embodiment, the infection is Human papilloma virus (HPV). HPV primarily affects keratinocytes and occurs in two forms: cutaneous and genital. Transmission is believed to occur through direct contact and/or sexual activity. Both cutaneous and genital HPV infection can result in warts and latent infections and sometimes recurring infections, which are controlled by host immunity which controls the symptoms and blocks the appearance of warts, but leaves the host capable of transmitting the infection to others.

Infection with HPV can also lead to certain cancers, such as cervical, anal, vulvar, penile and oropharynial cancer. There are no known cures for HPV infection, but current treatment is topical application of Imiquimod, which stimulates the immune system to attack the affected area. The clearance of HPV latent infections would be of great clinical benefit. The antibodies of the invention may be combined with conventional treatments for HPV infections for therapeutic advantage.

Bacterial Infections Some examples of pathogenic bacteria causing infections that may be treated with the antibodies of the invention include syphilis, *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria. The antibodies of the invention can be used in combination with existing treatment modalities for the aforesaid infections. For example, treatments for syphilis include penicillin (e.g., penicillin G.), tetracycline, doxycycline, ceftriaxone and azithromycin.

Lyme disease, caused by *Borrelia burgdorferi* is transmitted into humans through tick bites. The disease manifests initially as a localized rash, followed by flu-like symptoms including malaise, fever, headache, stiff neck and arthralgias. Later manifestations can include migratory and polyarticular arthritis, neurologic and cardiac involvement with cranial nerve palsies and radiculopathy, myocarditis and arrhythmias. Some cases of Lyme disease become persistent, resulting in irreversible damage analogous to tertiary syphilis. Current therapy for Lyme disease includes primarily the administration of antibiotics. Antibiotic-resistant strains may be treated with hydroxychloroquine or methotrexate. Antibiotic refractory patients with neuropathic pain can be treated with gabapentin. Minocycline may be helpful in late/chronic Lyme disease with neurological or other inflammatory manifestations.

Other forms of borreliois, such as those resulting from *B. recurrentis, B. hermsii, B. turicatae, B. parikeri, B. hispanica, B. duttonii* and *B. persica*, as well leptospirosis (E.g., *L.* interrogans), typically resolve spontaneously unless blood titers reach concentrations to cause intrahepatic obstruction.

Fungi and Parasites

Some examples of pathogenic fungi causing infections that may be treated with the antibodies of the invention include *Candida* (*albicans, krusei, glabrata, tropicalis*, etc.), *Cryptococcus neoformans, Aspergillus* (*fumigatus, niger*, etc.), Genus Mucorales (*mucor, absidia*, rhizophus), *Sporothrix schenkii, Blastomyces dermatitidis, Paracoccidioides brasiliensis, Coccidioides immitis* and *Histoplasma capsulatum*.

Some examples of pathogenic parasites causing infections treatable with the antibodies of the invention described herein include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Diagnostic Uses and Kits

Kits

The invention also provides a kit comprising the antagonistic antibody specifically binding PD-1 of the invention.

The invention also provides a kit comprising the antagonistic antibody specifically binding TIM-3 of the invention.

The invention also provides a kit comprising the antagonistic bispecific PD-1/TIM-3 antibody comprising a first domain specifically binding PD-1 and a second domain specifically binding TIM-3 of the invention.

The kit may be used for therapeutic uses and as diagnostic kits.

The kit may be used to detect the presence of PD-1, TIM-3, or PD-1 and TIM-3 in a biological sample.

In some embodiments, the kit comprises the antibody of the invention described herein and reagents for detecting the antibody. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

In some embodiments, the kit comprises the antibody of the invention in a container and instructions for use of the kit.

In some embodiments, the antibody in the kit is labeled.

In some embodiments, the kit comprises the antagonistic antibody specifically binding PD-1, comprising the VH of SEQ ID NO: 41 and the VL of SEQ ID NO: 49;
the VH of SEQ ID NO: 41 and the VL of SEQ ID NO: 50;
the VH of SEQ ID NO: 42 and the VL of SEQ ID NO: 51;
the VH of SEQ ID NO: 42 and the VL of SEQ ID NO: 52;
the VH of SEQ ID NO: 42 and the VL of SEQ ID NO: 53;
the VH of SEQ ID NO: 43 and the VL of SEQ ID NO: 49;
the VH of SEQ ID NO: 43 and the VL of SEQ ID NO: 54;
the VH of SEQ ID NO: 43 and the VL of SEQ ID NO: 50;
the VH of SEQ ID NO: 43 and the VL of SEQ ID NO: 55;
the VH of SEQ ID NO: 43 and the VL of SEQ ID NO: 56;
the VH of SEQ ID NO: 43 and the VL of SEQ ID NO: 57;
the VH of SEQ ID NO: 44 and the VL of SEQ ID NO: 49;
the VH of SEQ ID NO: 45 and the VL of SEQ ID NO: 49;
the VH of SEQ ID NO: 46 and the VL of SEQ ID NO: 49;
the VH of SEQ ID NO: 47 and the VL of SEQ ID NO: 49;
the VH of SEQ ID NO: 48 and the VL of SEQ ID NO: 53;
the VH of SEQ ID NO: 48 and the VL of SEQ ID NO: 52;
the VH of SEQ ID NO: 48 and the VL of SEQ ID NO: 56;
the VH of SEQ ID NO: 47 and the VL of SEQ ID NO: 58;
the VH of SEQ ID NO: 47 and the VL of SEQ ID NO: 59;
the VH of SEQ ID NO: 45 and the VL of SEQ ID NO: 60;
the VH of SEQ ID NO: 45 and the VL of SEQ ID NO: 61;
the VH of SEQ ID NO: 45 and the VL of SEQ ID NO: 62;
the VH of SEQ ID NO: 63 and the VL of SEQ ID NO: 65; or
the VH of SEQ ID NO: 64 and the VL of SEQ ID NO: 65.

In some embodiments, the kit comprises the antagonistic antibody specifically binding PD-1 comprising the VH of SEQ ID NO: 48 and the VL of SEQ ID NO: 56.

In some embodiments, the kit comprises the antagonistic antibody specifically binding PD-1 comprising the VH of SEQ ID NO: 64 and the VL of SEQ ID NO: 65.

In some embodiments, the kit comprises the antagonistic antibody specifically binding TIM-3, comprising
- the VH of SEQ ID NO: 145 and the VL of SEQ ID NO: 155;
- the VH of SEQ ID NO: 146 and the VL of SEQ ID NO: 156;
- the VH of SEQ ID NO: 148 and the VL of SEQ ID NO: 157;
- the VH of SEQ ID NO: 147 and the VL of SEQ ID NO: 155;
- the VH of SEQ ID NO: 149 and the VL of SEQ ID NO: 158;
- the VH of SEQ ID NO: 150 and the VL of SEQ ID NO: 159;
- the VH of SEQ ID NO: 151 and the VL of SEQ ID NO: 160;
- the VH of SEQ ID NO: 152 and the VL of SEQ ID NO: 161;
- the VH of SEQ ID NO: 153 and the VL of SEQ ID NO: 162;
- the VH of SEQ ID NO: 154 and the VL of SEQ ID NO: 163; or the VH of SEQ ID NO: 172 and the VL of SEQ ID NO: 173.

In some embodiments, the kit comprises the antagonistic antibody specifically binding TIM-3 comprising the VH of SEQ ID NO: 146 and the VL of SEQ ID NO: 156.

In some embodiments, the kit comprises the antagonistic antibody specifically binding TIM-3 comprising the VH of SEQ ID NO: 172 and the VL of SEQ ID NO: 173.

In some embodiments, the kit comprises the antagonistic bispecific PD-1/TIM-3 antibody comprising the HC1, the LC1, the HC2 and the LC2 of
- SEQ ID NOs: 186, 188, 190 and 193, respectively;
- SEQ ID NOs: 186, 188, 191 and 194, respectively;
- SEQ ID NOs: 187, 189, 190 and 193, respectively;
- SEQ ID NOs: 187, 189, 191, 194, respectively;
- SEQ ID NOs: 186, 188, 192 and 195, respectively;
- SEQ ID NOs: 186, 188, 248 and 194, respectively;
- SEQ ID NOs: 241, 188, 244, 195, respectively;
- SEQ ID NOs: 241, 188, 245, 194, respectively;
- SEQ ID NOs: 242, 189, 246, 194, respectively;
- SEQ ID NOs: 243, 188, 246, 194, respectively; or
- SEQ ID NOs: 243, 188, 247, 195, respectively.

Methods of Detecting PD-1, TIM-3 or PD-1 and TIM-3

The invention also provides a method of detecting PD-1 in a sample, comprising obtaining the sample, contacting the sample with the antagonistic antibody specifically binding PD-1 of the invention, and detecting the antibody bound to PD-1 in the sample.

The invention also provides a method of detecting TIM-3 in a sample, comprising obtaining the sample, contacting the sample with the antagonistic antibody specifically binding TIM-3 of the invention, and detecting the antibody bound to TIM-3 in the sample.

The invention also provides a method of detecting PD-1 and TIM-3 in a sample, comprising obtaining the sample, contacting the sample with the antagonistic bispecific PD-1/TIM-3 antibody comprising a first domain specifically binding PD-1 and a second domain specifically binding TIM-3 of the invention, and detecting the antibody bound to PD-1 and TIM-3 in the sample.

In some embodiments, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like.

The antibodies of the invention bound to PD-1, TIM-3 or PD-1 and TIM-3 may be detected using known methods. Exemplary methods include direct labeling of the antibodies using fluorescent or chemiluminescent labels, or radiolabels, or attaching to the antibodies of the invention a moiety which is readily detectable, such as biotin, enzymes or epitope tags. Exemplary labels and moieties are ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes and Alexafluor® dyes.

The antibodies of the invention may be used in a variety of assays to detect PD-1, TIM-3 or PD-1 and TIM-3 in the sample. Exemplary assays are western blot analysis, radioimmunoassay, surface plasmon resonance, immunoprecipitation, equilibrium dialysis, immunodiffusion, electrochemiluminescence (ECL) immunoassay, immunohistochemistry, fluorescence-activated cell sorting (FACS) or ELISA assay.

The present invention will now be described with reference to the following specific, non-limiting examples.

Example 1. General Methods

Purified Human Mixed Lymphocyte Reaction (MLR)

A purified human mixed lymphocyte reaction (MLR assay) was used to measure changes in cytokine production induced by addition of test antibodies to co-cultures of CD4$^+$ T cells and dendritic cells.

Peripheral blood mononuclear cells (PBMCs) were isolated from a leukopak (Biological Specialty Corporation) using a Ficoll gradient. CD4$^+$ T cells were then freshly isolated by negative selection from PBMCs using the Miltenyi AutoMACS and CD4$^+$ T cell isolation beads per manufacturer's instructions or were commercially purchased as frozen CD4$^+$ T cells (Hemacare Corporation). One dendritic cell donor (Hemacare Corporation) was used. Post-isolation or thaw, CD4$^+$ T cells and dendritic cells were washed and resuspended in assay media (RMPI1640 media supplemented with 10% fetal bovine serum, 1% penicillin/streptomycin, 1× non-essential amino acids, and 1× sodium pyruvate-Invitrogen). The purified human CD4$^+$ T cells were diluted to 1×10$^6$ cells/mL and seeded at 100,000 cells/100 µL/well. Dendritic cells were diluted to 0.1×10$^6$ cells/mL and seeded at 5,000 cells/50 µL/well in U-bottom plates. Test antibodies or control antibodies were prepared at a 4× concentration in assay media yielding 1× when 50 µL of antibody was added to 150 µL of cells.

10-point serial dilutions of test or control antibodies were added to the wells at a final concentration of: 30, 10, 3.33, 1.11, 0.37, 0.12, 0.04, 0.01, 0.0046 and 00015 nM. CD4$^+$ T cells plus dendritic cells and dendritic cells alone were included as controls to measure basal cytokine secretion. Cells were maintained at 37° C., 5% CO$_2$ for 5 days. On Day 5, 100 µL of tissue culture supernatant was removed from culture plates and transferred to V-bottom plates. Supernatant was frozen at least overnight at −80° C. Cumulative cytokine production was measured in tissue culture supernatant using Meso Scale Discovery (MSD) Th1/Th2 human cytokine 10-plex plates following manufacturer's protocol. Briefly, MSD plates were blocked with 1% blocker B overnight at 4° C. The following day, blocker was removed and plates were washed using the Biotek 406 plate washer. An 8-point standard curve were prepared and added in duplicate to the plates. Thawed tissue culture supernatant was added at 25 μL/well, plates were sealed and shaken vigorously for 1.5 hours. Without removing standards or supernatant, 25 μL of detection antibody was added to each well. Plates were sealed, and shaken vigorously for 1.5 hours. Plates were washed, read buffer was added and plates were read using Meso Scale Discovery's plate reader.

Cytokine concentrations were calculated by MSD software. The concentration of cytokine in unknown samples is calculated by comparing the unknown's output signal to the output signal and known cytokine concentrations in the standard curve. Calculated concentrations were uploaded in Spotfire TIBCO software for visualization. After a visual inspection of the data, MAD-median outlier procedure with a threshold of 3.5 was used to identify and exclude outliers on log-transformed data. Robust analysis of the half-maximal effective concentration (Robust EC50) was carried out on each cytokine for each antibody.

CMV Assay

A cytomegalovirus antigen recall assay (CMV assay) was used to measure changes in cytokine production induced by addition of test antibodies to cultures of peripheral blood mononuclear cells (PBMCs) with CMV whole antigen (for PD-1 antibodies) or with a pool of 138 15-mer peptides that overlap through the 65 kd phosphoprotein (pp65) (for TIM-3 mAbs and PD1/TIM-3 bispecific mAbs).

Post-thaw, PBMCs (Astarte Biologics and Hemcare Corporation) were washed and resuspended in assay media (RMPI1640 media supplemented with 10% fetal bovine serum, 1% penicillin/streptomycin, 1× non-essential amino acids, and 1× sodium pyruvate-Invitrogen). The PBMCs were diluted to $1.5 \times 10^6$ cells/mL and seeded at 150,000 cells/100 μL/well. CMV antigen (Astarte Biologics) was prepared at a 4× concentration of 0.4 μg/mL in assay media yielding 0.1 μg/mL when 50 μL of antigen was added to 100 μL of cells and 50 μL of antibody. Antibodies were prepared at a 4× concentration in assay media yielding 1× when 50 μL of antibody was added to cells and peptide.

Serial dilutions of test antibodies were added to the wells at a final concentration between 150-0.001 nM. Cells plus CMV antigen or pp65 pool, cells alone, and isotype control prepared at a final concentration of 50 or 30 nM were included as controls to measure basal cytokine secretion. Cells were maintained at 37° C., 5% $CO_2$ for 6 days. For MSD analysis, on Day 6, 100 μL of tissue culture supernatant was removed from culture plates and transferred to V-bottom plates. Supernatant was frozen at least overnight at −80° C. Cumulative cytokine production was measured in tissue culture supernatant using Meso Scale Discovery (MSD) Th1/Th2 human cytokine 10-plex plates following manufacturer's protocol. Briefly, MSD plates were blocked with 1% blocker B overnight at 4° C. The following day, blocker was removed and plates were washed using the Biotek 406 plate washer. An 8-point standard curve was prepared and added in duplicate to the plates. Thawed tissue culture supernatant was added at 25 μL/well, plates were sealed and shaken vigorously for 1.5 hours. Without removing standards or supernatant, 25 μL of detection antibody was added to each well. Plates were sealed, and shaken vigorously for 1.5 hours. Plates were washed, read buffer was added and plates were read using Meso Scale Discovery's plate reader.

Cytokine concentrations were calculated by MSD software. The concentration of cytokine in unknown samples is calculated by comparing the unknown's output signal to the output signal and known cytokine concentrations in the standard curve. Calculated concentrations were uploaded in Spotfire TIBCO software for visualization. After a visual inspection of the data, MAD-median outlier procedure with a threshold of 3.5 was used to identify and exclude outliers on log-transformed data. Robust analysis of the half-maximal effective concentration (Robust EC50) was carried out on each cytokine for each antibody.

For TIM-3 antibodies and PD1/TIM-3 bispecific antibodies, at day 6, after supernatant was collected for MSD analysis, cells were washed once with PBS and subsequently stained for Live/Dead discrimination and the following cell surface markers: CD3, CD4, CD8, CD137, PD-1 and TIM-3. Flow cytometry was performed on a LSR Fortessa (BD). Data was analyzed using the Flow Jo software. CD137+ cells were identified based on Fluorescence Minus One (FMO) method on viable CMV-treated CD8+ and CD4+ cells.

For the sequential treatment experiments, CMV recall assays were carried out as above with pp65 peptide pool stimulation for six days. On day six, supernatant was removed and cells were restimulated with pp65 pool in the presence of anti-TIM-3 antibodies. Twenty-four hours later, supernatant was removed and IFN-γ levels were measured by MSD, as described above.

PD-1 Ligand Inhibition Assay

The ligand inhibition assay design was MSD (Mescoscale Discovery) based. A MSD plate was directly coated with ligand (cynoPDL1-ECD, huPDL1-ECD or huPDL2-ECD) and incubated overnight at 4° C. The following day, the coating solution was removed and the plate was blocked. A fixed concentration of biotinylated PD-1 (huPD1-ECD) was pre incubated with antibodies or with an isotype control antibody as a negative control. Depending on the panel of antibodies to be tested, the antibodies were tested as titrations or at a fixed concentration. The MSD plate was washed and the biotinylated PD-1/antibody mixture was added to the ligand coated MSD plate. The plate was washed and biotinylated PD-1 bound to ligand was detected by ruthenylated streptavidin. Inhibition of PD-1 binding by an antibody resulted in decreased signal in the MSD assay. Maximal biotinylated PD-1 binding in the absence of inhibitor was determined and sometimes used to normalize the data to a percentage of maximal biotinylated PD-1 signal. The mAbs that were positive for inhibition of ligand binding at one concentration were also tested in dose responses for inhibition of various PD-1 ligands.

Jurkat Cell Binding

Jurkat cells were stimulated overnight with 20 ng/ml of PHA, harvested, washed, and checked for viability. The cells were then incubated at 6-10° C. for 45-60 minutes with various concentrations of test antibodies, washed and incubated at 6-10° C. for 45-60 minutes with FITC-labeled goat anti-human IgG. The cells were washed and fixed with BD Cytofix, refrigerated overnight and analyzed on a MACSQuant flow cytometer. The percentage of PD-1 positive cells at each antibody concentration was plotted vs log of the antibody concentration and $EC_{50}$ values were generated in Prism.

Affinity Measurements

PD-1 mAbs

Anti-PD-1 mAbs were tested for binding affinity to huPD1-ECD and cynoPD-1-ECD. Affinity measurements using Surface Plasmon Resonance (SPR) were performed using a ProteOn XPR36 system. A biosensor surface was prepared by coupling a mixture of anti-IgG Fc modified alginate polymer layer surface of a GLC chip using the manufacturer instructions for amine-coupling chemistry. Test mAbs were captured and their interactions with analytes (huPD1-ECD or cynoPD1-ECD) were monitored in PBS-based buffer at 25° C. The collected data were processed and fitted to a Langmuir 1:1 binding model. The result for each mAb was reported in the format of $k_{on}$ (On-rate), $k_{off}$ (Off-rate) and $K_D$ (equilibrium dissociation constant).

TIM-3 Ligand Inhibition Assay

TIM-3/galectin-9 competition ELISAs were done by binding 1 µg/ml recombinant human Fc-TIM-3 chimera (R&D Systems-cat #: 2365-TM-05) in PBS per well of a 96-well White Maxisorp plate (Nunc). The plates were washed and blocked with StartingBlock T20 (Pierce) and inhibitor at a 10 µg/ml concentration was added to the wells. Without washing, 7.5 µg/ml galectin-9 at was added to the wells and incubated for 30 min. Anti-galectin-9-biotin antibody polyclonal antibody (R&D Systems) at 0.5 µg/mL was then added and incubated for 30 minutes. The plates were washed and neutravidin-HRP-conjugated (Pierce) was added and the plates incubated for an additional 45 minutes. The plates were washed and POD Chemiluminescence substrate (Roche) was added immediately prior to reading plates and the luminescence was read on a luminometer.

Generation of Antigens Used in the Study

Cloning, expression and purification of the antigens was done using standard methods. Various protein fragments were expressed as hexahistidine tag or Fc fusion proteins. The amino acid sequences of the used proteins without the tag sequences are shown in SEQ ID NOs: 1-9, 138 and 89.

```
Full length human PD1 (huPD1);
                                             SEQ ID NO: 1
PGWFLDSPDRPWNPPTFSPALLVVTEGDNATFTCSFSNTSESFVLNWYRM

SPSNQTDKLAAFPEDRSQPGQDCRFRVTQLPNGRDFHMSVVRARRNDSGT

YLCGAISLAPKAQIKESLRAELRVTERRAEVPTAHPSPSPRPAGQFQTLV

VGVVGGLLGSLVLLVWVLAVICSRAARGTIGARRTGQPLKEDPSAVPVFS

VDYGELDFQWREKTPEPPVPCVPEQTEYATIVFPSGMGTSSPARRGSADG

PRSAQPLRPE DGHCSWPL

Extracellular domain of human PD1 (huPD1-ECD);
                                             SEQ ID NO: 2
PGWFLDSPDRPWNPPTFSPALLVVTEGDNATFTCSFSNTSESFVLNWYRM

SPSNQTDKLAAFPEDRSQPGQDCRFRVTQLPNGRDFHMSVVRARRNDSGT

YLCGAISLAPKAQIKESLRAELRVTERRAEVPTAHPSPSPRPAGQFQTL

Macaca fascicularis (cynomolgous, herein
referred to as cyno) PD1 (cPD1);
                                             SEQ ID NO: 3
PGWFLESPDRPWNAPTFSPALLLVTEGDNATFTCSFSNASESFVLNWYRM

SPSNQTDKLAAFPEDRSQPGQDCRFRVTRLPNGRDFHMSVVRARRNDSGT

YLCGAISLAPKAQIKESLRAELRVTERRAEVPTAHPSPSPRPAGQFQALV

VGVVGGLLGSLVLLVWVLAVICSRAAQGTIEARRTGQPLKEDPSAVPVFS

VDYGELDFQWREKTPEPPAPCVPEQTEYATIVFPSGLGTSSPARRGSADG

PRSPRPLRPEDGHCSWPL

Extracellular domain of cyno PD1 (cPD1-ECD);
                                             SEQ ID NO: 4
PGWFLESPDRPWNAPTFSPALLLVTEGDNATFTCSFSNASESFVLNWYRM

SPSNQTDKLAAFPEDRSQPGQDCRFRVTRLPNGRDFHMSVVRARRNDSGT

YLCGAISLAPKAQIKESLRAELRVTERRAEVPTAHPSPSPRPAGQFQAL

Full length human PD-L1 (huPD-L1);
                                             SEQ ID NO: 5
FTVTVPKDLYVVEYGSNMTIECKFPVEKQLDLAALIVYWEMEDKNIIQFV

HGEEDLKVQHSSYRQRARLLKDQLSLGNAALQITDVKLQDAGVYRCMISY

GGADYKRITVKVNAPYNKINQRILVVDPVTSEHELTCQAEGYPKAEVIWT

SSDHQVLSGKTTTTNSKREEKLFNVTSTLRINTTTNEIFYCTFRRLDPEE

NHTAELVIPELPLAHPPNER

Extracellular domain of human PD-L1 (huPDL1-ECD)
                                             SEQ ID NO: 6
FTVTVPKDLYVVEYGSNMTIECKFPVEKQLDLAALIVYWEMEDKNIIQFV

HGEEDLKVQHSSYRQRARLLKDQLSLGNAALQITDVKLQDAGVYRCMISY

GGADYKRITVKVNAPYNKINQRILVVDPVTSEHELTCQAEGYPKAEVIWT

SSDHQVLSGKTTTTNSKREEKLFNVTSTLRINTTTNEIFYCTFRRLDPEE

NHTAELVIPELPLAHPPNERT

Extracellular domain of cynomolgus PD-L1
(cynoPDL1-ECD)
                                             SEQ ID NO: 7
AFTVTVPKDLYVVEYGSNMTIECKFPVEKQLDLTSLIVYWEMEDKNIIQF

VHGEEDLKVQHSNYRQRAQLLKDQLSLGNAALRITDVKLQDAGVYRCMIS

YGGADYKRITVKVNAPYNKINQRILVVDPVTSEHELTCQAEGYPKAEVIW

TSSDHQVLSGKTTTTNSKREEKLLNVTSTLRINTTANEIFYCIFRRLDPE

ENHTAELVIPELPLALPPNERT

Extracellular domain of human PD-L2
(huPDL2-ECD)
                                             SEQ ID NO: 8
LFTVTVPKELYIIEHGSNVTLECNFDTGSHVNLGAITASLQKVENDTSPH

RERATLLEEQLPLGKASFHIPQVQVRDEGQYQCIIIYGVAWDYKYLTLKV

KASYRKINTHILKVPETDEVELTCQATGYPLAEVSWPNVSVPANTSHSRT

PEGLYQVTSVLRLKPPPGRNFSCVFWNTHVRELTLASIDLQSQMEPRTHP

T

Extracellular domain of mouse PD1 (musPD1-ECD)
                                             SEQ ID NO: 9
LEVPNGPWRSLTFYPAWLTVSEGANATFTCSLSNWSEDLMLNWNRLSPSN

QTEKQAAFCNGLSQPVQDARFQIIQLPNRHDFHMNILDTRRNDSGIYLCG

AISLHPKAKIEESPGAELVVTERILETSTRYPSPSPKPEGRFQ

Full length human TIM-3,
                                           SEQ ID NO: 138
SEVEYRAEVGQNAYLPCFYTPAAPGNLVPVCWGKGACPVFECGNVVLRTD

ERDVNYWTSRYWLNGDFRKGDVSLTIENVTLADSGIYCCRIQIPGIMNDE

KFNLKLVIKPAKVTPAPTRQRDFTAAFPRMLTTRGHGPAETQTLGSLPDI

NLTQISTLANELRDSRLANDLRDSGATIRIGIYIGAGICAGLALALIFGA

LIFKWYSHSKEKIQNLSLISLANLPPSGLANAVAEGIRSEENIYTIEENV

YEVEEPNEYYCYVSSRQQPSQPLGCRFAMP
```

-continued

Extracellular domain of human TIM-3
(huTIM-3-ECD)

SEQ ID NO: 89
SEVEYRAEVGQNAYLPCFYTPAAPGNLVPVCWGKGACPVFECGNVVLRTD

ERDVNYWTSRYWLNGDFRKGDVSLTIENVTLADSGIYCCRIQIPGIMNDE

KFNLKLVIKPAKVTPAPTRQRDFTAAFPRMLTTRGHGPAETQTLGSLPDI

NLTQISTLANELRDSRLANDLRDSGATIR

Example 2. Selection of Human Anti-PD-1 Antibodies from Phage Display Libraries

PD-1 binding Fabs were selected from de novo pIX phage display libraries as described in Shi et al., J Mol Biol 397:385-96, 2010, Int. Patent Publ. No. WO2009/085462 and U.S. Patent Publ. No. US2010/0021477. Briefly, the libraries were generated by diversifying human scaffolds where germline VH genes IGHV1-69*01, IGHV3-23*01, and IGHV5-51*01 were recombined with the human IGHJ-4 minigene via the H3 loop, and human germline VL kappa genes O12 (IGKV1-39*01), L6 (IGKV3-11*01), A27 (IGKV3-20*01), and B3 (IGKV4-1*01) were recombined with the IGKJ-1 minigene to assemble complete VH and VL domains. The positions in the heavy and light chain variable regions around H1, H2, L1, L2 and L3 loops corresponding to positions identified to be frequently in contact with protein and peptide antigens were chosen for diversification. Sequence diversity at selected positions was limited to residues occurring at each position in the IGHV or IGLV germline gene families of the respective IGHV or IGLV genes. Diversity at the H3 loop was generated by utilizing short to mid-sized synthetic loops of lengths 7-14 amino acids. The amino acid distribution at H3 was designed to mimic the observed variation of amino acids in human antibodies. Library design is detailed in Shi et al., (2010) J Mol Biol 397:385-96. The scaffolds utilized to generate libraries were named according to their human VH and VL germline gene origin. The three heavy chain libraries were combined with the four germline light chains or combined with the diversified light chain libraries to generate 12 unique VH:VL combinations. These libraries were later combined further based on library versions to generate additional libraries for panning experiments against PD-1.

The libraries were panned against huPD1-ECD, cynoPD1-ECD, musPD1-ECD, huPD1-Fc and/or musPD1-Fc. The recombinant proteins were biotinylated (bt) and captured on streptavidin magnetic beads (Dynal), then exposed to the de novo pIX Fab libraries at a final concentration of 100 nM or 10 nM. Non-specific phages were washed away in PBS-Tween and bound phages were recovered by infection of MC1061F' E. coli cells. Phages were amplified from these cells overnight and panning was repeated for a total of three or four rounds. Following the final round of biopanning, monoclonal Fab was screened for binding to huPD1-ECD, huPD1-Fc, musPD1-Fc and/or cynoPD1-Fc in two ELISA formats. In Format 1, Fab was captured on an ELISA plate by anti-Fd antibody and the various forms of btPD1's were added to captured Fab, followed by detection of bt-PD1's with Streptavidin:HRP. In Format 2, the various forms of btPD1's were captured on ELISA plates by Streptavidin and secreted Fab was added to the captured antigen, followed by detection of the Fab with GoatAntiFab'2HRP. Clones that demonstrated binding to the proteins were sequenced in the heavy and light chain variable regions.

Fabs from the human PD-1 or mouse PD-1 selections were then tested for cross-reactivity to cynoPD1-Fc secreted in mammalian cell supernatant. Fab was captured on an ELISA plate by anti-Fd antibody and the cynoPD1-Fc supernatant was added to the captured Fab, followed by detection of cynoPD1-Fc with GoatAntiHumanFc:HRP. Based on binding characteristics to cynoPD1-Fc, select antibodies were chosen for further characterization.

Select Fabs were chosen for further characterization and were cloned as IgG2sigma/κ. IgG2sigma has abolished effector functions and has V234A, G237A, P238S, H268A, V309L, A330S and P331S substitutions when compared to the wild type IgG2. IgG2sigma is described in U.S. Pat. No. 8,961,967. The antibodies were evaluated for their ability to block human PD-1 binding to cynomolgus PD-L1, affinity to human and cynomolgus PD-1 proteins, and their ability to bind to cells endogenously expressing human PD-1 (Jurkat cells). The antibodies were subsequently evaluated for their ability to block human PD-L1 and human PD-L2 binding to huPD1.

Based on the results, several antibodies were chosen for affinity maturation. Characteristics of select antibodies chosen for affinity maturation are shown in Table 7.

TABLE 7

| | Ligand inhibition; IC$_{50}$ (µg/ml) | | | | ProteOn SPR affinity | | |
|---|---|---|---|---|---|---|---|
| mAb | cynoPD-L1 | huPD-L1 | huPD-L2 | Jurkat binding; EC$_{50}$ µg/ml | k$_{on}$ (1/Ms) | k$_{off}$ (1/s) | K$_D$ (nM) |
| PD1B11 | 0.017-0.018 | 0.019 | 0.029 | 0.03-0.24 | 4.68E+05 | 8.96E−03 | 19.2 |
| PD1B70 | 0.010-0.021 | 0.040 | 0.059 | 0.69-1.32 | 1.84E+05 | 3.04E−02 | 166 |
| PD1B71 | 0.014-0.015 | 0.024 | 0.035 | 0.13-0.47 | 2.31E+05 | 2.77E−02 | 120 |

Hu: human
Cyno: cynomolgus

Example 3. Affinity-Maturation of Human Anti-PD-1 Antibodies

Antibodies PD1B70, PD1B71 and PD1B114 (close homolog to PD1B11), were affinity matured in Fab format using phage display libraries with diversity at select VL positions and at HCDR1 and HCDR2. The design of affinity-maturation libraries for each Fab is shown in Table 8. Residue numbering is according to PD1B114 VH SEQ ID NO: 41 in Table 8.

TABLE 8

Diversification of PD1B114, PD1B70 and PD1B71 VH

| Position | Parent amino acid | Residues used for diversification |
|---|---|---|
| 30 | S | D, K, S |
| 31 | S | D, N, S, T |
| 32 | Y | A, D, S, Y |
| 33 | A | A, D, G, S, W, Y |
| 35 | S | H, N, S |

TABLE 8-continued

| 50 | G | A, E, G, N, R, T, W, Y |
| 52 | I | A, D, I, N, R, S |
| 54 | I | E, I, N, S, Y |
| 55 | F | E, F, Q, S, Y |
| 57 | T | D, N, R, S, T, Y |
| 59 | N | E, G, N, Q, R, Y |

Diversification of PD1B114, PD1B70 and PD1B71 VL

| Position | Parent amino acid | Residues used for diversification |
|---|---|---|
| 30 | S | D, N, R, S |
| 31 | S | N, S, T |
| 32 | Y | D, N, R, S, Y |
| 49 | Y | E, H, K, Y |
| 50 | D | D, G, S, W, Y |
| 53 | N | D, N, S, T, Y |
| 91 | R | A, D, E, G, H, N, R, S, W, Y |
| 92 | S | A, D, E, G, H, N, R, S, W, Y |
| 93 | N | A, D, E, G, H, N, R, S, W, Y |
| 94 | W | A, D, E, G, H, N, R, S, W, Y |
| 96 | L | F, I, L, N, R, W, Y |

The libraries were constructed and phage was generated. The VH and the VL phage libraries were then used for phage panning against huPD1-ECD and cynoPD1-ECD biotinylated recombinant proteins. Following phage panning, soluble Fabs were screened for binding to both human and cyno PD-1. Select Fabs were cloned as IgG2sigma isotype and characterized for their Jurkat cell binding and cynomolgus PD-L1 ligand inhibition at concentrations 1 µg/ml and 10 µg/ml.

Table 9 shows the characterization results of the parental and affinity-matured antibodies.

TABLE 9

| mAb | Ligand inhibition at indicated concentration* | | Jurkat Cell binding; $EC_{50}$ (µg/ml) |
|---|---|---|---|
| | 1 µg/ml | 10 µg/ml | |
| PD1B11 | 5% | 5% | 0.05 |
| PD1B114 | 8% | 13% | 0.47 |
| PD1B149 | 7% | 7% | 0.08 |
| PD1B160 | 4% | 3% | 0.08 |
| PD1B162 | 7% | 6% | 0.05 |
| PD1B164 | 6% | 3% | 0.06 |
| PD1B183 | 5% | 5% | 0.08 |
| PD1B184 | 4% | 4% | 0.08 |
| PD1B185 | 8% | 5% | 0.09 |
| PD1B187 | 7% | 5% | 0.09 |
| PD1B192 | 5% | 5% | 0.06 |
| PD1B70 | 6% | 6% | 0.69 |
| PD1B175 | 6% | 5% | 0.09 |
| PD1B71 | 6% | 9% | 0.13 |
| PD1B177 | 7% | 8% | 0.05 |

*value indicates percentage ligand not blocked

The affinity matured antibodies were assessed in affinity experiments as described above using ProteOn SPR analyses for binding to huPD1-ECD and cynoPD1-ECD. The binding characteristics of the mAbs to cyno PD-1 are shown in Table 10 and to human PD-1 in Table 11. STDEV were calculated for 3 or more replicates generated for human and cyno proteins. If less than 3 replicates were calculated, RANGE was indicated. RANGE is defined as the low and high values for the replicates tested. For samples in the Table 10 or Table 11 without value indicated in RANGE or STDEV, only one experiment was performed. The best affinity matured variants had affinities for human and cyno PD-1 in the single digit nM range following ~4-20 fold gains in affinity compared to their parental mAbs.

TABLE 10

| | antigen: cyno PD-1 | | | | | |
|---|---|---|---|---|---|---|
| Sample | $k_{on}$ (1/Ms) | STDEV. kon or RANGE | $k_{off}$ (1/s) | STDEV. koff or RANGE | $K_D$ (nM) | STDEV. $K_D$ or RANGE |
| PD1B70 | 2.10E+05 | (1.99-2.25)E+05 | 2.58E−02 | (2.45-2.75)E−02 | 123 | 109-138 |
| PD1B175 | 2.14E+05 | (1.98-2.30)E+05 | 6.40E−03 | (6.06-6.73)E−03 | 30 | 26-34 |
| PD1B71 | 3.04E+05 | 2.35 E+04 | 2.03E−02 | 7.27E−04 | 66.8 | 5.68 |
| PD1B177 | 2.92E+05 | (2.80-3.04)E+05 | 1.89E−03 | (1.84-1.93)E−03 | 6.47 | 6.1-6.9 |
| PD1B114 | 2.94E+05 | 1.69 E+04 | 2.39E−02 | 1.45E−03 | 81.5 | 6.8 |
| PD1B149 | 3.20E+05 | (3.04-3.36)E+05 | 3.57E−03 | (3.48-3.65)E−03 | 11.2 | (10.9-11.4) |
| PD1B160 | 3.17E+05 | (3.16-3.17)E+05 | 1.66E−03 | (1.63-1.68)E−03 | 5.23 | 5.1-5.3 |
| PD1B162 | 3.87E+05 | (3.84-3.89)E+05 | 9.79E−04 | (9.59-9.98)E−04 | 2.53 | 2.5-2.6 |
| PD1B164 | 2.67E+05 | (2.67-2.67)E+05 | 2.87E−04 | (2.82-2.91)E−04 | 1.07 | 1.06-1.09 |
| PD1B11 | 2.93E+05 | (2.85-3.01)E+05 | 9.17E−03 | (0.8-1.00)E−02 | 31.3 | (27.7-35.1) |
| PD1B183 | 3.20E+05 | (3.04-3.37)E+05 | 8.39E−03 | (8.01-8.76)E−03 | 26.3 | 23.9-28.8 |
| PD1B184 | 2.38E+05 | (2.08-2.68)E+05 | 2.74E−03 | (2.55-2.92)E−03 | 11.5 | 9.5-14.1 |
| PD1B185 | 3.11E+05 | (2.80-3.43)E+05 | 9.47E−03 | (9.38-9.55)E−03 | 30.5 | 27.5-34.1 |
| PD1B187 | 2.94E+05 | (2.20-3.70)E+05 | 1.57E−03 | (1.28-1.85)E−03 | 5.32 | 3.5-8.4 |
| PD1B192 | 3.07E+05 | (2.90-3.24)E+05 | 5.04E−03 | (4.86-5.22)E−03 | 16.4 | 15.0-18.0 |

TABLE 11

Antigen: human PD-1

| Sample | $k_{on}$ (1/Ms) | $k_{off}$ (1/s) | $K_D$ (nM) |
|---|---|---|---|
| PD1B70 | 4.15E+05 | 4.18E−02 | 101 |
| PD1B175 | 4.22E+05 | 9.72E−03 | 23 |
| PD1B71 | 5.48E+05 | 2.73E−02 | 49.9 |
| PD1B177 | 5.15E+05 | 2.57E−03 | 5 |
| PD1B114 | 5.17E+05 | 2.79E−02 | 54.1 |
| PD1B149 | 5.32E+05 | 6.20E−03 | ~12* |
| PD1B160 | 5.40E+05 | 3.71E−03 | 6.87 |
| PD1B162 | 6.49E+05 | 3.86E−03 | 5.95 |
| PD1B164 | 4.48E+05 | 1.31E−03 | 2.92 |
| PD1B11 | 5.16E+05 | 8.52E−03 | ~17* |
| PD1B183 | 5.27E+05 | 8.44E−03 | 16 |
| PD1B184 | 4.45E+05 | 5.09E−03 | 11.4 |
| PD1B185 | 5.85E+05 | 7.65E−03 | 13.1 |
| PD1B187 | 5.35E+05 | 2.78E−03 | 5.2 |
| PD1B192 | 5.41E+05 | 1.17E−02 | ~228 |

*Values did not pass the data acceptance criteria (chi2 > 20%) and were therefore considered approximations.

Example 4. Combinatorial Variant PD-1 mAb Production

Following the analysis of the affinity results, combinatorial sequences were considered.

PD1B11 and PD1B114 have very similar sequences. Because PD1B11 had approximately a 3-fold tighter affinity to human PD-1 and a 2-fold tighter affinity to cyno PD-1 compared to PD1B114, antibodies having combinations of their various CDRs were made. The HCDR3 of PD1B11 was placed into PD1B164 and PD1B162 (affinity-matured variants of PD1B114), using site directed mutagenesis while the HCDR2 of PD1B164 (affinity matured variant of PD1B114) was placed into PD1B187 (affinity matured variant of PD1B11). The resulting heavy chains were paired with parental light chains resulting in new antibodies PD1B194, PD1B195 and PD1B196, respectively.

PD1B175 and PD1B177 both contained the parental light chain even though the antibodies were generated using diversified VL libraries during affinity maturation. In an attempt to increase antibody affinities, PD1B175 heavy chain was paired with PD1L185 or PD1L187 affinity matured light chains, and PD1B177 heavy chain was paired with PD1L86, PD1L168 or PD1L190 affinity matured light chains, resulting in antibodies PD1B197, PD1B198, PD1B199, PD1B200 and PD1B201. VH and VL pairing of the antibodies is shown in Table 20 in Example 5.

The HCDR, LCDR, VH and VL sequences of these antibodies are shown in Tables 14, 15, 16, 17, 18, 19, 21 and 22 in Example 5. The antibodies were cloned as IgG2sigma/x mAbs and transiently expressed in HEK293 expi cells for affinity measurements.

Affinities of the resulting antibodies were determined as described above. Table 12 shows the measured affinities of the combinatorial mAb variants to cyno PD-1 and Table 13 shows the affinities to human PD-1. STDEV were calculated for 3 or more replicates generated for human and cyno proteins. If less than 3 replicates were calculated, RANGE is indicated. RANGE is defined as the low and high values for the replicates tested. For samples without RANGE or STDEV, only one experiment was performed

TABLE 12

| | binding to cyno PD-1 | | | | | |
|---|---|---|---|---|---|---|
| Sample | $k_{on}$ (1/Ms) | STDEV. kon or RANGE | $k_{off}$ (1/s) | STDEV. koff or RANGE | $K_D$ (nM) | STDEV. KD or RANGE |
| PD1B70 (Parent) | 2.50E+05 | (2.25-2.74) E+05 | 2.22E−02 | (2.18-2.26) E−02 | 88.98 | (79.6-100) |
| PD1B197 | 2.75E+05 | 1.27 E+04 | 1.26E−03 | 4.04E−05 | 4.6 | 0.3 |
| PD1B198 | 3.72E+05 | 1.61 E+04 | 4.16E−03 | 9.29E−05 | 11.18 | 0.54 |
| PD1B11 (Parent) | 3.50E+05 | (3.49-3.50) E+05 | 9.42E−03 | (9.38-9.46) E−03 | 26.95 | (26.8-27.1) |
| PD1B194 | 3.22E+05 | 2.86 E+04 | 1.93E−04 | 5.86E−06 | 0.6 | 0.06 |
| PD1B195 | 4.32E+05 | (4.30-4.34) E+05 | 4.08E−04 | (3.96-4.19) E−04 | 0.94 | (0.91-0.97) |
| PD1B196 | 3.03E+05 | 6.66 E+03 | 1.76E−04 | 9.85E−06 | 0.58 | 0.03 |
| PD1B71 (Parent) | 3.77E+05 | (3.37-4.17) E+05 | 1.96E−02 | (1.85-2.07) E−02 | 51.99 | (44.4-61.4) |
| PD1B199 | 3.40E+05 | 7.94 E+03 | 1.77E−04 | 1.55E−05 | 0.52 | 0.05 |
| PD1B200 | 3.80E+05 | 2.21 E+04 | 4.22E−04 | 1.99E−05 | 1.11 | 0.08 |
| PD1B201 | 3.05E+05 | 1.80 E+04 | 2.93E−04 | 2.35E−05 | 0.96 | 0.1 |

TABLE 13

| | binding to human PD-1 | | | | | |
|---|---|---|---|---|---|---|
| Sample | $k_{on}$ (1/Ms) | STDEV. kon or RANGE | $k_{off}$ (1/s) | STDEV. koff or RANGE | $K_D$ (nM) | STDEV. KD or RANGE |
| PD1B70 (Parent) | 7.69E+05 | (7.37-8.00) E+05 | 3.49E−02 | (3.41-3.56) E−02 | 45.35 | (42.6-43.8) |
| PD1B197 | 6.58E+05 | 2.26 E+04 | 3.24E−03 | 1.74E−04 | 4.9 | 0.3 |
| PD1B198 | 8.95E+05 | 6.44 E+04 | 9.34E−03 | 9.90E−04 | 10.43 | 1.34 |
| PD1B11 (Parent) | 9.33E+05 | (8.84-9.82) E+05 | 9.05E−03 | (8.67-9.43) E−03 | 9.7 | (9.6-9.81) |
| PD1B194 | 8.97E+05 | 1.45 E+05 | 9.60E−04 | 2.78E−05 | 1.07 | 0.18 |
| PD1B195 | 1.23E+06 | 1.79 E+05 | 1.52E−03 | 6.51E−05 | 1.23 | 0.19 |
| PD1B196 | 8.83E+05 | 6.39 E+04 | 3.66E−04 | 2.01E−05 | 0.41 | 0.04 |

TABLE 13-continued

| | | | | | | |
|---|---|---|---|---|---|---|
| | | | binding to human PD-1 | | | |
| Sample | $k_{on}$ (1/Ms) | STDEV. kon or RANGE | $k_{off}$ (1/s) | STDEV. koff or RANGE | $K_D$ (nM) | STDEV. KD or RANGE |
| PD1B71 (Parent) | 9.55E+05 | (9.33-9.76) E+05 | 2.25E-02 | (2.19-2.30) E-02 | 23.52 | (22.4-24.7) |
| PD1B199 | 9.33E+05 | 6.92 E+04 | 5.64E-04 | 1.98E-05 | 0.6 | 0.05 |
| PD1B200 | 1.05E+06 | 1.40 E+05 | 1.22E-03 | 3.21E-05 | 1.17 | 0.16 |
| PD1B201 | 8.58E+05 | 8.22 E+04 | 9.57E-04 | 3.06E-05 | 1.12 | 0.11 |

Example 5. Structural Characterization of Anti-PD1 Antibodies Derived from Phage Display Libraries The cDNA sequences and amino acid translations of the antibodies were obtained using standard techniques throughout the generation of the antibodies using various campaigns. After polypeptide sequence determination, some antibody cDNAs encoding the variable regions or full length antibodies were codon optimized using standard methods for scale-up expression.

Table 14 shows the HCDR1 sequences of select PD-1 antibodies.

Table 15 shows the HCDR2 sequences of select PD-1 antibodies.

Table 16 shows the HCDR3 sequences of select PD-1 antibodies.

Table 17 shows the LCDR1 sequences of select PD-1 antibodies.

Table 18 shows the LCDR2 sequences of select PD-1 antibodies.

Table 19 shows the LCDR3 sequences of select PD-1 antibodies.

Table 20 shows the VH and the VL pairing of select PD-1 antibodies.

Table 21 shows the VH sequences of select PD-1 antibodies.

Table 22 shows the VL sequences of select PD-1 antibodies.

TABLE 14

| | HCDR1 | | | | | |
|---|---|---|---|---|---|---|
| Antibody | | | Sequence | | | SEQ ID NO: |
| PD1B114 | S | Y | A | I | S | 10 |
| PD1B149 | S | Y | A | I | S | 10 |
| PD1B160 | S | Y | A | I | S | 10 |
| PD1B162 | S | Y | A | I | S | 10 |
| PD1B164 | S | Y | A | I | S | 10 |
| PD1B11 | S | Y | A | I | S | 10 |
| PD1B183 | S | Y | A | I | S | 10 |
| PD1B184 | S | Y | A | I | S | 10 |
| PD1B185 | S | Y | A | I | S | 10 |
| PD1B187 | S | Y | A | I | S | 10 |
| PD1B192 | S | Y | A | I | S | 10 |
| PD1B71 | S | Y | A | I | S | 10 |
| PD1B177 | D | Y | V | I | S | 11 |
| PD1B70 | S | Y | A | I | S | 10 |
| PD1B175 | S | Y | V | I | H | 12 |
| PD1B194 | S | Y | A | I | S | 10 |
| PD1B195 | S | Y | A | I | S | 10 |
| PD1B196 | S | Y | A | I | S | 10 |
| PD1B197 | S | Y | V | I | H | 12 |
| PD1B198 | S | Y | V | I | H | 12 |
| PD1B199 | D | Y | V | I | S | 11 |
| PD1B200 | D | Y | V | I | S | 11 |
| PD1B201 | D | Y | V | I | S | 11 |

TABLE 15

| | HCDR2 | | | | | | | | | | | | | | |
|---|---|---|---|---|---|---|---|---|---|---|---|---|---|---|---|
| Antibody | | | | | Sequence | | | | | | | | | | SEQ ID NO: |
| PD1B114 | G | I | I | P | I | F | G | T | A | N | Y | A | Q | K | F | Q | G | 13 |
| PD1B149 | G | I | I | P | I | F | G | T | A | N | Y | A | Q | K | F | Q | G | 13 |
| PD1B160 | G | I | I | P | I | F | D | T | A | N | Y | A | Q | K | F | Q | G | 14 |
| PD1B162 | G | I | I | P | I | F | D | T | A | N | Y | A | Q | K | F | Q | G | 14 |
| PD1B164 | G | I | I | P | I | F | D | T | A | N | Y | A | Q | K | F | Q | G | 14 |
| PD1B11 | G | I | I | P | I | F | G | T | A | N | Y | A | Q | K | F | Q | G | 13 |
| PD1B183 | G | I | I | P | I | F | G | T | A | N | Y | A | Q | K | F | Q | G | 13 |
| PD1B184 | G | I | I | P | I | F | G | T | A | N | Y | A | Q | K | F | Q | G | 13 |
| PD1B185 | G | I | I | P | I | F | G | T | A | N | Y | A | Q | K | F | Q | G | 13 |
| PD1B187 | G | I | I | P | I | F | G | T | A | N | Y | A | Q | K | F | Q | G | 13 |
| PD1B192 | G | I | I | P | I | F | G | T | A | N | Y | A | Q | K | F | Q | G | 13 |
| PD1B71 | G | I | I | P | I | F | G | T | A | N | Y | A | Q | K | F | Q | G | 13 |
| PD1B177 | G | I | I | P | I | Y | G | T | A | N | Y | A | Q | K | F | Q | G | 15 |
| PD1B70 | G | I | I | P | I | F | G | T | A | N | Y | A | Q | K | F | Q | G | 13 |
| PD1B175 | G | I | I | P | I | F | G | T | A | N | Y | A | Q | K | F | Q | G | 13 |
| PD1B194 | G | I | I | P | I | F | D | T | A | N | Y | A | Q | K | F | Q | G | 14 |
| PD1B195 | G | I | I | P | I | F | D | T | A | N | Y | A | Q | K | F | Q | G | 14 |
| PD1B196 | G | I | I | P | I | F | D | T | A | N | Y | A | Q | K | F | Q | G | 14 |
| PD1B197 | G | I | I | P | I | F | G | T | A | N | Y | A | Q | K | F | Q | G | 13 |
| PD1B198 | G | I | I | P | I | F | G | T | A | N | Y | A | Q | K | F | Q | G | 13 |

TABLE 15-continued

| | HCDR2 | |
|---|---|---|
| Antibody | Sequence | SEQ ID NO: |
| PD1B199 | G I I P I Y G T A N Y A Q K F Q G | 15 |
| PD1B200 | G I I P I Y G T A N Y A Q K F Q G | 15 |
| PD1B201 | G I I P I Y G T A N Y A Q K F Q G | 15 |

TABLE 16

| | HCDR3 | |
|---|---|---|
| Antibody | Sequence | SEQ ID NO: |
| PD1B114 | P G L A A A Y D T G N L D Y | 16 |
| PD1B149 | P G L A A A Y D T G N L D Y | 16 |
| PD1B160 | P G L A A A Y D T G N L D Y | 16 |
| PD1B162 | P G L A A A Y D T G N L D Y | 16 |
| PD1B164 | P G L A A A Y D T G N L D Y | 16 |
| PD1B11 | P G L A A A Y D T G S L D Y | 17 |
| PD1B183 | P G L A A A Y D T G S L D Y | 17 |
| PD1B184 | P G L A A A Y D T G S L D Y | 17 |
| PD1B185 | P G L A A A Y D T G S L D Y | 17 |
| PD1B187 | P G L A A A Y D T G S L D Y | 17 |
| PD1B192 | P G L A A A Y D T G S L D Y | 17 |
| PD1B71 | G T L D R T G H L D Y | 18 |
| PD1B177 | G T L D R T G H L D Y | 18 |
| PD1B70 | G Y V R A T G M L D Y | 19 |
| PD1B175 | G Y V R A T G M L D Y | 19 |
| PD1B194 | P G L A A A Y D T G S L D Y | 17 |
| PD1B195 | P G L A A A Y D T G S L D Y | 17 |
| PD1B196 | P G L A A A Y D T G S L D Y | 17 |
| PD1B197 | G Y V R A T G M L D Y | 19 |
| PD1B198 | G Y V R A T G M L D Y | 19 |
| PD1B199 | G T L D R T G H L D Y | 18 |
| PD1B200 | G T L D R T G H L D Y | 18 |
| PD1B201 | G T L D R T G H L D Y | 18 |

TABLE 17

| | LCDR1 | |
|---|---|---|
| Antibody | Sequence | SEQ ID NO: |
| PD1B114 | R A S Q S V S S Y L A | 20 |
| PD1B149 | R A S Q S V R N Y L A | 21 |
| PD1B160 | R A S Q S V D S Y L A | 22 |

TABLE 17-continued

| | LCDR1 | |
|---|---|---|
| Antibody | Sequence | SEQ ID NO: |
| PD1B162 | R A S Q S V D S Y L A | 22 |
| PD1B164 | R A S Q S V R S Y L A | 23 |
| PD1B11 | R A S Q S V S S Y L A | 20 |
| PD1B183 | R A S Q S V S S Y L A | 20 |
| PD1B184 | R A S Q S V R N Y L A | 21 |
| PD1B185 | R A S Q S V R N Y L A | 21 |
| PD1B187 | R A S Q S V R S Y L A | 23 |
| PD1B192 | R A S Q S V D S Y L A | 22 |
| PD1B71 | R A S Q S V S S Y L A | 20 |
| PD1B177 | R A S Q S V S S Y L A | 20 |
| PD1B70 | R A S Q S V S S Y L A | 20 |
| PD1B175 | R A S Q S V S S Y L A | 20 |
| PD1B194 | R A S Q S V R S Y L A | 23 |
| PD1B195 | R A S Q S V D S Y L A | 22 |
| PD1B196 | R A S Q S V R S Y L A | 23 |
| PD1B197 | R A S Q S V S N Y L A | 24 |
| PD1B198 | R A S Q S V S S Y L A | 20 |
| PD1B199 | R A S Q S V S S Y L A | 20 |
| PD1B200 | R A S Q S V D N Y L A | 25 |
| PD1B201 | R A S Q S V S N Y L A | 24 |

TABLE 18

| | LCDR2 | |
|---|---|---|
| Antibody | Sequence | SEQ ID NO: |
| PD1B114 | D A S N R A T | 26 |
| PD1B149 | D A S N R A T | 26 |
| PD1B160 | D A S D R A T | 27 |
| PD1B162 | D A S N R A T | 26 |
| PD1B164 | D A S Y R A T | 28 |

TABLE 18-continued

| Antibody | LCDR2 Sequence | | | | | | | SEQ ID NO: |
|---|---|---|---|---|---|---|---|---|
| PD1B11 | D | A | S | N | R | A | T | 26 |
| PD1B183 | D | A | S | N | R | A | T | 26 |
| PD1B184 | D | A | S | N | R | A | T | 26 |
| PD1B185 | D | A | S | D | R | A | T | 27 |
| PD1B187 | D | A | S | N | R | A | T | 26 |
| PD1B192 | D | A | S | N | R | A | T | 26 |
| PD1B71 | D | A | S | N | R | A | T | 26 |
| PD1B177 | D | A | S | N | R | A | T | 26 |
| PD1B70 | D | A | S | N | R | A | T | 26 |
| PD1B175 | D | A | S | N | R | A | T | 26 |
| PD1B194 | D | A | S | Y | R | A | T | 28 |
| PD1B195 | D | A | S | N | R | A | T | 26 |
| PD1B196 | D | A | S | N | R | A | T | 26 |
| PD1B197 | D | A | S | N | R | A | T | 26 |
| PD1B198 | D | A | S | S | R | A | T | 29 |
| PD1B199 | D | A | S | T | R | A | T | 30 |
| PD1B200 | D | A | S | N | R | A | T | 26 |
| PD1B201 | D | A | S | N | R | A | T | 26 |

TABLE 19

| Antibody | LCDR3 Sequence | | | | | | | | | SEQ ID NO: |
|---|---|---|---|---|---|---|---|---|---|---|
| PD1B114 | Q | Q | R | S | N | W | P | L | T | 31 |
| PD1B149 | Q | Q | R | N | Y | W | P | L | T | 32 |
| PD1B160 | Q | Q | R | G | N | W | P | L | T | 33 |
| PD1B162 | Q | Q | R | E | Y | W | P | L | T | 34 |
| PD1B164 | Q | Q | R | D | Y | W | P | L | T | 35 |
| PD1B11 | Q | Q | R | S | N | W | P | L | T | 31 |
| PD1B183 | Q | Q | R | G | Y | W | P | L | T | 36 |
| PD1B184 | Q | Q | R | N | Y | W | P | L | T | 32 |
| PD1B185 | Q | Q | R | W | N | W | P | L | T | 37 |
| PD1B187 | Q | Q | R | N | Y | W | P | L | T | 32 |
| PD1B192 | Q | Q | R | N | Y | W | P | L | T | 32 |
| PD1B71 | Q | Q | R | S | N | W | P | L | T | 31 |
| PD1B177 | Q | Q | R | S | N | W | P | L | T | 31 |
| PD1B70 | Q | Q | R | S | N | W | P | L | T | 31 |
| PD1B175 | Q | Q | R | S | N | W | P | L | T | 31 |
| PD1B194 | Q | Q | R | D | Y | W | P | L | T | 35 |
| PD1B195 | Q | Q | R | E | Y | W | P | L | T | 34 |
| PD1B196 | Q | Q | R | N | Y | W | P | L | T | 32 |
| PD1B197 | Q | Q | R | A | Y | W | P | L | T | 38 |
| PD1B198 | Q | Q | R | A | E | W | P | L | T | 39 |
| PD1B199 | Q | Q | R | N | Y | W | P | L | T | 32 |
| PD1B200 | Q | Q | R | S | A | W | P | L | T | 40 |
| PD1B201 | Q | Q | R | N | Y | W | P | L | T | 32 |

TABLE 20

| Antibody | VH peptide ID | VH SEQ ID NO: | VL peptide ID | VL SEQ ID NO: |
|---|---|---|---|---|
| PD1B114 | PD1H24 | 41 | PH9L3 | 49 |
| PD1B149 | PD1H24 | 41 | PD1L128 | 50 |
| PD1B160 | PD1H131 | 42 | PD1L101 | 51 |
| PD1B162 | PD1H131 | 42 | PD1L67 | 52 |
| PD1B164 | PD1H131 | 42 | PD1L71 | 53 |
| PD1B11 | PD1H3 | 43 | PH9L3 | 49 |
| PD1B183 | PD1H3 | 43 | PD1L109 | 54 |
| PD1B184 | PD1H3 | 43 | PD1L128 | 50 |
| PD1B185 | PD1H3 | 43 | PD1L132 | 55 |
| PD1B187 | PD1H3 | 43 | PD1L148 | 56 |
| PD1B192 | PD1H3 | 43 | PD1L133 | 57 |
| PD1B71 | PD1H108 | 44 | PH9L3 | 49 |
| PD1B177 | PD1H164 | 45 | PH9L3 | 49 |
| PD1B70 | PD1H107 | 46 | PH9L3 | 49 |
| PD1B175 | PD1H163 | 47 | PH9L3 | 49 |
| PD1B194 | PD1H170 | 48 | PD1L71 | 53 |
| PD1B195 | PD1H170 | 48 | PD1L67 | 52 |
| PD1B196 | PD1H170 | 48 | PD1L148 | 56 |
| PD1B197 | PD1H163 | 47 | PD1L185 | 58 |
| PD1B198 | PD1H163 | 47 | PD1L187 | 59 |
| PD1B199 | PD1H164 | 45 | PD1L86 | 60 |
| PD1B200 | PD1H164 | 45 | PD1L168 | 61 |
| PD1B201 | PD1H164 | 45 | PD1L190 | 62 |

TABLE 21

| VH peptide ID | VH SEQ ID NO: | VH sequence |
|---|---|---|
| PD1H24 | 41 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARPGLAAAYDTGNLDYWGQGTLVTVSS |
| PD1H131 | 42 | QVQLVQSGAEVKKPGSSVKVSCKASGGTFSSYAISWVRQAPGQGLEWMGGIIPIFDTANYAQKFQGRVTITADESTSTAYMELSSLRSEDTAVYYCARPGLAAAYDTGNLDYWGQGTLVTVSS |

TABLE 21-continued

| VH peptide ID | VH SEQ ID NO: | VH sequence |
|---|---|---|
| PD1H3 | 43 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARPGLAAAYDTGSLDYWGQGTLVTVSS |
| PD1H108 | 44 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARGTLDRTGHLDYWGQGTLVTVSS |
| PD1H164 | 45 | QVQLVQSGAEVKKPGSSVKVSCKASGGTFSDYVISWVRQAPGQGLEWMGGIIPIYGTANYAQKFQGRVTITADESTSTAYMELSSLRSEDTAVYYCARGTLDRTGHLDYWGQGTLVTVSS |
| PD1H107 | 46 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARGYVRATGMLDYWGQGTLVTVSS |
| PD1H163 | 47 | QVQLVQSGAEVKKPGSSVKVSCKASGGTFKSYVIHWVRQAPGQGLEWMGGIIPIFGTANYAQKFQGRVTITADESTSTAYMELSSLRSEDTAVYYCARGYVRATGMLDYWGQGTLVTVSS |
| PD1H170 | 48 | QVQLVQSGAEVKKPGSSVKVSCKASGGTFSSYAISWVRQAPGQGLEWMGGIIPIFDTANYAQKFQGRVTITADESTSTAYMELSSLRSEDTAVYYCARPGLAAAYDTGSLDYWGQGTLVTVSS |

TABLE 22

| VL peptide ID | VL SEQ ID NO: | VL sequence |
|---|---|---|
| PH9L3 | 49 | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIK |
| PD1L128 | 50 | EIVLTQSPATLSLSPGERATLSCRASQSVRNYLAWYQQKPGQAPRLLIHDASNRATGIPARFSGSGSGTDFTLTISSLEPEDFAVYYCQQRNYWPLTFGQGTKVEIK |
| PD1L101 | 51 | EIVLTQSPATLSLSPGERATLSCRASQSVDSYLAWYQQKPGQAPRLLIKDASDRATGIPARFSGSGSGTDFTLTISSLEPEDFAVYYCQQRGNWPLTFGQGTKVEIK |
| PD1L67 | 52 | EIVLTQSPATLSLSPGERATLSCRASQSVDSYLAWYQQKPGQAPRLLIYDASNRATGIPARFSGSGSGTDFTLTISSLEPEDFAVYYCQQREYWPLTFGQGTKVEIK |
| PD1L71 | 53 | EIVLTQSPATLSLSPGERATLSCRASQSVRSYLAWYQQKPGQAPRLLIYDASYRATGIPARFSGSGSGTDFTLTISSLEPEDFAVYYCQQRDYWPLTFGQGTKVEIK |
| PD1L109 | 54 | EIVLTQSPATLSLSPGERATLSCRASQSVSSYLAWYQQKPGQAPRLLIKDASNRATGIPARFSGSGSGTDFTLTISSLEPEDFAVYYCQQRGYWPLTFGQGTKVEIK |
| PD1L132 | 55 | EIVLTQSPATLSLSPGERATLSCRASQSVRNYLAWYQQKPGQAPRLLIYDASDRATGIPARFSGSGSGTDFTLTISSLEPEDFAVYYCQQRWNWPLTFGQGTKVEIK |
| PD1L148 | 56 | EIVLTQSPATLSLSPGERATLSCRASQSVRSYLAWYQQKPGQAPRLLIYDASNRATGIPARFSGSGSGTDFTLTISSLEPEDFAVYYCQQRNYWPLTFGQGTKVEIK |
| PD1L133 | 57 | EIVLTQSPATLSLSPGERATLSCRASQSVDSYLAWYQQKPGQAPRLLIHDASNRATGIPARFSGSGSGTDFTLTISSLEPEDFAVYYCQQRNYWPLTFGQGTKVEIK |

TABLE 22-continued

| VL peptide ID | VL SEQ ID NO: | VL sequence |
|---|---|---|
| PD1L185 | 58 | EIVLTQSPATLSLSPGERATLSCRASQSVSNYLAWYQQKPGQAPRLLIYDASNRATGIPARFSGSGSGTDFTLTISSLEPEDFAVYYCQQRAYWPLTFGQGTKVEIK |
| PD1L187 | 59 | EIVLTQSPATLSLSPGERATLSCRASQSVSSYLAWYQQKPGQAPRLLIEDASSRATGIPARFSGSGSGTDFTLTISSLEPEDFAVYYCQQRAEWPLTFGQGTKVEIK |
| PD1L86 | 60 | EIVLTQSPATLSLSPGERATLSCRASQSVSSYLAWYQQKPGQAPRLLIHDASTRATGIPARFSGSGSGTDFTLTISSLEPEDFAVYYCQQRNYWPLTFGQGTKVEIK |
| PD1L168 | 61 | EIVLTQSPATLSLSPGERATLSCRASQSVDNYLAWYQQKPGQAPRLLIHDASNRATGIPARFSGSGSGTDFTLTISSLEPEDFAVYYCQQRSAWPLTFGQGTKVEIK |
| PD1L190 | 62 | EIVLTQSPATLSLSPGERATLSCRASQSVSNYLAWYQQKPGQAPRLLIYDASNRATGIPARFSGSGSGTDFTLTISSLEPEDFAVYYCQQRNYWPLTFGQGTKVEIK |

All anti-PD-1 antibodies were identified to have VH1-69 (SEQ ID NO: 170) and IGKV3-11 (L6) (SEQ ID NO: 171) frameworks.

SEQ ID NO: 170
QVQLVQSGAEVKKPGSSVKVSCKASGGTFS SYAIS

WVRQAPGQGLEWMG GIIPIFGTANYAQKFQG

RVTITADESTSTAYMELSSLRSEDTAVYYCAR

SEQ ID NO: 171
EIVLTQSPATLSLSPGERATLSCRASQSVSSYLAWYQQKPGQAPRLLIYD

ASNRATGIPARFSGSGSGTDFTLTISSLEPEDFAVYYCQQRSNWP

Example 6. Generation and Characterization of PD-1 Antibodies in Mice

BALB/c were immunized intraperitoneally with huPD1-ECD and assessed for specific IgG titers. Once sufficient titers were obtained, splenocytes were isolated and fused with FO cells. The resulting hybridomas were plated in 96 well plates and cultured for 10 days. Antigen specific clones were identified by standard capture ELISA for binding to huPD1-ECD. Human PD-1-specific hybridomas were further tested for their affinity to human and cyno PD-1, binding to Jurkat cells and cyno PD-L1 inhibition. Based on the results, clone PD1B28 was selected for humanization using framework adaptation.

Framework adaptation process was done as essentially described in U.S. Patent Publ. No. 2009/0118127 and Fransson et al., (2010) *J Mol Biol* 398:214-231. Briefly, the heavy and light chain sequences were compared with the human germline sequences (only the "01" alleles as of Oct. 1, 2007) using BLAST search against the IMGT database (Kaas, et al., (2004) *Nucl Acids Res* 32, D208-D210; Lefranc et al., (2005) *Nucl Acid Res* 33, D593-D597). From this set of human germline genes, redundant genes (100% identical at amino acid level) and those with unpaired cysteine residues were removed. The remaining closest matching human germline genes in both the framework and CDR regions were chosen as the acceptor human frameworks. Several VL and VH germline human frameworks were selected based upon overall sequence homology and CDR lengths as well as CDR similarity. FR-4 was selected based on sequence similarity of the IGHJ/IGJK germline genes. Then, the CDRs of PD1B28 were transferred into the selected acceptor human frameworks to generate the HFA variants, except in the region corresponding to the HCDR1 of $V_H$. For this region a combination of CDR and HV, or a shorter HCDR2 (referred to as Kabat-7, see U.S. Patent Publ. No. 2009/0118127) were transferred from the non-human antibody into the human FRs because the remaining HCDR2 residues have not been found in contact in antigen-antibody complexes of known structures (Almagro, (2004) *J Mol Recognit.* 17:132). Backumtations were introduced into certain residue positions in the humanized antibodies. PD1B131 backmutations: VH: V37I_Q39L_W47S_R98S, VL: Y49K. PD1B132: VH W47S_R98S, VL: Y49K (residue numbering according to Chothia). Select antibodies were expressed as IgG2sigma/κ. The resulting antibodies were characterized for their binding to recombinant PD-1 and PD-1 expressed on cells (Jurkat cells), and their ligand inhibition (cyno PD-L1 and human PD-L1). Characteristics of select humanized antibodies are shown in Table 23. The VH and the VL sequences of the generated antibodies are shown in Table 24 and Table 25, respectively.

TABLE 23

| mAb | Jurkat cell binding relative to PD1B28 | Human PD-1 Affinity | | | PD-L1 Inhibition, $IC_{50}$ (ng/ml) | |
|---|---|---|---|---|---|---|
| | | kon (1/Ms) | koff (1/s) | $K_D$ (pM) | Human PD-L1 | Cyno PD-L1 |
| PD1B28 | 100% | 9.70E+05 | 1.18E−04 | 122 | 67 | 96 |
| PD1B131 | 100% | 8.27E+05 | 1.05E−04 | 127 | 79 | 96 |
| PD1B132 | 100% | 9.14E+05 | 8.80E−05 | 96 | 55 | 79 |

TABLE 24

| mAb | VH ID | VL ID | VH sequence | VH SEQ ID NO: |
|---|---|---|---|---|
| PD1B131 | PD1H130 | PD1L62 | EVQLVESGGGLVQPGG SLRLSCAASGFAFSRY DMSWIRLAPGKGLESV AYISGGGANTYYLDNV KGRFTISRDNAKNSLY LQMNSLRAEDTAVYYC ASPYLSYFDVWGQGTL VTVSS | 63 |
| PD1B132 | PD1H129 | PD1L62 | EVQLVESGGGLVQPGG SLRLSCAASGFAFSRY DMSWVRQAPGKGLESV AYISGGGANTYYLDNV KGRFTISRDNAKNSLY LQMNSLRAEDTAVYYC ASPYLSYFDVWGQGTL VTVSS | 64 |

TABLE 25

| mAb | VH ID | VL ID | VL sequence | VL SEQ ID NO: |
|---|---|---|---|---|
| PD1B131 | PD1H130 | PD1L62 | EIVMTQSPATLSVSPG ERATLSCRASQSLSDY LHWYQQKPGQAPRLLI KSASQSISGIPARFSG SGSGTEFTLTISSLQS EDFAVYYCQNGHSFPY TFGQGTKLEIK | 65 |
| PD1B132 | PD1H129 | PD1L62 | EIVMTQSPATLSVSPG ERATLSCRASQSLSDY LHWYQQKPGQAPRLLI KSASQSISGIPARFSG SGSGTEFTLTISSLQS EDFAVYYCQNGHSFPY TFGQGTKLEIK | 65 |

The CDR sequences of PD1B131 and PD1B132 are shown below:
HCDR1 (SEQ ID NO: 66)
RYDMS
HCDR2 (SEQ ID NO: 67)
YISGGGANTYYLDNVKG
HCDR3 (SEQ ID NO: 68)
PYLSYFDV
LCDR1 (SEQ ID NO: 69)
RASQSLSDYLH
LCDR2 (SEQ ID NO: 70)
SASQSIS
LCDR3 (SEQ ID NO: 71)
QNGHSFPYT Example 7. Effect of Isotype Switching on Anti-PD-1 Antibody Properties Variable regions of antibodies PD1B196 and PD1B199 (of IgG2sigma/x isotype) were cloned as IgG4 S228P isotypes and variable regions from antibody PD1B132 (of IgG2) into IgG2sigma isotype to assess possible differences in functionality and developability.

The antibodies were named PD1B244 (PD1B196 VH/VL on IgG4 S228P) PD1B245 (PD1B199 VH/VL on IgG4 S228P) AND PD1B243 (PD1B132 VH/VL on IgG2sigma).

Isotype switch had no consistent effect on the antibody properties however, for some of the antibodies, some change in $EC_{50}$ values were seen in the CMV assay.

Exemplified below are heavy chain and light chain amino acid sequences of various antibodies. Table 26 shows the summary of the VH, VL, heavy chain and light chain SEQ ID NOs: for select antibodies.

TABLE 26

| Antibody | VH peptide ID | VH SEQ ID NO: | VL peptide ID | VL SEQ ID NO: | HC SEQ ID NO | LC SEQ ID NO: |
|---|---|---|---|---|---|---|
| PD1B114 | PD1H24 | 41 | PH9L3 | 49 | 212 | 213 |
| PD1B149 | PD1H24 | 41 | PD1L128 | 50 | 214 | 215 |
| PD1B160 | PD1H131 | 42 | PD1L101 | 51 | 216 | 217 |
| PD1B162 | PD1H131 | 42 | PD1L67 | 52 | 218 | 219 |
| PD1B164 | PD1H131 | 42 | PD1L71 | 53 | 220 | 221 |
| PD1B183 | PD1H3 | 43 | PD1L109 | 54 | 222 | 223 |
| PD1B184 | PD1H3 | 43 | PD1L128 | 50 | 224 | 225 |
| PD1B185 | PD1H3 | 43 | PD1L132 | 55 | 226 | 227 |
| PD1B192 | PD1H3 | 43 | PD1L133 | 57 | 228 | 229 |
| PD1B243 | PD1H129 | 64 | PD1L62 | 65 | 74 | 75 |
| PD1B244 | PD1H170 | 48 | PD1L148 | 56 | 72 | 73 |
| PD1B245 | PD1H164 | 45 | PD1L86 | 60 | 76 | 77 |

HC of PD1B244
SEQ ID NO: 72
QVQLVQSGAEVKKPGSSVKVSCKASGGTFSSYAISWVRQAPGQGLEW
MGGIIPIFDTANYAQKFQGRVTITADESTSTAYMELSSLRSEDTAVY
YCARPGLAAAYDTGSLDYWGQGTLVTVSSASTKGPSVFPLAPCSRST
SESTAALGCLVKDYFPEPVTVSWNSGALTSGVHTFPAVLQSSGLYSL
SSVVTVPSSSLGTKTYTCNVDHKPSNTKVDKRVESKYGPPCPPCPAP
EFLGGPSVFLFPPKPKDTLMISRTPEVTCVVVDVSQEDPEVQFNWYV
DGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFY
PSDIAVEWESNGQPENNYKTTPPVLDSDGSFFLYSRLTVDKSRWQEG
NVFSCSVMHEALHNHYTQKSLSLSLGK

LC of PD1B244
SEQ ID NO: 73
EIVLTQSPATLSLSPGERATLSCRASQSVRSYLAWYQQKPGQAPRLL
IYDASNRATGIPARFSGSGSGTDFTLTISSLEPEDFAVYYCQQRNYW
PLTFGQGTKVEIKRTVAAPSVFIFPPSDEQLKSGTASVVCLLNNFYP
REAKVQWKVDNALQSGNSQESVTEQDSKDSTYSLSSTLTLSKADYEK
HKVYACEVTHQGLSSPVTKSFNRGEC

HC of PD1B243
SEQ ID NO: 74
EVQLVESGGGLVQPGGSLRLSCAASGFAFSRYDMSWVRQAPGKGLES
VAYISGGGANTYYLDNVKGRFTISRDNAKNSLYLQMNSLRAEDTAVY
YCASPYLSYFDVWGQGTLVTVSSASTKGPSVFPLAPCSRSTSESTAA
LGCLVKDYFPEPVTVSWNSGALTSGVHTFPAVLQSSGLYSLSSVVTV
PSSSLGTKTYTCNVDHKPSNTKVDKRVESKYGPPCPPCPAPEFLGGP
SVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAV
EWESNGQPENNYKTTPPVLDSDGSFFLYSRLTVDKSRWQEGNVFSCS
VMHEALHNHYTQKSLSLSLGK

LC of PD1B243
SEQ ID NO: 75
EIVMTQSPATLSVSPGERATLSCRASQSLSDYLHWYQQKPGQAPRLL
IKSASQSISGIPARFSGSGSGTEFTLTISSLQSEDFAVYYCQNGHSF
PYTFGQGTKLEIKRTVAAPSVFIFPPSDEQLKSGTASVVCLLNNFYP
REAKVQWKVDNALQSGNSQESVTEQDSKDSTYSLSSTLTLSKADYEK
HKVYACEVTHQGLSSPVTKSFNRGEC

HC of PD1B245
SEQ ID NO: 76
QVQLVQSGAEVKKPGSSVKVSCKASGGTFSDYVISWVRQAPGQGLEW
MGGIIPIYGTANYAQKFQGRVTITADESTSTAYMELSSLRSEDTAVY
YCARGTLDRTGHLDYWGQGTLVTVSSASTKGPSVFPLAPCSRSTSES
TAALGCLVKDYFPEPVTVSWNSGALTSGVHTFPAVLQSSGLYSLSSV
VTVPSSSLGTKTYTCNVDHKPSNTKVDKRVESKYGPPCPPCPAPEFL
GGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLP
SSIEKTISKAKGQPREPQVYTLPPSQEEMTKNQVSLTCLVKGFYPSD
IAVEWESNGQPENNYKTTPPVLDSDGSFFLYSRLTVDKSRWQEGNVF
SCSVMHEALHNHYTQKSLSLSLGK

LC of PD1B245
SEQ ID NO: 77
EIVLTQSPATLSLSPGERATLSCRASQSVSSYLAWYQQKPGQAPRLL
IHDASTRATGIPARFSGSGSGTDFTLTISSLEPEDFAVYYCQQRNYW
PLTFGQGTKVEIKRTVAAPSVFIFPPSDEQLKSGTASVVCLLNNFYP
REAKVQWKVDNALQSGNSQESVTEQDSKDSTYSLSSTLTLSKADYEK
HKVYACEVTHQGLSSPVTKSFNRGEC

HC of PD1B114
SEQ ID NO: 212
QVQLVQSGAEVKKPGSSVKVSCKASGGTFSSYAISWVRQAPGQGLEW
MGGIIPIFGTANYAQKFQGRVTITADESTSTAYMELSSLRSEDTAVY
YCARPGLAAAYDTGNLDYWGQGTLVTVSSASTKGPSVFPLAPCSRST
SESTAALGCLVKDYFPEPVTVSWNSGALTSGVHTFPAVLQSSGLYSL
SSVVTVTSSNFGTQTYTCNVDHKPSNTKVDKTVERKCCVECPPCPAP
PAAASSVFLFPPKPKDTLMISRTPEVTCVVVDVSAEDPEVQFNWYVD
GVEVHNAKTKPREEQFNSTFRVVSVLTVLHQDWLNGKEYKCKVSNKG
LPSSIEKTISKTKGQPREPQVYTLPPSREEMTKNQVSLTCLVKGFYP
SDIAVEWESNGQPENNYKTTPPMLDSDGSFFLYSKLTVDKSRWQQGN
VFSCSVMHEALHNHYTQKSLSLSPGK

LC of PD1B114
SEQ ID NO: 213
EIVLTQSPATLSLSPGERATLSCRASQSVSSYLAWYQQKPGQAPRLL
IYDASNRATGIPARFSGSGSGTDFTLTISSLEPEDFAVYYCQQRSNW
PLTFGQGTKVEIKRTVAAPSVFIFPPSDEQLKSGTASVVCLLNNFYP
REAKVQWKVDNALQSGNSQESVTEQDSKDSTYSLSSTLTLSKADYEK
HKVYACEVTHQGLSSPVTKSFNRGEC

HC of PD1B149
SEQ ID NO 214
QVQLVQSGAEVKKPGSSVKVSCKASGGTFSSYAISWVRQAPGQGLEW
MGGIIPIFGTANYAQKFQGRVTITADESTSTAYMELSSLRSEDTAVY
YCARPGLAAAYDTGNLDYWGQGTLVTVSSASTKGPSVFPLAPCSRST
SESTAALGCLVKDYFPEPVTVSWNSGALTSGVHTFPAVLQSSGLYSL
SSVVTVTSSNFGTQTYTCNVDHKPSNTKVDKTVERKCCVECPPCPAP
PAAASSVFLFPPKPKDTLMISRTPEVTCVVVDVSAEDPEVQFNWYVD
GVEVHNAKTKPREEQFNSTFRVVSVLTVLHQDWLNGKEYKCKVSNKG
LPSSIEKTISKTKGQPREPQVYTLPPSREEMTKNQVSLTCLVKGFYP
SDIAVEWESNGQPENNYKTTPPMLDSDGSFFLYSKLTVDKSRWQQGN
VFSCSVMHEALHNHYTQKSLSLSPGK

LC of PD1B149

SEQ ID NO: 215

EIVLTQSPATLSLSPGERATLSCRASQSVRNYLAWYQQKPGQAPRLL
IHDASNRATGIPARFSGSGSGTDFTLTISSLEPEDFAVYYCQQRNYW
PLTFGQGTKVEIKRTVAAPSVFIFPPSDEQLKSGTASVVCLLNNFYP
REAKVQWKVDNALQSGNSQESVTEQDSKDSTYSLSSTLTLSKADYEK
HKVYACEVTHQGLSSPVTKSFNRGEC

HC of PD1B160

SEQ ID NO: 216

QVQLVQSGAEVKKPGSSVKVSCKASGGTFSSYAISWVRQAPGQGLEW
MGGIIPIFDTANYAQKFQGRVTITADESTSTAYMELSSLRSEDTAVY
YCARPGLAAAYDTGNLDYWGQGTLVTVSSASTKGPSVFPLAPCSRST
SESTAALGCLVKDYFPEPVTVSWNSGALTSGVHTFPAVLQSSGLYSL
SSVVTVTSSNFGTQTYTCNVDHKPSNTKVDKTVERKCCVECPPCPAP
PAAASSVFLFPPKPKDTLMISRTPEVTCVVVDVSAEDPEVQFNWYVD
GVEVHNAKTKPREEQFNSTFRVVSVLTVLHQDWLNGKEYKCKVSNKG
LPSSIEKTISKTKGQPREPQVYTLPPSREEMTKNQVSLTCLVKGFYP
SDIAVEWESNGQPENNYKTTPPMLDSDGSFFLYSKLTVDKSRWQQGN
VFSCSVMHEALHNHYTQKSLSLSPGK

LC of PD1B160

SEQ ID NO: 217

EIVLTQSPATLSLSPGERATLSCRASQSVDSYLAWYQQKPGQAPRLL
IKDASDRATGIPARFSGSGSGTDFTLTISSLEPEDFAVYYCQQRGNW
PLTFGQGTKVEIKRTVAAPSVFIFPPSDEQLKSGTASVVCLLNNFYP
REAKVQWKVDNALQSGNSQESVTEQDSKDSTYSLSSTLTLSKADYEK
HKVYACEVTHQGLSSPVTKSFNRGEC

HC of PD1B162

SEQ ID NO: 218

QVQLVQSGAEVKKPGSSVKVSCKASGGTFSSYAISWVRQAPGQGLEW
MGGIIPIFDTANYAQKFQGRVTITADESTSTAYMELSSLRSEDTAVY
YCARPGLAAAYDTGNLDYWGQGTLVTVSSASTKGPSVFPLAPCSRST
SESTAALGCLVKDYFPEPVTVSWNSGALTSGVHTFPAVLQSSGLYSL
SSVVTVTSSNFGTQTYTCNVDHKPSNTKVDKTVERKCCVECPPCPAP
PAAASSVFLFPPKPKDTLMISRTPEVTCVVVDVSAEDPEVQFNWYVD
GVEVHNAKTKPREEQFNSTFRVVSVLTVLHQDWLNGKEYKCKVSNKG
LPSSIEKTISKTKGQPREPQVYTLPPSREEMTKNQVSLTCLVKGFYP
SDIAVEWESNGQPENNYKTTPPMLDSDGSFFLYSKLTVDKSRWQQGN
VFSCSVMHEALHNHYTQKSLSLSPGK

LC of PD1B162

SEQ ID NO: 219

EIVLTQSPATLSLSPGERATLSCRASQSVDSYLAWYQQKPGQAPRLL
IYDASNRATGIPARFSGSGSGTDFTLTISSLEPEDFAVYYCQQREYW
PLTFGQGTKVEIKRTVAAPSVFIFPPSDEQLKSGTASVVCLLNNFYP
REAKVQWKVDNALQSGNSQESVTEQDSKDSTYSLSSTLTLSKADYEK
HKVYACEVTHQGLSSPVTKSFNRGEC

HC of PD1B164

SEQ ID NO: 220

QVQLVQSGAEVKKPGSSVKVSCKASGGTFSSYAISWVRQAPGQGLEW
MGGIIPIFDTANYAQKFQGRVTITADESTSTAYMELSSLRSEDTAVY
YCARPGLAAAYDTGNLDYWGQGTLVTVSSASTKGPSVFPLAPCSRST
SESTAALGCLVKDYFPEPVTVSWNSGALTSGVHTFPAVLQSSGLYSL
SSVVTVTSSNFGTQTYTCNVDHKPSNTKVDKTVERKCCVECPPCPAP
PAAASSVFLFPPKPKDTLMISRTPEVTCVVVDVSAEDPEVQFNWYVD
GVEVHNAKTKPREEQFNSTFRVVSVLTVLHQDWLNGKEYKCKVSNKG
LPSSIEKTISKTKGQPREPQVYTLPPSREEMTKNQVSLTCLVKGFYP
SDIAVEWESNGQPENNYKTTPPMLDSDGSFFLYSKLTVDKSRWQQGN
VFSCSVMHEALHNHYTQKSLSLSPGK

LC of PD1B164

SEQ ID NO: 221

EIVLTQSPATLSLSPGERATLSCRASQSVRSYLAWYQQKPGQAPRLL
IYDASYRATGIPARFSGSGSGTDFTLTISSLEPEDFAVYYCQQRDYW
PLTFGQGTKVEIKRTVAAPSVFIFPPSDEQLKSGTASVVCLLNNFYP
REAKVQWKVDNALQSGNSQESVTEQDSKDSTYSLSSTLTLSKADYEK
HKVYACEVTHQGLSSPVTKSFNRGEC

HC of PD1B183

SEQ ID NO: 222

QVQLVQSGAEVKKPGSSVKVSCKASGGTFSSYAISWVRQAPGQGLEW
MGGIIPIFGTANYAQKFQGRVTITADESTSTAYMELSSLRSEDTAVY
YCARPGLAAAYDTGSLDYWGQGTLVTVSSASTKGPSVFPLAPCSRST
SESTAALGCLVKDYFPEPVTVSWNSGALTSGVHTFPAVLQSSGLYSL
SSVVTVTSSNFGTQTYTCNVDHKPSNTKVDKTVERKCCVECPPCPAP
PAAASSVFLFPPKPKDTLMISRTPEVTCVVVDVSAEDPEVQFNWYVD
GVEVHNAKTKPREEQFNSTFRVVSVLTVLHQDWLNGKEYKCKVSNKG
LPSSIEKTISKTKGQPREPQVYTLPPSREEMTKNQVSLTCLVKGFYP
SDIAVEWESNGQPENNYKTTPPMLDSDGSFFLYSKLTVDKSRWQQGN
VFSCSVMHEALHNHYTQKSLSLSPGK

LC of PD1B183

SEQ ID NO: 223

EIVLTQSPATLSLSPGERATLSCRASQSVSSYLAWYQQKPGQAPRLL
IKDASNRATGIPARFSGSGSGTDFTLTISSLEPEDFAVYYCQQRGYW
PLTFGQGTKVEIKRTVAAPSVFIFPPSDEQLKSGTASVVCLLNNFYP
REAKVQWKVDNALQSGNSQESVTEQDSKDSTYSLSSTLTLSKADYEK
HKVYACEVTHQGLSSPVTKSFNRGEC

HC of PD1B184

SEQ ID NO: 224

QVQLVQSGAEVKKPGSSVKVSCKASGGTFSSYAISWVRQAPGQGLEW
MGGIIPIFGTANYAQKFQGRVTITADESTSTAYMELSSLRSEDTAVY
YCARPGLAAAYDTGSLDYWGQGTLVTVSSASTKGPSVFPLAPCSRST
SESTAALGCLVKDYFPEPVTVSWNSGALTSGVHTFPAVLQSSGLYSL
SSVVTVTSSNFGTQTYTCNVDHKPSNTKVDKTVERKCCVECPPCPAP
PAAASSVFLFPPKPKDTLMISRTPEVTCVVVDVSAEDPEVQFNWYVD

GVEVHNAKTKPREEQFNSTFRVVSVLTVLHQDWLNGKEYKCKVSNKG

LPSSIEKTISKTKGQPREPQVYTLPPSREEMTKNQVSLTCLVKGFYP

SDIAVEWESNGQPENNYKTTPPMLDSDGSFFLYSKLTVDKSRWQQGN

VFSCSVMHEALHNHYTQKSLSLSPGK

LC of PD1B184
SEQ ID NO: 225

EIVLTQSPATLSLSPGERATLSCRASQSVRNYLAWYQQKPGQAPRLL

IHDASNRATGIPARFSGSGSGTDFTLTISSLEPEDFAVYYCQQRNYW

PLTFGQGTKVEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

HC of PD1B185
SEQ ID NO: 226

QVQLVQSGAEVKKPGSSVKVSCKASGGTFSSYAISWVRQAPGQGLEW

MGGIIPIFGTANYAQKFQGRVTITADESTSTAYMELSSLRSEDTAVY

YCARPGLAAAYDTGSLDYWGQGTLVTVSSASTKGPSVFPLAPCSRST

SESTAALGCLVKDYFPEPVTVSWNSGALTSGVHTFPAVLQSSGLYSL

SSVVTVTSSNFGTQTYTCNVDHKPSNTKVDKTVERKCCVECPPCPAP

PAAASSVFLFPPKPKDTLMISRTPEVTCVVVDVSAEDPEVQFNWYVD

GVEVHNAKTKPREEQFNSTFRVVSVLTVLHQDWLNGKEYKCKVSNKG

LPSSIEKTISKTKGQPREPQVYTLPPSREEMTKNQVSLTCLVKGFYP

SDIAVEWESNGQPENNYKTTPPMLDSDGSFFLYSKLTVDKSRWQQGN

VFSCSVMHEALHNHYTQKSLSLSPGK

LC of PD1B185
SEQ ID NO: 227

EIVLTQSPATLSLSPGERATLSCRASQSVRNYLAWYQQKPGQAPRLL

IYDASDRATGIPARFSGSGSGTDFTLTISSLEPEDFAVYYCQQRWNW

PLTFGQGTKVEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

HC of PD1B192
SEQ ID NO: 228

QVQLVQSGAEVKKPGSSVKVSCKASGGTFSSYAISWVRQAPGQGLEW

MGGIIPIFGTANYAQKFQGRVTITADESTSTAYMELSSLRSEDTAVY

YCARPGLAAAYDTGSLDYWGQGTLVTVSSASTKGPSVFPLAPCSRST

SESTAALGCLVKDYFPEPVTVSWNSGALTSGVHTFPAVLQSSGLYSL

SSVVTVTSSNFGTQTYTCNVDHKPSNTKVDKTVERKCCVECPPCPAP

PAAASSVFLFPPKPKDTLMISRTPEVTCVVVDVSAEDPEVQFNWYVD

GVEVHNAKTKPREEQFNSTFRVVSVLTVLHQDWLNGKEYKCKVSNKG

LPSSIEKTISKTKGQPREPQVYTLPPSREEMTKNQVSLTCLVKGFYP

SDIAVEWESNGQPENNYKTTPPMLDSDGSFFLYSKLTVDKSRWQQGN

VFSCSVMHEALHNHYTQKSLSLSPGK

LC or PD1B192
SEQ ID NO: 229

EIVLTQSPATLSLSPGERATLSCRASQSVDSYLAWYQQKPGQAPRLL

IHDASNRATGIPARFSGSGSGTDFTLTISSLEPEDFAVYYCQQRNYW

PLTFGQGTKVEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

Example 8. Characterization of PD-1 Antibodies in Cell-Based Assays

Select antibodies were characterized in MLR and CMV assays using protocols described in Example 1. The $EC_{50}$ values for IFN-γ induction from MLR and CMV assays are shown in Table 27. In most cases, anti-PD-1 antibodies showed a dose-dependent increase in IFN-γ levels in both MLR and CMV assays.

TABLE 27

| Origin | mAb | MLR $EC_{50}$, nM | CMV $EC_{50}$, nM |
|---|---|---|---|
| Phage display | PD1B3 | 0.29 | 0.06 |
| | PD1B91 | 0.05 | 0.03 |
| | PD1B194 | NT | NC |
| | PD1B195 | NT | 1.64 |
| | PD1B196 | 0.14 | 0.31 |
| | PD1B199 | 0.63 | NC |
| | PD1B200 | NT | 3.81 |
| | PD1B201 | NT | 2.60 |
| | PD1B244 | 0.08 | 0.03 |
| HFA | PD1B132 | NT | 0.07 |
| | PD1B243 | 0.07 | 0.02 |

NT: not tested
NC: no convergence
HFA: human framework adaptation

In addition to IFN-γ, secreted levels of additional cytokines were also affected by PD-1 blockade in the two assays. Upon CMV stimulation, anti-PD-1 antibodies led to a dose-dependent induction of TNF-α and IL-4, whereas in the MLR assay they increased TNF-α and IL-2 levels.

Example 9. Generation of Human Anti-TIM-3 Antibodies Using Phage Display Libraries The de novo pIX Fab libraries described in Example 2 were panned against the extracellular domain of recombinant human TIM-3-Fc fusion protein (R&D Systems, #2365-TM; residues Ser22-Arg200 of full length TIM-3) (huTIM-3-Fc).

The recombinant protein was biotinylated (bt) and captured on streptavidin magnetic beads (Dynal), then exposed to the de novo pIX Fab libraries at a final concentration of 100 nM. Non-specific phages were washed away in PBS-Tween and bound phages were recovered by infection of MC1061F' E. coli cells. Phages were amplified from these cells overnight and panning was repeated for a total of three rounds. Following the final round of biopanning, monoclonal Fab was screened for binding to biotinylated human TIM-3-Fc captured on ELISA plates by Streptavidin and secreted Fab was added to the captured antigen, followed by detection of the Fab with Goat Anti human kappa:HRP. Select antibodies were expressed and cloned on various IgG isotypes as indicated below, and characterized further.

Example 10. Generation of Anti-TIM-3 Antibodies in Mice

Balb/c mice were immunized with recombinant human TIM-3-Fc fusion protein (R&D Systems, catalog #2365-TM) over the course of 18 days. Spleens were harvested, and a B cell enriched population was fused with FO mouse myeloma cells to generate mAb secreting hybridomas. The hybridoma supernatants were screened for binding by ELISA to TIM-3-Fc protein and an irrelevant human IgG1 Fc. TIM-3 specific supernatants were then assayed for the ability to bind to TIM-3 expressing THP-1 cells.

Select mAb HC and LC v-genes were cloned from the TIM-3 positive hybridomas using standard molecular biology techniques (RT-PCR followed by PCR fragment ligation into plasmid expression vectors). mAbs were expressed recombinantly, and the ELISA was repeated to confirm TIM-3 specific binding. Molecular models for murine antibody sequences to be human framework adapted were constructed using MOE (CCG, Montreal) and visually inspected. Potential problem positions that might influence antigen binding, VL/VH packing and/or core residues that might affect domain stabilities were identified. For both VL and VH, multiple human frameworks were proposed with or without back mutations to mouse framework sequences if problem positions were identified. The designed sequences were cloned into heavy and light chain plasmids and expressed in Expi293F cells. Expressed antibody in the culture supernatants were quantified and assessed for binding to HEK293 cells transfected with recombinant human TIM-3.

Example 11. Isotypes of Anti-TIM-3 Antibodies

The VH and VL of isolated anti-TIM-3 antibodies were cloned onto various heavy chain isotypes, optionally with various Fc substitutions, and allotypes with K light chains during the course of antibody characterization to evaluate the effect, if any, of isotype switch on functionality or developability of the antibodies. The various isotypes used are shown in Table 28.

TABLE 28

| Isotype | Substitution when compared to wild type* | Purpose of substitution |
|---|---|---|
| IgG2sigma | V234A, G237A, P238S, H268A, V309L, A330S, P331S | Abolishing effector functions |
| IgG2sigma_K409R | V234A, G237A, P238S, H268A, V309L, A330S, P331S, K409R | Abolishing effector functions, improving heterodimer formation in bispecific antibody |
| IgG2sigma_F405L | V234A, G237A, P238S, H268A, V309L, A330S, P331S, F405L | Abolishing effector functions, improving heterodimer formation in bispecific antibody |
| IgG4_PAA | S228P, F234A, L235A | Antibody stability, abolishing effector functions |
| IgG4_PAA_F405L_R409K | S228P, F234A, L235A, F450L, R409K | Antibody stability, abolishing effector functions, improving heterodimer formation in bispecific antibody |
| IgG4_S228P | S228P | Antibody stability |
| IgG1 | Wild type | |
| IgG1sigma | L234A, L235A, G237A, P238S, H268A, A330S, P331S | Abolishing effector functions |
| IgG1sigma_K409R | L234A, L235A, G237A, P238S, H268A, A330S, P331S, K409R | Abolishing effector functions, improving heterodimer formation in bispecific antibody |

TABLE 28-continued

| Isotype | Substitution when compared to wild type* | Purpose of substitution |
|---|---|---|
| IgG1sigma_F405L | L234A, L235A, G237A, P238S, H268A, A330S, P331S, F405L | Abolishing effector functions, improving heterodimer formation in bispecific antibody |
| IgG1_AA | L234A, L235A | Abolishing effector functions |

*Residue numbering according to the EU Index

The various allotypes used in the generated antibodies are shown in Table 29. Some of the antibodies had chimeric allotypes. Antibodies TM3B105 and TM3B403 for example differ by one amino acid substitution in a constant region at position 189. TM3B105 heavy and light chains SEQ ID NOs: 240 and 79, respectively; TM3B403 heavy and light chains SEQ ID NOs: 78 and 79, respectively. The two antibodies are expected to have the same characteristics.

TABLE 29

| Isotype/Allotype/Substitutions |
|---|
| IgG2sigma_G2m(n-)/(n)_K409R |
| IgG2sigma_G2m(n-)_K409R |
| IgG2sigma_G2m(n-)/(n) |
| IgG2sigma_F405L |
| IgG2_K409R |
| IgG2sigma_G2m(n-) |
| IgG2 |
| IgG4_S228P |
| IgG4_S228P_F405L_R409K |
| IgG4_nG4m(a)_PAA_F405L_R409K |
| IgG4_PAA |
| IgG1sigma |
| IgG1_G1m(17) |
| IgG1_ G1m(17,1)_AA |

In general, anti-TIM-3 antibodies with IgG2sigma Fc had greater activity in the CMV assay than anti-TIM-3 antibodies with huIgG4 Fc. In addition, antibodies with huIgG2 Fc demonstrated functionality that was intermediate between IgG2sigma and IgG4. Allotype had no effect on antibody activity.

Example 12. Structural Characterization of Anti-TIM-3 Antibodies

The cDNA sequences and amino acid translations of the antibodies were obtained using standard techniques throughout the generation of the antibodies using various campaigns. After polypeptide sequence determination, some antibody cDNAs encoding the variable regions or full length antibodies were codon optimized using standard methods for scale-up expression. Antibodies TM3B103, TM3B105, M3B108, TM3B109 and TM3B1113 were isolated from phage display libraries. Antibodies TM3B189, TM3B190, TM3B193, TM3B195 and TM3B196 were generated by immunizing mice.

Table 30 shows the HCDR1 sequences of select anti-TIM-3 antibodies.
Table 31 shows the HCDR2 sequences of select anti-TIM-3 antibodies.
Table 32 shows the HCDR3 sequences of select anti-TIM-3 antibodies.
Table 33 shows the LCDR1 sequences of select anti-TIM-3 antibodies.
Table 34 shows the LCDR2 sequences of select anti-TIM-3 antibodies.
Table 35 shows the LCDR3 sequences of select anti-TIM-3 antibodies.
Table 36 shows the VH sequences of select anti-TIM-3 antibodies.
Table 37 shows the VL sequences of select anti-TIM-3 antibodies.
Table 38 shows the frameworks of select anti-TIM-3 antibodies.
Table 30.

TABLE 30

| mAb name | HCDR1 Sequence | | | | | | SEQ ID NO: |
|---|---|---|---|---|---|---|---|
| TM3B103 | N | Y | W | M | S | | 90 |
| TM3B105 | S | Y | A | M | S | | 91 |
| TM3B109 | S | Y | A | M | S | | 91 |
| TM3B108 | G | Y | W | M | H | | 92 |
| TM3B113 | D | Y | W | M | S | | 93 |
| TM3B189 | S | Y | V | M | Y | | 94 |
| TM3B190 | S | D | Y | A | W | N | 95 |
| TM3B193 | D | T | Y | L | H | | 96 |
| TM3B195 | S | Y | W | M | Q | | 97 |
| TM3B196 | S | Y | G | V | H | | 98 |
| TM3B291 | S | Y | W | M | Q | | 97 |

TABLE 31

| mAb | HCDR2 Sequence | | | | | | | | | | | | | | | SEQ ID NO: |
|---|---|---|---|---|---|---|---|---|---|---|---|---|---|---|---|---|
| TM3B103 | A | I | S | G | S | G | G | S | T | Y | Y | A | D | S | V | K | G | 99 |
| TM3B105 | A | I | S | G | S | G | G | S | T | Y | Y | A | D | S | V | K | G | 99 |
| TM3B109 | A | I | S | G | S | G | G | S | T | Y | Y | A | D | S | V | K | G | 99 |
| TM3B108 | A | I | S | Y | S | G | S | S | T | Y | Y | A | D | S | V | K | G | 100 |
| TM3B113 | V | I | K | Y | S | G | G | S | K | Y | Y | A | D | S | V | K | G | 101 |
| TM3B189 | Y | I | N | P | Y | N | G | T | K | Y | N | E | K | F | K | G | | 102 |
| TM3B190 | Y | I | N | Y | S | G | R | T | S | Y | N | P | S | L | K | S | | 103 |

TABLE 31-continued

| | HCDR2 | |
|---|---|---|
| mAb | Sequence | SEQ ID NO: |
| TM3B193 | R I D P T N G N I K Y D P K F Q G | 104 |
| TM3B195 | A I Y P G D G D I R Y T Q N F K G | 105 |
| TM3B196 | V I W S D G S T T Y N S A L K S | 106 |
| TM3B291 | A I Y P G D G D I R Y T Q N F K G | 105 |

TABLE 32

| | HCDR3 | |
|---|---|---|
| mAb | Sequence | SEQ ID NO: |
| TM3B103 | D H W D P N F L D Y | 107 |
| TM3B105 | S P Y A P L D Y | 108 |
| TM3B109 | N E E P D D R L D Y | 109 |
| TM3B108 | G T N W L D Y | 110 |
| TM3B113 | E L E G V F D Y | 111 |
| TM3B189 | D D Y D V A P F A Y | 112 |
| TM3B190 | G G N F D Y | 113 |
| TM3B193 | P Y Y G F F D Y | 114 |
| TM3B195 | W E K S T T V V Q R N Y F D Y | 115 |
| TM3B196 | Q A N Y R Y D S A M D Y | 116 |
| TM3B291 | W E K S T T V V Q R N Y F D Y | 115 |

TABLE 33

| | LCDR1 | |
|---|---|---|
| mAb | Sequence | SEQ ID NO: |
| TM3B103 | R A S Q S V S S S Y L A | 117 |
| TM3B105 | R A S Q S V N D Y L A | 118 |
| TM3B109 | K S S Q S V L A S S N N K N Y L A | 119 |
| TM3B108 | R A S Q S V S S S Y L A | 117 |
| TM3B113 | R A S Q S V S N S T L A | 120 |
| TM3B189 | R A S E S L D S Y G N S Y I H | 121 |
| TM3B190 | Q A T Q D I V K N L N | 122 |
| TM3B193 | K A S Q D V N T A V A | 123 |
| TM3B195 | K A S E N V G T F V S | 124 |
| TM3B196 | K A S Q S V D Y D G D S Y M N | 125 |
| TM3B291 | K A S E N V G T F V S | 124 |

TABLE 34

| | LCDR2 | |
|---|---|---|
| mAb | Sequence | SEQ ID NO: |
| TM3B103 | G A S S R A T | 126 |
| TM3B105 | D A S N R A T | 127 |
| TM3B109 | W A S T R E S | 128 |
| TM3B108 | G A S S R A T | 126 |
| TM3B113 | T A S S R A T | 129 |
| TM3B189 | L A S N L E S | 130 |
| TM3B190 | Y V T E L A E | 131 |
| TM3B193 | S A T Y R Y T | 132 |
| TM3B195 | G A S N R Y T | 133 |
| TM3B196 | T A A N L Q S | 134 |
| TM3B291 | G A S N R Y T | 133 |

TABLE 35

| | LCDR3 | |
|---|---|---|
| mAb | Sequence | SEQ ID NO: |
| TM3B103 | Q Q Y G S S P L T | 135 |
| TM3B105 | Q Q G G H A P I T | 136 |
| TM3B109 | Q Q Y Y S T P L T | 137 |
| TM3B108 | Q Q Y G S S P L T | 135 |
| TM3B113 | Q Q S Y T S P W T | 139 |
| TM3B189 | Q Q N N E D P F T | 140 |
| TM3B190 | L Q F Y E F P L T | 141 |
| TM3B193 | Q Q H Y S T P Y T | 142 |
| TM3B195 | G Q S Y S Y P T | 143 |
| TM3B196 | Q Q S N E D P F T | 144 |
| TM3B291 | G Q S Y S Y P T | 143 |

TABLE 36

| mAb name | VH name | VH sequence | SEQ ID NO: |
|---|---|---|---|
| TM3B103 | TM3H21 | EVQLLESGGGLVQPGGSLRLSCAASGFTFSNYWMSWVRQAPGKGLEWVSAISGSGGSTYYADSVKGRFTISRDNSKNTLYLQMNSLRAEDTAVYYCAKDHWDPNFLDYWGQGTLVTVSS | 145 |

TABLE 36-continued

| mAb name | VH name | VH sequence | SEQ ID NO: |
|---|---|---|---|
| TM3B105 | TM3H24 | EVQLLESGGGLVQPGGSLRLS CAASGFTFSSYAMSWVRQAPG KGLEWVSAISGSGGSTYYADS VKGRFTISRDNSKNTLYLQMN SLRAEDTAVYYCAKSPYAPLD YWGQGTLVTVSS | 146 |
| TM3B108 | TM3H30 | EVQLLESGGGLVQPGGSLRLS CAASGFTFSGYWMHWVRQAPG KGLEWVSAISYSGSSTYYADS VKGRFTISRDNSKNTLYLQMN SLRAEDTAVYYCAKGTNWLDY WGQGTLVTVSS | 147 |
| TM3B109 | TM3H31 | EVQLLESGGGLVQPGGSLRLS CAASGFTFSSYAMSWVRQAPG KGLEWVSAISGSGGSTYYADS VKGRFTISRDNSKNTLYLQMN SLRAEDTAVYYCAKNEEPDDR LDYWGQGTLVTVSS | 148 |
| TM3B113 | TM3H65 | EVQLLESGGGLVQPGGSLRLS CAASGFTFSDYWMSWVRQAPG KGLEWVSVIKYSGGSKYYADS VKGRFTISRDNSKNTLYLQMN SLRAEDTAVYYCAKELEGVFD YWGQGTLVTVSS | 149 |
| TM3B189 | TM3H141 | EVQLQQSGPELLKPGASVKMS CKASGYTFTSYVMYWVKQKPG QGLEWIGYINPYNDGTKYNEK FKGKATLTSDKSSSTAYMELS RLTSEDSAVYYCTRDDYDVAP FAYWGQGTLVTVSA | 150 |
| TM3B190 | TM3H96 | DVQLQESGPGLVKPSQSLSLT CTVTGYSITSDYAWNWIRQFP GNKLEWMGYINYSGRTSYNPS LKSRISITRDTSKNQFFLQLN SVTTEDTATYYCTSGGNFDYW GQGTTLTVSS | 151 |
| TM3B193 | TM3H99 | EVQLQQSGAELVKPGASVKLS CTASGPHIKDTYLHWVKQRPE QGLEWIGRIDPTNGNIKYDPK FQGKATITSDTSSNTAYLQLS SLTSEDTAVYYCARPYYGFFD YWGQGTTLTVSS | 152 |
| TM3B195 | TM3H144 | EVQLQQSGAELARPGASVKLS CKASGYTFTSYWMQWVKQRPG QGLEWIGAIYPGDGDIRYTQN FKGKATLTADKSSSTAYMQLS SLASEDSAVYYCARWEKSTTV VQRNYFDYWGQGTTLTVSS CORRECT? | 153 |
| TM3B196 | TM3H102 | QVQLKESGPGLVAPSQSLSIT CTISGFSLTSYGVHWVRQPPG KGLEWLVVIWSDGSTTYNSAL KSRLSISKDNSKSQVFLKMNS LQTDDTAMYYCARQANYRYDS AMDYWGQGTSVTVSS | 154 |
| TM3B291 | TM3H162 | EVQLVQSGAEVKKPGESLKIS CKGSGYSFTSYWMQWVRQMPG KGLEWMGAIYPGDGDIRYTQN FKGQVTISADKSISTAYLQWS SLKASDTAMYYCARWEKSTTV VQRNYFDYWGQGTTLTVSS | 172 |

TABLE 37

| mAb name | VL name | VL sequence | SEQ ID NO: |
|---|---|---|---|
| TM3B103 | PH9L1 | EIVLTQSPGTLSLSPGERATL SCRASQSVSSSYLAWYQQKPG QAPRLLIYGASSRATGIPDRF SGSGSGTDFTLTISRLEPEDF AVYYCQQYGSSPLTFGQGTKV EIK | 155 |
| TM3B105 | TM3L33 | EIVLTQSPATLSLSPGERATL SCRASQSVNDYLAWYQQKPGQ APRLLIYDASNRATGIPARFS GSGSGTDFTLTISSLEPEDFA VYYCQQGGHAPITFGQGTKVE IK | 156 |
| TM3B108 | PH9L1 | EIVLTQSPGTLSLSPGERATL SCRASQSVSSSYLAWYQQKPG QAPRLLIYGASSRATGIPDRF SGSGSGTDFTLTISRLEPEDF AVYYCQQYGSSPLTFGQGTKV EIK | 155 |
| TM3B109 | PYYL6 | DIVMTQSPDSLAVSLGERATI NCKSSQSVLASSNNKNYLAWY QQKPGQPPKLLIYWASTRESG VPDRFSGSGSGTDFTLTISSL QAEDVAVYYCQQYYSTPLTFG QGTKVEIK | 157 |
| TM3B113 | TM3L12 | EIVLTQSPGTLSLSPGERATL SCRASQSVSNSTLAWYQQKPG QAPRLLIYTASSRATGIPDRF SGSGSGTDFTLTISRLEPEDF AVYYCQQSYTSPWTFGQGTKV EIK | 158 |
| TM3B189 | TM3L61 | DIVLTQSPASLAVSLGQRATI SCRASESLDSYGNSYIHWYQQ KPGQPPKLLIYLASNLESGVP ARFSGSGSKTDFTLTIDPVEA DDPATYYCQQNNEDPFTFGSG TKLEIK | 159 |
| TM3B190 | TM3L62 | DIVMTQSPSSMSASLGDRITI TCQATQDIVKNLNWYQQKPGK PPSFLIHYVTELAEGVPSRFS GSGSGSDYSLTISNLESEDFA DYYCLQFYEFPLTFGAGTKLE LK | 160 |
| TM3B193 | TM3L52 | DIVMTQSHKFMSTSVGDRVSI TCKASQDVNTAVAWYQQKPGQ SPKLLIYSATYRYTGVPDRFT GSGSGTDFTFTISSVQAEDLA VYYCQQHYSTPYTFGSGTKLE IK | 161 |
| TM3B195 | TM3L67 | DVQMIQSPKSMSMSVGERVTL SCKASENVGTFVSWYQQKPDQ SPKLLIYGASNRYTGVPDRFT GSGSATDFTLTISSVQAEDLA DYHCGQSYSYPTFGSGTKLEM | 162 |
| TM3B196 | TM3L64 | DIQMTQSPASLAVSLGQRATI SCKASQSVDYDGDSYMNWYQQ KPGQPPKLLIYTAANLQSGIP ARFSGSGSGTDFTLNIHPVEE EDAATYYCQQSNEDPFTFGSG TKLEIK | 163 |
| TM3B291 | TM3L85 | DIQMTQSPSSLSASVGDRVTI TCKASENVGTFVSWYQQKPGK APKLLIYGASNRYTGVPSRFS GSGSGTDFTLTISSLQPEDFA TYYCGQSYSYPTFGQGTKLEI K | 173 |

TABLE 38

| mAb name | VH name | VH framework Name | SEQ ID NO: | VL name | VL framework Name | SEQ ID NO: |
|---|---|---|---|---|---|---|
| TM3B103 | TM3H21 | IGHV3-23 | 174 | PH9L1 | IGKV3-20 | 180 |
| TM3B105 | TM3H24 | IGHV3-23 | 174 | TM3L33 | IGKV3-11 | 171 |
| TM3B108 | TM3H30 | IGHV3-23 | 174 | PH9L1 | IGKV3-20 | 180 |
| TM3B109 | TM3H31 | IGHV3-23 | 174 | PYYL6 | IGKV4-1 | 181 |
| TM3B113 | TM3H65 | IGHV3-23 | 174 | TM3L12 | IGKV3-20 | 180 |
| TM3B189 | TM3H141 | IGHV1-02 | 175 | TM3L61 | IGKV4-1 | 181 |
| TM3B190 | TM3H96 | IGHV4-30 | 176 | TM3L62 | IGKV1-39 | 182 |
| TM3B193 | TM3H99 | IGHV1-03 | 177 | TM3L52 | IGKV1-33 | 183 |
| TM3B195 | TM3H144 | IGHV1-03 | 177 | TM3L67 | IGKV1-39 | 182 |
| TM3B196 | TM3H102 | IGHV2-26 | 178 | TM3L64 | IGKV4-1 | 181 |
| TMB291 | TM3H162 | IGHV5-51 | 179 | TM3L85 | IGKV1-39 | 182 |

IGHV3-23
SEQ ID NO: 174
EVQLLESGGGLVQPGGSLRLSCAASGFTFSSYAMSWVRQAPGKGLEWVS
AISGSGGSTYYADSVKGRFTISRDNSKNTLYLQMNSLRAEDTAVYYCAK

IGHV1-02
SEQ ID NO: 175
QVQLVQSGAEVKKPGASVKVSCKASGYTFTGYYMHWVRQAPGQGLEWMG
RINPNSGGTNYAQKFQGRVTSTRDTSISTAYMELSRLRSDDTVVYYCAR

IGHV4-30
SEQ ID NO: 176
QVQLQESGPGLVKPSQTLSLTCTVSGGSISSGDYYWSWIRQPPGKGLEW
IGYIYYSGSTYYNPSLKSRVTISVDTSKNQFSLKLSSVTAADTAVYYCA
R

IGHV1-03
SEQ ID NO: 177
QVQLVQSGAEVKKPGASVKVSCKASGYTFTSYAMHWVRQAPGQRLEWMG
WINAGNGNTKYSQKFQGRVTITRDTSASTAYMELSSLRSEDTAVYYCAR

IGHV2-26
SEQ ID NO: 178
QVTLKESGPVLVKPTETLTLTCTVSGFSLSNARMGVSWIRQPPGKALEW
LAHIFSNDEKSYSTSLKSRLTISKDTSKSQVVLTMTNMDPVDTATYYCA
RI

IGHV5-51
SEQ ID NO: 179
EVQLVQSGAEVKKPGESLKISCKGSGYSFTSYWIGWVRQMPGKGLEWMG
HYPGDSDTRYSPSFQGQVTISADKSISTAYLQWSSLKASDTAMYYCAR

IGKV3-20
SEQ ID NO: 180
EIVLTQSPGTLSLSPGERATLSCRASQSVSSSYLAWYQQKPGQAPRLLI
YGASSRATGIPDRFSGSGSGTDFTLTISRLEPEDFAVYYCQQYGSSP

IGKV3-11
SEQ ID NO: 171
EIVLTQSPATLSLSPGERATLSCRASQSVSSYLAWYQQKPGQAPRLLIY
DASNRATGIPARFSGSGSGTDFTLTISSLEPEDFAVYYCQQRSNWP

IGKV4-1
SEQ ID NO: 181
EIVLTQSPGTLSLSPGERATLSCRASQSVSSSYLAWYQQKPGQAPRLLI
YGASSRATGIPDRFSGSGSGTDFTLTISRLEPEDFAVYYCQQYGSSP

IGKV1-39
SEQ ID NO: 182
DIQMTQSPSSLSASVGDRVTITCRASQSISSYLNWYQQKPGKAPKLLIY
AASSLQSGVPSRFSGSGSGTDFTLTISSLQPEDFATYYCQQSYSTPI

GKV1-33
SEQ ID NO: 183
DIQMTQSPSSLSASVGDRVTITCQASQDISNYLNWYQQKPGKAPKLLIY
DASNLETGVPSRFSGSGSGTDFTFTISSLQPEDIATYYCQQYDNLP

Example 13. Characterization of Anti-TIM-3 Antibodies

Select antibodies were characterized for their binding to human or cyno cells, and their ability to block ligand galectin 9 binding. Table 39 shows the characteristics of select antibodies in these assays. The cell binding data represents the calculated $EC_{50}$ values of the antibodies binding to cells transfected with the indicated TIM-3 recombinant protein expressed in µg/ml units. The galectin-9 inhibition represents the maximal level of inhibition of galectin-9 binding to human TIM-3 seen with the indicated antibodies. The tested antibodies were tested as IgG2sigma isotypes.

Epitope mapping assays were performed by coating recombinant huTIM-3-Fc protein on MSD plates. Plates were blocked and washed, followed by the addition of the mixture of the MSD-tag-labeled anti-TIM-3 mAbs incubated with increasing concentrations of unlabeled anti-TIM-3 mABs. After incubation with gentle shaking at room temperature, plates were washed and analyzed with a SECTOR Imager 6000. Antibodies that competed with each other for binding to human TIM-3 were considered to bind to similar epitopes. Positive inhibition was noted if >75% of the binding was inhibited. Partial inhibition was 40-75% inhibition. <40% inhibition was denoted as negative.

TABLE 39

| | Cell binding $EC_{50}$, µg/ml | | Galectin 9 Inhibition, | |
|---|---|---|---|---|
| mAb | Human cells | Cyno cells | % inhibition | Epitope Bin |
| TM3B103 | 0.71 | 0.09 | 71.2 | 1 |
| TM3B105 | 0.46 | 0.03 | 69.8 | 1 |
| TM3B107 | | | 74.8 | 2 |
| TM3B108 | 0.42 | 0.03 | 64.2 | 1 |
| TM3B109 | | | 77.0 | 1 |
| TM3B113 | | | 75.6 | 2 |
| TM3B189 | 0.74 | 0.19 | 76.4 | 3 |
| TM3B190 | 0.35 | 0.08 | 60.7 | 1 |
| TM3B193 | | | 47.4 | 3 |
| TM3B219 | 0.60 | 0.10 | 38.0 | 3 |
| TM3B196 | | | 57.0 | 4 |

Example 14. Development of a Functional In Vitro Assay to Characterize Anti-TIM-3 Antibodies Functional assessment of inhibitory receptors such as PD-1 can be done using T cells from normal donor that are stimulated by allogeneic dendritic cells or specific antigens, such as Tetanus toxoid or CMV. In this setting, changes in T cell function with antibody treatment can be detected by measuring supernatant cytokine levels or markers of T cell activation. Effects of anti-TIM-3 antibodies can be very variable in these types of assays, with little overall change in the state of activation or functionality of bulk T cell (non-antigen-specific). On the other hand, using tetramer approaches to follow single T cell sub-populations/clones in these assays does not provide the resolution needed to detect functional effects of anti-TIM-3 antibodies, due to the low frequency and heterogeneous functional profile of these T cell clones. In addition, this approach necessitates the prior identification of the epitopes recognized by CMV-specific T cells in each donor.

CD137 was recently described as a surrogate marker for activated antigen-specific T cells (Wolf et al., (2007) *Blood*

110(1):201-210; Klinger et al., (2013) *PLoS One* 8(9): e74231). In our assays, using CD137 enabled the identification of antigen specific CD8+ and CD4+ T cells that expand in response to CMV antigen stimulation and allowed the detection of the functional effects of anti-TIM-3 antibodies. In addition to CD137 expression, cytokine secretion by MSD was also evaluated in these assays.

The activity of select anti-TIM-3 antibodies was tested in CMV pp65-stimulated PBMCs. In these assays, anti-TIM-3 antibodies augmented T cell activation, as evidenced by increased CD137 expression on both CD8+ and CD4+ T cells. In addition, selected anti-TIM-3 antibodies also enhanced secretion of IFN-γ and TNF-α in this assay.

Table 40 shows the results of the CMV assay where enhanced surface expression of CD137 was evaluated on CD8+ or CD4+ cells for select TIM-3 antibodies. The table shows the p values generated using the Two-tailed T-test (unequal variance).

TABLE 40

| | CD8+ CD137+, p values | | | CD4+ CD137+, p values | | |
|---|---|---|---|---|---|---|
| | Mean | Std Dev | n | Mean | Std Dev | n |
| TM3B103 | 0.043 | 0.025 | 5 | 0.071 | 0.112 | 3 |
| TM3B105 | 0.029 | 0.036 | 6 | 0.01 | 0.017 | 3 |
| TM3B107 | 0.182 | 0.188 | 5 | 0.157 | 0.125 | 3 |
| TM3B108 | 0.022 | 0.018 | 5 | 0.01 | 0.01 | 3 |
| TM3B109 | 0.035 | 0.041 | 5 | 0.017 | 0.015 | 3 |
| TM3B113 | 0.082 | 0.064 | 6 | 0.05 | 0.026 | 3 |
| TM3B189 | 0.027 | 0.026 | 6 | 0.007 | 0.011 | 3 |
| TM3B190 | 0.078 | 0.159 | 6 | 0.004 | 0.005 | 3 |
| TM3B193 | 0.467 | 0.252 | 3 | 0.1 | NA | 1 |
| TM3B195 | 0.035 | 0.043 | 7 | 0.01 | 0.01 | 3 |
| TM3B196 | 0.328 | 0.183 | 6 | 0.733 | 0.058 | 3 |
| TM3B197 | 0.473 | 0.303 | 4 | 0.3 | NA | 1 |

Example 15. Generation of Bispecific PD-1/TIM-3 Antibodies

Select monospecific PD-1 and TIM-3 antibodies were expressed as IgG1/κ, IgG2/κ or IgG4/κ. Substitutions were made at positions 405 and 409 (EU numbering) in the monospecific antibodies to promote subsequent in vitro arm exchange and formation of the bispecific antibodies. The IgG1 and IgG2 anti-PD-1 and anti-TIM-3 antibodies were engineered to have a F405L and a K409R substitution, respectively, to promote arm exchange and generation the bispecific antibodies. On IgG4, the 409 WT position is R, hence the IgG4 anti-PD-1 antibody was not engineered and the IgG4 anti-TIM-3 antibody was engineered to have F405L and R409K substitutions. In addition to position 405 and 409 substitutions, the IgG4 mAbs were engineered to have S228P substitution and the IgG2 antibodies were optionally engineered to include IgG2sigma substitution (V234A, G237A, P238S, H268A, V309L, A330S and P331S).

The monospecific antibodies were expressed and purified using standard methods using a Protein A column (HiTrap MabSelect SuRe column). After elution, the pools were dialyzed into D-PBS, pH 7.2

Bispecific PD-1/TIM-3 antibodies were generated by combining a monospecific PD-1 mAb and a monospecific TIM-3 mAb in in vitro Fab arm exchange as described in Int. Patent Publ. No. WO2011/131746. Briefly, at about 1-20 mg/ml at a molar ratio of 1:1 of each antibody in PBS, pH 7-7.4 and 75 mM 2-mercaptoethanolamine (2-MEA) was mixed together and incubated at 25-37° C. for 2-6 h, followed by removal of the 2-MEA via dialysis, diafiltration, tangential flow filtration and/or spinned cell filtration using standard methods.

The bispecific antibodies were further purified after the in vitro Fab-arm exchange using hydrophobic interaction chromatography to minimize residual parental PD-1 and TIM-3 antibodies using standard methods.

Select monospecific anti-PD-1 antibodies and anti-TIM-3 antibodies were combined in matrix in in vitro Fab arm exchange to generate bispecific antibodies. Table 41, Table 42 and Table 43 show the VH, the VL, the HC and the LC sequences of the generated bispecific antibodies and their isotypes. The G2 antibody allotypes were G2m(n)/(n−) or G2m(n−).

In some experiments, control antibodies were used that were monovalent for either PD-1 or TIM-3 with the second arm being inert binding to gp120. The gp120 binding arm had a VH of SEQ ID NO: 184 and the VL of SEQ ID NO: 185. Table 44 shows the generated control antibodies.

SEQ ID NO: 184 VH of gp120 binding mAb QVQLVQS-GAEVKKP-
GASVKVSCQASGYRFSNFVIHWVRQAPGQR-FEWMGWINP
YNGNKEFSAKFQDRVTFTADTSANTAYMELRSLR-SADTAVYYCARVGPYSWDDS
PQDNYYMDVWGKGTTVIVSS
SEQ ID NO: 185 VL of gp120 binding mAb EIVLTQSPGTLSLSPGERATFSCRSSHSIRSRR-VAWYQHKPGQAPRLVIHGVSNRAS GIS-DRFSGSGSGTDFTLTITRVEPEDFALYYCQVYGAS-SYTFGQGTKLERK

TABLE 41

| | PD-1 binding arm | | | | |
|---|---|---|---|---|---|
| mAb | VH1 | VH1 SEQ ID NO: | VL1 | VL1 SEQ ID NO: | Isotype |
| PTBB14 | PD1H170 | 48 | PD1L148 | 56 | IgG2sigma |
| PTBB15 | PD1H170 | 48 | PD1L148 | 56 | IgG2sigma |
| PTBB16 | PD1H129 | 64 | PD1L62 | 65 | IgG2sigma |
| PTBB17 | PD1H129 | 64 | PD1L62 | 65 | IgG2sigma |
| PTBB24 | PD1H170 | 48 | PD1L148 | 56 | IgG2sigma |
| PTBB30 | PD1H170 | 48 | PD1L148 | 56 | IgG2sigma |
| PTBB27 | PD1H170 | 48 | PD1L148 | 56 | IgG2 |
| PTBB28 | PD1H170 | 48 | PD1L148 | 56 | IgG2 |
| PTBB18 | PD1H129 | 64 | PD1L62 | 65 | IgG4_S228P |
| PTBB20 | PD1H170 | 48 | PD1L148 | 56 | IgG4_S228P |
| PTBB21 | PD1H170 | 48 | PD1L148 | 56 | IgG4_S228P |

TABLE 42

| | TIM-3 binding arm | | | | |
|---|---|---|---|---|---|
| mAb | VH2 | VH2 SEQ ID NO: | VL2 | VL2 SEQ ID NO: | Isotype |
| PTBB14 | TM3H144 | 153 | TM3L67 | 162 | IgG2sigma |
| PTBB15 | TM3H24 | 146 | TM3L33 | 156 | IgG2sigma |
| PTBB16 | TM3H144 | 153 | TM3L67 | 162 | IgG2sigma |
| PTBB17 | TM3H24 | 146 | TM3L33 | 156 | IgG2sigma |
| PTBB24 | TM3H162 | 172 | TM3L85 | 173 | IgG2sigma |
| PTBB30 | TM3H24 | 146 | TM3L33 | 156 | IgG2sigma |
| PTBB27 | TM3H162 | 172 | TM3L85 | 173 | IgG2 |
| PTBB28 | TM3H24 | 146 | TM3L33 | 156 | IgG2 |
| PTBB18 | TM3H24 | 146 | TM3L33 | 156 | IgG4_S228 |
| PTBB20 | TM3H24 | 146 | TM3L33 | 156 | IgG4_S228 |
| PTBB21 | TM3H162 | 172 | TM3L85 | 173 | IgG4_S228 |

TABLE 43

| | SEQ ID NO: | | | |
|---|---|---|---|---|
| | PD-1 binding arm | | TIM-3 binding arm | |
| mAb | HC1 | LC1 | HC2 | LC2 |
| PTBB14 | 186 | 188 | 190 | 193 |
| PTBB15 | 186 | 188 | 191 | 194 |
| PTBB16 | 187 | 189 | 190 | 193 |
| PTBB17 | 187 | 189 | 191 | 194 |
| PTBB24 | 186 | 188 | 192 | 195 |
| PTBB30 | 186 | 188 | 248 | 194 |
| PTBB27 | 241 | 188 | 244 | 195 |
| PTBB28 | 241 | 188 | 245 | 194 |
| PTBB18 | 242 | 189 | 246 | 194 |
| PTBB20 | 243 | 188 | 246 | 194 |
| PTBB21 | 243 | 188 | 247 | 195 |

SEQ ID NO: 186
QVQLVQSGAEVKKPGSSVKVSCKASGGTFSSYAISWVRQAPGQGLEWMG
GIIPIFDTANYAQKFQGRVTITADESTSTAYMELSSLRSEDTAVYYCAR
PGLAAAYDTGSLDYWGQGTLVTVSSASTKGPSVFPLAPCSRSTSESTAA
LGCLVKDYFPEPVTVSWNSGALTSGVHTFPAVLQSSGLYSLSSVVTVTS
SNFGTQTYTCNVDHKPSNTKVDKTVERKCCVECPPCPAPPAAASSVFLF
PPKPKDTLMISRTPEVTCVVVDVSAEDPEVQFNWYVDGVEVHNAKTKPR
EEQFNSTFRVVSVLTVLHQDWLNGKEYKCKVSNKGLPSSIEKTISKTKG
QPREPQVYTLPPSREEMTKNQVSLTCLVKGFYPSDIAVEWESNGQPENN
YKTTPPMLDSDGSFLLYSKLTVDKSRWQQGNVFSCSVMHEALHNHYTQK
SLSLSPGK

SEQ ID NO: 187
EVQLVESGGGLVQPGGSLRLSCAASGFAFSRYDMSWVRQAPGKGLESVA
YISGGGANTYYLDNVKGRFTISRDNAKNSLYLQMNSLRAEDTAVYYCAS
PYLSYFDVWGQGTLVTVSSASTKGPSVFPLAPCSRSTSESTAALGCLVK
DYFPEPVTVSWNSGALTSGVHTFPAVLQSSGLYSLSSVVTVTSSNFGTQ
TYTCNVDHKPSNTKVDKTVERKCCVECPPCPAPPAAASSVFLFPPKPKD
TLMISRTPEVTCVVVDVSAEDPEVQFNWYVDGVEVHNAKTKPREEQFNS
TFRVVSVLTVLHQDWLNGKEYKCKVSNKGLPSSIEKTISKTKGQPREPQ
VYTLPPSREEMTKNQVSLTCLVKGFYPSDIAVEWESNGQPENNYKTTPP
MLDSDGSFLLYSKLTVDKSRWQQGNVFSCSVMHEALHNHYTQKSLSLSP
GK

SEQ ID NO: 188
EIVLTQSPATLSLSPGERATLSCRASQSVRSYLAWYQQKPGQAPRLLIY
DASNRATGIPARFSGSGSGTDFTLTISSLEPEDFAVYYCQQRNYWPLTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC

SEQ ID NO: 189
EIVMTQSPATLSVSPGERATLSCRASQSLSDYLHWYQQKPGQAPRLLIK
SASQSISGIPARFSGSGSGTEFTLTISSLQSEDFAVYYCQNGHSFPYTF
GQGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC

SEQ ID NO: 190
EVQLQQSGAELARPGASVKLSCKASGYTFTSYWMQWVKQRPGQGLEWIG
AIYPGDGDIRYTQNFKGKATLTADKSSSTAYMQLSSLASEDSAVYYCAR
WEKSTTVVQRNYFDYWGQGTTLTVSSASTKGPSVFPLAPCSRSTSESTA
ALGCLVKDYFPEPVTVSWNSGALTSGVHTFPAVLQSSGLYSLSSVVTVT
SSNFGTQTYTCNVDHKPSNTKVDKTVERKCCVECPPCPAPPAAASSVFL
FPPKPKDTLMISRTPEVTCVVVDVSAEDPEVQFNWYVDGVEVHNAKTKP
REEQFNSTFRVVSVLTVLHQDWLNGKEYKCKVSNKGLPSSIEKTISKTK
GQPREPQVYTLPPSREEMTKNQVSLTCLVKGFYPSDIAVEWESNGQPEN
NYKTTPPMLDSDGSFFLYSRLTVDKSRWQQGNVFSCSVMHEALHNHYTQ
KSLSLSPGK

SEQ ID NO: 191
EVQLLESGGGLVQPGGSLRLSCAASGFTFSSYAMSWVRQAPGKGLEWVS
AISGSGGSTYYADSVKGRFTISRDNSKNTLYLQMNSLRAEDTAVYYCAK
SPYAPLDYWGQGTLVTVSSASTKGPSVFPLAPCSRSTSESTAALGCLVK
DYFPEPVTVSWNSGALTSGVHTFPAVLQSSGLYSLSSVVTVTSSNFGTQ
TYTCNVDHKPSNTKVDKTVERKCCVECPPCPAPPAAASSVFLFPPKPKD
TLMISRTPEVTCVVVDVSAEDPEVQFNWYVDGVEVHNAKTKPREEQFNS
TFRVVSVLTVLHQDWLNGKEYKCKVSNKGLPSSIEKTISKTKGQPREPQ
VYTLPPSREEMTKNQVSLTCLVKGFYPSDIAVEWESNGQPENNYKTTPP
MLDSDGSFFLYSRLTVDKSRWQQGNVFSCSVMHEALHNHYTQKSLSLSP
GK

SEQ ID NO: 192
EVQLVQSGAEVKKPGESLKISCKGSGYSFTSYWMQWVRQMPGKGLEWMG
AIYPGDGDIRYTQNFKGQVTISADKSISTAYLQWSSLKASDTAMYYCAR
WEKSTTVVQRNYFDYWGQGTTVTVSSASTKGPSVFPLAPCSRSTSESTA
ALGCLVKDYFPEPVTVSWNSGALTSGVHTFPAVLQSSGLYSLSSVVTVT
SSNFGTQTYTCNVDHKPSNTKVDKTVERKCCVECPPCPAPPAAASSVFL
FPPKPKDTLMISRTPEVTCVVVDVSAEDPEVQFNWYVDGVEVHNAKTKP
REEQFNSTFRVVSVLTVLHQDWLNGKEYKCKVSNKGLPSSIEKTISKTK
GQPREPQVYTLPPSREEMTKNQVSLTCLVKGFYPSDIAVEWESNGQPEN
NYKTTPPMLDSDGSFFLYSRLTVDKSRWQQGNVFSCSVMHEALHNHYTQ
KSLSLSPGK

SEQ ID NO: 193
DVQMIQSPKSMSMSVGERVTLSCKASENVGTFVSWYQQKPDQSPKLLIY
GASNRYTGVPDRFTGSGSATDFTLTISSVQAEDLADYHCGQSYSYPTFG
SGTKLEMKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC

SEQ ID NO: 194
EIVLTQSPATLSLSPGERATLSCRASQSVNDYLAWYQQKPGQAPRLLIY
DASNRATGIPARFSGSGSGTDFTLTISSLEPEDFAVYYCQQGGHAPITF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC

SEQ ID NO: 195
DIQMTQSPSSLSASVGDRVTITCKASENVGTFVSWYQQKPGKAPKLLIY
GASNRYTGVPSRFSGSGSGTDFTLTISSLQPEDFATYYCGQSYSYPTFG
QGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC

SEQ ID NO: 241
QVQLVQSGAEVKKPGSSVKVSCKASGGTFSSYAISWVRQAPGQGLEWMG
GIIPIFDTANYAQKFQGRVTITADESTSTAYMELSSLRSEDTAVYYCAR
PGLAAAYDTGSLDYWGQGTLVTVSSASTKGPSVFPLAPCSRSTSESTAA
LGCLVKDYFPEPVTVSWNSGALTSGVHTFPAVLQSSGLYSLSSVVTVPS
SNFGTQTYTCNVDHKPSNTKVDKTVERKCCVECPPCPAPPVAGPSVFLF
PPKPKDTLMISRTPEVTCVVVDVSHEDPEVQFNWYVDGVEVHNAKTKPR
EEQFNSTFRVVSVLTVVHQDWLNGKEYKCKVSNKGLPAPIEKTISKTKG
QPREPQVYTLPPSREEMTKNQVSLTCLVKGFYPSDIAVEWESNGQPENN
YKTTPPMLDSDGSFLLYSKLTVDKSRWQQGNVFSCSVMHEALHNHYTQK
SLSLSPGK

SEQ ID NO: 242
EVQLVESGGGLVQPGGSLRLSCAASGFAFSRYDMSWVRQAPGKGLESVA
YISGGGANTYYLDNVKGRFTISRDNAKNSLYLQMNSLRAEDTAVYYCAS
PYLSYFDVWGQGTLVTVSSASTKGPSVFPLAPCSRSTSESTAALGCLVK
DYFPEPVTVSWNSGALTSGVHTFPAVLQSSGLYSLSSVVTVPSSSLGTK
TYTCNVDHKPSNTKVDKRVESKYGPPCPPCPAPEFLGGPSVFLFPPKPK
DTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREP
QVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLS
LGK

SEQ ID NO: 243
QVQLVQSGAEVKKPGSSVKVSCKASGGTFSSYAISWVRQAPGQGLEWMG
GIIPIFDTANYAQKFQGRVTITADESTSTAYMELSSLRSEDTAVYYCAR
PGLAAAYDTGSLDYWGQGTLVTVSSASTKGPSVFPLAPCSRSTSESTAA
LGCLVKDYFPEPVTVSWNSGALTSGVHTFPAVLQSSGLYSLSSVVTVPS
SSLGTKTYTCNVDHKPSNTKVDKRVESKYGPPCPPCPAPEFLGGPSVFL
FPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPEN
NYKTTPPVLDSDGSFFLYSRLTVDKSRWQEGNVFSCSVMHEALHNHYTQ
KSLSLSLGK

SEQ ID NO: 244
EVQLVQSGAEVKKPGESLKISCKGSGYSFTSYWMQWVRQMPGKGLEWMG
AIYPGDGDIRYTQNFKGQVTISADKSISTAYLQWSSLKASDTAMYYCAR
WEKSTTVVQRNYFDYWGQGTTVTVSSASTKGPSVFPLAPCSRSTSESTA
ALGCLVKDYFPEPVTVSWNSGALTSGVHTFPAVLQSSGLYSLSSVVTVP
SSNFGTQTYTCNVDHKPSNTKVDKTVERKCCVECPPCPAPPVAGPSVFL
FPPKPKDTLMISRTPEVTCVVVDVSHEDPEVQFNWYVDGVEVHNAKTKP
REEQFNSTFRVVSVLTVVHQDWLNGKEYKCKVSNKGLPAPIEKTISKTK
GQPREPQVYTLPPSREEMTKNQVSLTCLVKGFYPSDIAVEWESNGQPEN
NYKTTPPMLDSDGSFFLYSRLTVDKSRWQQGNVFSCSVMHEALHNHYTQ
KSLSLSPGK

SEQ ID NO: 245
EVQLLESGGGLVQPGGSLRLSCAASGFTFSSYAMSWVRQAPGKGLEWVS
AISGSGGSTYYADSVKGRFTISRDNSKNTLYLQMNSLRAEDTAVYYCAK
SPYAPLDYWGQGTLVTVSSASTKGPSVFPLAPCSRSTSESTAALGCLVK
DYFPEPVTVSWNSGALTSGVHTFPAVLQSSGLYSLSSVVTVPSSNFGTQ
TYTCNVDHKPSNTKVDKTVERKCCVECPPCPAPPVAGPSVFLFPPKPKD
TLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQ
VYTLPPSREEMTKNQVSLTCLVKGFYPSDIAVEWESNGQPENNYKTTPP
MLDSDGSFFLYSRLTVDKSRWQQGNVFSCSVMHEALHNHYTQKSLSLSP
GK

SEQ ID NO: 246
EVQLLESGGGLVQPGGSLRLSCAASGFTFSSYAMSWVRQAPGKGLEWVS
AISGSGGSTYYADSVKGRFTISRDNSKNTLYLQMNSLRAEDTAVYYCAK
SPYAPLDYWGQGTLVTVSSASTKGPSVFPLAPCSRSTSESTAALGCLVK
DYFPEPVTVSWNSGALTSGVHTFPAVLQSSGLYSLSSVVTVPSSSLGTK
TYTCNVDHKPSNTKVDKRVESKYGPPCPPCPAPEFLGGPSVFLFPPKPK
DTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREP
QVYTLPPSQEEMTKNQVSLTCLVKGFYPSDIAVEWESNGQPENNYKTTP
PVLDSDGSFLLYSKLTVDKSRWQEGNVFSCSVMHEALHNHYTQKSLSLS
LGK

SEQ ID NO: 247
EVQLVQSGAEVKKPGESLKISCKGSGYSFTSYWMQWVRQMPGKGLEWMG
AIYPGDGDIRYTQNFKGQVTISADKSISTAYLQWSSLKASDTAMYYCAR
WEKSTTVVQRNYFDYWGQGTTVTVSSASTKGPSVFPLAPCSRSTSESTA
ALGCLVKDYFPEPVTVSWNSGALTSGVHTFPAVLQSSGLYSLSSVVTVP
SSSLGTKTYTCNVDHKPSNTKVDKRVESKYGPPCPPCPAPEFLGGPSVF
LFPPKPKDTLMISRTPEVTCVVVDVSQEDPEVQFNWYVDGVEVHNAKTK
PREEQFNSTYRVVSVLTVLHQDWLNGKEYKCKVSNKGLPSSIEKTISKA

-continued

KGQPREPQVYTLPPSQEEMTKNQVSLTCLVKGFYPSDIAVEWESNGQPE

NNYKTTPPVLDSDGSFLLYSKLTVDKSRWQEGNVFSCSVMHEALHNHYT

QKSLSLSLGK

SEQ ID NO: 248
EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYCAK

SPYAPLDYWGQGTLVTVSSASTKGPSVFPLAPCSRSTSESTAALGCLVK

DYFPEPVTVSWNSGALTSGVHTFPAVLQSSGLYSLSSVVTVPSSNFGTQ

TYTCNVDHKPSNTKVDKTVERKCCVECPPCPAPPAAASSVFLFPPKPKD

TLMISRTPEVTCVVVDVSAEDPEVQFNWYVDGVEVHNAKTKPREEQFNS

TFRVVSVLTVLHQDWLNGKEYKCKVSNKGLPSSIEKTISKTKGQPREPQ

VYTLPPSREEMTKNQVSLTCLVKGFYPSDIAVEWESNGQPENNYKTTPP

MLDSDGSFFLYSRLTVDKSRWQQGNVFSCSVMHEALHNHYTQKSLSLSP

GK

TABLE 44

| Control mAb | Arm 1 VH/VL with F405L substitution | Arm 2 VH/VL with K409R substitution | Isotype |
|---|---|---|---|
| TM3B342 | gp120 | TM3B195 | IgG2sigma |
| TM3B343 | gp120 | TM3B299 | IgG2sigma |
| B23B74 | gp120 | B23B32 | IgG2sigma |
| PTBB23 | gp120 | TM3B291 | IgG2sigma |
| PD1B355 | PD1B246 | gp120 | IgG2sigma |
| PD1B356 | PD1B248 | gp120 | IgG2sigma |

Example 16. Characterization of Bispecific PD-1/TIM-3 Antibodies

The generated antagonistic bispecific antibodies were tested in the CMV assay for their ability to enhance antigen-specific T cell responses. Functionality was measured by assessing CD137 expression on both CD4$^+$ and CD T cells and by IFN-γ and TNF-α levels in the culture supernatants as described in Example 14. Table 45 and Table 46 summarize the activity of bispecific PD-1/TIM-3 antibodies in this assay for the different readouts. As shown in this table, select bispecific molecules led to significant increases in CD137 expression on CD4$^+$ and CD8$^+$ T cells and in levels of secreted IFN-γ and TNF-α. Overall, the PD-1/TIM-3 bispecifics with huIgG2sigma Fc had the most robust activity, followed by those molecules with huIgG2 and then huIgG4.

TABLE 45

| mAb | | Statistical Significance | | | |
|---|---|---|---|---|---|
| | | CD4$^+$CD137$^+$ | | CD8$^+$CD137$^+$ | |
| Isotype | name | Avg p value | St Dev | Avg p value | St Dev |
| IgG2sigma | PTBB14 | 0.1144 | 0.1591 | 0.0002 | 0.0001 |
| IgG2sigma | PTBB15 | 0.0467 | 0.0988 | 0.0001 | 0.0000 |
| IgG2sigma | PTBB16 | 0.0017 | 0.0023 | 0.0001 | 0.0000 |
| IgG2sigma | PTBB17 | 0.4148 | 0.5051 | 0.0001 | 0.0001 |
| IgG2sigma | PTBB24 | 0.0031 | 0.0051 | 0.0001 | 0.0000 |
| IgG2 | PTBB27 | 0.0009 | 0.0011 | 0.0001 | 0.0000 |
| IgG2 | PTBB28 | 0.0003 | 0.0002 | 0.0001 | 0.0000 |
| IgG4 | PTBB18* | 0.0353 | | 0.0071 | |
| IgG4 | PTBB20 | 0.6025 | 0.1710 | 0.0004 | 0.0004 |
| IgG4 | PTBB21 | 0.1071 | 0.1372 | 0.0059 | 0.0081 |

*one p value reported

TABLE 46

| mAb | | Statistical significance | | | |
|---|---|---|---|---|---|
| | | IFN-γ | | TNF-α | |
| Isotype | name | Avg p value | St Dev | Avg p value | St Dev |
| IgG2sigma | PTBB14 | 0.0001 | 0.0000 | 0.0112 | 0.0157 |
| IgG2sigma | PTBB15 | 0.0001 | 0.0000 | 0.0005 | 0.0008 |
| IgG2sigma | PTBB16 | 0.0001 | 0.0000 | 0.0012 | 0.0016 |
| IgG2sigma | PTBB17 | 0.0001 | 0.0000 | 0.0001 | 0.0000 |
| IgG2sigma | PTBB24 | 0.0001 | 0.0001 | 0.0008 | 0.0008 |
| IgG2 | PTBB27 | 0.0026 | 0.0030 | 0.3406 | 0.4757 |
| IgG2 | PTBB28 | 0.0001 | 0.0000 | 0.1437 | 0.1229 |
| IgG4 | PTBB18 | 0.0001 | #DIV/0! | 0.0008 | #DIV/0! |
| IgG4 | PTBB20 | 0.0544 | 0.0768 | 0.1754 | 0.2140 |
| IgG4 | PTBB21 | 0.0174 | 0.0245 | 0.2685 | 0.1103 |

*one p value reported

Example 17. Anti-PD1 Antibodies Upregulate TIM-3 Expression on Tumors

Effect of anti-PD-1 antibody treatment in expression of TIM-3 on tumors were evaluated in CT26 or MC38 colon carcinoma mouse model.

Balb/c mice were implanted subcutaneously with 1×10$^6$ CT26 colon carcinoma tumors. Seven days after tumor cell implant, tumors were measured and mice were randomized by tumor size. Treatment with PBS or 10 mg/kg anti-mouse PD-1 antibodies (clone RMP1-14, BioXCell) began on day 7 after tumor cell implant and continued biweekly for the remainder of the study. To analyze T cell expression of TIM-3, tumors were harvested at day 22 and dissociated using GentleMACS (Miltenyi). Staining for flow cytometry was carried out with Live/Dead and markers for CD3, CD4, CD8 and TIM-3. Flow cytometry was performed on a LSR Fortessa (BD). Data was analyzed using the Flow Jo software.

Wild-type C57B1/6 female mice were implanted subcutaneously with 5×10$^5$ MC-38 colon carcinoma cells suspended in PBS. Tumors were measured and mice were randomized by tumor size (50-100 mm$^3$). Treatment with PBS or 10 mg/kg anti-mouse PD-1 (clone RMP1-14, BioX-Cell) began after randomization and continued biweekly for the remainder of the study. To profile tumor infiltrating T cells, tumors were harvested and dissociated using GentleMACS (Miltenyi) 12, 15, 19, or 22 days after implant.

Staining for flow cytometry was carried out with Live/Dead and markers for CD45, Thy1, CD3, CD4, CD8, TIM-3, CD137, OX40, GITR, TIGIT. Flow cytometry data was collected on a LSR Fortessa (BD). Data was analyzed using the FlowJo software (v9.9.4) and visualized with GraphPad Prism. Statistics were generated by GraphPad Prism.

Analysis of TIM-3 expression on CD8+ T cells isolated from CT26 tumors at day 22 revealed an increase of TIM-3 expression in the PD-1 treated samples, compared to PBS control. FIG. 1A shows the mean fluorescent intensity of TIM-3 expression in the two treatment groups.

Figure 1B:
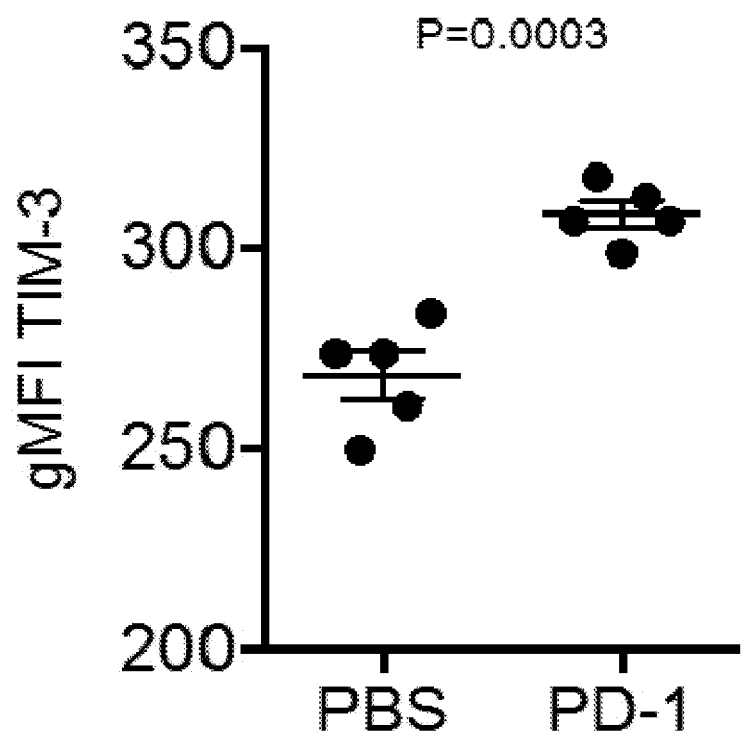
FIG. 1B shows that TIM-3 surface expression is elevated on tumor infiltrated lymphocytes (TIL) after treatment with anti-PD-1 antibodies. Balb/c mice with established MC38 colon carcinoma tumors were treated biweekly with anti-PD-1 antibody or vehicle. Geometric mean fluorescent intensity (gMFI) of TIM-3 expression on total CD8 TIL population is shown in vehicle treated (PBS) or anti-PD-1 antibody treated (PD-1) animals. p=0.003 vehicle vs anti-PD-1 antibody treated groups.
Figure 1C:
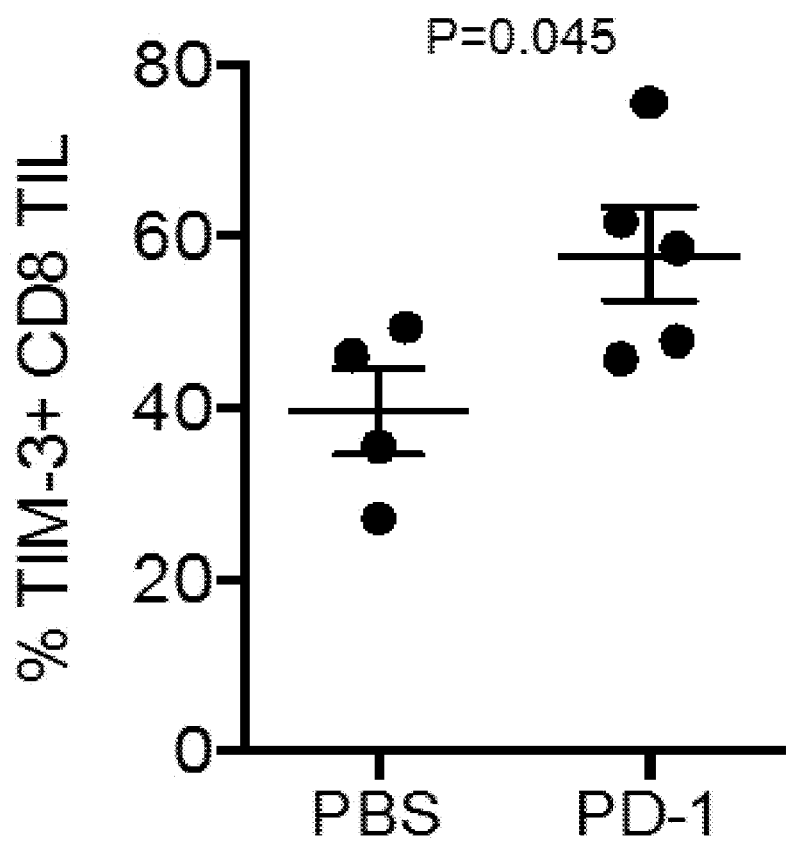
FIG. 1C shows the relative frequency of TIM-3$^+$ CD8 cells of total CD8$^+$ TILs in MC38 tumors harvested from mice treated with vehicle (PBS) or anti-PD-1 antibody (PD-1). p=0.045 vehicle vs anti-PD-1 antibody treated groups.

TIM-3 expression was also increased in MC-38 tumors in the anti-PD-1 mAb treated samples when compared to PBS control. FIG. 1B shows the geometric mean fluorescent intensity of TIM-3 expression in the CD8$^+$ TIL population. FIG. 1C shows the percentage (%) relative frequency of TIM-3$^+$ CD8$^+$ cells of total CD8$^+$ TILs.

These data show that TIM-3 is upregulated in response to anti-PD-1 treatment, supporting the rational for targeting TIM-3 in PD-1 treated subjects.

Figure 2A:
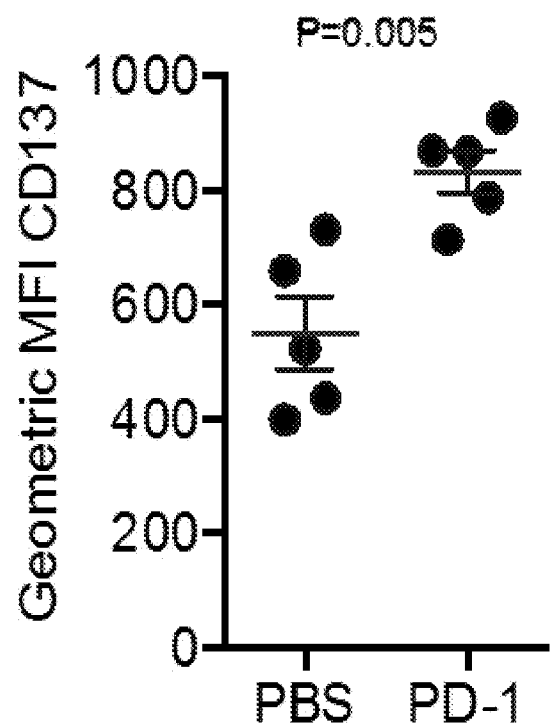
FIG. 2A shows that CD137 surface expression (gMFI) is elevated on TILs in MC38 colon carcinoma tumors in animals treated with anti-PD-1 antibodies (PD-1 group) when compared to vehicle treated (PBS) group. p=0.005 vehicle vs anti-PD-1 antibody treated groups. Each point represents one mouse. Data are representative of at least 2 independent experiments.
Figure 2B:
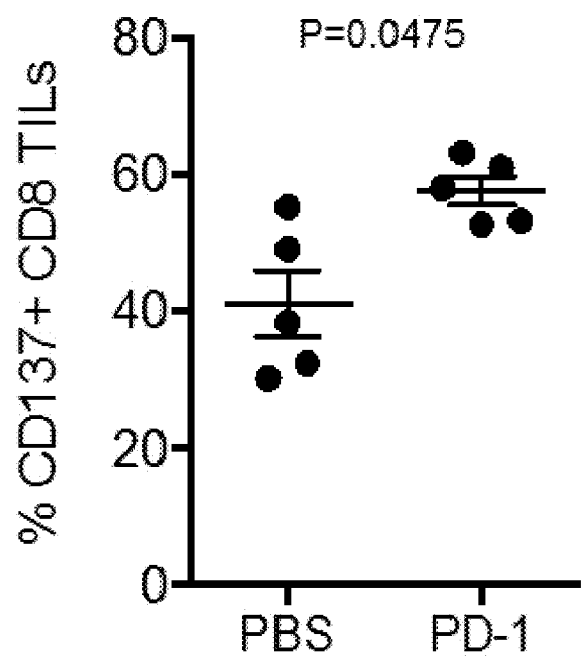
FIG. 2B shows that the relative frequency of CD137$^+$ CD8 cells of total CD8+ TILs in is elevated in MC38 colon carcinoma tumors in animals treated with anti-PD-1 antibodies (PD-1 group) when compared to vehicle treated (PBS) group. p=0.0475 vehicle vs anti-PD-1 antibody treated groups. Each point represents one mouse. Data are representative of at least 2 independent experiments.
Figure 3A:
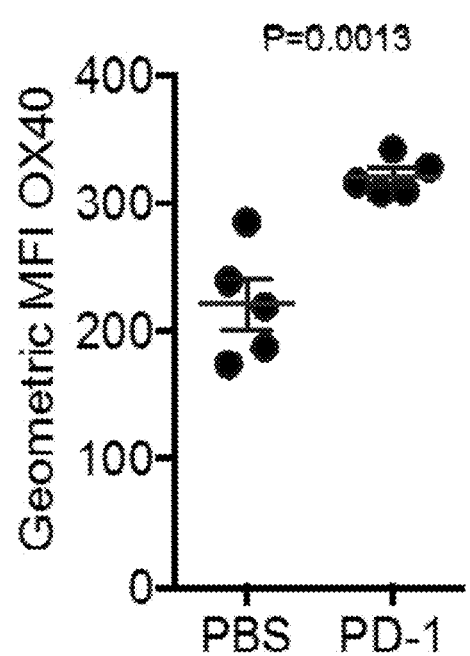
FIG. 3A shows that OX40 surface expression (gMFI) is elevated on TILs in MC38 colon carcinoma tumors in animals treated with anti-PD-1 antibodies (PD-1 group) when compared to vehicle treated (PBS) group. p=0.0013 vehicle vs anti-PD-1 antibody treated groups. Each point represents one mouse. Data are representative of at least 2 independent experiments.
Figure 3B:
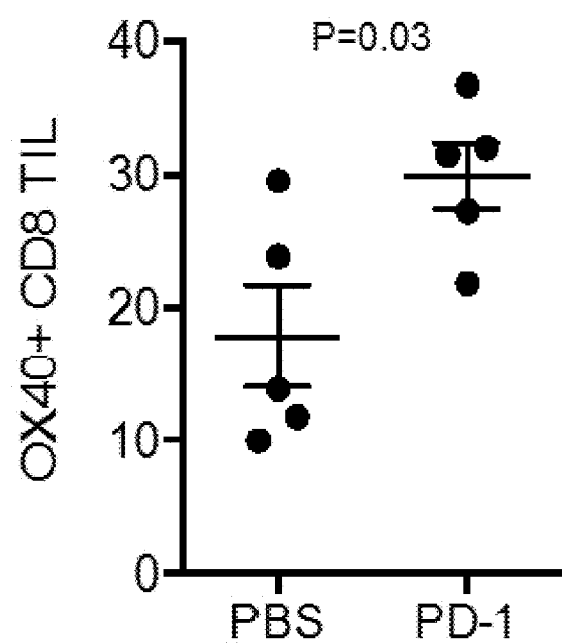
FIG. 3B shows that the relative frequency of OX40$^+$ CD8 cells of total CD8$^+$ TILs in is elevated in MC38 colon carcinoma tumors in animals treated with anti-PD-1 antibodies (PD-1 group) when compared to vehicle treated (PBS) group. p=0.03 vehicle vs anti-PD-1 antibody treated groups. Each point represents one mouse. Data are representative of at least 2 independent experiments.
Figure 4A:
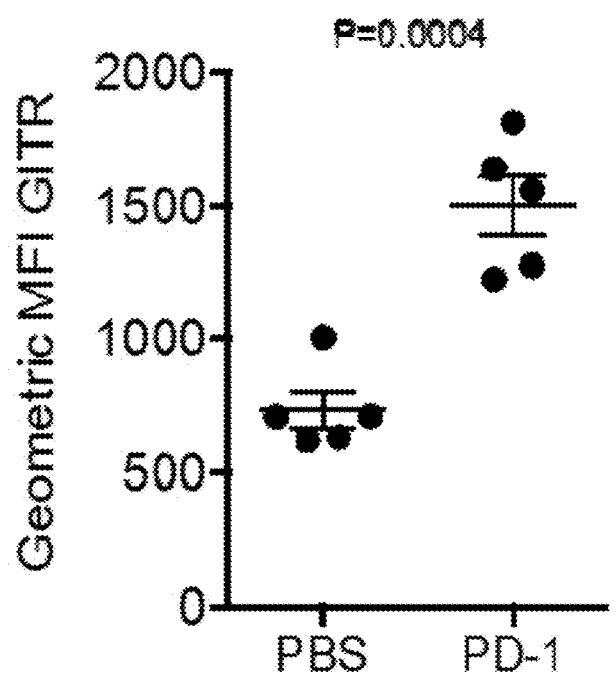
FIG. 4A shows that GITR surface expression (gMFI) is elevated on TILs in MC38 colon carcinoma tumors in animals treated with anti-PD-1 antibodies (PD-1 group) when compared to vehicle treated (PBS) group. p=0.0004 vehicle vs anti-PD-1 antibody treated groups. Each point represents one mouse. Data are representative of at least 2 independent experiments.
Figure 4B:
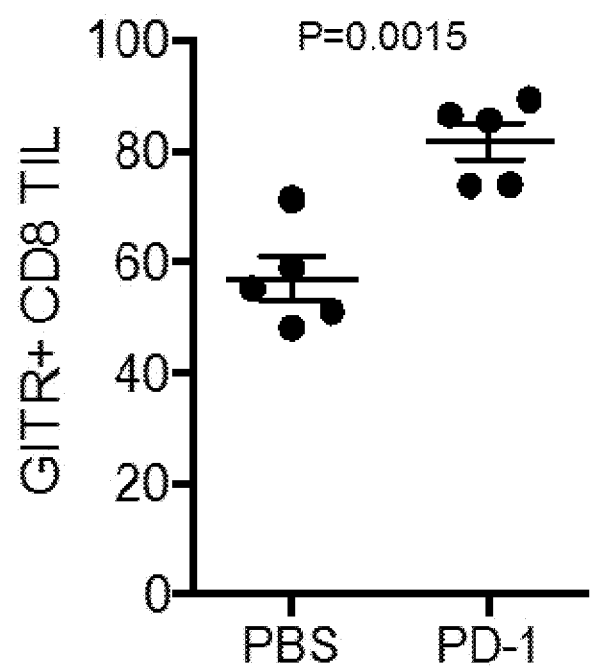
FIG. 4B shows that the relative frequency of GITR$^+$ CD8 cells of total CD8$^+$ TILs in is elevated in MC38 colon carcinoma tumors in animals treated with anti-PD-1 antibodies (PD-1 group) when compared to vehicle treated (PBS) group. p=0.0015 vehicle vs anti-PD-1 antibody treated groups. Each point represents one mouse. Data are representative of at least 2 independent experiments.

CD137, OX40 and GITR expression was also analyzed on CD8+ T cells infiltrating MC38 tumors isolated from mice treated with anti-mouse PD-1 antibodies. These results showed that both the frequency and level (gMFI) of TNF family costimulatory receptors CD137, OX40 and GITR expression was increased following PD-1 blockade. FIG. 2A and FIG. 2B show the gMFI and relative frequency of CD137 expression on CD8 TILs, respectively. FIG. 3A and FIG. 3B show the gMFI and relative frequency of OX40 expression on CD8 TILs, respectively, and FIG. 4A and FIG. 4B show the gMFI and relative expression of GITR on CD8 TILs, respectively.

These data support the rational for targeting CD137, OX40 and/or GITR in PD-1 treated subjects.

Example 18. Activity of Anti-TIM-3 Antibodies Following PD-1 Blockade

Figure 5:
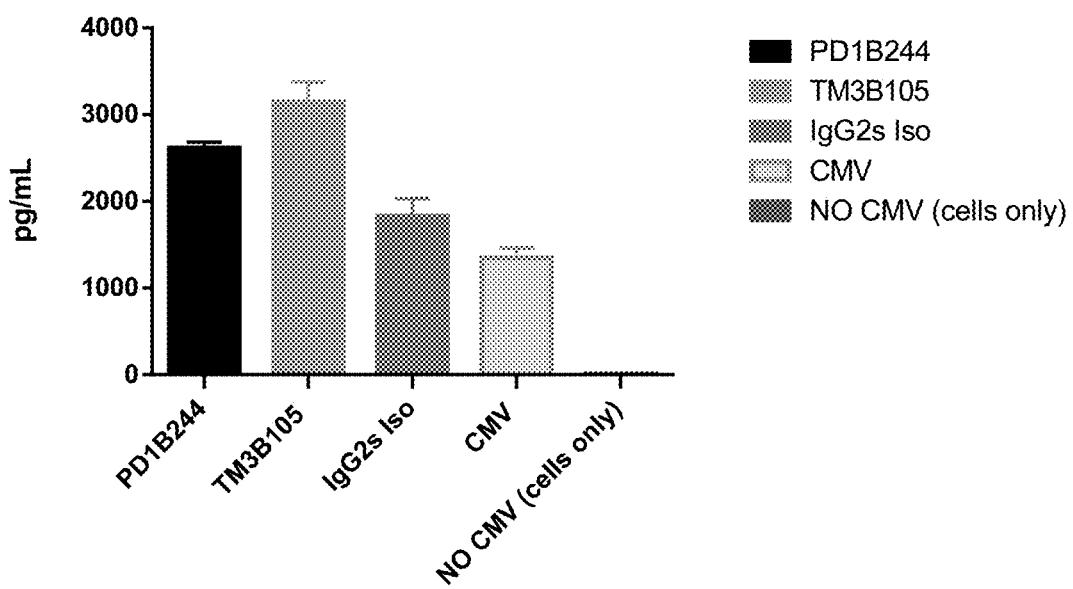
FIG. 5 shows that treatment with anti-TIM-3 antibodies after anti-PD-1 antibody treatment further induces antigen-specific immune response. The antibodies were tested in the CMV assay using PBMCs from CMV positive donors, in which antigen-specific immune responses were induced with pp65 peptide pools. The cells were treated for 5 days with anti-PD-1 antibody PD1B244, re-stimulated, and treated for 24 hours with anti-TIM-3 antibody TM3B105. Immune response was determined by measuring increases in IFN-γ secretion. IgG2s Iso: IgG2sigma isotype control. CMV: sample treated with cytomegalovirus p65 peptides in the absence of antibodies.

The activity of anti-TIM-3 antibodies was also tested following anti-PD-1 antibody blockade in the CMV assay. In these experiments, PBMCs from one normal donor (CMV-sera positive) were incubated with pp65 peptide pools and anti-PD-1 antibodies for 5 days. On day 5, supernatants were harvested and cells were re-stimulated with pp65 peptide pool in the presence of either anti-TIM-3 or anti-PD-1 antibody. IFN-γ levels in the supernatant were measured 24 hours later. Treatment with anti-TIM-3 antibodies after 5 days of anti-PD-1 blockade resulted in a significant increase of IFN-γ levels. This effect was significant (p=0.0183) compared to continued anti-PD-1 treatment. In the experiment, anti-TIM-3 antibody TM3B403 and anti-PD-1 antibody PD1B244 were used. FIG. 5 shows the increased IFN-γ levels in the CMV assay, where PBMCs were treated with anti-TIM-3 antibody TM3B105 following 5 days of treatment with anti-PD-1 PD1B244. Values represent average of six biological replicates used for each condition.

Example 19. Epitope Mapping of Anti-TIM-3 Antibodies

Solution hydrogen/deuterium exchange-mass spectrometry (HDX-MS) was performed to identify the binding epitopes of TMB403 and TMB291. For the experiments, the VH and the VL of TM3B403 and TM3B291 were cloned as IgG1 Fabs with a hexahistidine tag in the C-terminus. The Fabs, were generated from transient transfections of HEK293 Expi cells in suspension shake flasks. TIM-3 IgG1 Fc Chimera, Ser22-Arg200 (Accession #Q8TDQ0), produced in Mouse myeloma cell line (NS0 derived) from R&D Systems (Catalog #2365-TM) was used.

For H/D exchange, the procedures used to analyze the Fab perturbation were similar to those described previously (Hamuro et al., Biomolecular Techniques 14: 171-182, 2003; Horn et al., Biochemistry 45: 8488-8498, 2006) with some modifications. Briefly, deglycosylated human TIM-3/Fc fusion protein or deglycosylated human TIM-3-Fc plus Fab mixture was incubated with deuterium oxide labeling buffer at 0° C. for various times up to 2 hours. Deuterium exchange was quenched by adding guanidine hydrochloride and the quenched sample was subjected to on-column pepsin digestion and LC-MS analysis. The mass spectra were recorded in MS only mode. For the calculation of deuterium incorporation, the mass spectra for a given peptide were combined across the extracted ion chromatogram peak and the weighted average m/z was calculated. The mass increase from the mass of the native peptide (0 min) to the weighted averaged mass corresponds to the level of deuterium incorporation. About 98.4% of the protein could be mapped to specific peptides.

The deuterium levels at the identified peptides were monitored from the mass shift on LC-MS. The selected deuterium buildup curves, which show significant difference in deuterium levels and/or slopes, over exchange time for the peptides were plotted. Deglycosylated human Tim-3/Fc fusion protein showed significant reduction in deuterium uptakes upon binding to TM3B403 at sequences $_{32}$WGK-GACPVFECGNVVL$_{47}$, (SEQ ID NO: 261) and upon binding to TM3B291 at sequences $_{90}$RIQIPGIMNDEKF$_{102}$. (SEQ ID NO: 262). These regions with significant reduction in deuterium uptakes upon binding to Fabs can thus be regarded as main epitopes of the mAbs.

A segment, $_{50}$DERDVNY$_{56}$, (SEQ ID NO: 263) demonstrated modest reduction in deuterium exchange upon binding to TM3B403 or TM3B291. This region may be also considered as a potential epitope for both antibodies.

The major binding epitopes for TM3B403 or TM3B291 are different. However, they may share the similar modest protection region, $_{50}$DERDVNY$_{56}$, (SEQ ID NO: 263) based on the HDX mapping results. To help assess if this region contributes to common binding epitope region for both Fab molecules, competition ELISA was performed. Recombinant human Tim-3/Fc protein was directly coated on plates which were then blocked and washed. A mixture of Ruthenium (Ru)-labeled TM3B291 Fab which was pre-incubated with different concentrations of unlabeled TM3B105 or TM3B291. Plates were incubated, washed and MSD Read Buffer T was dispensed into each well followed by reading with a SECTOR Imager 6000 (Meso Scale Discovery, Gaithersburg, MD).

The competition analysis demonstrated that that TM3B403 competed for binding to TIM-3 with TM3B291. This result could indicate that the modestly protected region, DERDVNY (SEQ ID NO: 263) is part of the epitope for both antibodies or that the antibodies may be sterically blocking each other's binding due to the close proximity of their epitopes.

Example 20. TIM-3 Blockade Increases TIGIT Expression on CD8$^+$ TILs

Effect of anti-TIM-3 antibody treatment on expression of TIGIT in tumors was evaluated in CT26 and MC38 colon carcinoma mouse models. The studies were conducted as described in Example 17 except that 10 mg/ml anti-TIM-3 antibody RMT3-23 was used.

Figure 19A:
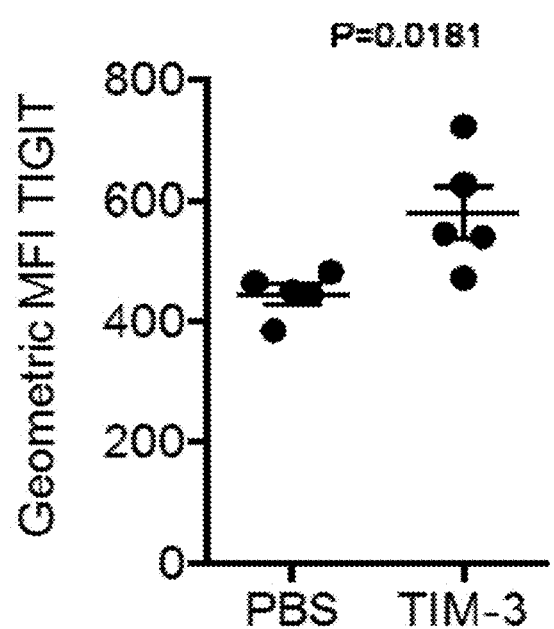
FIG. 19A shows that TIGIT surface expression (gMFI) is elevated on TILs in MC38 colon carcinoma tumors in animals treated with anti-TIM-3 antibodies (TIM-3 group) when compared to vehicle treated (PBS) group. p=0.0181 vehicle vs anti-TIM-3 antibody treated groups. Each point represents one mouse. Data are representative of at least 2 independent experiments.
Figure 19B:
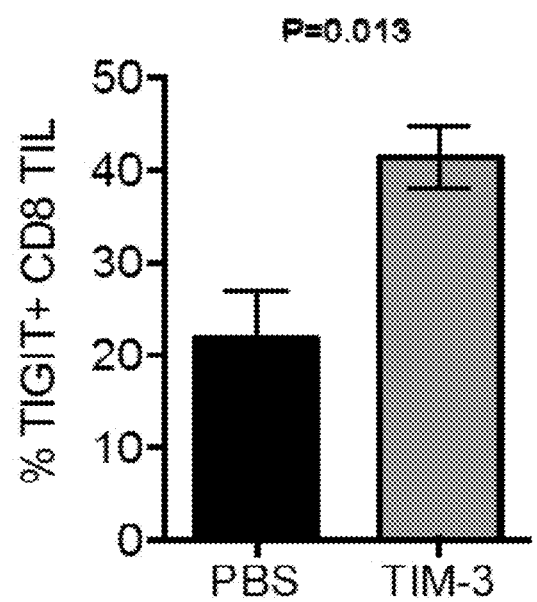
FIG. 19B shows that the relative frequency of TIGIT+ CD8 cells of total CD8$^+$ TILs in is elevated in MC38 colon carcinoma tumors in animals treated with anti-TIM-3 antibodies (TIM-3 group) when compared to vehicle treated (PBS) group. p=0.0475 vehicle vs anti-TIM-3 antibody treated groups. Each point represents one mouse. Data are representative of at least 2 independent experiments.
Figure 20A:
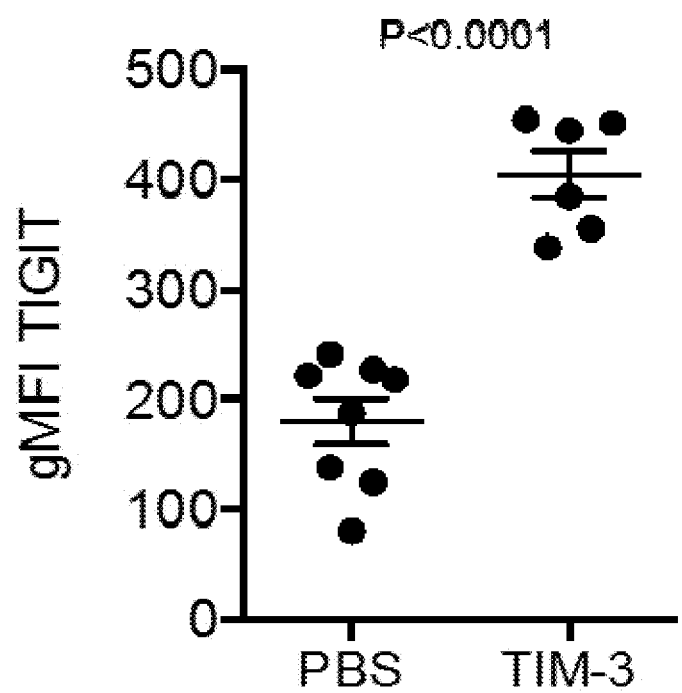
FIG. 20A shows that TIGIT surface expression (gMFI) is elevated on TILs in CT26 colon carcinoma tumors in animals treated with anti-TIM-3 antibodies (TIM-3 group) when compared to vehicle treated (PBS) group. p<0.001 vehicle vs anti-TIM-3 antibody treated groups. Each point represents one mouse. Data are representative of at least 2 independent experiments.
Figure 20B:
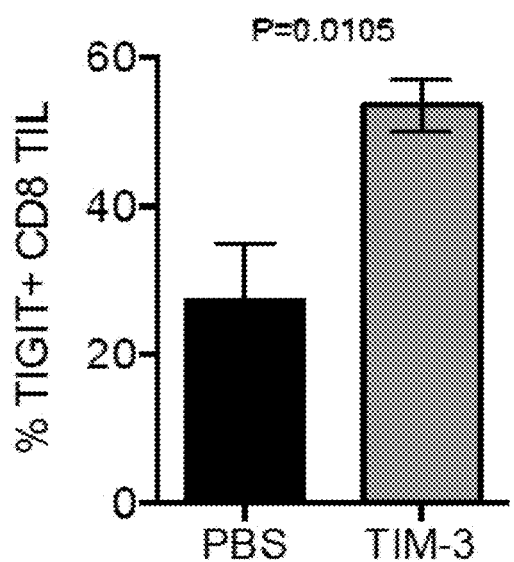
FIG. 20B shows that the relative frequency of TIGIT+ CD8 cells of total CD8+ TILs in is elevated in CT26 colon carcinoma tumors in animals treated with anti-TIM-3 antibodies (TIM-3 group) when compared to vehicle treated (PBS) group. p=0.0105 vehicle vs anti-TIM-3 antibody treated groups. Each point represents one mouse. Data are representative of at least 2 independent experiments.

TIGIT expression on CD8+ TILs (FIG. 19A, FIG. 20A) and relative frequency of TIGIT+ TILs f (FIG. 19B, FIG. 20B) were elevated in both CT26 (FIG. 19A, FIG. 19B) and MC38 (FIG. 20A, FIG. 20B) tumor models following TIM-3 blockage.

Example 21. TIM-3 Expression is Increased after Ex Vivo PD-1 Blockade in Melanoma Patient PBMC PBMCs from treatment naïve melanoma patients were stimulated with melanoma antigen peptide pools (NY-ESO, gp100, MART-1) in the presence of anti-PD-1 or anti-TIM-3 function blocking antibodies. Expression of TIM-3 was evaluated on peptide-restimulated cells on day 6. Results showed significant increases in the frequency of TIM-3+ CD8+ T cells in the anti-PD-1 treated samples compared to controls or TIM-3 treated PBMCs (FIG. 21).

On day 0, frozen PBMCs from treatment naïve melanoma patients were rapidly thawed in a 37° C. water bath. Cells were thawed, washed and counted in complete RPMI media (RPMI+10% FBS+1% sodium pyruvate+1% NEAA+1% pen/strep). Cells were plates at 200,000 cells per well in a 96 well, U-bottom plate in the presence or absence of anti-PD-1 or anti-TIM-3 function blocking antibodies (PD1B244 and TM3B403, respectively) and 1 μg/mL of melanoma antigen peptide pools (NY-ESO, gp100, MART-1) for 6 days at 37 C. Cells were restimulated with the peptide pool at day 6 and analyzed by flow cytometry for expression of PD-1 and TIM-3 as well as T cell activation and proliferation markers.

Figure 22A:
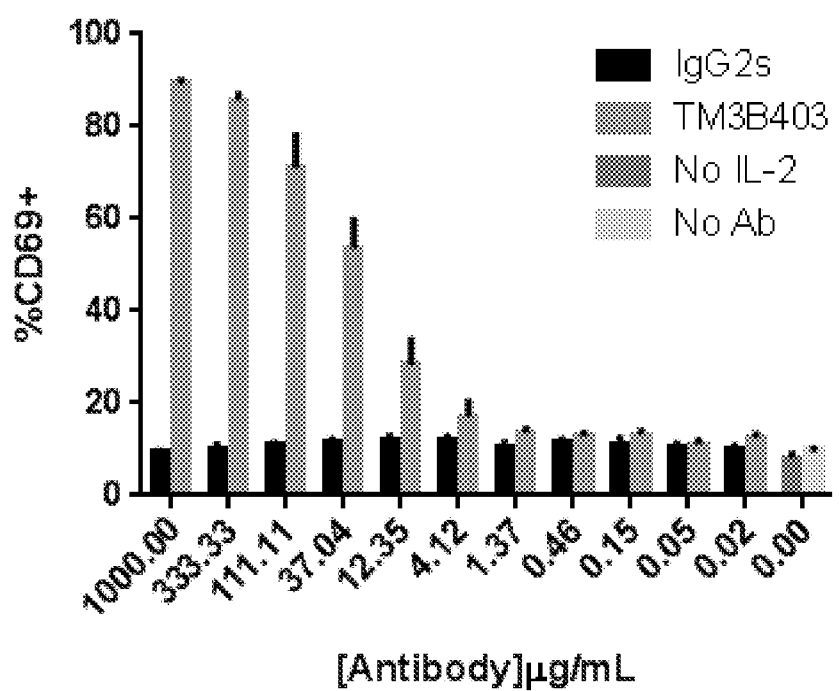
FIG. 22A shows that TM3B403 treatment increases frequency of activated NK cells in IL-2 stimulated human PBMCs. IgG2s: Isotype control. NK cell activation was assessed as percentage (%) of CD69 expressing cells in the stimulated PBMCs.
Figure 22B:
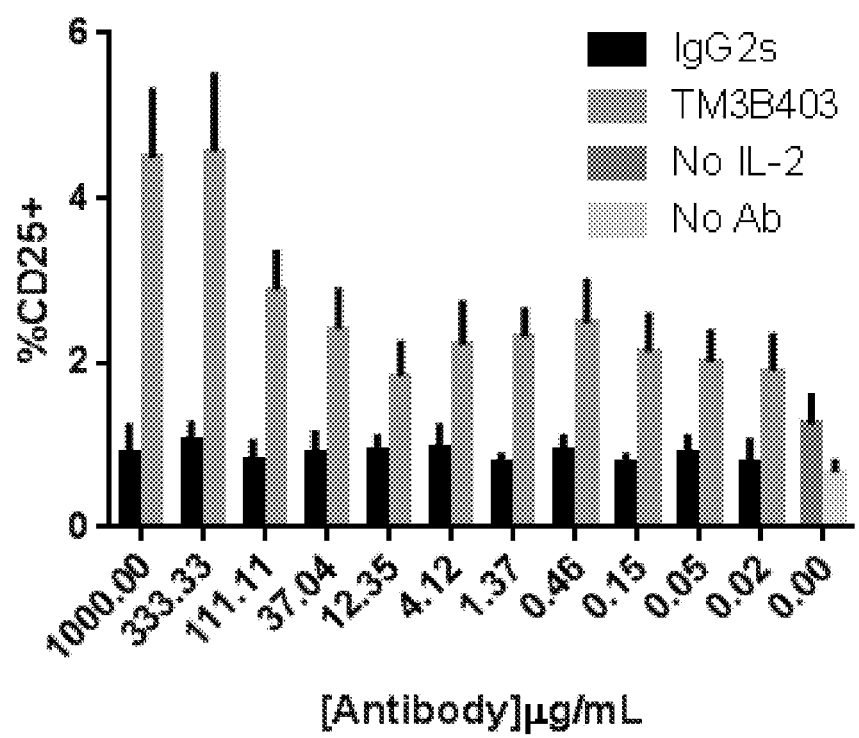
FIG. 22B shows that TM3B403 treatment increases frequency of activated NK cells in IL-2 stimulated human PBMCs. IgG2s: Isotype control. NK cell activation was assessed as percentage (%) of CD25 expressing cells in the stimulated PBMCs.

Example 22. Anti-TIM-3 Antibodies Increase the Frequency of Activated NK Cells in IL-2 Stimulated PBMCs The effects of anti-TIM-3 antibody TM3B403 on the frequency of activated NK cells was determined in assays where human PBMCs were stimulated with IL-2 (20U). Frequency of CD69 and CD25, markers of NK cell activation, were evaluated by flow cytometry 48 hours post-treatment at a range of mAb concentrations. TM3B403 increased the frequency of activated NK cells when the activation was assessed by percentage of CD69 positive cells (FIG. 22A) or percentage of CD25 positive cells (FIG. 22B).

What is claimed is:

1. A polynucleotide
   (a) encoding the VH of SEQ ID NOs: 41, 42, 43 or 48 and the VL of SEQ ID NOs: 49, 50, 51, 52, 53, 54, 55 or 56, wherein the encoding VH and VL comprise SEQ ID NOs: 41 and 49, 41 and 50, 42 and 51, 42 and 52, 42 and 53, 43 and 49, 43 and 54, 43 and 50, 43 and 55, 43 and 56, 48 and 53, 48 and 52, 48 and 56; or
   (b) comprising the polynucleotide sequences of SEQ ID NOs: 196 and 197.

2. A vector comprising the polynucleotide of claim 1.

3. A host cell comprising the vector of claim 2.

4. A method of producing an antagonistic antibody specifically binding PD-1 or an antigen-binding portion thereof, comprising culturing the host cell of claim 3 in conditions that the antibody of the antigen-binding portion thereof is expressed, and recovering the antibody or the antigen-binding portion thereof produced by the host cell.

5. A polynucleotide
   (a) encoding the VH of SEQ ID NO: 64 and the VL of SEQ ID NO: 65; or
   (b) comprising the polynucleotide sequences of SEQ ID NOs: 198 and 199.

6. A vector comprising the polynucleotide of claim 5.

7. A host cell comprising the vector of claim 6.

8. A method of producing an antagonistic antibody specifically binding PD-1 or an antigen-binding portion thereof, comprising culturing the host cell of claim 7 in conditions that the antibody or the antigen-binding portion thereof is expressed, and recovering the antibody or the antigen-binding portion thereof produced by the host cell.

9. A method of treating a cancer in a subject, comprising administering a therapeutically effective amount of-an isolated antibody or the antigen-binding portion thereof to the subject in need thereof for a time sufficient to treat the cancer wherein the isolated antibody or the antigen-binding portion thereof comprises an HCDR1, HCDR2, and HCDR3, and an LCDR1, LCDR2, and LCDR3 of SEQ ID NOs:
   (a) 10, 13, 16, 20, 26 and 31, respectively;
   (b) 10, 13, 16, 21, 26 and 32, respectively;
   (c) 10, 14, 16, 22, 27 and 33, respectively;
   (d) 10, 14, 16, 22, 26 and 34, respectively;
   (e) 10, 14, 16, 23, 28 and 35, respectively;
   (f) 10, 13, 17, 20, 26 and 31, respectively;
   (g) 10, 13, 17, 20, 26 and 36, respectively;
   (h) 10, 13, 17, 21, 26 and 32, respectively;
   (i) 10, 13, 17, 21, 27 and 37, respectively;
   (j) 10, 13, 17, 23, 26 and 32, respectively;
   (k) 10, 14, 17, 23, 28 and 35, respectively;
   (l) 10, 14, 17, 22, 26 and 34, respectively; or
   (m) 10, 14, 17, 23, 26 and 32, respectively.

10. A method of treating a cancer in a subject, comprising administering a therapeutically effective amount of the isolated antibody or the antigen-binding portion thereof to the subject in need thereof for a time sufficient to treat the cancer wherein the isolated antibody or the antigen-binding fragment thereof comprises (a) an HCDR1, HCDR2, and HCDR3, and an LCDR1, LCDR2, and LCDR3 of SEQ ID NOs: 66, 67, 68, 69, 70 and 71, respectively;
(b) a VH of SEQ ID NO: 64 and a VL of SEQ ID NO: 65; and/or
(c) a HC of SEQ ID NO: 74 and a LC of SEQ ID NO: 75.

11. The method of claim 9, wherein the cancer is a solid tumor or a hematological malignancy.

12. The method of claim 11, wherein the solid tumor is a melanoma, a lung cancer, a squamous non-small cell lung cancer (NSCLC), a non-squamous NSCLC, a colorectal cancer, a prostate cancer, a castration-resistant prostate cancer, a stomach cancer, an ovarian cancer, a gastric cancer, a liver cancer, a pancreatic cancer, a thyroid cancer, a squamous cell carcinoma of the head and neck, carcinomas of the esophagus or gastrointestinal tract, a breast cancer, a fallopian tube cancer, a brain cancer, an urethral cancer, a genitourinary cancer, an endometriosis, a cervical cancer or a metastatic lesion of the cancer.

13. The method of claim 11, wherein the hematological malignancy is a lymphoma, a myeloma or a leukemia.

14. A method of enhancing an immune response in a subject, comprising administering a therapeutically effective amount of an antibody or the antigen-binding portion thereof to the subject in need thereof for a time sufficient to enhance the immune response wherein the antibody or the antigen-binding portion thereof comprises an HCDR1, HCDR2, and HCDR3, and an LCDR1, LCDR2, and LCDR3 of SEQ ID NOs:
(a) 10, 13, 16, 20, 26 and 31, respectively;
(b) 10, 13, 16, 21, 26 and 32, respectively;
(c) 10, 14, 16, 22, 27 and 33, respectively;
(d) 10, 14, 16, 22, 26 and 34, respectively;
(e) 10, 14, 16, 23, 28 and 35, respectively;
(f) 10, 13, 17, 20, 26 and 31, respectively;
(g) 10, 13, 17, 20, 26 and 36, respectively;
(h) 10, 13, 17, 21, 26 and 32, respectively;
(i) 10, 13, 17, 21, 27 and 37, respectively;
(j) 10, 13, 17, 23, 26 and 32, respectively;
(k) 10, 14, 17, 23, 28 and 35, respectively;
(l) 10, 14, 17, 22, 26 and 34, respectively; or
(m) 10, 14, 17, 23, 26 and 32, respectively.

15. The method of claim 14, wherein the subject has a cancer or a viral infection.

16. The method of claim 9, wherein the antibody or the antigen-binding portion thereof is administered in combination with a second therapeutic agent.

17. The method of claim 16, wherein the second therapeutic agent is
a) a standard of care drug for treatment of the solid tumor or the hematological malignancy;
b) an agonist of a T cell activating molecule;
c) an agonist of CD86 (SEQ ID NO: 264), CD80 (SEQ ID NO: 265), CD28 (SEQ ID NO: 266), ICOS (SEQ ID NO: 267), ICOS ligand (SEQ ID NO: 268), TMIGD2 (SEQ ID NO: 269), CD40 (SEQ ID NO: 270), GITR (SEQ ID NO: 271), 4-1BB ligand (SEQ ID NO: 271), OX40 ligand (SEQ ID NO: 272), CD70 (SEQ ID NO: 274), CD40L (SEQ ID NO: 275), TNFRSF25 (SEQ ID NO: 264), LIGHT (SEQ ID NO: 277), GITR ligand (SEQ ID NO: 278), OX-40 (SEQ ID NO: 279), CD27 (SEQ ID NO: 280), CD137 (SEQ ID NO: 281), NKG2D (SEQ ID NO: 282), CD48 (SEQ ID NO: 283), CD226 (SEQ ID NO: 284), or MICA (SEQ ID NO: 285);
d) an inhibitor of a T cell inhibitory molecule;
e) an inhibitor of PD-1 (SEQ ID NO: 1), PD-L1 (SEQ ID NO: 5), PD-L2 (SEQ ID NO: 8), VISTA (SEQ ID NO: 286), BTNL2 (SEQ ID NO: 287), B7-H3 (SEQ ID NO: 288), B7-H4 (SEQ ID NO: 289), HVEM (SEQ ID NO: 290), HHLA2 (SEQ ID NO: 291), CTLA-4 (SEQ ID NO: 292), LAG-3 (SEQ ID NO: 293), TIM-3 (SEQ ID NO: 138), BTLA (SEQ ID NO: 294), CD160 (SEQ ID NO: 295), CEACAM-1 (SEQ ID NO: 296), LAIR1 (SEQ ID NO: 297), TGFβ (SEQ ID NO: 298), IL-10 (SEQ ID NO: 299), CD96 (SEQ ID NO: 300), TIGIT (SEQ ID NO: 301), NKG2A (SEQ ID NO: 302), CD112 (SEQ ID NO: 303), CD47 (SEQ ID NO: 304), SIRPA (SEQ ID NO: 305) or CD244 (SEQ ID NO: 306);
f) an antagonistic antibody specifically binding TIM-3;
g) an antagonistic antibody specifically binding TIM-3 comprising the VH and the VL of
i) SEQ ID NOs: 145 and 155, respectively;
ii) SEQ ID NOs: 146 and 156, respectively;
iii) SEQ ID NOs: 148 and 157, respectively;
iv) SEQ ID NOs: 147 and 155, respectively;
v) SEQ ID NOs: 149 and 158, respectively;
vi) SEQ ID NOs: 150 and 159, respectively;
vii) SEQ ID NOs:151 and 160, respectively;
viii) SEQ ID NOs: 152 and 161, respectively;
ix) SEQ ID NOs: 153 and 162, respectively;
x) SEQ ID NOs: 154 and 163, respectively; or
xi) SEQ ID NOs: 172 and 173, respectively;
h) a fibroblast growth factor receptor (FGFR) inhibitor;
i) a vaccine;
j) an agonistic antibody specifically binding GITR;
k) an agonistic antibody specifically binding OX40;
l) An agonistic antibody specifically binding OX40, comprising the VH and the VL of SEQ ID NOs: 309 and 310, respectively;
m) an agonistic antibody specifically binding OX40, comprising the VH and the VL of SEQ ID NOs: 311 and 312, respectively;
n) an agonistic antibody specifically binding CD137;
o) radiation therapy; or
p) surgery.

18. The method of claim 17, wherein the antibody or the antigen-binding portion thereof and the second therapeutic agent are administered simultaneously, sequentially or separately.

19. The method of claim 9, wherein the antibody or the antigen-binding portion thereof comprises
a) a heavy chain variable region (VH) of SEQ ID NOs: 41, 42, 43 or 48;
b) a light chain variable region (VL) of SEQ ID NOs: 49, 50, 51, 52, 53, 54, 55 or 56; or
c) a VH of SEQ ID NOs: 41, 42, 43 or 48 and a VL of SEQ ID NOs: 49, 50, 51, 52, 53, 54, 55 or 56.

20. The method of claim 9, wherein the antibody or the antigen-binding portion thereof comprises
a) a VH of SEQ ID NO: 41 and a VL of SEQ ID NO: 49;
b) a VH of SEQ ID NO: 41 and a VL of SEQ ID NO: 50;
c) a VH of SEQ ID NO: 42 and a VL of SEQ ID NO: 51;
d) a VH of SEQ ID NO: 42 and a VL of SEQ ID NO: 52;
e) a VH of SEQ ID NO: 42 and a VL of SEQ ID NO: 53;
f) a VH of SEQ ID NO: 43 and a VL of SEQ ID NO: 49;
g) a VH of SEQ ID NO: 43 and a VL of SEQ ID NO: 54;
h) a VH of SEQ ID NO: 43 and a VL of SEQ ID NO: 50;
i) a VH of SEQ ID NO: 43 and a VL of SEQ ID NO: 55;
j) a VH of SEQ ID NO: 43 and a VL of SEQ ID NO: 56;
k) a VH of SEQ ID NO: 48 and a VL of SEQ ID NO: 53;

l) A VH of SEQ ID NO: 48 and a VL of SEQ ID NO: 52; or m) a VH of SEQ ID NO: 48 and a VL of SEQ ID NO: 56.

21. The method of claim 20, wherein the antibody or the antigen-binding portion thereof comprises a VH of SEQ ID NO: 48 and a VL of SEQ ID NO: 53.

22. The method of claim 20, wherein the antibody or the antigen-binding portion thereof comprises a VH of SEQ ID NO: 48 and a VL of SEQ ID NO: 52.

23. The method of claim 20, wherein the antibody or the antigen-binding portion thereof comprises a VH of SEQ ID NO: 48 and a VL of SEQ ID NO: 56.

24. The method of claim 9, wherein the antibody or the antigen-binding portion thereof comprises a HC of SEQ ID NO: 72 and a LC of SEQ ID NO: 73.

25. The method of claim 17, wherein the standard of care drug is capecitabine.

26. The polynucleotide of claim 1, wherein the encoding VH and VL comprise SEQ ID NOs: 48 and 56.

27. The polynucleotide of claim 1, wherein the polynucleotide sequences comprise SEQ ID NOs: 196 and 197.

28. The polynucleotide of claim 5, wherein the encoding VH and VL comprise SEQ ID NOs: 64 and 65.

29. The polynucleotide of claim 5, wherein the polynucleotide sequences comprise SEQ ID NOs: 198 and 199.

30. The method of claim 16, wherein the second therapeutic agent is gemcitabine.

* * * * *